United States Patent
Chamberlain et al.

(10) Patent No.: US 11,414,387 B2
(45) Date of Patent: *Aug. 16, 2022

(54) OXOACRIDINYL ACETIC ACID DERIVATIVES AND METHODS OF USE

(71) Applicant: Stingthera, Inc., Wilmington, DE (US)

(72) Inventors: Brian T. Chamberlain, Wilmington, DE (US); James M. Rice, Wilmington, DE (US); Finith E. Jernigan, III, Wilmington, DE (US); Woody Sherman, Wilmington, DE (US); Meghana M. Kulkarni, Wilmington, DE (US); Sharon Shechter, Wilmington, DE (US); Bryce K. Allen, Wilmington, DE (US); Dazhi Tan, Wilmington, DE (US); Kristen A. Marino, Wilmington, DE (US); Zhixiong Lin, Wilmington, DE (US)

(73) Assignee: STINGTHERA, INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/923,280

(22) Filed: Jul. 8, 2020

(65) Prior Publication Data

US 2021/0002230 A1    Jan. 7, 2021

Related U.S. Application Data

(63) Continuation of application No. 16/195,997, filed on Nov. 20, 2018, now Pat. No. 10,745,358.

(60) Provisional application No. 62/723,660, filed on Aug. 28, 2018, provisional application No. 62/631,530, filed on Feb. 16, 2018, provisional application No. 62/588,802, filed on Nov. 20, 2017.

(51) Int. Cl.
| | | |
|---|---|---|
| *C07D 219/06* | (2006.01) | |
| *C07D 219/08* | (2006.01) | |
| *C07D 405/12* | (2006.01) | |
| *C07D 401/12* | (2006.01) | |
| *C07D 209/86* | (2006.01) | |
| *C07D 405/04* | (2006.01) | |
| *C07D 413/04* | (2006.01) | |
| *C07D 417/04* | (2006.01) | |
| *C07D 401/04* | (2006.01) | |
| *C07D 209/88* | (2006.01) | |

(52) U.S. Cl.
CPC ......... *C07D 219/06* (2013.01); *C07D 209/86* (2013.01); *C07D 209/88* (2013.01); *C07D 219/08* (2013.01); *C07D 401/04* (2013.01); *C07D 401/12* (2013.01); *C07D 405/04* (2013.01); *C07D 405/12* (2013.01); *C07D 413/04* (2013.01); *C07D 417/04* (2013.01)

(58) Field of Classification Search
CPC .. C07D 219/06; C07D 209/88; C07D 219/08; C07D 405/12; C07D 401/12; C07D 209/86; C07D 405/04; C07D 413/04; C07D 417/04; C07D 401/04
See application file for complete search history.

(56) References Cited

U.S. PATENT DOCUMENTS

| | | |
|---|---|---|
| 3,681,360 A | 8/1972 | Fryer et al. |
| 9,642,830 B2 | 5/2017 | Chang et al. |
| 2005/0217038 A1 | 10/2005 | Glenn |

FOREIGN PATENT DOCUMENTS

| | | |
|---|---|---|
| CN | 103709122 | 4/2014 |
| EP | 0889037 A1 | 1/1999 |
| JP | 2006004736 | 1/2006 |
| JP | 2008067873 | 3/2008 |
| JP | 2008090130 | 4/2008 |
| JP | 2009271403 | 11/2009 |
| RU | 2118532 C1 | 9/1998 |
| WO | WO 96/26938 A1 | 9/1996 |
| WO | WO 97/12872 A1 | 10/1997 |
| WO | WO 02/020743 | 11 | 9/2002 |
| WO | WO 02/099424 A2 | 12/2002 |
| WO | WO 02/099432 A2 | 12/2002 |
| WO | WO 2004/106923 A1 | 12/2004 |
| WO | WO 2008/021745 A2 | 2/2008 |
| WO | WO 2009/112791 A1 | 9/2009 |
| WO | WO 2011/062182 A1 | 5/2011 |
| WO | WO 2012/096718 A2 | 7/2012 |
| WO | WO 2013/022740 A2 | 2/2013 |
| WO | WO 2015/046502 A1 | 4/2015 |
| WO | WO 2018/165494 A1 | 9/2018 |

OTHER PUBLICATIONS

Lao, W., "Microwave-assisted rapid preparation of substituted carbazole-9-acetic and propionic acids and their absorption and fluorescence spectra." Monatshefte für Chemie/Chemical Monthly 131.7 (2000): 803-811.*
Szulc, Z., "Synthesis of carbocyclic derivatives of 9 (10 H)-acridinone, 9H-carbazole and 10 H-phenothiazine 5, 5-dioxide as potential immunomodulating agents." Journal für Praktische Chemie 330.6 (1988): 1023-1029.*
Chemical Abstracts Service CAS Registry No. 908816-64-8, CAplus database entry date of Sep. 27, 2006 ; 1p.*
CAS Registry Reference 1581-44-8; p. 1; accessed in STN 2019.
CAS 1179362-81-2 (Entered STN: Sep. 2, 2009), 2 pages.

(Continued)

*Primary Examiner* — John M Mauro
(74) *Attorney, Agent, or Firm* — Barnes & Thornburg LLP; Ryan L. Marshall; Steve Sturlis

(57) ABSTRACT

Compounds of Formula I or pharmaceutically acceptable salts or esters thereof capable of binding to and modulating the activity of a stimulator of interferon genes (STING) protein are provided. Methods involving compounds of Formula I as effective modulators of STING are also provided.

23 Claims, No Drawings

(56) References Cited

OTHER PUBLICATIONS

CAS 1258222-14-8, registered Dec. 31, 2010.
CAS 1173022-07-5, registered Aug. 5, 2009.
CAS 231625-00-6, registered Aug. 10, 1999.
CAS 231625-88-0, registered Aug. 10, 1999.
CAS 231625-03-9, registered Aug. 10, 1999.
CAS 231625-02-8, registered Aug. 10, 1999.
CAS 231624-99-0, registered Aug. 10, 1999.
CAS 231624-32-1, registered Aug. 10, 1999.
CAS 231624-31-0, registered Aug. 10, 1999.
CAS 231624-30-9, registered Aug. 10, 1999.
CAS 231624-29-6, registered Aug. 10, 1999.
CAS 231624-28-5, registered Aug. 10, 1999.
CAS 231624-27-4, registered Aug. 10, 1999.
CAS 231624-26-3, registered Aug. 10, 1999.
Chen, C.-H., "Synthesis of new tetracyclic 7-ox0-pyrido [3, 2, 1 -de] acridine derivatives", Tetrahedron, 2011, vol. 67, No. 33, p. 5883-5893.
Faerman, C. H. et al., "Charge is the major discriminating factor for glutathione reductase versus trypanothione reductase inhibitors", Bioorganic & Medicinal Chemistry, 1996, vol. 4, No. 8, p. 1247-1253.
Kramer, M. J. et al. "Antiviral Activity of 10-Carboxymethyl-9-Acridanone", Antimicrobial Agents and Chemotherapy, 1976, vol. 9, No. 2, p. 233-238.
Kumar, R. et al., "Synthesis, cytotoxic activity, and computational analysis of N10 substituted acridone analogs", Medicinal Chemistry Research, 2015, vol. 24, No. 3, p. 921-933.
Szulc, B., "Choline and halogen derivatives of CMA (9-oxo-10-acridine acetic acids) as tools for monitoring the interaction of the interferon inducers via a specific receptor", Antiviral Research, 1987, vol. 7, No. 2, p. 109-117.
Szulc, Z. et al. "Synthesis of Halogen Derivatives of 9-Oxo-10-acridineacetic Acid as Potential Interferon Inducers", Journal f. prakt. Chemie. Band H:29, H<-'ft 4, 1987, p. 741-744.
Tijono, S. M., "Identification of human-selective analogues of the vascular-disrupting agent 5, 6-dimethylxanthenone-4-acetic acid (DMXAA)", British Journal of Cancer, 2013, vol. 108, No. 6, p. 1306.
Vargas, T. R., "Rationale for stimulator of interferon genes-targeted cancer immunotherapy", European Journal of Cancer, 2017, vol. 75, p. 86-97.
Verweij, M. F. "Preventive medicine between obligation and aspiration", 2013, vol. 4, Ch. 3, p. 25-48.
Office Action for corresponding Eurasian Appln. No. 202091270, dated Apr. 21, 2021.
Extended European Search Report for EP Appln. 18878928.3, dated Mar. 16, 2021.
Cavlar, T., et al. Species-specific detection of the antiviral small-molecule compound CMA by STING, The EMBO Journal, 2013, vol. 32, pp. 1440-1450.
Examination Report for corresponding Australian Appln. No. 2018368789, dated Aug. 9, 2021.
CAS Registry No. 908816-64-8; STN Entry Date Sep. 27, 2006; 10(9H)-Acridineacetic acid, 4-cyano-2,3-dimethyl-9-oxo-, ethyl ester.

\* cited by examiner

OXOACRIDINYL ACETIC ACID DERIVATIVES AND METHODS OF USE

RELATED APPLICATIONS

This application is a continuation of U.S. application Ser. No. 16/195,997, filed on Nov. 20, 2018, which claims priority to, and the benefit of, U.S. Provisional Application Nos. 62/588,820, filed on Nov. 20, 2017, 62/631,530, filed on Feb. 16, 2018, and 62/723,660, filed on Aug. 28, 2018, the contents of each of which are incorporated by reference in their entirety.

BACKGROUND

Modulating innate immune activity by agonizing or antagonizing pattern recognition receptors (PRRs) has vast potential for clinical applications both as monotherapy and in combination with other pharmaceutical or bio-pharmaceutical agents. The applications range from alleviating autoimmune disorders through immunosuppression to treating solid and hematological cancers by stimulating innate anti-tumor immunity, as well as uses in anti-viral therapy or as vaccine adjuvant.

One of the PRRs involved in the effective activation of antigen presenting cells (APCs) is the stimulator of interferon genes (STING) protein. STING is an evolutionarily conserved, cytosolic PRR that is part of the cGAS-CDN-STING axis. Aberrant dsDNA in the cytosol, as a consequence of cell stress, viral or intracellular bacterial infection, failed mitosis, or phagocytosis, is recognized by the cGAS enzyme, which synthesizes the non-canonical cyclic di-nucleotide (CDN), 2'3'cGAMP, 2'3'cGAMP binds to and stabilizes the STING dimer, resulting in IRF3 and NFkB activation and synthesis of type I interferon. STING protein plays an important role in innate cellular responses to viral infection and aberrant cytosolic DNA accumulation in both target cells and responding innate immune cells. The pleiotropic effects of STING activation are cell-type and context dependent. For example, overstimulation of T cells and B cells through STING leads to a pro-apoptotic phenotype, while in myeloid cells STING activation elevates type I IFN and pro-inflammatory cytokines without an increase in apoptosis.

Tumor derived dsDNA is phagocytosed by resident dendritic cells (DCs), which stimulates the cGAS-CDN-STING axis and activates DCs, leading to lymph node migration and, ultimately, proliferation of antigen specific CD4+ and CD8+ T cells. This process and the accompanying type I IFN response are often absent in tumors that lack a T cell infiltrate, highlighting the potential of STING agonization to directly address the mechanism of escape exploited by these tumors. Although several CDN derived ligands have shown pre-clinical promise as STING agonists, their relatively large molecular weight and polarity have limited their application to intratumoral injection. Moreover, binding and activation/inhibition of the cytosolic STING protein is limited in vivo by cell membrane permeability. Furthermore, despite their therapeutic efficacy via systemic administration (i.v. or i.p.), the previously identified small molecule STING agonists DMXAA and CMA exhibit species selectivity, prohibiting their use as human therapeutics. Thus, there is a need for human-active small molecule modulators of STING for use as effective therapeutic agents. The present application addresses this need. The novel compounds of this application overcome the limitations of CDN derived ligands.

SUMMARY

In one aspect, the present application relates to a compound of Formula I:

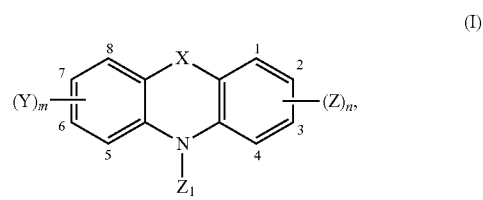

or a pharmaceutically acceptable salt or ester thereof, wherein X, Y, Z, $Z_1$, m, and n are each defined herein.

In another aspect, the present application relates to a pharmaceutical composition comprising a therapeutically effective amount of a compound of the application, or a pharmaceutically acceptable salt or ester thereof, and a pharmaceutically acceptable carrier.

Another aspect of the present application relates to a method of modulating (e.g., inhibiting or stimulating) a stimulator of interferon genes (STING) protein. The method comprises administering to a subject in need thereof an effective amount of a compound of the application or a pharmaceutically acceptable salt or ester thereof, or a pharmaceutical composition of the application. In one embodiment, the STING protein is a human STING protein.

Another aspect of the present application relates to a method of treating or preventing a disease, wherein the diseases is caused by, or associated with, STING expression, activity, and/or function (e.g., deregulation of STING expression, activity, and/or function). The method comprises administering to a subject in need thereof an effective amount of a compound of the application or a pharmaceutically acceptable salt or ester thereof, or a pharmaceutical composition of the application.

Another aspect of the present application relates to a method of treating or preventing a disease associated with deregulation of one or more of the intracellular pathways in which a STING protein is involved (e.g., deregulation of intracellular dsDNA mediated type I interferon activation). The method comprises administering to a subject in need thereof an effective amount of a compound of the application or a pharmaceutically acceptable salt or ester thereof, or a pharmaceutical composition of the application.

Another aspect of the present application relates to a kit comprising a compound of the application or a pharmaceutically acceptable salt or ester thereof, or a pharmaceutical composition of the application.

Another aspect of the present application relates to a compound of the application or a pharmaceutically acceptable salt or ester thereof, or a pharmaceutical composition of the application, for use in the manufacture of a medicament for modulating (e.g., inhibiting or stimulating) a STING protein, for treating or preventing a disease, wherein the diseases is caused by, or associated with STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type I interferon activation).

Another aspect of the present application relates to use of a compound of the application or a pharmaceutically acceptable salt or ester thereof, or a pharmaceutical composition of the application, in the manufacture of a medicament for modulating (e.g., inhibiting or stimulating) a STING protein, for treating or preventing a disease, wherein the diseases is caused by, or associated with, STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type I interferon activation).

Another aspect of the present application relates to a compound of the application or a pharmaceutically acceptable salt or ester thereof, or a pharmaceutical composition of the application, for use in modulating (e.g., inhibiting or stimulating) a STING protein, in treating or preventing a disease, wherein the diseases is caused by, or associated with STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type I interferon activation).

Another aspect of the present application relates to use of a compound of the application or a pharmaceutically acceptable salt or ester thereof, or a pharmaceutical composition of the application, in modulating (e.g., inhibiting or stimulating) a STING protein, in treating or preventing a disease, wherein the diseases is caused by, or associated with STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type-1 interferon activation).

The present application provides modulators of a STING protein that are therapeutic agents in the treatment or prevention of diseases such as cancer and immunological disorders.

The details of the disclosure are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

The contents of all references (including literature references, issued patents, published patent applications, and co-pending patent applications) cited throughout this application are hereby expressly incorporated herein in their entireties by reference. The references cited herein are not admitted to be prior art to the application.

DETAILED DESCRIPTION

The present application relates to compounds of Formula I that are shown to potently and selectively a STING protein (e.g., the human STING protein). In one embodiment, a compound of the present application is represented by Formula I:

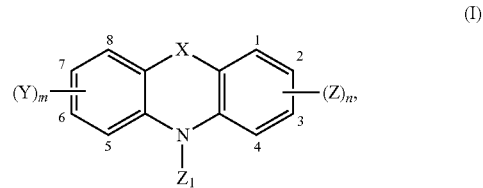

or a pharmaceutically acceptable salt or ester thereof, wherein

X is $C(R_X)_2$, O, S, CH=CH, or absent;

each $R_X$ is independently H, $CH_3$, $CF_3$, $CF_2H$, or F. or two $R_X$ together form =O, =$CH_2$, or =$CF_2$, or two $R_X$, together with the carbon atom to which they are bonded, form a cyclopropyl:

$Z_1$ is $(C(R_Z)_2)_p$-$T_1$;

p is 1, 2, 3, 4, 5, or 6;

each $R_Z$ is independently H, $C_1$-$C_4$ alkyl, $C_1$-$C_4$ alkyl substituted with one or more halogen, or halogen;

$T_1$ is $CHOR_1$, $C(O)R_1$, $C(O)OR_1$, $C(O)N(R_1)_2$, $NR_1C(O)R_1$, $C(S)R_1$, $C(S)N(R_1)_2$, $NR_1C(S)R_1$, $C(O)NHS(O)_2R_S$, $C(O)NHCOR_1$, $C(O)NHOH$, or $C(O)NHCN$;

$R_S$ is $R_1$, $C_3$-$C_8$ cycloalkyl, heterocyclyl comprising one 5- or 6-membered rings and 1-2 heteroatoms selected from N, O, and S, or $C_6$-$C_{10}$ aryl, wherein the cycloalkyl, heterocyclyl, or aryl is optionally substituted with one or more groups independently selected from $C_1$-$C_4$ alkyl;

each $R_1$ is independently H, $C_1$-$C_4$ alkyl, or $C_1$-$C_4$ alkyl substituted with one or more halogen;

m is 0, 1, 2, 3, or 4;

each Y is independently $C_1$-$C_6$ alkyl, $C_2$-$C_6$ alkenyl, $C_2$-$C_6$ alkynyl, halogen, CN, OH, O—($C_1$-$C_6$ alkyl), S—($C_1$-$C_6$ alkyl), O—($C_2$-$C_4$ alkenyl), O—($C_2$-$C_4$ alkynyl), $NH_2$, NH—$C_1$-$C_6$ alkyl, N—($C_1$-$C_6$ alkyl)$_2$, S(O)—($C_1$-$C_6$ alkyl), S(O)$_2$—($C_1$-$C_6$ alkyl), or Q-T, wherein the alkyl, alkenyl, or alkynyl moiety is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$, or two Y, together with the two adjacent carbon atoms to which they are bonded, form a 5- to 7-membered carbocycle or phenyl;

n is 0, 1, 2, 3, or 4;

each Z is independently $C_1$-$C_6$ alkyl, $C_2$-$C_6$ alkenyl, $C_2$-$C_6$ alkynyl, halogen, CN, OH O—($C_1$-$C_6$ alkyl), S—($C_1$-$C_6$ alkyl), O—($C_2$-$C_4$ alkenyl), O—($C_2$-$C_4$ alkynyl), $NH_2$, NH—$C_1$-$C_6$ alkyl, N—($C_1$-$C_6$ alkyl)$_2$, S(O)—($C_1$-$C_6$ alkyl), S(O)$_2$—($C_1$-$C_6$ alkyl), or Q-T, wherein the alkyl, alkenyl, or alkynyl moiety is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$;

each Q is independently a bond, NH, N($C_1$-$C_3$ alkyl), O, S, S(O), S(O)$_2$, Q', NH-Q', N($C_1$-$C_3$ alkyl)-Q', O-Q', S-Q', S(O)-Q', or S(O)$_2$-Q';

each Q' is independently a carbon linker comprising one or more $C(R_Q)_2$, $C(R_1)_2$—$C(R_Q)_2$, $CR_Q$=$CR_Q$, or C≡C;

each $R_Q$ is independently H or $C_1$-$C_3$ alkyl;

each T is independently C(O)—$C_1$-$C_6$ alkyl, C(O)O—$C_1$-$C_6$ alkyl, $C_3$-$C_8$ cycloalkyl, $C_3$-$C_8$ cycloalkenyl, heterocyclyl comprising one or two 5- or 6-membered rings and 1-4 heteroatoms selected from N, O, and S, $C_6$-$C_{10}$ aryl, or heteroaryl comprising one or two 5- or 6-membered rings and 1-4 heteroatoms selected from N, O, and S, wherein the cycloalkyl, cycloalkenyl, heterocyclyl, aryl, or heteroaryl is optionally substituted with one or more $R_T$;

each $R_T$ is independently $C_1$-$C_6$ alkyl, $C_1$-$C_6$ haloalkyl, OH, CN, halogen, O—($C_1$-$C_6$ alkyl), O—($C_1$-$C_6$ haloalkyl), S—($C_1$-$C_6$ alkyl), $NH_2$, NH—$C_1$-$C_6$ alkyl, N—($C_1$-$C_6$ alkyl)$_2$, NHS(O)$_2$—($C_1$-$C_6$ alkyl), (CH$_2$)—$C_3$-$C_8$ cycloalkyl, (CH$_2$)$_q$-heterocyclyl, (CH$_2$)$_q$-phenyl, or (CH$_2$)$_q$-heteroaryl, wherein the heterocyclyl or heteroaryl comprises one or two 5- or 6-membered rings and 1-4 heteroatoms selected from N, O, and S; and q is 0, 1, 2, or 3, wherein when X is C(O) and each $R_Z$ is H:

m and n are not both 0; and the compound of Formula I is not mono-substituted at the 2- or 7-position with Cl; and the compound of Formula I is not di-substituted at the 2- and 8-positions or at the 1- and 7-positions with halogens selected from F and Cl.

In one embodiment, a compound of Formula I is of Formula Ia or Ib:

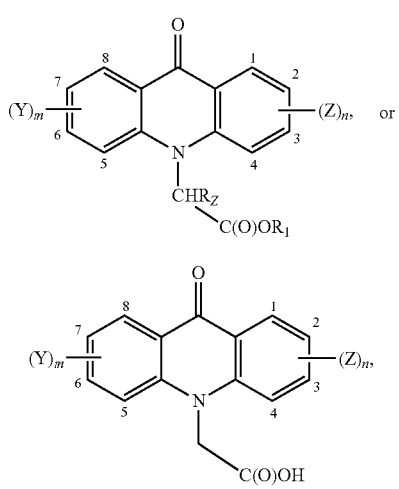

or a pharmaceutically acceptable salt or ester thereof.

For any of Formula I, Ia, or Ib, where applicable:

(a1) In one embodiment, X is C($R_X$)$_2$.

(b1) In one embodiment, each $R_X$ is H.

(b2) In one embodiment, at least one $R_X$ is CH$_3$, CF$_3$, CF$_2$H. or F.

(b3) In one embodiment, one $R_X$ is CH$_3$, CF$_3$. CF$_2$H, or F, and the other $R_X$ is H.

(b4) In one embodiment, each $R_X$ is independently CH$_3$, CF$_3$, CF$_2$H, or F. In one embodiment, each $R_X$ is CH$_3$. In one embodiment, each $R_X$ is CF$_3$. In one embodiment, each $R_X$ is CF$_2$H. In one embodiment, each $R_X$ is F.

(b5) In one embodiment, two $R_X$ together form =O, =CH$_2$, or =CF$_2$.

(b6) In one embodiment, two $R_X$ together form =O.

(b7) In one embodiment, two $R_X$ together form =CH$_2$.

(b8) In one embodiment, two $R_X$ together form =CF$_2$.

(b9) In one embodiment, two $R_X$, together with the carbon atom to which they are bonded, form a cyclopropyl.

(a2) In one embodiment, X is O.

(a3) In one embodiment, X is S.

(a4) In one embodiment, X is CH=CH.

(a5) In one embodiment, X is absent.

(a6) In one embodiment, X is not absent.

(c1) In one embodiment, p is 1, 2, or 3.

(c2) In one embodiment, p is 1 or 2.

(c3) In one embodiment, p is 1.

(c4) In one embodiment, p is 2, 3, 4, 5, or 6.

(d1) In one embodiment, each $R_Z$ is H.

(d2) In one embodiment, at least one $R_Z$ is $C_1$-$C_4$ alkyl (e.g., methyl, ethyl, n-propyl, i-propyl, n-butyl, i-butyl, s-butyl, or t-butyl), $C_1$-$C_4$ alkyl substituted with one or more halogen (e.g., methyl, ethyl, n-propyl, i-propyl, n-butyl, i-butyl, s-butyl, or t-butyl, each substituted with one or more halogen (e.g., F, Cl, Br, or I)), or halogen (e.g., F, Cl, Br, or I).

(d3) In one embodiment, at least one $R_Z$ is $C_1$-$C_4$ alkyl (e.g., methyl, ethyl, n-propyl, i-propyl, n-butyl, i-butyl, s-butyl, or t-butyl).

(d4) In one embodiment, at least one $R_Z$ is $C_1$-$C_4$ alkyl substituted with one or more halogen (e.g., methyl, ethyl, n-propyl, i-propyl, n-butyl, i-butyl, s-butyl, or t-butyl, each substituted with one or more halogen (e.g., F, Cl, Br, or I)).

(d5) In one embodiment, at least one $R_Z$ is halogen (e.g., F, Cl, Br, or I).

(e1) In one embodiment, $T_1$ is CHOR$_1$, C(O)R$_1$, C(O)OR$_1$, C(O)N(R$_1$)$_2$, or NR$_1$C(O)R$_1$.

(e2) In one embodiment, $T_1$ is C(O)R$_1$, C(O)OR, C(O)N(R$_1$)$_2$, or NR$_1$C(O)R$_1$.

(e3) In one embodiment, $T_1$ is C(O)R$_1$. C(O)OR$_1$, or C(O)N(R$_1$)$_2$.

(e4) In one embodiment, $T_1$ is C(O)OR, or C(O)N(R$_1$)$_2$.

(e5) In one embodiment, $T_1$ is C(O)R$_1$ or C(O)OR$_1$.

(e6) In one embodiment, $T_1$ is C(O)R$_1$, C(O)OR$_1$, C(O)N(R$_1$)$_2$, NR$_1$C(O)R$_1$, C(S)R$_1$, C(S)N(R$_1$)$_2$, or NR$_1$C(S)R$_1$.

(e7) In one embodiment, $T_1$ is C(O)OR$_1$, C(O)N(R$_1$)$_2$, NR$_1$C(O)R$_1$, C(S)N(R$_1$)$_2$, or NR$_1$C(S)R$_1$.

(e8) In one embodiment, $T_1$ is C(O)OR$_1$, C(O)N(R$_1$)$_2$, or C(S)N(R$_1$)$_2$.

(e9) In one embodiment, $T_1$ is C(S)R$_1$, C(S)N(R$_1$)$_2$, or NR$_1$C(S)R$_1$.

(e10) In one embodiment, $T_1$ is C(O)R$_1$, C(O)OR$_1$, C(O)N(R$_1$)$_2$, NR$_1$C(O)R$_1$, C(O)NHS(O)$_2$R$_S$, C(O)NHCOR$_1$, C(O)NHOH, or C(O)NHCN.

(e11) In one embodiment, $T_1$ is C(O)OR$_1$, C(O)N(R$_1$)$_2$, C(O)NHS(O)$_2$R$_S$, C(O)NHCOR$_1$, C(O)NHOH, or C(O)NHCN.

(f1) In one embodiment, each $R_1$ is H.

(f2) In one embodiment, at least one $R_1$ is $C_1$-$C_4$ alkyl (e.g., methyl, ethyl, n-propyl, i-propyl, n-butyl, i-butyl, s-butyl, or t-butyl), $C_1$-$C_4$ alkyl substituted with one or more halogen (e.g., methyl, ethyl, n-propyl, i-propyl, n-butyl, i-butyl, s-butyl, or t-butyl, each substituted with one or more halogen (e.g., F, Cl, Br, or I)), or halogen (e.g., F, Cl, Br, or I).

(f3) In one embodiment, at least one $R_1$ is $C_1$-$C_4$ alkyl (e.g., methyl, ethyl, n-propyl, i-propyl, n-butyl, i-butyl, s-butyl, or t-butyl).

(f4) In one embodiment, at least one $R_1$ is $C_1$-$C_4$ alkyl substituted with one or more halogen (e.g., methyl, ethyl, n-propyl, i-propyl, n-butyl, i-butyl, s-butyl, or t-butyl, each substituted with one or more halogen (e.g., F, Cl, Br, or I)).

(f5) In one embodiment, at least one $R_1$ is halogen (e.g., F, Cl, Br, or I).

(g1) In one embodiment, m is 0, 1, 2, or 3.

(g2) In one embodiment, m is 0, 1, or 2.

(g3) In one embodiment, m is 0.

(g4) In one embodiment, m is 1 or 2.

(g5) In one embodiment, m is 1.

(g6) In one embodiment, m is 2.

(h1) In one embodiment, at least one Y is $C_1$-$C_6$ straight-chain or $C_3$-$C_6$ branched alkyl (e.g., methyl, ethyl, n-propyl, i-propyl, n-butyl, i-butyl, s-butyl, t-butyl, pentyl, i-pentyl, or hexyl), optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Y is $C_1$-$C_4$ alkyl (e.g., methyl, ethyl, n-propyl, i-propyl, n-butyl, i-butyl, s-butyl, or t-butyl), optionally substituted as described herein. In one embodiment, at least one Y is $C_1$-$C_6$ straight-chain or $C_3$-$C_6$ branched alkyl and is substituted as described herein. In one embodiment, at least one Y is $C_1$-$C_6$ straight-chain or $C_3$-$C_6$ branched alkyl substituted with OH, $NH_2$, $N_3$, halogen, or O—($C_1$-$C_6$ alkyl). In one embodiment, at least one Y is methyl, optionally substituted as described herein. In one embodiment, at least one Y is ethyl, optionally substituted as described herein. In one embodiment, at least one Y is i-propyl, optionally substituted as described herein. In one embodiment, at least one Y is t-butyl, optionally substituted as described herein.

(h2) In one embodiment, at least one Y is $C_2$-$C_6$ straight-chain or $C_3$-$C_6$ branched alkenyl (e.g., ethenyl, propenyl, butenyl, pentenyl, or hexenyl), optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Y is $C_2$-$C_6$ straight-chain or $C_3$-$C_6$ branched alkenyl substituted with OH, $NH_2$, halogen, or O—($C_1$-$C_6$ alkyl).

(h3) In one embodiment, at least one Y is $C_2$—C straight-chain or $C_4$-$C_6$ branched alkynyl (e.g., ethynyl, propynyl, butynyl, pentynyl, or hexynyl), optionally substituted with one or more groups independently selected from OH, $NH_2$. $N_3$, halogen, O—($C_1$—C alkyl), S—($C_1$-$C_6$ alkyl), NH—$C_1$-$C_6$ alkyl, and N—($C_1$-$C_6$ alkyl)$_2$. In one embodiment, at least one Y is $C_2$-$C_6$ straight-chain or $C_4$-$C_6$ branched alkynyl substituted with OH $NH_2$, halogen, or O—($C_1$-$C_6$ alkyl).

(h4) In one embodiment, at least one Y is halogen (e.g., F, Cl, Br, or I). In one embodiment, at least one Y is F. In one embodiment, at least one Y is Cl. In one embodiment, at least one Y is Br.

(h5-1) In one embodiment, at least one Y is OH or O—($C_1$-$C_6$ straight-chain or $C_3$-$C_6$ branched alkyl) (e.g., methyl, ethyl, n-propyl, i-propyl, n-butyl, i-butyl, s-butyl, t-butyl, pentyl, i-pentyl, or hexyl), wherein the alkyl moiety is optionally substituted with one or more groups independently selected from OH, $NH_2$, $N_3$, halogen, O—($C_1$-$C_6$ alkyl), S—($C_1$-$C_6$ alkyl). NH—$C_1$-$C_6$ alkyl, and N—($C_1$-$C_6$ alkyl)$_2$. In one embodiment, at least one Y is O-methyl, optionally substituted as described herein. In one embodiment, at least one Y is O-ethyl, optionally substituted as described herein. In one embodiment, at least one Y is O-i-propyl, optionally substituted as described herein.

(h5-2) In one embodiment, at least one Y is O—($C_2$-$C_4$ alkenyl) (e.g., ethenyl, propenyl, or butenyl), wherein the alkenyl moiety is optionally substituted with one or more groups independently selected from OH $NH_2$, $N_3$, halogen, O—($C_1$-$C_6$ alkyl), S—($C_1$-$C_6$ alkyl). NH—$C_1$-$C_6$ alkyl, and N—($C_1$-$C_6$ alkyl)$_2$. In one embodiment, at least one Y is O-ethenyl, optionally substituted as described herein. In one embodiment, at least one Y is O-propenyl, optionally substituted as described herein.

(h5-3) In one embodiment, at least one Y is O—($C_2$-$C_4$ alkynyl) (e.g., ethynyl, propynyl, or butynyl), wherein the alkynyl moiety is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Y is O-ethynyl, optionally substituted as described herein. In one embodiment, at least one Y is O-propynyl, optionally substituted as described herein.

(h6-1) In one embodiment, at least one Y is S—($C_1$-$C_6$ straight-chain or $C_3$-$C_6$ branched alkyl) (e.g., methyl, ethyl, n-propyl, i-propyl, n-butyl, i-butyl, s-butyl, t-butyl, pentyl, i-pentyl, or hexyl), wherein the alkyl moiety is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Y is S-methyl, optionally substituted as described herein. In one embodiment, at least one Y is S-ethyl, optionally substituted as described herein. In one embodiment, at least one Y is S-i-propyl, optionally substituted as described herein.

(h6-2) In one embodiment, at least one Y is S(O)—($C_1$-$C_6$ alkyl) or S(O)—($C_1$-$C_6$ alkyl) (e.g., methyl, ethyl, n-propyl, i-propyl, n-butyl, i-butyl, s-butyl, t-butyl, pentyl, i-pentyl, or hexyl), wherein the alkyl moiety is optionally substituted with one or more groups independently selected from OH $NH_2$, $N_3$, halogen, O—($C_1$-$C_6$ alkyl), S—($C_1$-$C_6$ alkyl). NH—$C_1$-$C_6$ alkyl, and N—($C_1$-$C_6$ alkyl)$_2$. In one embodiment, at least one Y is $S(O)_2CH_3$, optionally substituted as described herein.

(h7) In one embodiment, at least one Y is $NH_2$, NH—$C_1$-$C_6$ straight-chain or $C_3$-$C_6$ branched alkyl (e.g., methyl, ethyl, n-propyl, i-propyl, n-butyl, i-butyl, s-butyl, t-butyl, pentyl, i-pentyl, or hexyl), or N—($C_1$-$C_6$ straight-chain or $C_3$-$C_6$ branched alkyl)$_2$ (e.g., methyl, ethyl, n-propyl, i-propyl, n-butyl, i-butyl, s-butyl, t-butyl, pentyl, i-pentyl, or hexyl), wherein the alkyl moiety is optionally substituted with one or more groups independently selected from OH, $NH_2$, $N_3$, halogen. O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Y is N—($C_1$-$C_6$ alkyl)$_2$, optionally substituted as described herein, and the two $C_1$-$C_6$ alkyls are the same. In one embodiment, at least one Y is N—($C_1$-$C_6$ alkyl)$_2$, optionally substituted as described herein, and the two $C_1$-$C_6$ alkyls are different. In one embodiment, at least one Y is $N(CH_3)_2$, optionally substituted as described herein. In one embodiment, at least one Y is $N(CH_3)(CH_2CH_3)$, optionally substituted as described herein.

(h8) In one embodiment, at least one Y is Q-T.

(h9) In one embodiment, at least one Y is Q-T $C_1$-$C_6$ alkyl, halogen, O—($C_1$-$C_6$ alkyl), S—($C_1$-$C_6$ alkyl), O—($C_2$-$C_4$ alkenyl), O—($C_2$-$C_4$ alkynyl), $NH_2$, NH—$C_1$-$C_6$ alkyl, N—($C_1$-$C_6$ alkyl)$_2$, S(O)—($C_1$-$C_6$ alkyl), or $S(O)_2$—($C_1$-$C_6$ alkyl), as described herein.

(h10) In one embodiment, at least one Y is Q-T, $C_1$-$C_6$ alkyl, halogen, O—($C_1$-$C_6$ alkyl). S—($C_1$-$C_6$ alkyl). $NH_2$, NH—$C_1$-$C_6$ alkyl, N—($C_1$-$C_6$ alkyl)$_2$, or $S(O)_2$—($C_1$-$C_6$ alkyl), as described herein.

(h11) In one embodiment, at least one Y is Q-T, $C_1$-$C_6$ alkyl, halogen, O—($C_1$-$C_6$ alkyl), S—($C_1$-$C_6$ alkyl), O—($C_2$-$C_4$ alkenyl), O—($C_2$-$C_4$ alkynyl), $NH_2$, NH—$C_1$-$C_6$ alkyl, N—($C_1$-$C_6$ alkyl)$_2$, S(O)—($C_1$-$C_6$ alkyl), or $S(O)_2$—($C_1$-$C_6$ alkyl), as described herein, and at least another Y is Q-T, $C_1$-$C_6$ alkyl, halogen, O—($C_1$-$C_6$ alkyl), S—($C_1$-$C_6$ alkyl), O—($C_2$-$C_4$ alkenyl), O—($C_2$-$C_4$ alkynyl), $NH_2$, NH—$C_1$-$C_6$ alkyl, N—($C_1$-$C_6$ alkyl)$_2$, S(O)—($C_1$-$C_6$ alkyl), or $S(O)_2$—($C_1$-$C_6$ alkyl), as described herein.

(h12) In one embodiment, at least one Y is Q-T, $C_1$-$C_6$ alkyl, halogen, O—($C_1$-$C_6$ alkyl), S—($C_1$-$C_6$ alkyl), $NH_2$, NH—$C_1$-$C_6$ alkyl, N—($C_1$-$C_6$ alkyl)$_2$, or $S(O)_2$—($C_1$-$C_6$ alkyl), as described herein, and at least another Y is Q-T, $C_1$-$C_6$ alkyl, halogen, O—($C_1$-$C_6$ alkyl), S—($C_1$-$C_6$ alkyl), $NH_2$, NH—$C_1$-$C_6$ alkyl, N—($C_1$-$C_6$ alkyl)$_2$, or S(O)$_2$—($C_1$-$C_6$ alkyl), as described herein.

(h13) In one embodiment, at least one Y is Q-T, as described herein, and at least another Y is $C_1$-$C_6$ alkyl, halogen. O—($C_1$-$C_6$ alkyl). S—($C_1$-$C_6$ alkyl). $NH_2$, NH—$C_1$-$C_6$ alkyl, N—($C_1$-$C_6$ alkyl)$_2$, or S(O)$_2$—($C_1$-$C_6$ alkyl), as described herein.

(h14) In one embodiment, at least one Y is halogen, OH, O—($C_1$-$C_6$ alkyl), S—($C_1$-$C_6$ alkyl), $NH_2$. NH—$C_1$-$C_6$ alkyl, or N—($C_1$-$C_6$ alkyl)$_2$, as described herein, and at least another Y is halogen, OH, O—($C_1$-$C_6$ alkyl), S—($C_1$-$C_6$ alkyl), $NH_2$, NH—$C_1$-$C_6$ alkyl, or N—($C_1$-$C_6$ alkyl)$_2$, as described herein.

(h15) In one embodiment, at least one Y is halogen, as described herein, and at least another Y is halogen, OH, O—($C_1$-$C_6$ alkyl), S—($C_1$-$C_6$ alkyl), $NH_2$. NH—$C_1$-$C_6$ alkyl, or N—($C_1$-$C_6$ alkyl)$_2$, as described herein. In one embodiment, at least one Y is Cl, and at least another Y is halogen, OH, O—($C_1$-$C_6$ alkyl), S—($C_1$-$C_6$ alkyl), $NH_2$. NH—$C_1$-$C_6$ alkyl, or N—($C_1$-$C_6$ alkyl)$_2$, as described herein. In one embodiment, at least one Y is Cl, and at least another Y is halogen, O—($C_1$-$C_6$ alkyl), S—($C_1$-$C_6$ alkyl), NH—$C_1$-$C_6$ alkyl, or N—($C_1$-$C_6$ alkyl)$_2$, as described herein. In one embodiment, at least one Y is Cl, and at least another Y is Cl, O—($C_1$-$C_6$ alkyl), or S—($C_1$-$C_6$ alkyl), as described herein. In one embodiment, at least one Y is Cl, and at least another Y is Cl or O—($C_1$-$C_6$ alkyl), as described herein.

(h16) In one embodiment, two Y, together with the two adjacent carbon atoms to which they are bonded, form a cyclopentyl, cyclohexyl, cycloheptyl, cyclopentenyl, cyclohexenyl, cycloheptenyl, cyclopentynyl, cyclohexynyl, or cycloheptynyl. In one embodiment, two Y, together with the two adjacent carbon atoms to which they are bonded, form a cyclohexyl.

(h17) In one embodiment, two Y, together with the two adjacent carbon atoms to which they are bonded, form phenyl.

(h18) In one embodiment, at least one Y is at the 6-position, as indicated in Formula I, Ia, or Ib.

(h19) In one embodiment, at least one Y is at the 5-position, as indicated in Formula I, Ia, or Ib.

(h20) In one embodiment, at least one Y is at the 7-position, as indicated in Formula I, Ia, or Ib.

(h21) In one embodiment, at least one Y is at the 5-position and at least one Y is at the 6-position, as indicated in Formula I, Ia, or Ib.

(h22) In one embodiment, at least one Y is at the 7-position and at least one Y is at the 6-position, as indicated in Formula I, Ia, or Ib.

(h23) In one embodiment, one Y is at the 5-position and the other Y is at the 6-position, as indicated in Formula I, Ia, or Ib.

(h24) In one embodiment, one Y is at the 7-position and the other Y is at the 6-position, as indicated in Formula I, Ia, or Ib.

(i1) In one embodiment, n is 0, 1, 2, or 3.

(i2) In one embodiment, n is 0, 1, or 2.

(i3) In one embodiment, n is 0.

(i4) In one embodiment, n is 1 or 2.

(i5) In one embodiment, n is 1.

(i6) In one embodiment, n is 2.

(j1) In one embodiment, at least one Z is $C_1$-$C_6$ straight-chain or $C_3$-$C_6$ branched alkyl (e.g., methyl, ethyl, n-propyl, i-propyl, n-butyl, i-butyl, s-butyl, t-butyl, pentyl, i-pentyl, or hexyl), optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Z is $C_1$-$C_4$ alkyl (e.g., methyl, ethyl, n-propyl, i-propyl, n-butyl, i-butyl, s-butyl, or t-butyl), optionally substituted as described herein. In one embodiment, at least one Z is $C_1$-$C_6$ straight-chain or $C_3$-$C_6$ branched alkyl and is substituted as described herein. In one embodiment, at least one Z is $C_1$-$C_6$ straight-chain or $C_3$-$C_6$ branched alkyl substituted with OH $NH_2$, $N_3$, halogen, or O—($C_1$-$C_6$ alkyl). In one embodiment, at least one Z is methyl, optionally substituted as described herein. In one embodiment, at least one Z is ethyl, optionally substituted as described herein. In one embodiment, at least one Z is i-propyl, optionally substituted as described herein. In one embodiment, at least one Z is t-butyl, optionally substituted as described herein.

(j2) In one embodiment, at least one Z is $C_2$-$C_6$ straight-chain or $C_3$-$C_6$ branched alkenyl (e.g., ethenyl, propenyl, butenyl, pentenyl, or hexenyl), optionally substituted with one or more groups independently selected from OH, $NH_2$. $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Z is $C_2$-$C_6$ straight-chain or $C_3$—C(branched alkenyl substituted with OH, $NH_2$, halogen, or O—($C_1$-$C_6$ alkyl).

(j3) In one embodiment, at least one Z is $C_2$-$C_6$ straight-chain or $C_4$-$C_6$ branched alkynyl (e.g., ethynyl, propynyl, butynyl, pentynyl, or hexynyl), optionally substituted with one or more groups independently selected from OH, $NH_2$, $N_3$, halogen, O—($C_1$-$C_6$ alkyl), S—($C_1$—C alkyl), NH—$C_1$-$C_6$ alkyl, and N—($C_1$-$C_6$ alkyl)$_2$. In one embodiment, at least one Z is $C_2$-$C_6$ straight-chain or $C_4$-$C_6$ branched alkynyl substituted with OH $NH_2$, halogen, or O—($C_1$-$C_6$ alkyl).

(j4) In one embodiment, at least one Z is halogen (e.g., F, Cl, Br, or I). In one embodiment, at least one Z is F. In one embodiment, at least one Z is Z is Cl. In one embodiment, at least one Z is Br.

(j5-1) In one embodiment, at least one Z is OH or O—($C_1$-$C_6$ straight-chain or $C_3$-$C_6$ branched alkyl) (e.g., methyl, ethyl, n-propyl, i-propyl, n-butyl, i-butyl, s-butyl, t-butyl, pentyl, i-pentyl, or hexyl), wherein the alkyl moiety is optionally substituted with one or more groups independently selected from OH, $NH_2$. $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Z is O-methyl, optionally substituted as described herein. In one embodiment, at least one Z is O-ethyl, optionally substituted as described herein. In one embodiment, at least one Z is O-i-propyl, optionally substituted as described herein.

(j5-2) In one embodiment, at least one Z is O—($C_2$-$C_4$ alkenyl) (e.g., ethenyl, propenyl, or butenyl), wherein the alkenyl moiety is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Z is O-ethenyl, optionally substituted as described herein. In one embodiment, at least one Z is O-propenyl, optionally substituted as described herein.

(j5-3) In one embodiment, at least one Z is O—($C_2$-$C_4$ alkynyl) (e.g., ethynyl, propynyl, or butynyl), wherein the alkynyl moiety is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Z is O-ethynyl, optionally substituted as described herein. In one embodiment, at least one Z is O-propynyl, optionally substituted as described herein.

(j6-1) In one embodiment, at least one Z is S—($C_1$-$C_6$ straight-chain or $C_3$-$C_6$ branched alkyl) (e.g., methyl, ethyl, n-propyl, i-propyl, n-butyl, i-butyl, s-butyl, t-butyl, pentyl, i-pentyl, or hexyl), wherein the alkyl moiety is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Z is S-methyl, optionally substituted as described herein. In one embodiment, at least one Z is S-ethyl, optionally substituted as described herein. In one embodiment, at least one Z is S-i-propyl, optionally substituted as described herein.

(h6-2) In one embodiment, at least one Z is S(O)—($C_1$-$C_6$ alkyl) or S(O)$_2$—($C_1$-$C_6$ alkyl) (e.g., methyl, ethyl, n-propyl, i-propyl, n-butyl, i-butyl, s-butyl, t-butyl, pentyl, i-pentyl, or hexyl), wherein the alkyl moiety is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Z is S(O)$_2$CH$_3$, optionally substituted as described herein.

(j7) In one embodiment, at least one Z is $NH_2$, NH—$C_1$-$C_6$ straight-chain or $C_3$-$C_6$ branched alkyl (e.g., methyl, ethyl, n-propyl, i-propyl, n-butyl, i-butyl, s-butyl, t-butyl, pentyl, i-pentyl, or hexyl), or N—($C_1$-$C_6$ straight-chain or $C_3$-$C_6$ branched alkyl)$_2$ (e.g., methyl, ethyl, n-propyl, i-propyl, n-butyl, i-butyl, s-butyl, t-butyl, pentyl, i-pentyl, or hexyl), wherein the alkyl moiety is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$. In one embodiment, at least one Z is N—($C_1$-$C_6$ alkyl)$_2$, optionally substituted as described herein, and the two $C_1$-$C_6$ alkyls are the same. In one embodiment, at least one Z is N—($C_1$-$C_6$ alkyl)$_2$, optionally substituted as described herein, and the two $C_1$-$C_6$ alkyls are different. In one embodiment, at least one Z is N(CH$_3$)$_2$, optionally substituted as described herein. In one embodiment, at least one Z is N(CH$_3$)(CH$_2$CH$_3$), optionally substituted as described herein.

(j8) In one embodiment, at least one Z is Q-T.

(j9) In one embodiment, at least one Z is Q-T, $C_1$-$C_6$ alkyl, halogen, O—($C_1$-$C_6$ alkyl), S—($C_1$-$C_6$ alkyl), O—($C_2$-$C_4$ alkenyl), O—($C_2$-$C_4$ alkynyl), $NH_2$, NH—$C_1$-$C_6$ alkyl, N—($C_1$-$C_6$ alkyl)$_2$, S(O)—($C_1$-$C_6$ alkyl), or S(O)$_2$—($C_1$—C(alkyl), as described herein.

(j10) In one embodiment, at least one Z is Q-T, $C_1$-$C_6$ alkyl, halogen, O—($C_1$-$C_6$ alkyl), S—($C_1$-$C_6$ alkyl), $NH_2$, NH—$C_1$-$C_6$ alkyl, N—($C_1$-$C_6$ alkyl)$_2$, or S(O)$_2$—($C_1$-$C_6$ alkyl), as described herein.

(j11) In one embodiment, at least one Z is Q-T, $C_1$-$C_6$ alkyl, halogen, O—($C_1$-$C_6$ alkyl), S—($C_1$-$C_6$ alkyl), O—($C_2$-$C_4$ alkenyl), O—($C_2$-$C_4$ alkynyl), $NH_2$, NH—$C_1$-$C_6$ alkyl, N—($C_1$-$C_6$ alkyl)$_2$, S(O)—($C_1$-$C_6$ alkyl), or S(O)$_2$—($C_1$-$C_6$ alkyl), as described herein, and at least another Z is Q-T, $C_1$-$C_6$ alkyl, halogen, O—($C_1$-$C_6$ alkyl), S—($C_1$-$C_6$ alkyl), O—($C_2$-$C_4$ alkenyl), O—($C_2$-$C_4$ alkynyl), $NH_2$, NH—$C_1$-$C_6$ alkyl, N—($C_1$-$C_6$ alkyl)$_2$, S(O)—($C_1$-$C_6$ alkyl), or S(O)$_2$—($C_1$-$C_6$ alkyl), as described herein.

(j12) In one embodiment, at least one Z is Q-T, $C_1$-$C_6$ alkyl, halogen, O—($C_1$-$C_6$ alkyl), S—($C_1$-$C_6$ alkyl), $NH_2$, NH—$C_1$-$C_6$ alkyl, N—($C_1$-$C_6$ alkyl)$_2$, or S(O)$_2$—($C_1$-$C_6$ alkyl), as described herein, and at least another Z is Q-T, $C_1$-$C_6$ alkyl, halogen, O—($C_1$-$C_6$ alkyl), S—($C_1$-$C_6$ alkyl), $NH_2$, NH—$C_1$-$C_6$ alkyl, N—($C_1$-$C_6$ alkyl)$_2$, or S(O)$_2$—($C_1$-$C_6$ alkyl), as described herein.

(j13) In one embodiment, at least one Z is Q-T, as described herein, and at least another Z is $C_1$-$C_6$ alkyl, halogen, O—($C_1$-$C_6$ alkyl), S—($C_1$-$C_6$ alkyl), $NH_2$, NH—$C_1$-$C_6$ alkyl, N—($C_1$-$C_6$ alkyl)$_2$, or S(O)$_2$—($C_1$-$C_6$ alkyl), as described herein.

(j14) In one embodiment, at least one Z is halogen, OH, O—($C_1$-$C_6$ alkyl), S—($C_1$-$C_6$ alkyl), $NH_2$, NH—$C_1$-$C_6$ alkyl, or N—($C_1$-$C_6$ alkyl)$_2$, as described herein, and at least another Z is halogen, OH O—($C_1$-$C_6$ alkyl), S—($C_1$-$C_6$ alkyl), $NH_2$, NH—$C_1$-$C_6$ alkyl, or N—($C_1$-$C_6$ alkyl)$_2$, as described herein.

(j15) In one embodiment, at least one Z is halogen, as described herein, and at least another Z is halogen, OH, O—($C_1$-$C_6$ alkyl), S—($C_1$-$C_6$ alkyl), $NH_2$. NH—$C_1$-$C_6$ alkyl, or N—($C_1$-$C_6$ alkyl)$_2$, as described herein. In one embodiment, at least one Z is Cl, and at least another Z is halogen, OH. O—($C_1$-$C_6$ alkyl), S—($C_1$-$C_6$ alkyl), $NH_2$, NH—$C_1$-$C_6$ alkyl, or N—($C_1$-$C_6$ alkyl)$_2$, as described herein. In one embodiment, at least one Z is Cl, and at least another Z is halogen, O—($C_1$-$C_6$ alkyl), S—($C_1$-$C_6$ alkyl), NH—$C_1$-$C_6$ alkyl, or N—($C_1$-$C_6$ alkyl)$_2$, as described herein. In one embodiment, at least one Z is Cl, and at least another Z is Cl, O—($C_1$-$C_6$ alkyl), or S—($C_1$-$C_6$ alkyl), as described herein. In one embodiment, at least one Z is Cl, and at least another Z is Cl or O—($C_1$-$C_6$ alkyl), as described herein.

(j16) In one embodiment, at least one Z is at the 3-position, as indicated in Formula I, Ia, or Ib.

(j17) In one embodiment, at least one Z is at the 4-position, as indicated in Formula I, Ia, or Ib.

(j18) In one embodiment, at least one Z is at the 3-position and at least one Z is at the 4-position, as indicated in Formula I, Ia, or Ib.

(j19) In one embodiment, one Z is at the 3-position and the other Z is at the 4-position, as indicated in Formula I, Ia, or Ib.

(k1) In one embodiment, at least one Q is a bond.

(k2) In one embodiment, each Q is independently NH. N($C_1$-$C_3$ alkyl), O, S, S(O), S(O)$_2$, Q', NH-Q', N($C_1$-$C_3$ alkyl)-Q', O-Q', S-Q', S(O)-Q', or S(O)$_2$-Q'.

(k3) In one embodiment, each Q is independently NH, O, S, or Q'.

(k4) In one embodiment, each Q is independently Q', NH-Q', O-Q', or S-Q'.

(k5) In one embodiment, each Q is independently NH, S, Q', NH-Q', or S-Q'

(k6) In one embodiment, each Q is independently NH, Q', or NH-Q'.

(k7) In one embodiment, each Q is independently O, Q', or O-Q'.

(k8) In one embodiment, each Q is independently S, S(O), S(O)$_2$, Q', S-Q', S(O)-Q', or S(O)$_2$-Q'.

(k9) In one embodiment, at least one Q is Q'.

(l1) In one embodiment, each Q' is independently a carbon linker comprising one or more C($R_Q$)$_2$ or C($R_Q$)$_2$—C($R_Q$)$_2$. In one embodiment, each Q' is independently a carbon linker comprising one or more C($R_Q$)$_2$. In one embodiment, each Q' is independently a carbon linker comprising one or more C($R_Q$)$_2$—C($R_Q$)$_2$.

(l2) In one embodiment, each Q' is independently a carbon linker comprising one or more C$R_Q$=C$R_Q$.

(l3) In one embodiment, each Q' is independently a carbon linker comprising one or more C≡C.

(l4) In one embodiment, each Q' is independently a carbon linker comprising one or more C($R_1$)$_2$ or C($R_1$)$_2$—C($R_Q$)$_2$ and $CR_Q=CR_Q$. In one embodiment, each Q' is independently a carbon linker comprising one or more $C(R_Q)_2$ and $CR_Q=CR_Q$. In one embodiment, each Q' is independently a carbon linker comprising one or more $C(R_Q)_2$—$C(R_Q)_2$ and $CR_Q=CR_Q$.

(l5) In one embodiment, each Q' is independently a carbon linker comprising one or more $C(R_1)_2$ or $C(R_Q)_2$—$C(R_Q)_2$ and C≡C. In one embodiment, each Q' is independently a carbon linker comprising one or more $C(R_Q)_2$ and C≡C. In one embodiment, each Q' is independently a carbon linker comprising one or more $C(R_Q)_2$—$C(R_Q)_2$ and C≡C.

(l6) In one embodiment, each Q' is independently a carbon linker comprising one or more $CR_Q=CR_Q$ and C≡C.

(l7) In one embodiment, each Q' is independently a carbon linker comprising one or more $C(R_Q)_2$, $C(R_Q)_2$—$C(R_Q)_2$, $CR_Q=CR_Q$, and C≡C.

(m1) In one embodiment, each R is H.

(m2) In one embodiment, at least one R is methyl, ethyl, or propyl.

(n1) In one embodiment, at least one T is cyclopropyl, cyclobutyl, cyclopentyl, cyclohexyl, cycloheptyl, or cyclooctyl, each of which is optionally substituted with one or more $R_T$.

(n2) In one embodiment, at least one T is cyclobutenyl, cyclopentenyl, cyclohexenyl, cycloheptenyl, or cyclooctenyl, each of which is optionally substituted with one or more $R_T$.

(n3) In one embodiment, at least one T is heterocyclyl comprising one or two 5- or 6-membered rings and 1-4 heteroatoms selected from N, O, and S (e.g., pyrrolidinyl, imidazolidinyl, pyrazolidinyl, oxazolidinyl, isoxazolidinyl, triazolidinyl, tetrahyrofuranyl, piperidinyl, piperazinyl, or morpholinyl), optionally substituted with one or more $R_T$. In one embodiment, at least one T is heterocyclyl comprising one or two 5- or 6-membered rings and 1-3 heteroatoms selected from N, O, and S, such as those described herein, optionally substituted with one or more $R_T$. In one embodiment, at least one T is heterocyclyl comprising one 5- or 6-membered rings and 1-3 heteroatoms selected from N, O, and S, such as those described herein, optionally substituted with one or more $R_T$. In one embodiment, at least one T is heterocyclyl comprising one 5- or 6-membered rings and 1-3 heteroatoms selected from N and O, such as those described herein, optionally substituted with one or more $R_T$. In one embodiment, at least one T is heterocyclyl comprising one 5-membered ring and 1-3 heteroatoms selected from N and O, such as those described herein, optionally substituted with one or more $R_T$. In one embodiment, at least one T is heterocyclyl comprising one 5-membered ring and 1-2 heteroatoms selected from N and O, such as those described herein, optionally substituted with one or more $R_T$. In one embodiment, at least one T is heterocyclyl comprising one 6-membered ring and 1-3 heteroatoms selected from N, O, and S, such as those described herein, optionally substituted with one or more $R_T$. In one embodiment, at least one T is heterocyclyl comprising one 6-membered ring and 1-3 heteroatoms selected from N and O, such as those described herein, optionally substituted with one or more $R_T$. In one embodiment, at least one T is heterocyclyl comprising one 6-membered ring and 1-2 heteroatoms selected from N and O, such as those described herein, optionally substituted with one or more $R_T$.

(n4) In one embodiment, at least one T is $C_6$-$C_{10}$ aryl optionally substituted with one or more $R_T$. In one embodiment, at least one T is phenyl optionally substituted with one or more $R_T$.

(n5) In one embodiment, at least one T is heteroaryl comprising one or two 5- or 6-membered rings and 1-4 heteroatoms selected from N, O, and S (e.g., pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, quinolinyl, isoquinolinyl, naphthyridinyl, indolyl, purinyl, indolizinyl, quinoxalinyl, benzoxazolyl, benzodioxazolyl, benzothiazolyl, benzoimidazolyl, benzothiophenyl, or benzofuranyl), optionally substituted with one or more $R_T$. In one embodiment, at least one T is heteroaryl comprising one or two 5- or 6-membered rings and 1-3 heteroatoms selected from N, O, and S, such as those described herein, optionally substituted with one or more $R_T$. In one embodiment, at least one T is heteroaryl comprising one 5- or 6-membered rings and 1-3 heteroatoms selected from N, O, and S, such as those described herein, optionally substituted with one or more $R_T$. In one embodiment, at least one T is heteroaryl comprising one 5- or 6-membered rings and 1-3 heteroatoms selected from N and O, such as those described herein, optionally substituted with one or more $R_T$. In one embodiment, at least one T is heteroaryl comprising one 5-membered ring and 1-3 heteroatoms selected from N, O, and S, such as those described herein, optionally substituted with one or more $R_T$. In one embodiment, at least one T is heteroaryl comprising one 5-membered ring and 1-3 heteroatoms selected from N and O, such as those described herein, optionally substituted with one or more $R_T$. In one embodiment, at least one T is heteroaryl comprising one 5-membered ring and 1-2 heteroatoms selected from N and O, such as those described herein, optionally substituted with one or more $R_T$. In one embodiment, at least one T is heteroaryl comprising one 5-membered ring and 1-2 N, such as those described herein, optionally substituted with one or more $R_T$. In one embodiment, at least one T is heteroaryl comprising one 6-membered ring and 1-3 heteroatoms selected from N, O. and S, such as those described herein, optionally substituted with one or more $R_T$. In one embodiment, at least one T is heteroaryl comprising one 6-membered ring and 1-3 heteroatoms selected from N and O, such as those described herein, optionally substituted with one or more $R_T$. In one embodiment, at least one T is heteroaryl comprising one 6-membered ring and 1-2 heteroatoms selected from N and O, such as those described herein, optionally substituted with one or more $R_T$. In one embodiment, at least one T is heteroaryl comprising one 6-membered ring and 1-2 N, such as those described herein, optionally substituted with one or more $R_T$.

(n6) In one embodiment, at least one T is C(O)—$C_1$-$C_6$ alkyl or C(O)O—$C_1$-$C_6$ alkyl, each optionally substituted with one or more $R_T$.

(o1) In one embodiment, at least one $R_T$ is $C_1$-$C_6$ straight-chain or $C_3$—C branched alkyl (e.g., methyl, ethyl, n-propyl, i-propyl, n-butyl, i-butyl, s-butyl, t-butyl, pentyl, i-pentyl, or hexyl). In one embodiment, at least one $R_T$ is $C_1$-$C_4$ alkyl (e.g., methyl, ethyl, n-propyl, i-propyl, n-butyl, i-butyl, s-butyl, or t-butyl).

(o2) In one embodiment, at least one $R_T$ is $C_1$-$C_6$ haloalkyl, i.e., $C_1$-$C_6$ straight-chain or $C_3$-$C_6$ branched alkyl (e.g., methyl, ethyl, n-propyl, i-propyl, n-butyl, i-butyl, s-butyl, t-butyl, pentyl, i-pentyl, or hexyl) substituted with one or more halogen (e.g., F, Cl, Br, or I). In one embodiment, at least one $R_T$ is $C_1$-$C_4$ haloalkyl, i.e., $C_1$-$C_4$ alkyl (e.g., methyl, ethyl, n-propyl, i-propyl, n-butyl, i-butyl, s-butyl, or t-butyl) substituted with one or more halogen (e.g., F, Cl, Br, or I).

(o3) In one embodiment, at least one $R_T$ is OH CN, halogen, or $NH_2$.

(o4) In one embodiment, at least one $R_T$ is halogen (e.g., F, Cl, Br, or I).

(o5) In one embodiment, at least one $R_T$ is O—($C_1$-$C_6$ straight-chain or $C_3$-$C_6$ branched alkyl) (e.g., methyl, ethyl, n-propyl, i-propyl, n-butyl, i-butyl, s-butyl, t-butyl, pentyl, i-pentyl, or hexyl). In one embodiment, at least one $R_T$ is O—$C_1$-$C_4$ alkyl (e.g., methyl, ethyl, n-propyl, i-propyl, n-butyl, i-butyl, s-butyl, or t-butyl).

(o6) In one embodiment, at least one $R_T$ is O—($C_1$-$C_6$ haloalkyl) (i.e., wherein the $C_1$-$C_6$ haloalkyl is $C_1$-$C_6$ straight-chain or $C_3$-$C_6$ branched alkyl (e.g., methyl, ethyl, n-propyl, i-propyl, n-butyl, i-butyl, s-butyl, t-butyl, pentyl, i-pentyl, or hexyl) substituted with one or more halogen (e.g., F, Cl, Br, or I). In one embodiment, at least one $R_T$ is O—($C_1$-$C_4$ haloalkyl) (i.e., wherein the $C_1$-$C_4$ haloalkyl is $C_1$-$C_4$ alkyl (e.g., methyl, ethyl, n-propyl, t-propyl, n-butyl, i-butyl, s-butyl, or t-butyl) substituted with one or more halogen (e.g., F, Cl, Br, or I)).

(o7) In one embodiment, at least one $R_T$ is S—($C_1$-$C_6$ straight-chain or $C_3$-$C_6$ branched alkyl) (e.g., methyl, ethyl, n-propyl, i-propyl, n-butyl, i-butyl, s-butyl, t-butyl, pentyl, i-pentyl, or hexyl). In one embodiment, at least one $R_T$ is S—$C_1$-$C_4$ alkyl (e.g., methyl, ethyl, n-propyl, i-propyl, n-butyl, i-butyl, s-butyl, or t-butyl).

(o8) In one embodiment, at least one $R_T$ is $NH_2$, NH—($C_1$-$C_6$ straight-chain or $C_3$-$C_6$ branched alkyl), N—($C_1$-$C_6$ straight-chain or $C_3$-$C_6$ branched alkyl)$_2$, or $NHS(O)_2$—($C_1$-$C_6$ alkyl). In one embodiment, at least one $R_T$ is NH—($C_1$-$C_6$ straight-chain or $C_3$-$C_6$ branched alkyl) (e.g., methyl, ethyl, n-propyl, i-propyl, n-butyl, i-butyl, s-butyl, t-butyl, pentyl, i-pentyl, or hexyl). In one embodiment, at least one $R_T$ is NH—$C_1$-$C_4$ alkyl (e.g., methyl, ethyl, n-propyl, i-propyl, n-butyl, i-butyl, s-butyl, or t-butyl). In one embodiment, at least one $R_T$ is NH—($C_1$-$C_6$ straight-chain or $C_3$-$C_6$ branched alkyl)$_2$ (e.g., methyl, ethyl, n-propyl, i-propyl, n-butyl, i-butyl, s-butyl, t-butyl, pentyl, i-pentyl, or hexyl). In one embodiment, at least one $R_T$ is NH—($C_1$-$C_4$ alkyl)$_2$ (e.g., methyl, ethyl, n-propyl, i-propyl, n-butyl, i-butyl, s-butyl, or t-butyl).

(o9) In one embodiment, at least one $R_T$ is $(CH_2)_q$—$C_3$-$C_8$ cycloalkyl, $(CH_2)_q$-heterocyclyl, $(CH_2)_q$-phenyl, or $(CH_2)$-heteroaryl.

(o10) In one embodiment, at least one $R_T$ is $(CH_2)_q$—$C_3$-$C_8$ cycloalkyl, wherein the $C_3$-$C_8$ cycloalkyl is selected from cyclopropyl, cyclobutyl, cyclopentyl, cyclohexyl, cycloheptyl, and cyclooctyl.

(o11) In one embodiment, at least one $R_T$ is $(CH_2)_q$-heterocyclyl, wherein the heterocyclyl comprises one or two 5- or 6-membered rings and 1-4 heteroatoms selected from N, O, and S (e.g., pyrrolidinyl, imidazolidinyl, pyrazolidinyl, oxazolidinyl, isoxazolidinyl, triazolidinyl, tetrahyrofuranyl, piperidinyl, piperazinyl, or morpholinyl). In one embodiment, the heterocyclyl comprises one or two 5- or 6-membered rings and 1-3 heteroatoms selected from N, O, and S such as those described herein. In one embodiment, the heterocyclyl comprises one 5- or 6-membered rings and 1-3 heteroatoms selected from N, O, and S, such as those described herein. In one embodiment, the heterocyclyl comprises one 5- or 6-membered rings and 1-3 heteroatoms selected from N and O, such as those described herein. In one embodiment, the heterocyclyl comprises one 5-membered ring and 1-3 heteroatoms selected from N, O, and S, such as those described herein. In one embodiment, the heterocyclyl comprises one 5-membered ring and 1-3 heteroatoms selected from N and O, such as those described herein. In one embodiment, the heterocyclyl comprises one 5-membered ring and 1-2 heteroatoms selected from N and O, such as those described herein. In one embodiment, the heterocyclyl comprises one 6-membered ring and 1-3 heteroatoms selected from N, O, and S, such as those described herein. In one embodiment, the heterocyclyl comprises one 6-membered ring and 1-3 heteroatoms selected from N and O, such as those described herein. In one embodiment, the heterocyclyl comprises one 6-membered ring and 1-2 heteroatoms selected from N and O, such as those described herein.

(o12) In one embodiment, at least one $R_T$ is $(CH_2)_q$-phenyl.

(o13) In one embodiment, at least one $R_T$ is $(CH_2)_q$-heteroaryl, wherein the heteroaryl comprises one or two 5- or 6-membered rings and 1-4 heteroatoms selected from N, O, and S (e.g., pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, quinolinyl, isoquinolinyl, naphthyridinyl, indolyl, purinyl, indolizinyl, quinoxalinyl, benzoxazolyl, benzodioxazolyl, benzothiazolyl, benzoimidazolyl, benzothiophenyl, or benzofuranyl). In one embodiment, the heteroaryl comprises one or two 5- or 6-membered rings and 1-3 heteroatoms selected from N, O, and S, such as those described herein. In one embodiment, the heteroaryl comprises one 5- or 6-membered rings and 1-3 heteroatoms selected from N, O, and S, such as those described herein. In one embodiment, the heteroaryl comprises one 5- or 6-membered rings and 1-3 heteroatoms selected from N and O, such as those described herein. In one embodiment, the heteroaryl comprises one 5-membered ring and 1-3 heteroatoms selected from N, O, and S, such as those described herein. In one embodiment, the heteroaryl comprises one 5-membered ring and 1-3 heteroatoms selected from N and O, such as those described herein. In one embodiment, the heteroaryl comprises one 5-membered ring and 1-2 heteroatoms selected from N and O, such as those described herein. In one embodiment, the heteroaryl comprises one 5-membered ring and 1-2 N, such as those described herein. In one embodiment, the heteroaryl comprises one 6-membered ring and 1-3 heteroatoms selected from N, O, and S, such as those described herein. In one embodiment, the heteroaryl comprises one 6-membered ring and 1-3 heteroatoms selected from N and O, such as those described herein. In one embodiment, the heteroaryl comprises one 6-membered ring and 1-2 heteroatoms selected from N and O, such as those described herein. In one embodiment, the heteroaryl comprises one 6-membered ring and 1-2 N, such as those described herein.

(o14) In one embodiment, at least one $R_T$ is $C_1$-$C_6$ alkyl, $C_1$-$C_6$ haloalkyl, OH, CN, halogen, O—($C_1$-$C_6$ alkyl), O—($C_1$-$C_6$ haloalkyl), S—($C_1$-$C_6$ alkyl), $NH_2$, NH—$C_1$-$C_6$ alkyl, N—($C_1$-$C_6$ alkyl)$_2$, $(CH_2)_q$-heterocyclyl, or $(CH_2)_q$-phenyl, as described herein.

(o15) In one embodiment, at least one $R_T$ is $C_1$-$C_6$ alkyl, $C_1$-$C_6$ haloalkyl, OH, CN, halogen, O—($C_1$-$C_6$ alkyl), O—($C_1$-$C_6$ haloalkyl), S—($C_1$-$C_6$ alkyl), $NH_2$, $(CH_2)_q$-heterocyclyl, or $(CH_2)_q$-phenyl, as described herein. In one embodiment, at least one $R_T$ is methyl, ethyl, propyl, i-propyl, $CF_3$, OH, CN, F, Cl, methoxy, ethoxy, $OCF_3$, $SCH_3$. $NH_2$, $(CH_2)$-morpholinyl, or $(CH_2)$-phenyl.

(p1) In one embodiment, q is 0, 1, or 2.

(p2) In one embodiment, q is 1, 2, or 3.

(p3) In one embodiment, q is 0 or 1.
(p4) In one embodiment, q is 1 or 2.
(p5) In one embodiment, q is 0.
(p6) In one embodiment, q is 1.
(p7) In one embodiment, q is 2.
(p8) In one embodiment, q is 3.
(q1) In one embodiment, $R_S$ is $R_1$.
(q2) In one embodiment, $R_S$ is $C_3$-$C_6$ cycloalkyl, heterocyclyl comprising one 5- or 6-membered rings and 1-2 heteroatoms selected from N, O, and S, or $C_6$-$C_{10}$ aryl, wherein the cycloalkyl, heterocyclyl, or aryl is optionally substituted with one or more groups independently selected from $C_1$-$C_4$ alkyl.
(q3) In one embodiment, $R_S$ is $C_3$-$C_8$ cycloalkyl or $C_6$-$C_{10}$ aryl, each optionally substituted with one or more groups independently selected from $C_1$-$C_4$ alkyl.
(q4) In one embodiment, $R_S$ is $C_3$-$C_6$ cycloalkyl or phenyl, each optionally substituted with one or more groups independently selected from $C_1$-$C_4$ alkyl.

Any of the groups described herein for any of X, Y, Z, $Z_1$, R, $R_Q$, $R_T$, $R_X$, $R_Z$, $R_S$, Q Q', $T_1$, T, m, n, p, and q can be combined with any of the groups described herein for one or more of the remainder of X, Y, Z, $Z_1$, R, $R_Q$, $R_T$, $R_X$, $R_Z$, $R_S$, Q, Q', $T_1$, T, m, n, p, and q.

(A1) In one embodiment, p is as described in any one of (c1)-(c3), and $R_Z$ is as described in (d1).
(A2) In one embodiment, p is as described in any one of (c1)-(c3), and $R_Z$ is as described in any one of (d2)-(d5).
(A3) In one embodiment, p is as described in (c3), and $R_Z$ is as described in (d1).
(A4) In one embodiment, p is as described in (c3), and $R_Z$ is as described in any one of (d2)-(d5).
(A5) In one embodiment, p is as described in (c4), and $R_Z$ is as described in (d1).
(A6) In one embodiment, p is as described in (c4), and $R_Z$ is as described in any one of (d2)-(d5).
(B1) In one embodiment, p and $R_Z$ are as described in any one of (A1)-(A6), and $T_1$ is as described in any one of (e1)-e5).
(B2) In one embodiment, p and $R_Z$ are as described in any one of (A1)-(A6), and $T_1$ is as described in any one of (e3)-(e5).
(B3) In one embodiment, p and $R_Z$ are as described in any one of (A1)-(A6), and $T_1$ is as described in (e4).
(B4) In one embodiment, p and $R_Z$ are as described in any one of (A1)-(A6), and $T_1$ is as described in (e5).
(B5) In one embodiment, p and $R_Z$ are as described in any one of (A1)-(A6), and $T_1$ is as described in any one of (e6)-(e9).
(B6) In one embodiment, p and $R_Z$ are as described in any one of (A1)-(A6), and $T_1$ is as described in any one of (e10)-(e11).
(B7) In one embodiment, p and $R_Z$ are as described in any one of (A3)-(A4), and $T_1$ is as described in any one of (e1)-(e5).
(B8) In one embodiment, p and $R_Z$ are as described in any one of (A3)-(A4), and $T_1$ is as described in any one of (e3)-(e5).
(B9) In one embodiment, p and $R_Z$ are as described in any one of (A3)-(A4), and $T_1$ is as described in (e4).
(B10) In one embodiment, p and $R_Z$ are as described in any one of (A3)-(A4), and $T_1$ is as described in (e5).
(B11) In one embodiment, p and $R_Z$ are as described in any one of (A3)-(A4), and $T_1$ is as described in any one of (e6)-(e9).
(B12) In one embodiment, p and $R_Z$ are as described in any one of (A3)-(A4), and $T_1$ is as described in any one of (e10)-(e11).
(B13) In one embodiment, p and $R_Z$ are as described in (A3), and $T_1$ is as described in any one of (e1)-(e5).
(B14) In one embodiment, p and $R_Z$ are as described in (A3), and $T_1$ is as described in any one of (e3)-(e5).
(B15) In one embodiment, p and $R_Z$ are as described in (A3), and $T_1$ is as described in (e4).
(B16) In one embodiment, p and $R_Z$ are as described in (A3), and $T_1$ is as described in (e5).
(B17) In one embodiment, p and $R_Z$ are as described in (A3), and $T_1$ is as described in any one of (e6)-(e9).
(B18) In one embodiment, p and $R_Z$ are as described in (A3), and $T_1$ is as described in any one of (e10)-(e11).
(C1) In one embodiment, m is as described in (g1) or (g2), and Y is as described in any one of (h1)-(h7) and (h8)-(h24).
(C2) In one embodiment, m is as described in any one of (g4)-(g6), and Y is as described in any one of (h1)-(h7) and (h8)-(h24).
(C3) In one embodiment, m is as described in (g5), and Y is as described in any one of (h1)-(h7) and (h18)-(h20).
(C4) In one embodiment, m is as described in (g6), and Y is as described in any one of (h1)-(h7) and (h8)-(h24).
(C5) In one embodiment, m is as described in (g1) or (g2), and Y is as described in (h8) and (h18)-(h24).
(C6) In one embodiment, m is as described in any one of (g4)-(g6), and Y is as described in (h8) and (h18)-(h24).
(C7) In one embodiment, m is as described in (g5), and Y is as described in (h8) and (h18)-(h20).
(C8) In one embodiment, m is as described in (g6), and Y is as described in (h8) and (h18)-(h24).
(C9) In one embodiment, m is as described in (g1) or (g2), and Y is as described in any one of (h9)-(h15) and (h8)-(h24).
(C10) In one embodiment, m is as described in any one of (g4)-(g6), and Y is as described in any one of (h9)-(h15) and (h8)-(h24).
(C11) In one embodiment, m is as described in (g5), and Y is as described in any one of (h9)-(h15) and (h18)-(h20).
(C12) In one embodiment, m is as described in (g6), and Y is as described in any one of (h9)-(h15) and (h18)-(h24).
(D1) In one embodiment, m and Y are as described, where applicable, in any one of (C1)-(C12), and n is as described in (i1) or (i2).
(D2) In one embodiment, m and Y are as described, where applicable, in any one of (C1)-($C_{12}$), and n is as described in (i3).
(D3) In one embodiment, m and Y are as described, where applicable, in any one of (C1)-(C12), and n is as described in any one of (i4)-(i6).
(D4) In one embodiment, m and Y are as described, where applicable, in any one of (C1)-(C12), and n is as described in (i5).
(D5) In one embodiment, m and Y are as described, where applicable, in any one of (C1)-(C12), and n is as described in (i6).
(E1) In one embodiment, Y is as described in (h6), and n is as described in (i1) or (i2).
(E2) In one embodiment, Y is as described in (h16), and n is as described in (i3).
(E3) In one embodiment, Y is as described in (h16), and n is as described in any one of (i4)-(i6).
(E4) In one embodiment, Y is as described in (h16), and n is as described in (i5).
(E5) In one embodiment, Y is as described in (h16), and n is as described in (i6).

(E6) In one embodiment, Y is as described in (h7), and n is as described in (i1) or (i2).

(E7) In one embodiment, Y is as described in (h17), and n is as described in (i3).

(E8) In one embodiment, Y is as described in (h17), and n is as described in any one of (i4)-(i6).

(E9) In one embodiment, Y is as described in (h17), and n is as described in (i5).

(E10) In one embodiment, Y is as described in (h17), and n is as described in (i6).

(F1) In one embodiment, n is as described in (i1) or (i2), and Z is as described in any one of (j1)-(j7) and (j16)-(j19).

(F2) In one embodiment, n is as described in any one of (i4)-(i6), and Z is as described in any one of (j1)-(j7) and (j16)-(j19).

(F3) In one embodiment, n is as described in (i5), and Z is as described in any one of (j1)-(j7) and (j16)-(j17).

(F4) In one embodiment, n is as described in (i6), and Z is as described in any one of (j1)-(j7) and (j16)-(j19).

(F5) In one embodiment, n is as described in (i1) or (i2), and Z is as described in any one of (j8) and (j16)-(j19).

(F6) In one embodiment, n is as described in any one of (i4)-(i6), and Z is as described in any one of (j8) and (16)-(j19).

(F7) In one embodiment, n is as described in (i), and Z is as described in any one of (j8) and (j16)-(j17).

(F8) In one embodiment, n is as described in (i6), and Z is as described in any one of (j8) and (j16)-(j19).

(F9) In one embodiment, n is as described in (i1) or (i2), and Z is as described in any one of (j9)-(j15) and (j16)-(j19).

(F10) In one embodiment, n is as described in any one of (i4)-(i6), and Z is as described in any one of (j9)-(j15) and (j16)-(j19).

(F11) In one embodiment, n is as described in (i5), and Z is as described in any one of (j9)-(j15) and (j16)-(j17).

(F12) In one embodiment, n is as described in (i6), and Z is as described in any one of (j9)-(j15) and (16)-(j19).

(G1) In one embodiment, n and Z are as described, where applicable, in any one of (F1)-(F12), and m is as described in (g1) or (g2).

(G2) In one embodiment, n and Z are as described, where applicable, in any one of (F1)-(F12), and m is as described in (g3).

(G3) In one embodiment, n and Z are as described, where applicable, in any one of (F1)-(F12), and m is as described in any one of (g4)-(g6).

(G4) In one embodiment, n and Z are as described, where applicable, in any one of (F1)-(F12), and m is as described in (g5).

(G5) In one embodiment, n and Z are as described, where applicable, in any one of (F1)-(F12), and m is as described in (g6).

(H1) In one embodiment, m, n, and Y are as described, where applicable, in any one of (C1)-(D1), (D3)-(E1), (E3)-(E6), and (E8)-(E10), and Z is as described in any one of (j1)-(j7).

(H2) In one embodiment, m, n, and Y are as described, where applicable, in any one of (C1)-(D1), (D3)-(E1), (E3)-(E6), and (E8)-(E10), and Z is as described in (j8).

(H3) In one embodiment, m, n, and Y are as described, where applicable, in any one of (C1)-(D1), (D3)-(E1), (E3)-(E6), and (E8)-(E10), and Z is as described in any one of (j9)-(j15).

(I1) In one embodiment, m, n, and Z are as described, where applicable, in any one of (F1)-(G1) and (G3)-(G5), and Y is as described in any one of (h1)-(h7).

(I2) In one embodiment, m, n, and Z are as described, where applicable, in any one of (F1)-(G1) and (G3)-(G5), and Y is as described in (h8).

(I3) In one embodiment, m, n, and Z are as described, where applicable, in any one of (F1)-(G1) and (G3)-(G5), and Y is as described in any one of (h9)-(h15).

(I4) In one embodiment, m, n, and Z are as described, where applicable, in any one of (F1)-(G1) and (G3)-(G5), and Y is as described in (h16).

(I5) In one embodiment, m, n, and Z are as described, where applicable, in any one of (F1)-(G1) and (G3)-(G5), and Y is as described in (h17).

(J1) In one embodiment, Y, Z, $R_Z$, $T_1$, m, n, and p are as described, where applicable, in any one of (A1)-(B18), (C5)-(D5), and (F5)-(I5), and Q is as described in (k1).

(J2) In one embodiment, Y, Z, $R_Z$, $T_1$, m, n, and p are as described where applicable, in any one of (A1)-(B18), (C5)-(D5), and (F5)-(I5), and Q is as described in any one of (k2)-(k9).

(J3) In one embodiment, Y, Z, $R_Z$, $T_1$, m, n, and p are as described, where applicable, in any one of (A1)-(B18). (C5)-(D5), and (F5)-(I5), and Q is as described in (k4).

(J4) In one embodiment, Y, Z, $R_Z$, $T_1$, m, n, and p are as described, where applicable, in any one of (A1)-(B18), (C5)-(D5), and (F5)-(I5), and Q is as described in (k5).

(J5) In one embodiment, Y, Z, $R_Z$, $T_1$, m, n, and p are as described, where applicable, in any one of (A1)-(B18), (C5)-(D5), and (F5)-(I5), and Q is as described in (k6).

(J6) In one embodiment, Y, Z, $R_Z$, $T_1$, m, n, and p are as described, where applicable, in any one of (A1)-(B18), (C5)-(D5), and (F5)-(I5), and Q is as described in (k7).

(J7) In one embodiment, Y, Z, $R_Z$, $T_1$, m, n, and p are as described, where applicable, in any one of (A1)-(B18), (C5)-(D5), and (F5)-(I5), and Q is as described in (k8).

(J8) In one embodiment, Y, Z, $R_Z$, $T_1$, m, n, and p are as described, where applicable, in any one of (A1)-(B18), (C5)-(D5), and (F5)-(I5), and Q is as described in (k9).

(K1) In one embodiment, Y, Z, $R_Z$, $T_1$, Q, m, n, and p are as described, where applicable, in any one of (A1)-(B18), (C5)-(D5), (F5)-(I5), and (J2)-(J8), and Q' is as described in (l1).

(K2) In one embodiment, Y, Z, $R_Z$, $T_1$, Q, m, n, and p are as described, where applicable, in any one of (A1)-(B18), (C5)-(D5), (F5)-(I5), and (J2)-(J8), and Q' is as described in (l2).

(K3) In one embodiment, Y, Z, $R_Z$, $T_1$, Q, m, n, and p are as described, where applicable, in any one of (A)-(B18), (C5)-(D5), (F5)-(I5), and (J2)-(J8), and Q' is as described in (l3).

(K4) In one embodiment, Y, Z, $R_Z$, $T_1$, Q, m, n, and p are as described, where applicable, in any one of (A1)-(B18). (C5)-(D5), (F5)-(I5), and (J2)-(J8), and Q' is as described in (l4).

(K5) In one embodiment, Y, Z, $R_Z$, $T_1$, Q, m, n, and p are as described, where applicable, in any one of (A1)-(B18), (C5)-(D5), (F5)-(I5), and (J2)-(J8), and Q' is as described in (l5).

(K6) In one embodiment, Y, Z, $R_Z$, $T_1$, Q, m, n, and p are as described, where applicable, in any one of (A1)-(B18), (C5)-(D5), (F5)-(I5), and (J2)-(J8), and Q' is as described in (l6).

(K7) In one embodiment, Y, Z, $R_Z$, $T_1$, Q, m, n, and p are as described, where applicable, in any one of (A)-(B18), (C5)-(D5), (F5)-(I5), and (J2)-(J8), and Q' is as described in (l7).

(L1) In one embodiment, Y, Z, $R_Z$, $T_1$, Q, Q', m, n, and p are as described, where applicable, in any one of (A1)-(B18), (C5)-(D5), (F5)-(I5), (J1)-(J8), and (K1)-(K7), and T is as described in (n1).

(L2) In one embodiment, Y, Z, $R_Z$, $T_1$, Q, Q', m, n, and p are as described, where applicable, in any one of (A1)-(B18), (C5)-(D5), (F5)-(I5), (J1)-(J8), and (K1)-(K7), and T is as described in (n2).

(L3) In one embodiment, Y, Z, $R_Z$, $T_1$, Q, Q', m, n, and p are as described, where applicable, in any one of (A1)-(B18), (C5)-(D5), (F5)-(I5), (J1)-(J8), and (K1)-(K7), and T is as described in (n3).

(L4) In one embodiment, Y, Z, $R_Z$, $T_1$, Q, Q', m, n, and p are as described, where applicable, in any one of (A1)-(B18), (C5)-(D5), (F5)-(I5), (J1)-(J8), and (K1)-(K7), and T is as described in (n4).

(L5) In one embodiment, Y, Z, $R_Z$, $T_1$, Q, Q', m, n, and p are as described, where applicable, in any one of (A1)-(B18), (C5)-(D5), (F5)-(I5), (J1)-(J8), and (K1)-(K7), and T is as described in (n5).

(M1) In one embodiment, Y, Z, $R_Z$, T, $T_1$, Q, Q', m, n, and p are as described, where applicable, in any one of (A1)-(L5), and X is as described in (a1).

(M2) In one embodiment, Y, Z, $R_Z$, T, $T_1$, Q, Q', m, n, and p are as described, where applicable, in any one of (A1)-(L5), and X is as described in (a2).

(M3) In one embodiment, Y, Z, $R_Z$, T, $T_1$, Q, Q', m, n, and p are as described, where applicable, in any one of (A1)-(L5), and X is as described in (a3).

(M4) In one embodiment, Y, Z, $R_Z$, $T_1$, Q, Q', m, n, and p are as described, where applicable, in any one of (A1)-(L5), and X is as described in (a4).

(M5) In one embodiment, Y, Z, $R_Z$, T, $T_1$, Q, Q', m, n, and p are as described, where applicable, in any one of (A1)-(L5), and X is as described in (a5).

(N1) In one embodiment, Y, Z, $R_Z$, T, $T_1$, Q, Q', X, m, n, and p are as described, where applicable, in any one of (A1)-(L5) and (M), and $R_X$ is as described in (b1).

(N2) In one embodiment, Y, Z, $R_Z$, T, $T_1$, Q, Q', X, m, n, and p are as described, where applicable, in any one of (A1)-(L5) and (M1), and $R_X$ is as described in (b2).

(N3) In one embodiment, Y, Z, $R_Z$, T, $T_1$, Q, Q', X, m, n, and p are as described, where applicable, in any one of (A1)-(L5) and (MI), and $R_X$ is as described in (b3).

(N4) In one embodiment, Y, Z, $R_Z$, T, $T_1$, Q, Q', X, m, n, and p are as described, where applicable, in any one of (A1)-(L5) and (M1), and $R_X$ is as described in (b4).

(N5) In one embodiment, Y, Z, $R_Z$, T, $T_1$, Q, Q', X, m, n, and p are as described, where applicable, in any one of (A1)-(L5) and (M1), and $R_X$ is as described in (b5).

(N6) In one embodiment, Y, Z, $R_Z$, T, $T_1$, Q, Q', X, m, n, and p are as described, where applicable, in any one of (A1)-(L5) and (MI), and $R_X$ is as described in (b6).

(N7) In one embodiment, Y, Z, $R_Z$, T, $T_1$, Q, Q', X, m, n, and p are as described, where applicable, in any one of (A1)-(L5) and (M1), and $R_X$ is as described in (b7).

(N8) In one embodiment, Y, Z, $R_Z$, T, $T_1$, Q, Q', X, m, n, and p are as described, where applicable, in any one of (A1)-(L5) and (M1), and $R_X$ is as described in (b8).

(N9) In one embodiment, Y, Z, $R_Z$, $T_1$, Q, Q', X, m, n, and p are as described, where applicable, in any one of (A1)-(L5) and (M1), and $R_X$ is as described in (b9).

(O1) In one embodiment, m is 1 and n is 0.
(O2) In one embodiment, m is 0 and n is 1.
(O3) In one embodiment, m is 1 and n is 1.
(O4) In one embodiment, m is 2 and n is 0.
(O5) In one embodiment, m is 2 and n is 1.
(O6) In one embodiment, m is 0 and n is 2.
(O7) In one embodiment, m is 1 and n is 2.
(O8) In one embodiment, m is 3 and n is 0.
(O9) In one embodiment, m is 3 and n is 1.
(O10) In one embodiment, m is 3 and n is 2.
(O11) In one embodiment, m is 0 and n is 3.
(O12) In one embodiment, m is 1 and n is 3.
(O13) In one embodiment, m is 2 and n is 3.

(P1) In one embodiment, m and n are as described in any one of (O1), (O3)-(O5), (O7)-(10), (O12), and (O13), and, where applicable, Y is as described in any one of (h1)-(h7) and (h18)-(h24).

(P2) In one embodiment, m and n are as described in any one of (O1), (O3)-(O5), (O7)-(10), (O12), and (O13), and, where applicable, Y is as described in (h8) and (h18)-(h24).

(P3) In one embodiment, m and n are as described in any one of (O1), (O3)-(O5), (O7)-(10), (O12), and (O13), and, where applicable. Y is as described in any one of (h9)-(h15) and (h18)-(h24).

(P4) In one embodiment, m and n are as described in any one of (O1), (O3)-(O5), (O7)-(10), (O12), and (O13), and, where applicable, Y is as described in (h16).

(P5) In one embodiment, m and n are as described in any one of (O1), (O3)-(O5), (O7)-(10), (O12), and (O13), and, where applicable, Y is as described in (h17).

(Q1) In one embodiment, m and n are as described in any one of (O2), (O3), (O5)-(O7), and (O9)-(O13), and, where applicable, Z is as described in any one of (j1)-(j7) and (j16)-(j19).

(Q2) In one embodiment, m and n are as described in any one of (O2), (O3), (O5)-(O7), and (O9)-(O13), and, where applicable, Z is as described in (j8) and (j16)-(j19).

(Q3) In one embodiment, m and n are as described in any one of (O2), (O3), (O5)-(O7), and (O9)-(O13), and, where applicable, Z is as described in any one of (j9)-(j15) and (j16)-(j19).

(R1) In one embodiment, m, n, and Y are as described in any one of (P1)-(P5), and, where applicable, Z is as described in any one of (j1)-(j7) and (j16)-(j19).

(R2) In one embodiment, m, n, and Y are as described in any one of (P1)-(P5), and, where applicable, Z is as described in (j8) and (j16)-(j19).

(R3) In one embodiment, m, n, and Y are as described in any one of (P1)-(P5), and, where applicable, Z is as described in any one of (j9)-(j15) and (j16)-(j19).

(S1) In one embodiment, m, n, and Z are as described in any one of (Q1)-(Q3), and, where applicable, Y is as described in any one of (h1)-(h7) and (h8)-(h24).

(S2) In one embodiment, m, n, and Z are as described in any one of (Q1)-(Q3), and, where applicable, Y is as described in (h8) and (h8)-(h24).

(S3) In one embodiment, m, n, and Z are as described in any one of (Q1)-(Q3), and, where applicable, Y is as described in any one of (h9)-(h15) and (h18)-(h24).

(S4) In one embodiment, m, n, and Z are as described in any one of (Q1)-(Q3), and, where applicable, Y is as described in (h16) and (h8)-(h24).

(S5) In one embodiment, m, n, and Z are as described in any one of (Q1)-(Q3), and, where applicable, Y is as described in (h17) and (h8)-(h24).

(T1) In one embodiment, m, n, Y, and Z are as described in any one of (O1)-(S5), and p, $R_Z$, and $T_1$ are as described, where applicable, in any one of (A1)-(B8).

(U1) In one embodiment, p, $R_Z$, $T_1$, m, n, Y, and Z are as described, where applicable, in any one of (O1)-(T1), and X is as described in (a1).

(U2) In one embodiment, p, $R_Z$, $T_1$, m, n, Y and Z are as described, where applicable, in any one of (O1)-(T1), and X is as described in (a2).

(U3) In one embodiment, p, $R_Z$, $T_1$, m, n, Y, and Z are as described where applicable, in any one of (O1)-(T1), and X is as described in (a3).

(U4) In one embodiment, p, $R_Z$, $T_1$, m, n, Y, and Z are as described, where applicable, in any one of (O1)-(T1), and X is as described in (a4).

(U5) In one embodiment, p, $R_Z$, $T_1$, m, n, Y and Z are as described, where applicable, in any one of (O1)-(T1), and X is as described in (a).

(V1) In one embodiment, p, $R_Z$, $T_1$, m, n, X, Y, and Z are as described, where applicable, in any one of (O1)-(T1) and (U1), and $R_X$ is as described in (b1).

(V2) In one embodiment, p, $R_Z$, $T_1$, m, n, X, Y, and Z are as described, where applicable, in any one of (O1)-(T1) and (U1), and $R_X$ is as described in (b2).

(V3) In one embodiment, p, $R_Z$, $T_1$, m, n, X, Y and Z are as described, where applicable, in any one of (O1)-(T1) and (U1), and $R_X$ is as described in (b3).

(V4) In one embodiment, p, $R_Z$, $T_1$, m, n, X, Y, and Z are as described, where applicable, in any one of (O1)-(T1) and (U1), and $R_X$ is as described in (b4).

(V5) In one embodiment, p, $R_Z$, $T_1$, m, n, X, Y, and Z are as described, where applicable, in any one of (O1)-(T1) and (UI), and $R_X$ is as described in (b5).

(V6) In one embodiment, p, $R_Z$, $T_1$, m, n, X, Y, and Z are as described, where applicable, in any one of (O1)-(T1) and (U1), and $R_X$ is as described in (b6).

(V7) In one embodiment, p, $R_Z$, $T_1$, m, n, X, Y and Z are as described, where applicable, in any one of (O1)-(T1) and (U1), and $R_X$ is as described in (b).

(V8) In one embodiment, p, $R_Z$, $T_1$, m, n, X, Y, and Z are as described, where applicable, in any one of (O1)-(T1) and (U1), and $R_X$ is as described in (b8).

(V9) In one embodiment, p, $R_Z$, $T_1$, m, n, X, Y, and Z are as described, where applicable, in any one of (O1)-(T1) and (U1), and $R_X$ is as described in (b9).

In one embodiment, a compound of Formula I is of Formula I1, I1a, or I1b:

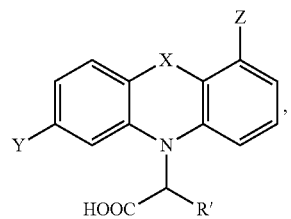
(I1)

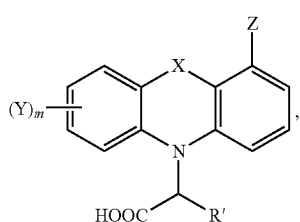
(I1a)

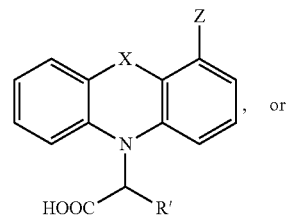
, or

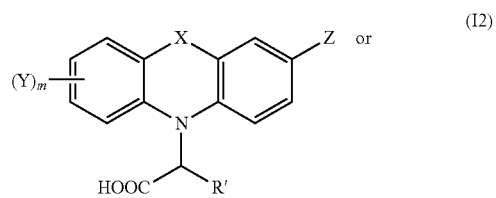
(I1b)

or a pharmaceutically acceptable salt or ester thereof, wherein R' is H or methyl.

In one embodiment, a compound of Formula I is of Formula I2 or I2a:

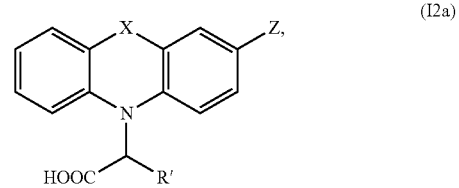
(I2)

(I2a)

or a pharmaceutically acceptable salt or ester thereof, wherein R' is H or methyl.

In one embodiment, a compound of Formula I is of Formula I3, I3a, or I3b:

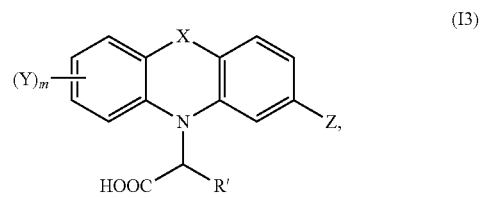
(I3)

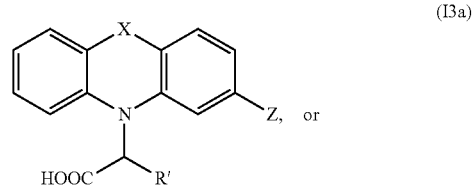
(I3a)

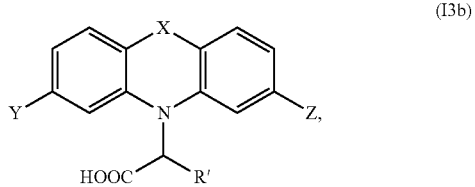
(I3b)

or a pharmaceutically acceptable salt or ester thereof, wherein R' is H or methyl.

In one embodiment, a compound of Formula I is of Formula I4, I4a, I4b, I4c, or I4d:

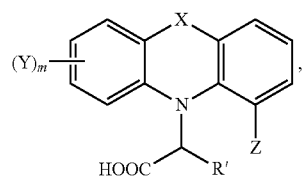 (I4)
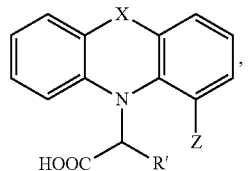 (I4a)
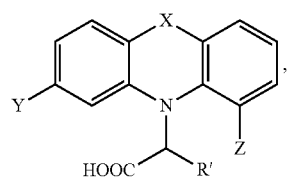 (I4b)
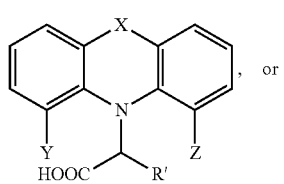 (I4c)
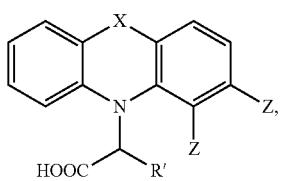 (I4d)
or a pharmaceutically acceptable salt or ester thereof, wherein R' is H or methyl.
In one embodiment, a compound of Formula I is of Formula I5, I5a, I5a2, I5a3, I5a4, I5a5, I5a6, I5b1, I5b2, I5b3, I5b4, I5b5, I5b6, I5c1, I5c2, I5c3, I5c4, I5c5, I5c6, I5d1, I5d2, I5d3, I5d4, I5d5, or I5d6:
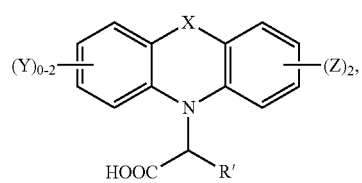 (I5)
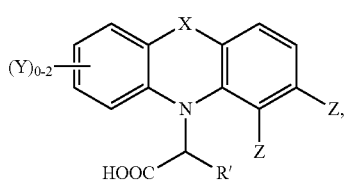 (I5a1)
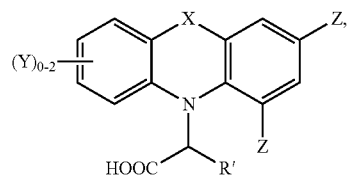 (I5a2)
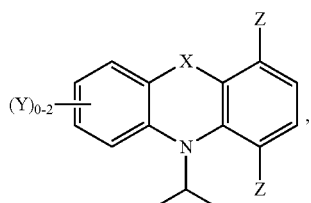 (I5a3)
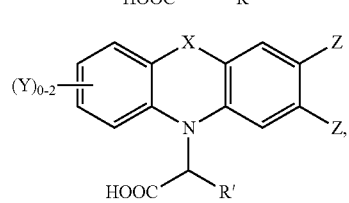 (I5a4)
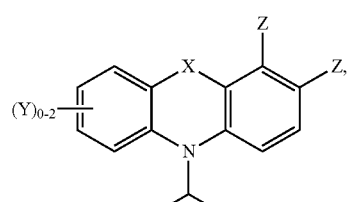 (I5a5)
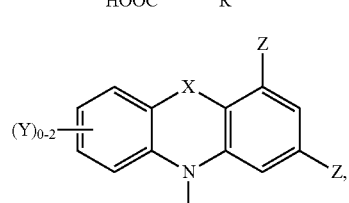 (I5a6)
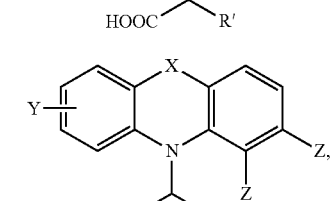 (I5b1)
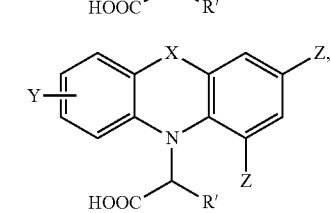 (I5b2)
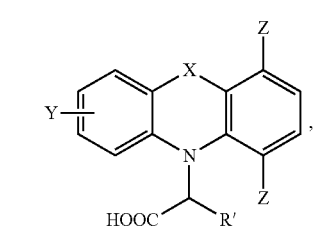 (I5b3)

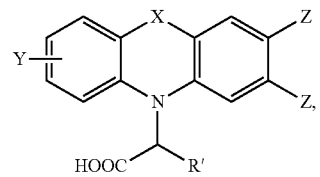
(I5b4)
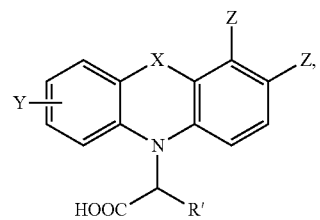
(I5b5)
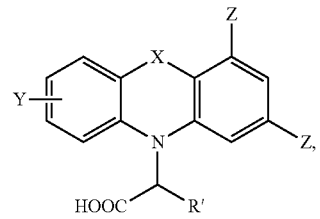
(I5b6)
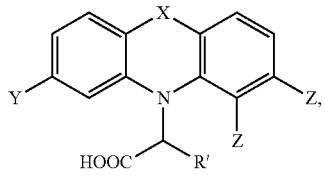
(I5c1)
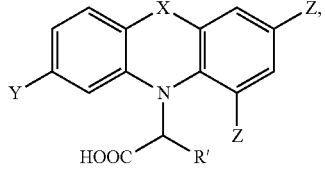
(I5c2)
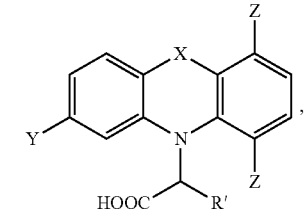
(I5c3)
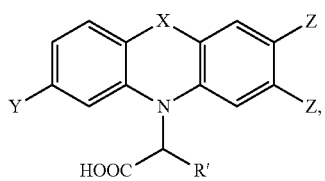
(I5c4)
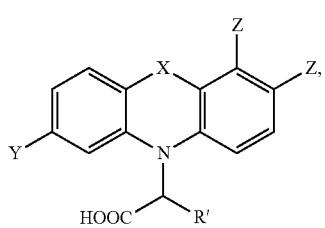
(I5c5)
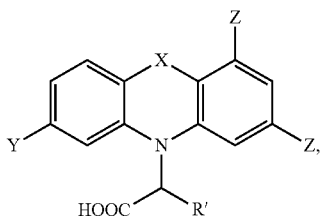
(Ic56)
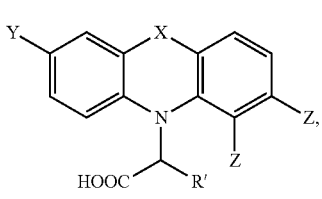
(I5d1)
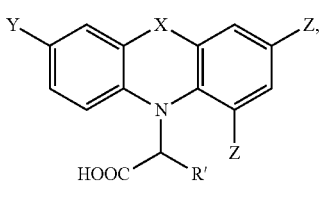
(I5d2)
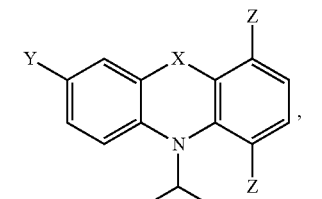
(I5d3)
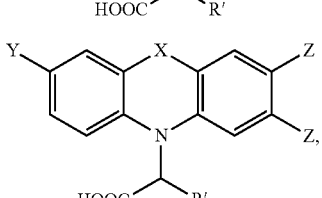
(I5d4)
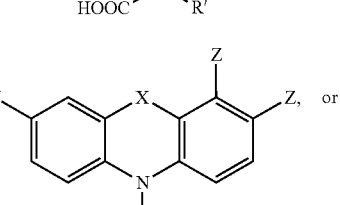
(I5d5)
or
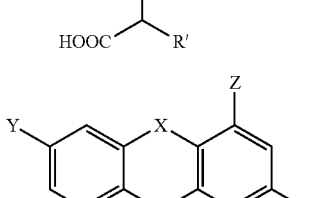
(I5d6)
or a pharmaceutically acceptable salt or ester thereof, wherein R' is H or methyl.
For a compound of any one of Formulae I1, I1a, I1b, I2, I2a, I3, I3a, I3b, I4, I4a, I4b, I4c, I4d, I5, I5a1, I5a2, I5a3, I5a4, I5a5, I5a6, I5b1, I5b2, I5b3, I5b4, I5b5. I5b6, I5c1, I5c2, I5c3, I5c4, I5c5, I5c6, I5d1, I5d2, I5d3, I5d4, I5d5, and I5d6, X, Y, Z, R, $R_T$, $R_X$, Q, Q', T, m, and q are each as defined herein in Formula I, and each of the groups described herein for any of X, Y, Z, R, $R_r$, $R_X$, Q, Q', T, m, and q can be combined as described herein above.

For example, for a compound of any one of Formulae Ia, Ib, I1, I1a, I1b, I2, I2a, I3, I3a, I3b, I4, I4a, I4b, I4c, I4d, I5, I5a1, I5a2, I5a3, I5a4, I5a5, I5a6, I5b1, I5b2, I5b3, I5b4, I5b5, I5b6, I5c1, I5c2, I5c3, I5c4, I5c5, I5c6, I5d1, I5d2, I5d3, I5d4, I5d5, and I5d6, where applicable:

In one embodiment, each Z is independently $C_1$-$C_6$ alkyl, $C_2$-$C_6$ alkenyl, $C_2$-$C_6$ alkynyl, halogen, CN, OH, O—($C_1$-$C_6$ alkyl), S—($C_1$-$C_6$ alkyl), $NH_2$, NH—$C_1$-$C_6$ alkyl, or N—($C_1$-$C_6$ alkyl)$_2$, each of which is as described herein.

In one embodiment, each Z is independently $C_1$-$C_6$ alkyl, halogen, CN, OH, O—($C_1$-$C_6$ alkyl), S—($C_1$-$C_6$ alkyl), $NH_2$, NH—$C_1$-$C_6$ alkyl, or N—($C_1$-$C_6$ alkyl)$_2$, each of which is as described herein.

In one embodiment, each Z is independently $C_1$-$C_6$ alkyl, halogen. CN, $NH_2$, NH—$C_1$-$C_6$ alkyl, or N—($C_1$-$C_6$ alkyl)$_2$, each of which is as described herein.

In one embodiment, each Z is independently $C_1$-$C_6$ alkyl, halogen, CN, or N—($C_1$-$C_6$ alkyl)$_2$, each of which is as described herein.

In one embodiment, each Z is independently methyl, ethyl, n-propyl, i-propyl, CN, F, Cl, Br, I, or $N(CH_3)_2$.

In one embodiment, each Z is independently methyl, F, Cl, Br, CN, or $N(CH_3)_2$.

In one embodiment, each Z is independently F, Cl, or Br.

In one embodiment, each Z is independently Cl or Br.

In one embodiment, each Z is Cl.

In one embodiment, each Z is Br.

In one embodiment, one Z is Br, and the other Z is Cl. In a further embodiment, one Z is Br at the 4-position, and the other Z is Cl at the 3-position.

In one embodiment, X is $C(R_X)_2$, and each $R_X$ is independently H, $CH_3$, $CF_3$, $CF_2H$, or F. In a further embodiment, each $R_X$ is independently H or $CH_3$. In another further embodiment, each $R_X$ is H. In another further embodiment, each $R_X$ is $CH_3$.

In one embodiment, X is $C(R_X)_2$, and two $R_X$ together form =O, =$CH_2$, or =$CF_2$. In a further embodiment, two $R_X$ together form =O.

In one embodiment, R' is H.

In one embodiment, R' is methyl. In a further embodiment, R' is (S)-methyl. In another further embodiment, R' is (R)-methyl.

Any of the groups described above for any of X, Z, and R' can be combined with any of the groups described above for the remainder of X, Z, and R', and the combination of X, Z, and R' can be further combined, where applicable, with any of the groups described herein for one or more of Y, $Z_1$, $R_1$, $R_Q$, $R_T$, $R_X$, $R_Z$, $R_S$, Q, Q', $T_1$, T, m, n, p, and q.

In one embodiment, a compound of Formula I is of Formula I5a1, I5b1, I5c1, or I5d1:

(I5a1)

(I5b1)

(I5c1)

(I5d1)

or a pharmaceutically acceptable salt or ester thereof, wherein R' is H or methyl.

For a compound of any one of Formulae I5a1, I5b1, I5c1, and I5d1, X, Y, Z, $R_Q$, $R_T$, $R_X$, Q, Q', T, m, and q are each as defined herein in Formula I, and each of the groups described herein for any of X, Y, Z, $R_Q$, $R_T$, $R_X$, Q, Q', T, m, and q can be combined as described herein above.

For example, for a compound of any one of Formulae I, Ia, Ib, I5a1, I5b1, I5c1, and I5d1, where applicable:

In one embodiment, each Z is independently $C_1$-$C_6$ alkyl, $C_2$-$C_6$ alkenyl, $C_2$-$C_6$ alkynyl, halogen, CN, OH, O—($C_1$-$C_6$ alkyl), S—($C_1$-$C_6$ alkyl), $NH_2$, NH—$C_1$-$C_6$ alkyl, or N—($C_1$-$C_6$ alkyl)$_2$, each of which is as described herein.

In one embodiment, each Z is independently $C_1$-$C_6$ alkyl, halogen, CN, OH, O—($C_1$-$C_6$ alkyl), S—($C_1$-$C_6$ alkyl), $NH_2$, NH—$C_1$-$C_6$ alkyl, or N—($C_1$-$C_6$ alkyl)$_2$, each of which is as described herein.

In one embodiment, each Z is independently $C_1$-$C_6$ alkyl, halogen, CN, $NH_2$, NH—$C_1$-$C_6$ alkyl, or N—($C_1$-$C_6$ alkyl)$_2$, each of which is as described herein.

In one embodiment, each Z is independently $C_1$-$C_6$ alkyl, halogen, CN, or N—($C_1$-$C_6$ alkyl)$_2$, each of which is as described herein.

In one embodiment, each Z is independently methyl, ethyl, n-propyl, i-propyl, CN, F, Cl, Br, I, or $N(CH_3)_2$.

In one embodiment, each Z is independently methyl, F, Cl, Br, CN, or $N(CH_3)_2$.

In one embodiment, each Z is independently F, Cl, or Br.

In one embodiment, each Z is independently Cl or Br.

In one embodiment, each Z is Cl.

In one embodiment, each Z is Br.

In one embodiment, one Z is Br, and the other Z is Cl. In a further embodiment, one Z is Br at the 4-position, and the other Z is Cl at the 3-position.

For any of the formulae described herein, wherein applicable:

In one embodiment, one Z is halogen, O—($C_1$-$C_6$ alkyl), S—($C_1$-$C_6$ alkyl), N—($C_1$-$C_6$ alkyl)$_2$, or Q-T, each of which is as described herein, and the other Z is Cl. In a further embodiment, Z is Cl at the 3-position, and the halogen. O—($C_1$-$C_6$ alkyl), S—($C_1$-$C_6$ alkyl), N—($C_1$-$C_6$ alkyl)$_2$, or Q-T is at the 4-position.

In one embodiment, one Z is halogen, O—($C_1$-$C_6$ alkyl), S—($C_1$-$C_6$ alkyl), or N—($C_1$-$C_6$ alkyl)$_2$, each of which is as described herein, and the other Z is Cl. In a further embodiment, Z is Cl at the 3-position, and the halogen, O—($C_1$-$C_6$ alkyl), S—($C_1$-$C_6$ alkyl), or N—($C_1$-$C_6$ alkyl)$_2$ is at the 4-position.

In one embodiment, one Z is halogen, and the other Z is Cl. In a further embodiment, Z is Cl at the 3-position. In a further embodiment, Z is Cl at the 3-position, and the halogen is at the 4-position. In a further embodiment, the halogen is Cl, Br, or I. In a further embodiment, the halogen is Cl.

In one embodiment, one Z is O—($C_1$-$C_6$ alkyl) as described herein, and the other Z is Cl. In a further embodiment, Z is Cl at the 3-position, and the O—($C_1$-$C_6$ alkyl) is at the 4-position. In a further embodiment, the O—($C_1$-$C_6$ alkyl) is O-methyl.

In one embodiment, one Z is S—($C_1$-$C_6$ alkyl) as described herein, and the other Z is Cl. In a further embodiment, Z is Cl at the 3-position, and the S—($C_1$-$C_6$ alkyl) is at the 4-position. In a further embodiment, the S—($C_1$-$C_6$ alkyl) is S-methyl.

In one embodiment, one Z is N—($C_1$-$C_6$ alkyl)$_2$ as described herein, and the other Z is Cl. In a further embodiment, Z is Cl at the 3-position, and the N—($C_1$-$C_6$ alkyl)$_2$ is at the 4-position. In a further embodiment, the N—($C_1$-$C_6$ alkyl)$_2$ is N($CH_3$)$_2$ or N($CH_3$)($CH_2CH_3$).

In one embodiment, one Z is Q-T as described herein, and the other Z is Cl. In a further embodiment, Z is Cl at the 3-position. In a further embodiment, Z is Cl at the 3-position, and Q-T is at the 4-position. In a further embodiment, Q is a bond and T is cycloalkyl, cycloalkenyl, heterocyclyl, $C_6$-$C_{10}$ aryl, or heteroaryl, each optionally substituted with one or more $R_T$, as described herein. In a further embodiment, Q is a bond and T is $C_6$-$C_{10}$ aryl optionally substituted with one or more $R_T$. In a further embodiment, T is phenyl optionally substituted with one or more $R_T$.

In one embodiment, Y is tert-butyl, one Z is S—$CH_3$, and the other Z is Cl. In a further embodiment, one Z is S—$CH_3$ at the 4-position, and the other Z is Cl at the 3-position.

In one embodiment, Y is tert-butyl, one Z is O—$CH_3$, and the other Z is Cl. In a further embodiment, one Z is O—$CH_3$ at the 4-position, and the other Z is Cl at the 3-position.

In one embodiment, Y is methyl, i-propyl, or t-butyl, one Z is phenyl, and the other Z is Cl. In a further embodiment, one Z is phenyl at the 4-position, and the other Z is Cl at the 3-position. In a further embodiment, Y is methyl or i-propyl. In a further embodiment, Y is at the 6-position.

In one embodiment, Y is methyl, i-propyl, or t-butyl, one Z is N($CH_3$)$_2$, and the other Z is Cl. In a further embodiment, one Z is N($CH_3$)$_2$ at the 4-position, and the other Z is Cl at the 3-position. In a further embodiment, Y is methyl or t-butyl. In a further embodiment, Y is at the 6-position.

In one embodiment, Y is NH-phenyl, one Z is N($CH_3$)$_2$, and the other Z is Cl. In a further embodiment, one Z is N($CH_3$)$_2$ at the 4-position, and the other Z is Cl at the 3-position. In a further embodiment, Y is at the 6-position.

In one embodiment, X is C($R_X$)$_2$, and each $R_X$ is independently H, $CH_3$, $CF_3$, $CF_2H$, or F. In a further embodiment, each $R_X$ is independently H or $CH_3$. In another further embodiment, each $R_X$ is H. In another further embodiment, each $R_X$ is $CH_3$.

In one embodiment, X is C($R_X$)$_2$, and two $R_X$ together form =O, =$CH_2$, or =$CF_2$. In a further embodiment, two $R_X$ together form =O.

In one embodiment, Y is NH-(phenyl) and one Z is N—($CH_3$)$_2$, and the other Z is halogen. In a further embodiment, the halogen is Cl.

In one embodiment, Y is $C_1$-$C_6$ alkyl and one Z is phenyl, and the other Z is halogen. In a further embodiment, Z is halogen at the 3-position. In a further embodiment, the halogen is Cl. In another further embodiment, Z is Cl at the 3-position. In another further embodiment, Y is methyl.

In one embodiment, Y is isopropyl and one Z is N—($CH_3$)$_2$, and the other Z is halogen. In a further embodiment, Z is halogen at the 3-position. In a further embodiment, the halogen is Cl. In another further embodiment, Z is Cl at the 3-position.

In one embodiment, Y is $C_1$-$C_6$ alkyl and one Z is N—($CH_3$)$_2$, and the other Z is halogen. In a further embodiment, the halogen is Cl. In another further embodiment, Z is Cl at the 3-position. In another further embodiment, Y is methyl. In another further embodiment, Y is methyl at the 6-position.

In one embodiment, Y is branched $C_1$-$C_6$ alkyl and one Z is phenyl, and the other Z is halogen. In a further embodiment, Z is halogen at the 3-position. In a further embodiment, the halogen is Cl. In another further embodiment, Y is isopropyl.

In one embodiment, R' is H.

In one embodiment, R' is methyl. In a further embodiment, R' is (S)-methyl. In another further embodiment, R' is (R)-methyl.

Any of the groups described above for any of X, Z, and R' can be combined with any of the groups described above for the remainder of X, Z, and R', and the combination of X, Z, and R' can be further combined, where applicable, with any of the groups described herein for one or more of Y, $Z_1$, $R_1$, $R_Q$, $R_T$, $R_X$, $R_Z$, $R_S$, Q, Q', $T_1$, T, m, n, p, and q.

Representative compounds of the present application are shown in Table 1.

TABLE 1

| Cmpd No. | Structure |
|---|---|
| 1 | 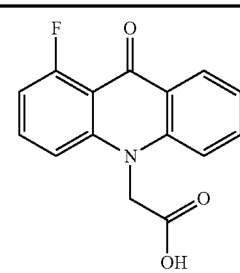 |
| 2 | 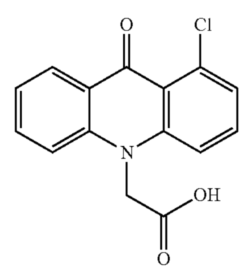 [SMILES: O=C(O)Cn1c2ccccc2c(=O)c2c(Cl)cccc21] |
| 3 | 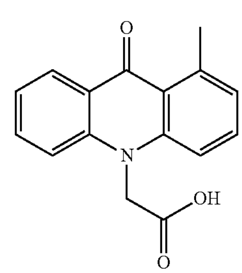 [SMILES: Cc1cccc2c1c(=O)c1ccccc1n2CC(=O)O] |

TABLE 1-continued
| Cmpd No. | Structure |
|---|---|
| 4 | 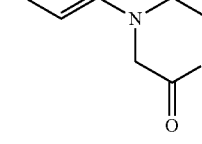 |
| 5 | 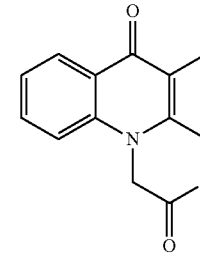 |
| 6 | 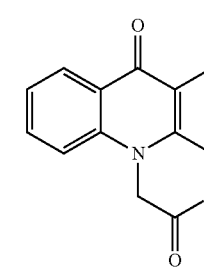 |
| 7 | 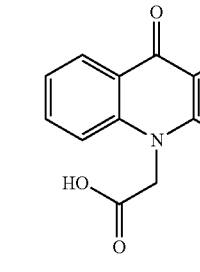 |
| 8 | 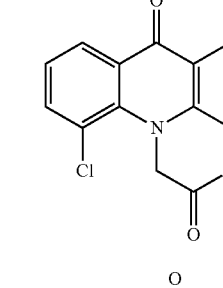 |
| 9 | 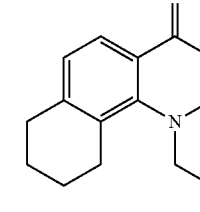 |
| 10 | 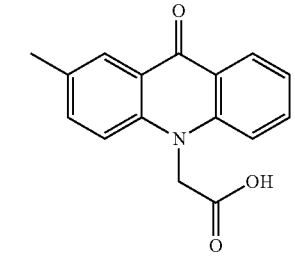 [SMILES: Cc1ccc2c(c1)c(=O)c1ccccc1n2CC(=O)O] |
| 11 | 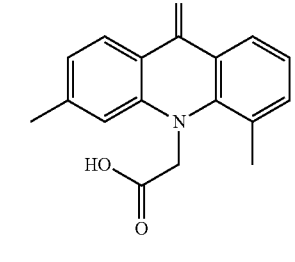 |
| 12 | 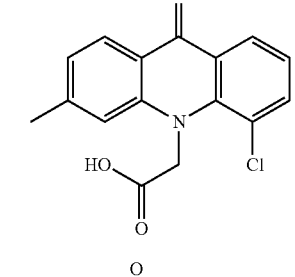 |
| 13 | 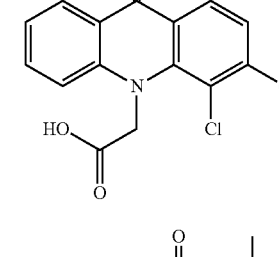 |
| 14 | 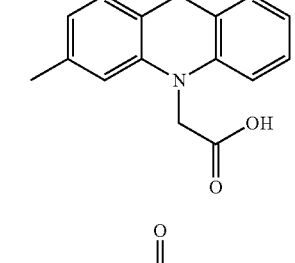 |
| 15 | 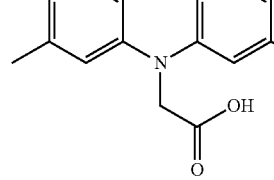 |

TABLE 1-continued

| Cmpd No. | Structure |
|---|---|
| 16 | 1-chloro-6-methyl acridin-9(10H)-one-10-yl acetic acid |
| 17 | 3-chloro-6-methyl acridin-9(10H)-one-10-yl acetic acid |
| 18 | 3-bromo acridin-9(10H)-one-10-yl acetic acid |
| 19 | 4-chloro-3-methyl acridin-9(10H)-one-10-yl acetic acid |
| 20 | 1-bromo acridin-9(10H)-one-10-yl acetic acid |
| 21 | 2-bromo acridin-9(10H)-one-10-yl acetic acid |
| 22 | 2-(phenylethynyl) acridin-9(10H)-one-10-yl acetic acid |
| 23 | 2-phenethyl acridin-9(10H)-one-10-yl acetic acid |
| 24 | 3,6-dimethyl acridin-9(10H)-one-10-yl acetic acid |
| 25 | 3-(phenylethynyl) acridin-9(10H)-one-10-yl acetic acid |
| 26 | 3-phenethyl acridin-9(10H)-one-10-yl acetic acid |

TABLE 1-continued

| Cmpd No. | Structure |
|---|---|
| 27 | 2-phenethyl-1-methyl acridone N-acetic acid |
| 28 | 2-cyclohexenyl-1-methyl acridone N-acetic acid |
| 29 | 1,2-dichloro-7-methyl acridone N-acetic acid |
| 30 | 2,3-dichloro-6-fluoro acridone N-acetic acid |
| 31 | 2,3-dichloro-8-fluoro acridone N-acetic acid |
| 32 | 7-methyl-1-methoxy acridone N-acetic acid |
| 33 | 6-fluoro-3-methyl acridone N-acetic acid |
| 34 | 6-methoxy-3-methyl acridone N-acetic acid |
| 35 | 6-methoxy-1-methyl acridone N-acetic acid |
| 36 | 3-methyl-8-fluoro acridone N-acetic acid |

TABLE 1-continued

| Cmpd No. | Structure |
|---|---|
| 37 | 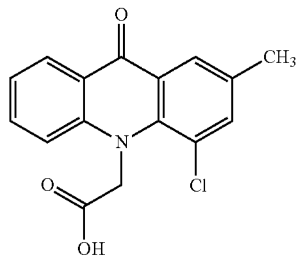 [SMILES: Cc1cc(Cl)c2c(c1)c(=O)c1ccccc1n2CC(=O)O] |
| 38 | 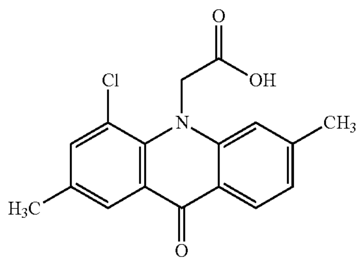 |
| 39 | 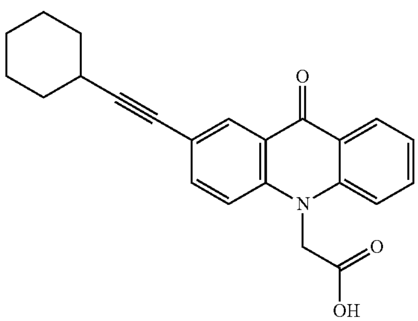 [SMILES: O=C(O)Cn1c2ccccc2c(=O)c2cc(C#CC3CCCCC3)ccc21] |
| 40 | 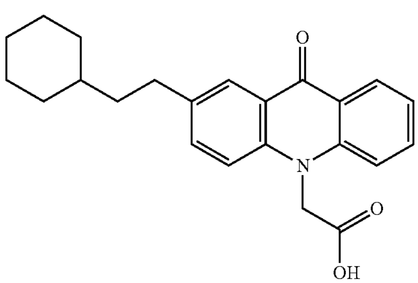 [SMILES: O=C(O)Cn1c2ccccc2c(=O)c2cc(CCC3CCCCC3)ccc21] |
| 41 | 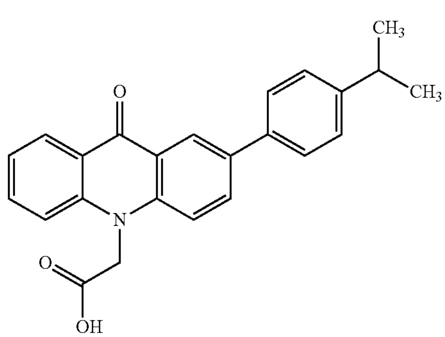 [SMILES: CC(C)c1ccc(-c2ccc3c(c2)c(=O)c2ccccc2n3CC(=O)O)cc1] |
| 42 | 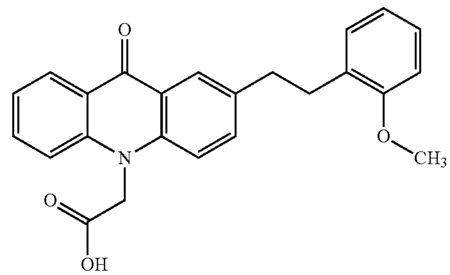 [SMILES: COc1ccccc1CCc1ccc2c(c1)c(=O)c1ccccc1n2CC(=O)O] |
| 43 | 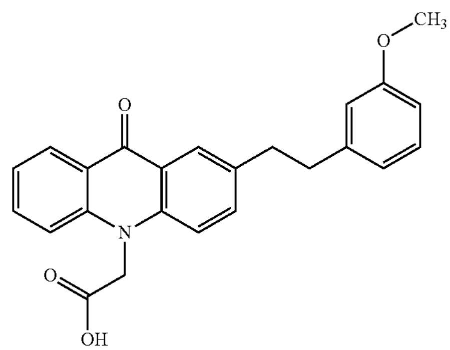 [SMILES: COc1cccc(CCc2ccc3c(c2)c(=O)c2ccccc2n3CC(=O)O)c1] |
| 44 | 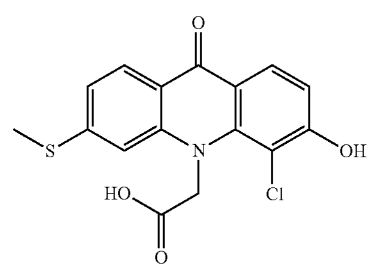 [SMILES: CSc1ccc2c(=O)c3ccc(O)c(Cl)c3n(CC(=O)O)c2c1] |
| 45 | 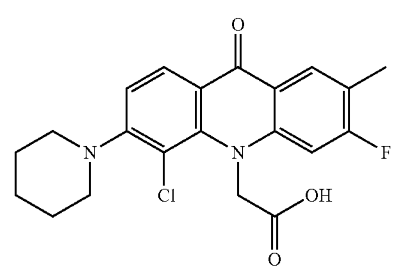 [SMILES: Cc1cc2c(=O)c3ccc(N4CCCCC4)c(Cl)c3n(CC(=O)O)c2cc1F] |
| 46 | 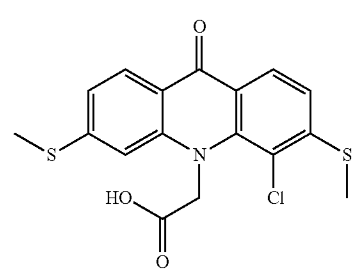 |

TABLE 1-continued

| Cmpd No. | Structure |
|---|---|
| 47 | 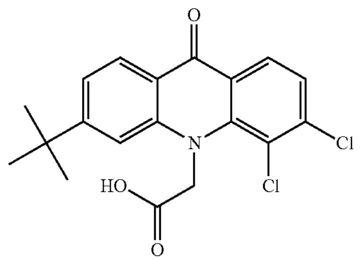 [SMILES: CC(C)(C)c1ccc2c(=O)c3ccc(Cl)c(Cl)c3n(CC(=O)O)c2c1] |
| 48 | 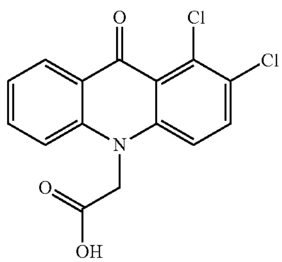 [SMILES: O=C(O)Cn1c2ccccc2c(=O)c2c(Cl)c(Cl)ccc21] |
| 49 | 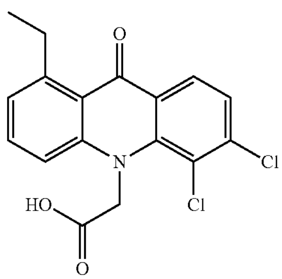 [SMILES: CCc1cccc2c1c(=O)c1ccc(Cl)c(Cl)c1n2CC(=O)O] |
| 50 | 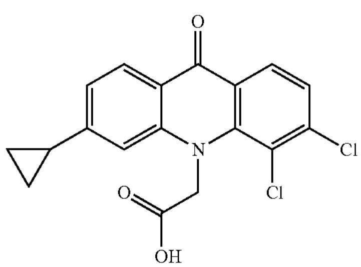 [SMILES: O=C(O)Cn1c2cc(C3CC3)ccc2c(=O)c2ccc(Cl)c(Cl)c21] |
| 51 | 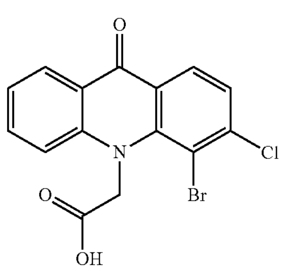 [SMILES: O=C(O)Cn1c2ccccc2c(=O)c2ccc(Cl)c(Br)c21] |
| 52 | 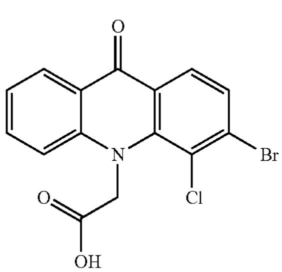 [SMILES: O=C(O)Cn1c2ccccc2c(=O)c2ccc(Br)c(Cl)c21] |
| 53 | |
| 54 | |
| 55 | |
| 56 | |
| 57 | |

TABLE 1-continued

| Cmpd No. | Structure |
|---|---|
| 58 | 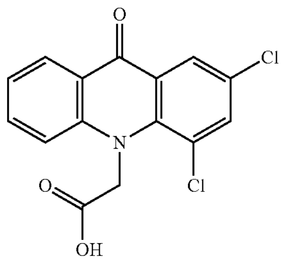 [SMILES: O=C(O)Cn1c2ccccc2c(=O)c2cc(Cl)cc(Cl)c21] |
| 59 | 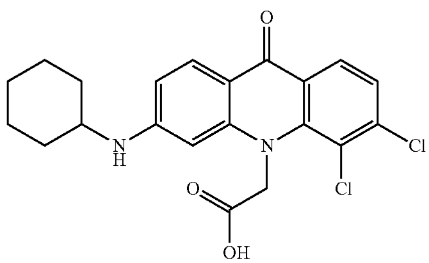 [SMILES: O=C(O)Cn1c2cc(NC3CCCCC3)ccc2c(=O)c2ccc(Cl)c(Cl)c21] |
| 60 | 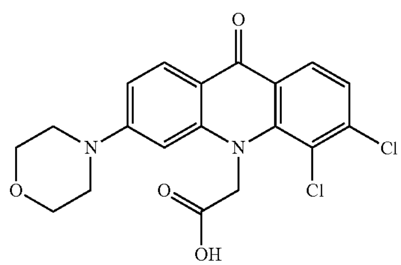 [SMILES: O=C(O)Cn1c2cc(N3CCOCC3)ccc2c(=O)c2ccc(Cl)c(Cl)c21] |
| 61 | 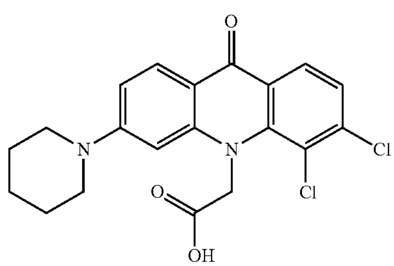 [SMILES: O=C(O)Cn1c2cc(N3CCCCC3)ccc2c(=O)c2ccc(Cl)c(Cl)c21] |
| 62 | 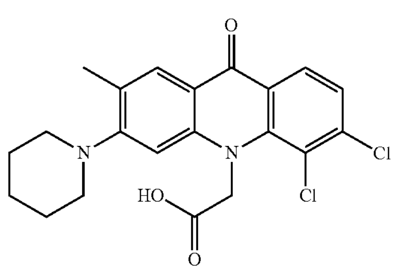 [SMILES: Cc1cc2c(=O)c3ccc(Cl)c(Cl)c3n(CC(=O)O)c2cc1N1CCCCC1] |
| 63 | 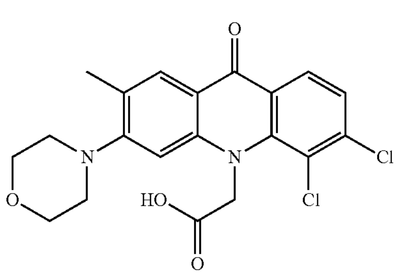 [SMILES: Cc1cc2c(=O)c3ccc(Cl)c(Cl)c3n(CC(=O)O)c2cc1N1CCOCC1] |
| 64 | |
| 65 | |
| 66 | |
| 67 | |
| 68 | |

TABLE 1-continued
| Cmpd No. | Structure |
|---|---|
| 69 | 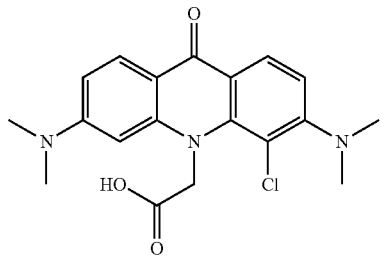 |
| 70 | 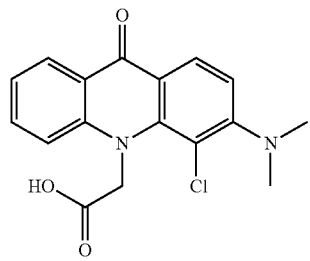 [SMILES: CN(C)c1ccc2c(=O)c3ccccc3n(CC(=O)O)c2c1Cl] |
| 71 | 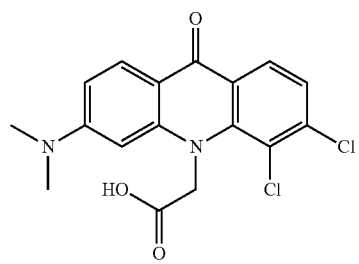 [SMILES: CN(C)c1ccc2c(=O)c3ccc(Cl)c(Cl)c3n(CC(=O)O)c2c1] |
| 72 | 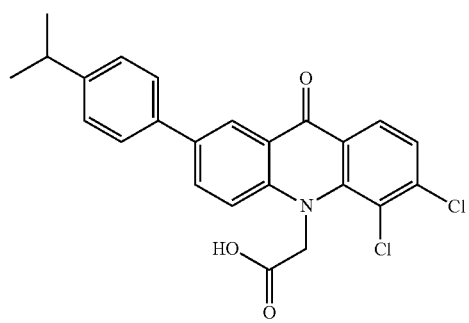 |
| 73 | 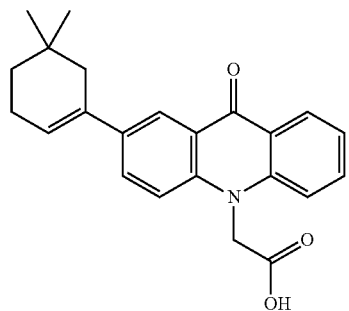 [SMILES: CC1(C)CCC=C(c2ccc3c(c2)c(=O)c2ccccc2n3CC(=O)O)C1] |
| 74 | 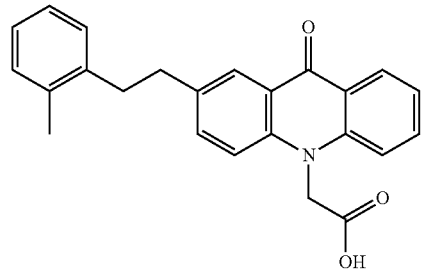 [SMILES: Cc1ccccc1CCc1ccc2c(c1)c(=O)c1ccccc1n2CC(=O)O] |
| 75 | 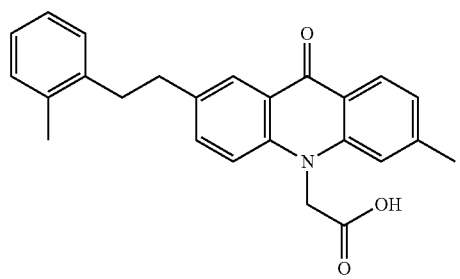 [SMILES: Cc1ccc2c(=O)c3cc(CCc4ccccc4C)ccc3n(CC(=O)O)c2c1] |
| 76 | 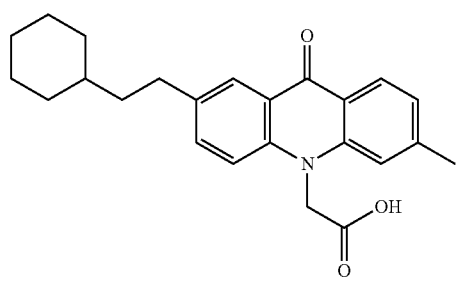 [SMILES: Cc1ccc2c(=O)c3cc(CCC4CCCCC4)ccc3n(CC(=O)O)c2c1] |
| 77 | 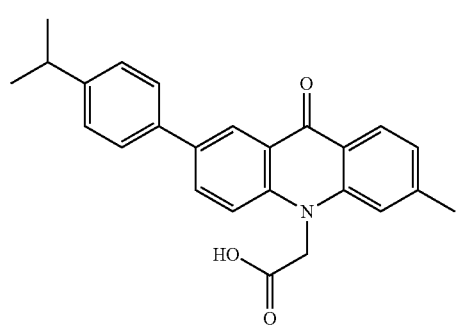 [SMILES: Cc1ccc2c(=O)c3cc(-c4ccc(C(C)C)cc4)ccc3n(CC(=O)O)c2c1] |
| 78 | 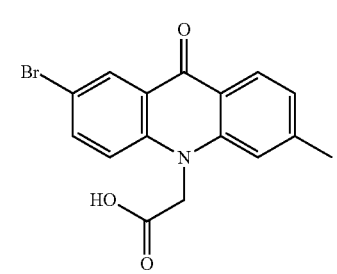 [SMILES: Cc1ccc2c(=O)c3cc(Br)ccc3n(CC(=O)O)c2c1] |

TABLE 1-continued

| Cmpd No. | Structure |
|---|---|
| 79 | 7-bromo-3,4-dichloro-9-oxoacridine-10(9H)-acetic acid |
| 80 | 7-styryl-9-oxoacridine-10(9H)-acetic acid |
| 81 | 7-isopropyl-3,4-dichloro-9-oxoacridine-10(9H)-acetic acid |
| 82 | 7-ethyl-3,4-dichloro-9-oxoacridine-10(9H)-acetic acid |
| 83 | 3-fluoro-4-chloro-9-oxoacridine-10(9H)-acetic acid |
| 84 | 3-chloro-4-fluoro-9-oxoacridine-10(9H)-acetic acid |
| 85 | 7-methyl-3,4-dichloro-9-oxoacridine-10(9H)-acetic acid |
| 86 | 2-bromo-9,9-dimethylacridine-10(9H)-acetic acid |
| 87 | 9,9-dimethylacridine-10(9H)-acetic acid |
| 88 | 7-phenethyl-3,4-dichloro-9-oxoacridine-10(9H)-acetic acid |

TABLE 1-continued
| Cmpd No. | Structure |
|---|---|
| 89 | 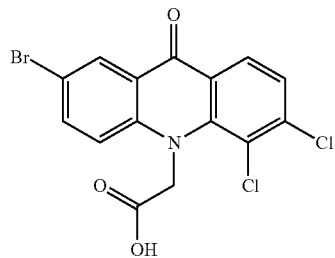 |
| 90 | 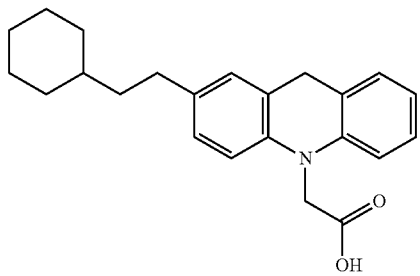 [SMILES: O=C(O)CN1c2ccccc2Cc2cc(CCC3CCCCC3)ccc21] |
| 91 | 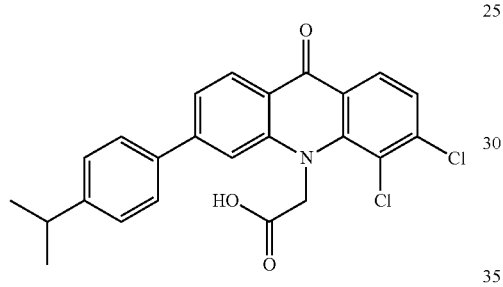 |
| 92 | 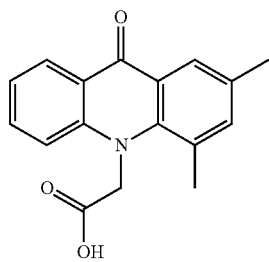 [SMILES: Cc1cc(C)c2c(c1)c(=O)c1ccccc1n2CC(=O)O] |
| 93 | 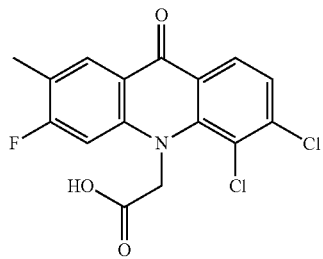 [SMILES: Cc1cc2c(=O)c3ccc(Cl)c(Cl)c3n(CC(=O)O)c2cc1F] |
| 94 | 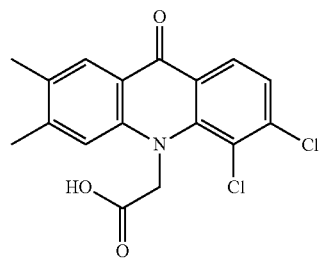 [SMILES: Cc1cc2c(=O)c3ccc(Cl)c(Cl)c3n(CC(=O)O)c2cc1C] |
TABLE 1-continued
| Cmpd No. | Structure |
|---|---|
| 95 | 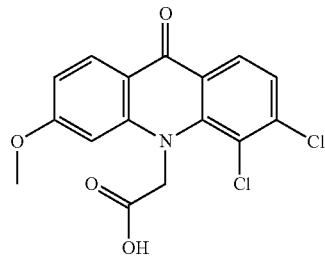 [SMILES: COc1ccc2c(=O)c3ccc(Cl)c(Cl)c3n(CC(=O)O)c2c1] |
| 96 | 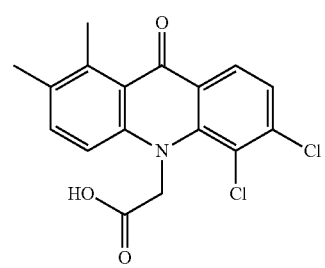 [SMILES: Cc1ccc2c(c1C)c(=O)c1ccc(Cl)c(Cl)c1n2CC(=O)O] |
| 97 | 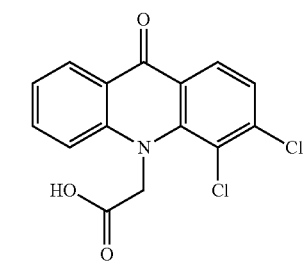 [SMILES: O=C(O)Cn1c2ccccc2c(=O)c2ccc(Cl)c(Cl)c21] |
| 98 | 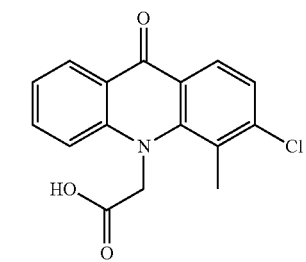 [SMILES: Cc1c(Cl)ccc2c(=O)c3ccccc3n(CC(=O)O)c12] |
| 99 | 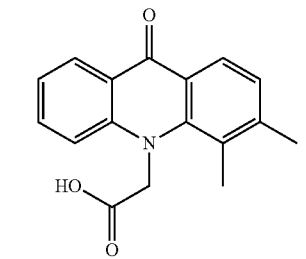 [SMILES: Cc1ccc2c(=O)c3ccccc3n(CC(=O)O)c2c1C] |
| 100 | 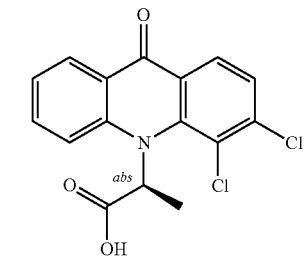 [SMILES: C[C@@H](C(=O)O)n1c2ccccc2c(=O)c2ccc(Cl)c(Cl)c21] |

TABLE 1-continued

| Cmpd No. | Structure |
|---|---|
| 101 | 9-oxo-acridine with N-CH(CH<sub>3</sub>)COOH (abs) and 3,4-diCl |
| 102 | 9-oxo-acridine with N-CH(CH<sub>3</sub>)COOH |
| 103 | 9-oxo-acridine with N-CH<sub>2</sub>COOH, 4-Cl, 3-I |
| 104 | 9-oxo-acridine with N-CH<sub>2</sub>COOH, 4-methyl, 3-Cl |
| 105 | 9-oxo-acridine with 2-(cyclohexylamino), 3-methyl, N-CH<sub>2</sub>COOH, 4,5-diCl |
| 106 | 9-oxo-acridine with N-CH<sub>2</sub>COOH, 4-CN, 3-Cl |
| 107 | 9-oxo-acridine with N-CH<sub>2</sub>COOH, 4-Cl, 3-CN |
| 108 | 9-oxo-acridine with N-CH<sub>2</sub>COOH, 4-Br, 3-Br |
| 109 | 9-oxo-acridine with 7-(4-isopropylphenyl), N-CH<sub>2</sub>COOH, 4-Br, 3-Cl |
| 110 | 9-oxo-acridine with 6-(cyclohexylamino), N-CH<sub>2</sub>COOH, 4-Br, 3-Cl |

TABLE 1-continued
| Cmpd No. | Structure |
|---|---|
| 111 | 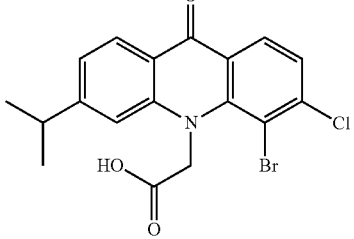 |
| 112 | 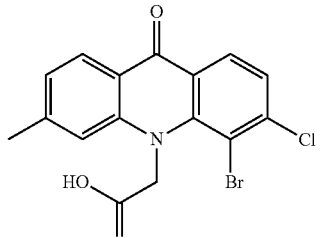 |
| 113 | 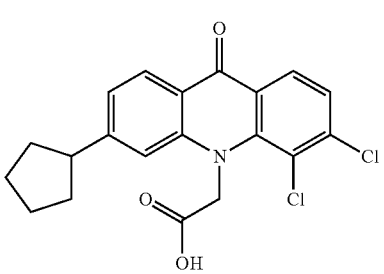 [SMILES: O=C(O)Cn1c2cc(C3CCCC3)ccc2c(=O)c2ccc(Cl)c(Cl)c21] |
| 114 | 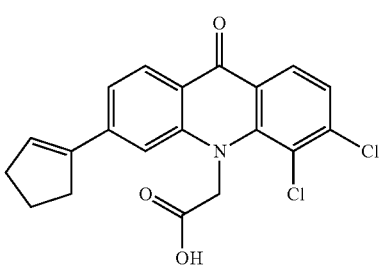 [SMILES: O=C(O)Cn1c2cc(C3=CCCC3)ccc2c(=O)c2ccc(Cl)c(Cl)c21] |
| 115 | 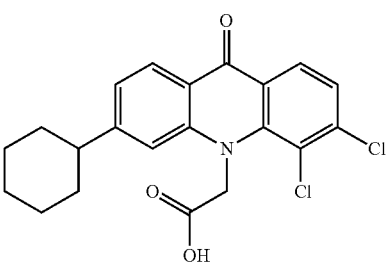 [SMILES: O=C(O)Cn1c2cc(C3CCCCC3)ccc2c(=O)c2ccc(Cl)c(Cl)c21] |
| 116 | 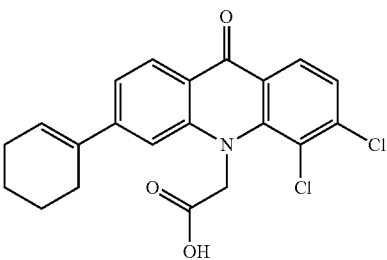 [SMILES: O=C(O)Cn1c2cc(C3=CCCCC3)ccc2c(=O)c2ccc(Cl)c(Cl)c21] |
| 117 | 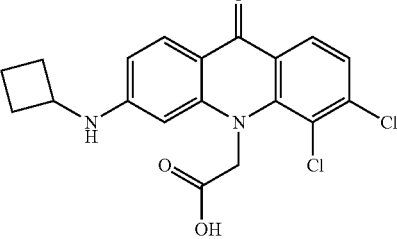 |
| 118 | 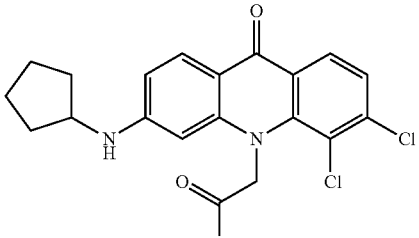 |
| 119 | 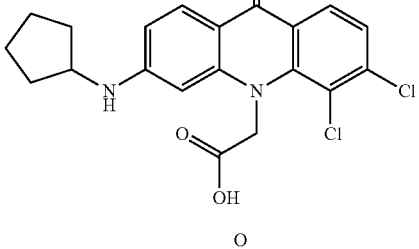 |
| 120 | 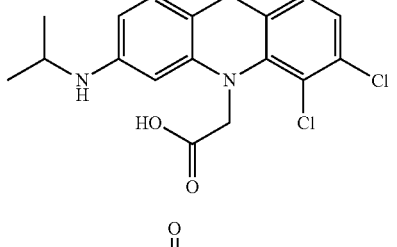 |
| 121 | 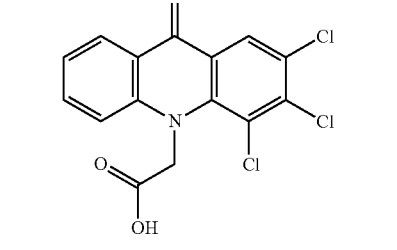 |
| 122 | 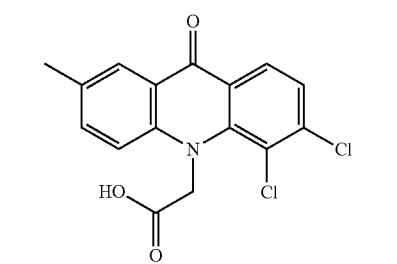 [SMILES: Cc1ccc2c(c1)c(=O)c1ccc(Cl)c(Cl)c1n2CC(=O)O] |

TABLE 1-continued

| Cmpd No. | Structure |
|---|---|
| 123 | (structure) |
| 124 | (structure) |
| 125 | (structure) |
| 126 | (structure) |
| 127 | (structure) |
| 128 | (structure) |
| 129 | (structure) |
| 130 | (structure) |
| 131 | (structure) |
| 132 | (structure) |
| 133 | (structure) |
| 134 | (structure) |

TABLE 1-continued

| Cmpd No. | Structure |
|---|---|
| 135 | 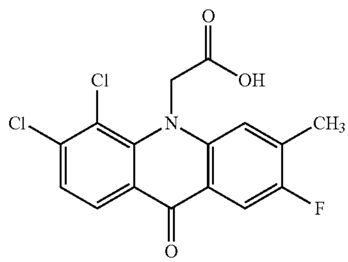 [SMILES: Cc1cc2c(cc1F)c(=O)c1ccc(Cl)c(Cl)c1n2CC(=O)O] |
| 136 | 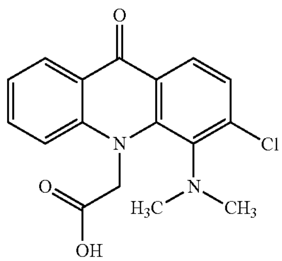 [SMILES: CN(C)c1c(Cl)ccc2c(=O)c3ccccc3n(CC(=O)O)c12] |
| 137 | 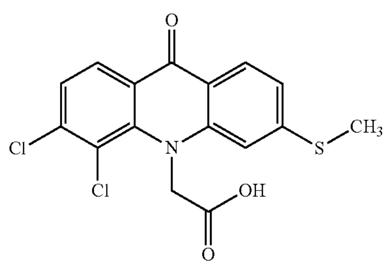 [SMILES: CSc1ccc2c(=O)c3ccc(Cl)c(Cl)c3n(CC(=O)O)c2c1] |
| 138 | 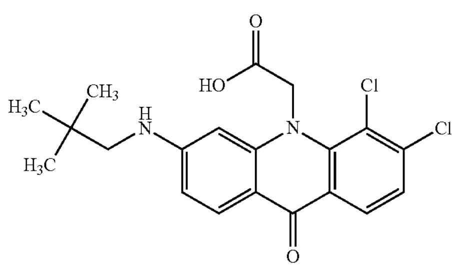 [SMILES: CC(C)(C)CNc1ccc2c(=O)c3ccc(Cl)c(Cl)c3n(CC(=O)O)c2c1] |
| 139 | 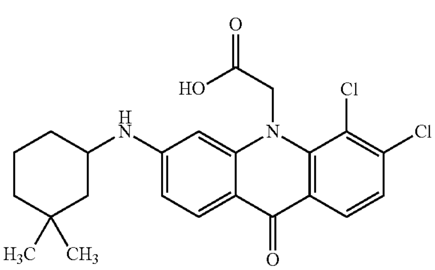 [SMILES: CC1(C)CCCC(Nc2ccc3c(=O)c4ccc(Cl)c(Cl)c4n(CC(=O)O)c3c2)C1] |
| 140 | 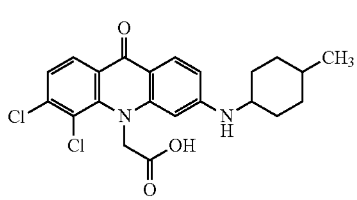 [SMILES: CC1CCC(Nc2ccc3c(=O)c4ccc(Cl)c(Cl)c4n(CC(=O)O)c3c2)CC1] |
| 141 | 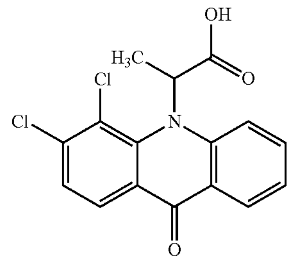 [SMILES: CC(C(=O)O)n1c2ccccc2c(=O)c2ccc(Cl)c(Cl)c21] |
| 142 | 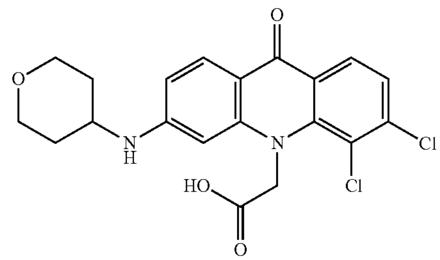 [SMILES: O=C(O)Cn1c2cc(NC3CCOCC3)ccc2c(=O)c2ccc(Cl)c(Cl)c21] |
| 143 | 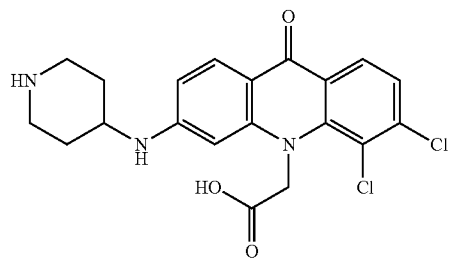 [SMILES: O=C(O)Cn1c2cc(NC3CCNCC3)ccc2c(=O)c2ccc(Cl)c(Cl)c21] |
| 144 | 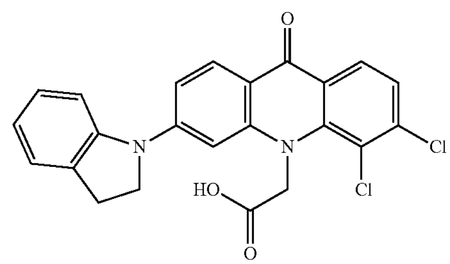 [SMILES: O=C(O)Cn1c2cc(N3CCc4ccccc43)ccc2c(=O)c2ccc(Cl)c(Cl)c21] |
| 145 | 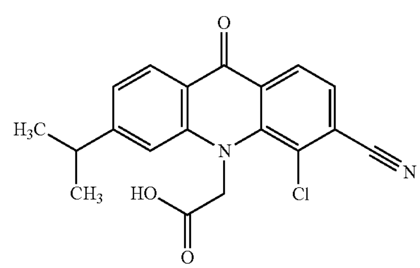 [SMILES: CC(C)c1ccc2c(=O)c3ccc(C#N)c(Cl)c3n(CC(=O)O)c2c1] |
| 146 | 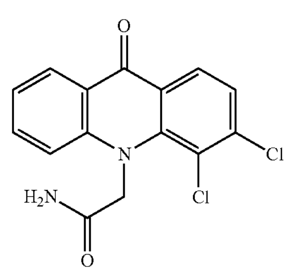 [SMILES: NC(=O)Cn1c2ccccc2c(=O)c2ccc(Cl)c(Cl)c21] |

TABLE 1-continued

| Cmpd No. | Structure |
|---|---|
| 147 | 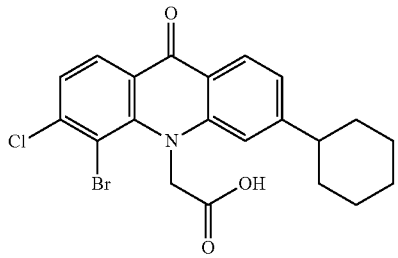 [SMILES: O=C(O)Cn1c2cc(C3CCCCC3)ccc2c(=O)c2ccc(Cl)c(Br)c21] |
| 148 | 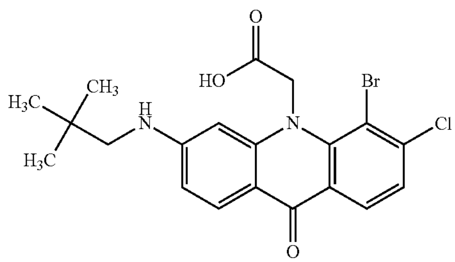 |
| 149 | 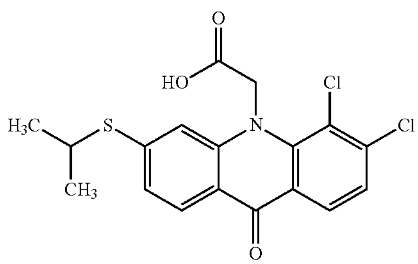 [SMILES: CC(C)Sc1ccc2c(=O)c3ccc(Cl)c(Cl)c3n(CC(=O)O)c2c1] |
| 150 | 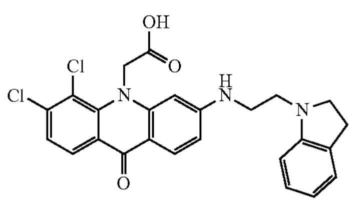 [SMILES: O=C(O)Cn1c2cc(NCCN3CCc4ccccc43)ccc2c(=O)c2ccc(Cl)c(Cl)c21] |
| 151 | 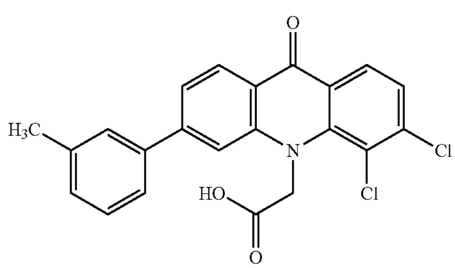 [SMILES: Cc1cccc(-c2ccc3c(=O)c4ccc(Cl)c(Cl)c4n(CC(=O)O)c3c2)c1] |
| 152 | 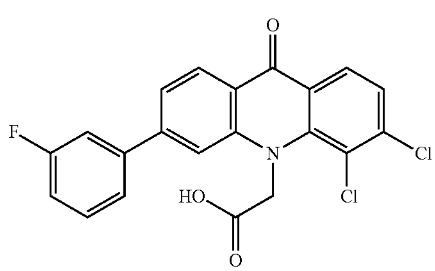 [SMILES: O=C(O)Cn1c2cc(-c3cccc(F)c3)ccc2c(=O)c2ccc(Cl)c(Cl)c21] |
| 153 | |
| 154 | |
| 155 | |
| 156 | |
| 157 | |
| 158 | |

TABLE 1-continued

| Cmpd No. | Structure |
|---|---|
| 159 | 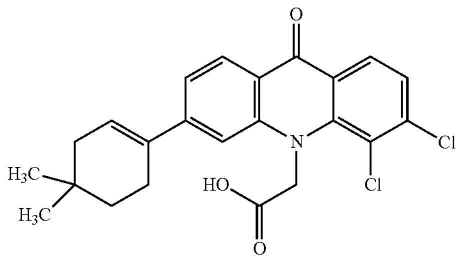 [SMILES: CC1(C)CC=C(c2ccc3c(=O)c4ccc(Cl)c(Cl)c4n(CC(=O)O)c3c2)CC1] |
| 160 | 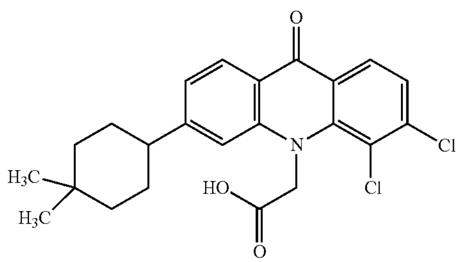 [SMILES: CC1(C)CCC(c2ccc3c(=O)c4ccc(Cl)c(Cl)c4n(CC(=O)O)c3c2)CC1] |
| 161 | 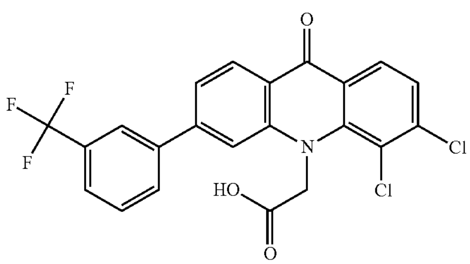 [SMILES: O=C(O)Cn1c2cc(-c3cccc(C(F)(F)F)c3)ccc2c(=O)c2ccc(Cl)c(Cl)c21] |
| 162 | 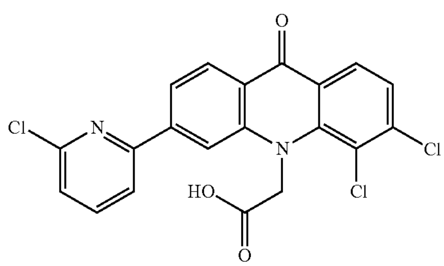 [SMILES: O=C(O)Cn1c2cc(-c3cccc(Cl)n3)ccc2c(=O)c2ccc(Cl)c(Cl)c21] |
| 163 | 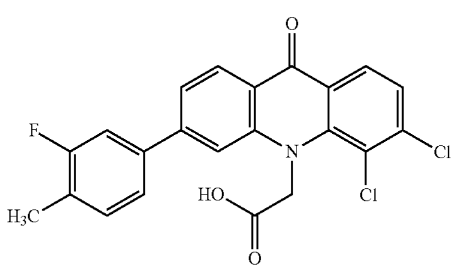 [SMILES: Cc1ccc(-c2ccc3c(=O)c4ccc(Cl)c(Cl)c4n(CC(=O)O)c3c2)cc1F] |
| 164 | 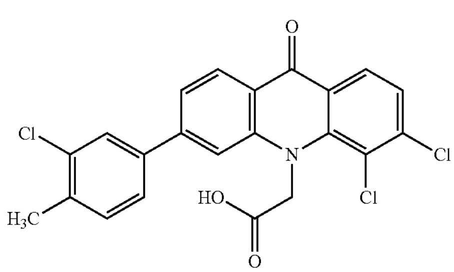 [SMILES: Cc1ccc(-c2ccc3c(=O)c4ccc(Cl)c(Cl)c4n(CC(=O)O)c3c2)cc1Cl] |
| 165 | |
| 166 | |
| 167 | |
| 168 | |
| 169 | |
| 170 | |

TABLE 1-continued
| Cmpd No. | Structure |
|---|---|
| 171 | 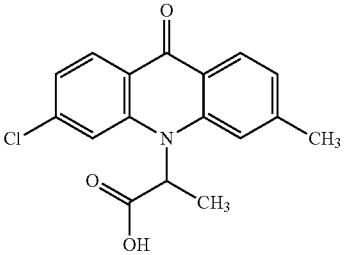 [SMILES: Cc1ccc2c(=O)c3ccc(Cl)cc3n(C(C)C(=O)O)c2c1] |
| 172 | 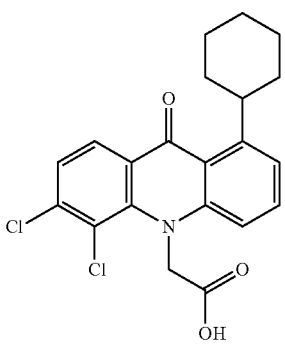 [SMILES: O=C(O)Cn1c2cccc(C3CCCCC3)c2c(=O)c2ccc(Cl)c(Cl)c21] |
| 173 | 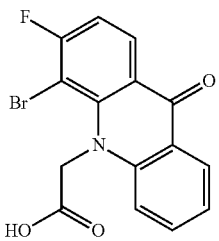 |
| 174 | 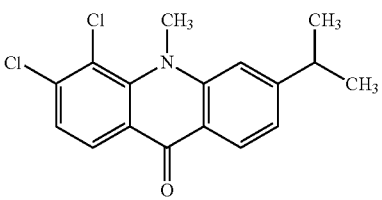 [SMILES: CC(C)c1ccc2c(=O)c3ccc(Cl)c(Cl)c3n(C)c2c1] |
| 175 | 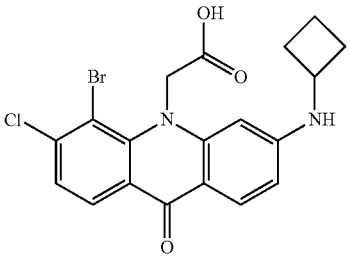 [SMILES: O=C(O)Cn1c2cc(NC3CCC3)ccc2c(=O)c2ccc(Cl)c(Br)c21] |
| 176 | 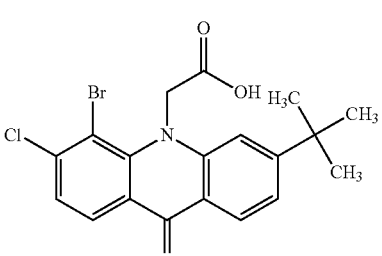 |
| 177 | 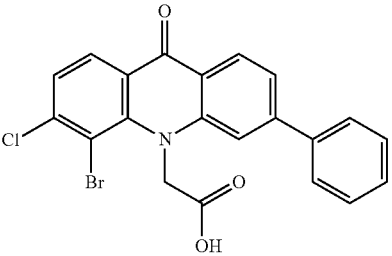 [SMILES: O=C(O)Cn1c2cc(-c3ccccc3)ccc2c(=O)c2ccc(Cl)c(Br)c21] |
| 178 | 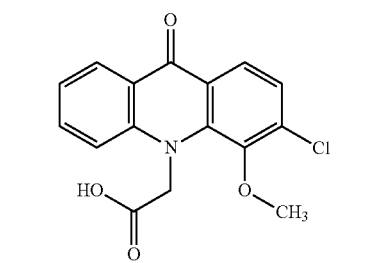 [SMILES: COc1c(Cl)ccc2c(=O)c3ccccc3n(CC(=O)O)c12] |
| 179 | 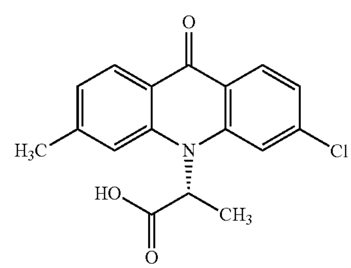 [SMILES: Cc1ccc2c(=O)c3ccc(Cl)cc3n([C@H](C)C(=O)O)c2c1] |
| 180 | 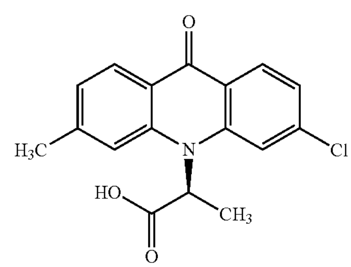 [SMILES: Cc1ccc2c(=O)c3ccc(Cl)cc3n([C@@H](C)C(=O)O)c2c1] |
| 181 | 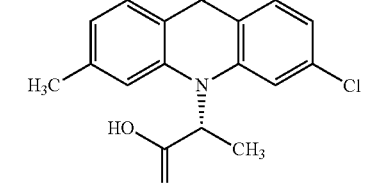 |
| 182 | 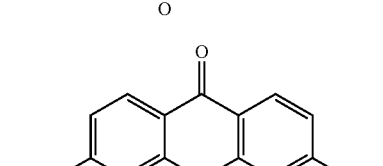 |

TABLE 1-continued

| Cmpd No. | Structure |
|---|---|
| 183 | (structure) |
| 184 | (structure) |
| 185 | (structure) |
| 186 | (structure) |
| 187 | (structure) |
| 188 | (structure) |
| 189 | (structure) |
| 190 | (structure) |
| 191 | (structure) |
| 192 | (structure) |
| 193 | (structure) |
| 194 | (structure) |

TABLE 1-continued
| Cmpd No. | Structure |
|---|---|
| 195 | 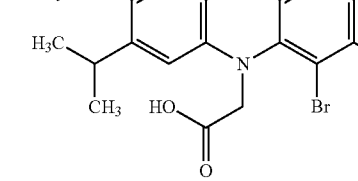 |
| 196 | 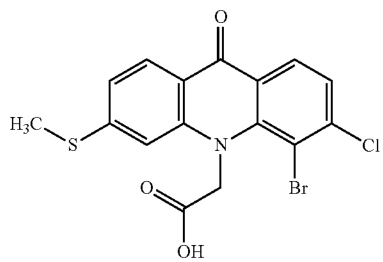 [SMILES: CSc1ccc2c(=O)c3ccc(Cl)c(Br)c3n(CC(=O)O)c2c1] |
| 197 | 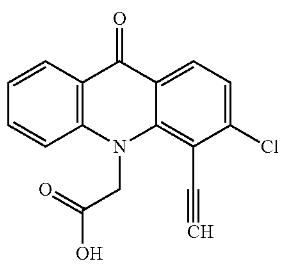 [SMILES: C#Cc1c(Cl)ccc2c(=O)c3ccccc3n(CC(=O)O)c12] |
| 198 | 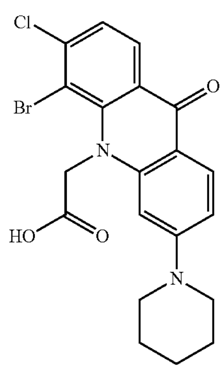 |
| 199 | 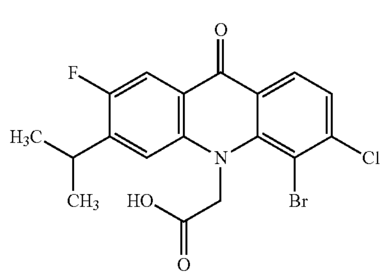 [SMILES: CC(C)c1cc2c(cc1F)c(=O)c1ccc(Cl)c(Br)c1n2CC(=O)O] |
TABLE 1-continued
| Cmpd No. | Structure |
|---|---|
| 200 | 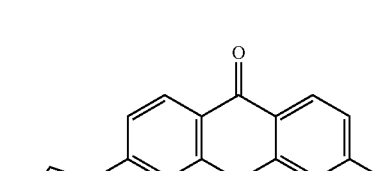 |
| 201 | 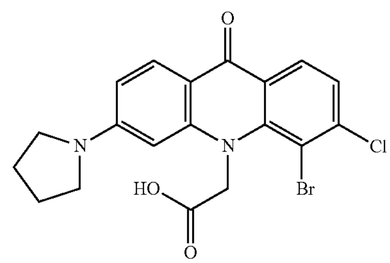 [SMILES: O=C(O)Cn1c2cc(N3CCCC3)ccc2c(=O)c2ccc(Cl)c(Br)c21] |
| 202 | 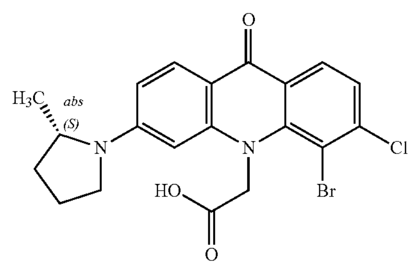 |
| 203 | 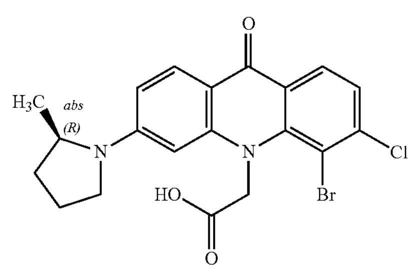 |
| 204 | 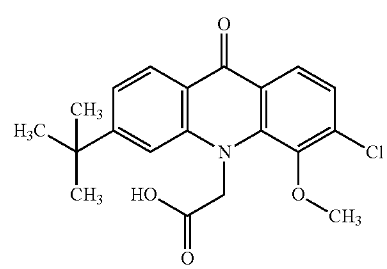 [SMILES: COc1c(Cl)ccc2c(=O)c3ccc(C(C)(C)C)cc3n(CC(=O)O)c12] |

TABLE 1-continued

| Cmpd No. | Structure |
|---|---|
| 205 | (structure) |
| 206 | (structure) |
| 207 | (structure) |
| 208 | (structure) |
| 209 | (structure) |
| 210 | (structure) |
| 211 | (structure) |
| 212 | (structure) |
| 213 | (structure) |
| 214 | (structure) |
| 215 | (structure) |

TABLE 1-continued

| Cmpd No. | Structure |
|---|---|
| 216 | 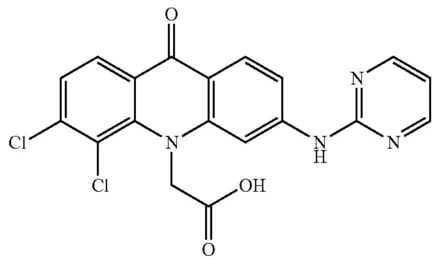 [SMILES: O=C(O)Cn1c2cc(Nc3ncccn3)ccc2c(=O)c2ccc(Cl)c(Cl)c21] |
| 217 | 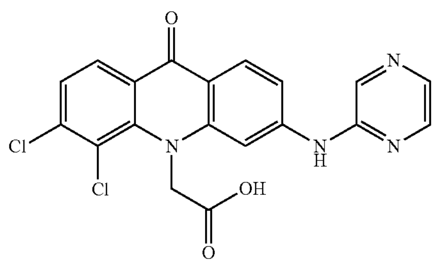 [SMILES: O=C(O)Cn1c2cc(Nc3cnccn3)ccc2c(=O)c2ccc(Cl)c(Cl)c21] |
| 218 | 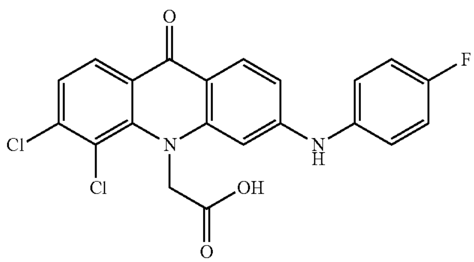 [SMILES: O=C(O)Cn1c2cc(Nc3ccc(F)cc3)ccc2c(=O)c2ccc(Cl)c(Cl)c21] |
| 219 | 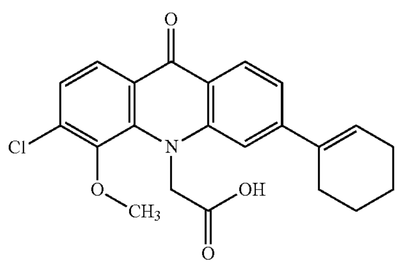 [SMILES: COc1c(Cl)ccc2c(=O)c3ccc(C4=CCCCC4)cc3n(CC(=O)O)c12] |
| 220 | 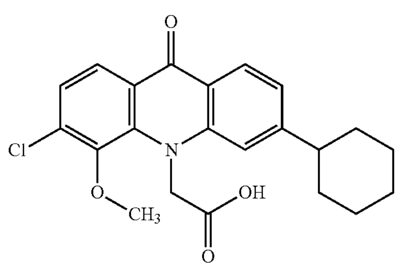 [SMILES: COc1c(Cl)ccc2c(=O)c3ccc(C4CCCCC4)cc3n(CC(=O)O)c12] |
| 221 | 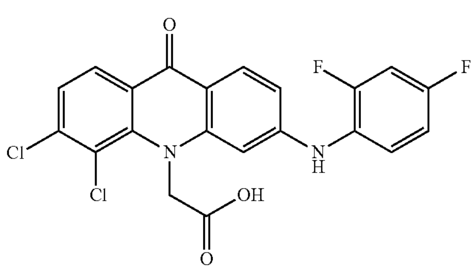 [SMILES: O=C(O)Cn1c2cc(Nc3ccc(F)cc3F)ccc2c(=O)c2ccc(Cl)c(Cl)c21] |
| 222 | 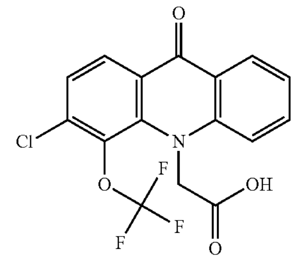 [SMILES: O=C(O)Cn1c2ccccc2c(=O)c2ccc(Cl)c(OC(F)(F)F)c21] |
| 223 | 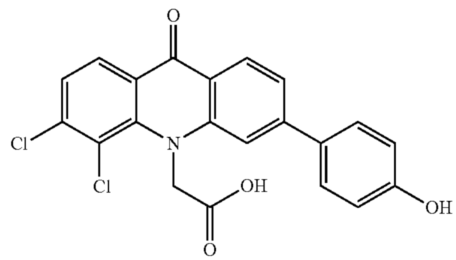 [SMILES: O=C(O)Cn1c2cc(-c3ccc(O)cc3)ccc2c(=O)c2ccc(Cl)c(Cl)c21] |
| 224 | 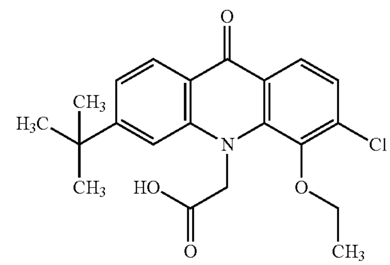 [SMILES: CCOc1c(Cl)ccc2c(=O)c3ccc(C(C)(C)C)cc3n(CC(=O)O)c12] |
| 225 | 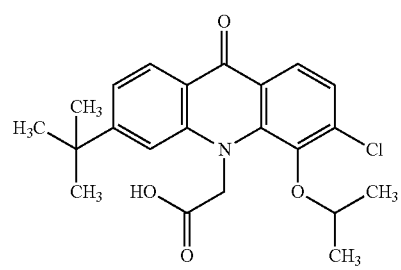 [SMILES: CC(C)Oc1c(Cl)ccc2c(=O)c3ccc(C(C)(C)C)cc3n(CC(=O)O)c12] |
| 226 | 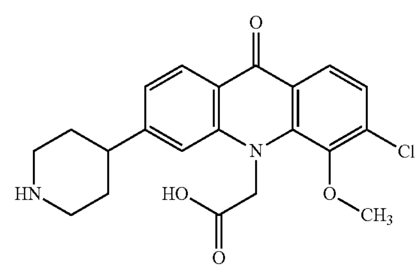 [SMILES: COc1c(Cl)ccc2c(=O)c3ccc(C4CCNCC4)cc3n(CC(=O)O)c12] |
| 227 | 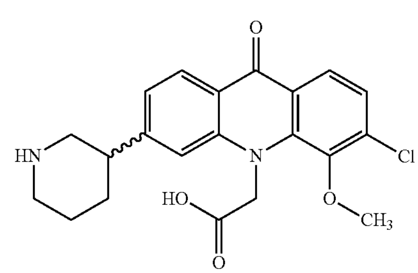 [SMILES: COc1c(Cl)ccc2c(=O)c3ccc(C4CCCNC4)cc3n(CC(=O)O)c12] |

TABLE 1-continued
| Cmpd No. | Structure |
|---|---|
| 228 | 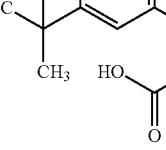 |
| 229 | 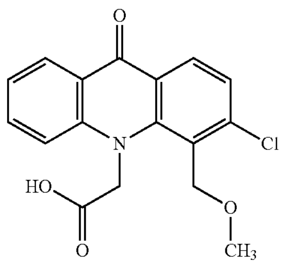 [SMILES: COCc1c(Cl)ccc2c(=O)c3ccccc3n(CC(=O)O)c12] |
| 230 | 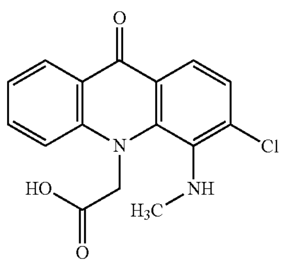 [SMILES: CNc1c(Cl)ccc2c(=O)c3ccccc3n(CC(=O)O)c12] |
| 231 | 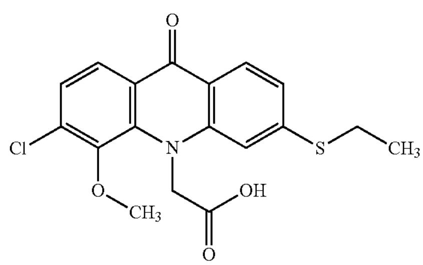 [SMILES: CCSc1ccc2c(=O)c3ccc(Cl)c(OC)c3n(CC(=O)O)c2c1] |
| 232 | 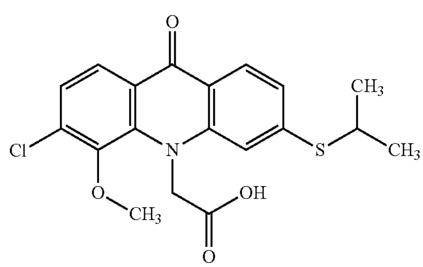 [SMILES: COc1c(Cl)ccc2c(=O)c3ccc(SC(C)C)cc3n(CC(=O)O)c12] |
| 233 | 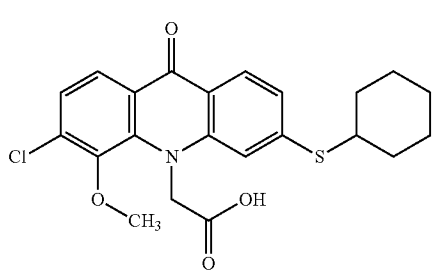 [SMILES: COc1c(Cl)ccc2c(=O)c3ccc(SC4CCCCC4)cc3n(CC(=O)O)c12] |
| 234 | 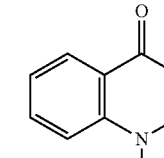 |
| 235 | |
| 236 | |
| 237 | |
| 238 | |
| 239 | |

TABLE 1-continued

| Cmpd No. | Structure |
|---|---|
| 240 | 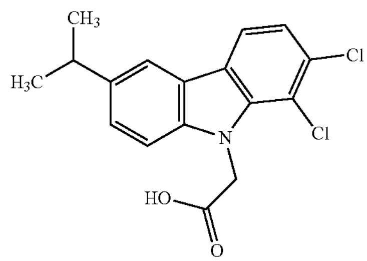 [SMILES: CC(C)c1ccc2c(c1)c1ccc(Cl)c(Cl)c1n2CC(=O)O] |
| 241 | 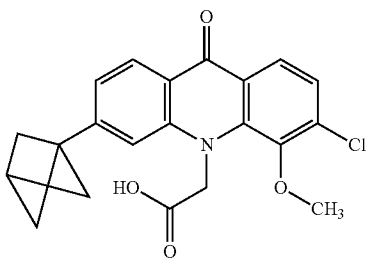 [SMILES: COc1c(Cl)ccc2c(=O)c3ccc(C45CC6CC64C5)cc3n(CC(=O)O)c12] |
| 242 | 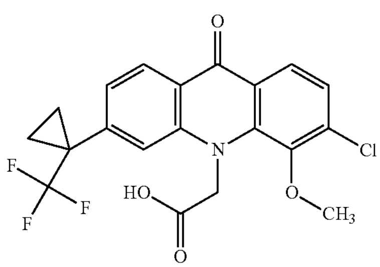 [SMILES: COc1c(Cl)ccc2c(=O)c3ccc(C4(C(F)(F)F)CC4)cc3n(CC(=O)O)c12] |
| 243 | 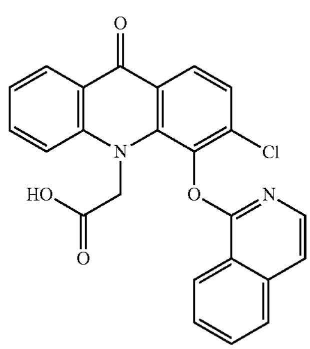 [SMILES: O=C(O)Cn1c2ccccc2c(=O)c2ccc(Cl)c(Oc3nccc4ccccc34)c21] |
| 244 | 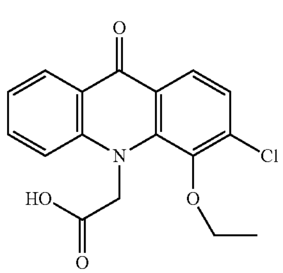 [SMILES: CCOc1c(Cl)ccc2c(=O)c3ccccc3n(CC(=O)O)c12] |
| 245 | 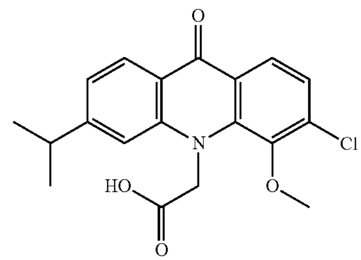 [SMILES: COc1c(Cl)ccc2c(=O)c3ccc(C(C)C)cc3n(CC(=O)O)c12] |
| 246 | 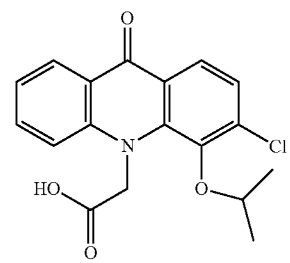 [SMILES: CC(C)Oc1c(Cl)ccc2c(=O)c3ccccc3n(CC(=O)O)c12] |
| 247 | 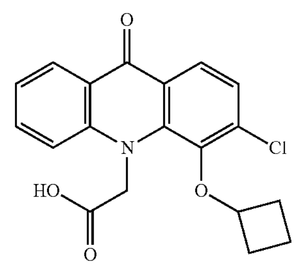 [SMILES: O=C(O)Cn1c2ccccc2c(=O)c2ccc(Cl)c(OC3CCC3)c21] |
| 248 | 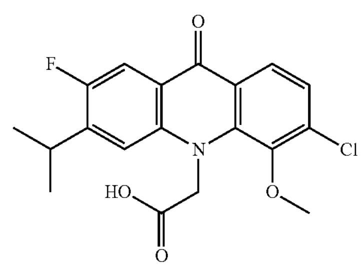 [SMILES: COc1c(Cl)ccc2c(=O)c3cc(F)c(C(C)C)cc3n(CC(=O)O)c12] |
| 249 | 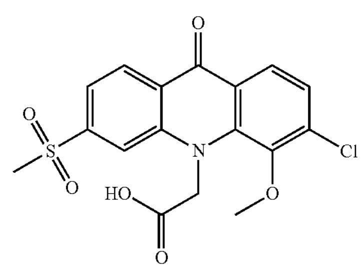 [SMILES: COc1c(Cl)ccc2c(=O)c3ccc(S(C)(=O)=O)cc3n(CC(=O)O)c12] |
| 250 | 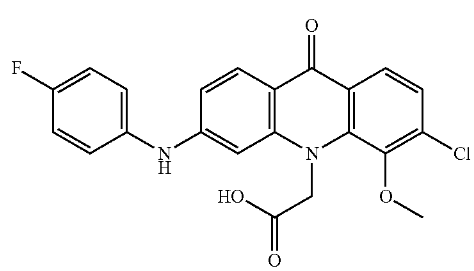 [SMILES: COc1c(Cl)ccc2c(=O)c3ccc(Nc4ccc(F)cc4)cc3n(CC(=O)O)c12] |

TABLE 1-continued

| Cmpd No. | Structure |
|---|---|
| 251 | 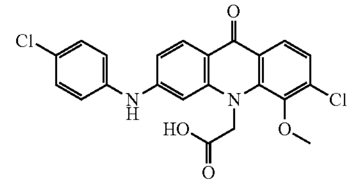 [SMILES: COc1c(Cl)ccc2c(=O)c3ccc(Nc4ccc(Cl)cc4)cc3n(CC(=O)O)c12] |
| 252 | 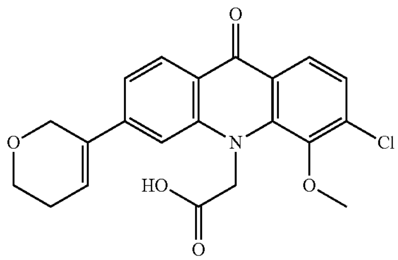 [SMILES: COc1c(Cl)ccc2c(=O)c3ccc(C4=CCCOC4)cc3n(CC(=O)O)c12] |
| 253 | 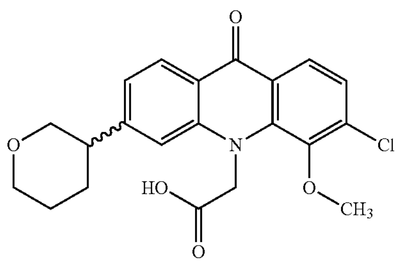 [SMILES: COc1c(Cl)ccc2c(=O)c3ccc(C4CCCOC4)cc3n(CC(=O)O)c12] |
| 254 | 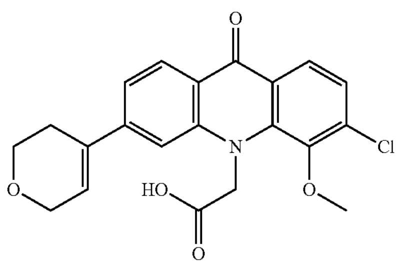 [SMILES: COc1c(Cl)ccc2c(=O)c3ccc(C4=CCOCC4)cc3n(CC(=O)O)c12] |
| 255 | 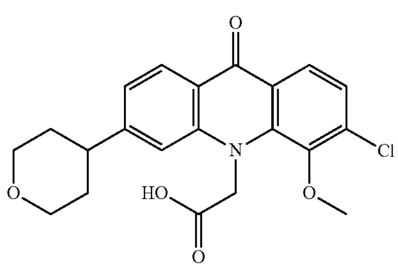 [SMILES: COc1c(Cl)ccc2c(=O)c3ccc(C4CCOCC4)cc3n(CC(=O)O)c12] |
| 256 | 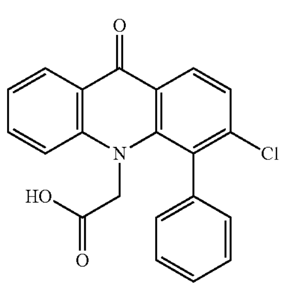 [SMILES: O=C(O)Cn1c2ccccc2c(=O)c2ccc(Cl)c(-c3ccccc3)c21] |
| 257 | 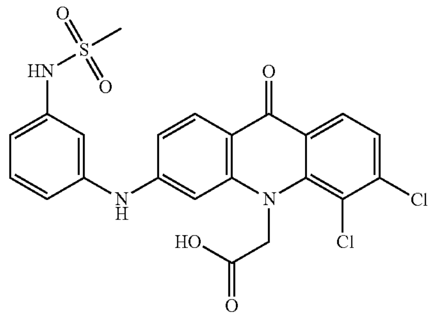 [SMILES: CS(=O)(=O)Nc1cccc(Nc2ccc3c(=O)c4ccc(Cl)c(Cl)c4n(CC(=O)O)c3c2)c1] |
| 258 | 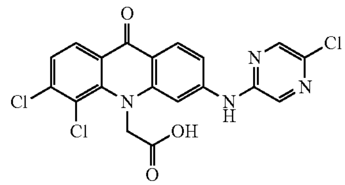 [SMILES: O=C(O)Cn1c2cc(Nc3cnc(Cl)cn3)ccc2c(=O)c2ccc(Cl)c(Cl)c21] |
| 259 | 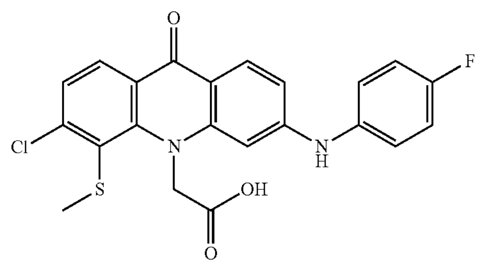 [SMILES: CSc1c(Cl)ccc2c(=O)c3ccc(Nc4ccc(F)cc4)cc3n(CC(=O)O)c12] |
| 260 | 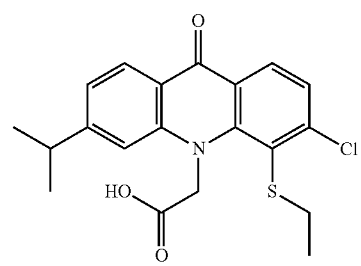 [SMILES: CCSc1c(Cl)ccc2c(=O)c3ccc(C(C)C)cc3n(CC(=O)O)c12] |
| 261 | 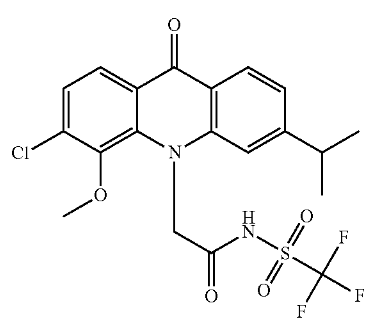 [SMILES: COc1c(Cl)ccc2c(=O)c3ccc(C(C)C)cc3n(CC(=O)NS(=O)(=O)C(F)(F)F)c12] |

TABLE 1-continued

| Cmpd No. | Structure |
|---|---|
| 262 | 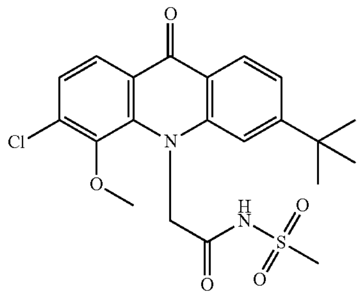 [SMILES: COc1c(Cl)ccc2c(=O)c3ccc(C(C)(C)C)cc3n(CC(=O)NS(C)(=O)=O)c12] |
| 263 | 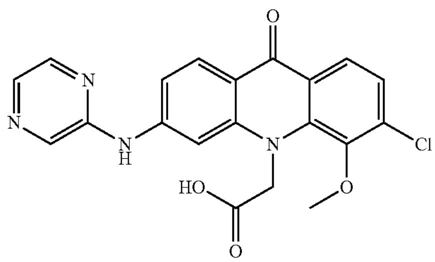 [SMILES: COc1c(Cl)ccc2c(=O)c3ccc(Nc4cnccn4)cc3n(CC(=O)O)c12] |
| 264 | 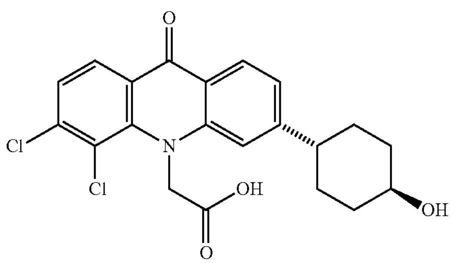 |
| 265 | 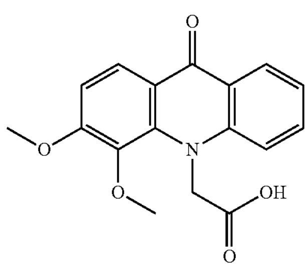 [SMILES: COc1ccc2c(=O)c3ccccc3n(CC(=O)O)c2c1OC] |
| 266 | 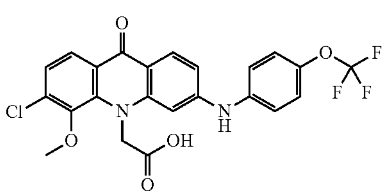 [SMILES: COc1c(Cl)ccc2c(=O)c3ccc(Nc4ccc(OC(F)(F)F)cc4)cc3n(CC(=O)O)c12] |
| 267 | 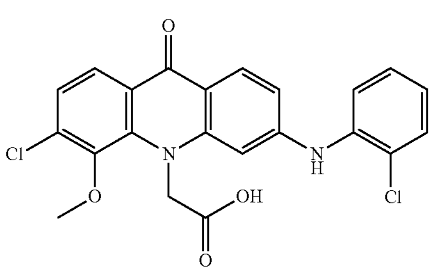 [SMILES: COc1c(Cl)ccc2c(=O)c3ccc(Nc4ccccc4Cl)cc3n(CC(=O)O)c12] |
| 268 | |
| 269 | |
| 270 | |
| 271 | |
| 272 | |

TABLE 1-continued

| Cmpd No. | Structure |
|---|---|
| 273 | (structure) |
| 274 | (structure) |
| 275 | (structure) |
| 276 | (structure) |
| 277 | (structure) |
| 278 | (structure) |
| 279 | (structure) |
| 280 | (structure) |
| 281 | (structure) |
| 282 | (structure) |
| 283 | (structure) |

TABLE 1-continued
| Cmpd No. | Structure |
|---|---|
| 284 | 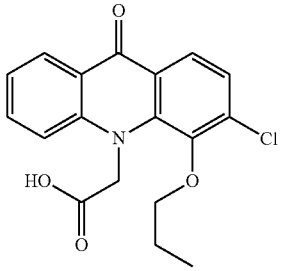 [SMILES: CCCOc1c(Cl)ccc2c(=O)c3ccccc3n(CC(=O)O)c12] |
| 285 | 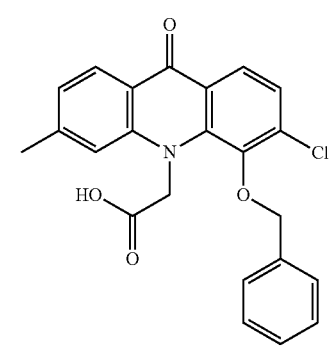 [SMILES: Cc1ccc2c(=O)c3ccc(Cl)c(OCc4ccccc4)c3n(CC(=O)O)c2c1] |
| 286 | 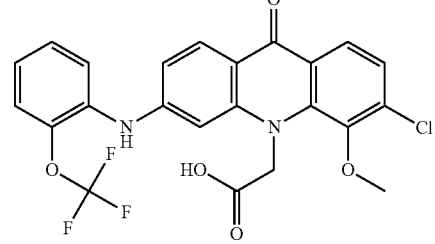 |
| 287 | 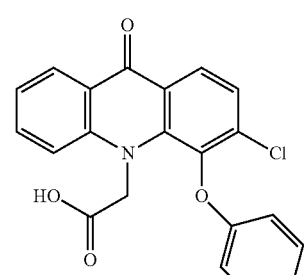 |
| 288 | 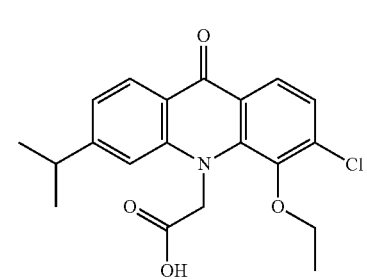 [SMILES: CCOc1c(Cl)ccc2c(=O)c3ccc(C(C)C)cc3n(CC(=O)O)c12] |
| 289 | 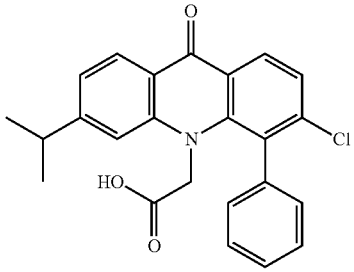 [SMILES: CC(C)c1ccc2c(=O)c3ccc(Cl)c(-c4ccccc4)c3n(CC(=O)O)c2c1] |
| 290 | 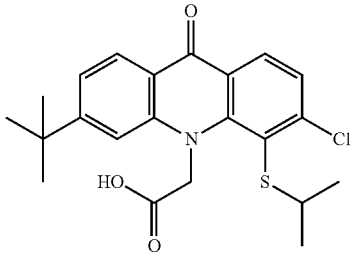 [SMILES: CC(C)Sc1c(Cl)ccc2c(=O)c3ccc(C(C)(C)C)cc3n(CC(=O)O)c12] |
| 291 | 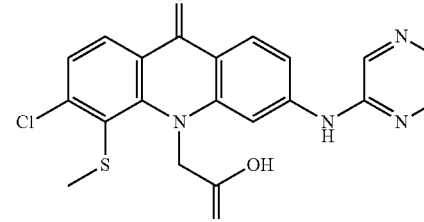 |
| 292 | 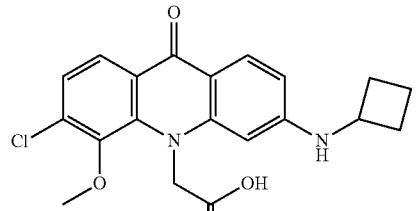 |
| 293 | 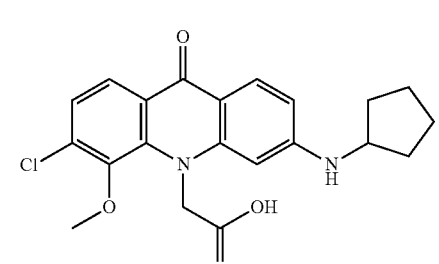 |
| 294 | 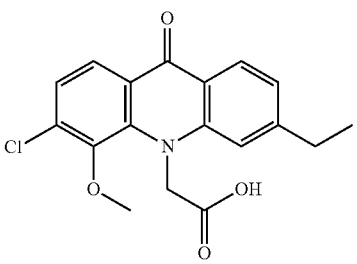 [SMILES: CCc1ccc2c(=O)c3ccc(Cl)c(OC)c3n(CC(=O)O)c2c1] |

TABLE 1-continued

| Cmpd No. | Structure |
| --- | --- |
| 295 | 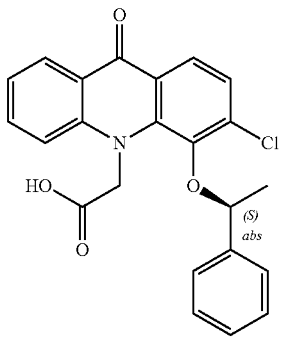 |
| 296 | 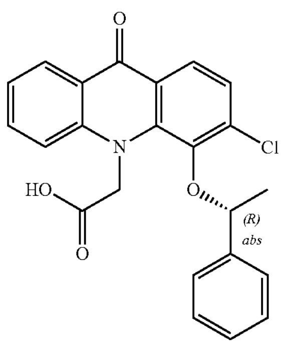 |
| 297 | 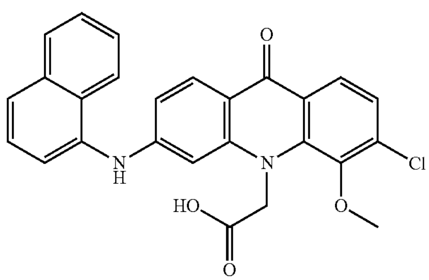 [SMILES: COc1c(Cl)ccc2c(=O)c3ccc(Nc4cccc5ccccc45)cc3n(CC(=O)O)c12] |
| 298 | 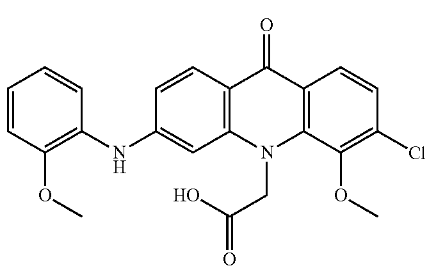 [SMILES: COc1ccccc1Nc1ccc2c(=O)c3ccc(Cl)c(OC)c3n(CC(=O)O)c2c1] |
| 299 | 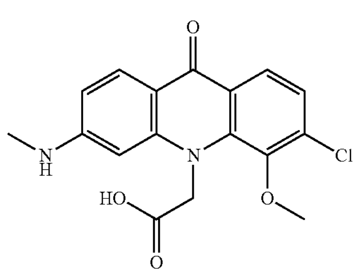 [SMILES: CNc1ccc2c(=O)c3ccc(Cl)c(OC)c3n(CC(=O)O)c2c1] |
| 300 | 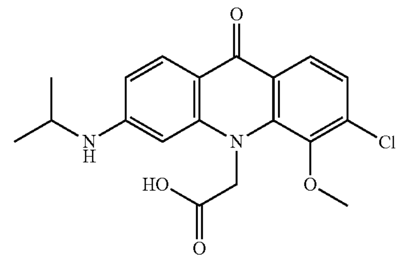 [SMILES: COc1c(Cl)ccc2c(=O)c3ccc(NC(C)C)cc3n(CC(=O)O)c12] |
| 301 | 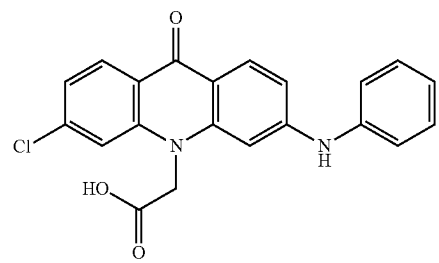 [SMILES: O=C(O)Cn1c2cc(Cl)ccc2c(=O)c2ccc(Nc3ccccc3)cc21] |
| 302 | 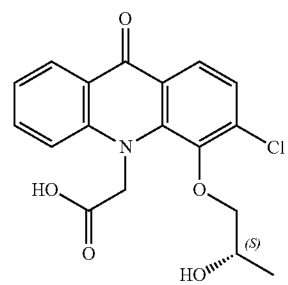 |
| 303 | 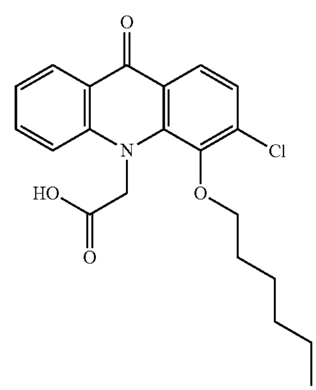 [SMILES: CCCCCCOc1c(Cl)ccc2c(=O)c3ccccc3n(CC(=O)O)c12] |
| 304 | 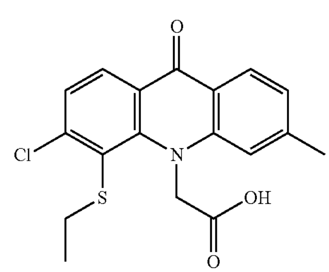 [SMILES: CCSc1c(Cl)ccc2c(=O)c3ccc(C)cc3n(CC(=O)O)c12] |

TABLE 1-continued

| Cmpd No. | Structure |
|---|---|
| 305 | (acridin-9(10H)-one with Cl, CH2-N3 substituents and N-CH2COOH) |
| 306 | (acridin-9(10H)-one with Cl, OEt substituents, ethyl group, and N-CH2COOH) |
| 307 | (acridin-9(10H)-one with Cl, N(Me)(Et) substituents, methyl group, and N-CH2COOH) |
| 308 | (acridin-9(10H)-one with Cl, NMe2 substituents, methyl group, and N-CH2COOH) |
| 309 | (acridin-9(10H)-one with Cl, SMe, Br substituents, and N-CH2COOH) |
| 310 | (acridin-9(10H)-one with Cl, N(Me)(CH2Ph) substituents, and N-CH2COOH) |
| 311 | (acridin-9(10H)-one with methyl, Cl, O-allyl substituents, and N-CH2COOH) |
| 312 | (acridin-9(10H)-one with Cl, O-CH2-C(O)-CH3 substituents, and N-CH2COOH) |
| 313 | (acridin-9(10H)-one with OMe, Cl, OMe substituents, and N-CH2COOH) |
| 314 | (acridin-9(10H)-one with OH, Cl, OMe substituents, and N-CH2COOH) |

TABLE 1-continued

| Cmpd No. | Structure |
|---|---|
| 315 | (structure) |
| 316 | (structure) |
| 317 | (structure) |
| 318 | (structure) |
| 319 | (structure) |
| 320 | (structure) |
| 321 | (structure) |
| 322 | (structure) |
| 323 | (structure) |
| 324 | (structure) |
| 325 | (structure) |

TABLE 1-continued

| Cmpd No. | Structure |
|---|---|
| 326 | (structure) |
| 327 | (structure) |
| 328 | (structure) |
| 329 | (structure) |
| 330 | (structure) |
| 331 | (structure) |
| 332 | (structure) |
| 333 | (structure) |
| 334 | (structure) |
| 335 | (structure) |

TABLE 1-continued

| Cmpd No. | Structure |
|---|---|
| 336 | (structure) |
| 337 | (structure) |
| 338 | (structure) |
| 339 | (structure) |
| 340 | (structure) |
| 341 | (structure) |
| 342 | (structure) |
| 343 | (structure) |
| 344 | (structure) |
| 345 | (structure) |
| 346 | (structure) |
| 347 | (structure) |

TABLE 1-continued

| Cmpd No. | Structure |
|---|---|
| 348 | 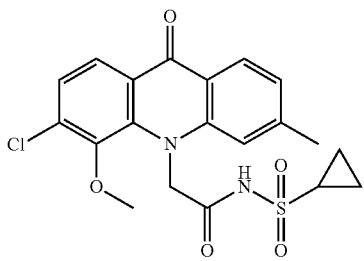 |
| 349 | 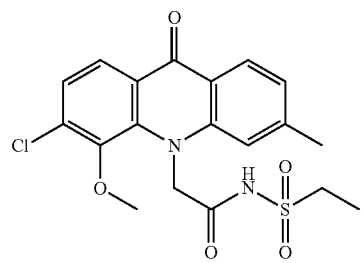 |
| 350 | 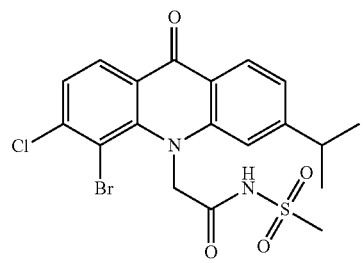 |
| 351 | 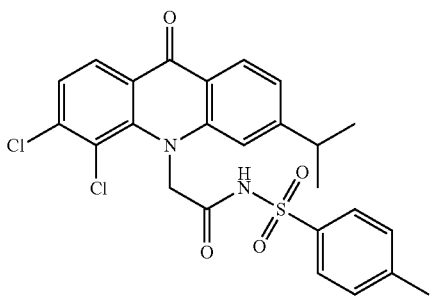 |
| 352 | 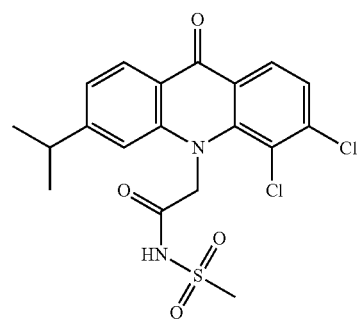 |

TABLE 1-continued

| Cmpd No. | Structure |
|---|---|
| 353 | 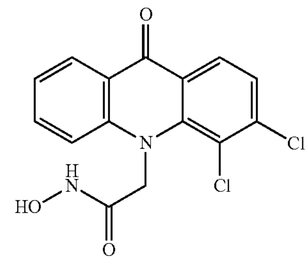 |

Some of the foregoing compounds can comprise one or more asymmetric centers, and thus can exist in various isomeric forms. e.g., stereoisomers and/or diastereomers. Accordingly, compounds of the application may be in the form of an individual enantiomer, diastereomer or geometric isomer, or may be in the form of a mixture of stereoisomers. In one embodiment, the compounds of the application are enantiopure compounds. In another embodiment, mixtures of stereoisomers or diastereomers are provided.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{18}F$, $^{35}S$, $^{32}P$, $^{125}I$, and $^{131}I$) introduced into the compound. Such compounds are useful for drug metabolism studies and diagnostics, as well as therapeutic applications.

Potency can also be determined by $IC_{50}$ value. A compound with a lower $IC_{50}$ value, as determined under substantially similar conditions, is more potent relative to a compound with a higher $IC_{50}$ value. In some embodiments, the substantially similar conditions comprise determining the level of binding of a known STING ligand to a STING protein, in vitro or in vivo, in the presence of a compound of the application.

In one embodiment, the compounds of the present application are useful as therapeutic agents, and thus may be useful in the treatment of a disease caused by, or associated with, STING expression, activity, and/or function (e.g., deregulation of STING expression, activity, and/or function) or a disease associated with one or more of the intracellular pathways that STING is involved in (e.g. regulation of intracellular DNA-mediated type I interferon activation), such as those described herein.

A "selective STING modulator" can be identified, for example, by comparing the ability of a compound to modulate STING expression/activity/function to its ability to modulate the other proteins or a STING protein from another species. In some embodiments, the selectivity can be identified by measuring the EC % or IC, of the compounds. In some embodiments, the compounds of the present application are "selective human STING modulator".

In certain embodiments, the compounds of the application are STING modulators (e.g., selective human STING modulator) that exhibit at least 2-fold, 3-fold, 5-fold, 10-fold, 25-fold, 50-fold or 100-fold selectivity over other proteins or a STING protein from another species (e.g., a non human animal, such as mouse). In various embodiments, the compounds of the application exhibit 1000-fold selectivity over other proteins or a STING protein from another species.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

In another aspect, the application provides a method of synthesizing a compound disclosed herein. The synthesis of the compounds of the application can be found herein and in the Examples below. Other embodiments are a method of making a compound of any of the formulae herein using any one, or combination of, reactions delineated herein. The method can include the use of one or more intermediates or chemical reagents delineated herein.

The application also provides for a pharmaceutical composition comprising a therapeutically effective amount of a compound of the application, or a pharmaceutically acceptable salt or ester thereof, and a pharmaceutically acceptable carrier.

Another aspect of the present application relates to a kit comprising a compound of the application or a pharmaceutically acceptable salt or ester thereof, or a pharmaceutical composition of the application. In another aspect, the application provides a kit comprising a compound capable of modulating STING activity selected from one or more compounds disclosed herein, or a pharmaceutically acceptable salt or ester thereof, optionally in combination with a second agent and instructions for use.

Another aspect of the present application relates to a compound of the application or a pharmaceutically acceptable salt or ester thereof, or a pharmaceutical composition of the application, for use in the manufacture of a medicament for modulating (e.g., inhibiting or stimulating) a STING protein, for treating or preventing a disease, wherein the diseases is caused by, or associated with, STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type 1 interferon activation).

Another aspect of the present application relates to use of a compound of the application or a pharmaceutically acceptable salt or ester thereof, or a pharmaceutical composition of the application, in the manufacture of a medicament for modulating (e.g., inhibiting or stimulating) a STING protein, for treating or preventing a disease, wherein the diseases is caused by, or associated with, STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type I interferon activation).

Another aspect of the present application relates to a compound of the application or a pharmaceutically acceptable salt or ester thereof, or a pharmaceutical composition of the application, for use in modulating (e.g., inhibiting or stimulating) a STING protein, in treating or preventing a disease, wherein the diseases is caused by, or associated with, STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type I interferon activation).

Another aspect of the present application relates to use of a compound of the application or a pharmaceutically acceptable salt or ester thereof, or a pharmaceutical composition of the application, in modulating (e.g., inhibiting or stimulating) a STING protein, in treating or preventing a disease, wherein the diseases is caused by, or associated with, STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type 1 interferon activation).

Method of Synthesizing the Compounds

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; and Greene, T. W., Wuts, P. G. M., *Protective Groups in Organic Synthesis*, $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application. The processes generally provide the desired final compound at or near the end of the overall process, although it may be desirable in certain instances to further convert the compound to a pharmaceutically acceptable salt, ester, or prodrug thereof. Suitable synthetic routes are depicted in the schemes below.

Those skilled in the art will recognize if a stereocenter exists in the compounds disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below.

Compounds of the present application can be synthesized by following the steps outlined in the following Schemes, which comprise different sequences of assembling intermediates. Starting materials are either commercially available or made by known procedures in the reported literature or as illustrated. As shown in the Schemes below, compounds of the present application may be synthesized from transition-metal catalyzed cross coupling reactions with known compounds. The cross-coupling reactions, as illustrated below, can provide the compounds of the present application or intermediates that can be further hydrogenated or deprotected to provide the target compounds.

Schemes 1a-1d

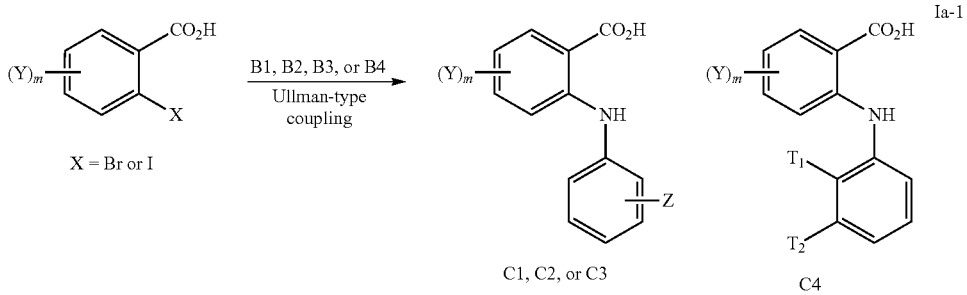

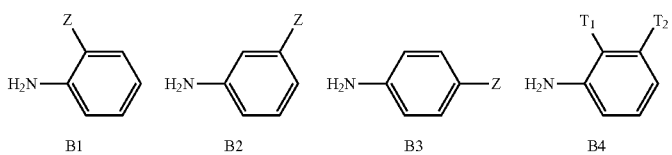

$T_1/T_2$ = H, Halogen, $OR_T$, $SR_T$, $NHR_T$, or $N(R_T)_2$
$R_T$ = a substituent such as alkyl

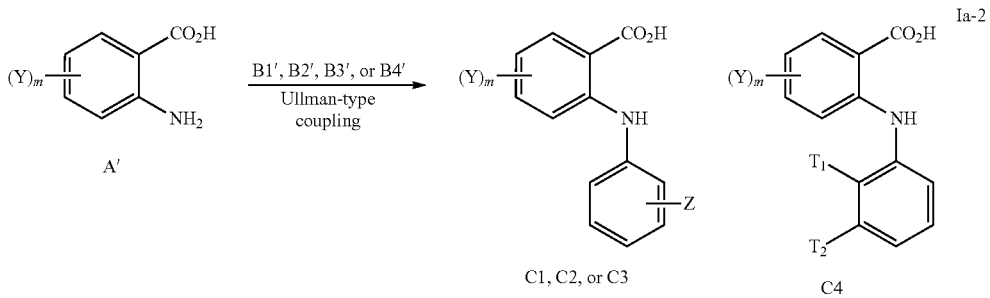

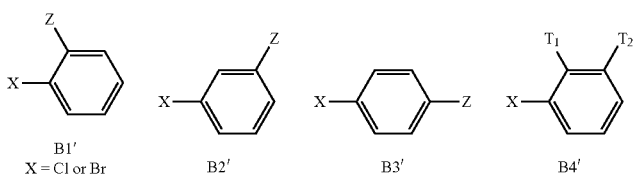

$T_1/T_2$ = H, Halogen, $OR_T$, $SR_T$, $NHR_T$, or $N(R_T)_2$
$R_T$ = a substituent such as alkyl -continued
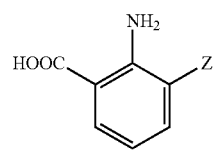
G1
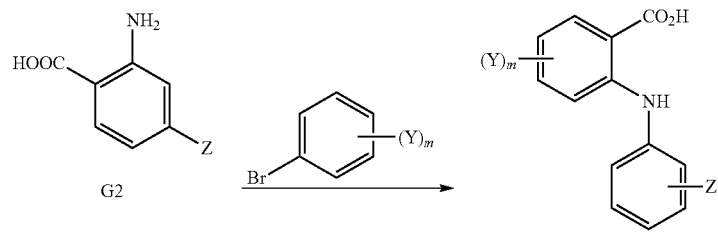
G2
C1, C2, or C3    1a'
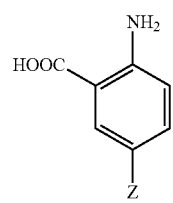
G3
C4
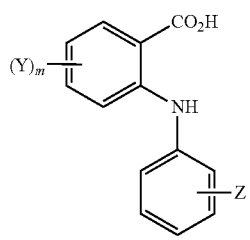
G4
$T_1/T_2$ = H, Halogen, $OR_T$, $SR_T$, $NHR_T$, or $N(R_T)_2$
$R_T$ = a substituent such as alkyl
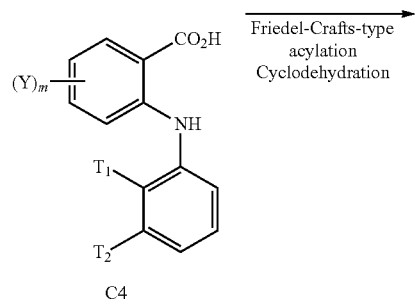
C1, C2, or C3
Friedel-Crafts-type acylation
Cyclodehydration
C4    1b -continued
i) from C1 (Y)$_m$ 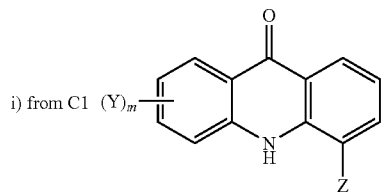
D1
ii) from C2 (Y)$_m$ 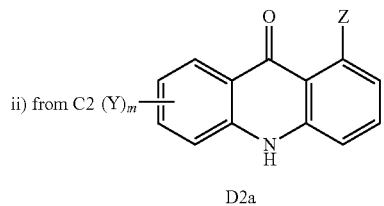 and (Y)$_m$ 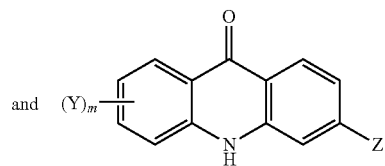
D2a          D2b
iii) from C3 (Y)$_m$ 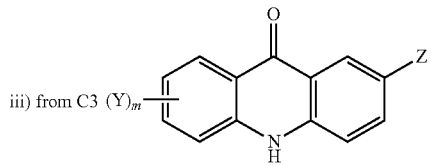
D3
iv) from C4 (Y)$_m$ 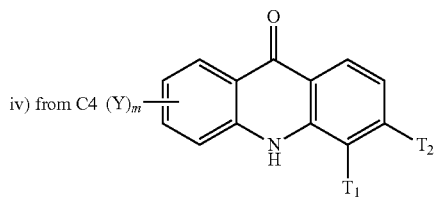
D4
D1, D2a, D2b, D3, or D4 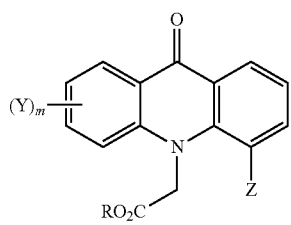 →  N-alkylation; saponification
Ic
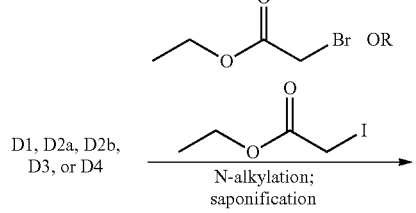
E1
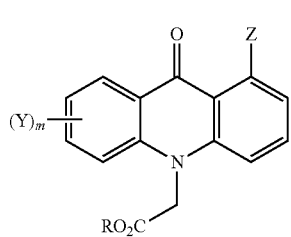 and 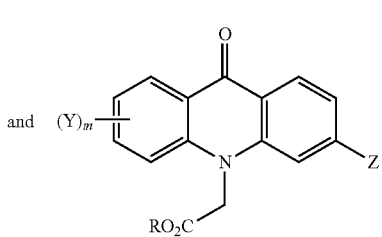
E2a          E2b -continued
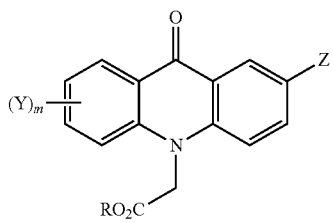
E3
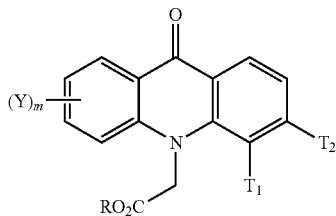
E4
i) R = ethyl
ii) R = H
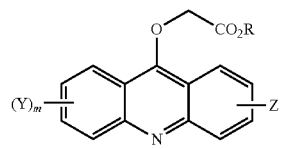
O-alkylation side-products
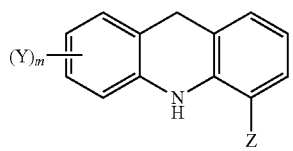
D1'
D1, D2a, D2b, D3, or D4 → 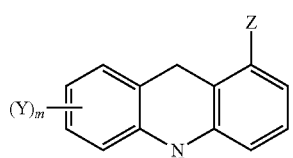 and 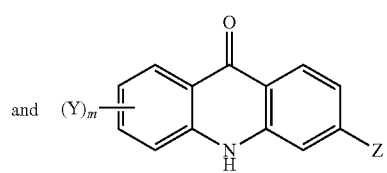 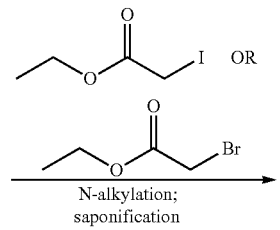
N-alkylation; saponification
D1a'     D2b'
Id
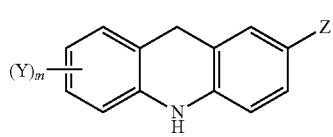
D3'
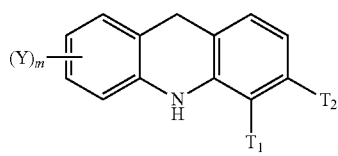
D4c'

-continued

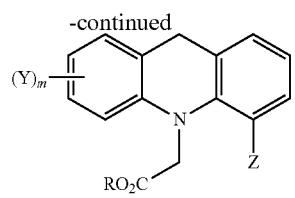

F1

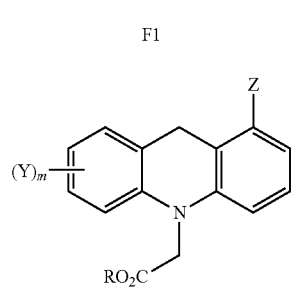

F2a   and   F2b

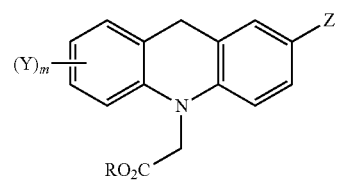

F3

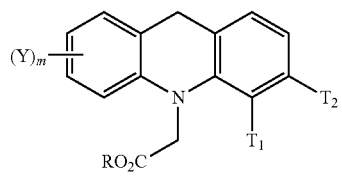

F4 i) R = ethyl
ii) R = H

As shown in Schemes 1a-1d, copper-catalyzed Ullmann-type coupling between the requisite aniline (BI, B2, B3, or B4) and the properly substituted 2-bromobenzoic acid or 2-iodobenzoic acid (A) yields the corresponding diphenylamines (C1, C2, C3, or C4) (1a-1). Alternatively, diphenylamines (C1, C2, C3, or C4) can be prepared according to 1a-2 or 1a'. Cyclodehydration of the diphenylamines (C1, C2, C3, C4) affords substituted 10H-acridin-9-one (D1, D2a, D2b, D3, or D4) (1b). Alkylation of the 10H-acridin-9-one (D1, D2a, D2b, D3, or D4), followed by saponification, generates the target compounds (E1, E2a, E2b, E3, or E4) (1c). Alternatively, hydrogenation of the 10H-acridin-9-one (D1, D2a, D2b, D3, or D4), followed by saponification, generates additional target compounds (F1, F2a, F2b, F3, or F4) (1d).

Scheme 2

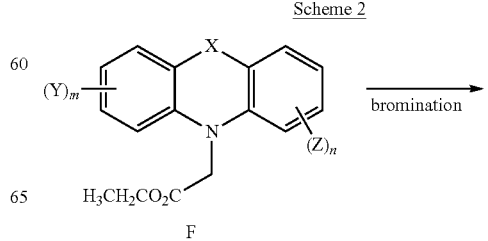

bromination

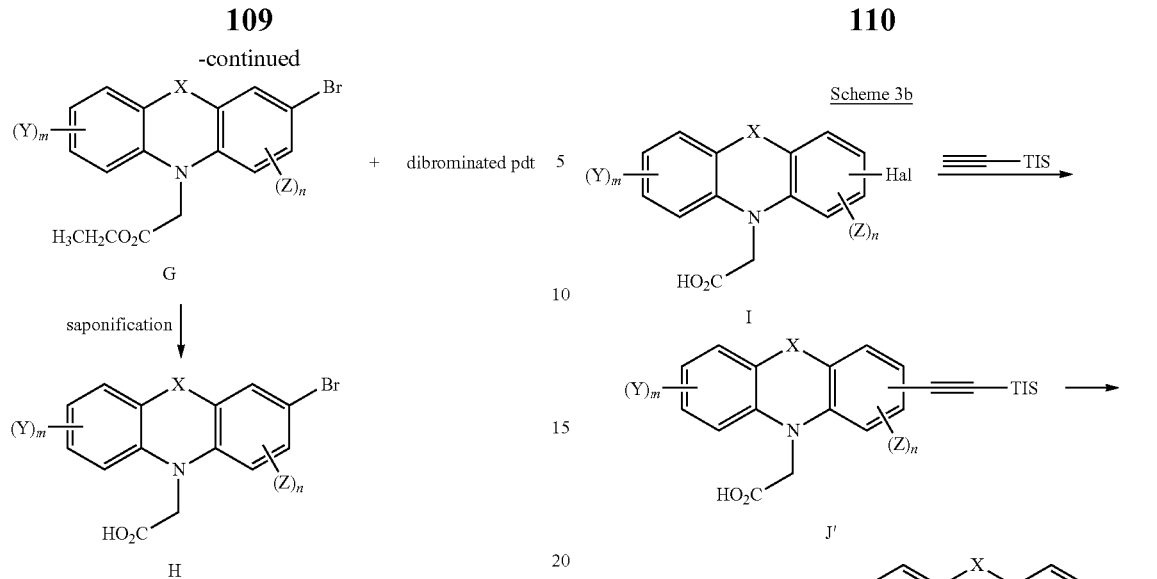

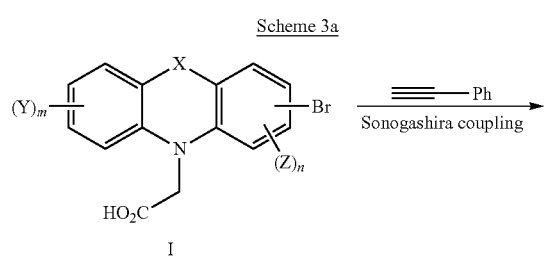

As shown in Scheme 2, compounds of the present application or precursors thereof can be prepared through bromination of compound F, followed by saponification in the Hal = Br or I
TIS = triisopropylsilyl As shown in Schemes 3a and 3b, compounds of the present application can be prepared through Sonogashira coupling, the product of which may be subject to hydrogenation to produce additional compounds of the present application.

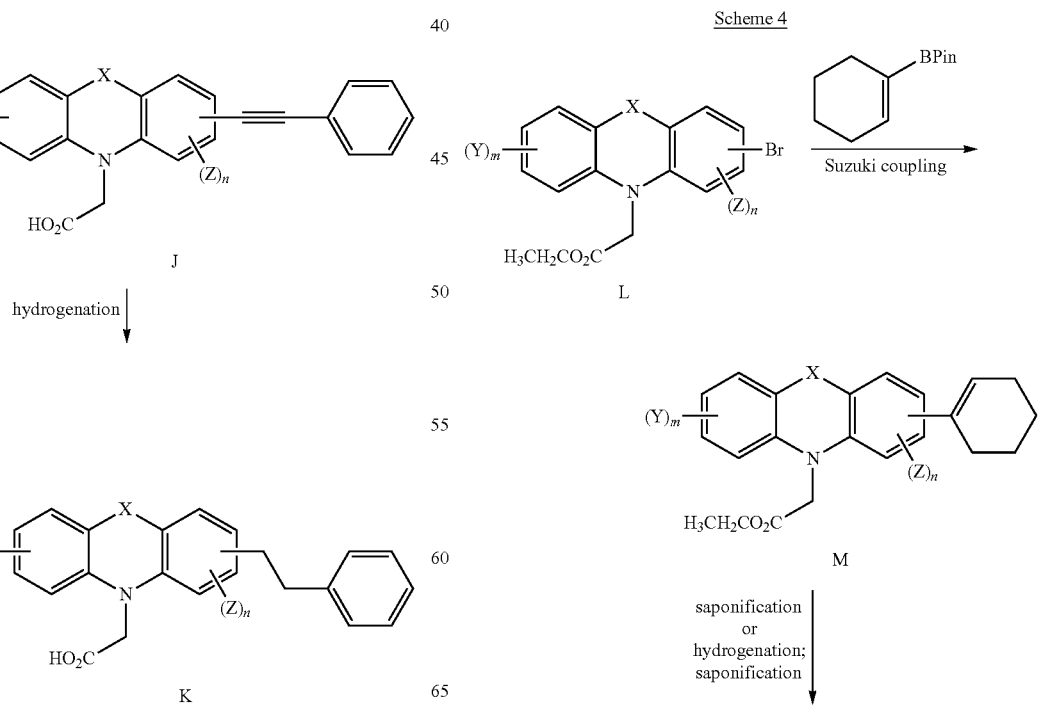

111

-continued

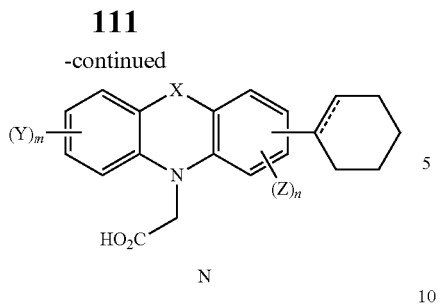

112

-continued

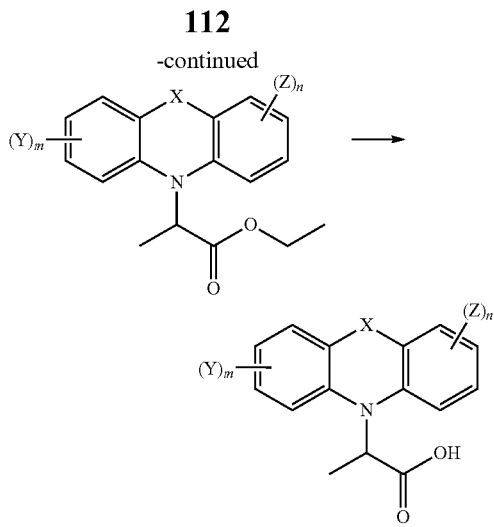

As shown in Scheme 4, compounds of the present application can be prepared through Suzuki coupling, the product of which may be subject to saponification or hydrogenation to produce additional compounds of the present application.

Scheme 5

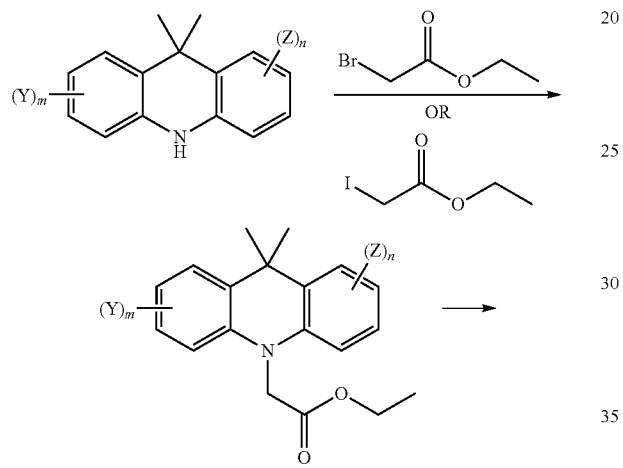

Schemes 7a and 7b

7a

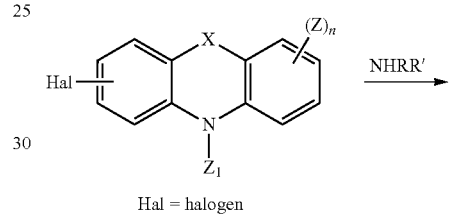

Hal = halogen

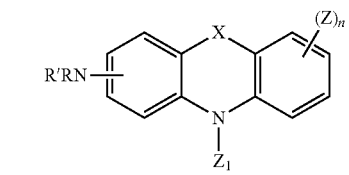

7b

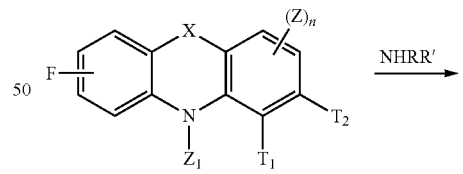

Scheme 6

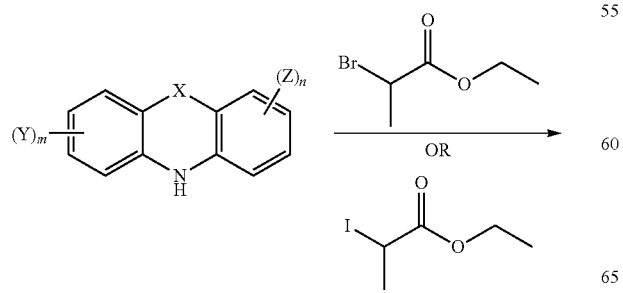

$T_1/T_2$ = H, Halogen, $OR_T$, $SR_T$, $NHR_T$, or $N(R_T)_2$
$R_T$ = a substituent such as alkyl

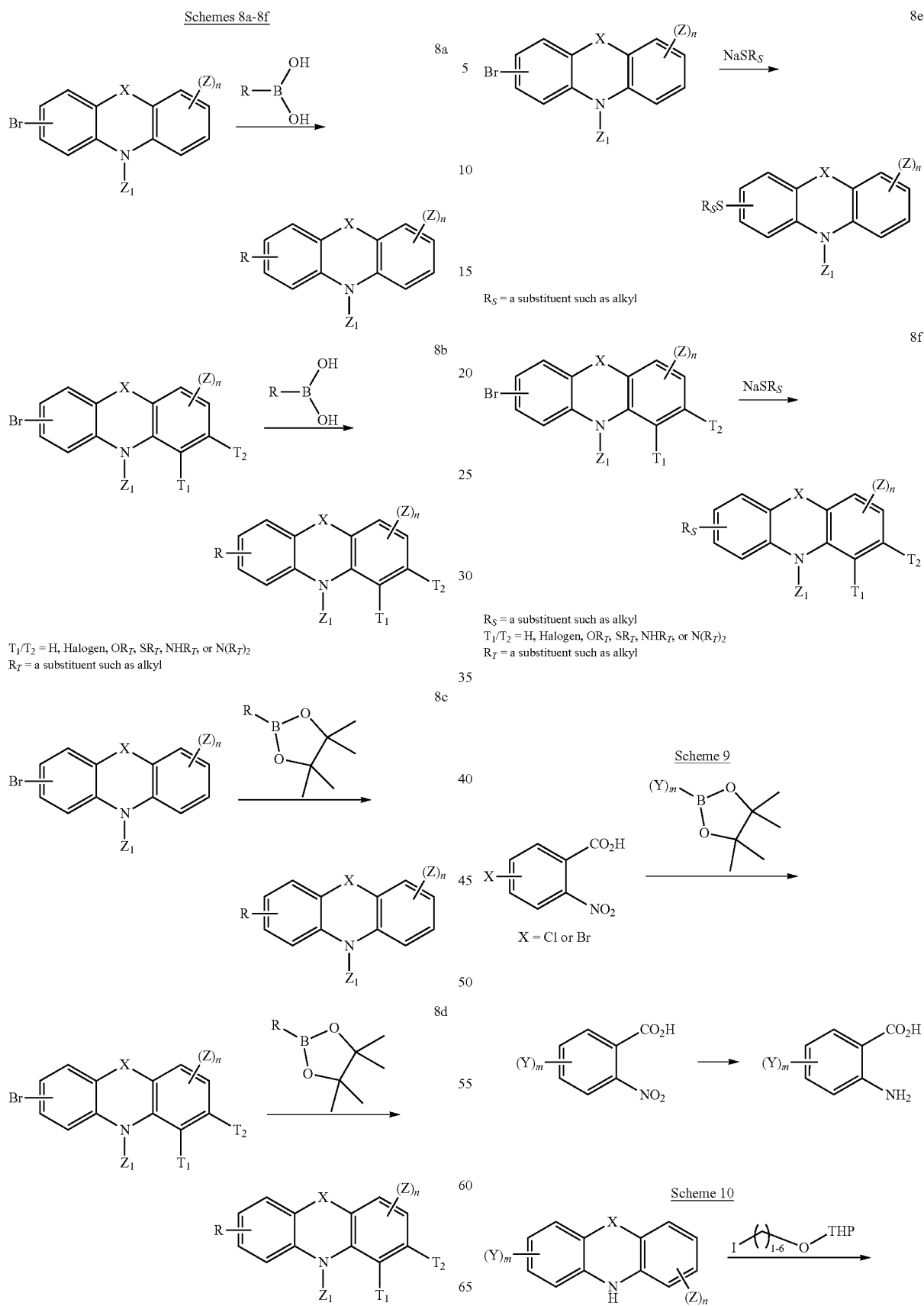

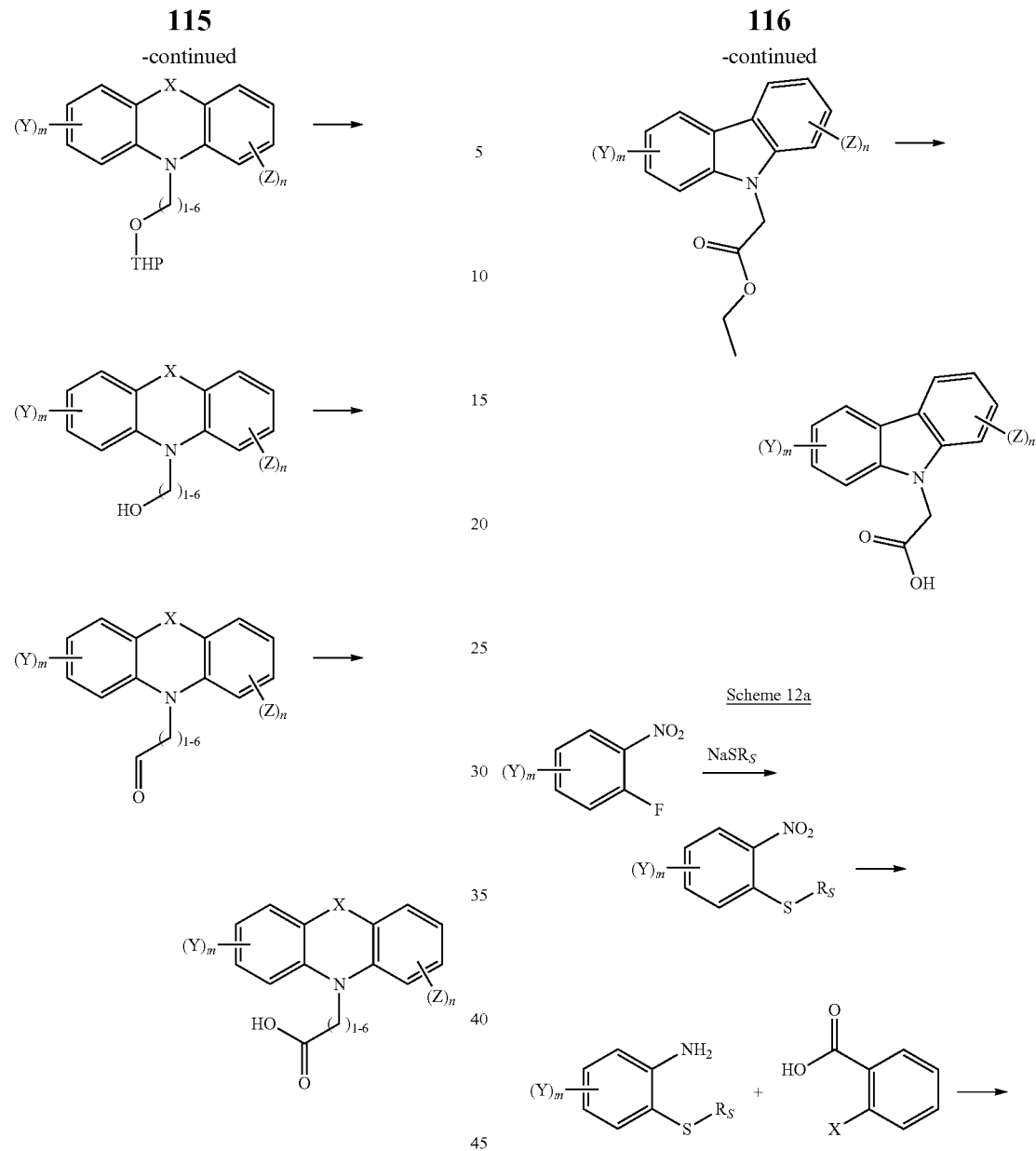
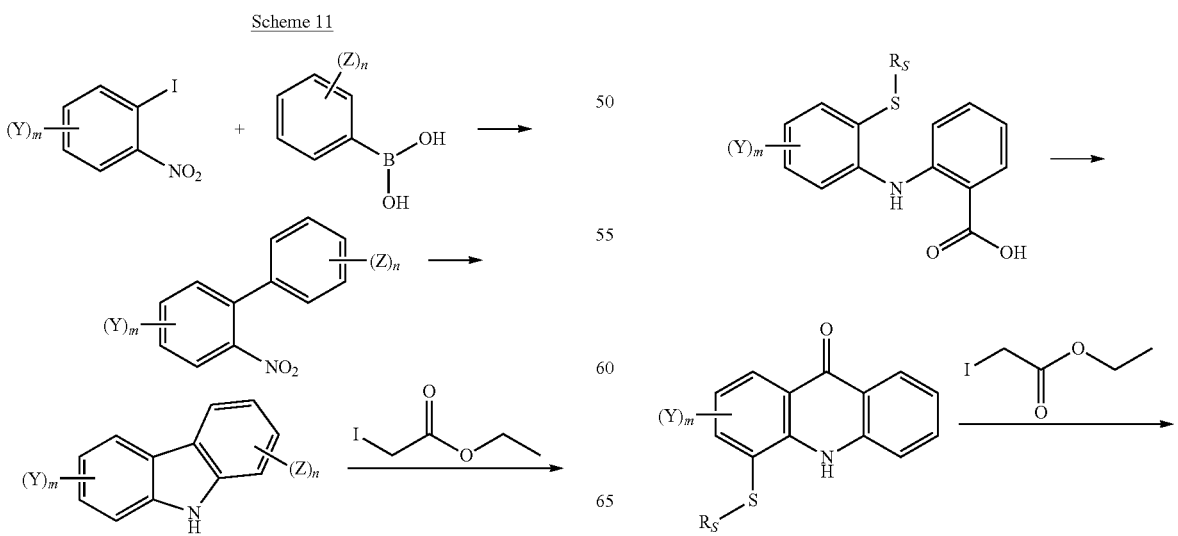

117
-continued
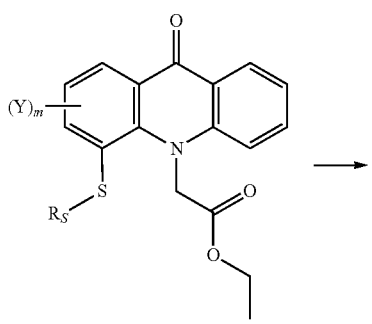
$R_S$ = a substituent such as alkyl
X = Br or I
118
-continued
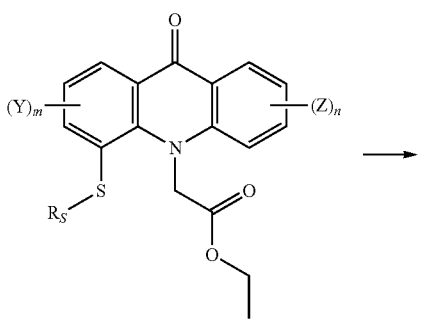
$R_S$ = a substituent such as alkyl
X = Br or I
Scheme 12b
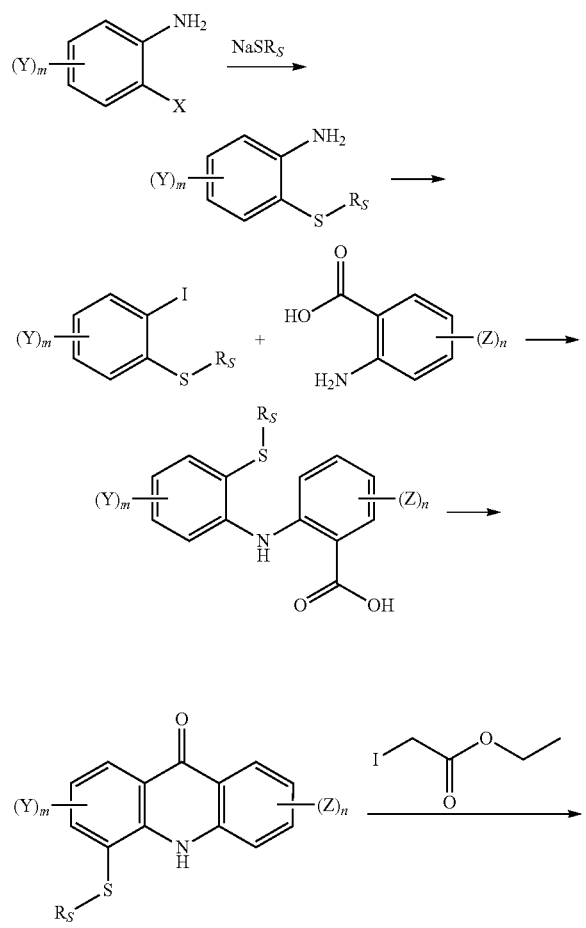
Scheme 13
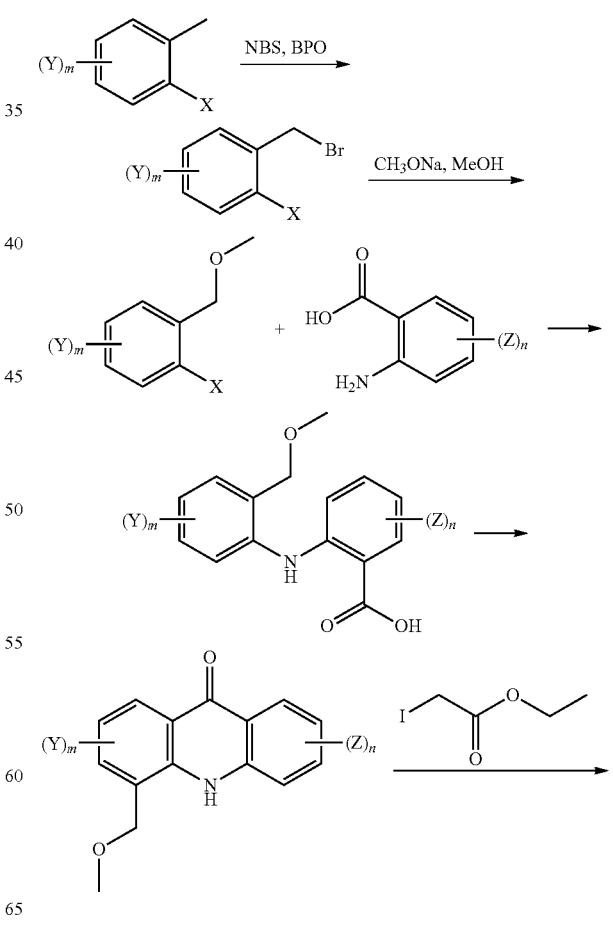

119

-continued

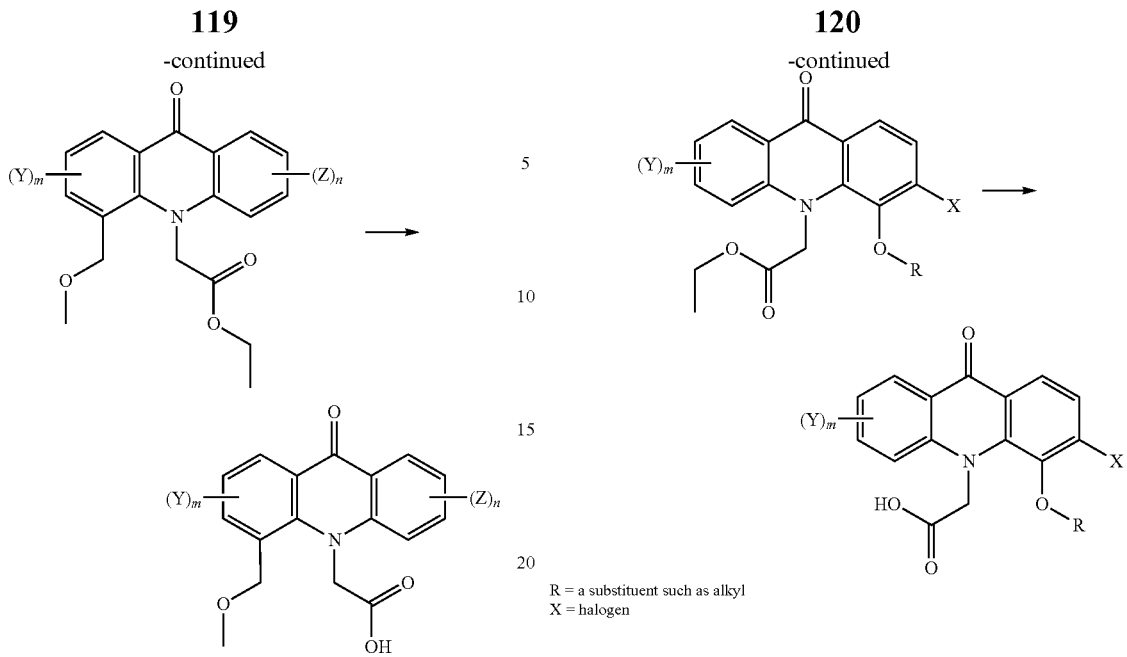

$R_S$ = a substituent such as alkyl
X = Br or I

Scheme 14

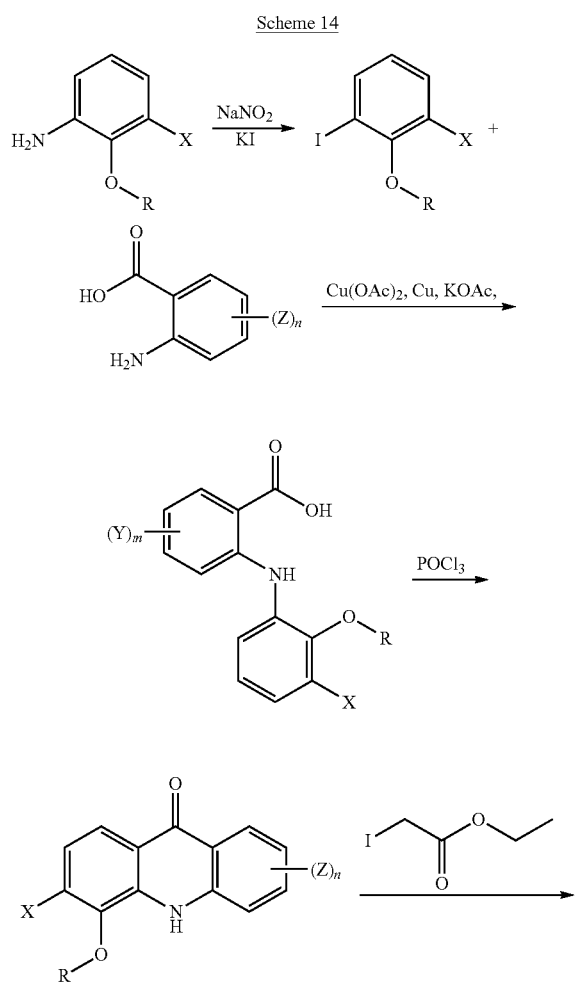

120

-continued

R = a substituent such as alkyl
X = halogen

Additional compounds of the present application can be prepared using the procedures according to Schemes 5-14.

A compound of the application can be prepared as a pharmaceutically acceptable acid addition salt by reacting the free base form of the compound with a pharmaceutically acceptable inorganic or organic acid. Alternatively, a pharmaceutically acceptable base addition salt of a compound of the application can be prepared by reacting the free acid form of the compound with a pharmaceutically acceptable inorganic or organic base. The pharmaceutically acceptable salt may include various counterions, e.g., counterions of the inorganic or organic acid, counterions of the inorganic or organic base, or counterions afforded by counterion exchange.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alternatively, the salt forms of the compounds of the application can be prepared using salts of the starting materials or intermediates. The free acid or free base forms of the compounds of the application can be prepared from the corresponding base addition salt or acid addition salt from, respectively. For example, a compound of the application in an acid addition salt form can be converted to the corresponding free base by treating with a suitable base (e.g., ammonium hydroxide solution, sodium hydroxide, and the like). A compound of the application in a base addition salt form can be converted to the corresponding free acid by treating with a suitable acid (e.g., hydrochloric acid, etc.).

Compounds of the present application that contain nitrogens can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or N⁺—O⁻). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

Prodrugs of the compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the application with a suitable carbamylating agent (e.g., 1,1-acyloxyalkyl-carbanochloridate, para-nitrophenyl carbonate, or the like). Specifically, the central N-acetic acid moeity, and other analogous carboxylic acid groups, of the compounds of the present invention can be modified through techniques known in the art to produce effective prodrugs of the present invention.

Protected derivatives of the compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present application can be conveniently prepared, or formed during the process of the application, as solvates (e.g., hydrates). Hydrates of compounds of the present application can be conveniently prepared by recrystallization from an aqueous/organic solvent mixture, using organic solvents such as dioxin, tetrahydrofuran or methanol.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Biological Assays

Biological activities of the compounds of the present application can be measured by various biochemical or cellular assays known to one of ordinary skill in the art. Non-limiting examples of biochemical and cellular assays are listed herein below.

SWAT Protein FP Competition Dose Response Assay

A validated STING ligand, such as c-di-GMP, which is labeled with a read-out signal (e.g., a fluorescence signal such as fluorescein), is mixed with STING-CTD (e.g., mouse STING-CTD or human STING-CTD) with or without the presence of a compound of the present application. Changes in the read-out signal are measured (e.g., by fluorescence anisotropy) to determine the binding of the compound to STING-CTD.

Pharmaceutical Compositions

In another aspect, a pharmaceutical composition is provided. The pharmaceutical composition comprises a therapeutically effective amount of a compound of the application, or a pharmaceutically acceptable salt or ester thereof, and a pharmaceutically acceptable carrier.

Compounds of the application may be administered as pharmaceutical compositions by any conventional route, in particular enterally. e.g., orally, e.g., in the form of tablets or capsules, or parenterally, e.g., in the form of injectable solutions or suspensions, or topically, e.g., in the form of lotions, gels, ointments or creams, or in a nasal or suppository form.

Pharmaceutical compositions including a compound of the present application in free form or in a pharmaceutically acceptable salt form in association with at least one pharmaceutically acceptable carrier or diluent may be manufactured in a conventional manner by mixing, granulating or coating methods. For example, oral compositions can be tablets or gelatin capsules comprising the active ingredient together with a) diluents. e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier may include absorbable pharmacologically acceptable solvents to assist passage through the skin of the host. For example, transdermal devices may be in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which may serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application may be administered to humans and other animals orally, rectally, parenterally, intracistemally, intravaginally, intraperitoneally, topically (as by powders, ointments, or drops), buccally, or as an oral or nasal spray.

Liquid dosage forms for oral administration may include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds may also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

The pharmaceutical compositions containing active compounds of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Techniques for formulation and administration of the disclosed compounds of the application can be found in Remington: the Science and Practice of Pharmacy, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

Methods of Use

In one aspect, the present application provides a method of modulating (e.g., inhibiting or stimulating) a STING protein. The method comprises administering to a subject in need thereof an effective amount of a compound of the application or a pharmaceutically acceptable salt or ester thereof, or a pharmaceutical composition of the application.

In some embodiments, the modulation of a STING protein activity is measured by $IC_{50}$. In some embodiments, the modulation of a STING protein activity is measured by $EC_{50}$.

A compound of the present application (e.g., a compound of any of the formulae described herein, or selected from any compounds described herein) is capable of treating or preventing a disease, wherein the diseases is caused by, or associated with, STING expression, activity, and/or function (e.g. deregulation of STING expression, activity, and/or function) or a disease associated with deregulation of one or more of the intracellular pathways in which a STING protein is involved (e.g., deregulation of intracellular dsDNA mediated type I interferon activation).

In one aspect, the present application provides a method of treating or preventing a disease, wherein the diseases is caused by, or associated with, STING expression, activity, and/or function (e.g., deregulation of STING expression, activity, and/or function). The method comprises administering to a subject in need thereof an effective amount of a compound of the application or a pharmaceutically acceptable salt or ester thereof, or a pharmaceutical composition of the application. In one aspect, the disease is a STING mediated disorder.

In one aspect, the present application provides a method of treating or preventing a disease associated with deregulation of one or more of the intracellular pathways in which a STING protein is involved (e.g., deregulation of intracellular dsDNA mediated type I interferon activation). The method comprises administering to a subject in need thereof an effective amount of a compound of the application or a pharmaceutically acceptable salt or ester thereof, or a pharmaceutical composition of the application.

In one embodiment, the present application provides a method of treating or preventing any of the diseases, disorders, and conditions described herein, wherein the subject is a human. In one embodiment, the application provides a method of treating. In one embodiment, the application provides a method of preventing.

As modulators of a STING protein, the compounds and compositions of this application are particularly useful for treating or lessening the severity of a disease, condition, or disorder where a STING protein or one or more of the intracellular pathways that STING is involved is implicated in the disease, condition, or disorder. In one embodiment, the present application provides a method for treating or lessening the severity of a disease, condition, or disorder with compounds that modulate binding of a non-canonical cyclic di-nucleotide (CDN), such as 2'3'cGAMP, to a STING protein. In one embodiment, the present application provides a method for treating or lessening the severity of a disease, condition, or disorder with compounds that modulate the synthesis of type I interferon and/or type I IFN response.

In one aspect, the present application also provides a method of treating or preventing cell proliferative disorders such as hyperplasias, dysplasias, or pre-cancerous lesions. Dysplasia is the earliest form of pre-cancerous lesion recognizable in a biopsy by a pathologist. The compounds of the present application may be administered for the purpose of preventing hyperplasias, dysplasias, or pre-cancerous lesions from continuing to expand or from becoming cancerous. Examples of pre-cancerous lesions may occur in skin, esophageal tissue, breast, and cervical intra-epithelial tissue.

In one embodiment, the disease or disorder includes, but is not limited to, immune disorders, autoimmunity, a cell proliferative disease or disorder, cancer, inflammation, cachexia, neurodegenerative disease or disorders, neurological diseases or disorders, cardiac dysfunction, transplantation, or infection (e.g., viral, bacterial, and/or fungi infection, or infection caused by other microorganism).

In one embodiment, the disease or disorder is a cell proliferative disease or disorder.

As used herein, the term "cell proliferative disorder" refers to conditions in which unregulated or abnormal growth, or both, of cells can lead to the development of an unwanted condition or disease, which may or may not be cancerous. Exemplary cell proliferative diseases or disorders encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disease or disorder includes a precancer or a precancerous condition. A cell proliferative disease or disorder includes cancer.

In one embodiment, the proliferative disease or disorder is a non-cancerous. In one embodiment, the non-cancerous disease or disorder includes, but is not limited to, rheumatoid arthritis; inflammation; autoimmune disease; lymphoproliferative conditions; acromegaly; rheumatoid spondylitis; osteoarthritis; gout; other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; skin-related hyperproliferative disorders; psoriasis; eczema; atopic dermatitis; hyperpigmentation disorders; eye-related hyperproliferative disorders; age-related macular degeneration; ulcerative colitis; pancreatic fibrosis; hepatic fibrosis; acute and chronic renal disease irritable bowel syndrome; pyresis; restenosis; cerebral malaria; stroke and ischemic injury; neural trauma; Alzheimer's disease Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; fibroadipose hyperplasia; spinocerebullar ataxia type 1; CLOVES syndrome; Harlequin ichthyosis; macrodactyly syndrome; Proteus syndrome (Wiedemann syndrome); LEOPARD syndrome; systemic sclerosis; Multiple Sclerosis; lupus; fibromyalgia; AIDS and other viral diseases such as Herpes Zoster, Herpes Simplex I or II, influenza virus and cytomegalovirus; diabetes mellitus; hemihyperplasia-multiple lipomatosis syndrome; megalencephaly; rare hypoglycemia, Klippel-Trenaunay syndrome; harmatoma; Cowden syndrome; or overgrowth-hyperglycemia.

In one embodiment, the proliferative disease or disorder is cancer. In one embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

The term "cancer" includes, but is not limited to, the following cancers; breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers; myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" also refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Cancer may also include colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

Cancer may also include colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In one embodiment, the compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

Exemplary cancers may also include, but are not limited to, adrenocortical carcinoma. AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disease or disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Compounds and compositions of the present application may be used to treat a cancer selected from the group consisting of a hematologic cancer or a hematologic cell proliferative disorder. A hematologic cancer can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms, and mast cell neoplasms.

A "cell proliferative disorder of the lung" is a cell proliferative disease or disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Compounds and compositions of the present application may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can also include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. A cell proliferative disorder of the colon includes colon cancer. Compounds and compositions of the present application may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome, and juvenile polyposis.

Cell proliferative disorders of the colon can also include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Compounds and compositions of the present application may be used to treat pancreatic cancer or cell proliferative disorders of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Compounds and compositions of the present application may be used to treat prostate cancer or cell proliferative disorders of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Compounds and compositions of the present application may be used to treat skin cancer or cell proliferative disorders of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Compounds and compositions of the present application may be used to treat ovarian cancer or cell proliferative disorders of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Compounds and compositions of the present application may be used to treat breast cancer or cell proliferative disorders of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

In one embodiment, the disease or disorder includes, but is not limited to, a disease or disorders caused by or associated with Eniamoeba hisiolyttca, *Pneumocystis carmzit, Trygmtsonia cruzi, Trypanosona brucei, Leishmania nexicana, Clostrdiwn hisolyticum, Staphylcoccus aureus*, foot-and-mouth disease virus, or *Crithidia fasciculala*, as well as disease or disorder associated with osteoporosis, autoimmunity, schistosomiasis, malaria, tumor metastasis, metachromatic leukodvstrophy, muscular dystrophy, or amytrophy.

Additional examples of the diseases or disorders include, but are not limited to, diseases or disorders caused by or associated with veterinary and human pathogenic protozoa, intracellular active parasites of the phylum *Apicomplexa* or *Sarcomastigophora, Trypanosoma, Plasmodia, Leishmania, Babesia* and *Theileria, Cryptosporidia, Sacrocystida. Amoeba, Coccidia*, and *Trichomonadia*. For example, the diseases or disorders include, but are not limited to, *Malaria tropica*, caused by, for example, *Plasmodium falciparum; Malaria tertiana*, caused by *Plasmodium vivax* or *Plasmodium ovale, Malaria quartana*, caused by *Plasmodium malariae*; Toxoplasmosis, caused by *Toxoplasma gondii*; Coccidiosis, caused for instance by *Isospora belh*; intestinal Sarcosporidiosis, caused by *Sarcocystic suihominis*; dysentery caused by *Entamoeba histolytica*; Cryptosporidiosis, caused by *Cryptosporidium parvum*; Chagas' disease, caused by *Typinosoma cruzi*; sleeping sickness, caused by *Trypanooma brucei rhodesiense* or *gambiense*, the cutaneous and visceral as well as other forms of Leishmaniosis; diseases or disorders caused by veterinary pathogenic protozoa, such as *Theileria parva*, the pathogen causing bovine East coast fever, *Trypanosoma cungulense cungulense* or *Trypanosoma vivax vivax, Trypanosoma brucei brucei*, pathogens causing Nagana cattle disease in Africa, *Trypanosoma brucei evansi* causing Surra, *Babesia bigemina*, the pathogen causing Texas fever in cattle and buffalos. *Babesia bovis*, the pathogen causing European bovine Babesiosis as well as Babesiosis in dogs, cats and sheep, *Sarcocyvtis uvicanis* and ovifelis pathogens causing Sarcocystiosis in sheep, cattle and pigs, Cryptosporidia, pathogens causing Cryptosporidioses in cattle and birds. *Eimeria* and *Isospora* species, pathogens causing Coccidiosis in rabbits, cattle, sheep, goats, pigs and birds, especially in chickens and turkeys. *Rickettsia* comprise species such as *Rickettsia felis, Rickettsia prowayek, Rickettsia rickettsi, Rickettsia typhi, Rickettsia conorii, Rickettsia africae* and cause diseases such as typhus, rickettsialpox, Boutonneuse fever, African Tick Bite Fever. Rocky Mountain spotted fever, Australian Tick Typhus, Flinders Island Spotted Fever and Queensland Tick Typhus.

In one embodiment, the disease or disorder is caused by, or associated with, one or more bacteria. Examples of the bacteria include, but are not limited to, the Gram positive organisms (e.g., *Staphylocuccus aureus, Staphyloccus epidermidis. Enterococcus faecalis* and *E. faecium, Streptococcus pneunoniae*) and the Gram negative organisms (e.g., *Pseudoinonas aerugnosa, Burkholdia cepacia, Xanhononas maltophila. Escherichia coli, Enterobacter* spp. *Klebsiella pneumoniae* and *Salmonella* spp).

In one embodiment, the disease or disorder is caused by, or associated with, one or more fungi. Examples of the fungi include, but are not limited to, *Candida albicans, Histoplasma neoormnans, Coccidioides immitis*, and *Penicillium marneffei*.

In one embodiment, the disease or disorder is a neurological disease or disorder. In one embodiment, the neurological disease or disorder involves the central nervous system (e.g., brain, brainstem and cerebellum), the peripheral nervous system (e.g., cranial nerves), and/or the autonomic nervous system (e.g., parts of which are located in both central and peripheral nervous system).

Examples of the neurological disorders include, but are not limited to, acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease, alternating hemiplegia; Alzieimer's disease; Vascular dementia; amyotrophic lateral sclerosis; anencephaly; Angelman syndrome; angiomatosis; anoxia; aphasia; apraxia arachnoid cysts; arachnoiditis; Anronl-Chiari malformation; arteriovenous malformation; Asperger syndrome, ataxia telegiectasia attention deficit hyperactivity disorder, autism; autonomic dysfunction, back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury, brain abscess; brain injury, brain tumors (including glioblastoma multiforme); spinal tumor; Brown-Sequard syndrome; Canavan disease, carpal tunnel syndrome; causalgia; central pain syndrome; central pontine myelinolysis; cephalic disorder; cerebral aneurysm; cerebral arteriosclerosis; cerebral atrophy, cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state, congenital facial diplegia; corticobasal degeneration, cranial arteritis; craniosynostosis; Creutzfeldt-Jakob disease; cumulative trauma disorders; Cushing's syndrome; cytomegalic inclusion body disease; cytomegalovirus infection, dancing eyes-dancing feet syndrome; Dandy-Walker syndrome; Dawson disease; De Morsier's syndrome; Dejerine-Klumke palsy; dementia, dermatomyositis; diabetic neuropathy; diffuse sclerosis, dysautonomia; dysgraphia; dyslexia; dystonias; early infantile epileptic encephalopathy; empty sella syndrome; encephalitis encephaloceles; encephalotrigenunal angiomatosis; epilepsy; Erb's palsy, essential tremor; Fabry's disease; Fahr's syndrome, fainting; familial spastic paralysis, febrile seizures, Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; bead injury; headache; hemifacial spasm; hereditary spastic paraplegia; heredopathia atactica polyneuritiformis; herpes zoster oticus, herpes oster, Hirayama syndrome, HIV-associated dementia and neuropathy (also neurological manifestations of AIDS) holoprosencephaly; Huntington's disease and other polyglutamine repeat diseases hydranencephaly; hydrocephalus; hypercortisolism; hypoxia; immune-mediated encephalomyelitis, inclusion body myositis; incontinentia pigmenti; infantile phytanic acid storage disease; infantile refsum disease; infantile spasms; inflammatory myopathy; intracranial cyst intracranial hypertension Joubert syndrome; Kearns-Sayre syndrome; Kennedy disease Kinsboume syndrome; Klippel Feil syndrome; Krabbe disease; Kugelberg-Welander disease, kuru; Lafora disease, Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy, Lewy body dementia; Lissencephaly; locked-in syndrome; Lou Gehrig's disease (i.e., motor neuron disease or amyotrophic lateral sclerosis); lumbar disc disease; Lyme disease-neurological sequelae; Machado-Joseph disease; macrencephaly; megalencephaly; Melkersson-Rosenthal syndrome; Menueres disease; meningitis; Menkes disease; metachromatic leukodystrophy; microcephaly, migraine, Miller Fisher syndrome; mini-strokes; mitochondrial myopathies; Mobius syndrome; monomelic amyotrophy, motor neuron disease; Moamoya disease; mucopolysacchandoses; milti-infarct dementia; multifocal motor neuropathy; multiple sclerosis and other demelinating disorders; multiple system atrophy with postural hypotension; p muscular dystrophy; myasthenia gravis; myelinoclastic diffuse sclerosis, myoclonic encephalopathy of infants myoclonus; myopathy; myotonia congenital; narcolepsy; neurofibromatosis; neuroleptic malignant syndrome; neurological manifestations of AIDS; neurological sequelae of lupus; neuromy otonia, neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease, paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain, persistent vegetative state; pervasive developmental disorders; photic sneeze relex; phytanic acid storage disease, Pick's disease; pinched nerve; pituitary tumors: polymyositis; porencephaly; post-polio syndrome, postherpetic neuralgia postinfectious encephalomyelitis, postural hypotension; Prader-Willi syndrome; primary lateral sclerosis, prion diseases; progressive hemifacial atrophy; progressive multifocal leukoencephalopathy; progressiNe sclerosing poliodystrophy; progressive supranuclear palsy; pseudotumor cerebri; Ramsay-Hlunt syndrome (types I and II); Rasmussen's encephalitis, reflex sympathetic dystrophy syndrome; Refsum disease; repetitive motion disorders; repetitive stress injuries, restless legs syndrome; retrovirus-associated myelopathy; Rett syndrome; Reye's syndrome; Saint Vitus dance; Sandhoff disease Schilder's disease schizencephaly; septo-optic dysplasia, shaken baby syndrome, shingles; Shy-Drager syndrome; Sjagrei's syndrome, sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack, transmissible spongiform encephalopathies; transverse myelitis, traumatic brain injury; tremor; trigeminal neuralgia; tropical spastic paraparesis; tuberous sclerosis; vascular dementia (multi-infarct dementia); vasculitis including temporal arteritis; Von Hippel-Lndau disease; Wallenberg's syndrome; Werdnig-Hoffinan disease, West syndrome; whiplash; Williams syndrome; Wildon's disease, and Zellweger syndrome.

Examples of neurodegenerative diseases may also include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia. Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy. Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy. Steele-Richardson-Olszewski disease, Tabes dorsalis, and Toxic encephalopathy.

In one embodiment, the disease or disorder is an autoimmune disease. Examples of autoimmune diseases include, but are not limited to, rheumatoid arthritis, systemic lupus ervthematosus, inflammatory bowel diseases (IBDs) comprising Crohn disease (CD), and ulcerative colitis (UC) which are chronic inflammator conditions with polygenic susceptibility.

In one embodiment, the disease or disorder is inflammation, arthritis, rheumatoid arthritis, spondyiarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, peripheral neuropathy, or B-Cell Lymphoma.

In one embodiment, the disease or disorder is selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In one embodiment, the disease or disorder is selected from a proliferative disorder and an immune disorder.

As modulators of a STING protein, the compounds and compositions of this application are also useful in assessing, studying, or testing biological samples. One aspect of the application relates to modulating the activity of a STING protein in a biological sample, comprising contacting the biological sample with a compound or a composition of the application.

The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Modulation (e.g., inhibition or stimulation) of protein kinase activity in a biological sample is useful for a variety of purposes that are known to one of skill in the art. Examples of such purposes include, but are not limited to, blood transfusion, organ transplantation, and biological specimen storage.

Another aspect of this application relates to the study of a STING protein in biological and pathological phenomena; the study of intracellular signal transduction pathways mediated by STING protein. Examples of such uses include, but are not limited to, biological assays such as enzyme assays and cell-based assays.

The activity of the compounds and compositions of the present application as STING modulators may be assayed in vitro, in vivo, or in a cell line. In vitro assays include assays that determine modulation (e.g., inhibition or stimulation) of binding of a STING ligand to a STING protein through competitive binding assay. Alternate in vitro assays quantitate the ability of the modulator (e.g., inhibitor or stimulator) to bind to the protein kinase and may be measured either by radio labelling the modulator (e.g., inhibitor or stimulator) prior to binding, isolating the ligand/protein complex and determining the amount of radio label bound. Detailed conditions for assaying a compound utilized in this application as a modulator or a STING protein are set forth in the Examples below.

In accordance with the foregoing, the present application provides a method for preventing or treating any of the diseases or disorders described herein in a subject in need of such treatment, comprising administering to the subject a therapeutically effective amount of a compound of the application or an enantiomer, diastereomer, stereoisomer, or pharmaceutically acceptable salt thereof, or a pharmaceutical composition of the application. For any of the above uses, the required dosage will vary depending on the mode of administration, the particular condition to be treated and the effect desired.

Compounds and compositions of the application can be administered in therapeutically effective amounts in a combinational therapy with one or more therapeutic agents (pharmaceutical combinations) or modalities, e.g., anti-proliferative, anti-cancer, immunomodulatory (e.g., CTLA-4 and PD-1 pathway antagonists and other immunomodulatory agents), anti-inflammatory, and/or anti-viral agent, and/ or non-drug therapies, etc. For example, synergistic effects can occur with anti-proliferative, anti-cancer, immunomodulatory (e.g., CTLA-4 and PD-1 pathway antagonists and other immunomodulatory agents), anti-inflammatory, and/or anti-viral substances. Where the compounds of the application are administered in conjunction with other therapies, dosages of the co-administered compounds will of course vary depending on the type of co-drug employed, on the specific drug employed, on the condition being treated and so forth.

Combination therapy may include the administration of the subject compounds in further combination with one or more other biologically active ingredients (such as, but not limited to, a second STING modulator, a modulator of the cGAS-CDN-STING axis, or a modulator involved in the intracellular dsDNA mediated type-1 interferon activation. Other biologically active ingredients may also include antiproliferative agents, anti-cancer agents (e.g., chemotherapeutic agents), immunomodulatory (e.g., CTLA-4 and PD-1 pathway antagonists and other immunomodulatory agents) agents, antibodies, lipids, liposomes, peptides, etc. For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In one embodiment, the chemotherapeutic agent is an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g. a kinase inhibitor), a cytidine analogue drug, or any chemotherapeutic, anti-neoplastic or anti-proliferative agent listed in www.cancer.org/docroot/cdg/cdg_0.asp.

Alkylating agents are non-phase specific agents and strong electrophiles. Typically, alkylating agents form covalent linkages, by alkylation, to DNA through nucleophilic moieties of the DNA molecule such as phosphate, amino, sulfhydryl, hydroxy, carboxyl, and imidazole groups. Such alkylation disrupts nucleic acid function leading to cell death. Examples of alkylating agents include, but are not limited to, nitrogen mustards such as cyclophosphamide (e.g., CYTOXAN®), melphalan (e.g., ALKERAN®), and chlorambucil (e.g., LEUKERAN®); alkyl sulfonates such as busulfan (e.g., MYLERAN®); nitrosoureas such as carmustine (e.g., BiCNU®); and triazenes such as dacarbazine (e.g., DTIC-Dome®).

Exemplary alkylating agents also include, but are not limited to, busulfan (Busulfex), lomustine (CeeNU), oxaliplatin (Eloxatin), carmustine (Gliadel), ifosfamide (Ifex), mechlorethamine (Mustargen), busulfan (Myleran), carboplatin (PARAPLATIN®), cisplatin (CDDP, PLATINOL®), temozolomide (Temodar), thiotepa (Thioplex), bendamustine (Treanda), streptozocin (Zanosar), 5-azacytidine (e.g., VIDAZA), decitabine (e.g., DECOGEN), temozolomide (e.g., TEMODAR and TEMODAL), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (e.g., BCNU), bendamustine (e.g., TREANDA), carboplatin (e.g., PARAPLATIN®), lomustine (also known as CCNU, sold under the tradename CEENU®), cisplatin (also known as CDDP, sold under the tradenames PLATINOL® and PLATINOL®-AQ), cyclophosphamide (sold under the tradenames CYTOXAN® and NEOSARI®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (e.g., IFEX®), procarbazine (e.g., MATULANE®), mechlorethamine (also known as nitrogen mustard, mustine and mechloroethamine hydrochloride, sold under the tradename MUSTARGEN®), streptozocin (e.g., ZANOSAR®), and thiotepa (also known as thiophosphoamide, TESPA and TSPA, and sold under the tradename THIOPLEX®).

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin (e.g., COSMEGEN®), anthracyclines such as daunorubicin (e.g., as a liposomal injectable form as DAUNOXOME® or as an injectable as CERUBIDINE®) and doxorubicin (e.g., RUBEX® or ADRIAMYCIN RDF®)), and bleomycins (e.g., BLENOXANE®).

Exemplary antibiotics also include, but are not limited to, doxorubicin (Adriamycin), doxorubicin liposomal (Doxil), mitoxantrone (Novantrone), bleomycin (Blenoxane), daunorubicin (Cerubidine), daunorubicin liposomal (DaunoXome), dactinomycin (Cosmegen), epirubicin (Ellence), idarubicin (Idamycin), plicamycin (Mithracin), mitomycin (Mutamycin), pentostatin (Nipent), valrubicin (Valstar), doxorubicin (e.g., ADRIAMYCIN® and RUBEX®), bleomycin (e.g., LENOXANE®), daunorubicin (also known as daurubicin hydrochloride, daunomycin, and rubidomycin hydrochloride, sold under the tradename CERUBIDINE®), daunorubicin liposomal (daunorubicin citrate liposome, sold under the tradename DAUNOXOME), mitoxantrone (also known as DHAD, sold under the tradename NOVANTRONE®), epirubicin (e.g., ELLENCE™), idarubicin (e.g., IDAMYCIN®, IDAMYCIN PFS®), and mitomycin C (e.g., MUTAMYCIN®).

Anti-metabolite anti-neoplastic agents are phase specific agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil and analogs thereof (e.g., 5-fluoro deoxyuridine (floxuridine), 5-fluorodeoxyuridine monophosphate methotrexate), cytarabine (commonly known as Ara-C, available as CYTOSAR-U®) and analogs thereof (e.g., azacytidine, 2',2'-difluorodeoxycytidine (gemcitabine)), mercaptopurine (e.g., PURINETHOL®) and analogs thereof (e.g., azathioprine), thioguanine (e.g., TABLOID®) and analogs thereof (e.g., pentostatin, erythrohydroxy-nonyladenine (EHNA), fludarabine phosphate, and cladribine), gemcitabine (e.g., GEMZAR®), and methotrexate.

Exemplary anti-metabolites also include, but are not limited to, fluorouracil (Adrucil) capecitabine (Xeloda), hydroxyurea (Hydrea), mercaptopurine (Purinethol), pemetrexed (Alimta), fludarabine (Fludara), nelarabine (Arranon), cladribine (Cladribine Novaplus), clofarabine (Clolar), cytarabine (Cytosar-U), decitabine (Dacogen), cytarabine liposomal (DepoCyt), hydroxyurea (Droxia), pralatrexate (Folotyn), floxuridine (FUDR), gemcitabine (Genvar), cladribine (Leustatin), fludarabine (Oforta), methotrexate (MTX, Rheumatrex), methotrexate (Trexall), thioguanine (Tabloid), TS-1 or cytarabine (Tarabine PFS), claribine (2-chlorodeoxyadenosine, sold under the tradename LEUSTATIN®), 5-fluorouracil (sold under the tradename ADRUCIL®), 6-thioguanine (sold under the tradename PURINETHOL®), pemetrexed (sold under the tradename ALIMTA®), cytarabine (also known as arabinosylcytosine (Ara-C), sold under the tradename CYTOSAR-U®), cytarabine liposomal (also known as Liposomal Ara-C, sold under the tradename DEPOCYT™), decitabine (sold under the tradename DACOGEN®), hydroxyurea and (sold under the tradenames HYDREA®, DROXIA™ and MYLOCEL™), fludarabine (sold under the tradename FLUDARA®), floxuridine (sold under the tradename FUDR-k), cladribine (also known as 2-chlorodeoxyadenosine (2-CdA) sold under the tradename LEUSTATIN™), methotrexate (also known as amethopterin, methotrexate sodium (MTX), sold under the tradenames RHEUMATREX® and TREXALL™), and pentostatin (sold under the tradename NIPENT®).

Exemplary detoxifying agents include, but are not limited to, amifostine (Ethyol), and mesna (Mesnex).

Exemplary interferons include, but are not limited to, interferon alfa-2b (Intron A), and interferon alfa-2a (Roferon-A).

Exemplary polyclonal or monoclonal antibodies include, but are not limited to, trastuzumab (Herceptin), ofatumumab (Arzerra), bevacizumab (Avastin), rituximab (Rituxan), cetuximab (Erbitux), panitumumab (Vectibix), tositumomab/iodine[131] tositumomab (Bexxar), alemtuzumab (Campath), ibritumomab (Zevalin, In-111, Y-90 Zevalin), gemtuzumab (Mylotarg), eculizumab (Soliris), and ordenosumab.

Exemplary EGFR inhibitors include, but are not limited to, gefitinib (Iressa), lapatinib (Tykerb), cetuximab (Erbitux), erlotinib (Tarceva), panitumumab (Vectibix). PKI-166, canertinib (CI-1033), matuzumab (Emd7200), and EKB-569.

Exemplary HER2 inhibitors include, but are not limited to, trastuzumab (Herceptin); lapatinib (Tykerb), and AC-480.

Exemplary histone deacetylase Inhibitors include, but are not limited to, vorinostat (Zolinza).

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone; aminoglutethimide and other aromatase inhibitors such as anastrozole, letrozole, vorozole, and exemestane; progestins such as megestrol acetate; estrogens, and anti-estrogens such as fulvestrant, flutamide, nilutamide, bicalutamide, cyproterone acetate and 5-reductases such as finasteride and dutasteride; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716; and gonadotropin-releasing hormone (GnRH) and analogues thereof; and LHRH agonists and antagonists such as goserelin acetate and luprolide.

Exemplary hormones also include, but are not limited to, tamoxifen (Soltamox, Nolvadex), raloxifene (Evista), megestrol (Megace), leuprolide (Lupron, Lupron Depot, Eligard, Viadur), fulvestrant (Faslodex), letrozole (Femara), triptorelin (Trelstar LA, Trelstar Depot), exemestane (Aromasin), goserelin (Zoladex), bicalutamide (Casodex), anastrozole (Arimidex), fluoxymesterone (Androxy. Halotestin), medroxyprogesterone (Provera, Depo-Provera), estramustine (Emcyt), flutamide (Eulexin), toremifene (Fareston), degarelix (Firmagon), nilutamide (Nilandron), abarelix (Plenaxis), or testolactone (Teslac).

Anti-microtubule or anti-mitotic agents or mitotic inhibitors are phase specific agents active against the microtubules of tumor cells during M or the mitosis phase of the cell cycle. Examples of anti-microtubule agents include, but are not limited to, diterpenoids and vinca alkaloids. Examples of diterpenoids include, but are not limited to, paclitaxel (e.g., TAXOL®) and its analog docetaxel (e.g., TAXOTERE®). Examples of vinca alkaloids include, but are not limited to, vinblastine (e.g., VELBAN®), vincristine (e.g., ONCOVIN®), and vinorelbine (e.g., NAVELBINE®).

Exemplary mitotic inhibitors also include, but are not limited to, paclitaxel (Taxol, Onxol, Abraxane), docetaxel (Taxotere), vincristine (Oncovin, Vincasar PFS), vinblastine (Velban), etoposide (Toposar, Etopophos, VePesid), teniposide (Vumon), ixabepilone (Ixempra), nocodazole, epothilone, vinorelbine (Navelbine), camptothecin (CPT), irinotecan (Camptosar), topotecan (Hycamtin), amsacrine, and lamellarin D (LAM-D).

Exemplary MTOR inhibitors also include, but are not limited to, everolimus (Afinitor), temsirolimus (Torisel), rapamune, ridaforolimus, and AP23573.

Exemplary multi-kinase inhibitors include, but are not limited to, sorafenib (Nexavar), sunitinib (Sutent), BIBW 2992, E7080, Zd6474, PKC-412, motesanib, and AP24534.

Exemplary serine/threonine kinase inhibitors include, but are not limited to, ruboxistaurin, eril/easudil hydrochloride, flavopiridol, seliciclib (CYC202, Roscovitrine), SNS-032 (BMS-387032), Pkc412, bryostatin, KAI-9803, SF1126, VX-680, Azd1152, Arry-142886 (AZD-6244), SCIO-469, GW681323, CC-401, CEP-1347, and PD 332991.

Inhibitors of serine/threonine kinases also include MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta), IkB kinase family (IKKa, IKKb), PKB family kinases, AKT kinase family members, and TGF beta receptor kinases. Inhibitors of serine/threonine kinases are also described in *J. Biochem.* 126, 799 (1999), *Biochem. Pharmacol.* 60, 1101 (2000); Cancer Surveys 27, 41 (1996); *Cancer Treatment Res.* 78, 3 (1995); *Bioorg. Med. Chem. Letters* 10, 223 (2000); U.S. Pat. No. 6,268,391; and *Int. J. Cancer* 88, 44 (2000).

Tyrosine kinases (also nonreceptor tyrosine kinases) include, but are not limited to, cSrc, Lck, Fyn, Yes, Jak, cAbl, FAK (Focal adhesion kinase), Brutons tyrosine kinase, and Bcr-Abl. Inhibitors of non-receptor tyrosine kinase are described in *J. Hematotherapy Stem Cell Res.* 8, 465 (1999) and *Annual Rev. Immunol.* 15, 371 (1997).

Exemplary tyrosine kinase inhibitors also include, but are not limited to, erlotinib (Tarceva), gefitinib (Iressa), imatinib (Gleevec), sorafenib (Nexavar), sunitinib (Sutent), trastuzumab (Herceptin), bevacizumab (Avastin), rituximab (Rituxan), lapatinib (Tykerb), cetuximab (Erbitux), panitumumab (Vectibix), everolimus (Afinitor), alemtuzumab (Campath), gemtuzumab (Mylotarg), temsirolimus (Torisel), pazopanib (Votrient), dasatinib (Sprycel), nilotinib (Tasigna), vatalanib (Ptk787, ZK222584), CEP-701, SU5614, MLN518, XL999, VX-322, Azd0530, BMS-354825, SKI-606 CP-690, AG-490, WHI-P154, WHI-P131, AC-220, and AMG888.

Exemplary VEGF/VEGFR inhibitors include, but are not limited to, bevacizumab (Avastin), sorafenib (Nexavar), sunitinib (Sutent), ranibizumab, pegaptanib, and vandetinib, axitinib, brivanib alaninate ((S)-((R)-1-(4-(4-Fluoro-2-methyl-1H-indol-5-yloxy)-5-methylpyrrolo[2, 1-f][1,2,4]triazin-6-yloxy)propan-2-yl)2-aminopropanoate, also known as BMS-582664), motesanib (TST-(2,3-dihydro-3,3-dimethyl-IH-indol-6-yl)-2-(4-pyridinylmethyl)aminol-3-pyridinecarboxamide), and pasireotide (also known as SO 230).

Inhibitors of phosphotidyl inositol-3 kinase family members including blockers of Pekinese, ATM, DNA-PK, and Ku may also be combined with the compounds of the present application. Such inhibitors are discussed in *Curr. Opinion Immunol.* 8, 412 (19%); Oncogene 17, 3301 (1998); *Int. J. Biochem. Cell Biol.* 29, 935 (1997); and *Cancer Res.* 60, 1541 (2000).

Exemplary kinase inhibitors also include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3). MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-B, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including F13).

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin, and idarubicin.

Additional topoisomerase poison drugs include topoisomerase II inhibitors, such as epipodophyllotoxins. Examples of epipodophyllotoxins include, but are not limited to, etoposide (VP-16, VePESID®) and teniposide (VM-26, VUMON®).

Exemplary taxanes or taxane derivatives include, but are not limited to, paclitaxel and docetaxol.

Antibody antagonists to receptor kinase ligand binding may also serve as inhibitors. Examples include Imclone C225 EGFR specific antibody (see *Cancer Treat. Rev.* 26, 269 (2000)), Herceptint erbB2 antibody (see *Breast Cancer Res.* 2, 176 (2000)), and 2CB VEGFR2 specific antibody (see *Cancer Res.* 60, 5117 (2000)).

Anti-angiogenic therapeutic agents including non-receptor MEK angiogenesis inhibitors may also be combined with the compounds of the present application. Anti-angiogenic agents such as those which inhibit the effects of vascular endothelial growth factor (for example, bevacizumab [Avastin™]) and compounds that work by other mechanisms (for example, linomide, inhibitors of integrin αvβ3 function, endostatin and angiostatin).

Additional therapeutic agents which may be combined with the compounds of the present application also include SH2/SH3 domain blockers that disrupt SH2 or SH3 domain binding in a variety of enzymes or adaptor proteins including, P3-K p85 subunit, Src family kinases, adaptor molecules (She, Crk, Nek, Grb2), and Ras-GAP. SH2/SH3 domains blockers as anticancer drugs are discussed in *J. Pharm. Toxicol. Methods* 34, 125 (1995).

Additional therapeutic agents which may be combined with the compounds of the present application also include Myo-inositol signalling inhibitors such as phospholipase C blockers and Myoinositol analogues. Such signal inhibitors are described in *New Molecular Targets for Cancer Chemotherapy* ed., Paul Workman and David Kerr, CRC press 1994, London.

Additional therapeutic agents which may be combined with the compounds of the present application also include inhibitors of Ras oncogene, including inhibitors of farnesyl-transferase, geranyl-geranyl transferase, and CAAX proteases, as well as anti-sense oligonucleotides, ribozymes and immunotherapy. Such inhibitors are discussed in *J. Biomed. Sci.* 7, 292 (2000); *Curr. Opin. Lipidology* 9, 99 (1998); and *BioChim. Biophys. Acta,* 1423, 19 (1989).

Additional exemplary general chemotherapeutic, antineoplastic, or anti-proliferative agents which may be combined with the compounds of the present application also include, but are not limited to, altretamine (Hexalen), isotretinoin (Accutane, Amnesteem, Claravis, Sotret), tretinoin (Vesanoid), azacitidine (Vidaza), bortezomib (Velcade) asparaginase (Elspar), levamisole (Ergamisol), mitotane (Lysodren), procarbazine (Matulane), pegaspargase (Oncaspar), denileukin diftitox (Ontak), porfimer (Photofrin), aldesleukin (Proleukin), lenalidomide (Revlimid), bexarotene (Targretin), thalidomide (Thalomid), temsirolimus (Torisel), arsenic trioxide (Trisenox), verteporfin (Visudyne), mimosine (Leucenol), (1M tegafur-0.4 M 5-chloro-2,4-dihydroxypyrimidine-1 M potassium oxonate), and lovastatin.

Additional therapeutic agents which may be combined with the compounds of the present application also include anti-viral agents including, but not limited to, hepatitis B virus (HBV) inhibitors, hepatitis C virus (HCV) protease inhibitors, HCV polymerase inhibitors, HCV NS4A inhibitors, HCV NS5 A inhibitors, HCV NS5b inhibitors, and human immunodeficiency virus (HIV) inhibitors.

Additional therapeutic agents which may be combined with the compounds of the present application also include antigens or adjuvants including, but not limited to, B7 costimulatory molecule, interleukin-2, interferon-y, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. In one embodiment, adjuvants, such as aluminum hydroxide or aluminum phosphate, can be added to increase the ability of the vaccine to trigger, enhance, or prolong an immune response. In one embodiment, additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryllipid A, lipoteichoic acid, imiquimod, resiquimod, and in addition retinoic acid-inducible gene I (RIG-I) agonists such as poly I:C, can also be used.

Additional therapeutic agents which may be combined with the compounds of the present application also include cytotoxic agents including, but not limited to, arsenic trioxide (TRISENOX®), asparaginase (also known as L-asparaginase, and *Erwinia* L-asparaginase, sold under the tradenames ELSPAR® and KIDROLASE®).

Additional therapeutic agents which may be combined with the compounds of the present application also include retinoids including, but not limited to, alitretinoin (sold under the tradename PANRETIN®), tretinoin (all-trans retinoic acid, also known as ATRA, sold under the tradename VESANOID®), Isotretinoin (13-c/s-retinoic acid, sold under the tradenames ACCUTANE®, AMNESTEEM®, CLARAVIS®, CLARUS®, DECUTAN®, ISOTANE®, IZOTECHX. ORATANEX, ISOTRETX, and SOTRET®), and bexarotene (sold under the tradename TARGRETIN®).

Additional exemplary chemotherapeutic agents that may be used in combination with the compounds of present application include, but are not limited to, abiraterone acetate, altretamine, anhydrovinblastine, auristatin, bexarotene, bicalutamide, BMS 184476, 2,3,4,5,6-pentafluoro-N-(3-fluoro-4-methoxyphenyl) benzene sulfonamide, bleomycin. N,N-dimethyl-L-valyl-L-valyl-N-methyl-L-valyl-L-prolyl- 1-Lproline-t-butylamide, cachectin, cemadotin, chlorambucil, cyclophosphamide, 3',4'-didehydro-4'deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyurea andtaxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine.

Additional therapeutic agents which may be combined with the compounds of the present application also include inhibitors of cell cycle signaling, proapoptotic agents, PARP inhibitors, checkpoint therapeutics, and immune modulators.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in Exp. Opin. Ther. Patents 10, 215 (2000).

Therapeutic agents used in proapoptotic regimens (e.g., bcl-2 antisense oligonucleotides) may also be used in combination of the compounds of the present application.

As used herein, PARP inhibitors refer to a group of pharmacological inhibitors of the enzyme poly ADP ribose polymerase (PARP). Exemplary PARP inhibitors include, but are not limited to, Olaparib (AZD-2281, Lynparza® by Astra Zeneca), Rucaparib (PF-01367338, Rubraca® by Clovis Oncology), Niraparib (MK-4827, Zejula® by Tesaro), Talazoparib (BMN-673), Veliparib (ABT-888), Olaparib (AZD-2281), Olaparib TOPARP-A, Rucaparib (PF-01367338, AG014699), CEP 9722, E7016 (developed by Eisai), BGB-2901, Iniparib (BSI 201), and 3-aminobezamide.

Agents used in immunotherapeutic regimens may also be useful in combination with the compounds of the present application. Immunotherapy approaches, including ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine transfected tumor cell lines, and approaches using anti-idiotypic antibodies.

As used herein, checkpoint inhibitor therapy refers to a form of cancer treatment immunotherapy that targets immune checkpoints, key regulators of the immune system that stimulate or inhibit its actions, which may allow tumors to protect themselves from attacks by the immune system. Checkpoint therapy can block inhibitory checkpoints, restoring immune system function.

As used herein, "immune-modulators" or "immunomodulartors" refer to any substance including monoclonal antibodies that affect the immune system. Immuno-modulators can be used as anti-neoplastic agents for the treatment of cancer. For example, immune-modulators include, but are not limited to, anti-CTLA-4 antibodies such as ipilimumab (YERVOY) and anti-PD-1 antibodies (Opdivo/nivolumab and Keytruda/pembrolizumab). Other immuno-modulators include, but are not limited to, ICOS antibodies, OX-4) antibodies, PD-L1 antibodies. LAG3 antibodies, TIM-3 antibodies, 41BB antibodies, and GITR antibodies.

CLTA-4 and PD-1 pathways are important negative regulators of immune response. Activated T-cells up-regulate CTLA-4, which binds on antigen-presenting cells and inhibits T-cell stimulation, IL-2 gene expression, and T-cell proliferation. PD-1 binds to active T-cells and suppresses T-cell activation. PD-1 antagonists have demonstrated anti-tumor effects. CTLA-4 and PD-1 pathway antagonists that may be used in combination with the compounds of the present application include ipilimumab, tremelimumab, nivolumab, pembrolizumab, CT-011, AMP-224, and MDX-1106.

As used herein, PD-1 inhibitors and PD-L1 inhibitors refer to a group of checkpoint inhibitors or immune checkpoint inhibitors useful in the treatment of cancer. PD1 and PD-L1 are both proteins present on the surface of cells. PD-1 and PD-L1 inhibitors act to inhibit the association of the programmed death-ligand (PD-L1) with its receptor, programmed cell death protein 1 (PD-1). Exemplary PD-1 and/or PD-L inhibitors include, but are not limited to Nivolumab (Opdivo), Pembrolizumab (MK-3475 or lambrolizumab, Keytruda), Atezolizumab (Tecentriq), Avelumab (Bavencio), Durvalumab (Imfinzi), pidilizumab, AMP-224, AMP-514, PDR001, cemiplimab, BMS-936559, and CK-301.

Anti-PD-L1 antibodies and methods of making the same are known in the art. Such antibodies to PD-L1 may be polyclonal or monoclonal, and/or recombinant, and/or humanized. Exemplary PD-L1 antibodies are disclosed in U.S. Pat. Nos. 8,217,149, 8,383,796, 8,552,154, 9,212,224, and 8,779,108, and US Patent Appln. Pub. Nos. 20110280877, 20140341902, and 20130045201. Additional exemplary antibodies to PD-L1 (also referred to as CD274 or B7-H1) and methods for use are disclosed in U.S. Pat. Nos. 7,943,743, 8,168,179, and 7,595,048; WO2014055897, WO2016007235; and US Patent Appln. Pub. Nos. 20130034559 and 20150274835. In one embodiment, the anti-PD-L antibody is BMS-936559 (MDX-1105), MPDL3280A (RG7446), MEDI4736, TECENTRIQ™ (atezolizumab), YW243.55.570, MPDL3280A, BMS-936559, MEDI4736, or MSB0010718C, or an antibody that comprises the $V_H$ and $V_L$ described in WO2013019906 (e.g., SEQ ID NOs: 21 and 24 therein). Examples of anti-PD-LI antibodies and methods for making thereof are also described in WO 2010077634, WO 2007005874, WO 2011066389, WO 2013019906, WO 2010077634, U.S. Pat. Nos. 8,217,149 and 8,383,796, and US Patent Appln. Pub. No. 2013034559.

PD-1 antagonists or PD-1 inhibitors refer to any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1. CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1 are described in U.S. Pat. Nos. 7,488,802, 7,521,051, 8,008,449, 8,354,509, and 8,168,757, WO 2004004771, WO 2004072286, WO 2004056875, and US Patent Appln. Pub. No. 20110271358. In one embodiment, anti-human PD-1 mAbs useful as the PD-1 antagonists include: MK-3475, nivolumab, the humanized antibodies h409A11, h409A16 and h409A17, which are described in WO 2008156712, and AMP-514.

Other PD-1 antagonists useful in the any of the aspects and embodiments of the present application include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO 2010027827 and WO 2011066342. In one embodiment, the PD-1 antagonists include AMP-224 (also known as B7-DCIg), which is a PD-L2-FC fusion protein and binds to human PD-1.

In one embodiment, the anti-PD-1 antibody is KEYTRUDA/pembrolizumab, disclosed in U.S. Pat. No. 8,168,757 or Opdivo/nivolumab (also known as BMS-936558, MDX-1106, and ONO-4538, disclosed in U.S. Pat. No. 8,008,449.

In one embodiment, the CTLA-4 antagonist is Yervoy (ipilimumab), described in U.S. Pat. Nos. 6,984,720 and 7,605,238.

Additional examples of other therapeutic agents (anti-neoplastic agent) for use in combination or co-administration with a compound of the present application include antibodies to ICOS. Agonist antibodies to ICOS or ICOS binding proteins are disclosed in WO 2012013004, WO 2014033327, WO 2016120789, US Patent Appln. Pub. Nos. 20160215059 and US20160304610, for example, SEQ ID NOs: 1-6 or a direct equivalent thereof disclosed in WO 2016120789, a $V_H$ domain comprising an amino acid sequence at least 90% identical to SEQ ID NO: 7 as disclosed in WO 2016120789, and/or a $V_L$ domain comprising an amino acid sequence at least 90% identical to SEQ ID NO: 8 as disclosed in WO 2016120789.

Additional examples of other therapeutic agents (anti-neoplastic agent) for use in combination or co-administration with a compound of the present application include antibodies to OXO40. Such antibodies are described in WO 2012027328, WO 2013028231 (e.g., an antibody comprising a $V_L$ having a sequence at least 90% identical to SEQ ID NO: 10 and/or a $V_H$ having a sequence at least 90% identical to SEQ ID NO:4 therein)

Additional examples of other therapeutic agents for use in combination or co-administered with a compound of the present application include immunostimulatory agents. As used herein immunostimulatory agent refers to any agent that can stimulate the immune system. As used herein immunostimulatory agents include, but are not limited to, vaccine adjuvants, such as Toll-like receptor agonists, T-cell checkpoint blockers, such as mAbs to PD-1 and CTL4 and T-cell checkpoint agonist, such as agonist mAbs to OX-40 and ICOS. As used herein "immunostimulator agent" refers to any agent that can stimulate the immune system. As used herein immunostimulatory agents include, but are not limited to, vaccine adjuvants.

In one embodiment, TLR agonists include, but are not limited to, Pam3Cys, a TLR1/2 agonist; CFA, a TLR2 agonist; MALP2, a TLR2 agonist; Pam2Cys, a TLR2 agonist; FSL-I, a TLR-2 agonist; Hib-OMPC, a TLR-2 agonist; polyinosinic:polycytidylic acid (Poly I:C), a TLR3 agonist: polyadenosine-polyuridylic acid (poly AU), a TLR3 agonist; Polyinosinic-Polycytidylic acid stabilized with poly-L-lysine and carboxymethylcellulose (Hiltonol), a TLR3 agonist: bacterial flagellin a TLR5 agonist; imiquimod, a TLR7 agonist: resiquimod, a TLR7/8 agonist: loxoribine, a TLR7/8 agonist; and unmethylated CpG dinucleotide (CpG-ODN), a TLR9 agonist. Additional TLR agonists include, but are not limited to aminoalkyl glucosaminide phosphates (AGPs). An example of a naturally occurring TLR4 agonist is bacterial LPS. An example of a semisynthetic TLR4 agonist is monophosphoryl lipid A (MPL). Additional AGP derivatives are disclosed in U.S. Pat. Nos. 7,129,219, 6,525,028, and 6,911,434.

In one embodiment, the immunostimulatory agent for use in combination with the compounds of the present application is a TLR4 agonist. In one embodiment, the TLR4 agonist is CRX-601, CRX-527, or CRX 547. Other embodiments include AGPs such as CRX 602 or CRX 526.

In addition, the compounds of the present application may be combined with other therapeutic agents which, because of their adjuvant nature, can act to stimulate the immune system to respond to the cancer antigens present on the inactivated tumor cell(s). Such adjuvants include, but are not limited to, lipids, liposomes, inactivated bacteria which induce innate immunity (e.g., inactivated or attenuated Listeriamonocytogenes), compositions which mediate innate immune activation via, (NOD)-like receptors (NLRs), Retinoic acid inducible gene-based (RIG)-I-like receptors (RLRs), and/or C-type lectin receptors (CLRs). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacteria, rt-Galactosylceramide (rt.-GalCer) is an activator of natural killer T (NKT) cells. Muramyl dipeptide is a bioactive peptidoglycan motif common to all bacteria.

Additional examples of other therapeutic agents for use in combination or co-administered with a compound of the present application include IDO inhibitors (e.g., Epacadostat, as disclosed in U.S. Pat. No. 8,034,953), CD73 inhibitors, and A2a and A2b adenosine antagonists.

In one embodiment, the compounds may be administered in combination with one or more separate pharmaceutical agents, e.g., a chemotherapeutic agent, an immunotherapeutic agent, or an adjunctive therapeutic agent.

The compounds of the present application may be used in combination with at least one other therapeutic agent useful in the prevention or treatment of bacterial and viral infections. Examples of such agents include, without limitation: polymerase inhibitors such as those disclosed in WO 2004037818 and WO 2006045613; JTK-003, JTK-019, NM-283, HCV-796, R-803, R1728, R1626, as well as those disclosed in WO 2006018725, WO 2004074270, WO 2003095441. US Appl. Pub. No. 20050176701, WO 2006020082, WO 2005080388, WO 2004064925, WO 2004065367, WO 2003007945, WO 2002004425, WO 2005014543, WO 2003000254, EP 1065213, WO 2001047883, WO 2002057287, WO 2002057245; replication inhibitors such as acyclovir, famciclovir, ganciclovir, cidofovir, lamivudine, and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034, and similar agents; nucleoside and nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, tenofovir disproxil fumarate, tenofovir alafenamide fumarate/hemifumarate, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, rilpivirine, and similar agents; entry inhibitors such as enfuvirtide (T-20), T-1249, PRO-542, PRO-140, TNX-355, BMS-806, 5-Helix, and similar agents; integrase inhibitors such as dolutegravir, elvitegravir, raltegravir L-870,180, and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 2002074769, WO 20040054974, WO 2004055012, WO 2004055010, WO 2004055016, WO 2004055011, and WO 2004054581, and similar agents; pharmacokinetic enhancers such as cobicistat; neuraminidase inhibitors such as CS-8958, zanamivir, oseltamivir, peramivir, and similar agents; ion channel blockers such as amantadine or rimantadine, and similar agents; interfering RNA and antisense oligonucleotides and such as ISIS-14803 and similar agents; and antiviral agents of undetermined mechanism of action, for example those disclosed in WO 2005105761, WO 2003085375, WO 2006122011, ribavirin, and similar agents.

The compounds of the present application may be used in combination with at least one other therapeutic agent which may be useful in the treatment of Kaposi's sarcoma-associated herpesvirus infections (KSHV and KSHV-related) including, without limitation, chemotherapeutic agents such as bleomycin, vinblastine, vincristine, cyclophosphamide, prednisone, alitretinoin and liposomal anthracyclines such as doxorubicin, daunorubicin, immiunotherapeutics such as Rituximab, Tocilizumab, Siltuximab, and others such as Paclitaxel and Rapamycin.

The compounds of the present application may be used in combination with at least one other therapeutic agent which may be useful in the treatment of TB infection *Mycobacterium tuberculosis*) and Tularemia (*Franciseiia tularensis*), including, without limitation, first line oral agents isoniazid, Rifampicin, pyrazinamide, ethambutol, streptomycin, rifabutin; injectable agents including kanamycin, amikacin, capreomycin, streptomycin; fluoroquinolones including levofloxacin moxifloxacin ofloxacin; oral bacteriostatic agents para-aminosalicylic acid cycloserine terizidone thionamide protionamide; SQ-109 PNU-100480, Rifapentine Linezolid, PA-824 AZD5847, Gatifloxacin Moxifloxacin, Sirturo (bedaquiline) Delamanid (OPC-67683) and agents with undetermined mechanism of action in the treatment of drug-resistant TB, including clofazimine, linezolid, amoxicillin/clavulanate thioacetazone imipenem/cilastatin high dose isoniazid clarithromycin, and ciprofloxacin.

The compounds of the present application may be used in combination with at least one antimycobacterial agent (such as isoniazid (INH), ehambutol (Myambutol®), rifampin (Rifadin®), and pyrazinamide (PZA)), a bactericidal antibiotic (such as rifabutin (Mycobutin®) or rifapentine (Priftin®)), an aminoglycoside (Capreomycint®), a fluorquinolone (levofloxacin, moxifloxicin, ofloxacin), thioamide (ehionamide), cyclosporine (Sandimmune®), para-aminosalicyclic acid (Paser®), cycloserine (Seromycin®), kanamycin (Kantrex®), streptomycin, viomycin, capreomycin (Capastat®)), bedaquiline fumarate (Sirturot®), oxazolidinone (Sutezolid®), PNU-100480, or delamanid (OPC-67683).

The compounds of the present application may be used in combination with at least one other therapeutic agent which may be useful in the treatment of *Chlamydia* including, without limitation, Azithromycin, Doxycycline, Erythromycin, Levofloxacin, and Ofloxacin.

The compounds of the present application may be used in combination with at least one other therapeutic agent which may be useful in the treatment of *Plasmodium* infection including, without limitation, chloroquine, atovaquone-proguanil, artemether-lumefantrine, mefloquine, quinine, quinidine, doxocycline, cindamycin, artesunate, and primaquine.

In the treatment of amyotrophic lateral sclerosis (ALS), the compounds of the present application may be used in combination with a glutamate blocker (Riluzole (Riluteke®)), quinidine (Nuedexta®), anticholinergics (Amitriptyline®, Artane®, scopolamine patch (Transderm Scop®)), sympathomimetics (pseudoephedrine), mucolytics (guaifenesin), or analgesics (tramadol (Ultram®), ketorolac (Toradol®); morphine; or fentanyl patch (Duragesic®)).

In the treatment of multiple scelrosis, the compounds of the present application may be used in combination with corticosteroids (prednisone, methylprednisolone), Interferon Beta 1-A (Avonex®, Extavia®, Rebif, Betaseron®), peginterferon beta-IA (Plegridy®), Glatiramer acetate (Copaxone®); glatiramer acetate (Glatopa®-generic equivalent of Copaxone); Dimethyl fumarate (Tecfidera®); Fingolimod (Gilenya®)); teriflunomide (Aubagio®); dalfampridine (Ampyra®); daclizumab (Zinbryta) alemtuzumab (Lemtrada®); natalizumab (Tysabri®); or mitoxantrone hydrochloride (Novantrone®).

The compounds of the present application may be used in combination with one or more vaccines or immunogenic antigens useful in the prevention or treatment of viral infections. Such vaccines or immunogenic antigens include, without limitation, pathogen derived proteins or particles such as attenuated viruses, virus particles, and viral proteins typically used as immunogenic substances. Examples of viruses and viral antigens include, without limitation. Polioviruses, Coronaviridae and Coronaviruses, Rhinovirus (all subtypes), Adenoviruses (all subtypes), Hepatitis A, Hepatitis B, Hepatitis C. Hepatitis D, Human papillomavirus (including all subtypes), Rabies viruses, Human T-cell lympotropic virus (all subtypes), Rubella virus, Mumps virus, Coxsackie virus A (all subtypes), Cosackie virus B (all subtypes), human enteroviruses, herpesviruses including cytomegalovirus, Epstein-Barr virus, human herepesviruses (all subtypes), herpes simplex virus, varicella zoster virus, human immunodeficiency virus (HIV) (all subtypes), Epstein-Barr virus, Reoviruses (all subtypes), Filoviruses including Marburg virus and Ebola virus (all stains), Arenaviruses including Lymphocytic choriomeningitis virus, Lassa virus, Junin virus, and Machupo virus, Arboviruses including West Nile virus, Dengue viruses (all serotypes), Zika virus, Colorado tick fever virus, Sindbis virus, Togaviraidae, Flaviviridae, Bunyaviridae, Reoviridae, Rhabdoviridae, Orthomyxoviridae, Poxviruses including orthopoxvirus (variola virus, monkypox virus, vaccinia virus, cowpox virus), yatapoxviruses (tanapox virus, Yaba monkey tumor virus), parapoxvirus, molluscipoxvirus, Yellow fever, Hantaviruses including Hantaan, Seoul, Dobrava. Sin Nombre, Puumala. and Dobrava-like Saaremaa, human para influenza viruses and influenza viruses (all types), HINI influenza and swine influenza viruses, respiratory syncytial virus (all subgroups), rotaviruses including human rotaviruses A-E, bovine rotavirus, rhesus monkey rotavirus, Polyomaviruses including simian virus 40, JC virus, BK virus, Coltiviruses, eyach virus, calciviruses, and Parvoviridae including dependovirus, parvovirus and erythrovirus.

The compounds of the present application may be used in combination with at least one other therapeutic agent which may be useful in the prevention or treatment of viral infections for example immune therapies (e.g., interferon or other cytokines/chemokines, cytokine/chemokine receptor modulators, cytokine agonists or antagonists and similar agents); and therapeutic vaccines, anti-fibrotic agents, anti-inflammatory agents such as corticosteroids or NSAIDs (non-steroidal anti-inflammatory agents) and similar agents.

The compounds of the present application may be used in combination with other anti-inflammatory agents, including oral or topical corticosteroids, anti-TNF agents, 5-aminosalicyclic acid and mesalamine preparations, hydroxycloroquine, thiopurines, methotrexate, cyclophosphamide, cyclosporine, calcineurin inhibitors, mycophenolic acid, mTOR inhibitors, JAK inhibitors, Syk inhibitors, anti-inflammatory biologic agents, including anti-IL6 biologies, anti-IL1 agents, anti-IL17 biologies, anti-CD22, anti-integrin agents, anti-IFNa, anti-CD20 or CD4 biologies and other cytokine inhibitors or biologies to T-cell or B-cell receptors or interleukins.

For example, in the treatment of systemic lupus erythematosus and related lupus disorders, the compounds of the present application may be used in combination with at least one other therapeutic agent, including, a corticosteroid (such as prednisolone (Delatsone®, Orapred, Millipred, Omnipred, Econopred, Flo-Pred), an immunosuppressive agent (such as methotrexate (Rhuematrex®, Trexall®), dexamethasone (Decadron®, Solurex®), Mycophenolate mofetil (Cellcept®), Tacrolimus®. Sirolimus®), B-cell therapy (belimumab (Benlysta®), B-cell inhibitor (Atacicept®, Apratuzumab® (anti-CD22), SBI-087 (anti-CD20), an anti-BAFF antibody (LY2127399, A623), Velcade®), azathioprine (Azasan®, Imuran®), triamcinolone (Clinacort®, Kenalog-10®), hydroxychloroquine (Plaquenil®), thalidomide (Immunoprin®, Contergan®), immunoglobulin therapy (HyQiva®, Flebogamma®), Gamunex®, Privigen®, Gammagard®), anti-interferon-alpha therapy (Rontalizumab®, Sifalimumab®, AGS-009®, IFN Kinoid), TLR7 and TLR9 blockers (IMO-3100), anti-cytokine therapies (anti-IL6 (CNTO-136), anti-interferon-gamma (AMG811), immunomodulatory therapy (Lupuzor™, Abatacept, Orenciat®, AMG557, Laquinimod, Paquinimod, Leflunomide, anti-ICOS (Medi-570), anti-CD40 ligand antibody (CDP7657)), and/or a platelet aggregation inhibitor (aspirin).

In treatment of vasculitis and disease with inflammation of small or medium size blood vessels, the compounds of the present application may be used in combination with alkylating agents (cyclophosphamide, Cytoxan®), anti-rheumatic anti-CD20 antibody (Rituxan®, Rituximab®), and anti-TNF inhibitors (Etanrcept®).

In the treatment of psoriasis, the compounds of the present application may be used in combination with ixekizumab, tildrakizumab (MK-3222), or secukinumab (AIN457).

In one embodiment, the at least one other therapeutic agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarinic antagonist. For example, in the treatment of asthma, the compounds of the present application may be used in combination with an inhaled corticosteroid ((ICS) such as fluticasone proprionate (Flovent®), beclomethasone dipropionate (QVAR®), budesonide (Pulmicort), trimcinolone acetonide (Azmacort®), flunisolide (Aerobid®), mometasone fuorate (Asmanex® Twisthaler®), or Ciclesonide (Alvesco®)), a long acting beta agonist ((LABA) such as formoterol fumarate (Foradil®), salmeterol xinafoate (Serevent®)), a combination of an ICS and LABA (such as fluticasone furoate and vilanterol (Breo Ellipta®), formoterol/budesonide inhalation (Symbicort®), beclomethasone dipropionate/formoterol (Inuvair®), and fluticasone propionate/salmeterol (Advair®), a short acting beta agonist ((SABA) such as albuterol sulfate (ProAir®, Proventil HFA®, Ventolin HFA®, AccuNeb® Inhalation Solution), levalbuterol tartrate (Xopenex® HFA), ipratropium bromide/albuterol (Combivent® Respimat®), ipratropium bromide (Atrovent® HFA), a leukotriene modifier (such as montelukast sodium (Singulair®), zafirlukast (Accolate®), or zileuton (Zyflo®), and anti-IgE (such as omalizumab (Xolair®)), a methylxanthine bronchodilator (such as theophylline (Accurbron®, Aerolate®, Aquaphyllin®, Asbron®, Bronkodyl®, Duraphyl®, Elixicon®, Elixomin®, Elixophyllin®, Labid®, Lanophyllin®, Quibron-T®, Slo-Bid®, Slo-Phyllin®, Somophyllin®, Sustaire®, Synophylate®, T-Phyll®, Theo-24®, Theo-Dur®, Theobid®, Theochron®, Theoclear®, Theolair®, Theolixir®, Theophyl®, Theovent®, Uni-Dur®, Uniphyl®), a mast cell inhibitor (such as cromulyn sodium (Nasalcrom®) and nedocromil sodium (Tilade®)), a long-acting muscarinic antagonist ((LAMA) such as mometasone furoate/formoterol fumarate dihydrate (Dulera®)).

Other agents that may be suitable for use in combination therapy in the treatment of asthma include a protein tyrosine kinase inhibitor (masitinib), CRTH2/D-prostanoid receptor antagonist (AMG 853), indacaterol (Arcapta® Neohalert®), an epinephrine inhalation aerosol (E004), fluticasone furoate/fluticasone proprionate, vinanterol inhalation/ fluticasone furoate powder (Relovair™), fluticasone propionate/eformoterol fumarate dehydrate (Flutiform®), reslizumab, salbutamol dry-powder inhalation, tiotropium bromide (Spiriva® HandiHaler®), formoterol/budesonide (Symbicort® SMART®), fluticasone furoate (Veramyst®), Vectura's VR506, lebrikizumab (RG3637), a combination phosphodiesterase (PDE)-3 and (PDE)-4 inhibitor (RPL554).

In one embodiment, the at least one other therapeutic agent is selected from a long acting beta agonist, a long-acting inhaled anticholinergic or muscarinic antagonist, a phosphodiesterase inhibitor, a combination an inhaled corticosteroid long acting beta agonist, a short acting beta agonist, and an inhaled corticosteroid. For example, in the treatment of COPD, the compounds of the present application may be used in combination with a LABA (such as salmeterol xinafoate (Serevent), umeclidinium/vilanterol (Anoro Ellipta®), umeclidinium (Incruse Ellipta®), aformoterol tartrate (Brovana®), formoterol fumarate inhalation powder (Foradil®), indacterol maleate (Arcapta® Neohaler®), or fluticasone propionate/eformoterol fumarate dehydrate (Flutiform®)), a long-acting inhaled anticholinergic (or muscarinic antagonist, such as tiotropium bromide (Spiriva®), and aclidinium bromide (Tudorza® Pressair®), a phosphodiesterase (PDE-r) inhibitor (such as roflumilast, Daliresp®), a combination ICS/LABA (such as fluticasone furoate and vilanterol (Breo Ellipta), fluticasone propionate/salmeterol (Advair®), budesonide/formoterol (Symbicort®), mometasone/formoterol (Dulera®), ipratropium bromide/albuterol sulfate (Duoneb®, Atrovent®), albuterol/ipratropium (Combivent Respimat®)), a SABA (such as ipratropium bromide (Atrovent®), and albuterol sulfate (ProAir®, Proventil®)), and an ICS (such as budesonide (Pulmicort®) and fluticasone propionate (Flovent®10), beclometasone dipropionate (QVAR®).

Other agents that may be suitable for use in combination therapy in the treatment of COPD include SCH527123 (a CXCR2 antagonist), glycoprroniun bromide ((NVA237) Seebri® Breezhaler®), glycopyrronium bromide and indacaterol maleate ((QVA149) Ultibro® Breezhaler®), glycopyrrolate and formoterol fumarate (PT003), indacaterol maleate (QVA149), olodaterol (Striverdi® Respimat®), tiotropium (Spiriva®)/olodaterol (Striverdi® Respimat®), and aclidinium/formoterol inhalation.

In one embodiment, the at least one other therapeutic agent is selected from an oral corticosteroid, anti-thymocyte globulin, thalidomide, chlorambucil, a calcium channel blocker, a topical emollient, an ACE inhibitor, a serotonin reuptake inhibitor, an endothelin-1 receptor inhibitor, an anti-fibrotic agent, a proton-pump inhibitor or imatinib, ARG201, and tocilizumab.

For example, in the treatment of systemic scleroderma the compounds of the present application may be used in combination with an oral corticosteroid (such as prednisolone (Delatsone®, Orapred, Millipred, Omnipred, Econopred, Flo-Pred), an immunosuppressive agent (such as methotrexate (Rhuematrex®, Trexall®), cyclosporine (Sandimmune®), anti-thymocyte globulin (Atgam®), mycophenolate mofetil (CellCept®), cyclophosphamide (Cytoxan®)), FK506 (tacrolimus), thalidomide (Thalomid®), chlorambucil (Leukeran®), azathioprine (Imuran®, Azasan®)), a calcium channel blocker (such as nifedipine (Procardia®, Adalat®) or nicardipine (Cardene®), a topical emollient (nitroglycerin ointment), an ACE inhibitor (such as lisinopril (Zestri®, Prinivil®), diltaizem (Cardizem®, Cardizem SR®, Cardizem CD®, Cardia®, Dilacor®, Tiazac®)), a serotonin reuptake inhibitor (such as fluoxetine (Prozac®)), an endothelin-1 receptor inhibitor (such as bosentan (Tracleer®) or epoprostenol (Flolan®, Veletri®, Prostacyclin®)) an anti-fibrotic agent (such as colchicines (Colcrys®), para-aminobenzoic acid (PABA), dimethyl sulfoxide (DMSO), and D-penicillamine (Cuprimine®, Depen®), interferon alpha and interferon gamma (INF-g)), a proton-pump Inhibitor (such as omeprazole (Prilosec®), metoclopramide (Reglan)), lansoprazole (Prevacid®), esomeprazole (Nexium®), pantoprazole (Protonix®), rabeprazole (Aciphex®)) or imatinib (Gleevec®) ARG201 (arGentis Pharmaceutical), belimumab (Benlysta®), tocilizumnab (Actema®).

In the treatment of Sjogren's syndrome, the compounds of the present application may be used in combination with anti-rheumatic agents (hydroxychloroquine and Plaquenil®, Ridaura®, Kineret®), cholinergic agonists (Salagen®, Evoxac®), a JAK inhibitor (Xelijanz®, and anti-TNF treatments (Remicade®, Humira®, Enbre®, Cimzia®, Simponi®).

In one embodiment of this invention, the at least one other therapeutic agent is a ciliary neurotrophic growth factor or a gene transfer agent. For example, in the treatment of retinitis pigmentosa, the compounds of the present application may be used in combination with a ciliary neurotrophic growth factor (NT-501-CNTF) or gene transfer agent, Ush-Stat®.

In one embodiment of this invention, the at least one other therapeutic agent is selected from a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, or inactivated influenza vaccine. For example, in the treatment of influenza, the compounds of the present application may be used in combination with a trivalent (IIV3) inactivated influenza vaccine (such as Afluria®, Fluarix®, Flucelvax®, FluLaval®, Fluvirin®, Fluzone®), a quadrivalent (IIV4) inactivated influenza vaccine (such as Fluarix® Quadrivalent, Flulaval® Quadrivalent, Fluzone® Quadrivalent), a trivalent recombinant influenza vaccine (such as FluBlok®), a quadrivalent live attenuated influenza vaccine (such as FluMist® Quadrivalent), an antiviral agent (such as oseltamivir (Tamiflu®), zanamivir (Relenza®), rimantadine (Flumadine®), or amantadine (Symmetrel®)), or Fluad®, Fludase, FluNhance®, Preflucel, or VaxiGrip®.

In the treatment of a *staphylococcus* infection, the compounds of the present application may be used in combination with an antibiotic (such as a P-Lactam cephalosporin (Duricef®, Kefzolt®, Ancef®, Biocef®, etc), nafcillin (Unipen®), a sulfonamide (sulfamethoxazole and trimethoprim (Bacrim®, Septra®,) sulfasalazine (Azulfidine®), acetyl sulfisoxazole (Gantrisin®), etc), or vancomycin (Vancocin®)).

In one embodiment, the at least one other therapeutic agent is selected from a topical immunomodulator or calcineurin inhibitor, a topical corticosteroid, an oral corticosteroid, an interferon gamma, an antihistamine, or an antibiotic. For example, in the treatment of atopic dermatitis, the compounds of the present application may be used in combination with a topical immunomodulator or calcineurin inhibitor (such as pimecrolimus (Elidel®) or tacrolimus ointment (Protopic®)), a topical corticosteroid (such as hydrocortizone (Synacort®, Westcort®), betamethasone (Diprolene®), flurandrenolide (Cordan®), fluticasone (Cutivate®), triamcinolone (Kenalog®), fluocinonide (Lidex®), and clobetasol (Temovate®)), an oral corticosteroid (such as hydrocortisone (Cortef®), methyl prednisolone (Medrol®), or prednisolone (Pediapred®, Prelone®), an immunosuppressant (such as cyclosporine (Neoral®) or interferon gamma (Alferon N®, Infergen®, Intron A, Roferon-A®)), an antihistamine (for itching such as Atarax®, Vistaril®, Benadryl®), an antibiotic (such as penicillin derivatives flucloxacillin (Floxapen®) or dicloxacillin (Dynapen®), erythromycin (Eryc®, T-Stat®, Erythra-Derm®, etc.)), a non-steroidal immunosuppressive agent (such as azathioprine (Imuran®, Azasan®), methotrexate (Rhuematrex®, Trexall®), cyclosporin (Sandimmune®), or mycophenolate mofetil (CellCept®)).

In one embodiment, the compounds may be administered in combination with one or more separate pharmaceutical agents, e.g., a chemotherapeutic agent, an immunotherapeutic agent, or an adjunctive therapeutic agent, and one or more of the other second agents as described herein.

As used herein, "combination therapy" or "co-therapy" includes the administration of a compound of the present application, or a pharmaceutically acceptable salt or ester thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present application.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described herein in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As used herein, the term "immune response" relates to any one or more of the following: specific immune response, non-specific immune response, both specific and nonspecific response, innate response, primary immune response, adaptive immunity, secondary immune response, memory immune response, immune cell activation, immune cell proliferation, immune cell differentiation, and cytokine expression. In one embodiment, a compound of the present application, or a pharmaceutically acceptable salt or ester thereof, is administered in conjunction with one or more additional therapeutic agents including anti-viral compounds, vaccines intended to stimulate an immune response to one or more predetermined antigens, adjuvants, CTLA-4 and PD-1 pathway antagonists and other immunomodulatory agents, lipids, liposomes, peptides, anti-cancer agents, and chemotherapeutic agents, etc.

Definitions

Listed below are definitions of various terms used in this application. These definitions apply to the terms as they are used throughout this specification and claims, unless otherwise limited in specific instances, either individually or as part of a larger group.

The term "alkyl," as used herein, refers to saturated, straight or branched-chain hydrocarbon radicals containing, in certain embodiments, between one and six carbon atoms. Examples of $C_1$-$C_6$ alkyl radicals include, but are not limited to, methyl, ethyl, propyl, isopropyl, n-butyl, tert-butyl, neopentyl, and n-hexyl radicals.

The term "alkenyl," as used herein, denotes a monovalent group derived from a hydrocarbon moiety containing, in certain embodiments, from two to six carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, pentenyl, hexenyl, heptenyl, octenyl, nonenyl, decenyl, and the like.

The term "alkynyl," as used herein, denotes a monovalent group derived from a hydrocarbon moiety containing, in certain embodiments, from two to six carbon atoms having at least one carbon-carbon triple bond. The triple bond may or may not be the point of attachment to another group. Alkynyl groups include, but are not limited to, for example, ethynyl, propynyl, butynyl, pentynyl, hexynyl, heptynyl, octynyl, nonynyl, decynyl, and the like.

The term "alkoxy" refers to an —O-alkyl radical.

The terms "hal," "halo," and "halogen," as used herein, refer to an atom selected from fluorine, chlorine, bromine and iodine.

The term "cycloalkyl," as used herein, denotes a monovalent group derived from a monocyclic or polycyclic saturated or partially unsaturated carbocyclic ring compound. Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_2$-cycloalkyl include, but not limited to, cyclopropyl, cyclobutyl, cyclopentyl, cyclohexyl, bicyclo [2.2.1] heptyl, and bicyclo [2.2.2] octyl.

The term "cycloalkenyl," as used herein, denotes a monovalent group derived from a monocyclic or polycyclic saturated or partially unsaturated carbocyclic ring compound comprising at least one carbon-carbon double bond. Examples of $C_4$-$C_8$ cycloalkenyl include, but not limited to, cyclobutenyl, cyclopentenyl, cyclohexenyl, cyclopentenyl and cyclooctenyl.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl, and the like.

The term "aralkyl." as used herein, refers to an alkyl residue, such as those described herein, attached to an aryl ring, such as those described herein. Examples include, but are not limited to, benzyl, phenethyl, and the like.

The term "heteroaryl." as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, indazoyl, cinnolinyl, phthalazinyl, pyridazinyl, indolyl, acridinyl, benzoquinolinyl, pyrimidinyl, a purinyl, pyrrolopyrimidinyl, quinoxalinyl, quinazolinyl, indazolinyl, and phthalazinyl, and the like.

The term "heteroaralkyl," as used herein, refers to an alkyl residue, such as those described herein, attached to a heteroaryl ring, such as those described herein. Examples include, but are not limited to, pyridinylmethyl, pyrimidinylethyl, and the like.

In accordance with the application, any of the aryls, substituted aryls, heteroaryls and substituted heteroaryls described herein, can be any aromatic group. Aromatic groups can be substituted or unsubstituted.

The term "heterocyclyl," as used herein, refers to a non-aromatic mono- or poly-cyclic (e.g., bi-, or tri-cyclic or more) fused or non-fused, radical or ring system having from three to ten ring atoms of which one ring atoms is selected from S, O, and N; zero, one, or two ring atoms are additional heteroatoms independently selected from S, O, and N; and the remaining ring atoms are carbon. Representative heterocycloalkyl groups include, but are not limited to, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl, and the like.

The term "alkylamino" refers to a group having the structure —NH($C_1$-$C_{12}$ alkyl), e.g., —NH($C_1$—C(alkyl), where $C_1$-$C_6$ alkyl is as previously defined.

The term "dialkylamino" refers to a group having the structure —N($C_1$-$C_{12}$ alkyl)$_2$, e.g., —NH($C_1$-$C_6$ alkyl), where $C_1$-$C_6$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

As described herein, compounds of the application and moieties present in the compounds may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocyclyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I, —OH, protected hydroxy, —NO$_2$, —CN, —NH$_2$, protected amino, —NH—$C_1$-$C_2$-alkyl, —NH—$C_2$-$C_{12}$-alkenyl, —NH—$C_2$-$C_{12}$-alkenyl. —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)— heteroaryl, —C(O)-heterocycloalkyl, —CONH$_2$, —CONH—$C_1$-$C_{12}$-alkyl, —CONH—$C_2$-$C_2$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl. —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_2$-alkenyl, —OCONH—$C_3$-$C_{12}$-cycloalkyl, —OCONH-aryl. —OCONH-heteroaryl, —OCONH— heterocycloalkyl, —NHC(O)—$C_1$-$C_2$-alkyl, —NHC(O)—$C_2$-$C_{12}$-alkenyl, —NHC(O)—$C_2$-$C_2$-alkenyl, —NHC(O)—$C_3$-$C_{12}$-cycloalkyl, —NHC(O)-aryl, —NHC(O)-heteroaryl, —NHC(O)— heterocycloalkyl, —NHCO$_2$—$C_1$-$C_2$-alkyl, —NHCO$_2$—$C_2$-$C_{12}$-alkenyl, —NHCO$_2$—$C_2$-$C_{12}$-alkenyl, —NHCO$_2$—$C_3$-$C_{12}$-cycloalkyl, —NHCO$_2$-aryl, —NHCO$_2$-heteroaryl, —NHCO$_2$— heterocycloalkyl, NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{1f}$-cycloalkyl, —NHC(O)NH-aryl, —NHC(O)NH-heteroaryl. NHC(O)NH-heterocycloalkyl, —NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_{12}$-alkenyl, —NHC(NH)NH—$C_2$-$C_2$-alkenyl, —NHC(NH)NH—$C_3$-$C_{12}$-cycloalkyl, —NHC(NH)NH-aryl, —NHC(NH)NH-heteroaryl, —NHC(NH)NHheterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl. —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_1$-alkenyl, C(NH)NH—$C_3$-$C_{12}$-cycloalkyl, —C(NH)NH-aryl, —C(NH)NH-heteroaryl, —C(NH)NHheterocycloalkyl, —S(O)—$C_1$-$C_{12}$-alkyl, —S(O)—$C_2$-$C_2$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-SO$_2$NH$_2$, —SO$_2$NH—$C_1$-$C_2$-alkyl, —SO$_2$NH—$C_2$-$C_{12}$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract; kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands; neuroblastoma. Thus, the term "cancerous cell" as provided herein, includes a cell afflicted by any one of the above-identified conditions.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

The terms "disease(s)", "disorder(s)", and "condition(s)" are used interchangeably, unless the context clearly dictates otherwise.

The term "therapeutically effective amount" of a compound or pharmaceutical composition of the application, as used herein, means a sufficient amount of the compound or pharmaceutical composition so as to decrease the symptoms of a disorder in a subject. As is well understood in the medical arts a therapeutically effective amount of a compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific modulatory (e.g., inhibitory or stimulatory) dose for any particular patient will depend upon a variety of factors including the disorder being treated and the severity of the disorder; the activity of the specific compound employed; the specific composition employed; the age, body weight, general health, sex and diet of the patient the time of administration, route of administration, and rate of excretion of the specific compound employed; the duration of the treatment; drugs used in combination or coincidental with the specific compound employed; and like factors well known in the medical arts.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, 7-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein, refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application.

"Prodrug", as used herein, means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology." John Wiley and Sons, Ltd. (2002).

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

This application also encompasses pharmaceutical compositions containing, and methods of treating disorders through administering, pharmaceutically acceptable prodrugs of compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews*. 1996, 19, 1-15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described herein, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

When any variable (e.g., $R_1$) occurs more than one time in any constituent or formula for a compound, its definition at each occurrence is independent of its definition at every other occurrence. Thus, for example, if a group is shown to be substituted with one or more R moieties, then R at each occurrence is selected independently from the definition of R. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center, e.g., carbon. Absolute configuration refers to the arrangement in space of the substituents attached to the chiral center. The substituents attached to the chiral center under consideration are ranked in accordance with the Sequence Rule of Cahn, Ingold and Prelog. (Cahn et al., Angew. Chem. Inter. Edit. 1966, 5, 385: errata 511; Cahn et al., Angew. Chem. 1966, 78, 413; Cahn and Ingold, J Chem. Soc. 1951 (London), 612; Cahn et al., Experientia 1956, 12, 81: Cahn, J. Chem. Educ. 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques: it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present application, the structural formula of the compound represents a certain isomer for convenience in some cases, but the present application includes all isomers, such as geometrical isomers, optical isomers based on an asymmetrical carbon, stereoisomers, tautomers, and the like. In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

EXAMPLES

The purity of all compounds was over 95% and was analyzed with Waters LC/MS system. $^1$H NMR was obtained at 400 MHz. Chemical shifts are reported relative to dimethyl sulfoxide ($\delta$=2.50) for H NMR Data are reported as (br=broad, s=singlet, d=doublet, t=triplet, q=quartet, m=multiplet).

Abbreviations used in the following examples and elsewhere herein are:
AcOH acetic acid
atm atmosphere
BOC2O di-tert-butyl dicarbonate
br broad
$CuSO_4$ copper sulfate
$CDCl_3$ deuterated chloroform DCM dichloromethane
DIEA N,N-diisopropylethylamine
DMA N,N-dimethylacetamide
DMAP 4-dimethylaminopyridine
DMF N,N-dimethylformamide
DMSO dimethyl sulfoxide
DMSO-$d_6$ deuterated dimethyl sulfoxide
EDCl 1-ethyl-3-(3-dimethylaminopropyl) carbodiimide
ESI electrospray ionization
EtOAc ethyl acetate
HCl hydrochloric acid
h hour(s)
HATU bis(dimethylamino)methylene-1H-1,2,3-triazolo[4,5-b]pyridinium 3-oxide hexafluoro-phosphate
HPLC high-performance liquid chromatography
KHMDS potassium hexamethylsilazide
LCMS liquid chromatography-mass spectrometry
m multiplet
mL milliliter
MeCN acetonitrile
MeOH methanol
mg milligram
mmol millimole
$MgSO_4$ magnesium sulfate
MHz megahertz
min minutes
MS mass spectrometry
$Na_2CO_3$ sodium carbonate
$NaHCO_3$ sodium bicarbonate
NMR nuclear magnetic resonance
Tf triflate
$Pd_2(dba)_3$ tris(dibenzylideneacetone)dipalladium(0)
$Pd(PPh_3)_2Cl_2$ bis(triphenylphosphine)palladium(II) dichloride
$PhN(SO_2CF_3)_2$ N-phenyl-bis(trifluoromethanesulfonamide
$PMe_3$ trimethylphosphine
ppm parts per million
PTSA para-toluene sulfonic acid
rt room temperature
TBAF tetra-n-butylammonium fluoride
t-BuOH tert-butanol
TFA trifluoroacetic acid
TMS trimethylsilane
THF tetrahydrofuran
TLC thin layer chromatography
μL microliter
Xphos 2-dicyclohexylphosphino-2',4',6'-triisopropylbiphenyl
Z' Z-factor statistical value Example 1: Synthesis of Compounds 1-20 and 29-38

Compounds 1-20 and 29-38 were prepared according to Schemes 1a-1c. The first step was a copper-catalyzed Ullmann-type coupling between the requisite aniline and the properly substituted 2-bromobenzoic acid or 2-iodobenzoic acid to form the corresponding diphenylamine. Representative reaction conditions include either $Cu_2O$ (0.05 eq), Cu (0.1 eq), and $K_2CO_3$ (1.2 eq), refluxed in DMF overnight. Variations in base, solvent, and copper source could be employed.

The second step was a cyclodehydration in $H_2SO_4$: $H_2O$ (10:1) at elevated temperature (80° C. or higher, overnight) to afford the substituted 10H-acridin-9-one. Other strongly acidic reagents, for example, polyphosphoric acid, were also effective for this purpose. In cases where the diphenylamine was synthesized from a starting aniline that did not possess an ortho-substituent, a mixture of regioisomers was obtained from the cyclodehydration. This mixture could be separated using normal phase silica gel chromatography.

Alkylation of the 10H-acridin-9-one was accomplished with ethyl bromoacetate and an excess of $Cs_2CO_3$ with heating in DMF (80° C., 2 hr). The ester of the bromoacetate, the base, and the solvent utilized in this step could be modified as needed. If the alkylation during produced a putative mixture of N- and O-alkylated products, the ratio depended on the 10H-acridin-9-one substituents. These products were saponified as a mixture using metal hydroxide (NaOH, LiOH, or KOH) in a protic solvent, such as methanol or a THF/water mixture. Purification by extraction or reverse phase prep-HPLC delivered the desired substituted 10-carboxymethyl-9-acridinone.

Example 2: Synthesis of Compound 13

Step 1: Synthesis of N-(2,3-dichloro-phenyl)-anthranilic acid 2-bromobenzoic acid (4.0 g, 19.9 mmol, 1 eq), 2,3-dichloroaniline (3.55 g, 21.9 mmol, 1.1 eq), $Cu_2O$ (849 mg, 5.9 mmol, 0.3 eq), Cu (384 mg, 5.9 mmol, 0.3 eq), and $K_2CO_3$ (5.8 g, 41.3 mmol, 2.05 eq) were combined in DMF and heated to 140° C. for 4 hrs. The mixture was cooled to room temperature, pour onto ice-water, acidified with 2M aqueous HCl, and extracted with ethyl acetate (25 mL×5). The combined organic layers were washed with brine and concentrated to give the crude product which was triturated petroleum ether to give 2.9 g of the desired material as a solid. Calc for $C_{13}H_9C_2NO_2$+H: 282.0 found: 282.1 m/z.

Step 2: Synthesis of 3,4-dichloroacridone 2.9 g of crude N-(2,3-dichloro-phenyl)-anthranilic acid was combined with 30 mL of polyphosphoric acid and then heated to 140° C. for 4 hrs. The mixture was cooled to room temperature and poured into ice-water. The pH was neutralized with a saturated aqueous solution of sodium bicarbonate. The mixture was then extracted with ethyl acetate (20 mL×3). The organic layer was dried, filtered, and concentrated to give 880 mg of crude 3,4-dichloroacridone as a solid. Calc for $C_{13}H_7C_2NO$+H: 264.0; found: 264.2 m/z.

Step 3: Synthesis of 9-oxoacridine-10-acetic acid ethyl ester

Crude 3,4-dichloroacridone (360 mg, 1.36 mmol, 1 eq) was combined with bromo ethylacetate (295 mg, 1.8 mmol, 1.3 eq) and $Cs_2CO_3$ (886 mg, 2.72 mmol, 2 eq) in acetonitrile (10 mL). The mixture was heated with stirring to 80° C. overnight, and then cooled to room temperature, filtered, and concentrated in vacuo to give 294 mg of a crude oil, which was used directly in the next step. Calc for $C_{17}H_3Cl_2NO_3$+H: 350.0; found: 350.2 m/z.

Step 4: Synthesis of Compound 13

Crude 9-oxoacridine-10-acetic acid ethyl ester (294 mg, 0.82 mmol, 1 eq) was stirred in THF (5 mL) at room temperature. LiOH (133 mg, 3.28 mmol, 4 eq) was dissolved in 2 mL of $H_2O$ and added dropwise to the reaction mixture. The mixture was stirred at room temperature for 5 hrs. The reaction mixture was then diluted into water and extracted with ethyl acetate (5 mL×3). The organic layer was then washed with water (5 mL). The aqueous layers were combined, pH adjusted to ~2 with 2M aqueous HCl, and extracted with ethyl acetate (5 mL×3). The organic layer was dried and concentrated to give a residue that was triturated with petroleum ether: ethyl acetate (3:1, 4 mL) to give the target compound as a yellow solid (37.1 mg, 14%).

Example 3: Synthesis of Compound 26

Compound 26 was prepared from 3-bromo-4-methyl-9-oxoacridine-10-acetic acid ethyl ester by Sonogashira coupling (NaI, 1 eq; CuI, 1 eq; $PPh_3$, 1 eq; $Pd(PPh_3)_4$, 0.1 eq; TEA, 75° C. overnight: 43%) followed by catalytic hydrogenation (Pd/C. MeOH/THF, rt overnight, 84%) and saponification in the usual manner.

Example 4: Synthesis of Compound 27

Compound 27 was prepared from 3-bromo-4-methyl-9-oxoacridine-10-acetic acid ethyl ester by Suzuki reaction of I-cyclohexen-1-yl-boronic acid pinacol ester with 3-bromo-4-methyl-9-oxoacridine-10-acetic acid ethyl ester by Sonogashira coupling ($PdCl_2(dppf)CH_2Cl_2$, 0.1 eq; $K_2CO_3$, 2 eq; dioxane/water, 15 mL/3 mL; 78° C., overnight, 19%) followed by saponification of the ethyl ester in the usual manner.

Example 5: Synthesis of Compound 21

Compound 21 was prepared by bromination of 10-carboxymethyl-9-acridone ($Br_2$, 1.3 eq: AcOH, rt) which yielded a 2:1 mixture of the mono- and di-brominated product. The mixture was alkylated with bromo ethylacetate and saponified using the standard conditions.

Example 6: Synthesis of Compound 22

Compound 22 was prepared from Sonogashira coupling of phenyl acetylene with Compound 21 (NaI, 1 eq; CuI, 1 eq; $PPh_3$, 1 eq: $Pd(PPh_3)_4$, 0.1 eq: TEA, 75° C. overnight: 22%) followed by saponification using the standard conditions.

Example 7: Synthesis of Compound 25

Compound 25 was prepared by Suzuki coupling of 1-cyclohexen-1-yl-boronic acid pinacol ester with Compound 21 ($PdCl_2(dppf)CH_2Cl_2$, 0.1 eq; $K_2CO_3$, 2 eq; dioxane/water, 15 mL/3 mL; 78° C., overnight, 16%), followed by catalytic hydrogenation on palladium and then saponification in the usual manner to yield the target compound.

Example 8: Synthesis of Compounds 47-49, 51-53, 55-58, 66, 78, 79, 81-85, 89, 92-94, 96-99, 102, 111, 112, 120, 121, 124, 127, and 128

Compounds 47-49, 51-53, 55-58, 66, 78, 79, 81-85, 89, 92-94, 96-99, 102, 111, 112, 120, 121, 124, 127, and 128 were prepared according to the steps described in Scheme 1 with the appropriate starting materials.

Example 9: Synthesis of Compounds 86 and 90

Compounds 86 and 90 were prepared according to the steps described in Scheme 2 with the appropriate starting materials.

Example 10: Synthesis of Compounds 39,40,42,43,74-76, 80, 88 and 90

Compounds 39, 40, 42, 43, 74-76, 80, 88 and 90 were prepared according to the steps described in Scheme 3 with the appropriate starting materials.

Example 11: Synthesis of Compounds 41, 50, 54, 65, 67, 68, 72, 73, 77, 91, 114-116 and 125

Compounds 41, 50, 54, 65, 67, 68, 72, 73, 77, 91, 114-116 and 125 were prepared according to the steps described in Scheme 4 with the appropriate starting materials.

Example 12: Synthesis of Compounds 44-46, 59-64, 69, 70, 71, 95, 107.117-119, 122, 123, 126, and 129

Compounds 44, 46, 59-61, 69, 71, 95, 117-119, 122, 123, 126, and 129 were prepared through nucleophilic substitution from Compound 30.
Compounds 70 and 107 were prepared through nucleophilic substitution from Compound 83.
Compounds 45 and 62-64 were prepared through nucleophilic substitution from Compound 93.

Example 13: Synthesis of Compound 90

Compound 90 was prepared according to the steps described in Scheme 3 with the appropriate starting materials.

Example 14: Synthesis of Compounds 67, 68, 72, 88, and 125

Compound 88 and Compounds 67, 68, 72, and 125 were prepared from Compound 89, according to Scheme 3 and Scheme 4, respectively.

Example 15: Synthesis of Compounds 73, 74, and 80

Compound 73 and Compounds 74 and 80 were prepared from Compound 21, according to Scheme 4 and Scheme 3, respectively.

Example 16: Synthesis of Compounds 75-77

Compounds 75 and 76 and Compound 77 were prepared from Compound 78, according to Scheme 3 and Scheme 4, respectively.

Example 17: Synthesis of Compounds 50, 65, 91, and 114-116

Compounds 50, 65, 91, and 114-116 were prepared from Compound 79, according to Scheme 4.

Example 18: Synthesis of Compound 87

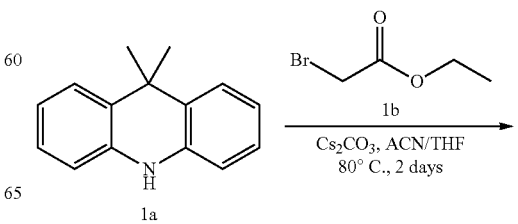

-continued

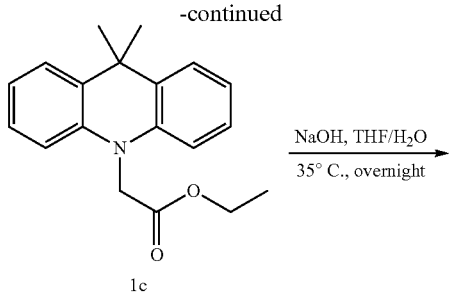
1c

NaOH, THF/H₂O
35° C., overnight
→

87

Step 1
To a mixture of 1a (880 mg, 4.2 mmol, 1.0 eq) and Cs₂CO₃ (3.4 g, 10.5 mmol, 2.5 eq) in acetonitrile/THF (5.0 mL/4.0 mL) was added 1b (1.02 mg, 6.3 mmol, 1.50 eq) at rt. The mixture was then stirred at 80° C. for 2 days, cooled to room temperature and filtered through celite. The filtrate was concentrated in vacuo to give crude product, which was purified by silica gel chromatography (PE/EtOAc, v/v=10:1-1:2) to afford 1c (80 mg, 6.4%) as a yellow solid. LC/MS: 296.2 [M+H]⁺.

Step 2
To mixture of 1c (15.0 mg: 0.05 mmol, 1.0 eq) in THF (3 mL) was added dropwise a solution of NaOH (8.0 mg, 0.2 mmol, 4.0 eq) in H₂O (1.0 mL). The reaction mixture was stirred at 35° C. overnight, then cooled to room temperature, and diluted with ice-water (3.0 mL), extracted with DCM (3.0 mL×3). The aqueous layer was acidified to pH=3 with 2 N HCl and extracted with EtOAc (5.0 mL×4). The combined organic layers were dried over anhydrous Na₂SO₄ and filtered. The filtrate was concentrated in vacuo. The residue was triturated with PE/EtOAc (v/v=3:1) and filtered to afford Compound 87 (5.0 mg, 37.6%) as a yellow solid. ¹H NMR (400 MHz, DMSO-d₆): δ 7.43 (m, 2H), 7.18-7.14 (m, 2H), 6.98-6.94 (m, 2H), 6.81 (d, J=8.0 Hz, 2H), 4.68 (s, 2H), 1.51 (s, 6H). LC/MS: 268.4 [M+H]⁺.

Example 19: Synthesis of Compound 85

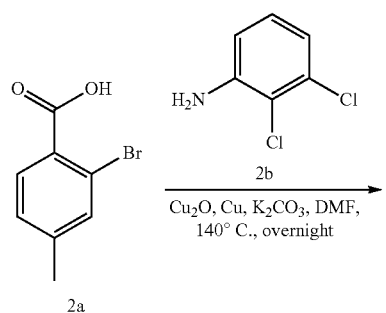

-continued

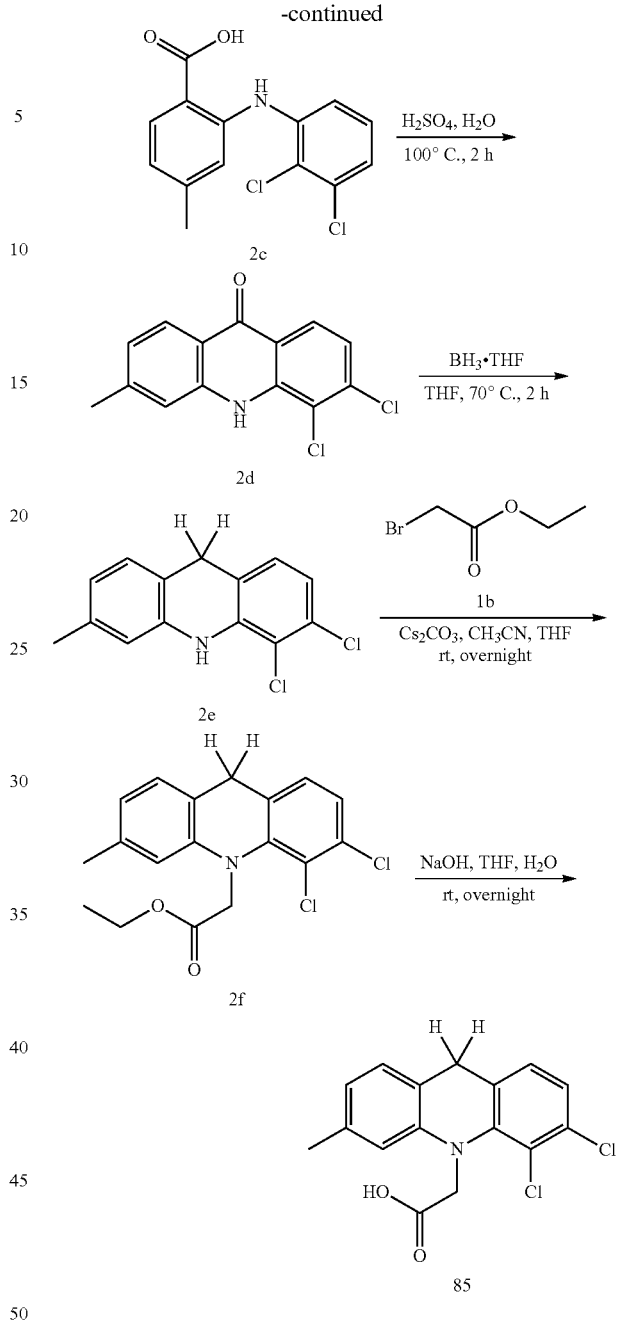

Step 1
A mixture of 2a (5.0 g, 23.25 mmol, 1.0 eq), 2b (4.14 g, 25.58 mmol, 1.1 eq), potassium carbonate (8.02 g, 58.13 mmol, 2.5 eq), copper powder (443.0 mg, 6.98 mmol, 0.3 eq) and Copper(I) oxide (997.0 mg, 6.98 mmol, 0.3 eq) in DMF (100.0 mL) was stirred at 140° C. overnight under argon atmosphere, then cooled to room temperature. Water (50.0 mL) was added. The mixture was filtered through celite. The filtrate was acidified to pH=2 with 2 N HCl, then water (50.0 mL) was added. The resulting mixture was extracted with EtOAc (50.0 mL×3). The combined organic layers were washed with brine (20.0 mL×5), dried over anhydrous Na₂SO₄ and filtered. The filtrate was concentrated in vacuo to afford crude 2c (crude, 4.61 g, 67.0%). LCMS: 296.1 [M+H]⁺.

Step 2

A mixture of 2c (4.61 g, 15.6 mmol), sulfuric acid (20.0 mL) and H$_2$O (2.0 mL) was heated at 100° C. for 2 hours, then cooled and poured into a mixture of ice and water. The suspension was filtered and the filter cake was washed with water (20.0 mL×3), dried in vacuo to afford crude 2d (1.0 g, 20.4%). LCMS: 278.1 [M+H]$^+$.

Step 3

To a mixture of 2d (300.0 mg, 1.08 mmol) in THF (10.0 mL) was added BH$_3$.THF (1 M in THF, 5.5 mL). The mixture was stirred at 70° C. for 2 h, diluted with water (30.0 mL), extracted with EtOAc (15.0 mL×3). The combined organic layers were concentrated in vacuo. The residue was triturated with PE/EtOAc (v/v=20:1) and filtered to afford 2e (120 mg, 42.0%) as a yellow solid. LC/MS: 264.1 [M+H]$^+$.

Step 4

To a mixture of 2e (120.0 mg, 0.46 mmol, 1.0 eq) and Cs$_2$CO$_3$ (446.0 mg, 1.37 mmol, 3.0 eq) in a mixture solvent of acetonitrile/THF (5.0 mL/5.0 mL) was added 1b (153.0 mg, 0.92 mmol, 2.0 eq). The mixture was stirred at room temperature overnight, then filtered through celite. The filtrate was concentrated in vacuo. The residue was triturated with PE/EtOAc (v/v=10:1) and filtered to afford 2f (40 mg, 25.5%) as a yellow solid. LC/MS: 350.1 [M+H]$^+$.

Step 5

To mixture of 2f (40 mg; 0.12 mmol, 1.0 eq) in THF (20.0 mL) was added dropwise a solution of NaOH (19.0 mg, 0.46 mmol, 4.0 eq) in H2O (8.0 mL). The reaction mixture was stirred at room temperature overnight, diluted with ice-water (30.0 mL), extracted with EtOAc (15.0 mL×3). The aqueous layer was acidified to pH=3 with 2 N HCl and extracted with EtOAc (25.0 mL×3). The combined organic layers were dried over anhydrous Na$_2$SO$_4$ and filtered. The filtrate was concentrated in vacuo to afford Compound 85 (15.0 mg, 40.8%) as a yellow solid. $^1$H NMR (400 MHz, DMSO-d$_6$): δ 7.27 (d, J=8.0 Hz, 1H), 7.18 (d, J=8.0 Hz, 1H), 7.08 (s, 1H), 7.03 (d, J=7.6 Hz, 1H), 6.80 (d, J=7.2 Hz, 1H), 4.75 (s, 2H), 3.92 (s, 2H), 2.26 (s, 3H). LC/MS: 322.1 [M+H]$^+$.

Example 20: Synthesis of Compound 81

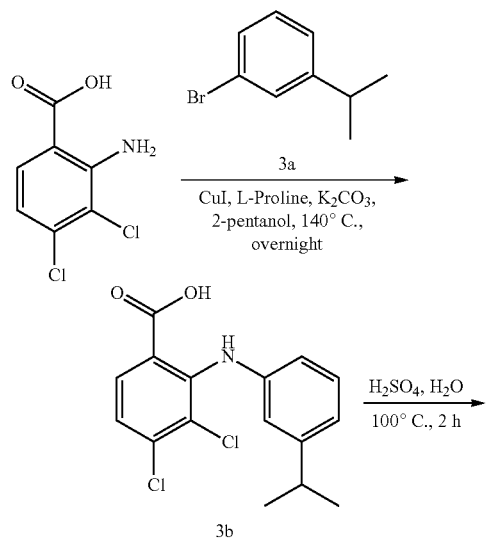

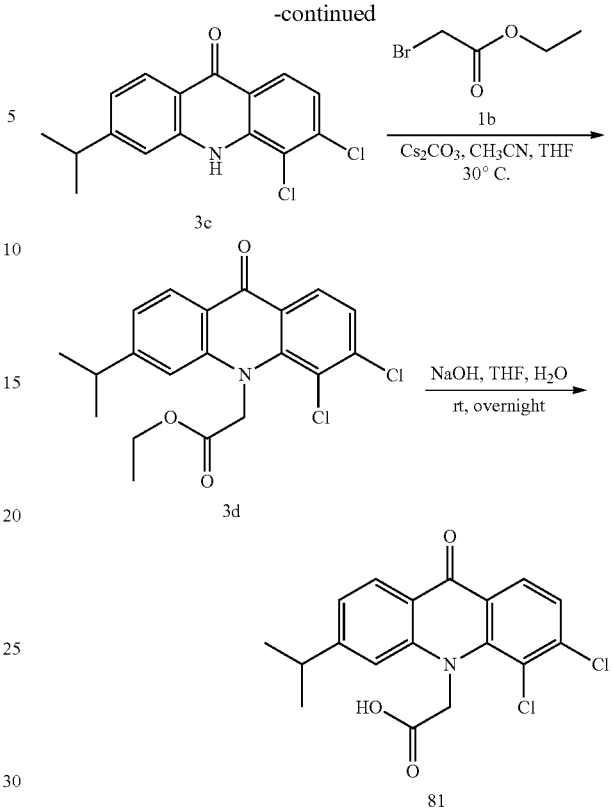

Step 1

A mixture of 2-amino-3,4-dichlorobenzoic acid (1.0 g, 4.85 mmol, 1.0 eq), 3a (1.93 g, 9.70 mmol, 2.0 eq), potassium carbonate (1.34 g, 9.70 mmol, 2.0 eq), L-proline (0.17 g, 1.46 mmol, 0.3 eq), and Copper(I) iodide (0.28 g, 1.46 mmol, 0.3 eq) in 2-Pentanol (30 mL) was stirred at 140° C. overnight under argon atmosphere, then cooled to room temperature, water (30.0 mL) was added. The mixture was filtered through celite. The filtrate was acidified to pH=2 with 2 N HCl, then water (30.0 mL) was added. The resulting mixture was extracted with EtOAc (30.0 mL×3). The combined organic layers were washed with brine (30.0 mL×3), dried over anhydrous Na$_2$SO$_4$ and filtered. The filtrate was concentrated in vacuo to afford crude 3b (1 g, 63.6%). LC/MS: 324.0 [M+H]$^+$.

Step 2

A mixture of 3b (1.0 g, 3.09 mmol, 1.0 eq), sulfuric acid (20.0 mL) and H$_2$O (2.0 mL) was heated at 100° C. for 2 hours, then cooled and poured into a mixture of ice and water (20.0 mL). The solid was collected by filtration and dried in vacuo to afford crude 3c (0.3 g, 31.9%). LC/MS: 306.0 [M+H]$^+$.

Step 3

To a mixture of 3c (0.3 g, 0.98 mmol, 1.0 eq) and Cs$_2$CO$_3$ (0.96 g, 2.94 mmol, 3.0 eq) in acetonitrile/THF (15.0 mL/15.0 mL) was added 1b (0.33 g, 1.96 mmol, 2.0 eq). The mixture was stirred at 30° C. overnight, cooled to room temperature and filtered through celite. The filtrate was concentrated in vacuo. The residue was triturated with PE/EtOAc (v/v=10:1) and filtered to afford 3d (0.05 g, 13.2%) as a yellow solid. LC/MS: 392.1 [M+H]$^+$.

Step 4

To mixture of 3d (50.0 mg; 0.13 mmol, 1.0 eq) in THF (4.0 mL) was added dropwise a solution of NaOH (20.8 mg, 0.52 mmol, 4.0 eq) in H₂O (1 mL). The reaction mixture was stirred at room temperature for overnight, diluted with ice-water (20.0 mL), extracted with EtOAc (15.0 mL×3). The aqueous layer was acidified to pH=3 with 2 N HC and extracted with EtOAc (25.0 mL×3). The combined organic layers were dried over anhydrous Na₂SO₄ and filtered. The filtrate was concentrated in vacuo to afford Compound 81(40.0 mg, 86.9%) as a yellow solid. ¹H NMR (400 MHz, DMSO-d₆): δ 13.11 (br, 1H), 8.21 (d, J=8.8 Hz, 1H), 8.12 (d, J=8.4 Hz, 1H), 7.62 (d, J=8.4 Hz, 1H), 7.50 (s, 1H), 7.31 (d, J=7.6 Hz, 1H), 5.22 (s, 2H), 3.65 (m, 1H), 1.27 (d, J=68 Hz, 6H). LC/MS: 364.2[M+H]⁺.

Example 21: Synthesis of Compound 79

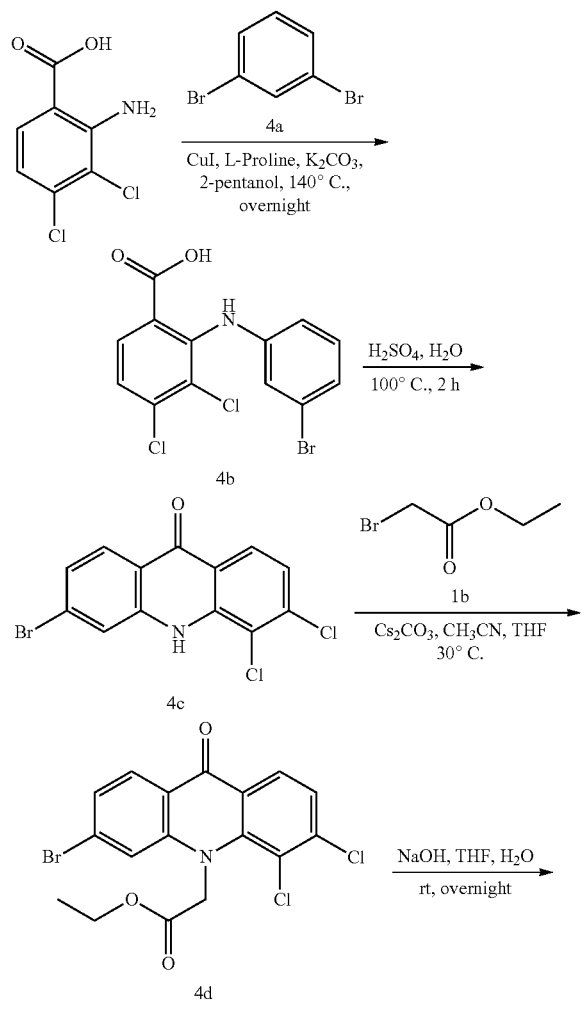

Step 1

A mixture of 2-amino-3,4-dichlorobenzoic acid (5.0 g, 24.3 mmol, 1.0 eq), 4a (17.2 g, 72.9 mmol, 3.0 eq), potassium carbonate (10 g, 72.9 mmol, 3.0 eq), L-proline (0.84 g, 7.29 mmol, 0.3 eq), and Copper(I) iodide (1.39 g, 7.29 mmol, 0.3 eq) in 2-Pentanol (50 mL) was stirred at 140° C. for overnight under argon atmosphere, then cooled to room temperature, water (50.0 mL) was added. The mixture was filtered through celite. The filtrate was acidified to pH=2 with 2 N HCl, then water (50.0 mL) was added. The resulting mixture was extracted with EtOAc (50.0 mL×3). The combined organic layers were washed with brine (30.0 mL×3), dried over anhydrous Na₂SO₄ and filtered. The filtrate was concentrated in vacuo to afford crude 4b (4.0 g, 48.0%). LC/MS: 359.9 [M+H]⁺.

Step 2

A mixture of 4b (4.0 g, 11.1 mmol, 1.0 eq), sulfuric acid (20.0 mL) and H₂O (2.0 mL) was heated at 100° C. for 2 hours, then cooled and poured into a mixture of ice and water (100.0 mL). The solid was collected by filtration and dried in vacuo to afford crude 4c (2.5 g, 65.8%). LC/MS: 341.9 [M+H]⁺.

Step 3

To a mixture of 4c (2.5 g, 7.29 mmol, 1.0 eq) and Cs₂CO₃ (7.13 g, 21.87 mmol, 3.0 eq) in acetonitrile/THF (15.0 mL/15.0 mL) was added 1b (2.43 g, 14.6 mmol, 2.0 eq). The mixture was stirred at 30° C. for overnight, cooled to room temperature and filtered through celite. The filtrate was concentrated in vacuo. The residue was triturated with PE/EtOAc (v/v=10:1) and filtered to afford 4d (0.2 g, 6.5%) as a yellow solid. LC/MS: 427.9 [M+H]⁺.

Step 4

To a mixture of 4d (0.2 g; 0.47 mmol, 1.0 eq) in THF (4.0 mL) was added dropwise a solution of NaOH (75.2 mg, 1.88 mmol, 4.0 eq) in H₂O (1 mL). The reaction mixture was stirred at room temperature overnight, diluted with ice-water (20.0 mL), extracted with EtOAc (15.0 mL×3). The aqueous layer was acidified to pH=3 with 2 N HCl and extracted with EtOAc (25.0 mL×3). The combined organic layers were dried over anhydrous Na₂SO₄ and filtered. The filtrate was concentrated in vacuo to afford Compound 79 (0.18 g, 95%) as a yellow solid. ¹H NMR (400 MHz, DMSO-d₆): δ 13.22 (s, 1H), 8.20 (d, J=8.4 Hz, 1H), 8.09 (d, J=8.4 Hz, 1H), 7.96 (d, J=1.6 Hz, 1H), 7.67 (d, J=8.4 Hz, 1H), 7.56 (dd, J=8.4 Hz, 1.6 Hz, 1H), 5.23 (s, 2H). LC/MS: 399.9 [M+H]⁺.

Example 22: Synthesis of Compound 59

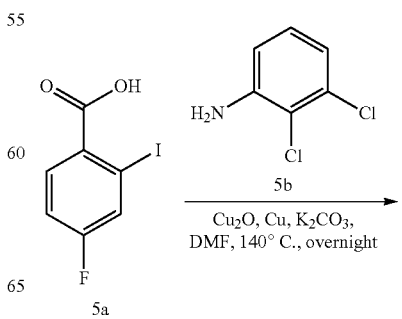

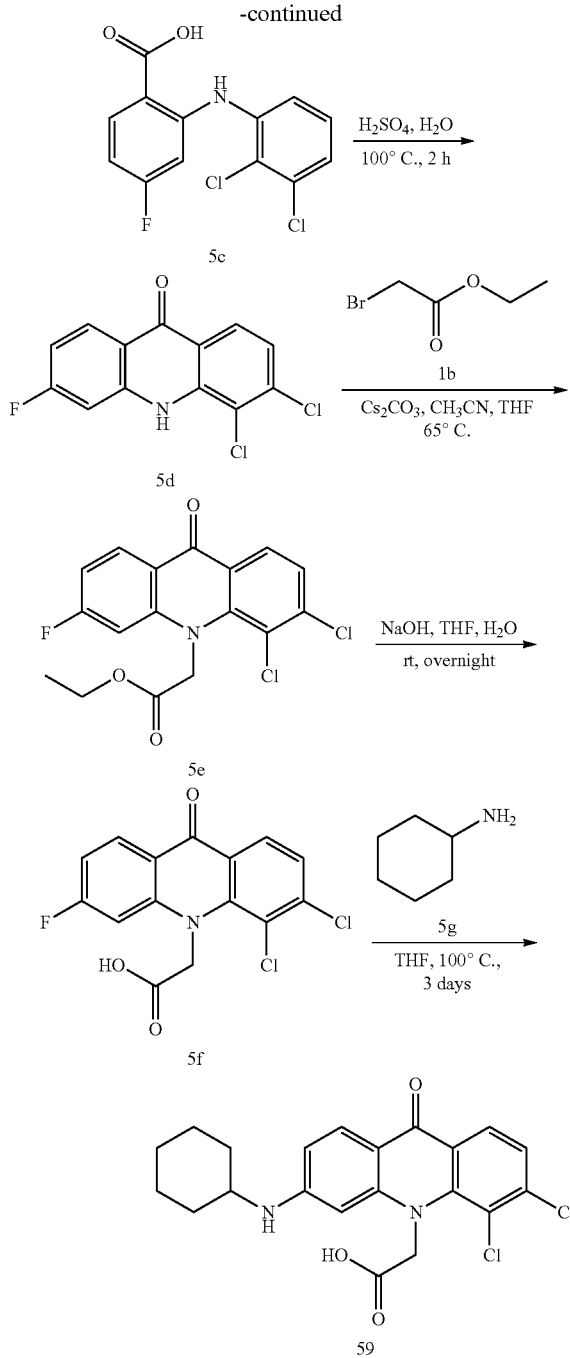

Step 2

A mixture of 5c (3.0 g, 10 mmol), sulfuric acid (15.0 mL) and $H_2O$ (2.0 mL) was heated at 100° C. for 2 hours, then cooled and poured into a mixture of ice and water (100.0 mL). The suspension was filtered and the filter cake was washed with water (20.0 mL×3) and dried in vacuo to afford crude 5d (1.7 g, 60.0%). LC/MS: 282.0 $[M+H]^+$.

Step 3

To a mixture of 5d (1.7 g, 6.05 mmol, 1.0 eq) and $Cs_2CO_3$ (5.92 g, 18.15 mmol, 3.0 eq) in a mixture solvent of acetonitrile/THF (15.0 mL/15.0 mL) was added 1b (2.02 g, 12.1 mmol, 2.0 eq). The mixture was stirred at 65° C. overnight, cooled to room temperature and filtered through celite. The filtrate was concentrated in vacuo. The residue was triturated with PE/EtOAc (v/v=10:1) and filtered to afford 5e (1.6 g, 73.0%) as a yellow solid. LC/MS: 368.0 $[M+H]^+$.

Step 4

To a mixture of 5e (1.6 g; 4.35 mmol, 1.0 eq) in THF (20.0 mL) was added dropwise a solution of NaOH (696.0 mg, 17.39 mmol, 4.0 eq) in $H_2O$ (8.0 mL). The reaction mixture was stirred at room temperature overnight, diluted with ice-water (30.0 mL), extracted with EtOAc (15.0 mL×3). The aqueous layer was acidified to pH=3 with 2 N HC and extracted with EtOAc (25.0 mL×3). The combined organic layers were dried over anhydrous $Na_2SO_4$ and filtered. The filtrate was concentrated in vacuo to afford 5f (1.5 g, 95%) as a yellow solid. LC/MS: 340.0 [M+H]+.

Step 5

To a mixture of 4f (60 mg, 0.18 mmol, 1.0 eq) in THF (2.0 mL) was added 4 g (3 mL). The mixture was stirred at 100° C. for three days, cooled to room temperature and purified by prep-HPLC to afford Compound 59 (45 mg, 60.8%) as a yellow solid. $^1$H NMR (400 MHz, DMSO-$d_6$): δ 13.17 (s, 1H), 8.15 (d, J=8.4 Hz, 1H), 7.88 (d, J=0.4 Hz, 1H), 7.54 (d, J=8.8 Hz, 1H), 6.88 (s, 1H), 6.66 (d, J=9.2 Hz, 1H), 6.40 (s, 1H), 5.00 (s, 2H), 1.96 (d, J=12.0 Hz, 2H), 1.74 (d, J=12.4 Hz, 2H), 1.63 (d, J=12.8 Hz, H), 1.41-1.18 (m, 6H). LC/MS: 419.1 $[M+H]^+$.

Example 23: Synthesis of Compound 71

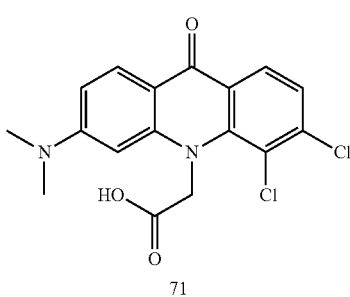

Step 1

A mixture of 5a (5.0 g, 18.8 mmol, 1.0 eq), 5b (4.60 g, 28.2 mmol, 1.5 eq), potassium carbonate (6.5 g, 47.0 mmol, 2.5 eq), copper powder (360.0 mg, 5.64 mmol, 0.3 eq), and Copper(I) oxide (810.0 mg, 5.64 mmol, 0.3 eq) in DMF (100.0 mL) was stirred at 140° C. overnight under argon atmosphere, then cooled to room temperature. Water (50.0 mL) was added. The mixture was filtered through celite. The filtrate was acidified to pH=2 with 2 N HCl, then water (50.0 mL) was added. The resulting mixture was extracted with EtOAc (50.0 mL×3). The combined organic layers were washed with brine (20.0 mL×5), dried over anhydrous $Na_2SO_4$ and filtered. The filtrate was concentrated in vacuo to afford crude 5c (3.0 g, 54.0%). LC/MS: 300.0 $[M+H]^+$.

A mixture of 5f (20 mg, 0.06 mmol, 1.0 eq) and Dimethylamine (2 mL, 2 M in THF) was stirred at 100° C. overnight in a sealed tube, then cooled to room temperature and purified by prep-HPLC to afford Compound 71 (20 mg, 93.0%) as a yellow solid. $^1$H NMR (400 MHz, DMSO-$d_6$): δ 8.16 (d, J=8.0 Hz, 1H), 7.98 (d, J=8.0 Hz, 1H), 7.57 (d, J=12 Hz, 1H), 6.84 (d, J=12 Hz, 1H), 6.54 (d, J=2 Hz, 1H), 5.14 (s, 2H), 3.09 (s, 6H). LC/MS: 365.1 [M+H]$^+$.

Example 24: Synthesis of Compound 72

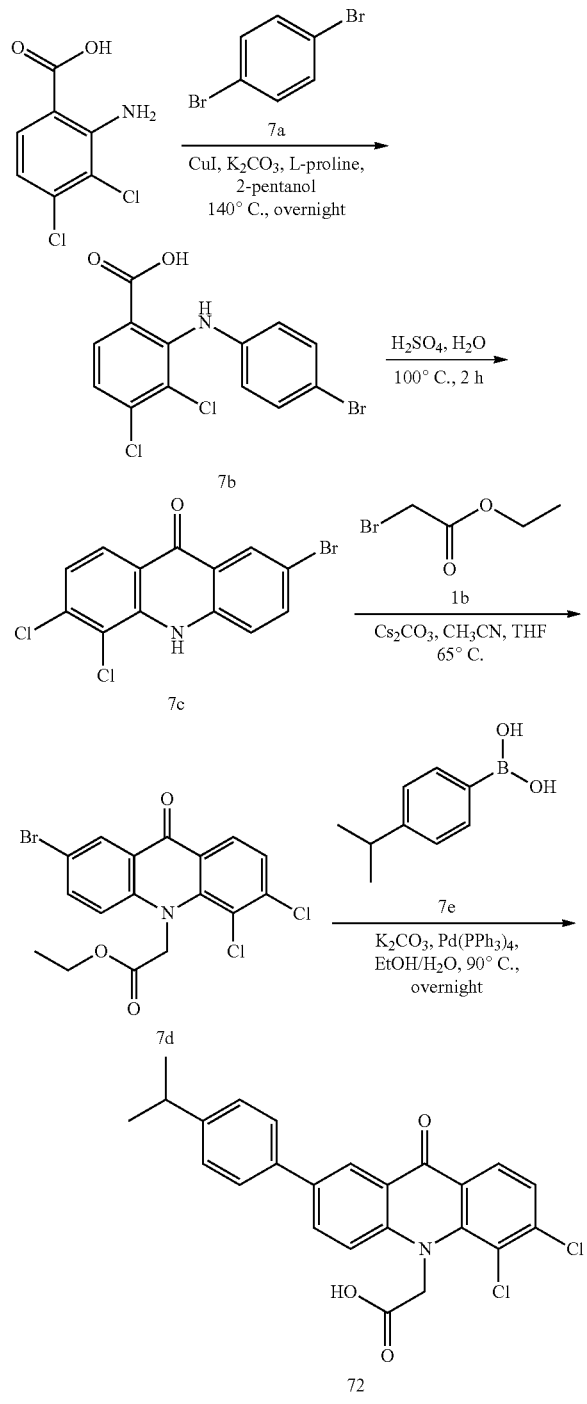

Step 1

A mixture of 2-amino-3,4-dichlorobenzoic acid (3.0 g, 14.56 mmol, 1.0 eq), 7a (10.27 g, 43.69 mmol, 3.0 eq), potassium carbonate (6.03 g, 43.69 mmol, 3.0 eq), Cuprous iodide (830.0 mg, 4.37 mmol, 0.3 eq), and L-proline (502.0 mg, 5.64 mmol, 0.3 eq) in 2-pentanol (100.0 mL) was stirred at 140° C. overnight under argon atmosphere, then cooled to room temperature. Water (50.0 mL) was added. The mixture was filtered through celite. The filtrate was acidified to pH=2 with 2 N HCl, then water (50.0 mL) was added. The resulting mixture was extracted with EtOAc (50.0 mL×3). The combined organic layers were washed with brine (20.0 mL×5), dried over anhydrous Na$_2$SO4 and filtered. The filtrate was concentrated in vacuo to afford crude 7b (crude, 4.0 g, 76.0%). LC/MS: 359.9 [M+H]$^+$ Step 2

A mixture of 7b (4.0 g, 11.14 mmol), sulfuric acid (20.0 mL) and H$_2$O (2.0 mL) was heated at 100° C. for 2 hours, then cooled and poured into a mixture of ice and water (100.0 mL). The suspension was filtered and the filter cake was washed with water (20.0 mL×3), dried in vacuo to afford 7c (crude, 1.0 g, 26.0%). LC/MS: 341.9 [M+H]$^+$.

Step 3

To a mixture of 7c (1.0 g, 2.92 mmol, 1.0 eq) and Cs$_2$CO$_3$ (2.90 g, 8.77 mmol, 3.0 eq) in a mixture solvent of acetonitrile/THF (15.0 mL/15.0 mL) was added 1b (950 mg, 5.85 mmol, 2.0 eq). The mixture was stirred at rt overnight, then cooled to room temperature and filtered through celite. The filtrate was concentrated in vacuo. The residue was triturated with PE/EtOAc (v/v=10:1) and filtered to afford 7d (crude, 350 mg, 28.0%) as a yellow solid. Crude 7d was used for the next step without purification. LC/MS: 427.9 [M+H]$^+$.

Step 4

To a mixture of 7d (100 mg, 0.233 mmol) and 7e (38 mg, 0.233 mmol, 1.0 eq) in EtOH/H$_2$O (8.0 mL/2.0 mL) were added K$_2$CO$_3$ (128 mg, 0.932 mmol, 4 eq) and Pd(PPh$_3$)$_4$ (14 mg, 0.017 mmol, 0.1 eq). The mixture was stirred at 50° C. overnight under N$_2$, then diluted with water (30.0 mL), extracted with EtOAc (15.0 mL×3). The extracts were concentrated in vacuo. The residue was purified by prep-HPLC to afford Compound 72 (7.5 mg, 8%) as a yellow solid. $^1$H NMR (400 MHz, DMSO-$d_6$): δ 13.21 (s, 1H), 8.40 (s, 1H), 8.27 (d, J=8.0 Hz, 1H), 8.16-8.14 (d, J=8.0 Hz, 1H), 7.77-7.66 (m, 1H), 7.44 (d, J=8.0 Hz, 1H), 5.24 (s, 2H), 3.09 (s, 6H), 1.27 (d, J=2.0 Hz, 6H). LC/MS: 440.1 [M+H]$^+$.

Example 25: Synthesis of Compound 68

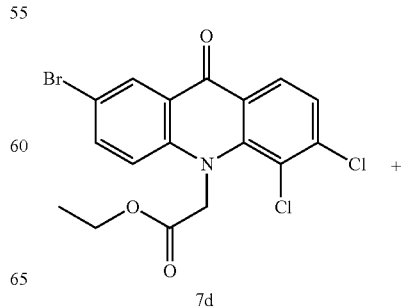

-continued

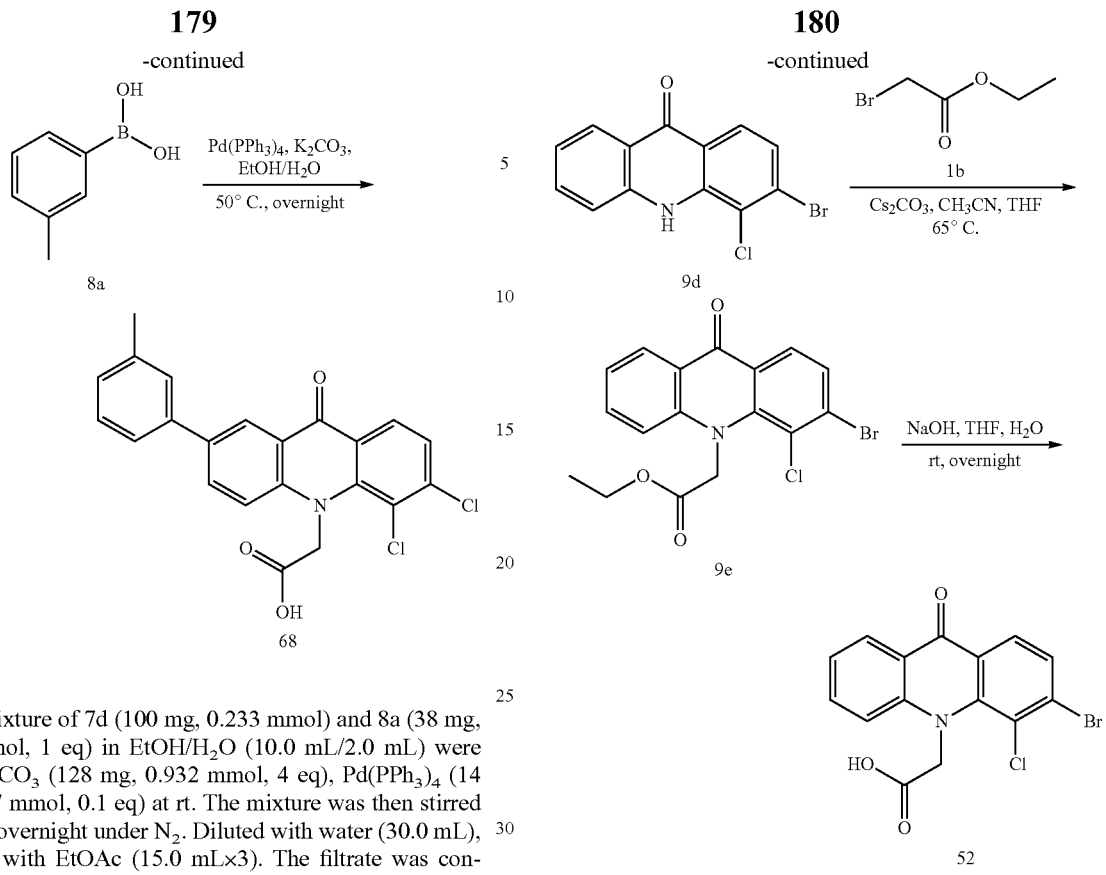

To a mixture of 7d (100 mg, 0.233 mmol) and 8a (38 mg, 0.233 mmol, 1 eq) in EtOH/H$_2$O (10.0 mL/2.0 mL) were added K$_2$CO$_3$ (128 mg, 0.932 mmol, 4 eq), Pd(PPh$_3$)$_4$ (14 mg, 0.017 mmol, 0.1 eq) at rt. The mixture was then stirred at 50° C. overnight under N$_2$. Diluted with water (30.0 mL), extracted with EtOAc (15.0 mL×3). The filtrate was concentrated in vacuo. The residue was purified by prep-HPLC to afford Compound 68 (7 mg, 7%) as a yellow solid. $^1$H NMR (400 MHz, DMSO-d$_6$): δ13.24 (s, 1H), 8.41 (s, 1H), 8.27 (d, J=8.8 Hz, 1H), 8.15 (d, J=11.6 Hz, 1H), 7.77 (d, J=8.8 Hz, 1H), 7.67 (d, J=8.4 Hz, 1H), 7.60 (s, 1H), 7.56 (d, J=7.6 Hz, 1H), 7.40 (t, J=8.0 Hz, 1H), 7.23 (d, J=7.2 Hz, 1H), 5.25 (s, 2H), 2.42 (s, 3H). LC/MS: 412.1 [M+H]$^+$.

Example 26: Synthesis of Compound 52

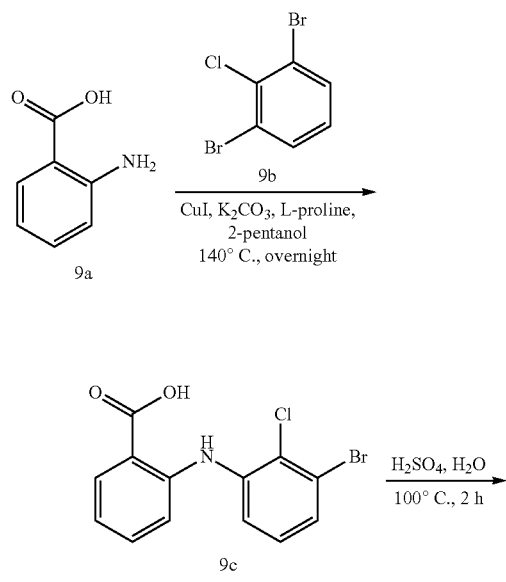

Step 1

A mixture of 9a (340 mg, 2.47 mmol, 1.0 eq), 9b (1.0 g, 3.70 mmol, 1.5 eq), potassium carbonate (1.03 g, 7.41 mmol, 3.0 eq), Cuprous iodide (141.0 mg, 0.74 mmol, 0.3 eq), and L-proline (85.0 mg, 0.74 mmol, 0.3 eq) in 2-pentanol (30.0 mL) was stirred at 140° C. overnight under argon atmosphere, then cooled to room temperature. Water (50.0 mL) was added. The mixture was filtered through celite. The filtrate was acidified to pH=2 with 2 N HCl, then water (50.0 mL) was added. The resulting mixture was extracted with EtOAc (50.0 mL×3). The combined organic layers were washed with brine (20.0 mL×5), dried over anhydrous Na$_2$SO$_4$ and filtered. The filtrate was concentrated in vacuo to afford 9c (crude, 600 mg, 74.5%). LC/MS: 326.0 [M+H]$^+$.

Step 2

A mixture of 9c (600 mg, 1.84 mmol), sulfuric acid (15.0 mL) and H$_2$O (2.0 mL) was heated at 100° C. for 2 h, then cooled and poured into a mixture of ice and water (50.0 mL), The solid was collected by filtration and dried in vacuo to afford 9d (crude, 500 mg, 88.4%). LC/MS: 307.9 [M+H]$^+$.

Step 3

To a mixture of 9d (300 mg, 0.97 mmol, 1.0 eq) and Cs$_2$CO$_3$ (950 mg, 2.91 mmol, 3.0 eq) in acetonitrile/THF (10.0 mL/10.0 mL) was added 1b (320 mg, 1.94 mmol, 1.2 eq). The mixture was stirred at 65° C. for 2 h, cooled to room temperature and filtered through celite. The filtrate was concentrated in vacuo. The residue was triturated with PE/EtOAc (v/v=10:1) and filtered to afford 9e (77 mg, 20.0%) as a yellow solid. LC/MS: 394.0 [M+H]$^+$.

Step 4

To a mixture of 9e (70 mg; 0.18 mmol, 1.0 eq) in THF (5.0 mL) was added dropwise a solution of NaOH (28.0 mg, 0.71 mmol, 4.0 eq) in H$_2$O (2.0 mL). The reaction mixture was stirred at room temperature overnight, diluted with ice-water (10.0 mL), extracted with EtOAc (15.0 mL×3). The aqueous layer was acidified to pH=3 with 2 N HCl and extracted with EtOAc (25.0 mL×3). The combined organic layers were dried over anhydrous $Na_2SO_4$ and filtered. The filtrate was concentrated in vacuo to afford Compound 52 (61.0 mg, 93.8%) as a yellow solid. $^1$H NMR (400 MHz, DMSO-$d_6$): S=13.1 (br, 1H), 8.19 (d, J=8.0 Hz, 1H), 8.13 (d, J=8.4 Hz, 1H), 7.78-7.85 (m, 2H), 7.68 (d, J=8.4 Hz, 1H), 7.39 (t, J=7.2 Hz, 1H), 5.18 (s, 2H). LC/MS: 366.0 $[M+H]^+$.

Example 27: Synthesis of Compound 51

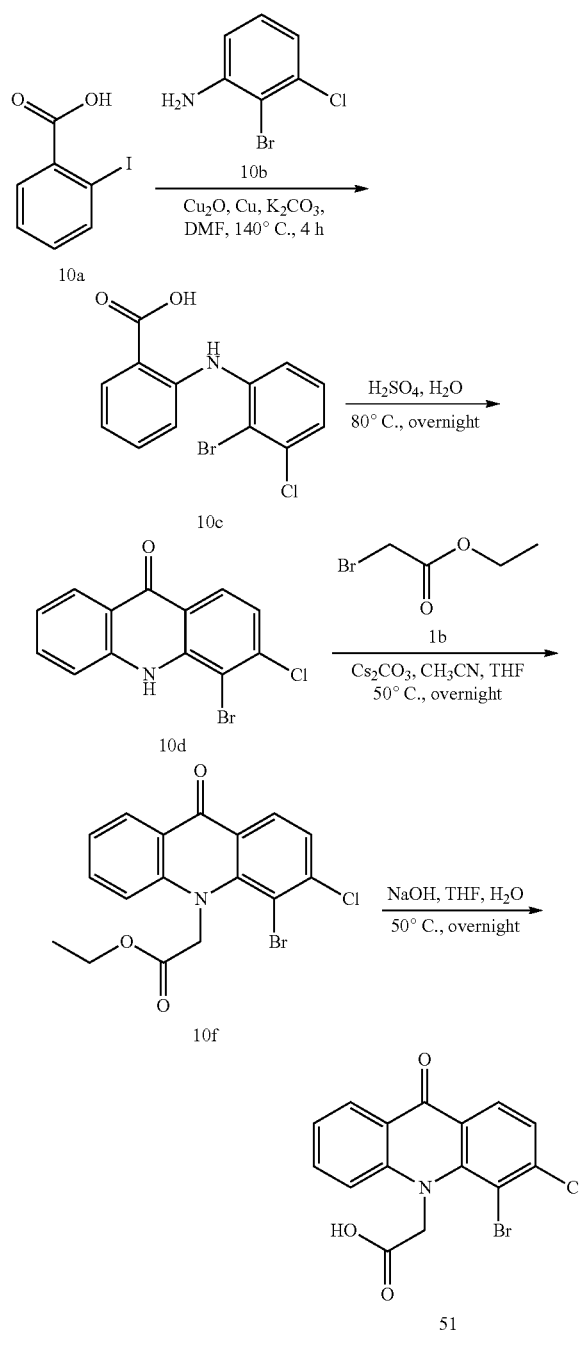

Step 1

A mixture of 10a (3.5 g, 14.1 mmol, 1.0 eq), 10b (2.9 g, 14.1 mmol, 1.0 eq), potassium carbonate (3.9 g, 28.2 mmol, 2.0 eq), copper powder (605 mg, 4.2 mmol, 0.3 eq), and Copper(I) oxide (267 mg, 4.2 mmol, 0.3 eq) in DMF (100.0 mL) was stirred at 140° C. for 4.0 h under argon atmosphere, then cooled to room temperature, water (50.0 mL) was added. The mixture was filtered through celite. The filtrate was acidified to pH=2 with 2 N HCl, then an additional of water (250.0 mL) was added. The resulting mixture was extracted with EtOAc (100.0 mL×3). The combined organic layers were washed with brine (100.0 mL×3), dried over anhydrous $Na_2SO_4$ and filtered. The filtrate was concentrated in vacuo to afford crude 10c (6.1 g, 100%). LC/MS: 326.0 $[M+H]^+$.

Step 2

A mixture of 10c (6.1 g, 18.8 mmol), sulfuric acid (40.0 mL) and $H_2O$ (4.0 mL) was heated at 80° C. overnight, then cooled and poured into a mixture of ice and water (140.0 mL), The solid was collected by filtration and dried in vacuo to afford crude 10d (2.0 g, 35.0%). LC/MS: 307.9 $[M+H]^+$.

Step 3

To a mixture of 10d (2.0 g, 6.5 mmol, 1.0 eq) and $Cs_2CO_3$ (6.4 g, 19.5 mmol, 3.0 eq) in acetonitrile/THF (30.0 mL/30.0 mL) was added 1b (1.3 g, 7.8 mmol, 1.2 eq). The mixture was stirred at 50° C. for overnight, cooled to room temperature and filtered through celite. The filtrate was concentrated in vacuo. The residue was triturated with PE/EtOAc (v/v=10:1) and filtered to afford 10f (150 mg, 1%) as a yellow solid. LC/MS: 394.0 $[M+H]^+$.

Step 4

To a mixture of 10f (150 mg; 0.38 mmol, 1.0 eq) in THF (15.0 mL) was added dropwise a solution of NaOH (153 mg, 3.80 mmol, 10.0 eq) in $H_2O$ (3.0 mL). The reaction mixture was stirred at 50° C. overnight, diluted with ice-water (30.0 mL), extracted with EtOAc (15.0 mL×3). The aqueous layer was acidified to pH=3 with 2 N HCl and extracted with EtOAc (25.0 mL×3). The combined organic layers were concentrated in vacuo and purified by Pre-HPLC to afford Compound 51 (110 mg, 73%) as a yellow solid. $^1$H NMR (400 MHz, DMSO-$d_6$): δ 13.0 (br, 1H), 8.23 (d, J=8.8 Hz, 1H), 8.18 (d, J=8.0 Hz, 1H), 7.77-7.80 (m, 2H), 7.64 (d, J=8.4 Hz, 1H), 7.37 (t, J=8.0 Hz, 1H), 5.29 (s, 2H). LC/MS: 366.0 $[M+H]^+$.

Example 28: Synthesis of Compound 47

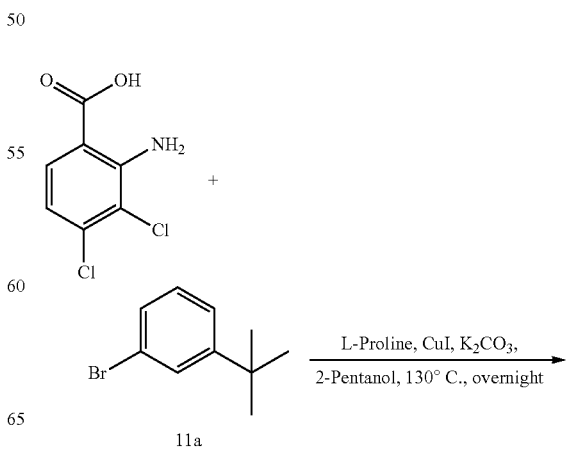

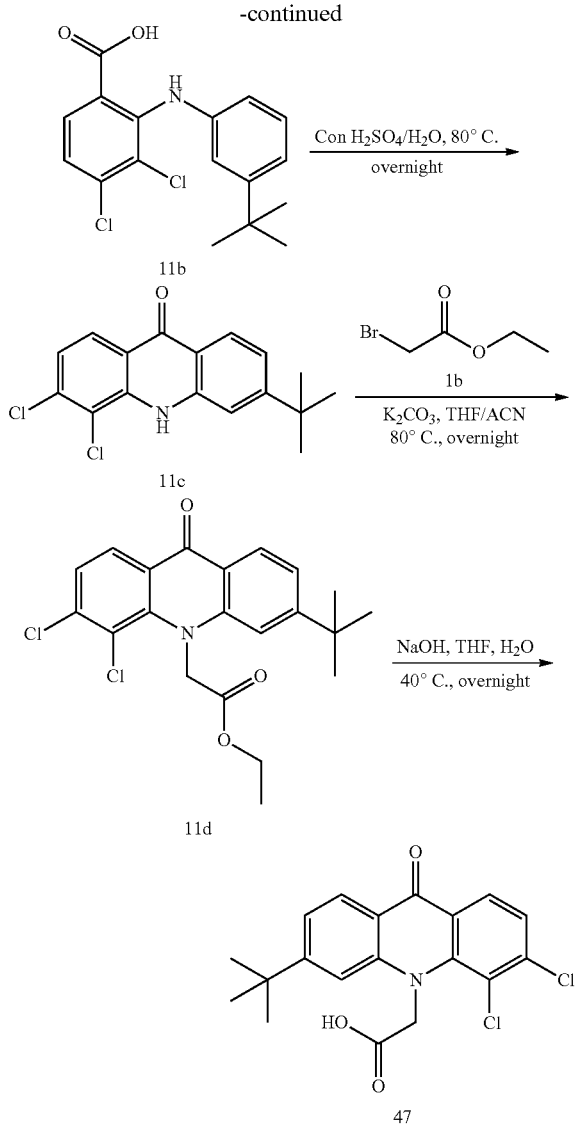

Step 3

To a mixture of 11c (1.05 g, 3.3 mmol, 1.0 eq) and K$_2$CO$_3$ (910.8 mg, 6.6 mmol, 2.0 eq) in acetonitrile/THF (20.0 mL/40.0 mL) was added 1b (651.0 mg, 3.9 mmol, 1.20 eq). The mixture was stirred at 80° C. overnight, cooled to room temperature and filtered through celite. The filtrate was concentrated in vacuo to give crude product which was purified by prep-HPLC to afford 11d (97 mg, 7.2%) as a yellow solid. LC/MS: 406.1 [M+H]$^+$.

Step 4

To mixture of 11d (197.0 mg; 0.24 mmol, 1.0 eq) in THF (15 mL) was added dropwise a solution of NaOH (38.0 mg, 0.96 mmol, 4.0 eq) in H$_2$O (4.0 mL). The reaction mixture was stirred at 40° C. overnight, cooled to room temperature, and diluted with ice-water (3.0 mL), extracted with DCM (3.0 mL×3). The aqueous layer was acidified to pH=3 with 2 N HCl and extracted with EtOAc (5.0 mL×4). The combined organic layers were dried over anhydrous Na$_2$SO$_4$ and filtered. The filtrate was concentrated in vacuo. The residue was triturated with PE/EtOAc (v/v=3:1) and filtered to afford Compound 47 (71.0 mg, 78.5%) as a yellow solid. $^1$H NMR (400 MHz, DMSO-d$_6$): δ 8.21 (d, J=8.8 Hz, 1H), 8.12 (d, J=8.4 Hz, 1H), 7.63 (d, J=8.8 Hz, 1H), 7.59 (s, 1H), 7.48 (d, J=8.4 Hz, 1H), 5.21 (s, 2H), 1.35 (s, 9H). LC/MS: 378.3 [M+H]$^+$.

Example 29: Synthesis of Compound 102

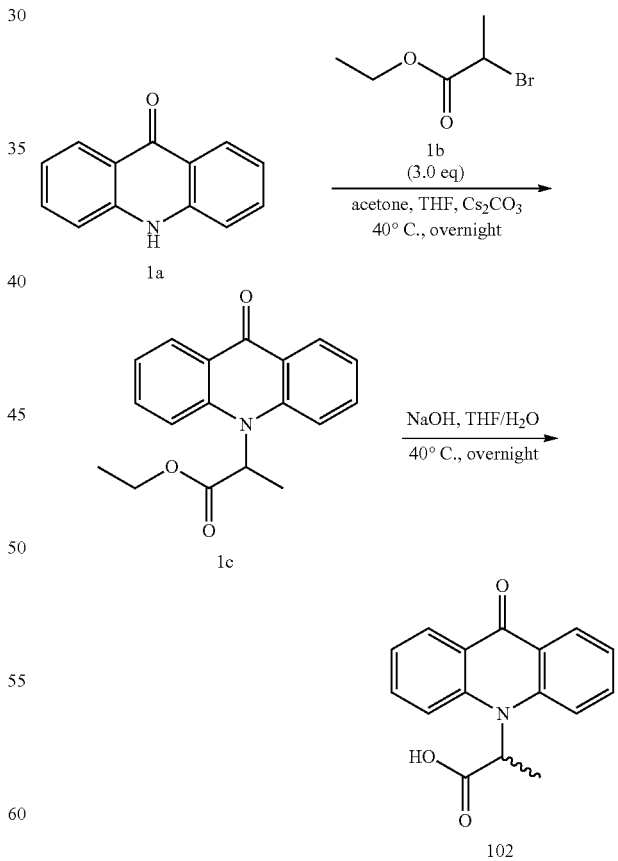

Step 1

A mixture of 2-amino-3,4-dichlorobenzoic acid (1.5 g, 7.3 mmol, 1.0 eq), 11a (3 g, 14.6 mmol, 2.0 eq), potassium carbonate (2.0 g, 14.6 mmol, 2.0 eq), L-proline (252.0 mg, 2.18 mmol, 0.3 eq), and Copper(I) oxide (406.0 mg, 2.19 mmol, 0.3 eq) in 2-Pentanol (30.0 mL) was stirred at 130° C. overnight under argon atmosphere, then cooled to room temperature, water (20.0 mL) was added. The mixture was filtered through celite. The filtrate was acidified to pH=2 with 2 N HCl, then water (50.0 mL) was added. The resulting mixture was extracted with EtOAc (50.0 mL×3). The combined organic layers were washed with brine (20.0 mL×5), dried over anhydrous Na$_2$SO$_4$ and filtered. The filtrate was concentrated in vacuo to afford crude 11b (1.7 g, 69%). LC/MS: 338.1 [M+H]$^+$.

Step 2

A mixture of 11b (1.7 g, 5.0 mmol) and con. H$_2$SO$_4$/H$_2$O (50 mL/5 mL) was heated at 80° C. overnight, then cooled and poured into a mixture of ice and water. The solid was collected by filtration and dried to afford crude 11c (1.05 g, 65.2%). LC/MS: 320.1 [M+H]$^+$ Step 1

To a mixture of 1a (500 mg, 2.6 mmol, 1.0 eq) and Cs$_2$CO$_3$ (3.4 g, 10.5 mmol, 2.5 eq) in acetone/THF (20 mL/10 mL) was added 1b (1.4 g, 7.8 mmol, 3.0 eq) at rt. The mixture was then stirred at 40° C. overnight, cooled to room temperature and filtered through celite. The filtrate was concentrated in vacuo to give crude product, which was purified by silica gel chromatography (PE/EtOAc, v/v=2:1) to afford 853 mg of crude which was further purified via prep-HPLC to provide 1c (182 mg, 24.1%). LC/MS: 296.1 [M+H]$^+$.

Step 2

To mixture of 1c (182 mg: 0.62 mmol, 1.0 eq) in THF (10 mL) was added dropwise a solution of NaOH (98.7 mg, 2.5 mmol, 4.0 eq) in H$_2$O (2 mL). The reaction mixture was stirred at 40° C. overnight, then cooled to room temperature, and diluted with ice-water (3.0 mL), extracted with DCM (3.0 mL×3). The aqueous layer was acidified to pH=3 with 2 N HCl and extracted with EtOAc (5.0 mL×4). The combined organic layers were dried over anhydrous Na$_2$SO$_4$ and filtered. The filtrate was concentrated in vacuo to afford Compound 102 (161 mg, 93.1%) as a yellow solid. $^1$H NMR (400 MHz, DMSO-d$_6$): δ 13.31 (s, 1H), 8.37 (d, J=8.0 Hz, 2H), 7.82 (t, J=7.6 Hz, 2H), 7.69 (br, 2H), 7.36 (t, J=7.6 Hz, 2H), 6.07 (q, J=6.8 Hz, 1H), 1.76 (d, J=6.8 Hz, 3H). LC/MS: 268.1 [M+H]$^+$.

Example 30: Synthesis of Compound 137

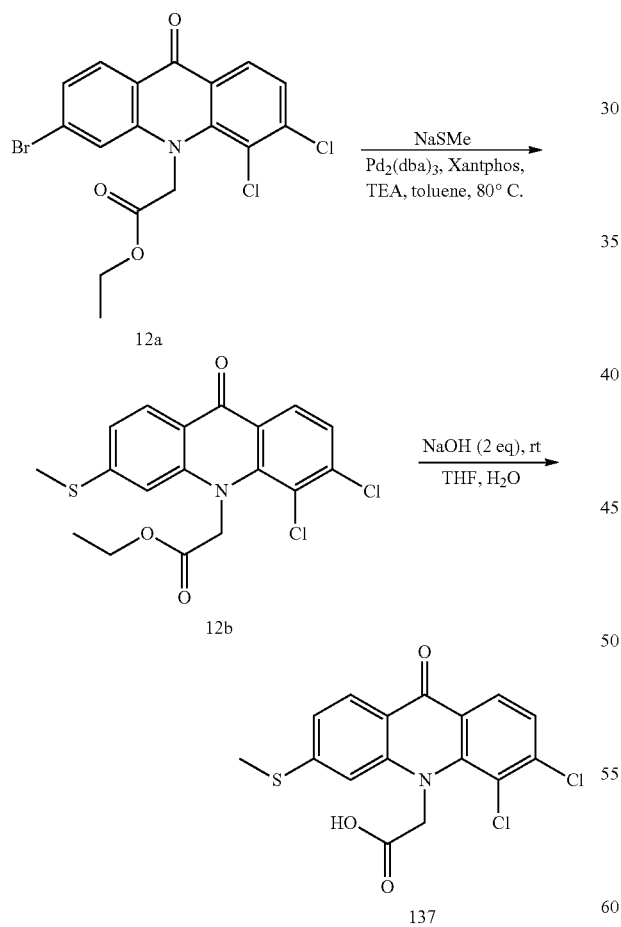

Step 1

A mixture of 12a (50 mg, 0.11 mmol), sodium thiomethoxide (11 mg, 0.13 mmol), Pd$_2$(dba)$_3$ (10 mg, 0.005 mmol), Xantphos (12 mg, 0.01 mmol), TEA (0.5 mL) in toluene (4 mL) under N$_2$ was stirred at 80° C. in a sealed-tube overnight. The mixture was cooled to room temperature, concentrated in vacuo. The residue was purified by Prep-HPLC to afford 12b (17.0 mg, 35.0%), LC/MS: 396.2 [M+H]$^+$.

Step 2

To a mixture of 12b (17 mg; 0.04 mmol) in THF (5 mL) was added a solution of NaOH (4 mg, 0.1 mmol) in H$_2$O (0.1 mL). The reaction mixture was stirred at room temperature overnight, diluted with water (10 mL), acidified to pH=3 with 2 N HCl and extracted with EtOAc (20 mL×2). The combined organic layers were dried over anhydrous Na$_2$SO$_4$ and filtered. The filtrate was concentrated in vacuo to afford 137 (10.0 mg, 62.5%). $^1$H NMR (400 MHz, DMSO-d$_6$): δ 113.16 (br, 1H), 8.19 (d, J=8.8 Hz, 1H), 8.07 (d, J=8.4 Hz, 1H), 7.64 (d, J=8.8 Hz, 1H), 7.39 (s, 1H), 7.28-7.24 (m, 1H), 5.23 (s, 2H), 2.60 (s, 3H) ppm, LC/MS: 368.0 [M+H]$^+$.

Example 31: Synthesis of Compound 145

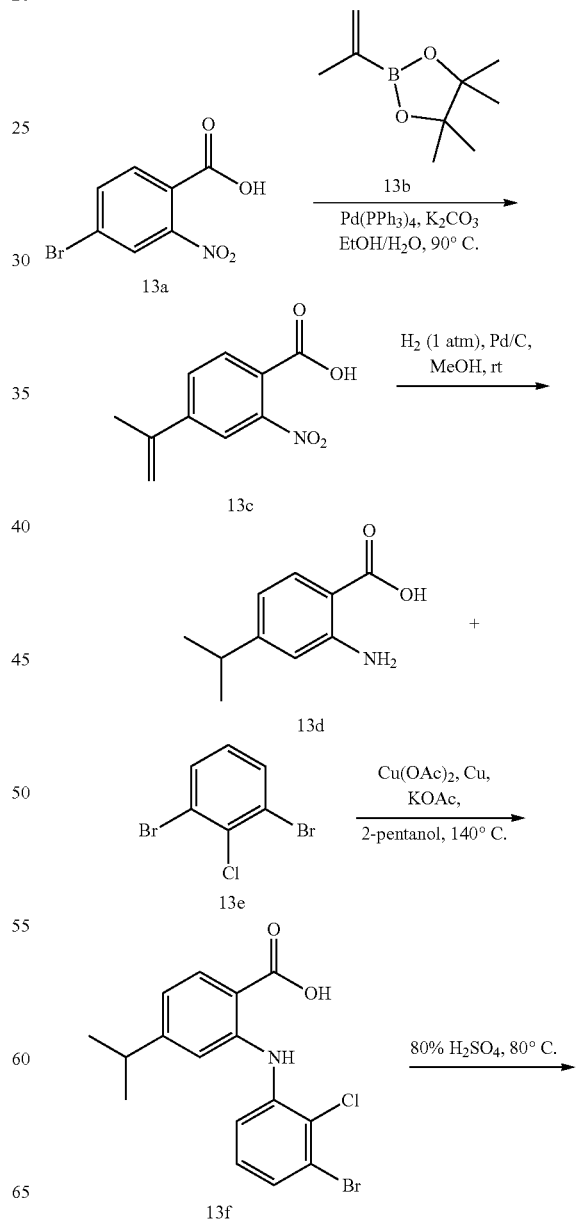

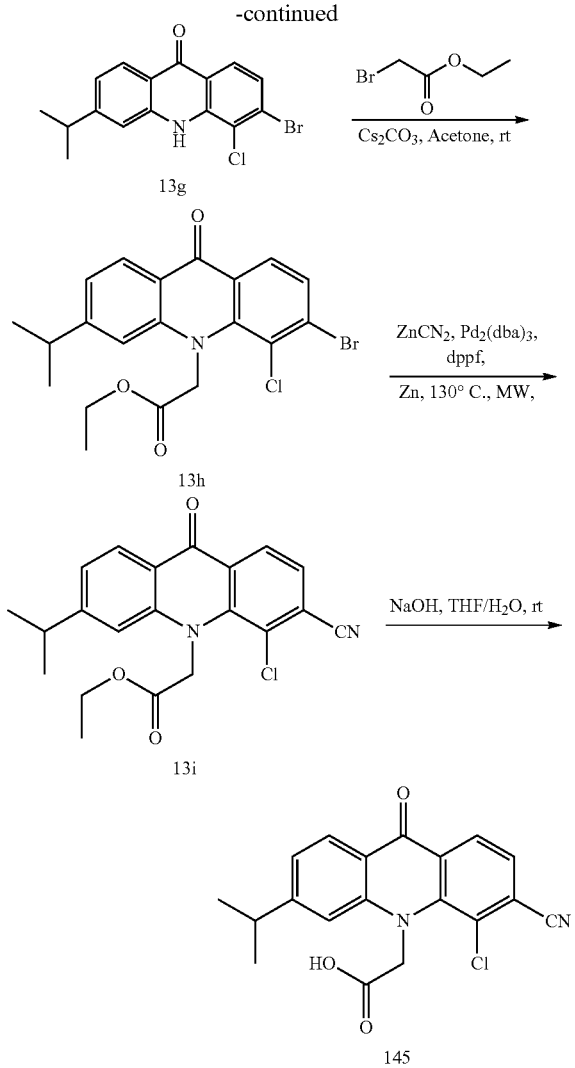

Step 1

To a mixture of 13a (2.46 g, 10 mmol) and I3b (3.3 g, 20 mmol) in EtOH/H₂O (50 mL/10.0 mL) were added K₂CO₃ (5.5 g, 40 mmol), Pd(PPh₃)₄ (580 mg, 0.5 mmol). The mixture was stirred at 80° C. overnight under N₂. The solvent was evaporated, diluted with water (100 mL), extracted with EtOAc (50 mL×2). The aqueous layer was acidified to pH=3 with 2 N HCl and extracted with EtOAc (50 mL×2). The combined organic layers were dried over anhydrous Na₂SO₄ and filtered. The filtrate was concentrated in vacuo to afford 13c (2.7 g, crude). LCMS: 206.2 [M−H]⁺.

Step 2

A mixture of 13c (2.7 g, crude) and Pd/C (500 mg, 20%) in MeOH (50 mL) was stirred at room temperature under H₂ (1 atm) for 5 h, then filtered off, The Pd/C was washed with MeOH (30 mL). The filtrate was concentrated in vacuo to afford 13d (2.4 g, 100%). LC/MS: 180.1 [M+H]⁺.

Step 3

A mixture of 13d (540 mg, 3.0 mmol), 13e (1.2 g, 4.5 mmol), KOAc (600 mg, 6.0 mmol), Cu(OAc)₂ (160 mg, 0.9 mmol), and Cu (60 mg, 0.9 mmol) in 2-Pentanol (10.0 mL) was stirred at 140° C. overnight under N₂ atmosphere, then cooled to room temperature. The reaction mixture was added water (50.0 mL), acidified to pH=2 with 2 N HCl, extracted with EtOAc (50.0 mL×2). The combined organic layers were washed with brine, dried over anhydrous Na₂SO₄ and filtered. The filtrate was concentrated in vacuo. The residue was purified by chromatography on silica gel (PE/EtOAc v/v=5/1) to afford 13f (680 mg, 61.8%). LC/MS: 368.0 [M+H]⁺.

Step 4

A mixture of 13f (680 mg, 1.85 mmol), sulfuric acid (80%, 20.0 mL) was heated at 70° C. overnight, then cooled and poured into a mixture of ice and water. The solid was collected by filtration and dried in vacuo to afford crude 13 g (610 mg, 95.3%). LCMS: 350.0 [M+H]⁺.

Step 5

To a mixture of 13 g (710 mg, 2.06 mmol) and Cs₂CO₃ (750 mg, 2.3 mmol) in acetonitrile (20 mL) was added methyl 2-bromoacetate (0.35 mL, 3.0 mmol). The mixture was stirred at room temperature overnight. The reaction mixture was added 2N HCl (20 mL), extracted with EtOAc (50.0 mL×2). The combined organic layers were dried over anhydrous Na₂SO₄ and filtered. The filtrate was concentrated in vacuo to afford the first batch of crude product. The same reaction was repeated with the first batch of crude product. The crude product from the second reaction was purified by Prep-HPLC to afford 13 h (300 mg, 31.7%), LC/MS: 422.1 [M+H]⁺.

Step 6

A mixture of 13 h (100 mg, 0.23 mmol), Zn(CN)₂ (45 mg, 0.35 mmol), Pd₂(dba)₃ (20 mg, 0.02 mmol), dppf (24 mg, 0.4 mmol), Zn (2 mg) in DMF (3 mL) was stirred at 130° C. under microwave for 15 min. The mixture was cooled to room temperature and water (20 mL) was added, extracted with EtOAc (20.0 mL×2). The combined organic layers were washed with brine, dried over anhydrous Na₂SO₄ and filtered. The filtrate was concentrated in vacuo. The residue was purified by chromatography on silica gel (PE/EtOAc v/v=5/1) to afford 13i (45 mg, 51.7% crude), LC/MS: 369.1 [M+H]⁺.

Step 7

To a mixture of 13i (45 mg; 0.12 mmol) in THF (5 mL) was added a solution of NaOH (10 mg, 0.24 mmol) in H₂O (0.1 mL). The reaction mixture was stirred at room temperature overnight, diluted with water (10 mL), acidified to pH=3 with 2 N HCl and extracted with EtOAc (20 mL×2). The combined organic layers were dried over anhydrous Na₂SO₄ and filtered. The filtrate was concentrated in vacuo. The residue was purified by Prep-HPLC to afford 145 (10.4 mg, 23.0%). ¹H NMR (400 MHz. DMSO-d₆): δ 13.25 (s, 1 H), 8.33 (d, J=8.0 Hz, 1H), 8.13 (d, J=8.4 Hz, 1H), 7.87 (d, J=8.0 Hz, 1H), 7.51 (s, 1H), 7.34 (d, J=8.0 Hz, 1H), 5.25 (s, 2H), 3.11-3.00 (m, 1H), 1.27 (d, J=7.2 Hz, 6H) ppm, LC/MS: 355.1 [M+H]⁺.

Example 32: Synthesis of Compound 146

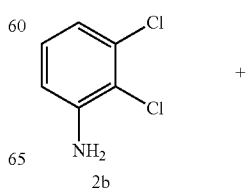

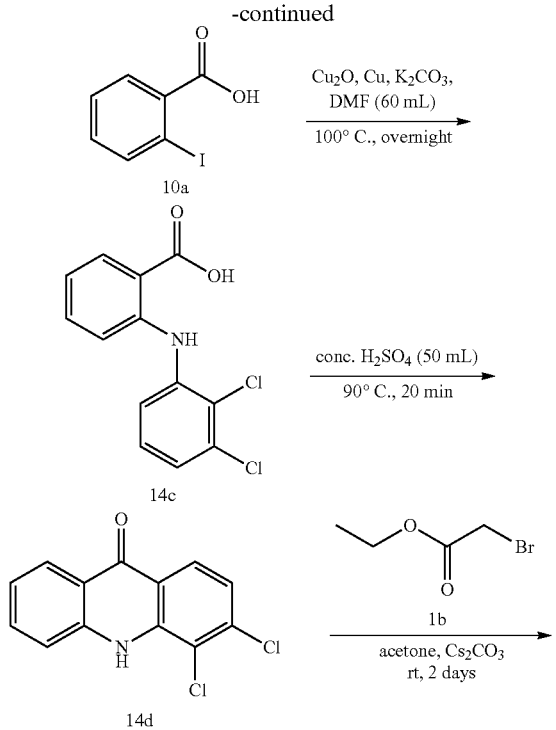

product which was triturated with acetonitrile, filtered and dried to afford 14d (3.5 g, 38.1%). LCMS: 264.0 [M+H]+.

Step 3

To a mixture of 14d (500.0 mg, 1.9 mmol, 1.0 eq) and $Cs_2CO_3$ (2.5 g, 7.6 mmol, 4.0 eq) in acetone (10.0 mL) was added ethyl 2-bromoacetate (952.0 mg, 5.7 mmol, 3.0 eq). The mixture was stirred at room temperature overnight, diluted with water (100 mL), extracted with EA. The organic layer was concentrated and the residue was purified by silica gel chromatography (PE/EtOAc, v/v=2:1) to afford the crude product which was further purified by reversed phase column to provide 14f (173 mg, 26.1%). LC/MS: 350.0 [M+H]+.

Step 4

A mixture of 14f (34.0 mg) and $NH_3$ in MeOH (6 M, 10.0 mL) was stirred at room temperature for 9 days. The reaction mixture was concentrated in vacuo to afford 146 (31.0 mg, ~100%). $^1$H NMR (400 MHz, DMSO-$d_6$): δ 8.18-8.25 (m, 2H), 7.82 (m, 2H), 7.62 (m, 2H), 7.32-7.38 (m, 2H), 5.03 (s, 2H). LCMS: 321.2 [M+H]+.

Example 33: Synthesis of Compound 197

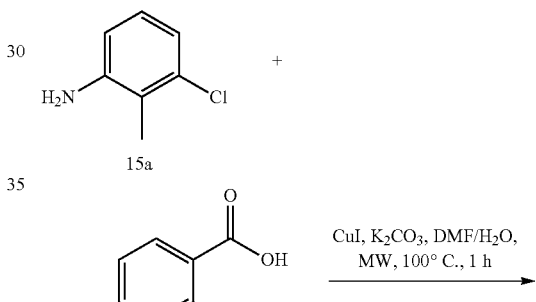

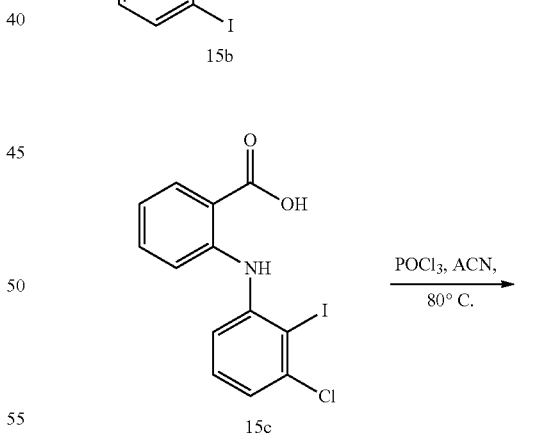

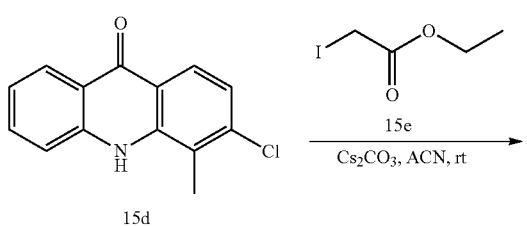

Step 1

A mixture of 2b (5.7 g, 35.2 mmol, 1.0 eq), 10a (17.5 g, 70.4 mmol, 2.0 eq), potassium carbonate (21.9 g, 158.4 mmol, 4.5 eq), copper powder (1.1 g, 17.6 mmol, 0.5 eq), and Copper(I) oxide (2.5 g, 17.6 mmol, 0.5 eq) in DMF (60.0 mL) was stirred at 100° C. overnight under argon atmosphere, then cooled to room temperature, 2 N NaOH (200.0 mL) was added. The mixture was filtered through celite. The filtrate was acidified to pH=2 with conc. HCl. The solid was collected by filtration and dried to provide crude 14c (containing 2b, 2b:14c=4:5). LC/MS: 282.0 [M+H]+.

Step 2

A mixture of crude 14c and conc. $H_2SO_4$ (50.0 mL) was heated at 90° C. for 20 min under argon atmosphere, then cooled and poured into a mixture of ice and water. The solid was collected by filtration and dried to afford the crude

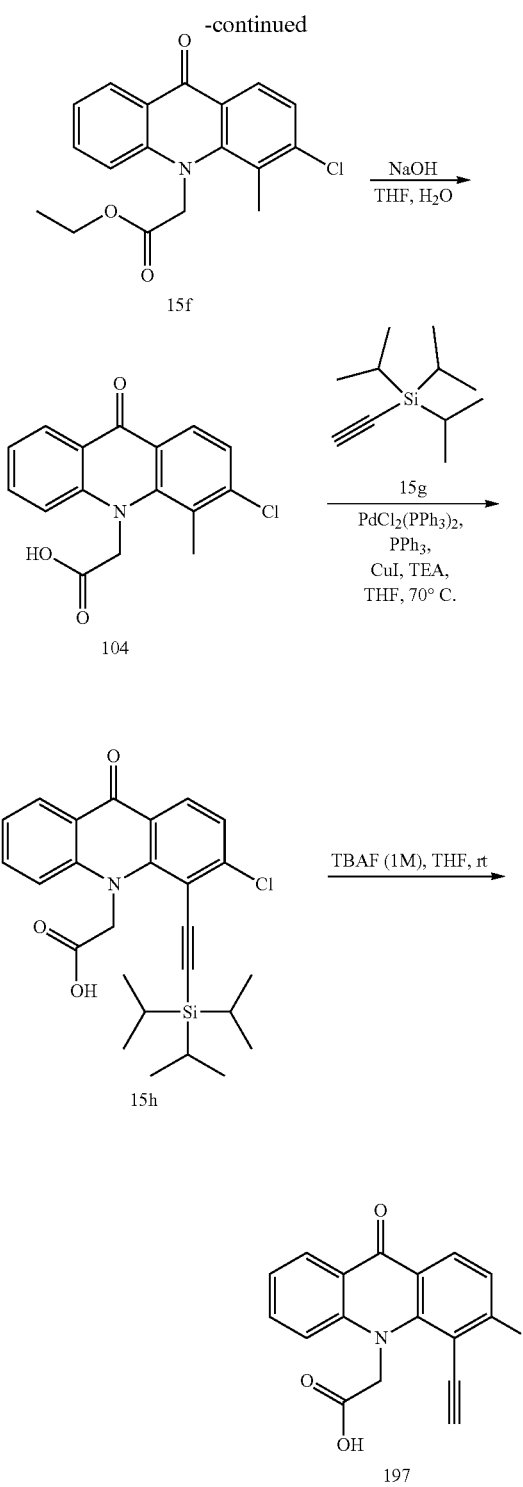

Step 1

A mixture of 15a (2.4 g, 9.6 mmol), 15b (2.0 g, 8.0 mmol), K₂CO₃ (3.4 g, 24.5 mmol), CuI (1.6 g, 8.4 mmol) in DMF (24 mL)/H₂O (2.4 mL) was stirred at 100° C. under microwave for 1 h. The mixture was cooled to room temperature, water (100 mL) was added, acidified to pH=2 with 2 N HCl, extracted with EtOAc (50.0 mL×2). The combined organic layers were washed with brine, dried over anhydrous Na₂SO₄ and filtered. The filtrate was concentrated in vacuo.

The residue was purified by chromatography on silica gel (PE/EtOAc v/v=5/1) to afford 15c (1.8 g, crude). LC/MS: 374.0 [M+H]⁺.

Step 2

To a solution of 15c (1.7 g, 4.5 mmol) in acetonitrile (50 mL) was added POCl₃ (1.1 mL, 11.4 mmol) dropwise at 80° C. The mixture was stirred at 80° C. for 2 hr, then cooled to room temperature, poured into water (100 mL), extracted with EA (100 mL×2). The combined organic layers were washed with sat. Na₂CO₃ and brine, dried over anhydrous Na₂SO₄ and filtered. The filtrate was concentrated in vacuo. The residue was purified by chromatography on silica gel (PE/EtOAc v/v=10/1) to afford 15d (270 mg, 16.9%). LCMS: 355.9 [M+H]⁺.

Step 3

To a mixture of 15d (270 mg, 0.76 mmol) and Cs₂CO₃ (750 mg, 2.3 mmol) in acetonitrile (20 mL) was added 15e (350 mg, 1.5 mmol). The mixture was stirred at room temperature overnight. The reaction mixture was added 2N HCl (20 mL), extracted with EtOAc (50.0 mL×2). The combined organic layers were dried over anhydrous Na₂SO₄ and filtered. The filtrate was concentrated in vacuo to afford the first batch of crude product. The same reaction was repeated with the first batch of crude product. The crude product from the second reaction was purified by Prep-HPLC to afford 15f (80 mg, 23.8%). LC/MS: 442.0 [M+H]⁺.

Step 4

To mixture of 15f (70 mg; 0.15 mmol) in THF (5 mL) was added a solution of NaOH (15 mg, 0.3 mmol) in H₂O (0.2 mL). The reaction mixture was stirred at room temperature overnight, diluted with water (30 mL), extracted with EtOAc (20 mL×2). The aqueous layer was acidified to pH=3 with 2 N HCl and extracted with EtOAc (40 mL×2). The combined organic layers were dried over anhydrous Na₂SO₄ and filtered. The filtrate was concentrated in vacuo to afford 104 (32.9 mg, 50.0%) as a yellow solid. H NMR (400 MHz, DMSO-d₆): δ 12.86 (s, 1H), 8.19 (d, J=8.4 Hz, 1H), 8.17-8.12 (m, 1H), 7.87-7.64 (m, 2H), 7.59 (d, J=8.4 Hz, 1H), 7.35 (t, J=7.6 Hz, 1H), 5.35 (s, 2H) ppm, LC/MS: 824.7 [2M−H]⁺.

Step 5

A mixture of 104 (30.4 mg, 0.07 mmol), 15 g (40 mg, 0.2 mmol), PdCl₂(PPh₃)₂ (5.0 mg, 0.007 mmol), CuI (1 mg), PPh₃ (1 mg), Et₃N (22 mg, 0.2 mmol) in THF (5 mL) was stirred at 70° C. under N₂. The mixture was cooled to room temperature, water (10 mL) was added, acidified to pH=2 with 2 N HCl, extracted with EtOAc (20 mL×2). The combined organic layers were washed with brine, dried over anhydrous Na₂SO₄ and filtered. The filtrate was concentrated in vacuo. The residue was purified by chromatography on silica gel (DCM/MeOH v/v=10/1) to afford 15 h (20.0 mg, 57.8). LC/MS: 468.3 [M+H]⁺.

Step 6

To a solution of 15 h (20.0 mg; 0.042 mmol) in THF (2 mL) was added TBAF (1N, 0.05 mL, 0.05 mmol) dropwise at 0° C. The mixture was stirred at 0° C. for 30 min. Water (10 mL) was added, acidified to pH=2 with 2 N HCl, extracted with EtOAc (20 mL×2). The combined organic layers were washed with brine, dried over anhydrous Na₂SO₄ and filtered. The filtrate was concentrated in vacuo. The residue was triturated with acetonitrile (2 mL) and filtered to afford 197 (7.1 mg, 54.3%) as a yellow solid. ¹H NMR (400 MHz, DMSO-d₆): δ 8.33 (d, J=8.8 Hz, 1H), 8.29-8.24 (m, 1H), 7.87-7.81 (m, 1H), 7.59-7.52 (m, 2H), 7.41 (t, J=7.6 Hz, 1H), 5.53 (s, 2H), 5.18 (s, 1H) ppm, LC/MS: 312.1 [M+H]⁺.

Example 34: Synthesis of Compound 205

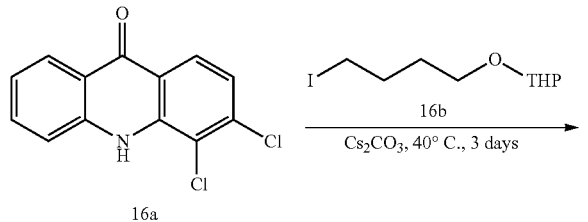

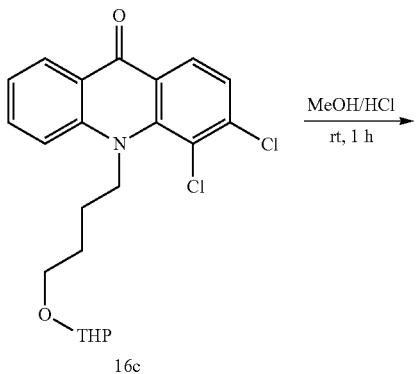

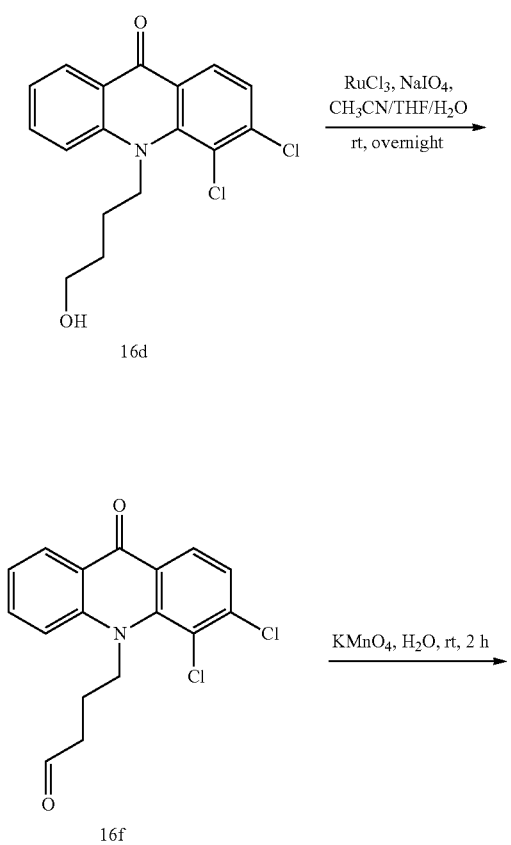

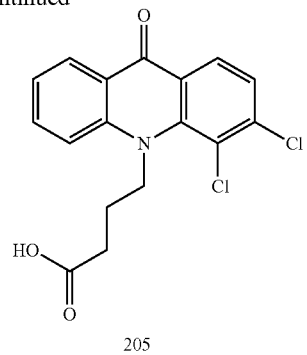

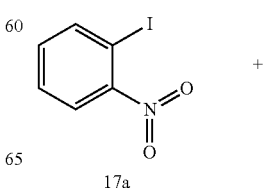

Step 1

A mixture of 16a (1 g, 3.8 mmol, 1.0 eq), 16b (2.2 g, 7.6 mmol, 2.0 eq), $Cs_2CO_3$ (3.7 g, 11.4 mmol, 3.0 eq) in acetonitrile (10.0 mL) was stirred at 40° C. for three days under argon atmosphere, then cooled to room temperature, diluted with water, extracted with EtOAc. The organic layer was concentrated and purified by silica gel chromatography (PE/EtOAc, v/v=10:1) to afford 16c (0.3 g, 18.9%) LC/MS: 338.1 $[M+H]^+$.

Step 2

A mixture of 16c (0.3 g) and HCl in MeOH (6 M, 10.0 mL) was stirred at room temperature for 1 h. The reaction mixture was concentrated in vacuo to afford 16d (0.2 g, 83%). LC/MS: 336.1 $[M+H]^+$.

Step 3

To a mixture of 16d (30 mg, 0.09 mmol, 1.0 eq) and $Na_1O_4$ (96 mg, 0.45 mmol, 5.0 eq) in a mixture solvent of acetonitrile/THF/water (2 mL/2 mL/3 mL) was added $RuCl_3$ (3 mg, 0.01 mmol, 0.15 eq). The mixture was stirred at room temperature overnight, diluted with water, extracted with EtOAc. The organic layer was concentrated to afford crude 16f (30 mg, 60% of 16d, 40% of 16f). LC/MS: 334.11 $[M+H]^+$.

Step 4

A mixture of 16d and 16f (30 mg, 60% of 16d, 40% of 16f, 0.09 mmol, 1.0 eq) in $H_2O$ (5.0 mL) was added $KMnO_4$ (2M, 0.5 mL, 0.18 mmol, 2.0 eq), The mixture stirred at room temperature for 2 h. The reaction was acidified to pH=2 with conc. HCl, extracted with EtOAc. The organic layer was concentrated to afford 205 (2.4 mg, 19.2%). $^1H$ NMR (400 MHz, DMSO-$d_6$): δ 12.07 (s, 1H), 8.17-8.20 (m, 1H), 7.93 (d, J=8.4 Hz, 1H), 7.84 (t, J=7.2 Hz, 1H), 7.65 (d, J=8.8 Hz, 2H), 7.39 (t, J=7.6 Hz, 1H), 4.66 (t, J=7.2 Hz, 2H), 1.89 (t, J=7.0 Hz, 2H), 1.55 (t, J=7.2 Hz, 2H) LC/MS: 350.1 $[M+H]^+$.

Example 35: Synthesis of Compound 209

-continued

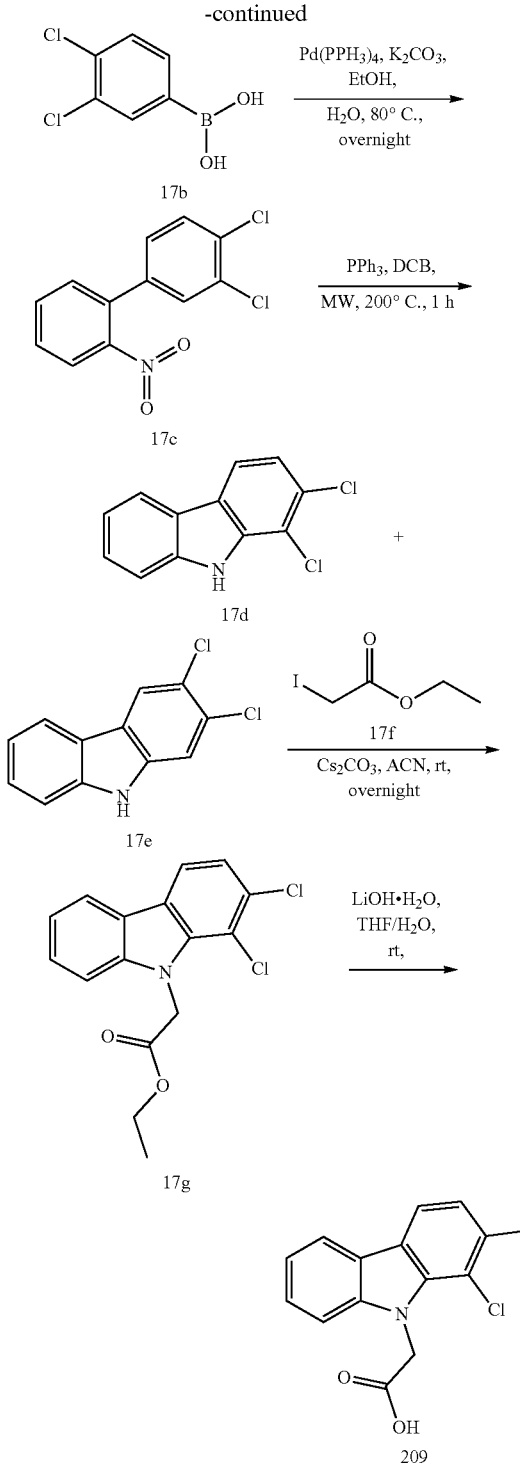

purified by chromatography on silica gel (PE/EtOAc v/v=100/1) to afford 17c (1.26 g, 91.3%) as a white solid.

Step 2

A mixture of 17c (130 mg, 0.5 mmol). PPh$_3$ (400 mg, 1.5 mmol) in dichlorobenzene (3 mL) was heated to 200° C. for 1 h under microwave. The reaction mixture was concentrated in vacuo. The residue was purified by chromatography on silica gel (PE/EtOAc v/v=201) to afford 17d (150 mg, crude). LCMS: 234.2 [M–H]$^+$.

Step 3

To a mixture of 17d (150 mg, crude) and Cs$_2$CO$_3$ (290 mg, 0.9 mmol) in acetonitrile (5.0 mL) was added 17f (130 mg, 0.6 mmol). The mixture was stirred at room temperature overnight. The reaction mixture was concentrated in vacuo. The residue was purified by chromatography on silica gel (PE/EtOAc v/v=30/1) to afford 17 g (88 mg, 91.3%).

Step 4

To a solution of 17 g (88 mg; 0.27 mmol) in THF (5.0 mL) was added a solution of LiOH.H$_2$O (25 mg, 0.59 mmol) in H$_2$O (0.3 mL). The reaction mixture was stirred at room temperature overnight, diluted with water (10 mL), extracted with EtOAc (15.0 mL×2). The aqueous layer was acidified to pH=3 with 2 N HCl and extracted with EtOAc (25.0 mL×2). The combined organic layers were dried over anhydrous Na$_2$SO$_4$ and filtered. The filtrate was concentrated in vacuo to afford 209 (60.6 mg, 76.6%) as a white solid. $^1$H NMR (400 MHz, DMSO-d$_6$): δ 13.16 (br, 1H), 8.24-8.17 (m, 2H), 7.72 (d, J=8.4 Hz, 1H), 7.52 (t, J=7.6 Hz, 1H), 7.72 (d, J=8.4 Hz, 1H), 7.30 (t, J=7.6 Hz, 1H), 5.52 (s, 2H) ppm, LC/MS: 292.1 [M–H]+.

Example 36: Synthesis of Compound 212

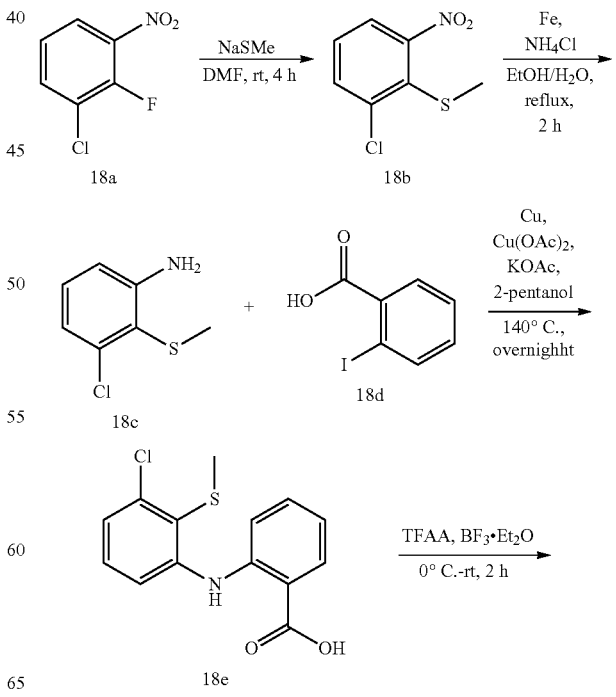

Step 1

To a mixture of 17a (1.25 g, 5.0 mmol) and 17b (1.15 g, 6.0 mmol) in EtOH/H$_2$O (30.0 mL/10.0 mL) were added K$_2$CO$_3$ (2.0 g, 15.0 mmol) and Pd(PPh$_3$)$_4$ (280 mg, 0.25 mmol). The mixture was stirred at 80° C. overnight under N$_2$, diluted with water (100 mL), extracted with EtOAc (50 mL×2). The combined organic layers were washed with brine (100 mL), dried over anhydrous Na$_2$SO$_4$ and filtered. The filtrate was concentrated in vacuo. The residue was

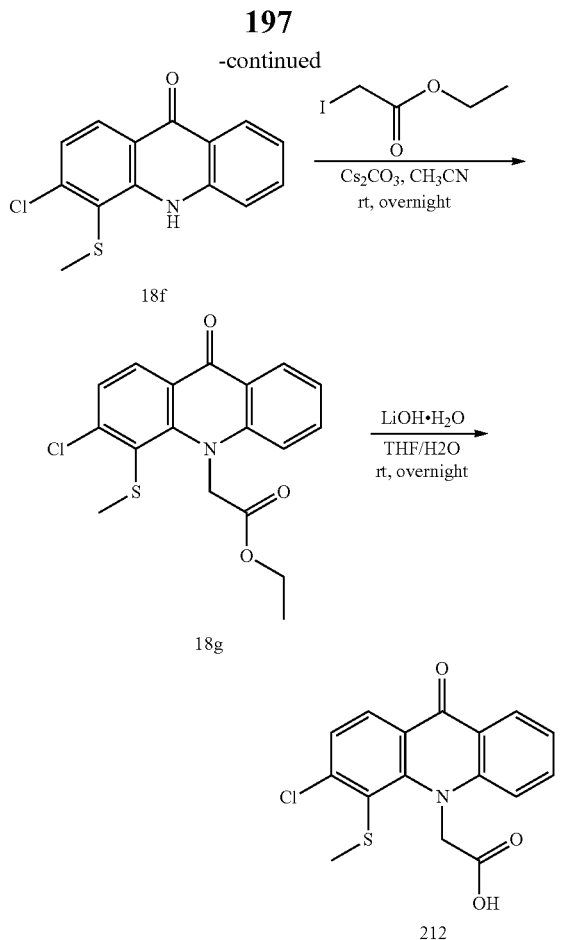

Step 1

A mixture of 18a (5.0 g, 28.48 mmol, 1.0 eq) and NaSMe (2.6 g, 37.03 mmol, 1.3 eq) in DMF (50.0 mL) was stirred at room temperature overnight under argon atmosphere, concentrated. The residue was purified by silica gel chromatography (PE/EA, v/v=50:1) to afford 18b (3.4 g, 59%). LC/MS: 204.0 [M+H]$^+$.

Step 2

A mixture of 18b (3.4 g, 16.75 mmol, 1.0 eq), Fe (4.7 g, 83.75 mmol, 5.0 eq) and NH$_4$C (4.5 g, 83.75 mmol, 5.0 eq) in EtOH/H$_2$O (25 mL/5 mL) was heated to reflux for 1 h. The reaction mixture was extracted with EtOAc. The organic layer was concentrated and purified by silica gel chromatography (PE/EA, v/v=30:1) to afford 18c (2.8 g, 96%). LC/MS: 174.0 [M+H]$^+$.

Step 3

A mixture of 18d (1.2 g, 4.8 mmol, 1.0 eq), 18c (1.0 g, 4.8 mmol, 1.2 eq), potassium acetate (940 mg, 9.6 mmol, 2.0 eq), copper powder (92 mg, 1.44 mmol, 0.3 eq) and cupric acetate (262 mg, 1.44 mmol, 0.3 eq) in 2-pentanol (30.0 mL) was stirred at 140° C. overnight under argon atmosphere, then cooled to room temperature. 2 N NaOH (100.0 mL) was added. The mixture was filtered through celite. The filtrate was acidified to pH=2 with conc. HCl, extracted with EtOAC. The organic layer was concentrated. The residue was triturated with PE and filtered to afford 18e (880 mg, 63%). LC/MS: 294.0 [M+H]$^+$.

Step 4

A mixture of 18e (400 mg, 1.37 mmol, 1 eq), TFAA (1 mL) and boron trifluoride etherate (1 M, 0.5 mL) was stirred at 0° C. The reaction mixture was warmed to room temperature and stirred for 2 h under argon atmosphere, poured into a mixture of ice and water. The solid was collected by filtration and dried to crude 18f (350 mg, 93%). LC/MS: 276.0 [M+H]$^+$.

Step 5

To a mixture of 18f (350 mg, 1.27 mmol, 1.0 eq) and Cs$_2$C$_3$ (1.25 g, 3.81 mmol, 3.0 eq) in MeCN (20 mL) was added ethyl iodoatetate (680 mg, 3.17 mmol, 5.0 eq) at room temperature. The mixture was then stirred at room temperature overnight, diluted with water, extracted with EtOAc. The organic layer was concentrated and the residue purified by reversed phase column to provide 18 g (130 mg, 28%). LC/MS: 362.0 [M+H]$^+$.

Step 6

To mixture of 18 g (120 mg; 0.33 mmol, 1.0 eq) in THF (5 mL) was added dropwise a solution of LiOH.H$_2$O (56 mg, 1.33 mmol, 4.0 eq) in H$_2$O (2 mL). The reaction mixture was stirred at room temperature overnight, and diluted with water, extracted with EtOAc. The aqueous layer was acidified to pH=3 with 2 N HCl and extracted with EA. The combined organic layers were dried over anhydrous Na$_2$SO$_4$ and filtered. The filtrate was concentrated in vacuo to afford 212 (85.2 mg, 77%). $^1$H NMR (400 MHz, DMSO-d$_6$): δ 12.96 (brs, 1H), 8.25-8.19 (m, 2H), 7.84-7.77 (m, 2H), 7.57 (d, J=8.4 Hz, 1H), 7.37 (t, J=8.0 Hz, 1H), 5.41 (s, 2H), 2.33 (s, 3H). LC/MS: 334.1 [M+H]$^+$.

Example 37: Synthesis of Compound 215

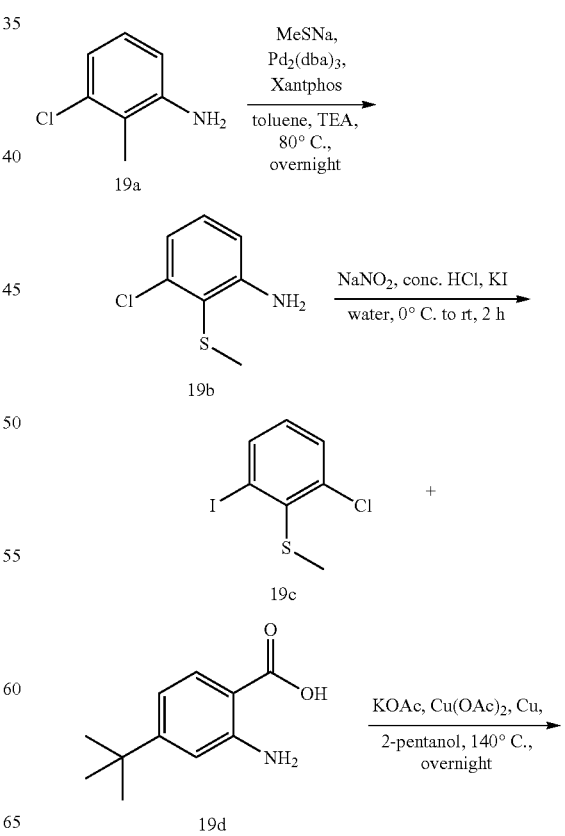

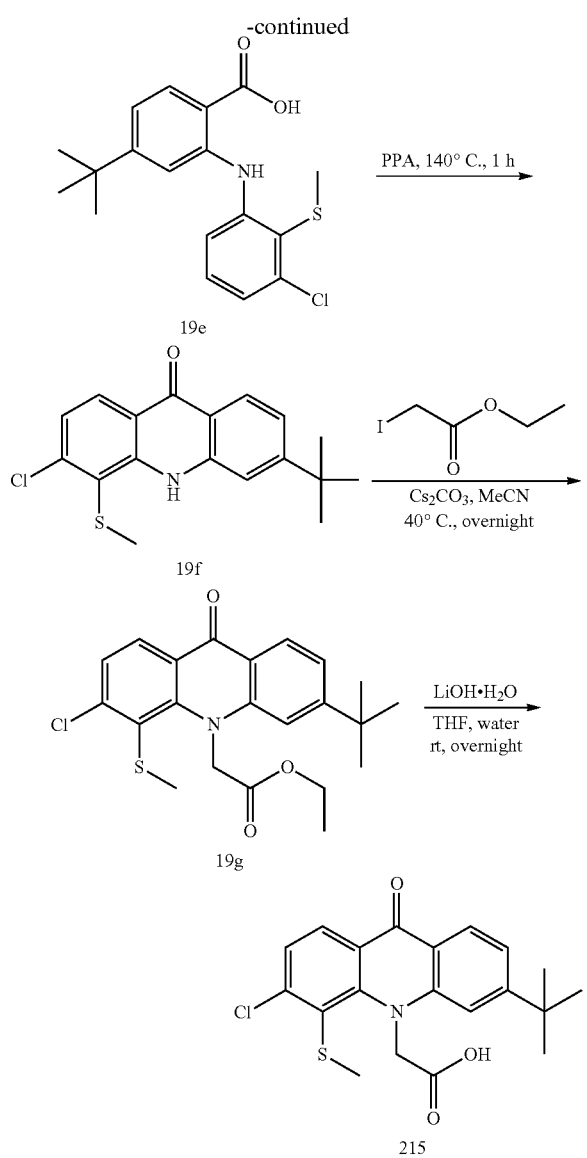

Step 1

A mixture of 19a (1.0 g, 4.0 mmol, 1.0 eq), Pd₂(dba)₃ (230 mg, 0.4 mmol, 0.1 eq), Xantphos (232 mg, 0.4 mmol, 0.1 eq), MeSNa (420 mg, 6.0 mmol, 1.5 eq) and TEA (1.0 mL) in Toluene (10.0 mL) was stirred at 80° C. overnight under argon atmosphere, then concentrated. The residue was purified by silica gel chromatography (PE/EtOAc, v/v=20:1) to afford 19b (912 mg, ca. 100%). LC/MS: 174.1 [M+H]⁺.

Step 2

A mixture of 19b (912 mg, 5.3 mmol, 1.0 eq) and 2 N HCl (20.0 mL) was stirred at room temperature for 5 min, then cooled to 0° C. and added NaNO₂ (439 mg, 6.4 mmol, 1.2 eq). The resulting mixture was stirred at 0° C. for 10 min, added KI (2.6 g, 15.9 mmol, 3.0 eq), stirred at room temperature for 1 h. The reaction mixture was extracted with EtOAc. The organic layer was concentrated and the residue was purified by silica gel chromatography (PE) to afford 19c (1.2 g, 80%).

Step 3

A mixture of 19d (600 mg, 3.1 mmol, 1.0 eq), 19c (1.3 g, 4.0 mmol, 1.3 eq), potassium acetate (608 mg, 6.2 mmol, 2.0 eq), copper powder (60 mg, 0.93 mmol, 0.3 eq), and cupric acetate (169 mg, 0.93 mmol, 0.3 eq) in 2-pentanol (60.0 mL) was stirred at 140° C. overnight under argon atmosphere, then cooled to room temperature. 2 N NaOH (200.0 mL) was added. The mixture was filtered through celite. The filtrate was acidified to pH=2 with conc. HCl, extracted with EtOAc. The organic layer was concentrated. The residue was triturated with PE and filtered to afford 19e (755 mg, 68.6%). LC/MS: 350.1 [M+H]⁺.

Step 4

A mixture of 19e (400 mg) and PPA (10.0 mL) was heated at 140° C. for 1 h under argon atmosphere, then cooled and poured into a mixture of ice and water, The solid was collected by filtration and dried to crude 19f (377 mg, ca 100%). LCMS: 332.1 [M+H]⁺.

Step 5

To a mixture of 19f (377 mg, 1.1 mmol, 1.0 eq) and Cs₂CO₃ (1.1 g, 3.4 mmol, 3.0 eq) in MeCN (20 mL) was added ethyl iodoatetate (1.2 g, 5.7 mmol, 5.0 eq) at room temperature. The mixture was heated to 40° C. and stirred overnight. The reaction mixture was cooled to room temperature, diluted with water, extracted with EtOAc. The organic layer was concentrated and the residue was purified by reverse-phase column to provide 19 g (210 mg, 44.2%). LCMS: 418.1 [M+H]⁺.

Step 6

To mixture of 19 g (50 mg: 0.12 mmol, 1.0 eq) in THF (10 mL) was added a solution of LiOH.H₂O (51 mg, 1.2 mmol, 10.0 eq) in H₂O (2 mL) dropwise. The reaction mixture was stirred at room temperature overnight, and diluted with water, extracted with EtOAc. The aqueous layer was acidified to pH=3 with 2 N HCl and extracted with EtOAc. The combined organic layers were washed with brine, dried over anhydrous Na₂SO₄ and filtered. The filtrate was concentrated in vacuo to afford 215 (34.6 mg, 62.5%). ¹H NMR (400 MHz, DMSO-d₆): δ 12.98 (s, 1H), 8.22 (d. J=7.6 Hz, 1H), 8.12 (d, J=7.6 Hz, 1H), 7.67 (s, 1H), 7.54 (d, J=7.6 Hz, 1H), 7.44 (d, J=7.6 Hz, 1H), 5.39 (s, 2H), 2.34 (s, 3H), 1.36 (s, 9H). LC/MS: 390.2 [M+H]⁺.

Example 38: Synthesis of Compound 229

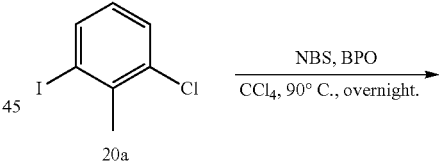

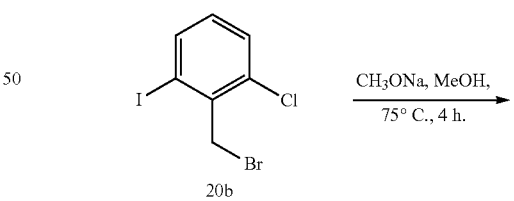

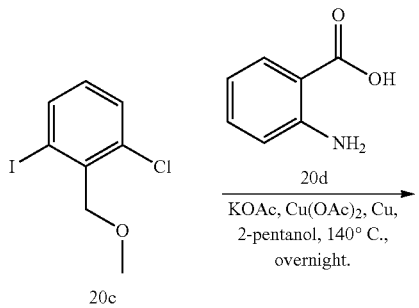

-continued

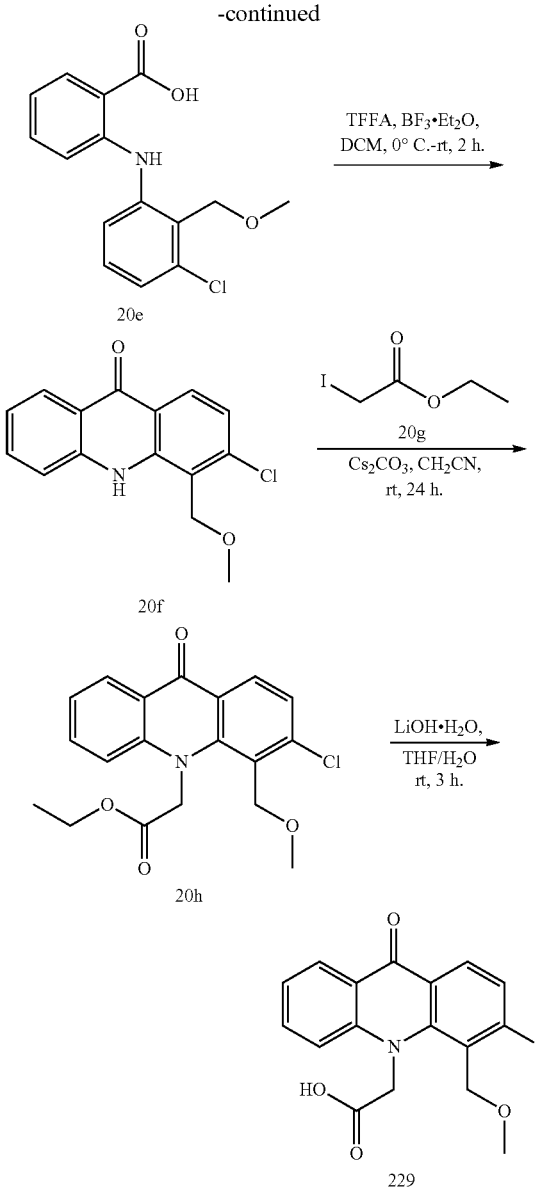

Step 1

To a solution of 20a (5.0 g, 19.8 mmol) in CCl₄ (50 mL) were added BPO (48.0 mg, 0.2 mmol) and NBS (3.52 g, 19.8 mmol) at room temperature. The resulting mixture was stirred at 90° C. overnight, cooled to room temperature, concentrated. The residue was purified by silica gel chromatography column (PE) to afford 20b (3.0 g, 46%) as a white solid.

Step 2

To a solution of 20b (3.0 g, 9.1 mmol) in MeOH (25 mL) was added CH₃ONa (491.4 mg, 9.1 mmol) at room temperature. The resulting mixture was stirred at 80° C. overnight, cooled to room temperature, evaporated. The residue was dissolved in EtOAc, washed with water and brine, dried over Na₂SO₄, filtered and concentrated in vacuo to afford the crude product which was purified by silica gel chromatography column (PE) to afford 20c (1.1 g, 43%) as yellow oil.

Step 3

A mixture of 20c (0.9 g, 3.2 mmol), 20d (364 mg, 2.7 mmol), potassium acetate (521 mg, 5.3 mmol), cupric acetate (160 mg, 0.8 mmol) and copper powder (51 mg, 0.8 mmol) in 2-Pentanol (30 mL) were stirred at 140° C. overnight under nitrogen atmosphere, then cooled to rt. Water (30 mL) was added. The mixture was filtered through celite. The filtrate was acidified to pH=2 with 1 N HCl, extracted with EtOAc (50 mL×2). The combined organic layers were washed with brine (50.0 mL), dried over anhydrous Na₂SO₄, filtered and concentrated in vacuo to afford the crude. The crude was purified by trituration with acetonitrile and filtered to afford 20e (560 mg, 60%) as a white solid. LC/MS: 290.2 [M−H].

Step 4

To solution of 20e (210 mg, 0.8 mmol) in DCM (15 mL) was added BF₃.Et₂O (1 M, 0.5 mL) and TFAA (1.0 mL) at 0° C. The resulting mixture was stirred at room temperature for 2 h under N₂ atmosphere. Water (10 mL) was added. The mixture was adjusted to pH=7-8 with sat. NaHCO₃ (aq.), extracted with DCM (20 mL). The organic layer was washed with brine, dried over anhydrous Na₂SO₄, filtered and concentrated in vacuo to afford 20f (190 mg, 96%) as a yellow solid. LC/MS: 274.2 [M+H]⁺.

Step 5

A mixture of 20f (100 mg, 0.37 mmol), 20 g (157 mg, 0.73 mmol) and Cs₂CO₃(359 mg, 1.10 mmol) in CH₃CN (10 mL) was stirred at room temperature for 24 h, and then concentrated. The residue was purified by silica gel chromatography column (PE/EA=10:1) to afford 20 h (25 mg, 17%) as a yellow solid. LC/MS: 360.2[M+H]⁺.

Step 6

To a solution of 20 h (25 mg, 0.07 mmol) in THF (5 mL) was added LiOH.H₂O (15 mg, 0.35 mmol) at room temperature. The resulting mixture was stirred at room temperature for 3 h, acidified by 2N HCl (20 mL), extracted with EtOAc (10 mL×3). The organic layers were washed with brine, dried over anhydrous Na₂SO₄, concentrated. The residue was purified by silica gel chromatography column (DCM/MeOH=10:1) to afford 229 (10 mg, 43%) as a yellow solid. ¹H NMR (400 MHz, d6-DMSO): δ 8.26 (d. J=8.4 Hz, 1H), 8.20 (d, J=8 Hz, 1H), 7.74 (t, J=7.2 Hz, 1H), 7.60 (d, J=8.8 Hz, H), 7.40 (d, J=8.8 Hz, 1H), 7.30 (t, J=7.2 Hz, 1H), 4.85 (s, 2H), 4.74 (s, 2H), 3.46 (s, 3H) ppm. LC/MS: 332.2 [M+H]⁺.

Example 39: Synthesis of Compound 204

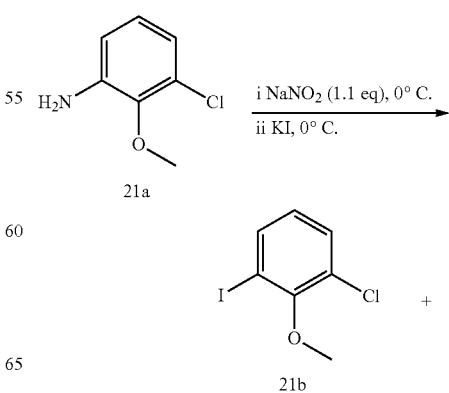

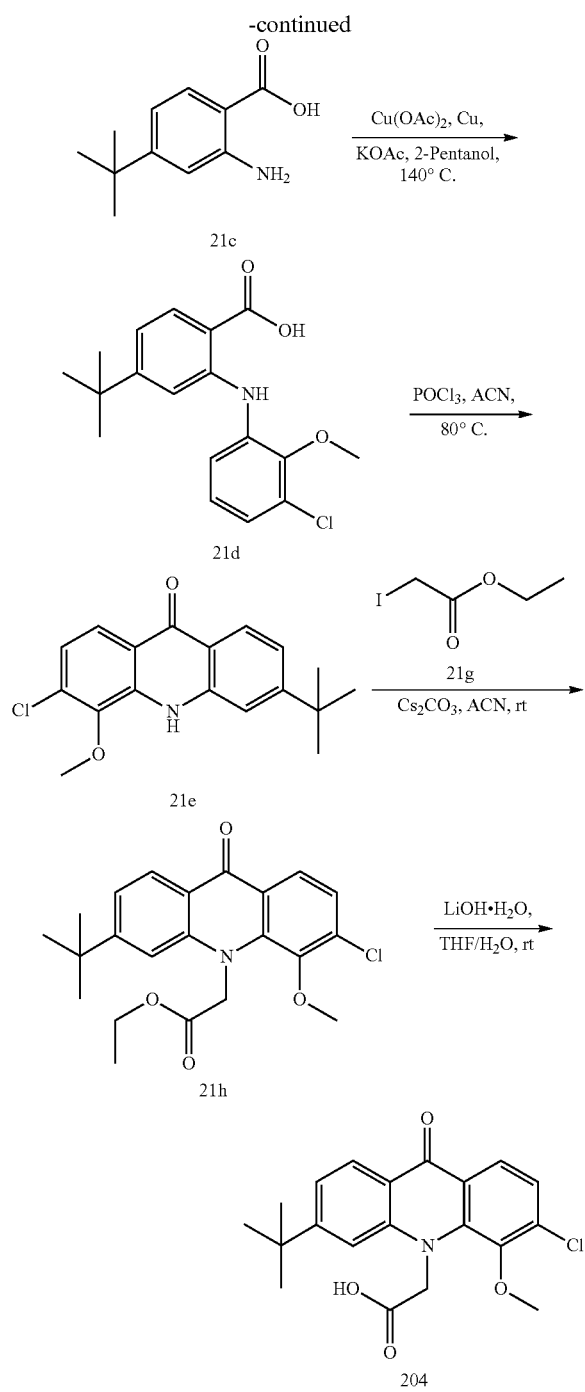

Step 1

A mixture of 21a (2.0 g, 12.7 mmol) and 4 N $H_2SO_4$ (20 mL) was stirred at room temperature for 5 min, then cooled to 0° C. and added a solution of $NaNO_2$ (0.96 g, 14.0 mmol) in water (5 mL). The resulting mixture was stirred at 5° C. for 20 min, then added to a solution of KI (10 g, 63.5 mmol) in water (40 mL) at 0° C. The resulting mixture was stirred for 30 min, and then extracted with EtOAc (50.0 mL×2). The combined organic layers were washed with $Na_2SO_3$ (50 mL×2) and brine, dried over anhydrous $Na_2SO_4$ and filtered. The filtrate was concentrated in vacuo to afford crude 21b (3.5 g, 100%).

Step 2

A mixture of 21b (1.1 g, 3.9 mmol), 21c (0.5 g, 2.6 mmol), KOAc (510 mg, 5.2 mmol), $Cu(OAc)_2$ (140 mg, 0.78 mmol), and Cu (50 mg, 0.78 mmol) in 2-Pentanol (10.0 mL) was stirred at 140° C. in sealed-tube overnight under $N_2$ atmosphere, then cooled to room temperature. Water (50.0 mL) was added. The mixture was acidified to pH=2 with 2 N HCl, extracted with EtOAc (50.0 mL×2). The combined organic layers were washed with brine, dried over anhydrous $Na_2SO_4$ and filtered. The filtrate was concentrated in vacuo. The residue was purified by chromatography on silica gel (PE/EtOAc v/v=5/1) to afford 21d (810 mg, 93.5%). LC/MS: 334.2 $[M+H]^+$.

Step 3

To a solution of 21d (810 mg; 2.43 mmol) in acetonitrile (30.0 mL) was added $POCl_3$ (0.56 mL, 6.1 mmol) dropwise at 80° C. The mixture was stirred at 80° C. for 5 h, cooled to room temperature. The residue was added EtOAc (50.0 mL), washed with sat.$Na_2CO_3$ and brine. The organic layer was dried over anhydrous $Na_2SO_4$ and filtered. The filtrate was concentrated in vacuo. The residue was purified by chromatography on silica gel (PE/EtOAc v/v=10/1) to afford 21e (350 mg, 46.8%). LC/MS: 316.2 $[M+H]^+$.

Step 4

To a mixture of 21e (350 mg, 1.11 mmol) and $Cs_2CO_3$ (1.08 g, 3.33 mmol) in acetonitrile (30 mL) was added 21 g (480 mg, 2.22 mmol). The mixture was stirred at room temperature overnight. The reaction mixture was added 2N HCl (20 mL), extracted with EtOAc (50.0 mL×2). The combined organic layers were dried over anhydrous $Na_2SO_4$ and filtered. The filtrate was concentrated in vacuo. The residue was purified by Prep-HPLC to afford 21 h (300 mg, 67.2%). LCMS: 402.4 $[M+H]^+$.

Step 5

To mixture of 21 h (300 mg; 0.76 mmol) in THF (15 mL) was added a solution of $LiOH.H_2O$ (70 mg, 1.5 mmol) in $H_2O$ (0.8 mL). The reaction mixture was stirred at room temperature overnight, diluted with water (30 mL), extracted with EtOAc (20 mL×2). The aqueous layer was acidified to pH=3 with 2 N HCl and extracted with EtOAc (40 mL×2). The combined organic layers were dried over anhydrous $Na_2SO_4$ and filtered. The filtrate was concentrated in vacuo to afford 204 (280 mg, 97.9%) as a yellow solid. $^1H$ NMR (400 MHz. DMSO-$d_6$): S13.41 (s, 1H), 8.17 (d, J=8.8 Hz, 1H), 8.05 (d, J=8.8 Hz, 1H), 7.49-7.42 (m, 3H), 5.16 (s, 2H), 3.76 (s, 3H), 1.36 (s, 9H) ppm, LC/MS: 374.3 $[M+H]^+$.

Example 40: Synthesis of Compound 237

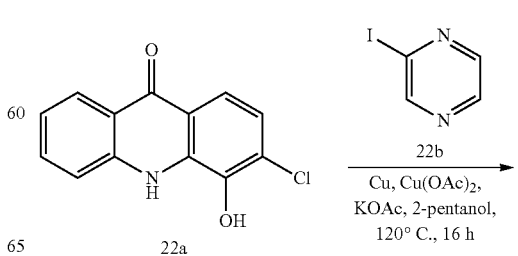

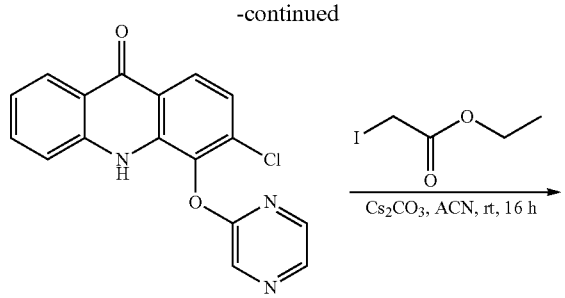

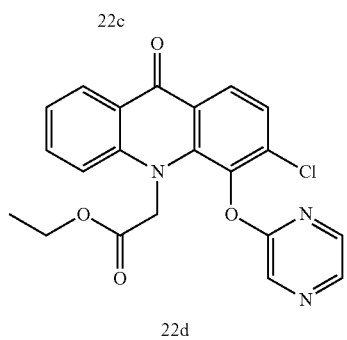

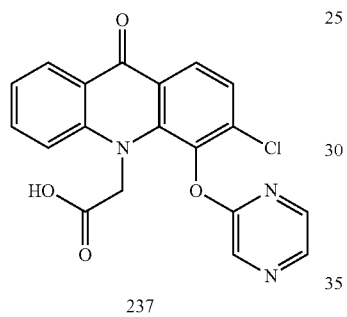

Step 1

A mixture of 22a (100 mg, 0.407 mmol, 1.0 eq), 22b (100 mg, 0.488 mmol, 1.2 eq), potassium acetate (100 mg, 1.018 mmol, 2.5 eq), cupric acetate (37 mg, 0.204 mmol, 0.5 eq), and copper powder (13 mg, 0.204 mmol, 0.5 eq) in 2-Pentanol (8.0 mL) was stirred at 120° C. overnight under nitrogen atmosphere. The reaction mixture was cooled to room temperature and filtered through celite. The filtrate was concentrated in vacuo to afford the crude product which was triturated with PE (2 mL) and filtered to afford 22c (112 mg, 85%) as a white solid. LCMS: 324.1 [M+H]$^+$.

Step 2

To a mixture of 22c (102 mg, 0.315 mmol, 1.0 eq) and Cs$_2$CO$_3$ (257 mg, 0.785 mmol, 2.5 eq) in acetonitrile (10 mL) was added ethyl iodoacetate (168 mg, 0.785 mmol, 2.5 eq). The reaction mixture was stirred at room temperature overnight. Water (10 mL) was added. The resulting mixture was extracted with EtOAc (10 mL×2). The combined organic layers were washed with brine (10 mL×2), dried over anhydrous Na$_2$SO$_4$ and filtered. The filtrate was concentrated in vacuo. The residue was purified by silicon column chromatography (PE:EA=4:1) to afford the crude product which was further purified by prep-HPLC to afford 22d (32 mg, 25%) as a white solid. LCMS: 410.2 [M+H]$^+$ Step 3

A mixture of 22d (32 mg; 0.078 mmol, 1.0 eq), LiOH H$_2$O (10 mg, 0.234 mmol, 3.0 eq) in THF (1 mL) and H$_2$O (0.5 mL) was stirred at room temperature overnight. The reaction mixture was diluted with water (1 mL). The resulting mixture was extracted with EtOAc (3 mL×2). The n the aqueous layer was acidified to pH=3 with 2 N HCl and extracted with EtOAc (3 mL×2). The combined organic layers were dried over anhydrous Na$_2$S04 and filtered. The filtrate was concentrated in vacuo to afford 237 (10 mg, 34%) as a white solid. $^1$H NMR (400 MHz, DMSO-d6): δ 12.86 (br, 1H), 8.98 (s, 1H), 8.83 (s, 1H), 8.75 (s, 1H), 8.36 (d, J=8.0 Hz, 1H), 8.22 (d, J=8.8 Hz, 1H), 7.67 (t, J=8.8 Hz, 1H), 7.53 (d. J=8.4 Hz, 1H), 7.42 (t, J=7.2 Hz, 1H), 6.78 (d, J=8.8 Hz, 1H), 4.12 (s, 2H). LC/MS: 382.3 [M+H]$^+$.

Example 41: Synthesis of Compound 244

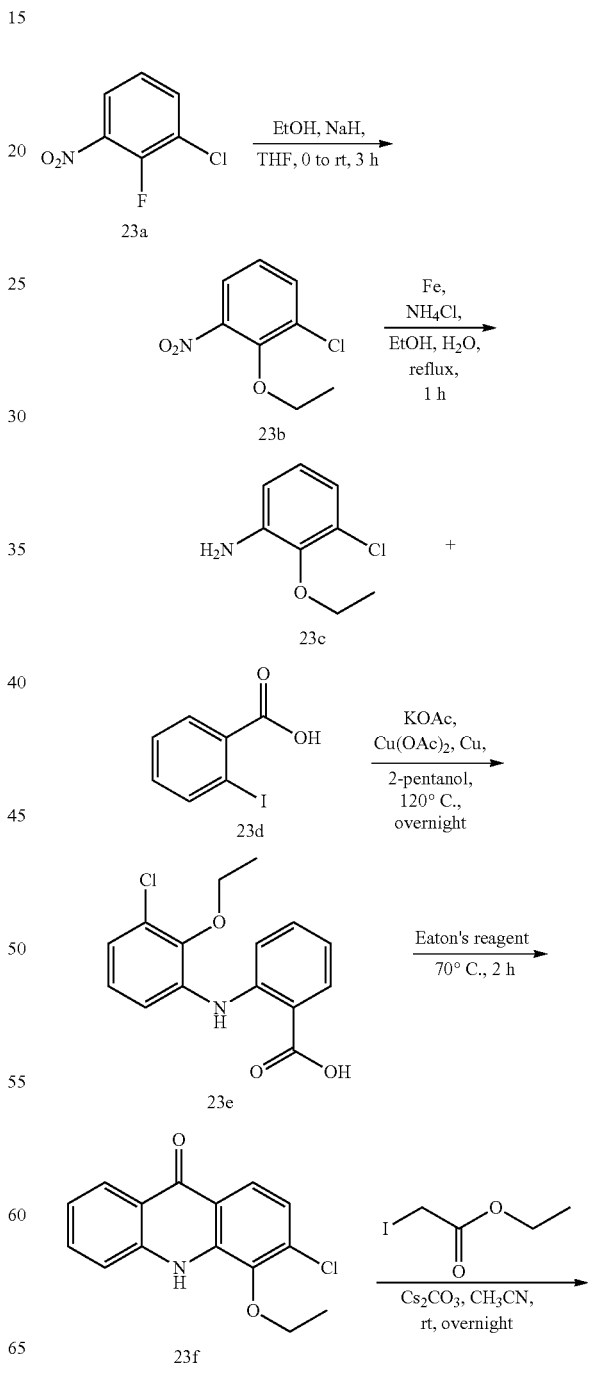

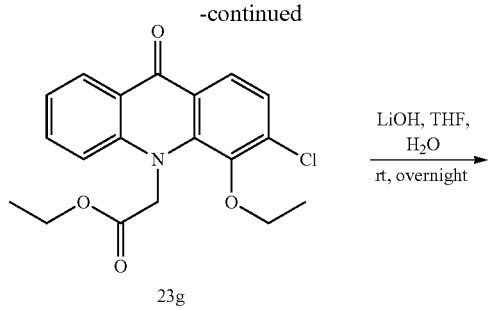

23g

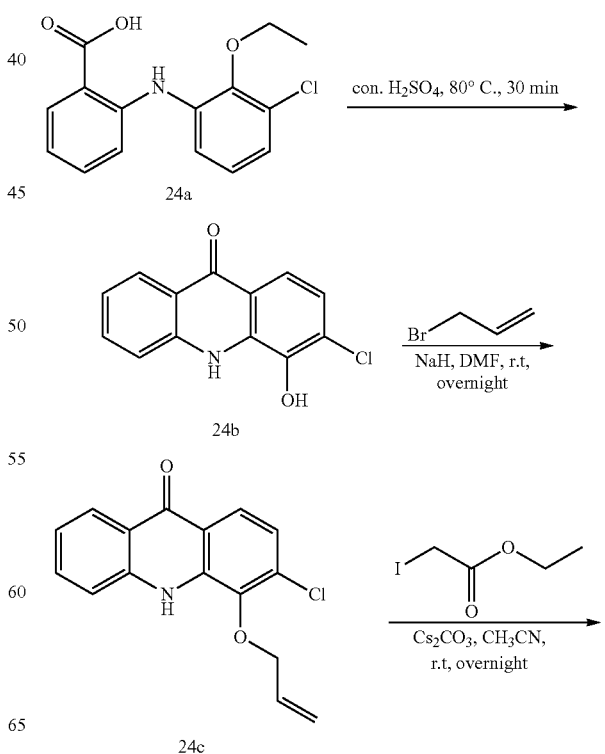

244

Step 1

To a mixture of ethanol (15.8 g, 342 mmol, 3.0 eq), NaH (60%) (16 g, 399 mmol, 3.5 eq) in THF (150 mL) was added a solution of 23a (20 g, 114 mmol, 1.0 eq) in THF (50 mL) slowly to keep the reaction temperature below 10° C. After addition, the mixture was stirred at room temperature for 2 h. Water (300 mL) was added and the resulting mixture was extracted with EtOAc (150.0 mL×2). The combined organic layers were washed with brine (150.0 mL×2), dried over anhydrous $Na_2SO_4$ and filtered. The filtrate was concentrated in vacuo to afford crude 23b as yellow oil (30 g, ca. 100%).

Step 2

A mixture of 23b (30 g, 114 mmol, 1.0 eq), $NH_4Cl$ (6.1 g, 114 mmol, 1.0 eq) in ethanol (210 mL) and water (90 mL) was heated to reflux and Fe (19 g, 342 mmol, 3.0 eq) was added in portions. After addition, the mixture was stirred under reflux for 2 h, and then cooled to room temperature. The mixture was filtered through celite. Water (400 mL) was added to the filtrate. The resulting mixture was extracted with EtOAc (200 mL×2). The combined organic layers were washed with brine (200 mL×2), dried over anhydrous $Na_2SO_4$ and filtered. The filtrate was concentrated in vacuo to afford crude 23c as yellow oil (26 g, ca. 100%). LC/MS: 172.1 $[M+H]^+$.

Step 3

A mixture of 23c (3.0 g, 17.5 mmol, 1.0 eq), 23d (4.3 g, 17.5 mmol, 1.0 eq), potassium acetate (3.5 g, 35.0 mmol, 2.0 eq), cupric acetate (0.96 g, 5.3 mmol, 0.3 eq), and copper powder (0.34 g, 5.3 mmol, 0.3 eq) in 2-Pentanol (50.0 mL) was stirred at 120° C. overnight under nitrogen atmosphere. Then the reaction mixture was cooled to room temperature and water (30.0 mL) was added. The mixture was filtered through celite. The filtrate was acidified to pH=2 with 2 N HCl, and water (50.0 mL) was added. The resulting mixture was extracted with EtOAc (50.0 mL×2). The combined organic layers were washed with brine (50.0 mL×2), dried over anhydrous $Na_2SO_4$ and filtered. The filtrate was concentrated in vacuo to afford crude. The crude was purified by trituration with PE (20 mL) to afford 23e (3.7 g, 60%). LC/MS: 292.2 $[M+H]^+$.

Step 4

A mixture of 23e (500 mg, 1.7 mmol) and Eaton's reagent (5 mL) was heated at 70° C. for 2 h, then cooled and poured into a mixture of ice and water. The solid was collected by filtration and dried to afford crude 23f (300 mg, 63%). LC/MS: 274.1 $[M+H]^+$ Step 5

To a mixture of 23f (230 mg, 0.84 mmol, 1.0 eq) and $Cs_2CO_3$ (824 mg, 2.5 mmol, 3.0 eq) in acetonitrile (10 mL) was added ethyl iodoacetate (363 mg, 1.68 mmol, 2.0 eq). The mixture was stirred at room temperature overnight, then filtered through celite. The filtrate was concentrated in vacuo to give crude product 23 g (310 mg, ca. 100%) as a yellow solid. LC/MS: 360.1 $[M+H]^+$.

Step 6

A mixture of 23 g (200 mg; 0.55 mmol, 1.0 eq), LiOH $H_2O$ (116 mg, 2.77 mmol, 5.0 eq) in THF (5.0 mL) and $H_2O$ (5.0 mL) was stirred at room temperature overnight, diluted with water (15.0 mL), extracted with EtOAc (10 mL×2). The aqueous layer was acidified to pH=3 with 2 N HCl and extracted with EtOAc (15.0 mL×2). The combined organic layers were washed with brine (10.0 mL×2), dried over anhydrous $Na_2SO_4$ and filtered. The filtrate was concentrated in vacuo to afford 244 (55 mg, 29%) as a yellow solid. $^1$H NMR (400 MHz, DMSO-$d_6$): δ 13.19 (s, 1H), 8.24 (dd, J=1.6 Hz, 8.0 Hz, 1H), 8.07 (d, J=8.4 Hz, 1H), 7.84-7.80 (m, 1H), 7.59 (d, J=8.8 Hz, 1H), 7.47 (d, J=8.8 Hz, 1H), 7.37 (m, 1H), 5.19 (s, 2H), 3.92 (q, J=6.8 Hz, 2H), 1.38 (t, J=6.8 Hz, 3H). LC/MS: 332.1 $[M+H]^+$.

Example 42: Synthesis of Compound 273

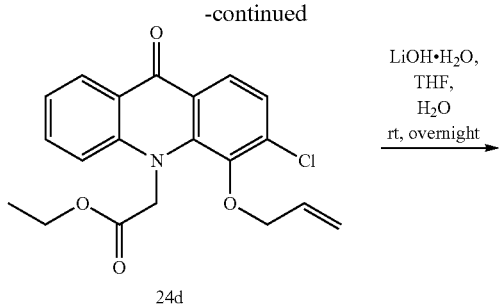

24d

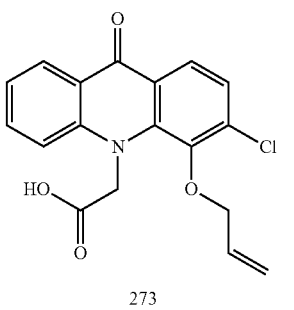

273

Step 1

A mixture of 24a (2.7 g, 9.3 mmol) and con. $H_2SO_4$ (27 mL) was heated at 80° C. for 30 min, then cooled and poured into a mixture of ice and water. The solid was collected by filtration and dried to afford crude. The crude was triturated with EtOAc (10 mL) and filtered to afford 24b (1.4 g, 55%). $^1$H NMR (400 MHz, DMSO-d6): δ11.29 (s, 1H), 10.51 (s, 1H), 8.21 (d, J=7.6 Hz, 1H), 7.98 (d, J=8.4 Hz, 1H), 7.76-7.69 (m, 2H), 7.27 (t, J=7.6 Hz, 1H), 7.21 (d, J=8.8 Hz, 1H). LC/MS: 246.1 [M+H]$^+$.

Step 2

To a mixture of 24b (245 mg, 1.0 mmol, 1.0 eq) in DMF (25 mL) was added NaH (60%) (48 mg, 1.2 mmol, 1.2 eq). The mixture was stirred at room temperature for 10 min. Allyl bromide (121 mg, 1.0 mmol, 1.0 eq) was added, and then the mixture was stirred at room temperature overnight under nitrogen atmosphere. Water (75 mL) was added. The resulting mixture was extracted with EtOAc (100 mL×2). The combined organic layers were washed with brine (100 mL×2), dried over anhydrous $Na_2SO_4$ and filtered. The filtrate was concentrated in vacuo to afford the crude product which was purified by trituration with EtOAc/PE (3 mL/9 mL) to afford 24c (130 mg, 45%). LC/MS: 286.1 [M+H]$^+$.

Step 3

To a mixture of 24c (130 mg, 0.46 mmol, 1.0 eq) and $Cs_2CO_3$ (446 mg, 1.38 mmol, 3.0 eq) in acetonitrile (15 mL) was added ethyl iodoacetate (196 mg, 0.92 mmol, 2.0 eq). The mixture was stirred at room temperature overnight, filtered through celite. The filtrate was concentrated in vacuo to give the crude product which was further purified by prep-HPLC to afford 24d (113 mg, 66%) as a yellow solid. LC/MS: 372.2 [M+H]$^+$.

Step 4

A mixture of 24d (105 mg; 0.28 mmol, 1.0 eq), LiOH $H_2O$ (60 mg, 1.4 mmol, 5.0 eq) in THF (10.0 mL) and $H_2O$ (10.0 mL) was stirred at room temperature overnight, diluted with water (30.0 mL), extracted with EtOAc (20 mL×2). The aqueous layer was acidified to pH=3 with 2 N HCl and extracted with EtOAc (30.0 mL×2). The combined organic layers were washed with brine (30.0 mL×2), dried over anhydrous $Na_2SO_4$ and filtered. The filtrate was concentrated in vacuo to afford 273 (30 mg, 30%) as a yellow solid. $^1$H NMR (400 MHz, DMSO-d$_6$): δ 13.14 (s, 1H), 8.25 (dd, J=0.8, 8.0 Hz, 1H), 8.07 (d, J=8.8 Hz, 1H), 7.84-7.80 (m, 1H), 7.61 (d, J=8.8 Hz, 1H), 7.47 (d, J=8.4 Hz, 1H), 7.37 (t, J=7.6 Hz, 1H), 6.11-6.04 (m, 1H), 5.44-5.39 (dd, J=1.6, 17.2 Hz, 1H), 5.28 (d, J=15.6 Hz, 1H), 5.24 (s, 2H), 4.44 (d, J=6.0 Hz, 2H). LC/MS: 344.2 [M+H]$^+$.

Example 43: Synthesis of Compound 336

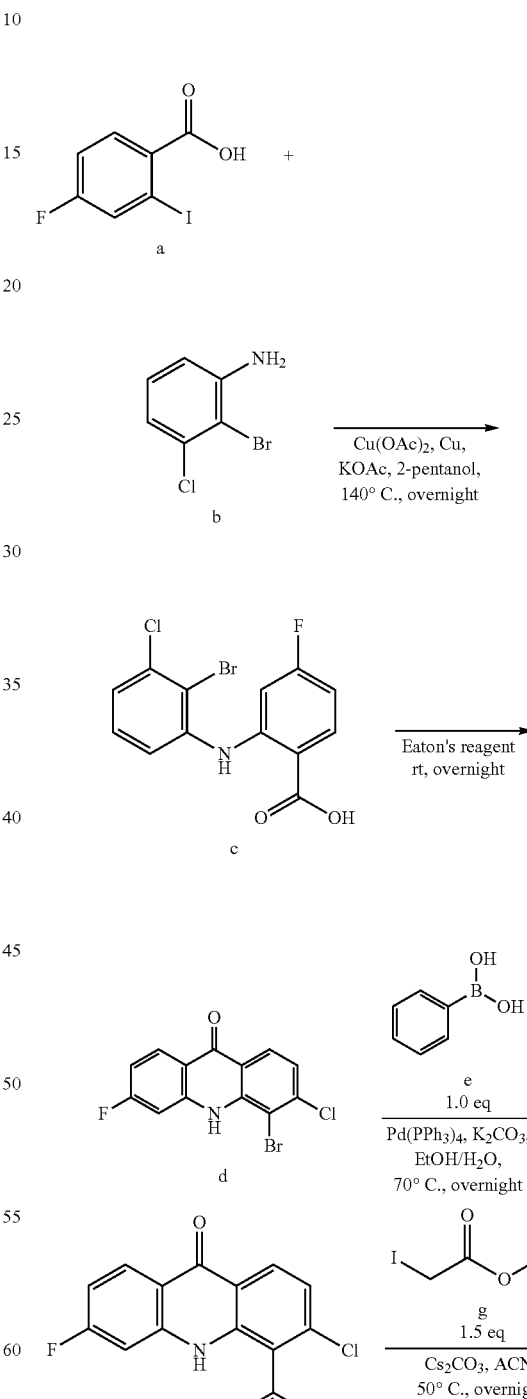

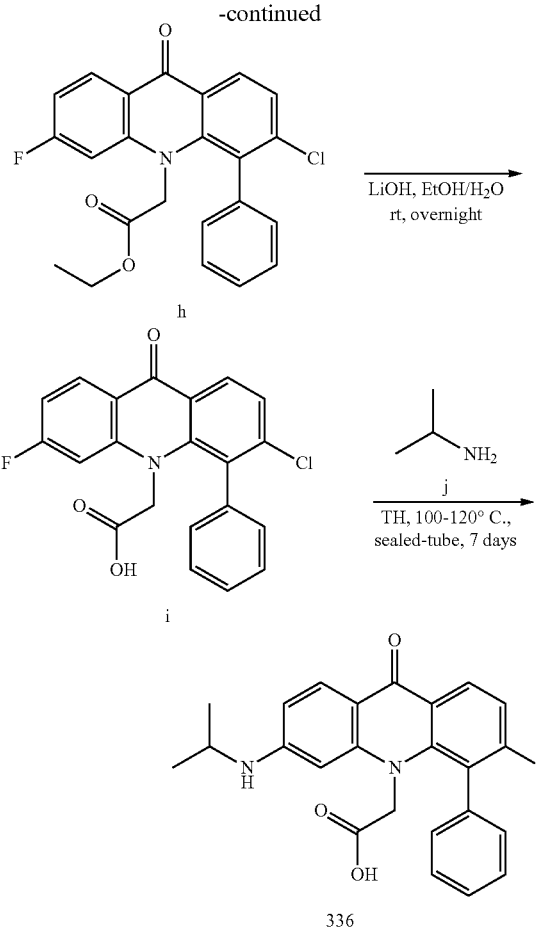

Step 1

A mixture of a (1.33 g, 5 mmol, 1.0 eq), b (1.5 g, 7.5 mmol, 1.5 eq), KOAc (1.3 g, 12.5 mmol, 2.5 eq), copper powder (100.0 mg, 1.5 mmol, 0.3 eq), and Cu(OAc)₂ (270.0 mg, 1.5 mmol, 0.3 eq) in 2-pentanol (30.0 mL) was stirred at 140° C. overnight under $N_2$ atmosphere, then cooled to room temperature. The mixture was diluted with water (100 mL), acidified to pH=3, with 2 N HCl and extracted with EtOAc (100 mL×2). The combined organic layers were dried over anhydrous $Na_2SO_4$ and concentrated. The residue was purified by chromatography on silica gel (EtOAc) to afford c (1.14 g, 66%). LC/MS: 341.9 [M−H]⁻.

Step 2

A mixture of c (1.14 g, 3.3 mmol) in Eaton's reagent (10 mL) was stirred at r.t. overnight. The mixture was poured into ice-water (50 g) and extracted with EtOAc (100 mL×2). The combined organic layers were dried over anhydrous $Na_2SO_4$ and concentrated to afford d (0.54 g, 50%). LC/MS: 325.9 [M+H]⁺.

Step 3

A mixture of d (540.0 mg, 1.66 mmol, 1.0 eq), e (205.0 mg, 1.66 mmol, 1.0 eq), Pd(PPh₃)₄ (96 mg, 0.08 mmol, 0.05 eq), $K_2CO_3$ (700.0 mg, 4.98 mmol, 3.0 eq) in EtOH/$H_2O$ (50.0 mL/10 mL) was stirred at 70° C. overnight. The reaction mixture was diluted with water (500 mL) and extracted with EtOAc (50 mL×2). The combined organic layers were dried over anhydrous $Na_2SO_4$ and concentrated. The residue was purified by chromatography on silica gel (PE/EtOAc=2/1) to afford f (480 mg, 89%). LC/MS: 324.11 [M+H]⁺.

Step 4

A mixture of f (480.0 mg, 1.48 mmol, 1.0 eq), g (475.1 mg, 2.22 mmol, 1.5 eq), $Cs_2CO_3$ (1.0 g, 2.96 mmol, 2.0 eq) in acetonitrile (20 mL) was heated to 50° C. overnight. The reaction mixture was diluted with 1N HCl to pH=3 and extracted with EtOAc (50 mL×2). The combined organic layers were dried over anhydrous $Na_2SO_4$ and concentrated. The residue was purified by Prep-HPLC to afford h (220 mg, 36%). LC/MS: 410.2 [M+H]

Step 5

A mixture of h (220.0 mg, 0.29 mmol), LiOH (40.0 mg, 0.88 mmol, 3.0 eq) in THF/$H_2O$/EtOH (5 mL/1 mL/2 mL) was stirred at r.t. overnight. The reaction mixture was diluted with water (20 mL) and extracted with EtOAc (20 mL×2). The aqueous phase was adjusted to pH=3 with 2 N HCl and extracted with EtOAc (20 mL×2). The combined organic layers were dried over anhydrous $Na_2SO_4$ and concentrated to afford i (170 mg, 83%). LC/MS: 382.0 [M+H]⁺.

Step 6

A mixture of i (60 mg, 0.15 mmol) in THF (5 mL) and j (2M in THF, 2 mL) was stirred at 120° C. in sealed tube for 7 days. The reaction mixture was evaporated and the residue was purified by Prep-HPLC (C18) to afford 336 (19.5 mg, 30%). LC/MS: 421.2 [M+H]', ¹H NMR (400 MHz, DMSO-d₆): δ 8.24 (d, J=8.4 Hz, 1H), 7.92 (d, J=8.8 Hz, H), 7.45-7.55 (m, 4H), 7.34-7.36 (m, 2H), 6.58-6.61 (m, 1H), 6.16 (s, 1H), 4.34 (s, 3H), 3.64-3.70 (m, 1H), 1.12-1.13 (m, 6H).

Example 44: Synthesis of Compound 334

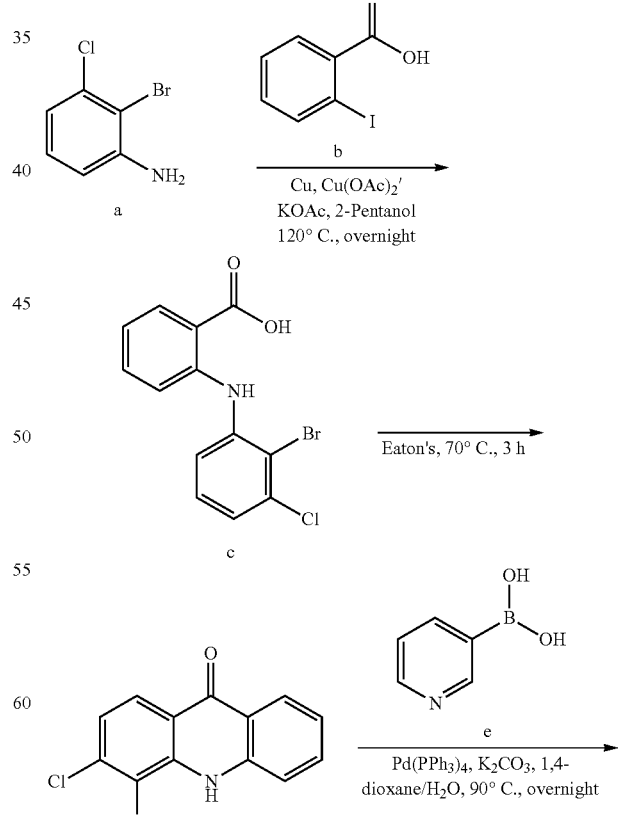

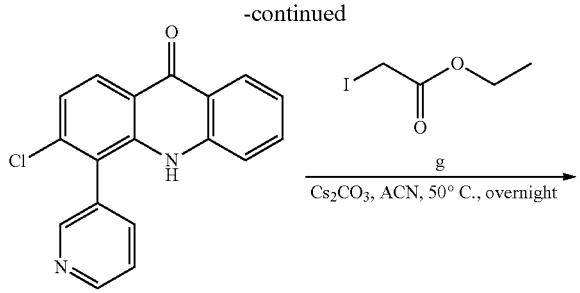

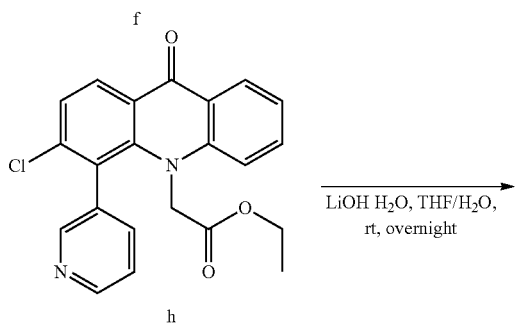

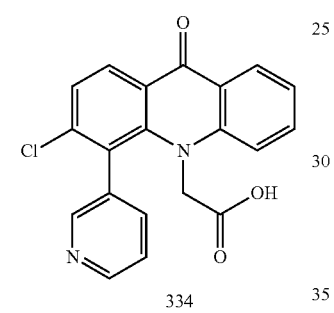

Step 1

A mixture of a (7.9 g, 38 mmol, 1.2 eq), b (8.0 g, 32 mmol, 1.0 eq), Cu powder (0.61 g, 9.6 mmol, 0.3 eq), Cu(OAc)$_2$ (1.7 g, 9.6 mmol, 0.3 eq), and KOAc (9.4 g, 96 mmol, 3.0 eq) in 2-pentanol (200 mL) was stirred at 120° C. overnight under N$_2$ atmosphere, and cooled to room temperature and filtered through celite. The filtrate was concentrated in vacuo. The residue was dissolved in H$_2$O (100 mL), acidified to pH=5 with 1 N HCl, and extracted with EtOAc (100 mL×2). The organic layer was washed with brine, dried over anhydrous Na$_2$SO$_4$, and concentrated to afford the crude which was triturated with acetonitrile (30 mL), filtered to afford c (4.2 g, 40%) as a yellow solid. LC/MS: 326.0 [M+H]$^+$.

Step 2

A mixture of c (4.2 g, 12.9 mmol, 1.0 eq) in Eaton's reagent (50 mL) was stirred at 70° C. for 3 h under N$_2$ atmosphere, and cooled to room temperature and poured into ice-water. The suspension was filtered and the solid was dried to afford d (4.0 g, ca. 100%) as a yellow solid. $^1$H NMR (400 MHz, DMSO-d$_6$): δ 10.76 (s, 1H), 8.26 (d, J=8.8 Hz, 1H), 8.21 (d, J=8.0 Hz, 1H), 8.13 (d, J=8.4 Hz, 1H), 7.79 (t, J=8.4 Hz, 1H), 7.49 (d, J=8.8 Hz, 1H), 7.35 (t, J=7.2 Hz, 1H). LC/MS: 307.9 [M+H]$^+$.

Step 3

A mixture of d (400.0 mg, 1.3 mmol, 1.0 eq), e (330.0 mg, 2.6 mmol, 2.0 eq), Pd(PPh$_3$)$_4$ (150.0 mg, 0.13 mmol, 0.1 eq), and K$_2$CO$_3$ (540.0 mg, 3.9 mmol, 3.0 eq) in 1,4-dioxane/ H$_2$O (20 mL/4 mL) was stirred at 90° C. overnight under N$_2$ atmosphere, and then concentrated. The residue was purified by silica gel column (EtOAc) to afford f (260.0 mg, 65%) as a yellow solid. LC/MS: 307.1 [M+H]$^+$.

Step 4

A mixture of f (260.0 mg, 0.85 mmol, 1.0 eq), g (370.0 mg, 1.7 mmol, 2.0 eq), and Cs$_2$CO$_3$ (830.0 mg, 2.55 mmol, 3.0 eq) in acetonitrile (20 mL) was stirred at 50° C. overnight under N$_2$ atmosphere, and then concentrated. The residue was purified by chromatography on silica gel (EA/ PE=1:1) to afford h (25.0 mg, 7%) as a yellow solid. LC/MS: 379.1 [M+H]$^+$.

Step 5

A mixture of h (25 mg, 0.06 mmol, 1.0 eq) and LiOH H$_2$O (25 mg, 0.6 mmol, 10.0 eq) in THF/H$_2$O (5 mL/1 mL) was stirred at r.t. overnight under N$_2$ atmosphere. H$_2$O (20 mL) was added and the resulting mixture was acidified to pH=1 with 1 N HC, and filtered to afford 334 (3.1 mg, 14%) as a yellow solid. H NMR (400 MHz, DMSO-d$_6$): δ. 12.74 (brs, 1H), 8.69 (s, 1H), 8.57 (s, 1H), 8.37 (d, J=8.4 Hz, 1H), 8.25 (d, J=8.0 Hz, 1H), 7.89 (d, J=7.6 Hz, 1H), 7.74 (t, J=7.6 Hz, 1H), 7.62-7.55 (m, 2H), 7.47 (d, J=8.8 Hz, 1H), 7.36 (t, J=7.6 Hz, 1H), 4.55 (s, 2H). LC/MS: 365.1 [M+H]$^+$.

Example 45: Synthesis of Compound 332

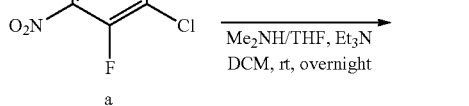

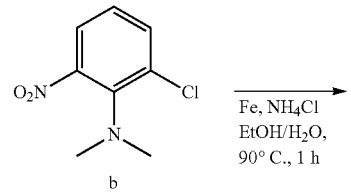

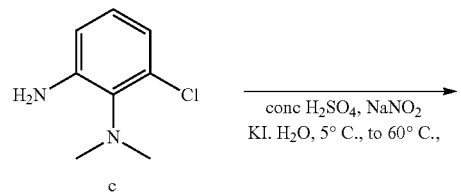

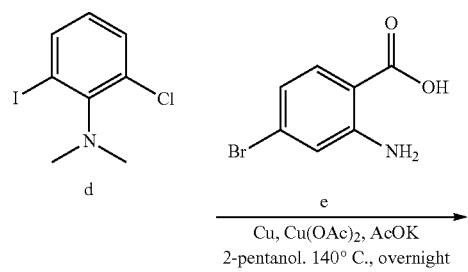

-continued

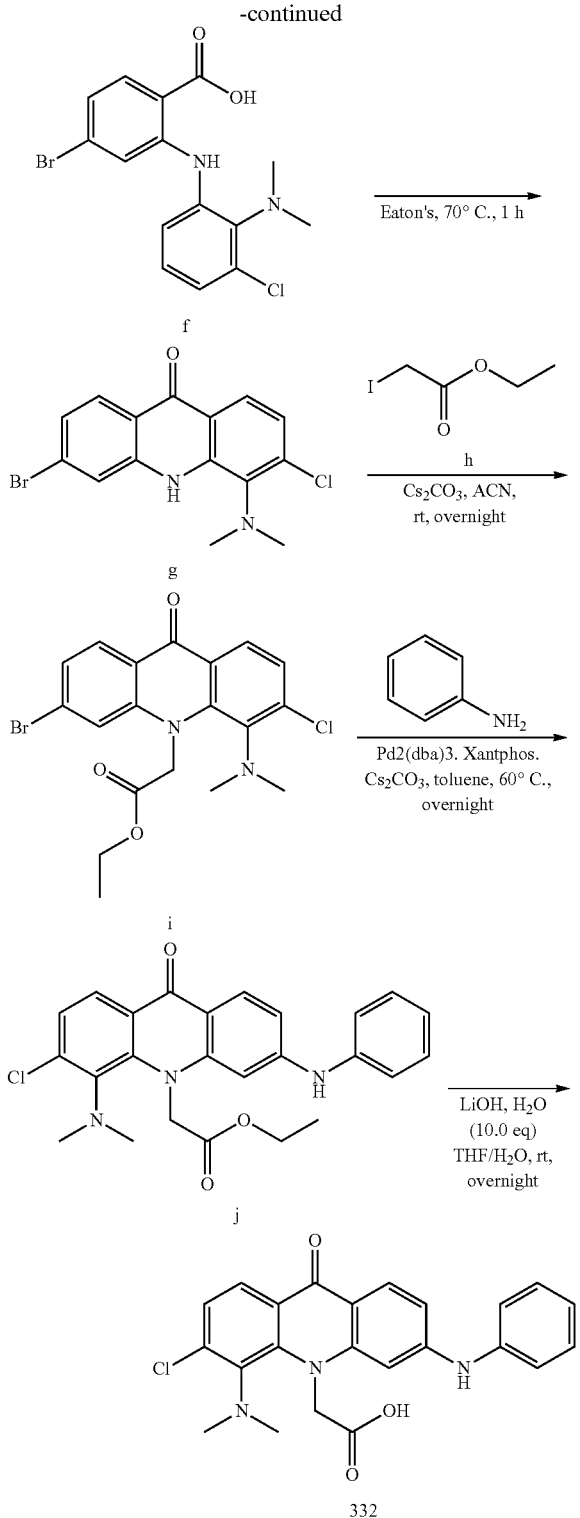

Step 1

To a solution of a (20 g, 114 mmol, 1.0 eq) and Et₃N (13.7 g, 136 mmol, 1.2 eq) in DCM (100 mL) was added Me₂NH (2 M in THF, 91 ml, 182 mmol, 1.6 eq). The mixture was stirred at r.t. overnight, added with DCM (300 mL), and washed with brine (100 mL). The organic layer was dried over anhydrous Na₂SO₄ and concentrated. The residue was purified by chromatography on silica gel (PE) to afford b (21.6 g, 95%) as colorless liquid. LCMS: 201.2 [M+H]⁺.

Step 2

A mixture of b (21.6 g, 108 mmol, 1.0 eq), Fe power (30.8 g, 550 mmol, 5.1 eq), and NH₄C₁ (59.0 g, 1.1 mol, 10.2 eq) in EtOH/H₂O (250 mL %50 mL) was stirred under reflux for 1 h. The reaction mixture was cooled to r.t. and filtered. The precipitate was washed with EtOAc. The filtrate was evaporated and the residue was purified by chromatography on silica gel (EA/PE=1/30) to afford c (18 g, 96%) as light-brown liquid. LCMS: 171.4 [M+H]⁺.

Step 3

To a mixture of c (18.0 g, 106 mmol, 1.0 eq) in water (240 mL) and conc. H₂SO₄ (60 mL) was added a solution of NaNO₂ (7.32 g, 106 mmol, 1.0 eq) in 30 mL of water maintaining the temperature below 10° C. After addition, the mixture was stirred for 30 minutes and poured into a solution of KI (21.9 g, 132 mmol, 1.25 eq) in water (120 mL). The resulting mixture was heated at 60° C. for 3 h, cooled, and added with CHCl₃ (300 mL). The organic layer was separated and successively washed with sat. Na₂CO₃(100 mL), 1 M sodium thiosulfate (10 mL), water (100 mL) and brine (100 mL), dried over anhydrous Na₂SO₄, and evaporated. The residue was purified by chromatography on silica gel (PE) to afford d (20.6 g, 69.2%) as colorless liquid. ¹H NMR (400 MHz, CDCl₃): 57.69 (dd, J=1.2, 8.0, 1H), 7.22 (dd, J=1.2, 8.0, 1H), 6.69 (t, J=8.0 Hz, 1H), 2.77 (s, 6H). LCMS: 282.0[M+H]⁺.

Step 4

A mixture of e (2.0 g, 9.3 mmol, 1.0 eq), d (3.9 g, 14.0 mmol, 1.5 eq), KOAc (2.7 g, 28.0 mmol, 3.0 eq), copper powder (179 mg, 2.8 mmol, 0.3 eq), and Cu(OAc)₂ (510 mg, 2.8 mmol, 0.3 eq) in 2-pentanol (30.0 mL) was stirred at 140° C. overnight under N₂ atmosphere, then cooled to room temperature. 2 N NaOH (100.0 mL) was added. The mixture was filtered through celite. The filtrate was acidified to pH=2 with conc. HCl, and extracted with EtOAc (100 mL×3). The combined organic layers were concentrated. The residue was triturated with PE/EA (10/1) and filtered to afford f (1.6 g, 47%). LC/MS: 369.0 [M+H]⁺.

Step 5

A solution of f (1.6 g, 4.3 mmol, 1.0 eq) in Eaton's reagent (20.0 mL) was stirred at 70° C. for 1 h. The mixture was poured into ice-water and filtered. The solid was dried to afford g (1.3 g, 87%). LCMS: 351.0 [M+H]⁺.

Step 6

A mixture of g (1.3 g, 3.7 mmol, 1.0 eq), h (1.6 g, 7.4 mmol, 2.0 eq), and Cs₂CO₃ (3.6 g, 11.1 mmol, 3.0 eq) in acetonitrile (50.0 mL) was stirred at r.t. overnight. Water (50 mL) was added to the reaction mixture water (50 mL), extracted with EtOAc (100 mL×2). The combined organic layers were dried over anhydrous Na₂SO₄ and concentrated. The residue was triturated with acetonitrile and filtered to give i (850.0 mg, 53%) as a yellow solid. LC/MS: 437.0 [M+H]⁺.

Step 7

A mixture of i (150.0 mg, 0.35 mmol, 1.0 eq), aniline (65.0 mg, 0.7 mmol, 2.0 eq), Pd₂(dba)₃ (32.0 mg, 0.035 mmol, 0.1 eq), Xantphos (20.0 mg, 0.035 mmol, 0.1 eq), and Cs₂CO₃ (343.0 mg, 1.05 mmol, 3.0 eq) in Toluene (5 mL) was heated to 60° C. and stirred overnight. The reaction mixture was cooled and concentrated. The residue was purified by column chromatography on silica gel (PE/EA=10/1 to 2/1) to afford j (103.0 mg, 67%). LC/MS: 450.2 [M+H]⁺.

Step 8

A mixture of j (103.0 mg, 0.67 mmol, 1.0 eq) and LiOH H$_2$O (281.0 mg, 6.7 mmol, 10.0 eq) in a mixed solvent of THF (10.0 mL), EtOH (6.0 mL), and H$_2$O (3.0 mL) was stirred at r.t. overnight, diluted with water (20 mL), and then extracted with EtOAc (20 mL×2). The aqueous layer was acidified to pH=3 with conc. HCl and extracted with EtOAc (20 mL×2). The combined organic layers were concentrated and purified by reversed phase chromatography (H$_2$O/MeCN=1/9 to 1/1, 1% TFA) to afford 332 (50.0 mg, 52.1%) as a yellow solid. $^1$H NMR (400 MHz, DMSO-d$_6$): δ 12.87 (s, 1H), 9.06 (s, 1H), 8.11 (d, J=8.8 Hz, 1H), 8.04 (d, J=8.8 Hz, 1H), 7.34 (m, 3H), 7.27 (m, 2H), 7.02 (m, 3H), 4.72 (s, 2H), 2.11 (s, 6H). LC/MS: 422.1 [M+H]$^+$.

Example 46: Synthesis of Compound 326

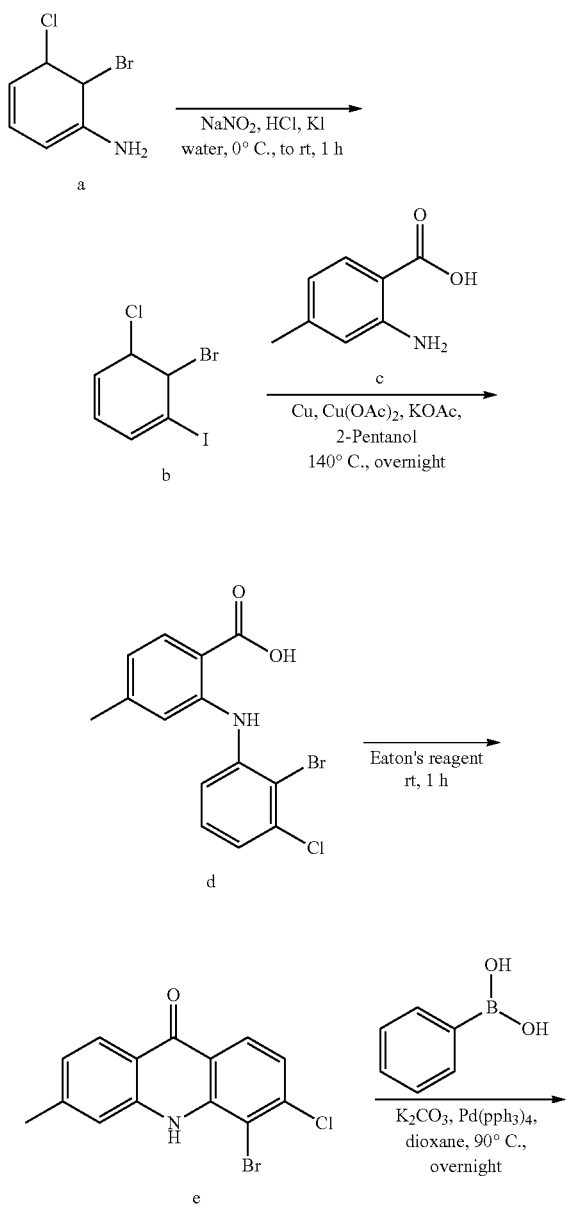

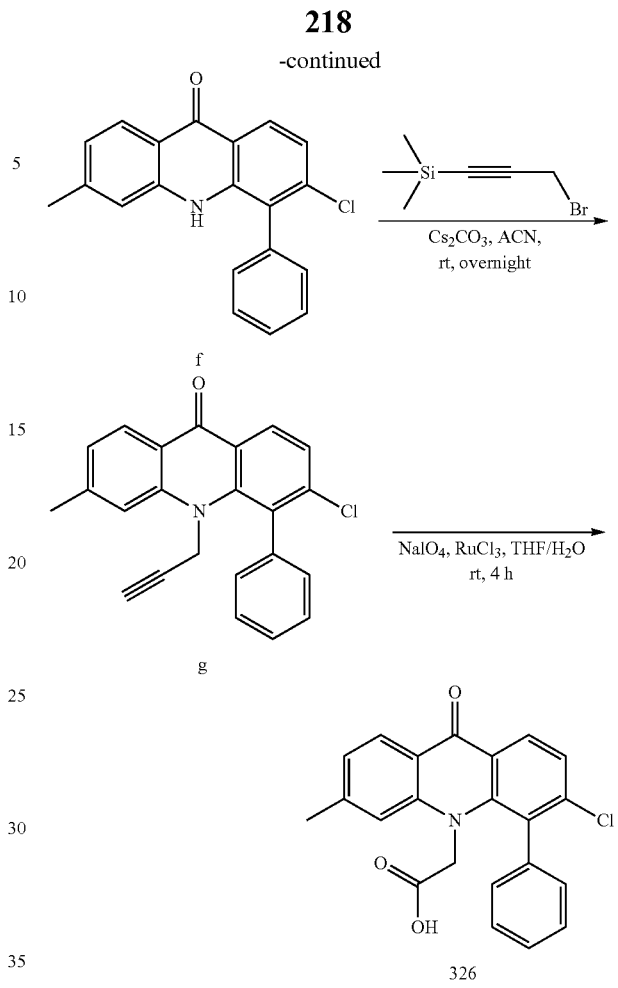

Step 1

A mixture of a (10.0 g, 48.4 mmol, 1.0 eq) and 2 N HCl (240.0 mL) was stirred at room temperature for 5 min, then cooled to 0° C. and added with NaNO$_2$ (4.0 g, 58.1 mmol, 1.2 eq). The resulting mixture was stirred at 0° C. for 10 min, added with KI (24.1 g, 145.3 mmol, 3.0 eq), and stirred at room temperature for 40 min, and extracted with DCM (100 mL×3). The extracts were dried over anhydrous Na$_2$SO$_4$ and concentrated. The residue was purified by column chromatography on silica gel (PE) to give b (10.8 g, 71%).

Step 2

A mixture of c (1.2 g, 7.95 mmol, 1.0 eq), b (3.0 g, 9.5 mmol, 1.2 eq), Cu (150.0 mg, 2.4 mmol, 0.3 eq), and KOAc (4.2 g, 23.4 mmol, 3 eq) in 2-pentanol (50 mL) was stirred at 140° C. overnight under nitrogen atmosphere. The reaction mixture was filtered and the filtrate was concentrated. The residue was purified by chromatography on silica gel (PE/EtOAc, 2/1) to afford d (2.3 g, 85%). LC/MS: 340.1 [M+H]$^+$.

Step 3

A mixture of d (2.3 g, 6.8 mmol, 1.0 eq) in Eaton's reagent (40 mL) was stirred at room temperature for 1 h. The reaction mixture was added with water (200 mL) and extracted with EtOAc (100 mL×2). The organic phase was washed with brine, dried and concentrated. The crude product was purified by chromatography on silica gel (PE/EtOAc, 2/1) to afford e (997 mg, 46%). LC/MS: 322.1 [M+H]$^+$.

Step 4

A mixture of e (500.0 mg, 1.46 mmol, 1.0 eq), phenylboronic acid (357.0 mg, 2.93 mmol, 2.0 eq), K$_2$CO$_3$ (504.0 mg, 3.65 mmol, 2.5 eq), and Pd(PPh$_3$)$_4$ (84.0 mg, 0.073 mmol, 0.05 eq) in 1,4-dioxane (10 mL) was stirred at 90° C. overnight under nitrogen atmosphere. The reaction mixture was filtered and the filtrate was concentrated. The crude product was purified by chromatography on silica gel (PE/EtOAc, 2/1) to afford f (325.0 mg, 69%). LC/MS: 320.1 [M+H]$^+$.

Step 5

A mixture of f (320.0 mg, 1.0 mmol, 1.0 eq), (3-bromoprop-1-yn-1-yl)trimethylsilane (391.0 mg, 2.05 mmol, 2.0 eq), and Cs$_2$CO$_3$ (653.0 mg, 1.79 mmol, 2.0 eq) in acetonitrile (40 mL) was stirred at room temperature overnight. The reaction mixture was filtered and the filtrate was concentrated. The crude product was purified by chromatography on silica gel (PE/EtOAc, 2/1) to afford g (120.0 mg, 33%). LCMS: 358.1 [M+H]$^+$.

Step 6

To a solution of g (50.0 mg, 0.14 mmol, 1.0 eq) and NaIO$_4$ (148.0 mg, 0.7 mmol, 5.0 eq) in THF/H$_2$O (10 mL/2 mL) was added RuCl$_3$ (6.2 mg, 0.028 mmol, 0.2 eq) at room temperature. The reaction mixture was stirred at room temperature for 2 h. The reaction mixture was filtered and the filtrate was concentrated. The crude was purified by prep-HPLC (acetonitrile and water with TFA as a modifier) to afford 326 (16 mg, 30.4%) as a white solid. $^1$H NMR (400 MHz, DMSO-d$_6$): δ 8.29 (d, J=8.4 Hz, 1H), 8.10 (d, J=8.4 Hz, 1H), 7.55-7.50 (m, 4H), 7.37-7.32 (m, 3H), 7.14 (d, J=8.0 Hz, 1H), 4.34 (s, 2H), 2.45 (s, 3H). LC/MS: 378.1 [M+H]$^+$.

Example 47: Synthesis of Compound 324

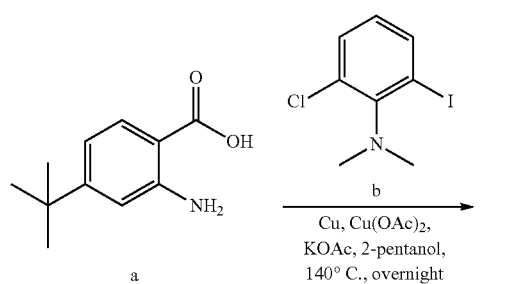

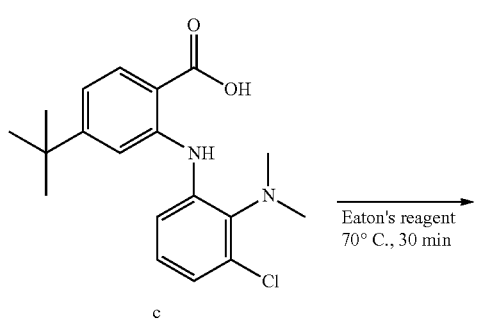

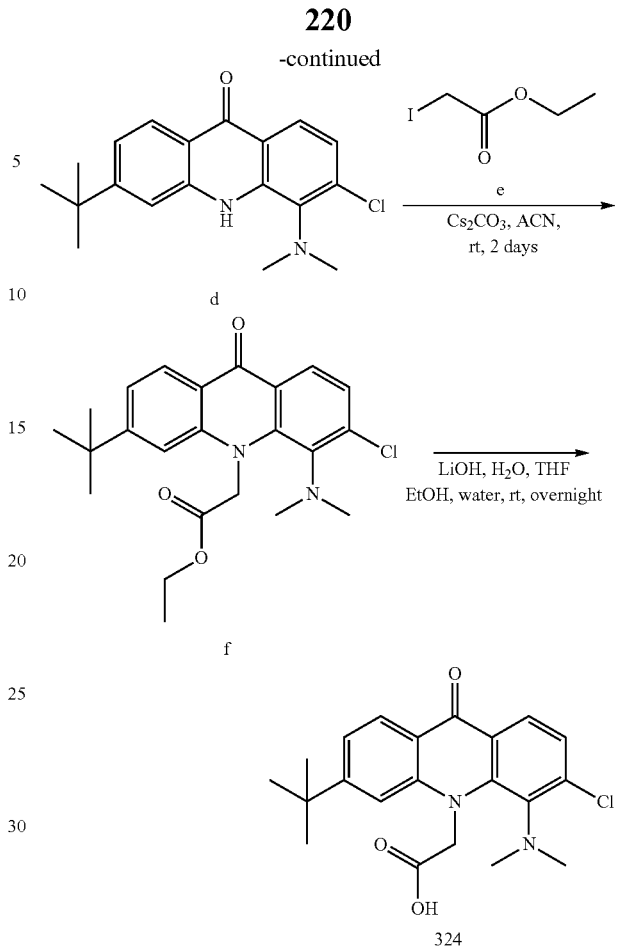

Step 1

A solution of a (1.0 g, 5.2 mmol, 1.0 eq), b (2.2 g, 7.8 mmol, 1.5 eq), KOAc (1.6 g, 15.6 mmol, 3.0 eq), copper powder (100.0 mg, 1.6 mmol, 0.3 eq), and Cu(OAc)$_2$ (291.0 mg, 1.6 mmol, 0.3 eq) in 2-pentanol (30.0 mL) was stirred at 140° C. overnight under N$_2$ atmosphere. The reaction was cooled to room temperature and 2 N NaOH (100.0 mL) was added. The mixture was filtered through celite. The filtrate was acidified to pH=2 with conc. HCl and extracted with EtOAc (100 mL×2). The combined organic layers were washed with brine, dried over anhydrous Na$_2$SO$_4$ and concentrated. The residue was purified by column chromatography on silica gel (PE/EA=10/1, 1% AcOH) to give c (950.0 mg, 53%). LC/MS: 347.1 [M+H]$^+$.

Step 2

A solution of c (950.0 mg, 2.7 mmol, 1.0 eq) in Eaton's reagent (20.0 mL) was stirred at 70° C. for 30 min. The mixture was poured into ice-water and filtered. The solid was dried to afford d (1.0 g, ca. 100%). LC/MS: 329.1 [M+H]$^+$.

Step 3

A solution of d (600.0 mg, 1.8 mmol, 1.0 eq), e (783.0 mg, 3.6 mmol, 2.0 eq), and Cs$_2$CO$_3$ (1.8 g, 5.4 mmol, 3.0 eq) in acetonitrile (20.0 mL) was stirred at r.t. overnight, diluted with water (50 mL), and extracted with EtOAc (50 mL×3). The organic layer was concentrated and purified by reversed phase chromatography (H$_2$O/MeCN=3/7 to 0/100, 1% NH$_3$.H$_2$O) to afford f (162.0 mg, 21.4%) as a yellow solid. LC/MS: 415.2 [M+H]$^+$.

Step 4

A mixture of f (162.0 mg; 0.39 mmol, 1.0 eq) and LiOH H2O (164.0 mg, 3.9 mmol, 10.0 eq) in a mixed solvent of THF (10.0 mL), EtOH (6.0 mL) and H$_2$O (3.0 mL) was stirred at r.t. overnight, diluted with water (20 mL), and extracted with EtOAc (20 mL×2). The aqueous layer was acidified to pH=3 with concentrated HCl and extracted with EtOAc (20 mL×2). The combined organic layers were dried over Na$_2$SO$_4$, concentrated to afford 324 (50 mg, 33.1%) as a yellow solid. $^1$H NMR (400 MHz, DMSO-d$_6$): δ 12.91 (s, 1H), 8.13 (d, J=8.8 Hz, 1H), 8.12 (d, J=8.4 Hz, 1H), 7.51 (s, 1H), 7.44 (d, J=8.4 Hz, 1H), 7.36 (d, J=8.4 Hz, 1H), 4.89 (s, 2H), 2.73 (s, 3H), 2.73 (s, 3H), 1.36 (s, 9H). LCMS: 387.1 [M+H]$^+$.

Example 48: Synthesis of Compound 322

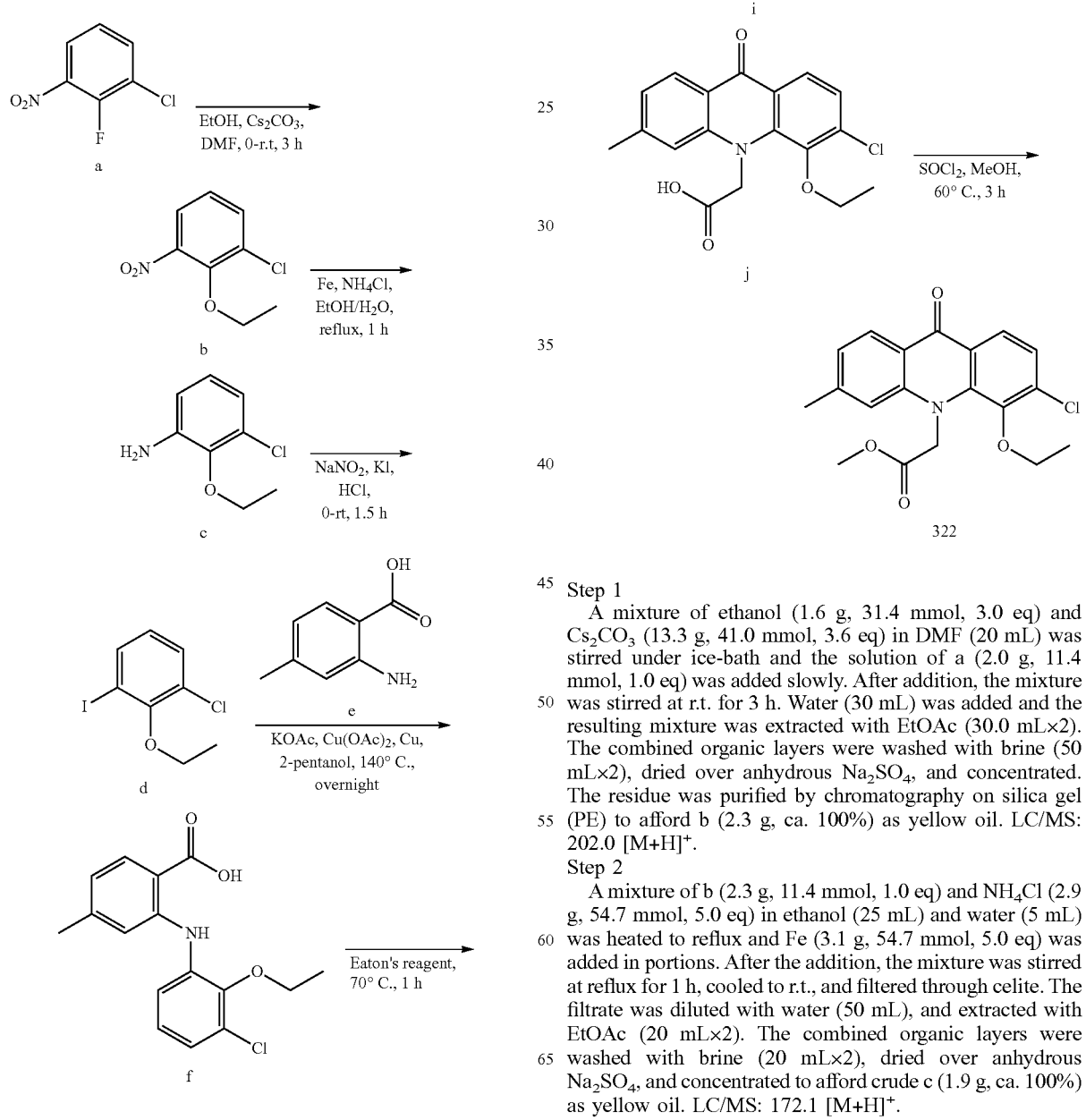

Step 1

A mixture of ethanol (1.6 g, 31.4 mmol, 3.0 eq) and Cs$_2$CO$_3$ (13.3 g, 41.0 mmol, 3.6 eq) in DMF (20 mL) was stirred under ice-bath and the solution of a (2.0 g, 11.4 mmol, 1.0 eq) was added slowly. After addition, the mixture was stirred at r.t. for 3 h. Water (30 mL) was added and the resulting mixture was extracted with EtOAc (30.0 mL×2). The combined organic layers were washed with brine (50 mL×2), dried over anhydrous Na$_2$SO$_4$, and concentrated. The residue was purified by chromatography on silica gel (PE) to afford b (2.3 g, ca. 100%) as yellow oil. LC/MS: 202.0 [M+H]$^+$.

Step 2

A mixture of b (2.3 g, 11.4 mmol, 1.0 eq) and NH$_4$Cl (2.9 g, 54.7 mmol, 5.0 eq) in ethanol (25 mL) and water (5 mL) was heated to reflux and Fe (3.1 g, 54.7 mmol, 5.0 eq) was added in portions. After the addition, the mixture was stirred at reflux for 1 h, cooled to r.t., and filtered through celite. The filtrate was diluted with water (50 mL), and extracted with EtOAc (20 mL×2). The combined organic layers were washed with brine (20 mL×2), dried over anhydrous Na$_2$SO$_4$, and concentrated to afford crude c (1.9 g, ca. 100%) as yellow oil. LC/MS: 172.1 [M+H]$^+$.

223

Step 3

A solution of c (1.9 g, 11.1 mmol, 1.0 eq) in 3M HCl (20 mL,) at 0° C. was added dropwise a solution of NaNO₂ (840.0 mg, 12.2 mmol, 1.1 eq) in water (2 mL). The mixture was stirred at 0° C. for 30 min, then added with a solution of KI (5.5 g, 33.3 mmol, 3.0 eq) in 5 mL of water. The mixture was stirred at r.t. for 1 h, poured into water (30 mL), and extracted with EtOAc (50 mL×2). The combined organic layers were successively washed with sat. Na₂SO₃ (25 mL×2) and brine (25 mL×2), dried over anhydrous Na₂SO₄, and concentrated. The residue was purified by chromatography on silica gel (PE) to afford d (2.6 g, 83%) as red liquid. LCMS: 282.1 [M+H]⁺.

Step 4

A mixture of d (580.0 mg, 3.8 mmol, 1.0 eq), e (1.3 g, 4.6 mmol, 1.2 eq), KOAc (753.0 mg, 7.7 mmol, 2.0 eq), Cu(OAc)₂ (210.0 mg, 1.2 mmol, 0.3 eq), and Cu (74.0 mg, 1.2 mmol, 0.3 eq) in 2-Pentanol (20.0 mL) was stirred at 140° C. overnight under nitrogen atmosphere, and then cooled to room temperature. Water (30 mL) was added and the mixture was filtered through celite. The filtrate was acidified to pH=2 with 2 N HCl. The resulting mixture was extracted with EtOAc (25 mL×2). The combined organic layers were washed with brine (25 mL×2), dried over anhydrous Na₂SO₄ and concentrated. The crude was purified by trituration with PE (20 mL) and filtered to afford f (800.0 mg, 68%). LC/MS: 306.1 [M+H]⁺.

Step 5

A mixture of f (400.0 mg, 1.3 mmol) and Eaton's Reagent (5 mL) was heated at 70° C. for 1 h. cooled and poured into a mixture of ice and water (20 g). The solid was collected by filtration and dried to afford g (380.0 mg, ca. 100%). LC/MS: 288.1 [M+H]⁺.

Step 6

A mixture of g (380.0 mg, 1.3 mmol, 1.0 eq) and Cs₂CO₃ (1.3 g, 3.9 mmol, 3.0 eq) in acetonitrile (20 mL) was added h (710.0 mg, 3.3 mmol, 2.5 eq). The mixture was stirred at r.t. overnight, diluted with water (20 mL), and extracted with EtOAc (25 mL×2). The combined organic layers were washed with brine (25 mL×2), dried over anhydrous Na₂SO₄ and concentrated. The residue was purified by chromatography on silica gel (PE/EA=30/1) to afford i (430.0 mg, 87%) as a yellow solid. LC/MS: 374.1 [M+H]⁺.

Step 7

A mixture of i (420.0 mg, 1.1 mmol, 1.0 eq) and LiOH H₂O (470 mg, 11.2 mmol, 10.0 eq) in THF (10.0 mL) and H₂O (4.0 mL) was stirred at r.t. overnight, diluted with water (15 mL), and extracted with EtOAc (10 mL×2). The aqueous layer was acidified to pH=3 with 2 N HCl and extracted with EtOAc (15 mL×2). The combined organic layers were washed with brine (10 mL×2), dried over anhydrous Na₂SO₄ and filtered. The filtrate was concentrated in vacuo to afford j (360.0 mg, 95%) as a yellow solid. LC/MS: 346.1 [M+H]⁺.

Step 8

A mixture of j (30.0 mg, 0.09 mmol, 1.0 eq) and SOCl₂ (470.0 mg, 0.18 mmol, 2.0 eq) in MeOH (5.0 mL) was stirred at 60° C. for 3 h, diluted with water (15.0 mL), and extracted with EtOAc (10 mL×2). The combined organic layers were washed with brine (10.0 mL×2), dried over anhydrous Na₂SO₄, and filtered. The filtrate was concentrated in vacuo to afford 322 (28.8 mg, 92%) as a yellow solid. LC/MS: 360.1 [M+H]⁺. ¹H NMR (400 MHz, DMSO-d₆): δ 8.13 (d, J=8.0 Hz, 1H), 8.05 (d, J=8.8 Hz, 1H), 7.46 (d, J=8.8 Hz, 1H), 7.43 (s, 1H), 7.21 (d, J=8.4 Hz, 1H), 5.25 (s, 2H), 3.93-3.88 (m, 2H), 3.78 (s, 3H), 2.48 (s, 3H), 1.33 (t, J=6.8 Hz, 3H).

224

Example 49: Synthesis of Compound 320

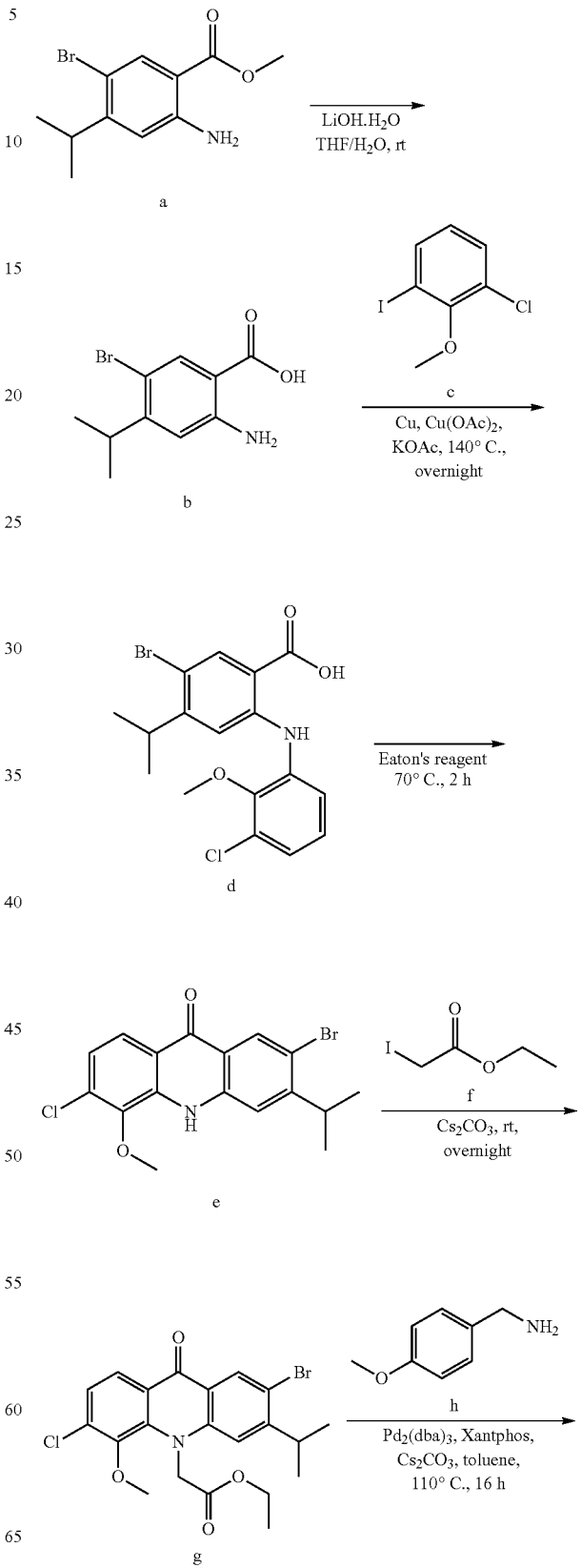

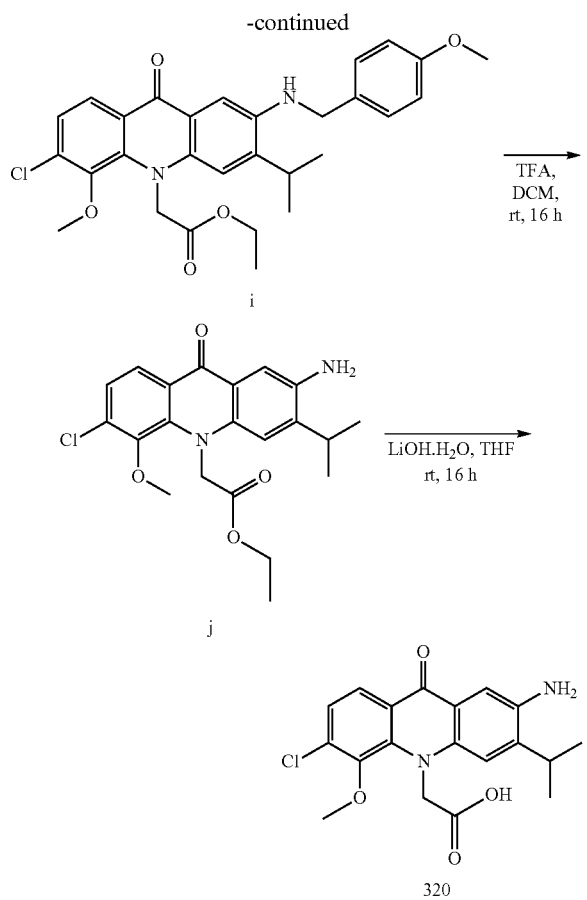

Step 1

A mixture of a (2 g, 7.38 mmol), LiOH H₂O (1.55 g, 36.9 mmol, 5.0 eq) in THF/H₂O (10 mL/10 mL) was stirred at r.t. overnight. The reaction mixture was diluted with water (20 mL), and extracted with EtOAc (20 mL×2). The aqueous phase was adjusted to pH=3 with 2 N HCl and extracted with EtOAc (20 mL×2). The combined organic layers were dried over anhydrous Na₂SO₄ and concentrated to afford b (1.7 g, 90%). LC/MS: 260.1 [M+H]⁺.

Step 2

A mixture of b (1.7 g, 6.61 mmol, 1.0 eq), c (2.7 g, 9.92 mmol, 1.5 eq), KOAc (1.9 g, 19.8 mmol, 3.0 eq), copper powder (127.0 mg, 1.98 mmol, 0.3 eq), and Cu(OAc)₂ (360.0 mg, 1.98 mmol, 0.3 eq) in 2-pentanol (20 mL) was stirred at 140° C. overnight under N₂ atmosphere, then cooled to room temperature. The mixture was diluted with water (20 mL), acidified to pH=3 with 2 N HCl, and extracted with EtOAc (30 mL×2). The combined organic layers were dried over anhydrous Na₂SO₄ and concentrated. The residue was purified by chromatography on silica gel (PE/EtOAc, 5/1) to afford d (1.8 g, 68%). LC/MS: 398.1 [M−H]⁻.

Step 3

A mixture of d (1.8 g, 4.5 mmol) in Eaton's reagent (20 mL) was stirred at 70° C. for 2 h. The mixture was poured into ice-water (50 g), and extracted with EtOAc (50 mL×2). The combined organic layers were dried over anhydrous Na₂SO₄ and concentrated to afford e (1.4 g, 81%). LC/MS: 382.1 [M+H]⁺.

Step 4

A mixture of e (1.4 g, 3.69 mmol, 1.0 eq), f (1.2 g, 5.54 mmol, 1.5 eq), Cs₂CO₃ (2.4 g, 7.38 mmol, 2.0 eq) in acetonitrile (20 mL) was stirred at r.t. overnight. The reaction mixture was diluted with 2N HCl (30 mL), and extracted with EtOAc (20 mL×2). The combined organic layers were dried over anhydrous Na₂SO₄ and concentrated. The residue was purified by Prep-HPLC (C18) to afford g (1.1 g, 63.9%). LC/MS: 466.2 [M+H]⁺.

Step 5

A mixture of g (50.0 mg, 0.107 mmol, 1.0 eq), h (30.0 mg, 0.214 mmol, 2.0 eq), Xantphos (13.0 mg, 0.0214 mmol, 0.2 eq), and Cs₂CO: (70.0 mg, 0.214 mmol, 2 eq) in toluene (10 mL) was degassed and charged with N₂ three times. Then Pd₂(dba)₃ was added under N₂ atmosphere. The reaction mixture was stirred at 110° C. overnight. The reaction was diluted with water (10 mL) and extracted with EtOAc (20 mL×3). The combined organic phase was dried over anhydrous Na₂SO₄ and filtered and concentrated. The crude product was purified by chromatography on silica gel (PE/EtOAc, 10/1) to afford i (28.0 mg, 50%). LC/MS: 523.3 [M+H]⁺.

Step 6

To a solution of i (22.0 mg, 0.042 mmol, 1.0 eq) in DCM (2 mL) was added TFA (2 mL) at 0° C. The reaction mixture was stirred at room temperature for 2 h and concentrated under reduced pressure. The resulting mixture was adjusted to pH=8 with sat. NaHCO₃(2 mL) and extracted with ethyl acetate (5 mL×3). The combined organic phase was dried over anhydrous Na₂SO₄, filtered, and the filtrate was concentrated. The crude product was purified by prep-TLC (PE/EtOAc, 5/1) to afford j (15.0 mg, 88%). LC/MS: 403.3 [M+H]⁺.

Step 7

To a mixture of j (13.0 mg, 0.032 mmol, 1.0 eq) and LiOH (4.0 mg, 0.16 mmol, 5.0 eq) in THF/H₂O (2 mL/2 mL) was stirred at r.t. overnight. The reaction mixture was concentrated under reduced pressure, and adjusted to PH=6~7 with 2N HCl, and extracted with ethyl acetate (5 mL×3). The combined organics were dried over anhydrous Na₂SO₄, filtered and concentrated to afford the crude which was purified by prep-HPLC (C18) to afford 320 (2.2 mg, 18%) as a white solid. ¹H NMR (400 MHz, CD₃OD): δ 8.15-8.13 (d. J=8.8 Hz, 1H), 7.60 (s, 1H), 7.47 (s, 1H), 7.27-7.25 (d, J=8.8 Hz, 1H), 5.05 (s, 2H), 3.87 (s, 3H), 3.19-3.16 (m, 1H), 1.34 (d, 6H). LC/MS: 375.4 [M+H]⁺.

Example 50: Synthesis of Compound 314

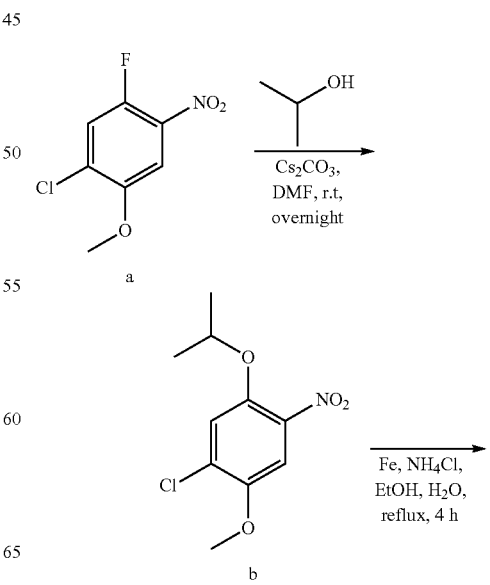

227
-continued

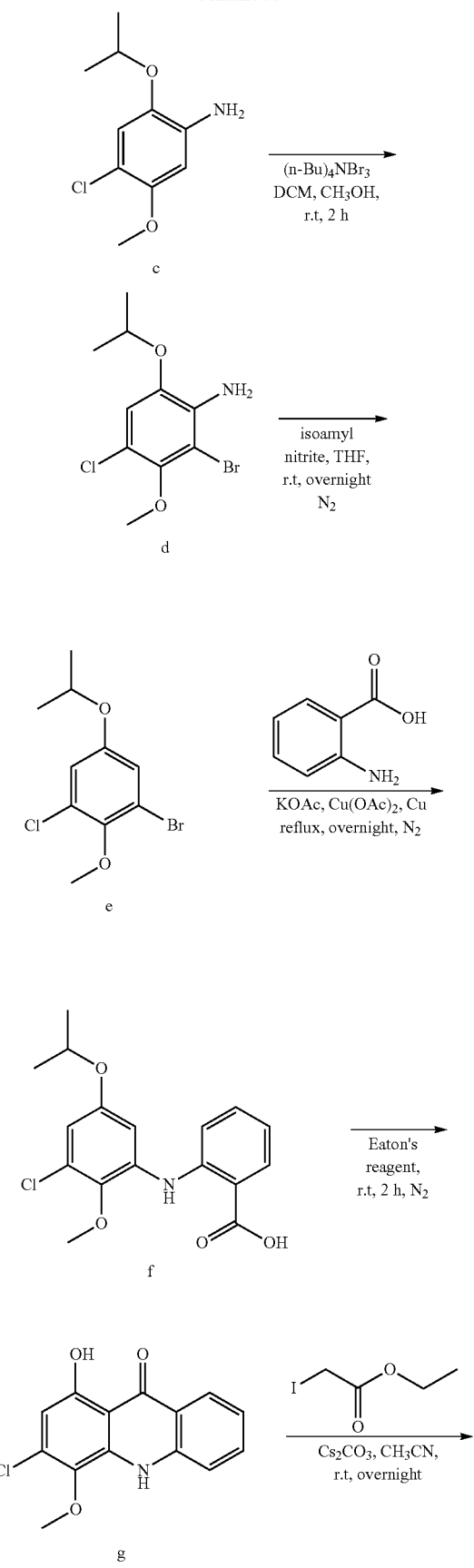

228
-continued

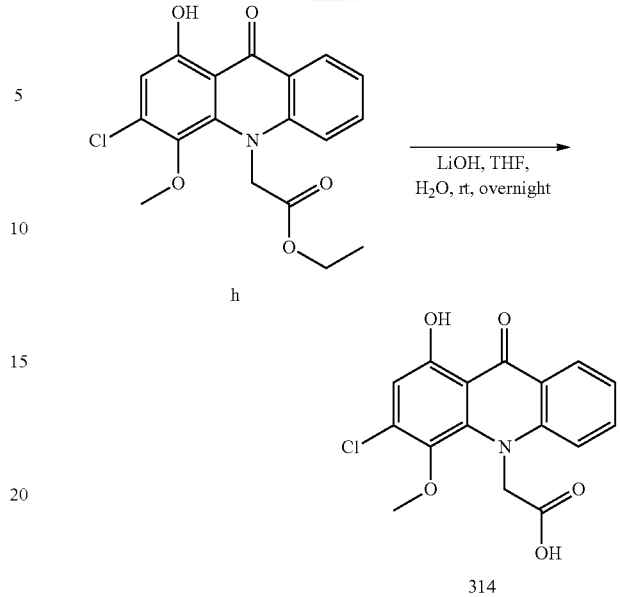

Step 1

To a mixture of a (6.0 g, 29.1 mmol, 1.0 eq) and Cs₂CO₃ (29.0 g, 87.4 mmol, 3.0 eq) in DMF (100 mL) was added isopropanol (5.3 g, 87.4 mmol, 3.0 eq). The mixture was stirred at room temperature overnight. Water (300 mL) was added and the mixture was extracted with EtOAc (100 mL×3). The combined organics were washed with brine and concentrated to afford b (7.1 g, 99%) as brown oil.

Step 2

A mixture of b (7.1 g, 28.8 mmol, 1.0 eq). NH₄Cl (1.5 g, 28.8 mmol, 1.0 eq) in ethanol (120 mL), and water (20 mL) was heated to reflux and Fe (4.8 g, 86.4 mmol, 3.0 eq) was added in portions. After the addition, the mixture was stirred under reflux for 2 h, cooled to r.t. and filtered through celite. Water (300 mL) was added to the filtrate. The resulting mixture was extracted with EtOAc (200 mL×2). The combined organic layers were washed with brine (200 mL×2), dried over anhydrous Na₂SO₄, and filtered. The filtrate was concentrated to afford crude c (6.0 g, 96.7%) as brown oil. LC/MS: 216.1 [M+H]⁺.

Step 3

A mixture of c (6.0 g, 27.8 mmol, 1.0 eq), (n-Bu)₄N Br₃ (14.0 g, 29.2 mmol, 1.05 eq) in DCM (180 mL) and CH₃OH (120 mL) was stirred at room temperature for 2 h. The reaction mixture was concentrated and the residue was purified by chromatography on silica gel (PE/EA=10/1) to afford d (4.9 g, 59%) as yellow oil. LC/MS: 294.0 [M+1]⁺.

Step 4

A mixture of d (4.9 g, 16.6 mmol, 1.0 eq) and isoamyl nitrite (3.9 g, 33.2 mmol, 2.0 eq) in THF (200 mL) was stirred at room temperature overnight under nitrogen atmosphere. The reaction mixture was concentrated and the residue was purified by chromatography on silica gel (PE) to afford e (4.2 g, 90%).

Step 5

A mixture of e (4.2 g, 15.0 mmol, 1.0 eq), anthranilic acid (1.44 g, 10.5 mmol, 0.7 eq), potassium acetate (2.94 g, 30.0 mmol, 2.0 eq), cupric acetate (0.8 g, 4.5 mmol, 0.3 eq), and copper powder (0.3 g, 4.5 mmol, 0.3 eq) in 2-pentanol (80 mL) was stirred under reflux overnight under nitrogen atmosphere. The reaction was cooled to room temperature and water (200 mL) was added. The mixture was acidified to pH=2 with 2 N HCl and filtered through celite. The filtrate was extracted with EtOAc (200 mL×2). The combined organic layers were washed with brine (200 mL×2), dried over anhydrous Na$_2$SO$_4$, and filtered. The filtrate was concentrated and the residue was triturated with PE (20 mL) and filtered to afford f (2.0 g, 40%). $^1$H NMR (400 MHz, CDCl$_3$): δ 9.56 (s, 1H), 8.09 (dd, J=1.6 Hz, 8.0 Hz, 1H), 7.47-7.38 (m, 2H), 6.92 (d, J=2.8 Hz, 1H), 6.88-6.83 (m, 1H), 6.60 (d, J=2.8 Hz, 1H), 4.47-4.40 (m, 1H), 3.82 (s, 3H), 1.32 (d, J=6.0 Hz, 6H). LC/MS: 336.2 [M+H]$^+$.

Step 6

A mixture of f (2.0 g, 5.95 mmol) in Eaton's reagent (50 mL) was stirred at room temperature under nitrogen atmosphere for 2 h, then poured into a mixture of ice and water (50 g). The solid was collected by filtration and dried. The crude residue was purified by chromatography on silica gel (PE/EA=10/1) to afford g (500.0 mg, 30%) as a yellow solid. $^1$H NMR (400 MHz, DMSO-d$_6$): δ 13.90 (s, 1H), 11.74 (s, 1H), 8.22 (d, J=8.0 Hz, 1H), 8.00 (d, J=8.4 Hz, 1H), 7.83 (t, J=7.2 Hz, 1H), 7.37 (t, J=7.2 Hz, 1H), 6.64 (s, 1H), 3.88 (s, 3H). LC/MS: 276.1 [M+H]$^+$.

Step 7

To a mixture of g (310.0 mg, 1.13 mmol, 1.0 eq) and Cs$_2$CO$_3$ (919.0 mg, 2.82 mmol, 2.5 eq) in acetonitrile (60 mL) was added ethyl iodoacetate (363.0 mg, 1.69 mmol, 1.5 eq). The mixture was stirred at r.t. overnight and filtered through celite. The filtrate was concentrated and purified by Prep-HPLC to afford h (20.0 mg, 4.9%) as a yellow solid. LC/MS: 362.0 [M+H]$^+$.

Step 8

A mixture of h (20.0 mg, 0.055 mmol, 1.0 eq), LiOH.H$_2$O (12.0 mg, 0.277 mmol, 5.0 eq) in THF (5.0 mL) and H$_2$O (5.0 mL) was stirred at r.t. overnight, diluted with water (15.0 mL), and extracted with EtOAc (10 mL×2). The aqueous layer was acidified to pH=3 with 2 N HCl and extracted with EtOAc (15.0 mL×2). The combined organic layers were washed with brine (10.0 mL×2), dried over anhydrous Na$_2$SO$_4$, and filtered. The filtrate was concentrated to afford 314 (15.0 mg, 81%) as a yellow solid. $^1$H NMR (400 MHz, DMSO-d$_6$): δ 8.26 (dd, J=1.6, 8.0 Hz, 1H), 7.90-7.86 (m, 1H), 7.64 (d, J=8.8 Hz, 1H), 7.42 (t, J=7.2 Hz, 1H), 6.85 (s, 1H), 5.14 (s, 2H), 3.66 (s, 3H). LC/MS: 334.0 [M+H]$^+$. NOESY.

Example 51: Synthesis of Compound 313

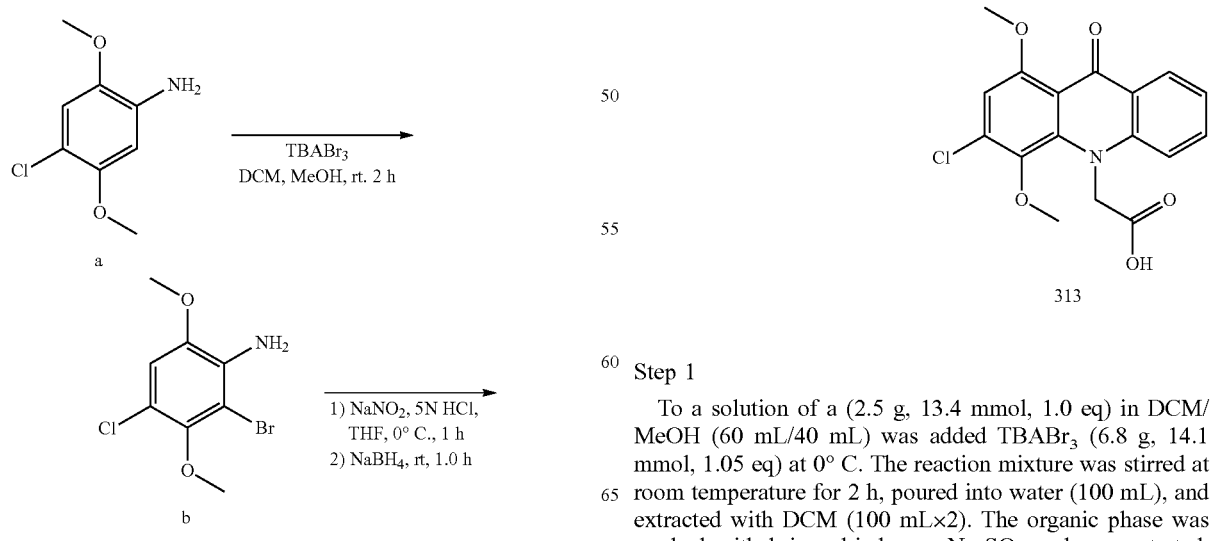

Step 1

To a solution of a (2.5 g, 13.4 mmol, 1.0 eq) in DCM/MeOH (60 mL/40 mL) was added TBABr$_3$ (6.8 g, 14.1 mmol, 1.05 eq) at 0° C. The reaction mixture was stirred at room temperature for 2 h, poured into water (100 mL), and extracted with DCM (100 mL×2). The organic phase was washed with brine, dried over Na$_2$SO$_4$ and concentrated.

The crude product was purified by chromatography on silica gel (PE/EtOAc, 10/1) to afford b (1.9 g, 54%).

Step 2

A mixture of b (1.9 g, 7.2 mmol, 1.0 eq) in 5N HCl/THF (6 mL3 mL) was added NaNO$_2$ (0.6 g, 8.6 mmol, 1.2 eq) at 0° C. The reaction mixture was stirred at 0° C. for 1 h and NaBH$_4$ (0.8 g, 21.6 mmol, 3.0 eq) was added. The reaction mixture was warmed to room temperature and stirred for another 1 h, poured into water (100 mL), and extracted with EtOAc (200 mL). The organic phase was washed with brine, dried over Na$_2$SO$_4$, and concentrated. The crude residue was purified by chromatography on silica gel (PE/EtOAc, 10/1) to afford c (1.2 g, 67%) as a white solid.

Step 3

A solution of c (1.2 g, 4.8 mmol, 1.0 eq), d (789.0 mg, 5.8 mmol, 1.2 eq). KOAc (1.4 g, 14.4 mmol, 3.0 eq), copper powder (92.0 mg, 1.4 mmol, 0.3 eq), and Cu(OAc)$_2$ (261.0 mg, 1.4 mmol, 0.3 eq) in 2-pentanol (15 mL) was stirred at 140° C. overnight under N$_2$ atmosphere, then cooled to room temperature and 2 N NaOH (100.0 mL) was added. The resulting mixture was filtered through celite. The filtrate was acidified to pH=2 with conc. HCl, then extracted with EtOAc (50 mL×3). The combined organic layers were washed with brine, dried over anhydrous Na$_2$SO$_4$ and filtered. The filtrate was concentrated in vacuo. The residue was purified by column chromatography on silica gel (PE/EA=10/1, 1% AcOH) to give e (620.0 mg, 34%). LC/MS: 308.2 [M+H]$^+$.

Step 4

A mixture of e (620.0 mg, 2.0 mmol, 1.0 eq) in Eaton's reagent (8 mL) was stirred at room temperature for 2 h. The reaction mixture was diluted with water (50 mL) and extracted with DCM (100 mL). The organic phase was washed with brine, dried over anhydrous Na$_2$SO$_4$, and concentrated. The crude product was purified by chromatography on silica gel (PE/EtOAc, 2/1) to afford f (280.0 mg, 48%). LC/MS 290.11 [M+H]+.

Step 5

A mixture of f (280.0 mg, 0.97 mmol, 1.0 eq), g (415.0 mg, 1.94 mmol, 2.0 eq) and Cs$_2$CO$_3$ (949.0 mg, 2.91 mmol, 3.0 eq) in acetonitrile (15 mL) was stirred at room temperature overnight. The reaction mixture was diluted with water (50 mL) and extracted with DCM (50 mL). The organic phase was washed with brine, dried over anhydrous Na$_2$SO$_4$, and concentrated. The crude product was purified by (C18) prep-HPLC (acetonitrile/water with TFA as a modifier) to afford h (180.0 mg, 49%). LC/MS: 376.2 [M+H]$^+$.

Step 6

A mixture of h (180.0 mg: 0.48 mmol, 1.0 eq), LiOH.H$_2$O (96.0 mg, 2.4 mmol, 5.0 eq) in THF (5.0 mL), and H$_2$O (5.0 mL) was stirred at r.t. overnight, diluted with water (20 mL) and extracted with EtOAc (20 mL×2). The aqueous layer was acidified to pH=3 with concentrated HCl and extracted with EtOAc (20 mL×2). The combined organic layers were concentrated and purified by reversed phase chromatography (H$_2$O/MeCN=1/9 to 1/1, 1% TFA) to afford 313 (46.2 mg, 28%) as a yellow solid. $^1$H NMR (400 MHz, DMSO-d$_6$): δ 8.07 (d, J=8.0 Hz, 1H), 7.74-7.70 (m, 1H), 7.53 (d, J=8.4 Hz, 1H), 7.32-7.28 (m, J=8.0, 1H), 7.00 (s, 1H), 4.94 (s, 2H), 3.87 (s, 3H), 3.65 (s, 3H). LC/MS: 348.1 [M+H]$^+$.

Example 52: Synthesis of Compound 309

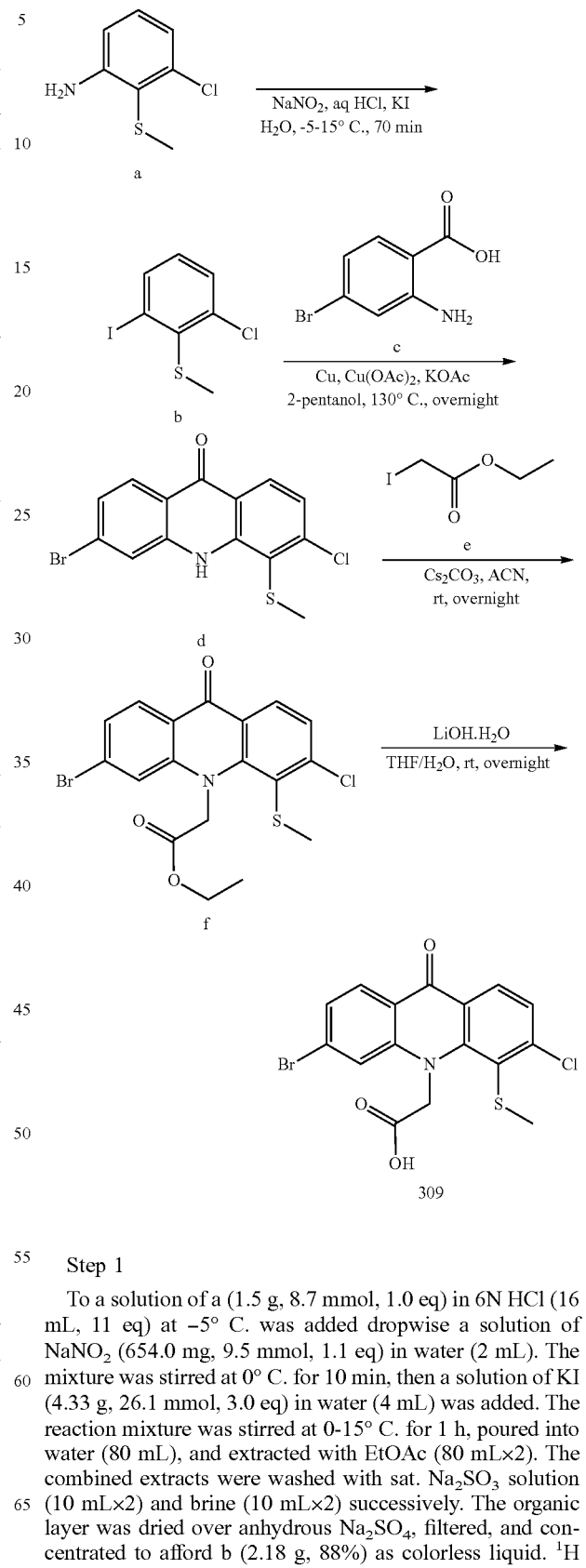

Step 1

To a solution of a (1.5 g, 8.7 mmol, 1.0 eq) in 6N HCl (16 mL, 11 eq) at −5° C. was added dropwise a solution of NaNO$_2$ (654.0 mg, 9.5 mmol, 1.1 eq) in water (2 mL). The mixture was stirred at 0° C. for 10 min, then a solution of KI (4.33 g, 26.1 mmol, 3.0 eq) in water (4 mL) was added. The reaction mixture was stirred at 0-15° C. for 1 h, poured into water (80 mL), and extracted with EtOAc (80 mL×2). The combined extracts were washed with sat. Na$_2$SO$_3$ solution (10 mL×2) and brine (10 mL×2) successively. The organic layer was dried over anhydrous Na$_2$SO$_4$, filtered, and concentrated to afford b (2.18 g, 88%) as colorless liquid. $^1$H NMR (400 MHz, CDCl$_3$): δ=7.83 (dd, J=1.2 Hz, J=8.0 Hz, 1H), 7.44 (dd, J=1.2 Hz, J=8.0 Hz, 1H), 6.90 (t, J=8.0 Hz, 1H), 2.43 (s, 3H).

Step 2

A solution of b (928.0 mg, 2.62 mmol, 1.0 eq), c (2.18 g, 7.67 mmol, 1.0 eq), Cu (147.0 mg, 2.3 mmol, 0.3 eq), Cu(OAc)$_2$ (460.0 mg, 2.3 mmol, 0.3 eq), and KOAc (2.25 g, 23 mmol, 3.0 eq) in 2-pentanol (30 mL) was stirred at 130° C. overnight under N$_2$ atmosphere. The reaction was poured into water (150 mL), acidified with 1N HCl to pH=3, and extracted with EA (50 mL×2). The organic layer was washed with brine and concentrated. The crude was purified by chromatography on silica gel (EA/PE=1/5) to afford d (1.77 g, 62%) as a yellow solid. LCMS: 374.0 [M+H]$^+$.

Step 3

A solution of d (1.65 g, 7.67 mmol, 1.0 eq), e (1.68 g, 7.86 mmol, 3.0 eq) and Cs$_2$CO$_3$ (2.56 g, 7.86 mmol, 3.0 eq) in acetonitrile (30 mL) was stirred at r.t. overnight, and then diluted with water (90 mL). The mixture was acidified with 2N HCl to pH=3, stirred at r.t. for 30 min, and then extracted with EtOAc (50 mL×2). The combined organic layers were washed with water (30 mL) and brine (30 ml), dried with anhydrous Na$_2$SO$_4$, and concentrated. The residue was purified by C18 Prep-HPLC to afford f (553.0 mg, 48%) as a yellow solid. LCMS: 442.2 [M+H]$^+$.

Step 4

A solution of f (50.0 mg, 0.11 mmol, 1.0 eq) and LiOH.H$_2$O (24.0 mg, 0.55 mmol, 5.0 eq) in THF/H$_2$O (5 mL5 mL) was stirred at r.t. overnight, and then diluted with water (10 mL). The mixture was acidified with 2N HCl to pH=5 and filtered. The filtrate was concentrated in vacuo to afford 309 (27.6 mg, 59%) as a yellow solid. $^1$H NMR (400 MHz, DMSO-d$_6$): δ 13.02 (brs, 1H), 8.19 (d, J=8.4 Hz, 1H), 8.10-8.08 (m, 2H), 7.58 (d, J=8.8 Hz, 1H), 7.54-7.52 (m, 1H), 5.47 (s, 2H), 2.34 (s, 3H). LCMS: 412.1[M+H]$^+$.

Example 53: Synthesis of Compound 308

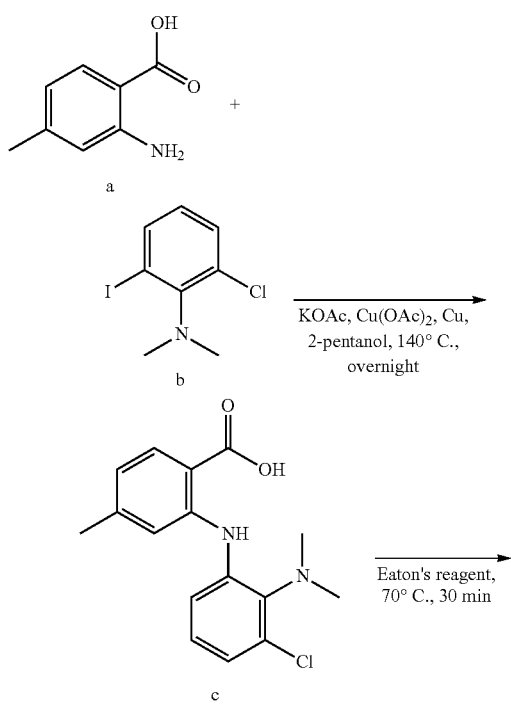

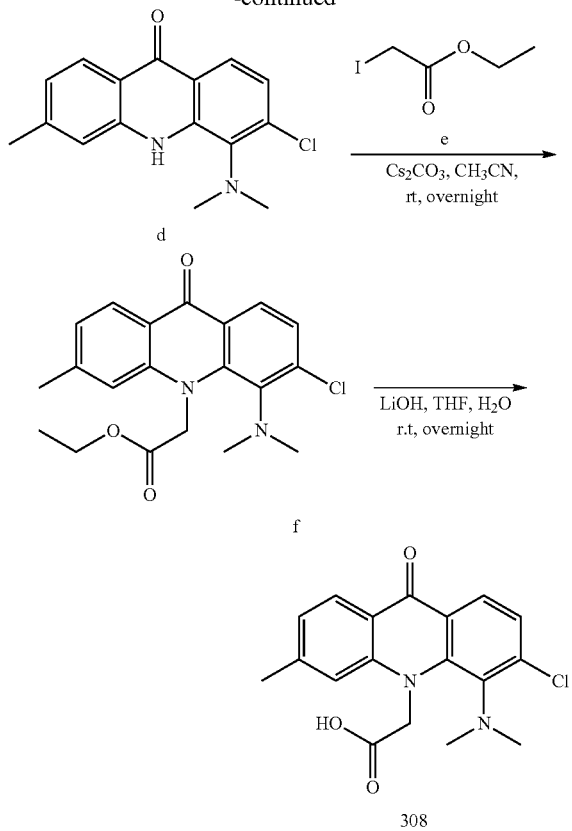

Step 1

A mixture of a (1.03 g, 6.82 mmol, 1.0 eq), b (2.3 g, 8.19 mmol, 1.2 eq), potassium acetate (2.0 g, 20.5 mmol, 3.0 eq), cupric acetate (373.0 mg, 2.05 mmol, 0.3 eq), and copper powder (131.0 mg, 2.05 mmol, 0.3 eq) in 2-pentanol (20.0 mL) was stirred at 140° C. overnight under nitrogen atmosphere, then cooled to room temperature and diluted with water (30.0 mL). The resulting mixture was filtered through celite. The filtrate was acidified to pH=2 with 2 N HCl, extracted with EtOAc (25 mL×2). The combined organic layers were washed with brine (25 mL×2), dried over anhydrous Na$_2$SO$_4$, and filtered. The filtrate was concentrated to afford the crude which was trituration with PE (20 mL) and filtered to afford c (1.6 g, 77%). LC/MS: 305.1 [M+H]$^+$.

Step 2

A mixture of c (1.6 g, 5.25 mmol) and Eaton's Reagent (20 mL) was heated at 70° C. for 30 min, then cooled and poured into a mixture of ice and water (30 g). The solid was collected by filtration and dried to afford crude d (1.5 g, 99%). LC/MS: 287.1 [M+H]$^+$.

Step 3

To a mixture of d (1.5 g, 5.25 mmol, 1.0 eq) and Cs$_2$CO$_3$ (5.1 g, 15.74 mmol, 3.0 eq) in acetonitrile (30 mL) was added e (2.3 g, 10.49 mmol, 2.0 eq). The mixture was stirred at r.t. overnight, diluted with water (25 mL), and extracted with EtOAc (25 mL×2). The combined organic layers were washed with brine (25 mL×2), dried over anhydrous Na$_2$SO$_4$, and filtered. The filtrate was concentrated in vacuo to give crude f (1.9 g, 98%) as a yellow solid. LC/MS: 373.1 [M+H]$^+$.

Step 4

A mixture of f (1.9 g crude, 5.1 mmol, 1.0 eq) and LiOH.H$_2$O (860.0 mg, 20.4 mmol, 4.0 eq) in THF (10.0 mL) and H$_2$O (4.0 mL) was stirred at r.t. overnight, and then diluted with water (30.0 mL), extracted with EtOAc (20 mL×2). The aqueous layer was acidified to pH=3 with 2 N HCl and extracted with EtOAc (15 mL×2). The combined organic layers were washed with brine (10 mL×2), dried over anhydrous Na$_2$SO$_4$, and filtered. The filtrate was concentrated in vacuo to afford 308 (640.0 mg, 37%) as a yellow solid. LCMS: 345.1 [M+H]$^+$. $^1$H NMR (400 MHz, DMSO-d$_6$): δ 12.84 (brs, 1H), 8.15 (d, J=8.4 Hz, 1H), 8.10 (d, J=8.0 Hz, 1H), 7.43 (s, 1H), 7.38 (d, J=8.4 Hz, 1H), 7.18 (d, J=8.4 Hz, 1H), 4.87 (s, 2H), 2.72 (s, 6H), 2.48 (s, 3H).

Example 54: Synthesis of Compound 305

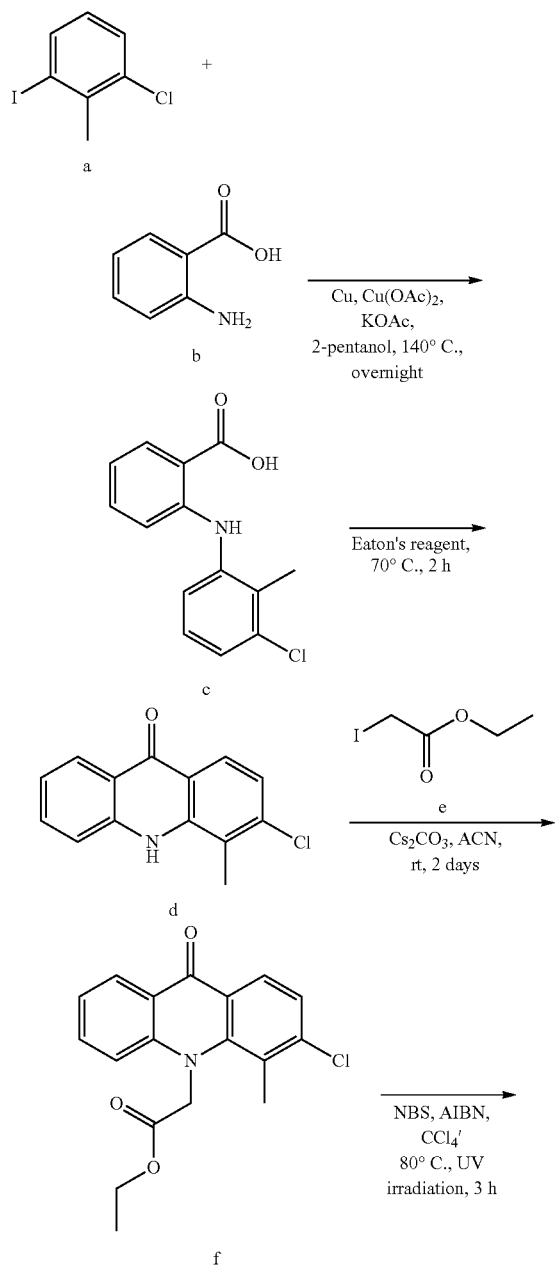

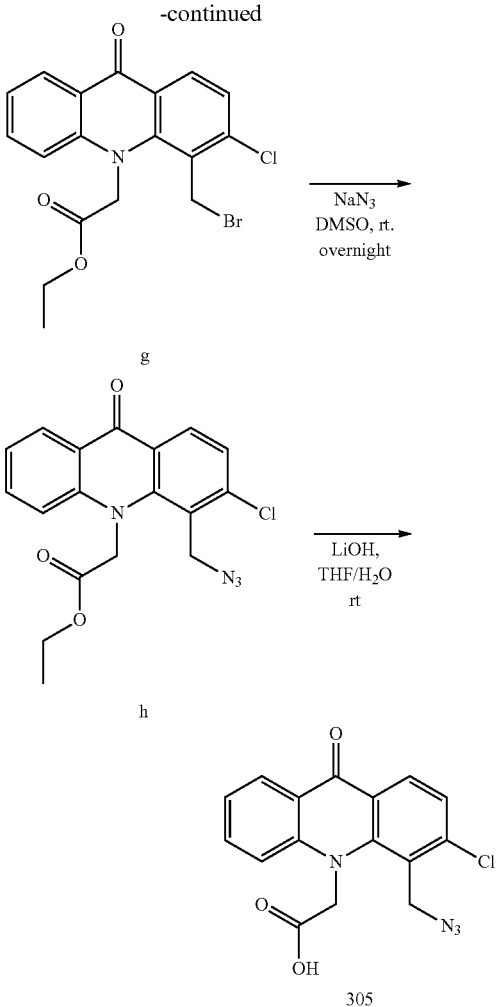

Step 1

A solution of a (1.8 g, 6.8 mmol, 1.0 eq), b (1.0 g, 7.5 mmol, 1.1 eq). KOAc (2.0 g, 20.4 mmol, 3.0 eq), copper powder (132.0 mg, 2.0 mmol, 0.3 eq), and Cu(OAc)$_2$ (364.0 mg, 2.0 mmol, 0.3 eq) in 2-pentanol (50.0 mL) was stirred at 140° C. overnight under N$_2$ atmosphere, then cooled to room temperature. The mixture was filtered and the filtrate was concentrated to give crude c (2.2 g, ca. 100%). LC/MS: 262.0 [M+H]$^+$.

Step 2

A solution of c (crude 2.2 g, 8.4 mmol, 1.0 eq) in Eaton's reagent (25.0 mL) was stirred at 70° C. for 2 hours, then cooled and poured into a mixture of ice and water (50 g). The solid was collected by filtration and dried to afford d (1.0 g, 60%). LCMS: 244.3 [M+H]$^+$.

Step 3

A solution of d (800.0 mg, 3.3 mmol, 1.0 eq), e (1.4 g, 6.6 mmol, 2.0 eq), Cs$_2$CO$_3$ (3.2 g, 9.9 mmol, 3.0 eq) in acetonitrile (50.0 mL) was stirred at r.t. overnight. 1 M HCl was added to the mixture until pH=5. The resulting mixture was extracted with EtOAc (100 mL×2). The organic layer was washed with brine, and concentrated. The residue was purified by column chromatography on silica gel to afford f (400.0 mg, 39%) as a yellow solid. LC/MS: 330.1 [M+H]$^+$.

Step 4

A mixture of f (50.0 mg, 0.15 mmol, 1.0 eq), NBS (31.0 mg, 0.17 mmol, 1.1 eq), and AIBN (1.0 mg) in CCl$_4$ (5 mL)

was heated to 70° C. under UV irradiation for 3 hours. The reaction mixture was cooled and concentrated. The residue was purified by column chromatography on silica gel to give g (33.0 mg, 54%). ¹H NMR (400 MHz, CDCl₃): δ 8.29-8.40 (m, 2H), 7.61-7.65 (m, 1H), 7.34 (d, J=8.4 Hz, 1H), 7.27 (t, J=7.6 Hz, 1H), 7.19 (d, J=6.0 Hz, 1H), 4.78 (s, 2H), 4.21 (q, J=16 Hz, 2H), 1.26-1.16 (m, 4H).

Step 5

A mixture of g (21.0 mg, 0.05 mmol, 1.0 eq) and NaN₃ (6.0 mg, 0.08 mmol, 1.6 eq) in DMSO (2 mL) was stirred at r.t. overnight. The reaction mixture was poured into water, and extracted with EtOAc (20 mL×2). The combined organic layers were dried over anhydrous Na₂SO₄ and concentrated. The residue was purified by prep-HPLC to afford h (15.0 mg, 80%). LC/MS: 371.2 [M+H]⁺.

Step 6

A mixture of h (15.0 mg, 0.04 mmol) and LiOH.H₂O (5.0 mg, 0.12 mmol) in THF/H₂O/EtOH (5 mL/1 mL/2 mL) was stirred at r.t. overnight. The reaction mixture was diluted with water and extracted with EtOAc (20 mL×2). The water phase was adjusted pH=4 with 1N HCl and extracted with EtOAc (20 mL×2). The combined organic layers were dried over anhydrous Na₂SO₄ and concentrated to afford 305 (8.6 mg, 63%). LC/MS: 343.2[M+H]⁺. ¹H NMR (400 MHz, DMSO-d₆): δ 13.34 (s, 1H), 8.26 (d, J=8.4 Hz, 1H), 8.18-8.20 (m, 1H), 7.84-7.80 (m, 1H), 7.55-7.60 (m, 2H), 7.37 (t, J=7.2 Hz, 1H), 5.11 (s, 2H), 4.90 (s, 2H).

Example 55: Synthesis of Compound 346

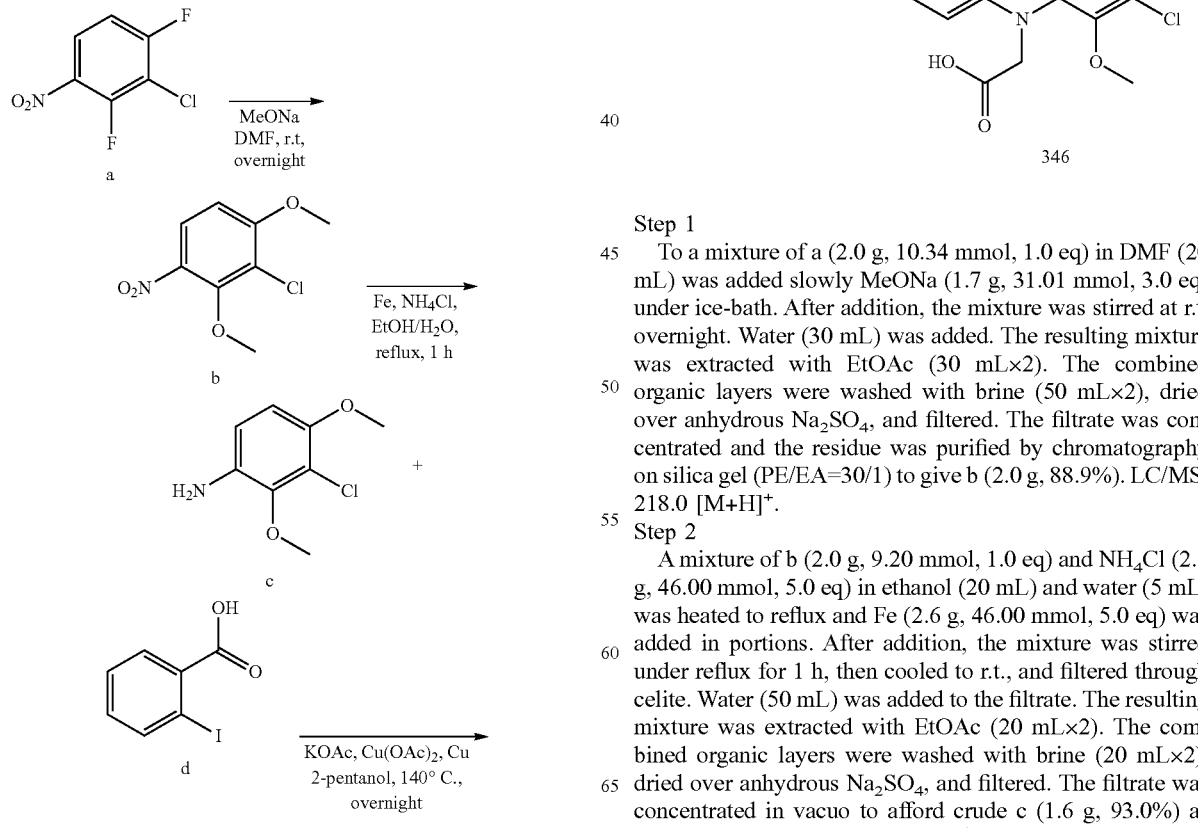

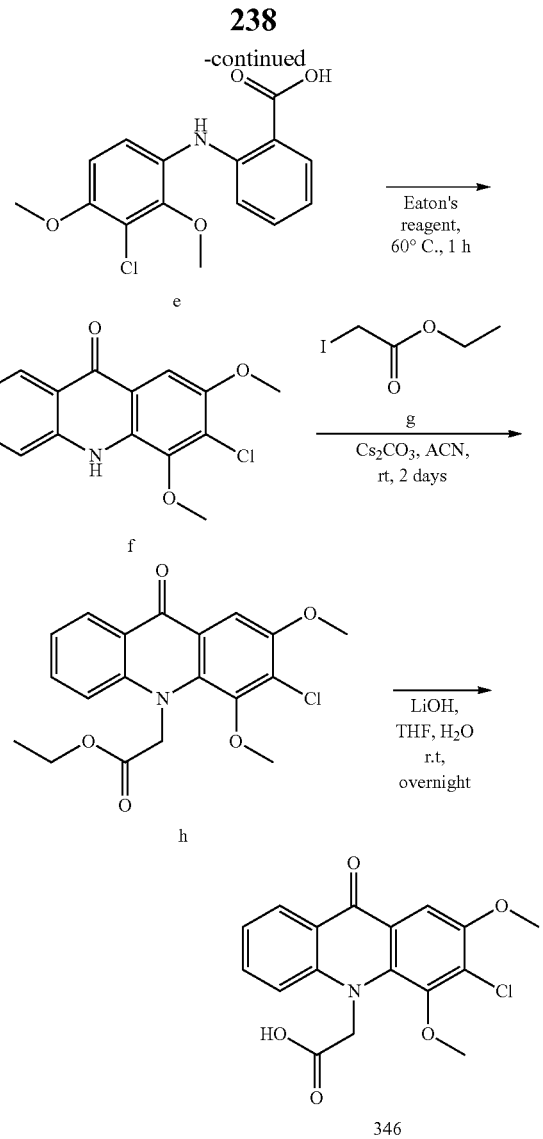

Step 1

To a mixture of a (2.0 g, 10.34 mmol, 1.0 eq) in DMF (20 mL) was added slowly MeONa (1.7 g, 31.01 mmol, 3.0 eq) under ice-bath. After addition, the mixture was stirred at r.t. overnight. Water (30 mL) was added. The resulting mixture was extracted with EtOAc (30 mL×2). The combined organic layers were washed with brine (50 mL×2), dried over anhydrous Na₂SO₄, and filtered. The filtrate was concentrated and the residue was purified by chromatography on silica gel (PE/EA=30/1) to give b (2.0 g, 88.9%). LC/MS: 218.0 [M+H]⁺.

Step 2

A mixture of b (2.0 g, 9.20 mmol, 1.0 eq) and NH₄Cl (2.5 g, 46.00 mmol, 5.0 eq) in ethanol (20 mL) and water (5 mL) was heated to reflux and Fe (2.6 g, 46.00 mmol, 5.0 eq) was added in portions. After addition, the mixture was stirred under reflux for 1 h, then cooled to r.t., and filtered through celite. Water (50 mL) was added to the filtrate. The resulting mixture was extracted with EtOAc (20 mL×2). The combined organic layers were washed with brine (20 mL×2), dried over anhydrous Na₂SO₄, and filtered. The filtrate was concentrated in vacuo to afford crude c (1.6 g, 93.0%) as yellow oil. LC/MS: 187.0 [M+H]⁺.

Step 3

A mixture of c (1.6 g, 8.56 mmol, 1.0 eq), d (2.7 g, 11.12 mmol, 1.3 eq), potassium acetate (2.5 g, 25.68 mmol, 3.0 eq), cupric acetate (470.0 mg, 2.57 mmol, 0.3 eq), and copper powder (164.0 mg, 2.57 mmol, 0.3 eq) in 2-Pentanol (30.0 mL) was stirred at 140° C. overnight under nitrogen atmosphere, then cooled to room temperature. Water (30.0 mL) was added. The resulting mixture was filtered through celite. The filtrate was acidified to pH=2 with 2 N HCl and extracted with EtOAc (25 mL×2). The combined organic layers were washed with brine (25 mL×2), dried over anhydrous $Na_2SO_4$, and filtered. The filtrate was concentrated in vacuo to afford the crude which was purified by trituration with PE (20 mL) to afford e (1.7 g, 65%). LC/MS: 308.1 $[M+H]^+$.

Step 4

A mixture of e (1.7 g, 5.54 mmol) and Eaton's reagent (20 mL) was heated at 60° C. for 1 h, then cooled, and poured into a mixture of ice and water (50 g). The solid was collected by filtration and dried to afford crude f (1.2 g, 75.0%). LC/MS: 290.1 [M+H]+

Step 5

To a mixture of f (300.0 mg, 1.04 mmol, 1.0 eq) and $Cs_2CO_3$ (1.0 g, 3.12 mmol, 3.0 eq) in acetonitrile (20 mL) was added g (450.0 mg, 2.08 mmol, 2.0 eq). The mixture was stirred at r.t. overnight, diluted with water (20 mL), and extracted with EtOAc (25 mL×2). The combined organic layers were washed with brine (25 mL×2), dried over anhydrous $Na_2SO_4$, and filtered. The residue was purified by prep-HPLC to give h (200.0 mg, 51.4%) as a yellow solid. LC/MS: 376.1 $[M+H]^+$.

Step 6

A mixture of h (200.0 mg, 0.53 mmol, 1.0 eq), $LiOH·H_2O$ (90.0 mg, 2.13 mmol, 4.0 eq) in THF (10 mL) and $H_2O$ (2 mL) was stirred at r.t. overnight, diluted with water (15 mL), and extracted with EtOAc (10 mL×2). The aqueous layer was acidified to pH=3 with 2 N HCl and extracted with EtOAc (15 mL×2). The combined organic layers were washed with brine (10 mL×2), dried over anhydrous $Na_2SO_4$ and filtered. The filtrate was concentrated in vacuo to afford 346 (165.0 mg, 89.2%) as a yellow solid. LC/MS: 348.1 $[M+H]^+$. $^1H$ NMR (400 MHz, DMSO-$d_6$): δ 13.16 (s, 1H), 8.26 (d, J=8.0 Hz, 1H), 7.80 (t, J=7.6 Hz, 1H), 7.68 (s, 1H), 7.60 (d, J=8.8 Hz, 1H), 7.35 (d, J=7.6 Hz, 1H), 5.11 (s, 2H), 3.98 (s, 3H), 3.78 (s, 3H).

Example 56: Synthesis of Compound 338

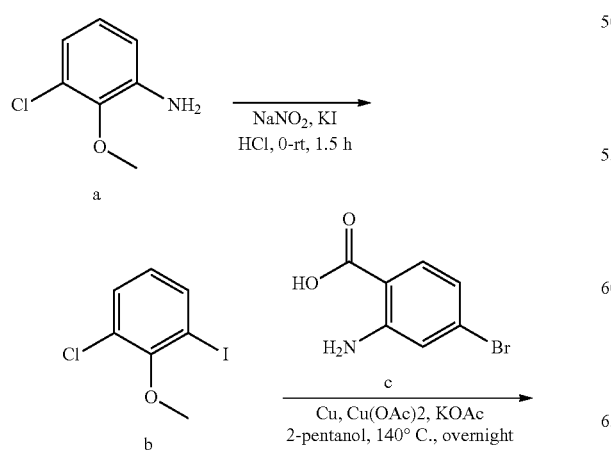

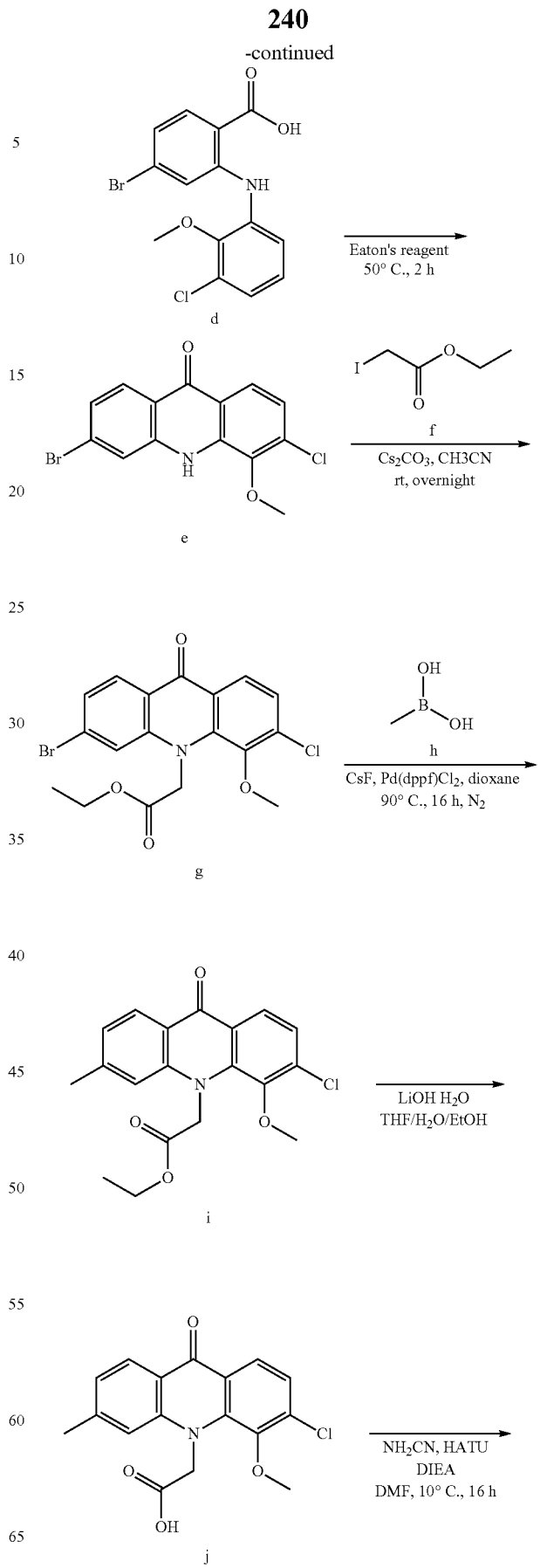

241

-continued

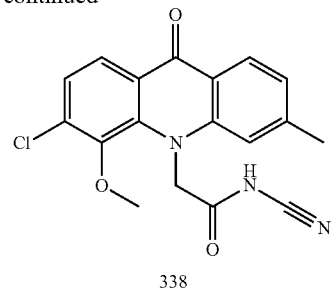

338

Step 1

A solution of a (15.76 g, 100 mmol, 1.0 eq) in 3M HCl (100 mL) at 0° C. was added dropwise a solution of NaNO$_2$ (7.59 g, 110 mmol, 1.1 eq) in water (20 mL). The mixture was stirred at 0° C. for 30 min, then added to a solution of KI (49.8 g, 300 mmol, 3.0 eq) in water (40 mL). The resulting mixture was stirred at r.t. for 1 h, poured into water (100 mL), and extracted with EtOAc (150 mL×2). The combined organic layers were washed with sat. Na$_2$SO$_3$ solution (50 mL×2) and brine (50 mL×2) successively, and then dried with anhydrous Na$_2$SO$_4$, filtered, and concentrated. The residue was purified by chromatography on silica gel (PE) to give b (26.0 g, 97%) as red liquid. LCMS: 268.9 [M+H]$^+$.

Step 2

A solution of b (7.5 g, 27.8 mmol, 1.2 eq), c (5.0 g, 23.2 mmol, 1.0 eq), KOAc (6.7 g, 69.5 mmol, 3.0 eq), copper powder (450 mg, 7.0 mmol, 0.3 eq), and Cu(OAc)$_2$ (1.3 g, 7.0 mmol, 0.3 eq) in 2-pentanol (50.0 mL) was stirred at 140° C. overnight under N$_2$ atmosphere, then cooled to room temperature. 2 N NaOH (100 mL) was added. The resulting mixture was filtered through celite. The filtrate was acidified to pH=2 with conc. HCl, and extracted with EtOAc (100 mL×3). The organic layer was concentrated. The residue was triturated with PE and filtered to afford d (5.5 g, 67%). LC/MS: 356.0 [M+H]$^+$.

Step 3

A solution of d (5.5 g, 15.5 mmol, 1.0 eq) in Eaton's Reagent (30.0 mL) was stirred at 50° C. for 2 hours. The mixture was poured into ice-water (50 g). The solid was collected by filtration and dried to afford e (5.2 g, 99%). LC/MS: 338.0 [M+H]$^+$.

Step 4

A solution of e (5.2 g, 15.4 mmol, 1.0 eq), f (6.6 g, 30.9 mmol, 2.0 eq) and Cs$_2$CO$_3$ (15.1 g, 40.3 mmol, 3.0 eq) in acetonitrile (100.0 mL) was stirred at 45° C. overnight, then added 1 N HCl until pH=23, and extracted with EtOAc (100 mL×3). The organic layer was washed with brine, then dried over anhydrous Na$_2$SO$_4$, filtered, and concentrated. The residue was purified by column chromatography on silica gel to afford g (6.2 g, 95%) as a yellow solid. LC/MS: 424.0 [M+H]$^+$. $^1$H NMR (400 MHz, DMSO-d$_6$): δ 8.13 (d, J=8.4 Hz, 1H), 8.04 (d, J=8.4 Hz, 1H), 7.88 (s, 1H), 7.55 (dd, J=8.4 Hz, 1H), 7.50 (d, J=8.4 Hz, 1H), 5.15 (s, 2H), 4.30-4.25 (m, 2H), 3.73 (s, 3H), 1.28 (t, J=7.2 Hz, 3H).

Step 5

A mixture of g (2.0 g, 4.8 mmol, 1.0 eq), h (864.0 mg, 14.4 mmol, 3.0 eq), Pd(dppf)C$_2$ (352.0 mg, 0.48 mmol, 0.1 eq), and CsF (2.4 g, 16.4 mmol, 3.4 eq) in dioxane (28 mL) was stirred at 90° C. under N$_2$ for 16 hours. The reaction mixture was filtrated with celite. The filtrate was concentrated and the residue purified by chromatography on silica gel (PE/EA=5/1) to afford i (1.45 g, 68%) as a yellow solid. LCMS: 360.11 [M+H]$^+$.

Step 6

A mixture of i (1.45 g, 4.0 mmol, 1.0 eq) and LiOH H$_2$O (1.1 g, 26.0 mmol, 6.5 eq) in THF/H$_2$O/EtOH (10 mL/2 mL/4 mL) was stirred at 25° C. overnight. The reaction mixture was heated to 45° C. and stirred for another 2 hours. The reaction mixture was diluted with H$_2$O (100 mL) and filtered. The filtrate was extracted with EtOAc (100 mL×2). The aqueous phase was acidified with conc. HCl to pH=2, and then extracted with EtOAc (100 mL×2). The organic phases were combined and concentrated to afford j (1.4 g, 96%) as a yellow solid. LCMS: [M+H]$^+$, Cal.: 332.0, Found: 332.0; $^1$HNMR: (DMSO-d$_6$, 400 MHz), δ 8.13 (d, J=8 Hz, 1H), 8.06 (d, J=8 Hz, 1H), 7.42-7.45 (m, 2H), 7.20 (d, J=7.6 Hz, 1H), 5.10 (s, 2H), 3.76 (s, 3H), 2.48 (s, 3H).

Step 7

A mixture of j (50.0 mg, 0.15 mmol, 1.0 eq), NH$_2$CN (7.6 mg, 0.18 mmol, 1.2 eq), HATU (68.0 mg, 0.18 mmol, 1.2 eq), and DIEA (58.0 mg, 0.45 mmol, 3 eq) in DMF (3.0 mL) was stirred at 10° C. overnight. The reaction mixture was diluted with H$_2$O (20 mL) and extracted with EtOAc (20 mL×3). The organic layers were combined and concentrated to give the crude which was purified by C18 prep-HPLC (acetonitrile/water with NH$_3$.H$_2$O as a modifier) to give 338 (16.7 mg, 31%) as a yellow solid. LCMS: [M+H]$^+$, Cal.: 356.1, Found: 356.1; $^1$H NMR: (CD$_3$OD, 400 MHz), 8.23 (d, J=8.4 Hz, 1H), 8.14 (d, J=8.8 Hz, 1H), 7.34-7.36 (m, 2H), 7.20 (d. J=8.4 Hz, 1H), 5.07 (s, 2H), 3.85 (s, 3H), 2.53 (s, 3H).

Example 57: Synthesis of Compound 339

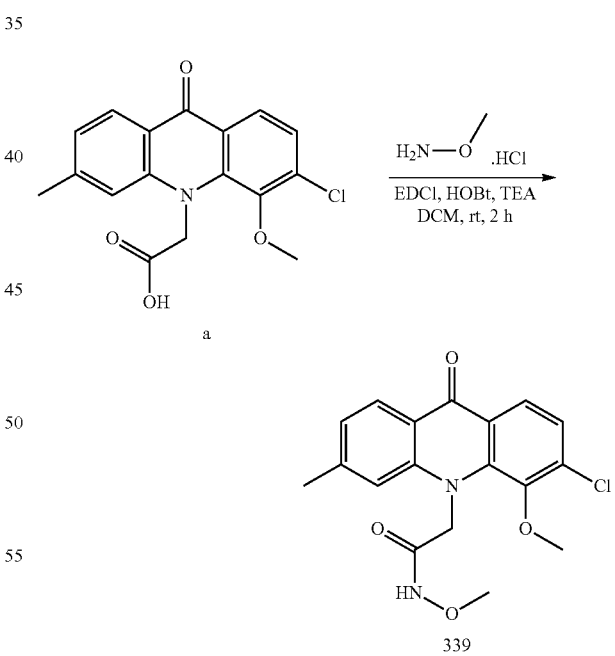

339

EDCl (69.0 mg, 0.36 mmol, 1.2 eq) was added to a solution of a (100 mg, 0.3 mmol, 1.0 eq), O-methylhydroxylamine hydrochloride (30 mg, 0.36 mmol, 1.2 eq), HOBt (49 mg, 0.36 mmol, 1.2 eq), and triethylamine (0.1 mL, 0.66 mmol, 2.2 eq) in DCM (8 mL) at room temperature. The reaction mixture was stirred at room temperature for 2 h. quenched with sat. aqueous NaHCO$_3$(30 mL), and extracted with DCM (25 mL×2). The combined organic layers were washed with brine (30 mL), dried over $Na_2SO_4$, and concentrated. The residue was purified by C18 Prep-HPLC (acetonitrile/water with TFA as a modifier) to afford 339 (63.6 mg, 58%) as a yellow solid. $^1$H NMR (400 MHz, DMSO-d6): δ=11.49 (s, 1H), 8.14 (d, J=8.4 Hz, 1H), 8.06 (d, J=8.4 Hz, 1H), 7.44 (d, J=8.4 Hz, 1H), 7.37 (s, 1H), 7.20 (d, J=8.0 Hz, 1H), 4.94 (s, 2H), 3.77 (s, 3H), 3.68 (s, 3H), 2.49 (s, 3H). LCMS: 361.3 [M+H]$^+$.

Example 58: Synthesis of Compound 347

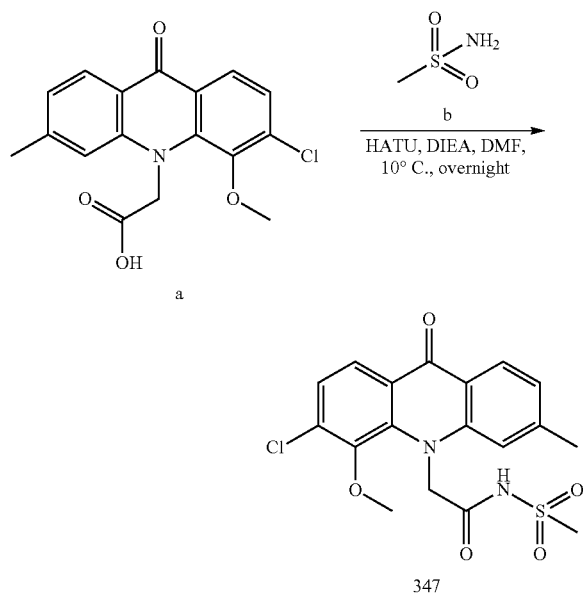

A mixture of a (50.0 mg, 0.15 mmol), b (17.0 mg, 0.18 mmol), HATU (68.0 mg, 0.18 mmol), and DIEA (58.0 mg, 0.45 mmol) in DMF (3.0 mL) was stirred at 10° C. overnight. The reaction mixture was diluted with $H_2O$ (10 mL) and extracted with EtOAc (5 mL×3). The organic layers were combined and concentrated to give the crude which was purified by C18 Prep-HPLC (acetonitrile/water with $NH_3H_2O$ as a modifier) to afford 347 (17.3 mg, 28.2%) as a yellow solid. LCMS: [M+H]$^+$, Cal.: 409.1, Found: 409.3. H NMR: (CD$_3$OD, 400 MHz), δ 8.21 (d, J=8.0 Hz, 1H), 8.12 (d, J=8.4 Hz, 1H), 7.36-7.38 (m, 2H), 7.20 (d, J=8.4 Hz, 1H), 5.06 (s, 2H), 3.85 (s, 3H), 3.28 (s, 3H), 2.52 (s, 3H).

Example 59: Synthesis of Compounds 261, 262, 348, 349, 351, and 352

Compounds 261, 262, 348, 349, 351, and 352 were prepared by following the synthesis of Compound 347 using the requisite sulfonamide.

Example 60: Human STING Protein FP Competition Concentration Response Assay

Fluorescein labeled c-di-GMP, a validated STING ligand, was mixed with recombinant hSTING-CTD in a homogenous assay format with or without the presence of a compound of the present application (titrated) in PBS in black 384-well plates (10 μL per well). The fluorescence anisotropy was determined on a PerkinElmer EnVisions multi-mode plate reader. The plate can be read immediately after mixing the reagents or after a few hours without change of signals.

Materials and Equipment
1) hSTING (Supplier: HDB)
2) 2'-Fluo-AHC-c-di GMP (BIOLOG #F009)
3) 2'3'-cGAMP (BIOLOG #C$_{161}$)
4) DMXAA (InvivoGen #tlrl-dmx)
5) DMSO (Sigma, #D5879-100 mL)
6) 10×PBS(HDB #MCP-020)
7) Assay plate, 384-well black plate, solid black bottom (Greiner #784076)
8) Compound dilution intermediate plate, 384 LDV plate (Labcyte #LP-0200)
9) Liquid handler, ECHO550 (Labcyte)
10) Liquid handler, Bravo (Aglient)
11) Reader, Envision (PerkinElmer)
12) Centrifuge (Eppendorf)
13) Multichannel Pipette (Raining)
14) 10 ml Reservoir (Corning)
15) 15 ml centrifuge tube (Corning)
16) Adhesive Plate seals (BioRad)

Compound Preparation
a) Containers of each compound were centrifuged at 1000 rpm for 5 min.
b) Compounds were dissolved in DMSO at 30 mM.
c) Compounds were sufficiently vortexed, and centrifuged at 1000 rpm for 1 min.
d) 16 uL of the compound solution was transferred into a LDV Compound Plate.
e) 2-fold serial dilutions of the compound solution were made with DMSO, and 14 concentrations were made in the 384-well LDV Compound Plate.
f) The LDV plate was spun at 1000 rpm for 60 sec and sealed with foil (stored at −20° C. if not used immediately).
g) 335 nL of each compound from the LDV Compound Plate was transferred to Assay Plate (ECHO550).

Probe Preparation
a) 200 uM probe stock (2'-Fluo-AHC-c-diGMP) was diluted by ddH$_2$O to 6 uM working concentration.
b) 10-12 uL 6 uM working solution of probe was transferred into the LDV plate.
c) 50 nL per well 6 uM working solution of probe was transferred from the LDV plate to each well of the empty Assay Plate (Greiner 784076) by ECHO550 Buffer mode.
d) Probe final concentration was 30 nM when assay system was 10 uL.
e) The Assay Plate was spun at 1000 rpm for 1 min.

Compound Addition
a) After the LDV Compound Plate was prepared, 335 nL compound (ECHO550 DMSO mode) was transferred from the LDV Compound Plate into the Assay Plate (Greiner 784076) containing 50 nL probe in each well according to the Assay Plate layout.
b) DMSO final concentration was 3.35% when assay system was 10 uL.
c) The Assay Plate was spun at 1000 rpm for 1 min.

Protein Addition
a) Aliquot of hSTING protein was thawed on ice, briefly to generate uniform solution.
b) 55 uM stock protein was diluted in 1×PBS assay buffer to generate 10 uM final solutions.
c) For test compound and ZPE wells, 10 μL per well of 10 uM protein solutions was added into the Assay Plate containing both the probe and test compounds or DMSO using multichannel pipette.

d) For HPE wells, 10 μL/well of 1×PBS assay buffer instead of protein was added into the Assay Plate containing both the probe and DMSO using multichannel pipette.

e) The Assay Plate was spun at 1000 rpm for 1min.

f) The Assay Plate was incubated at r.t. for 10-20 min.

|   |   | 1 | 2 | 3 | 4 | 5 | 6 | 7 | 8 | 9 | 10 | 11 | 12 |
|---|---|---|---|---|---|---|---|---|---|---|----|----|----|
| A | Dose (mM) | | | | | | HPE | | | | | | |
| B | 30 | Cmpd | Cmpd | Cmpd | Cmpd | Cmpd | Cmpd | Cmpd | Cmpd | Cmpd | Cmpd | Cmpd | Cmpd |
| C | 15 | 1 | 2 | 3 | 4 | 5 | 6 | 7 | 8 | 9 | 10 | 11 | 12 |
| D | 7.5 | | | | | | | | | | | | |
| E | 3.75 | | | | | | | | | | | | |
| F | 1.875 | | | | | | | | | | | | |
| G | 0.9375 | | | | | | | | | | | | |
| H | 0.48688 | | | | | | | | | | | | |
| I | 0.2344 | | | | | | | | | | | | |
| J | 0.1172 | | | | | | | | | | | | |
| K | 0.0586 | | | | | | | | | | | | |
| L | 0.0293 | | | | | | | | | | | | |
| M | 0.0146 | | | | | | | | | | | | |
| N | 0.0073 | | | | | | | | | | | | |
| O | 0.0037 | | | | | | | | | | | | |
| P | | | | | | | ZPE | | | | | | |

|   | 13 | 14 | 15 | 16 | 17 | 18 | 19 | 20 | 21 | 22 | 23 | 24 |
|---|----|----|----|----|----|----|----|----|----|----|----|----|
| A | | | | | | ZPE | | | | | | |
| B | Cmpd | Cmpd | Cmpd | Cmpd | Cmpd | Cmpd | Cmpd | Cmpd | Cmpd | Cmpd | Cmpd | Cmpd |
| C | 13 | 14 | 15 | 16 | 17 | 18 | 19 | 20 | 21 | 22 | 23 | 24 |
| D | | | | | | | | | | | | |
| E | | | | | | | | | | | | |
| F | | | | | | | | | | | | |
| G | | | | | | | | | | | | |
| H | | | | | | | | | | | | |
| I | | | | | | | | | | | | |
| J | | | | | | | | | | | | |
| K | | | | | | | | | | | | |
| L | | | | | | | | | | | | |
| M | | | | | | | | | | | | |
| N | | | | | | | | | | | | |
| O | | | | | | | | | | | | |
| P | | | | | | HPE | | | | | | |

Each Compound Plate contained HPE/ZPE, and 24 test compounds. Each assay included test compounds and two reference compounds: DMXAA and 2'3'-cGAMP.

Test compounds were dosed with 100% DMSO at 30 mM as the highest concentration and 14 decreasing concentrations through 2-fold serial dilution, in the 384-well LDV Compound Plate. DMXAA was dosed with 100% DMSO at 8.95 mM as the highest concentration and 14 decreasing concentrations through 2-fold serial dilution, in the 384-well LDV Compound Plate. 2'3'-cGAMP was dosed with 100% DMSO at 2.23 mM as the highest concentration and 14 decreasing concentrations through 2-fold serial dilution, in the 384-well LDV Compound Plate.

|   |   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|----|----|----|----|----|----|----|----|----|----|----|----|----|----|----|
| A | Dose (μM) | | | | | | HPE | | | | | | | | | | | | ZPE | | | | | | |
| B | 1000 | Cmpd 1 | | Cmpd 2 | | Cmpd 3 | | Cmpd 4 | | Cmpd 5 | | Cmpd 6 | | Cmpd 7 | | Cmpd 8 | | Cmpd 9 | | Cmpd 10 | | Cmpd 11 | | Cmpd 12 | |
| C | 500 | | | | | | | | | | | | | | | | | | | | | | | | |
| D | 250 | | | | | | | | | | | | | | | | | | | | | | | | |
| E | 125 | | | | | | | | | | | | | | | | | | | | | | | | |
| F | 62.5 | | | | | | | | | | | | | | | | | | | | | | | | |
| G | 31.25 | | | | | | | | | | | | | | | | | | | | | | | | |
| H | 15.625 | | | | | | | | | | | | | | | | | | | | | | | | |
| I | 7.8125 | | | | | | | | | | | | | | | | | | | | | | | | |
| J | 3.9063 | | | | | | | | | | | | | | | | | | | | | | | | |
| K | 1.9531 | | | | | | | | | | | | | | | | | | | | | | | | |
| L | 0.9766 | | | | | | | | | | | | | | | | | | | | | | | | |
| M | 0.4883 | | | | | | | | | | | | | | | | | | | | | | | | |
| N | 0.2441 | | | | | | | | | | | | | | | | | | | | | | | | |

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| O | 0.1221 | | | | | | | | | | | | | | | | | | | | | | | |
| P | | | | | ZPE | | | | | | | | | | | | | | HPE | | | | | |

Each Assay Plate contained HPE/ZPE, and 12 test compounds.
HPE well was 335 nL DMSO + 50 nL assay buffer containing 6 uM probe + 10 uL assay buffer.
ZPE well was 335 nL DMSO + 50 nL assay buffer containing 6 uM probe + 10 uL assay buffer containing 10 uM hSTING protein.
Test compound well was 335 nL DMSO containing compound (highest concentration at 1000 uM, and 14 decreasing concentrations through 2-fold serial dilution) + 50 nL assay buffer containing 6 uM probe + 10 uL assay buffer containing 10 uM hSTING protein.
For each assay, two reference compounds, DMXAA and 2'3'-cGAMP, were included in the last Assay Plate.
DMXAA well was 335 nL DMSO containing DMXAA (highest concentration at 8.95 mM, and 14 decreasing concentrations through 2-fold serial dilution) + 50 nL assay buffer containing 6 uM probe + 10 nL assay buffer containing 10 uM hSTING protein.
2'3'-cGAMP well was 335 nL DMSO containing 2'3'-cGAMP (highest concentration at 2.23 mM, and 14 decreasing concentrations through 2-fold serial dilution) + 50 nL assay buffer containing 6 uM probe + 10 uL assay buffer containing 10 uM hSTING protein.

Plate Reading

The EnVision plate reader was used to record the FA value of each well immediately after mixing the reagents or after a few hours without change of signals.

Data Analysis

The raw data and calculated data (Fluorescence anisotropy (FA)) was exported from the EnVision reader. Fluorescence anisotropy $(FA)=1000*(S-G*P)/(S+G*2*P)$, where S=<detector 2 or STING FP(1) channel 2>, P=<detector 1 or STING FP(1) channel 1>, G=G-factor. The FA value of each dose concentration was first normalized as a percentage of inhibition compared with ZPE (DMSO alone) and HPE (2'3'cGAMP+DMSO) controls, which provided a range of 0-100% inhibition. The data points were then plotted using non-linear regression modelling (4 Parameter Logistic Model, Sigmoidal Dose-Response Model) and least sum of squares. The resulting model was used to calculate an $IC_{50}$ value for the compound.

Example 61: Mouse STING Protein FP Competition Concentration Response Assay

Fluorescein labeled c-di-GMP was mixed with mSTING-CTD with or without the presence of a compound of the present application in PBS in black 384-well plates (10 μL per well). The fluorescence anisotropy was determined on a PerkinElmer EnVisions multi-mode plate reader. The plate can be read immediately after mixing the reagents or after a few hours without change of signals.

Materials and Equipment
1) 6×his-sumo-mSTING (Supplier: HDB)
2) 2'-Fluo-AHC-c-di GMP (BIOLOG #F009)
3) 23-cGAMP (BIOLOG #C161)
4) DMXAA (InvivoGen #tlrl-dmx)
5) DMSO (Sigma. #D5879-100 mL)
6) 10×PBS(HDB #MCP-020)
7) Assay plate, 384-well black plate, solid black bottom (Greiner #784076)
8) Compound dilution intermediate plate, 384 LDV plate (Labcyte #LP-0200)
9) Liquid handler, ECHO550 (Labcyte)
10) Liquid handler, Bravo (Aglient)
11) Reader, Envision (PerkinElmer)
12) Centrifuge (Eppendorf)
13) Multichannel Pipette (Raining)
14) 10 ml Reservoir (Corning)
15) 15 ml centrifuge tube (Corning)
16) Adhesive Plate seals (BioRad)

Compound Preparation
a) Containers of each compound were centrifuged at 1000 rpm for 5 min.
b) Compounds were dissolved in DMSO at 30 mM.
c) Compounds were sufficiently vortexed, and centrifuged at 1000 rpm for 1 min.
d) 16 uL of the compound solution was transferred into a LDV Compound Plate.
e) 2-fold serial dilutions of the compound solution were made with DMSO, and 14 concentrations were made in the 384-well LDV Compound Plate.
f) The LDV plate was spun at 1000 rpm for 60 sec and sealed with foil (stored at −20° C. if not used immediately).
g) 335 nL of each compound from the LDV Compound Plate was transferred to Assay Plate (ECHO550).

Probe Preparation
a) 200 uM probe stock (2'-Fluo-AHC-c-diGMP) was diluted by $dd_2O$ to 6 uM working concentration.
b) 10-12 uL 6 uM working solution of probe was transferred into the LDV plate.
c) 50 nL per well 6 uM working solution of probe was transferred from the LDV plate to each well of the empty Assay Plate (Greiner 784076) by ECHO550 Buffer mode.
d) Probe final concentration was 30 nM when assay system was 10 uL.
e) The Assay Plate was spun at 1000 rpm for 1 min.

Compound Addition
a) After the LDV Compound Plate was prepared, 100 nL compound (ECHO550 DMSO mode) was transferred from the LDV Compound Plate into the Assay Plate (Greiner 784076) containing 50 nL probe in each well according to the Assay Plate layout.
b) DMSO final concentration was 1% when assay system was 10 uL.
c) The Assay Plate was spun at 1000 rpm for 1 min.

Protein Addition
a) Aliquot of 6×his-sumo-mSTING protein was thawed on ice, briefly to generate uniform solution.
b) 66 uM stock protein was diluted in 1×PBS assay buffer to generate 8 uM final solutions.
c) For test compound and ZPE wells, 10 μL per well of 8 uM protein solutions was added into the Assay Plate containing both the probe and test compounds or DMSO using multichannel pipette.
d) For HPE wells, 10 L/well of 1×PBS assay buffer instead of protein was added into the Assay Plate containing both the probe and DMSO using multichannel pipette.
e) The Assay Plate was spun at 1000 rpm for 1 min.
f) The Assay Plate was incubated at r.t. for 10-20 min.

|   | 1 | 2 | 3 | 4 | 5 | 6 | 7 | 8 | 9 | 10 | 11 | 12 |
|---|---|---|---|---|---|---|---|---|---|----|----|----|
| A | Dose (mM) | | | | | HPE | | | | | | |
| B | 30 | Cmpd 1 | Cmpd 2 | Cmpd 3 | Cmpd 4 | Cmpd 5 | Cmpd 6 | Cmpd 7 | Cmpd 8 | Cmpd 9 | Cmpd 10 | Cmpd 11 | Cmpd 12 |
| C | 15 | | | | | | | | | | | | |
| D | 7.5 | | | | | | | | | | | | |
| E | 3.75 | | | | | | | | | | | | |
| F | 1.875 | | | | | | | | | | | | |
| G | 0.9375 | | | | | | | | | | | | |
| H | 0.4688 | | | | | | | | | | | | |
| I | 0.2344 | | | | | | | | | | | | |
| J | 0.1172 | | | | | | | | | | | | |
| K | 0.0586 | | | | | | | | | | | | |
| L | 0.0293 | | | | | | | | | | | | |
| M | 0.0146 | | | | | | | | | | | | |
| N | 0.0073 | | | | | | | | | | | | |
| O | 0.0037 | | | | | | | | | | | | |
| P | | | | | | ZPE | | | | | | | |

|   | 13 | 14 | 15 | 16 | 17 | 18 | 19 | 20 | 21 | 22 | 23 | 24 |
|---|----|----|----|----|----|----|----|----|----|----|----|----|
| A | | | | | | ZPE | | | | | | |
| B | Cmpd 13 | Cmpd 14 | Cmpd 15 | Cmpd 16 | Cmpd 17 | Cmpd 18 | Cmpd 19 | Cmpd 20 | Cmpd 21 | Cmpd 22 | Cmpd 23 | Cmpd 24 |
| C | | | | | | | | | | | | |
| D | | | | | | | | | | | | |
| E | | | | | | | | | | | | |
| F | | | | | | | | | | | | |
| G | | | | | | | | | | | | |
| H | | | | | | | | | | | | |
| I | | | | | | | | | | | | |
| J | | | | | | | | | | | | |
| K | | | | | | | | | | | | |
| L | | | | | | | | | | | | |
| M | | | | | | | | | | | | |
| N | | | | | | | | | | | | |
| O | | | | | | | | | | | | |
| P | | | | | | HPE | | | | | | |

Each Compound Plate contained HPE/ZPE, and 24 test compounds. Each assay included test compounds and two reference compounds: DMXAA and 2'3'-cGAMP.

Test compounds were dosed with 100% DMSO at 34 mM as the highest concentration and 14 decreasing concentrations through 2-fold serial dilution, in the 384-well LDV Compound Plate. DMXAA was dosed with 100% DMSO at 10 mM as the highest concentration and 14 decreasing concentrations through 2-fold serial dilution, in the 384-well LDV Compound Plate. 2'3'-cGAMP was dosed with 100% DMSO at 7.5 nM as the highest concentration and 14 decreasing concentrations through 2-fold serial dilution, in the 384-well LDV Compound Plate.

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|----|----|----|----|----|----|----|----|----|----|----|----|----|----|----|
| A | Dose ($\mu$M) | | | | | | HPE | | | | | | | | | | | | | ZPE | | | | |
| B | 1000 | Cmpd 1 | | Cmpd 2 | | Cmpd 3 | | Cmpd 4 | | Cmpd 5 | | Cmpd 6 | | Cmpd 7 | | Cmpd 8 | | Cmpd 9 | | Cmpd 10 | | Cmpd 11 | | Cmpd 12 |
| C | 500 | | | | | | | | | | | | | | | | | | | | | | | |
| D | 250 | | | | | | | | | | | | | | | | | | | | | | | |
| E | 125 | | | | | | | | | | | | | | | | | | | | | | | |
| F | 62.5 | | | | | | | | | | | | | | | | | | | | | | | |
| G | 31.25 | | | | | | | | | | | | | | | | | | | | | | | |
| H | 15.625 | | | | | | | | | | | | | | | | | | | | | | | |
| I | 7.8125 | | | | | | | | | | | | | | | | | | | | | | | |
| J | 3.9063 | | | | | | | | | | | | | | | | | | | | | | | |
| K | 1.9531 | | | | | | | | | | | | | | | | | | | | | | | |
| L | 0.9766 | | | | | | | | | | | | | | | | | | | | | | | |
| M | 0.4883 | | | | | | | | | | | | | | | | | | | | | | | |
| N | 0.2441 | | | | | | | | | | | | | | | | | | | | | | | |
| O | 0.1221 | | | | | | | | | | | | | | | | | | | | | | | |
| P | | | | | | | ZPE | | | | | | | | | | | | | HPE | | | | |

Each Assay Plate contained HPE/ZPE, and 12 test compounds.

HPE well was 100 nL DMSO + 50 nL assay buffer containing 6 uM probe + 10 uL assay buffer. ZPE well was 100 nL DMSO + 50 nL assay buffer containing 6 uM probe + 10 uL assay buffer containing 8 uM 6xhis-sumo-mSTING protein.

Test compound well was 100 nL DMSO containing compound (highest concentration at 30 mM and 14 decreasing concentrations through 2-fold serial dilution) + 50 nL assay buffer containing 6 uM probe + 10 uL assay buffer containing 8 uM 6xhis-sumo-mST1NG protein.

For each assay, two reference compounds, DMXAA and 2'3'-cGAMP, were included in the last Assay Plate.

DMXAA well was 100 nL DMSO containing DMXAA (highest concentration at 10 mM, and 14 decreasing concentrations through 2-fold serial dilution) + 50 nL assay buffer containing 6 uM probe + 10 nL assay buffer containing 8 uM 6xhis-sumo-mSTING protein.

2'3'-cGAMP well was 100 nL DMSO containing 2'3'-cGAMP (highest concentration at 7.5 mM, and 14 decreasing concentrations through 2-fold serial dilution) + 50 nL assay buffer containing 6 uM probe + 10 uL assay buffer containing 8 uM 6xhis-sumo-mSTING.

Plate Reading

The EnVision plate reader was used to record the FA value of each well immediately after mixing the reagents or after a few hours without change of signals.

Data Analysis

The raw data and calculated data (Fluorescence anisotropy (FA)) was exported from the EnVision reader. Fluorescence anisotropy (FA)=1000*(S−*P) (S+G*2*P), where S=<detector 2 or STING FP channel 2>, P=<detector or STING FP(1) channel 1>, G=G-factor. The FA value of each dose concentration was first normalized as a percentage of inhibition compared with ZPE (DMSO alone) and HPE (2'3'cGAMP+DMSO) controls, which provided a range of 0-1000% inhibition. The data points were then plotted using non-linear regression modelling (4 Parameter Logistic Model. Sigmoidal Dose-Response Model) and least sum of squares. The resulting model was used to calculate an $IC_{50}$ value for the compound.

Biological activities of the compounds of the application are shown in Table 2 below.

TABLE 2

| Cmpd No. | $^1$H NMR | Mass + HMass (calc) | Mass found | hSTING $IC_{50}$ (uM) | mSTING $IC_{50}$ (uM) |
|---|---|---|---|---|---|
| 1 | $^1$H NMR (400 MHz, DMSO-$d_6$): δ = 8.28 (d, 1 H), 7.80 (t, 1 H), 7.69 (t, 1 H), 7.59 (t, 2 H), 7.38 (t, 2 H), 5.26 (s, 2 H) ppm. | 272.1 | 272.2 | NA | C |
| 2 | $^1$H NMR (400 MHz, DMSO-$d_6$): δ = 8.28 (d, 1 H), 7.80 (t, 1 H), 7.69 (t, 1 H), 7.59 (t, 2 H), 7.38 (t, 2 H), 5.26 (s, 2 H) ppm. | 288.0 | 288.0 | NA | C |
| 3 | $^1$H NMR (400 MHz, CD$_3$OD): δ = 8.37 (d, 1 H), 7.75 (t, 1 H), 7.60 (t, 1 H), 7.54 (d, 1 H), 7.39 (d, 1 H), 7.32 (t, 1 H), 7.11 (d, 1 H), 5.21 (s, 2 H), 2.94 (s, 3 H) ppm. | 268.1 | 268.2 | NA | B |
| 4 | $^1$H NMR (400 MHz, DMSO-$d_6$): δ = 13.29 (brs, 1 H), 8.42 (t, 1 H), 8.36 (d, 1 H), 7.85 (t, 1 H), 7.65-7.58 (m, 2 H), 7.38 (t, 1 H), 7.21 (t, 1 H), 5.31 (s, 2 H) ppm. | 272.1 | 272.3 | NA | B |
| 5 | $^1$H NMR (400 MHz, DMSO-$d_6$): δ = 8.35 (d, 2 H), 7.83 (s, 2 H), 7.66 (d, 1 H), 7.39 (d, 2 H), 5.35 (s, 2 H) ppm. | 288.0 | 288.1 | NA | B |
| 6 | $^1$H NMR (400 MHz, DMSO-$d_6$): δ = 8.34 (d, 1 H), 8.25 (d, 1 H), 7.79 (t, 1 H), 7.63 (d, 1 H), 7.50 (s, 1 H), 7.35 (t, 1 H), 7.19 (d, 1 H), 5.19 (s, 2 H), 2.49 (s, 3 H) ppm. | 268.1 | 268.2 | NA | B |
| 7 | $^1$H NMR (400 MHz, DMSO-$d_6$): δ = 13.17 (bs, 1H), 8.21 (d, 1 H), 8.20 (d, 1 H), 7.79 (t, 1 H), 7.63 (d, 1 H), 7.54 (d, 1 H), 7.28 (m, 2 H), 5.08 (s, 2 H), 2.64 (s, 3 H) ppm. | 268.1 | 268.3 | D | B |
| 8 | $^1$H NMR (400 MHz, DMSO-$d_6$): δ = 13.20 (brs, 1 H), 8.30-8.22 (m, 2H), 7.93 (d, 1 H), 7.82 (t, 1 H), 7.62 (d, 1 H), 7.38 (t, 2 H), 5.20 (s, 2 H) ppm. | 288.0 | 288.2 | D | B |
| 9 | $^1$H NMR (400 MHz, DMSO-$d_6$): δ = 8.17 (d, 1 H), 8.02 (d, 1 H), 7.73 (t, 1 H), 7.62 (d, 1 H), 7.28 (t, 1 H), 7.13(d, 1 H), 4.99 (s, 2 H), 2.95-2.92 (m, 4 H), 1.84-1.81 (m, 2 H), 1.62-1.61 (m, 2 H) ppm. | 308.1 | 308.3 | C | A |
| 10 | $^1$H NMR (400 MHz, DMSO-$d_6$): δ = 13.32 (brs, 1 H), 8.34 (d, 1 H), 8.15 (s, 1 H), 7.80 (s, 1 H), 7.66 (d, 2 H), 7.64 (d, 1 H), 7.33 (t, 1 H), 5.31 (s, 2 H), 2.50 (s, 3 H) ppm. | 268.1 | 268.3 | D | B |
| 11 | $^1$H NMR (400 MHz, DMSO-$d_6$): δ = 13.10 (brs, 1 H), 8.14 (m, 2 H), 7.61 (d, 1 H), 7.34 (s, 1 H), 7.28 (t, 1 H), 7.15 (d, 1 H), 5.05 (s, 2 H), 2.63 (s, 3 H), 2.46 (s, 3 H) ppm. | 282.1 | 282.3 | C | A |
| 12 | $^1$H NMR (400 MHz, DMSO-$d_6$): δ = 13.15 (brs, 1 H), 8.28-8.25 (m, 1 H), 8.12-8.10 (d, 1 H), 7.91-7.89 (m, 1 H), 7.41 (s, 1 H), 7.37-7.34 (t, 1 H), 7.21-7.19 (d, 1 H), 5.20 (s, 2 H), 2.48 (s, 3 H) ppm. | 302.1 | 302.3 | C | A |
| 13 | $^1$H NMR (400 MHz, DMSO-$d_6$): δ = 13.12 (brs, 1 H), 8.25-8.19 (m, 2 H), 7.83 (t, 1 H), 7.67 (t, 2 H), 7.40 (t, 1 H), 5.19 (s, 2 H) ppm. | 322.0 | 322.2 | B | B |
| 14 | $^1$H NMR (400 MHz, DMSO-$d_6$): δ = 13.12 (brs, 1 H), 8.16 (d, 1 H), 7.62 (t, 1 H), 7.41 (s, 1 H), 7.38 (d, 1 H), 7.14 (d, 1 H), 7.08 (d, 1 H), 5.21 (s, 2 H), 2.88 (s, 3 H), 2.47 (s, 3 H) ppm. | 282.1 | 282.2 | NA | B |
| 15 | $^1$H NMR (400 MHz, DMSO-$d_6$): δ = 8.23 (d, 2 H), 7.45 (s, 2 H), 7.17 (d, 2 H), 5.29 (s, 2 H), 2.49 (s, 6 H) ppm. | 282.1 | 282.2 | D | B |
| 16 | $^1$H NMR (400 MHz, DMSO-$d_6$): δ = 13.32 (brs, 1 H), 8.16 (d, 1 H), 7.67 (t, 1 | 302.1 | 302.1 | NA | B |

TABLE 2-continued

| Cmpd No. | ¹H NMR | Mass + H (calc) | HMass found | hSTING IC$_{50}$ (uM) | mSTING IC$_{50}$ (uM) |
|---|---|---|---|---|---|
| | H), 7.54 (d, 1 H), 7.44 (s, 1 H), 7.34 (d, 1 H), 7.19 (d, 1H), 5.25 (s, 2 H), 2.43 (s, 3H) ppm. | | | | |
| 17 | ¹H NMR (400 MHz, DMSO-d$_6$): δ = 13.32 (brs, 1 H), 8.33 (d, 1 H), 8 24 (d, 1 H), 7.77 (s, 1 H), 7.49 (s, 1 H), 7.38 (d, 1 H), 7.22 (d, 1 H), 5.34 (s, 2 H), 2.49 (s, 3 H) ppm. | 302.1 | 302.1 | C | B |
| 18 | ¹H NMR (400 MHz, DMSO-d$_6$): δ = 13.36 (brs, 1 H), 8.35-8.33 (d, 1 H), 8.26-8.24 (d, 1 H), 7.97 (s, 1 H), 7.86-7.82 (t, 1 H), 7.66-7.62 (t, 1 H), 7.53-7.51 (d, 1 H), 7.41-7.37 (t, 1 H), 5.36 (s, 2 H) ppm. | 332.0 | 332.1 | NA | B |
| 19 | ¹H NMR (400 MHz, DMSO-d$_6$): δ = 13.07 (brs, 1 H), 8.20 (d, 1 H), 8.17 (d, 1 H), 7.79 (t, 1 H), 7.66 (d, 1 H), 7.42 (d, 1 H), 7.38 (t, 1 H), 5.16 (s, 2 H), 2.52 (s, 3 H) ppm. | 302.1 | 302.3 | D | B |
| 20 | ¹H NMR (400 MHz, DMSO-d$_6$): δ = 13.46 (brs, 1 H), 8.28-8.26 (d, 1 H), 7.81-7.77 (t, 1 H), 7.62-7.58 (m, 4 H), 7.37-7.34 (m, 1 H), 5.26 (s, 2 H) ppm. | 332.0 | 332.1 | NA | C |
| 21 | ¹H NMR (400 MHz, DMSO-d$_6$): δ = 8.38 (d, 1 H), 8.32 (d, 1 H), 7.87 (dd, 1 H), 7.78-7.76 (m, 1 H), 7.65-7.61 (m, 2 H), 7.33 (t, 1 H), 4.72 (s, 2 H) ppm. | 332.0 | 332.2 | NA | D |
| 22 | ¹H NMR (400 MHz, DMSO-d$_6$): δ = 8.47 (s, 1 H), 8.38 (d, 1 H), 7.96 (dd, 1 H), 7.86 (t, 1 H), 7.76 (d, 1 H), 7.71 (d, 1 H), 7.64-7.62 (m, 2H), 7.47-7.39 (m, 3 H), 5.38 (s, 2H) ppm. | 354.1 | 354.3 | C | B |
| 23 | ¹H NMR (400 MHz, DMSO-d$_6$): δ = 8.34 (dd, 1 H), 8.17 (d, 1 H), 7.78 (m, 1 H), 7.69 (d, 1 H), 7.65-7.59 (m, 2 H), 7.32 (t, 1 H), 7.28-7.27 (m, 4H), 7.18 (m, 1 H), 5.22 (s, 2H), 3.02 (m, 2H), 2.96 (m, 2H) ppm. | 358.1 | 358.4 | B | B |
| 24 | ¹H NMR (400 MHz, DMSO-d$_6$): δ = 8.32 (d, 1 H), 8.13 (s, 1 H), 7.73 (t, 1 H), 7.62 (d, 1 H), 7.56 (m, 2 H), 7.25 (t, 1 H), 4.66 (s, 2H), 2.65 (m, 1 H), 1.88-1.82 (m, 5H), 1.49-1.40 (m, 5H) ppm. | 336.2 | 336.3 | C | D |
| 25 | ¹H NMR (400 MHz, DMSO-d$_6$): δ = 8.33 (m, 2 H), 7.84-7.80 (m, 2 H), 7.66-7.64 (m, 3 H), 7.48-7.43 (m, 4 H), 7.34 (t, 1 H), 5.06 ppm. | 354.1 | 354.1 | NA | B |
| 26 | ¹H NMR (400 MHz, DMSO-d$_6$): δ = 8.32 (d, 1 H), 8.23 (d, 1 H), 7.75 (t, 1 H), 7.61 (d, 1 H), 7.54 (s, 1 H), 7.33-7.18 (m, 7H), 5.14 (s, 2H), 3.02 (d, 2 H), 2.96 (d, 2H) ppm. | 358.1 | 358.2 | C | A |
| 27 | ¹H NMR (400 MHz, DMSO-d$_6$): δ = 8.20 (d, 1 H), 8.03 (d, 1 H), 7.64 (m, 2 H), 7.29-7.21 (m, 7 H), 4.65 (s, 2 H), 3.00 (m, 2H), 2.91 (m, 2H), 2.50 (s, 3H) ppm. | 372.2 | 372.3 | D | C |
| 28 | ¹H NMR (400 MHz, DMSO-d$_6$): δ = 8.16 (d, 1 H), 8.05 (d, 1 H), 7.66 (d, 2 H), 7.21 (m, 1 H), 7.03 (d, 2 H), 5.68 (s, 1H), 4.40 (s, 2 H), 2.56 (s, 3 H), 2.24-2.18 (m, 4 H), 1.75-1.67 (m, 4 H) ppm. | 348.2 | 348.3 | C | B |
| 29 | ¹H NMR (400 MHz, DMSO-d$_6$): δ = 13.13 (br, 1 H), 8.21 (d, 1 H), 8.09 (d, 1 H), 7.63 (d, 1 H), 7.49 (s, 1 H), 7.22 (d, 1 H), 5.19 (s, 2 H), ~2.50 (s, 3 H) ppm. | 336.0 | 336 | B | B |
| 30 | ¹H NMR (400 MHz, DMSO-d$_6$): δ = 13.15 (br, 1 H), 8.12 (d, 1 H), 7.76 (m, 1 H), 7.66 (d, 1H), 7.52 (d, 1 H), 7.13 (d, 1H), 5.18 (s, 2H) ppm. | 340.0 | 340.0 | D | |
| 31 | ¹H NMR (400 MHz, DMSO-d$_6$): δ = 13.15 (br, 1 H), 7.78 (d, 1 H), 7.76 (ddd, 1 H), 7.65 (d, 1 H), 7.52 (d, 1 H), 7.12 (dd, 1 H), 5.79 (s, 2 H) ppm. | 340.0 | 340.0 | C | |
| 32 | ¹H NMR (400 MHz, DMSO-d$_6$): δ = 8.29 (d, 1 H), 7.67 (t, 1 H), 7.31 (s, 1 H), 7.15 (d, 1 H), 7.05 (d, 1 H), 6.86 (d, 1 H), 5.19 (s, 2 H), 3.96 (s, 3 H), 2.51 (s, 3 H) ppm. | 298.1 | 298.1 | NA | D |

TABLE 2-continued

| Cmpd No. | ¹H NMR | Mass + H (calc) | HMass found | hSTING IC$_{50}$ (uM) | mSTING IC$_{50}$ (uM) |
|---|---|---|---|---|---|
| 33 | ¹H NMR (400 MHz, DMSO-d$_6$): δ = 8.49 (dd, 1 H), 8.33 (d, 1 H), 7.38 (s, 1 H), 7.35 (d, 1 H), 7.24 (d, 1 H), 7.12 (ddd, 1 H), 5.28 (s, 2 H), 2.36 (s, 3 H) ppm. | 286.1 | 286.1 | NA | B |
| 34 | ¹H NMR (400 MHz, DMSO-d$_6$): δ = 13.33 (br, 1 H), 8.25 (d, 1 H), 8.20 (d, 1 H), 7.15 (s, 1 H), 6.98 (d, 1 H), 6.96-6.94 (m, 2 H), 5.3 (s, 2 H), 3.92 (s, 3 H), 2.5 (s, 3 H) ppm. | 298.1 | 298.1 | D | B |
| 35 | ¹H NMR (400 MHz, DMSO-d$_6$): δ = 13.33 (br, 1 H), 8.20 (d, 1 H), 7.58(t, 1 H), 7.38(d, 1 H), 7.07(d, 1 H), 6.92(d, 2 H), 5.20 (s, 2 H), 3.91 (s, 3 H), 2.87 (s, 3 H) ppm. | 298.1 | 298.1 | NA | B |
| 36 | ¹H NMR (400 MHz, DMSO-d$_6$): δ = 13.39 (br, 1 H), 8.16 (d, 1 H), 7.74 (dd, 1 H), 7.39 (s, 1 H), 7.18(d, 1 H), 7.06(d, 1 H), 7.03(dd, 1 H), 5.26 (s, 2 H), 2.49 (s, 3 H) ppm. | 286.1 | 286.1 | NA | B |
| 37 | ¹H NMR (400 MHz, DMSO-d$_6$): δ = 13.18 (br, 1 H), 8.21 (d, 1 H), 8.08 (s, 1 H), 7.80 (m, 2 H), 7.58 (d, 1 H), 7.34 (t, 1 H), 5.17 (s, 2 H), 2.42 (s, 3 H) ppm. | 302.1 | 302.0 | NA | |
| 38 | ¹H NMR (400 MHz, DMSO-d$_6$): δ = 13.12 (br, 1 H), 8.10 (d, 1 H), 8.07 (s, 1 H), 7.76 (s, 1 H), 7.39 (s, 1 H), 7.18 (d, 1 H), 5.17 (s, 2 H), 2.49 (s, 3 H), 2.41 (s, 3 H) ppm. | 316.1 | 316.2 | C | |
| 39 | ¹H NMR (400 MHz, DMSO-d$_6$): δ = 8.34 (d, 1 H), 8.27 (s, 1 H), 7.83 (t, 1 H), 7.77 (d, 1 H), 7.69 (t, 2 H), 7.38 (s, 2 H), 5.33 (s, 2 H), 2.49 (s, 1 H), 1.90 (m, 2 H), 1.70 (m, 2 H), 1.51 (m, 3 H), 1.34 (m, 3 H) ppm. | 360.2 | 360.3 | B | |
| 40 | ¹H NMR (400 MHz, DMSO-d$_6$): δ = 13.28 (br, 1 H), 8.34 (d, 1 H), 8.13 (s, 1 H), 7.94 (t, 1 H), 7.65 (d, 1 H), 7.59 (d, 1 H), 7.34 (t, 1 H), 5.30 (s, 2 H), 2.73 (t, 2 H), 1.76 (d, 2 H), 1.67 (m, 3 H), 1.53 (dt, 2 H), 1.16 (m, 4 H), 0.94 (m, 2 H) ppm. | 364.2 | 364.3 | A | |
| 41 | ¹H NMR (400 MHz, DMSO-d$_6$): δ = 13.50 (s, 1 H), 8.57 (s, 1 H), 8.37 (d, 1 H), 8.12 (d, 1 H), 7.84 (m, 3 H), 7.60 (d, 3 H), 7.36 (m, 3 H), 5.32 (s, 2 H), 2.95 (sept, 1 H), 1.24 (d, 6 H) ppm. | 372.2 | 372.4 | A | |
| 42 | ¹H NMR (400 MHz, DMSO-d$_6$): δ = 8.34 (d, 1 H), 8.15 (s, 1 H), 7.77 (t, 1 H), 7.66 (m, 3 H), 7.33 (t, 1 H), 7.16 (m, 2 H), 6.95 (d, 1 H), 6.84 (t, 1 H), 5.29 (s, 2 H), 3.79 (s, 3 H), 2.95 (m, 4 H) ppm. | 388.2 | 388.3 | C | |
| 43 | ¹H NMR (400 MHz, DMSO-d$_6$): δ = 8.35 (d, 1 H), 8.19 (s, 1 H), 7.75 (t, 1 H), 7.72 (d, 1 H), 7.63 (m, 2 H), 7.33 (t, 1 H), 7.18 (t, 1 H), 6.85 (d, 2 H), 6.74 (d, 1 H), 5.30 (s, 2 H), 3.72 (s, 3 H), 3.02 (m, 2 H), 2.92 (m, 2 H) ppm. | 388.2 | 388.3 | C | |
| 44 | ¹H NMR (400 MHz, DMSO-d$_6$): δ 8.30 (d, J = 9.2 Hz, 1 H), 8.17 (d, J = 8.8 Hz, 1 H), 8.31 (d, J = 8.0 Hz, 1 H), 6.89-6.80 (m, 2 H), 5.05 (s, 2 H), 2.60 (s, 3 H) ppm | 350.0256 | 350.0 [M + 1] | NA | |
| 45 | ¹H NMR (400 MHz, DMSO-d$_6$): δ 8.12-8.03 (m, 2 H), 7.45 (d, J = 12.8 Hz, 1 H), 7.08 (d, J = 8.4 Hz, 1 H), 4.78 (s, 2 H), 3.14 (s, 2 H), 2.93-2.90 (m, 2 H), 2.30 (s, 3 H), 1.75-1.53 (m, 6 H) ppm | 403.1226 | 403.3 [M + 1] | NA | |
| 46 | ¹H NMR (400 MHz, DMSO-d$_6$): δ 13.12 (s, 1 H), 8.19 (d, J = 8.8 Hz, 1 H), 8.16 (d, J = 6.4 Hz, 1 H), 7.36-7.23 (m, 2 H), 7.21 (d, J = 1.6 Hz 1 H), 5.17 (s, 2 H), 2.60 (s, 3 H), 2.58 (s, 3 H) ppm | 380.0184 | 380.0 [M + 1] | D | |
| 47 | ¹H NMR (400 MHz, DMSO-d$_6$): δ 8.21 (d, J = 8.8 Hz, 1 H), 8.12 (d, J = 8.4 Hz, 1 H), 7.63 (d, J = 8.8 Hz, 1 H), 7.59 (s, 1 H), 7.48 (d, J = 8.4 Hz, 1 H), 5.21 (s, 2 H), 1.35 (s, 9 H) pm | 378.0665 | 378.3 [M + 1] | A | B |

TABLE 2-continued

| Cmpd No. | $^1$H NMR | Mass + HMass (calc) found | hSTING IC$_{50}$ (uM) | mSTING IC$_{50}$ (uM) |
|---|---|---|---|---|
| 48 | $^1$H NMR (400 MHz, DMSO-d$_6$): δ 13.51 (br, 1 H), 8.30-8.24 (m, 1 H), 8.95 (d, J = 9.2 Hz, 1 H), 7.83-7.79 (m, 1 H), 7.64 (t, J = 10.0 Hz, 1 H), 7.38 (t, J = 7.4 Hz, 1 H), 5.29 (s, 2 H) ppm | 322.0039 322.0 [M + 1] | D | |
| 49 | $^1$H NMR (400 MHz, DMSO-d$_6$): δ 13.11 (br, 1 H), 8.12 (d, J = 8.4 Hz, 1 H), 7.69-7.51 (m, 3 H), 7.16 (d, J = 7.2 Hz 1 H), 5.16 (s, 2 H), 3.23 (q, J = 7.6 Hz, 2 H), 1.20 (t, J = 7.4 Hz, 3 H) ppm | 350.0352 350.2 [M + 1] | D | |
| 51 | $^1$H NMR (400 MHz, DMSO-d$_6$): δ 13.0 (br, 1 H), 8.23 (d, J = 8.8 Hz, 1 H), 8.18 (d, J = 8.0 Hz, 1 H), 7.77-7.80 (m, 2 H), 7.64 (d, J = 8.4 Hz, 1 H), 7.37 (t, J = 8.0 Hz, 1 H), 5.29 (s, 2 H) ppm | 365.9534 366.0 [M + 1] | B | |
| 52 | $^1$H NMR (400 MHz, DMSO-d$_6$): δ 13.1 (br, 1 H), 8.19 (d, J = 8.0 Hz, 1 H), 8.13 (d, J = 8.4 Hz, 1 H), 7.78-7.85 (m, 2 H), 7.68 (d, J = 8.4 Hz, 1 H), 7.39 (t, J = 7.2 Hz, 1 H), 5.18 (s, 2 H) ppm | 365.9534 366.0 [M + 1] | B | |
| 53 | $^1$H NMR (400 MHz, DMSO-d$_6$): δ 8.13 (d, J = 8.0 Hz, 1 H), 7.50-7.55 (m, 3 H), 7.39 (s, 1 H), 7.13 (d, J = 8.0 Hz, 1 H), 4.92 (s, 2 H), 2.44 (s, 3 H) ppm | 346.0081 346.1 [M + 1] | B | B |
| 54 | $^1$H NMR (400 MHz, DMSO-d$_6$): δ 13.1 (br, 1 H), 7.93 (d, J = 8.4 Hz, 1 H), 7.67-7.76 (m, 2 H), 7.60 (d, J = 8.4 Hz, 1 H), 7.24 (d, J = 8.4 Hz, 2 H), 7.18 (d, J = 8.4 Hz, 2 H), 7.11 (d, J = 6.8 Hz, 1 H), 5.19 (s, 2 H), 2.90-2.99 (m, 1 H), 1.26 (d, J = 7.2 Hz, 6 H) ppm | 440.0822 440.2 [M + 1] | B | |
| 55 | $^1$H NMR (400 MHz, DMSO-d$_6$): δ 13.0 (br, 1 H), 8.08 (d, J = 8.4 Hz, 1 H), 7.68 (t, J = 7.6 Hz, 1 H), 7.60 (d, J = 8.4 Hz, 1 H), 7.53 (d, J = 8.4 Hz, 1 H), 7.34 (d, J = 7.2 Hz, 1 H), 5.15 (s, 2 H), 4.42-4.45 (m, 1 H), 1.24 (d, J = 6.8 Hz, 6 H) ppm | 364.0509 364.1 [M + 1] | C | |
| 56 | $^1$H NMR (400 MHz, DMSO-d$_6$): δ 13.0 (br, 1 H), 8.05 (d, J = 8.4 Hz, 1 H), 7.83 (d, J = 8.8 Hz, 1 H), 7.74-7.78 (m, 1 H), 7.68 (d, J = 8.4 Hz, 1 H), 7.42 (d, J = 8.8 Hz, 1 H), 7.33-7.37 (m, 1 H), 5.16 (s, 2 H) ppm | 322.0039 322.2 [M + 1] | C | |
| 57 | $^1$H NMR (400 MHz, DMSO-d$_6$): δ 8.43 (s, 1 H), 8.37 (d, J = 7.2 Hz, 1 H), 8.12 (s, 1 H), 7.89 (s, 1 H), 7.70 (s, 1 H), 7.43 (s, 1 H), 5.32 (s, 2 H) ppm | 322.0039 322.0 [M + 1] | D | |
| 58 | $^1$H NMR (400 MHz, DMSO-d$_6$): δ 13.27 (s, 1 H), 8.22 (d, J = 7.2 Hz, 2 H), 8.09 (s, 1 H), 7.85 (s, 1 H), 7.63 (d, J = 8.0 Hz, 1 H), 7.40 (s, 1 H), 5.20 (s, 2 H) ppm | 322.0039 322.0 [M + 1] | D | |
| 59 | $^1$H NMR (400 MHz, DMSO-d$_6$): δ 13.17 (s, 1 H), 8.15 (d, J = 8.4 Hz, 1 H), 7.88 (d, J = 8.4 Hz, 1 H), 7.54 (d, J = 8.8 Hz, 1 H), 6.88 (s, 1 H), 6.66 (d, J = 9.2 Hz, 1 H), 6.40 (s, 1 H), 5.00 (s, 2 H), 1.96 (d, J = 12.0 Hz, 2 H), 1.74 (d, J = 12.4 Hz, 2 H), 1.63 (d, J = 12.8 Hz, 1 H), 1.41-1.18 (m, 6 H) ppm | 419.0931 419.1 [M + 1] | A | B |
| 60 | $^1$H NMR (400 MHz, DMSO-d$_6$): δ 13.03 (s, 1 H), 8.16 (d, J = 8.4 Hz, 1 H), 8.00 (d, J = 8.8 Hz, 1 H), 7.59 (d, J = 8.4 Hz, 1 H), 7.06 (dd, J = 8.8 Hz, 2.0 Hz, 1 H), 6.86 (d, J = 2.0 Hz, 1 H), 5.18 (s, 2 H), 3.76 (t, J$_1$ = 9.2 Hz, J$_2$ = 4.4 Hz, 4 H), 3.40-3.35 (m, 4 H) ppm | 407.0567 407.1 [M + 1] | A | B |
| 61 | $^1$H NMR (400 MHz, DMSO-d$_6$): δ 8.15 (d, J = 8.8 Hz, 1 H), 7.96 (d, J = 8.8 Hz, 1 H), 7.59 (d, J = 8.4 Hz, 1 H), 7.02 (d, J = 9.2 Hz, 1 H), 6.78 (s, 1 H), 5.14 (s, 2 H), 3.45 (s, 4 H), 1.62 (s, 6 H) ppm | 405.0774 405.1 [M + 1] | A | B |
| 62 | $^1$H NMR (400 MHz, DMSO-d$_6$): δ 8.19 (d, J = 8.4 Hz, 1 H), 7.91 (s, 1 H), 7.52 (d, J = 8.4 Hz, 1 H), 7.16 (s, 1 H), 4.78 (s, 2 H), 2.95-2.90 (m, 4 H), 1.69-1.49 (m, 6 H) ppm | 419.0931 419.2 [M + 1] | D | |

TABLE 2-continued

| Cmpd No. | ¹H NMR | Mass + HMass (calc) found | hSTING IC$_{50}$ (uM) | mSTING IC$_{50}$ (uM) |
|---|---|---|---|---|
| 63 | ¹H NMR (400 MHz, DMSO-d$_6$): δ 8.25 (d, J = 8.8 Hz, 1 H), 8.00 (s, 1 H), 7.45 (d, J = 8.4 Hz, 1 H), 7.01 (s, 1 H), 4.91 (s, 2 H), 3.86 (t, J = 8.0 Hz, 4 H), 3.05 (s, 4 H), 2.37 (s, 3 H), ppm | 421.0724 421.2 [M + 1] | B | |
| 64 | ¹H NMR (400 MHz, DMSO-d$_6$): δ 8.17 (d, J = 8.4 Hz, 1 H), 7.88 (s, 1 H), 7.50 (d, J = 8.4 Hz, 1 H), 7.07 (s, 1 H), 4.78 (s, 2 H), 2.80 (s, 6 H), 2.34 (s, 3 H), ppm | 379.0618 379.2 [M + 1] | B | |
| 65 | ¹H NMR (400 MHz, DMSO-d$_6$): δ 13.17 (s, 1H), 8.28-8.23 (m, 2H), 7.90 (s, 1H), 7.84-7.82 (d, J = 8.0 Hz, 2H), 7.72-7.67 (m, 2H), 7.58-7.54 (m, 2H), 7.50-7.47 (m, 1H) ppm | 398.0 398.1 [M + H] | A | |
| 66 | ¹H NMR (400 MHz, DMSO-d$_6$): δ 8.31-8.22 (m, 2 H), 7.37-7.48 (m, 2 H), 7.16-7.21 (m, 1 H), 4.81 (s, 2 H) ppm | 324.0241 324.2 [M + 1] | NA | |
| 67 | ¹H NMR (400 MHz, DMSO-d$_6$): δ13.17 (s, 1 H), 8.24 (d, J = 8.4 Hz, 1 H), 8.11 (s, 1 H), 8.15 (d, J = 11.6 Hz, 1 H), 7.95 (d, J = 9.6 Hz, 1 H), 7.63 (t, J = 8.8 Hz, 1 H), 6.29 (s, 1 H), 5.20 (s, 2 H), 2.24 (s, 4 H), 1.40 (s, 2 H), 1.00 (s, 6 H) ppm | 430.0978 430.2 [M + 1] | C | D |
| 68 | ¹H NMR (400 MHz, DMSO-d$_6$): δ13.24 (s, 1 H), 8.41 (s, 1 H), 8.27 (d, J = 8.8 Hz, 1 H), 8.15 (d, J = 11.6 Hz, 1 H), 7.77 (d, J = 8.8 Hz, 1 H), 7.67 (d, J = 8.4 Hz, 1 H), 7.60 (s, 1 H), 7.56 (d, J = 7.6 Hz, 1 H), 7.40 (1, J = 8.0 Hz, 1 H), 7.23 (d, J = 7.2 Hz, 1 H), 5.25 (s, 2 H), 2.42 (s, 3 H) ppm | 412.0509 412.1 [M + 1] | A | B |
| 69 | ¹H NMR (400 MHz, DMSO-d$_6$): δ 8.05 (d, J = 8 0 Hz, 1 H,), 7.96 (d, J = 8.0 Hz, 1 H), 7.05 (d, J = 8.0 Hz, 1 H), 6.76 (d, J = 12.0 Hz, 1 H), 6.50 (d, J = 4 Hz, 1 H), 5.07 (s, 2 H), 3.13 (s, 6 H), 2.94 (s, 6 H) ppm | 374.1273 374.3 [M + 1] | NA | |
| 70 | ¹H NMR (400 MHz, DMSO-d$_6$): δ 13.05 (s, 1 H), 8.18 (d, J = 8.0 Hz, 1 H,), 8.12 (d, J = 8.0 Hz, 1 H), 7.77-7.73 (m, 1 H), 7.60 (d, J = 8.0 Hz, 1 H), 7.34-7.31 (m, 1 H), 7.13(d, J = 8.0 Hz, 1 H), 5.14 (s, 2 H), 2.99 (s, 6H) ppm | 331.0851 331.0 [M + 1] | NA | |
| 71 | ¹H NMR (400 MHz, DMSO-d$_6$): δ 8.16 (d, J = 8 0 Hz, 1 H), 7.98 (d, J = 8.0 Hz, 1 H), 7.57 (d, J = 12 Hz, 1 H), 6.84 (d, J = 12 Hz, 1 H), 6.54 (d, J = 2 Hz, 1 H), 5.14 (s, 2 H), 3.09 (s, 6 H) ppm | 365.0461 365.1 [M + 1] | B | B |
| 72 | ¹H NMR (400 MHz, DMSO-d$_6$): δ13.21 (s, 1 H), 8.40 (s, 1 H), 8.27 (d, J = 8.0 Hz, 1 H), 8.16-8.14 (d, J = 8.0 Hz, 1 H,), 7.77-7.66 (m, 1H), 7.439 (d, J = 8.0 Hz, 1 H), 5.24 (s, 2 H), 3.09 (s, 6 H), 1.27 (d, J = 2.0 Hz, 6 H) ppm | 440.0822 440.1 [M + 1] | A | |
| 73 | ¹H NMR (400 MHz, DMSO-d$_6$): δ 8.32 (d, J = 8.0 Hz, 1 H), 8.25 (s, 1 H), 7.85 (d, J = 12.0 Hz, 1 H), 7.75-7.71 (m,, 1 H), 7.62-7.56 (m, 2 H), 7.29-7.26 (m, 1 H), 6.23 (s, 1 H), 4.78 (s, 2H), 2.25 (s, 4 H), 1.42-1.39 (m, 2H), 1.01 (s, 6H) ppm | 362.1758 362.1 [M + 1] | B | |
| 74 | ¹H NMR (400 MHz, DMSO-d$_6$): δ = 8.35 (d, J = 7.6 Hz, 1 H), 8.19 (d, J = 2 Hz, 1 H), 7.78 (1, J = 7.2 Hz, 1 H), 7.72 (d, J = 8.8 Hz, 1 H), 7.66-7.60 (m, 2 H), 7.34 (t, J = 7.2 Hz, 1 H), 7.22-7.19 (m, 1 H), 7.16-7.09 (m, 3 H), 5.22 (s, 2 H), 2.95-2.89 (m, 4 H), 2.31 (s, 3 H) ppm | 372.1601 372.2 [M + 1] | B | |
| 75 | ¹H NMR (400 MHz, DMSO-d$_6$): δ = 13.31 (br, 1 H), 8.25 (d, J = 8.0 Hz, 1 H), 8.18 (d, J = 1.6 Hz, 1 H), 7.72-7.69 (m, 1 H), 7.58 (d, J = 8.8 Hz, 1 H), 7.49 (s, 1 H), 7.22-7.09 (m, 5 H), 5.30(s, 2 H), 2.95-2.91 (m, 4 H), 2.49 (s, 3 H), 2.31 (s, 3 H) ppm | 386.1758 386.4 [M + 1] | B | D |
| 76 | ¹H NMR (400 MHz, DMSO-d$_6$): δ = 8.24 (d, J = 8 Hz, 1 H), 8.12 (s, 1 H), 7.65 (d, J = 8.4 Hz, 1 H), 7.56 (d, J = 9.2 Hz, 1 H), 7.48 (s, 1 H), 7.17 (d, J = 8.2 Hz, 1 H), | 378.207 378.4 [M + 1] | B | |

TABLE 2-continued

| Cmpd No. | ¹H NMR | Mass + HMass (calc) found | hSTING IC$_{50}$ (uM) | mSTING IC$_{50}$ (uM) |
|---|---|---|---|---|
| | 5.29 (s, 2 H), 2.74 (t, J = 7.6 Hz, 2 H), 2.49 (s, 3 H), 1.78-1.75 (m, 2 H), 1.69-1.62 (m, 3 H), 1.55-1.50 (m, 2 H), 1.25-1.2 (m, 4 H), 0.95-0.92 (m, 2 H) ppm | | | |
| 77 | ¹H NMR (400 MHz, DMSO-d$_6$): δ = 13.40 (br, 1 H), 8.56 (d, J = 2.4 Hz, 1 H), 8.28 (d, J = 8.0 Hz, 1 H), 8.33 (dd, J = 8.8, 6.8 Hz, 1 H), 7.74-7.69 (m, 3 H), 7.54 (s, 1 H), 7.38 (d, J = 8.4 Hz, 1 H), 7.21 (d, J = 8.4 Hz, 1 H), 5.37(s, 2 H), 3.34 (s, 3 H), 2.99-2.92 (m, 1 H), 1.26 (d, J = 6.8 Hz, 6 H) ppm | 386.1758 386.3 [M + 1] | B | |
| 78 | ¹H NMR (400 MHz, DMSO-d$_6$): δ = 13.43 (br, 1 H), 8.38 (s, 1 H), 8.24 (d, J = 8.4 Hz, 1 H), 7.95 (dd, J = 9.2, 6.8 Hz, 1 H), 7.65 (d, J = 9.6 Hz, 1 H), 7.53 (s, 1 H), 7.23 (d, J = 8.0 Hz, 1 H), 5.32 (s, 2 H), 2.50 (s, 3H) ppm | 346.0081 691.0 [2M − 1] | D | |
| 79 | ¹H NMR (400 MHz, DMSO-d$_6$): δ 13.22 (s, 1 H), 8.20 (d, J = 8.4 Hz, 1 H), 8.09 (d, J = 8.4 Hz, 1 H), 7.96 (d, J = 1.6 Hz, 1 H), 7.67 (d, J = 8.4 Hz, 1 H), 7.56 (dd, J = 8.4 Hz, 1.6 Hz, 1 H), 5.23 (s, 2 H) ppm | 399.9145 399.9 [M + 1] | B | |
| 80 | ¹H NMR (400 MHz, DMSO-d$_6$): δ 8.30 (m, 1 H), 8.26 (m, 1 H), 7.80 (m, 1 H), 7.63-7.70 (m, 4 H), 7.29 (m, 6 H), 6.76 (q, J = 12 Hz, 1 H), 5.27 (s, 2 H) ppm | 356.1288 356.3 [M + 1] | B | |
| 81 | H NMR (400 MHz, DMSO-d$_6$): δ 13.11 (br, 1 H), 8.21 (d, J = 8.8 Hz, 1 H), 8.12 (d, J = 8.4 Hz, 1 H), 7.62 (d, J = 8.4 Hz, 1 H), 7.50(s, 1 H), 7.31 (d, J = 7.6 Hz, 1 H), 5.22 (s, 2 H), 3.65 (m, 1 H), 1.27 (d, J = 6.8 Hz, 6 H) ppm | 364.0509 364.2 [M + 1] | A | B |
| 82 | ¹H NMR (400 MHz, DMSO-d$_6$): δ 13.12 (s, 1 H), 8.21 (d, J = 8.8 Hz, 1 H), 8.11 (d, J = 8.0 Hz, 1 H), 7.63 (d, J = 8.4 Hz, 1 H), 7.50(s, 1 H) 7.26 (d, J = 8 Hz, 1 H), 5.21 (s, 2 H), 2.75 (q, J = 7.2 Hz, 2 H), 1.25 (t, J = 7.6 Hz, 3 H) ppm | 350.0352 350.2 [M + 1] | B | C |
| 83 | ¹H NMR (400 MHz, DMSO-d$_6$): δ 1.30 (s, 1 H), 8.34 (dd, J = 6.4 Hz, 8.8 Hz, 1 H), 8.23 (dd, J = 1.6 Hz, 8 Hz, 1 H), 7.84 (m, 1 H), 7.61 (d, J = 8.4 Hz, 1 H), 7.38-7.48 (m, 2 H), 5.22 (s, 1 H) ppm | 306.0335 306.1 [M + 1] | D | |
| 84 | ¹H NMR (400 MHz, DMSO-d$_6$): δ 13.38 (s, 1 H), 8.29 (dd, J = 1.6 Hz, 8 Hz, 1 H), 8.14 (dd, J = 1.6 Hz, 8.8 Hz, 1 H), 7.86 (m, 1 H), 7.63 (d, J = 8.8 Hz, 1 H), 7.51 (dd, J = 6.4 Hz, 8.8 Hz, 1 H), 7.42 (t, J = 6.8 Hz, 1H), 5.19 (s, 1 H) ppm | 306.0335 306.1 [M + 1] | D | |
| 85 | ¹H NMR (400 MHz, DMSO-d$_6$): δ 7.27 (d, J = 8.0 Hz, 1 H), 7.18 (d, J = 8.0 Hz, 1 H), 7.08 (s, 1 H), 7.03 (d, J = 7.6 Hz, 1 H), 6.80 (d, J = 7.2 Hz, 1 H), 4.75 (s, 2H), 3.92 (s, 2 H), 2.26 (s, 3H) ppm | 322.0403 322.0 [M + 1] | C | |
| 86 | ¹H NMR (400 MHz, DMSO-d$_6$): δ 13.05 (s, 1 H), 7.51 (d, J = 2 Hz, 1 H), 7.43 (dd, J = 1.2 Hz, 7.6 Hz, 1 H), 7.34 (dd, J = 2 Hz, 8.8 Hz, 1 H)), 7.19 (m, 1 H), 6.99 (t, J = 7.2 Hz, 1 H), 6.82-6.77 (m, 2H), 4.67 (s, 2H), 1.47 (s, 6 H) ppm | 346.0444 346.2 [M + 1] | C | |
| 87 | ¹H NMR (400 MHz, DMSO-d$_6$): δ 7.43 (m, 2 H), 7.18-7.14 (m, 2 H), 6.98-6.94 (m, 2 H), 6.81 (d, J = 8 Hz, 2 H), 4.68 (s, 2H), 1.51 (s, 6H) ppm | 268.1339 268.4 [M + 1] | NA | NA |
| 88 | ¹H NMR (400 MHz, DMSO-d$_6$): δ 13.18 (s, 1 H), 8.23 (d, J = 8.4 Hz, 1 H), 8.02 (s, 1 H), 7.72 (dd, J = 2 Hz, 9.2 Hz, 1 H)), 7.64-7.59 (m, 2 H), 7.27 (m, 4 H), 7.18 (m, 1H), 5.17 (s, 2 H), 3.02 (dd, J = 5.2 Hz, 8.4 Hz, 2 H,), 2.94 (dd, J = 6 Hz, 9.6 Hz, 2 H,) ppm | 426.0665 426.0 [M + 1] | B | |
| 89 | ¹H NMR (400 MHz, DMSO-d$_6$): δ 8.21-8.26 (m, 2 H), 7.96-7.99 (m, 1 H), 7.67-7.69 (m, 2 H), 5.18 (s, 2 H) ppm | 399.9145 402.0 [M + 1] | B | |
| 90 | ¹H NMR (400 MHz, DMSO-d$_6$): δ 7.10-7.15 (m, 2 H), 6.93-6.97 (m, 2 H), 6.87 | 350.2122 350.3 [M + 1] | C | |

TABLE 2-continued

| Cmpd No. | ¹H NMR | Mass+H (calc) | HMass found | hSTING IC$_{50}$ (uM) | mSTING IC$_{50}$ (uM) |
|---|---|---|---|---|---|
| | (t, J = 7.2 Hz, 1 H), 6.71 (d, J = 8.0 Hz, 1 H), 6.64 (d, J = 8.4 Hz, 1 H), 4.56 (s, 2 H), 3.87 (s, 2H), 2.50 (s, 2 H), 1.57-1.75 (m, 6 H,), 1.40-1.46 (m, 2 H), 1.14-1.23 (m, 5 H) ppm | | | | |
| 91 | ¹H NMR (400 MHz, DMSO-d$_6$): δ 13.15 (s, 1H), 8.26-8.23 (m, 2H), 7.86 (s, 1H), 7.74 (d, J = 8.0 Hz, 2H), 7.67 (m, 2H), 7.42 (d, J = 8.0 Hz, 2H), 5.33 (s, 1H), 3.01-2.94 (m, 1H), 1.26 (d, J = 7.2 Hz, 6H) ppm | 440.1 | 440.2 [M + H] | A | |
| 92 | ¹H NMR (400 MHz, DMSO-d$_6$): δ 8.53 (d, J = 8.4 Hz, 1 H), 8.08-8.10 (m, 2 H), 7.74-7.77 (m, 1 H), 7.50-7.54 (m, 2 H), 4.39 (s, 2 H), 2.78 (s, 3 H), 1.59 (s, 3 H) ppm | 282.1132 | 282.2 [M + 1] | NA | |
| 93 | ¹H NMR (400 MHz, DMSO-d$_6$): δ 13.13 (brs, 1 H), 8.21 (d, J = 8.4 Hz, 1 H), 8.11 (d, J = 8.8 Hz, 1 H), 7.64 (d, J = 8.4 Hz, 1 H), 7.51 (d, J = 12.0 Hz, 1 H), 5.18 (s, 2 H), 2.34 (s, 3 H) ppm | 354.0102 | 354.2 [M + 1] | C | |
| 94 | ¹H NMR (400 MHz, DMSO-d$_6$): δ 13.11 (brs, 1 H), 8.22 (d, J = 8.4 Hz, 1 H), 7.94 (s, 1 H), 7.61 (d, J = 8.4 Hz, 1 H), 7.48 (s, 1 H), 5.18 (s, 2 H), 2.39 (s, 3 H), 2.34 (s, 3 H) ppm | 350.0352 | 350.2 [M + 1] | B | C |
| 95 | ¹H NMR (400 MHz, DMSO-d$_6$): δ 13.14 (s, 1H), 8.20 (d, J = 8.8 Hz, 1H), 8.12 (d, J = 9.2 Hz, 1H), 7.63 (d, J = 8.8 Hz, 1H), 7.08 (m, 1H), 7.01 (m, 1H), 5.20 (s, 2H), 3.91 (s, 3H) ppm | 352.0145 | 352.0 [M + 1] | B | |
| 96 | ¹H NMR (400 MHz, DMSO-d$_6$): δ 12.98 (s, 1H), 8.07 (d, J = 8.4 Hz, 1H), 7.56 (m, 2H), 7.45 (m, 1H), 5.14 (s, 2H), 2.67 (s, 3H), 2.32 (s, 3H) ppm | 350.0352 | 350.2 [M + 1] | B | |
| 97 | ¹H NMR (400 MHz, DMSO-d$_6$): δ 7.24 (d, J = 8.0 Hz, 1H), 7.16 (m, 4H), 6.94 (m, 1H), 4.61 (s, 2H), 3.98 (s, 2H) ppm | 308.0247 | 308.0 [M + 1] | C | D |
| 98 | ¹H NMR (400 MHz, DMSO-d$_6$): δ 8.17 (d, J = 8.4 Hz, 1H), 8.10 (d, J = 8.4 Hz, 1H), 7.70 (m, 2H), 7.37 (d, J = 8.8 Hz, 1H)), 7.28 (m, 1H), 4.49 (s, 2H), 2.69 (s, 3H) ppm | 302.0586 | 302.2 [M + 1] | C | B |
| 99 | ¹H NMR (400 MHz, DMSO-d$_6$): δ 8.28 (m, 1H), 8.12 (d, J = 8.0 Hz, 1H), ¹H NMR (400 MHz, DMSO-d$_6$): 7.74 (m, 1H), 7.61 (m, 1H)), 7.30 (m, 1H), 7.24 (d, J = 8.0 Hz, 1H), 5.03 (s, 2H), 2.53 (s, 3H), 2.47 (s, 3H) ppm | 282.1132 | 282.3 [M + 1] | C | C |
| 102 | ¹H NMR (400 MHz, DMSO-d$_6$): δ 13.31 (s, 1 H), 8.37 (d, J = 8.0 Hz, 2 H), 7.82 (t, J = 7.6 Hz, 2 H), 7.69 (br, 2 H), 7.36 (t, J = 7.6 Hz, 2 H), 6.07 (q, J = 6.8 Hz, 1 H), 1.76 (d, J = 6.8 Hz, 3 H) ppm | 268.1 | 268.1 [M + H] | NA | |
| 107 | ¹H NMR (400 MHz, DMSO-d$_6$): δ 8.35 (d, J = 8.4 Hz, 1H), 8.21 (d, J = 8.0 Hz, 1H), 7.88 (d, J = 8.4 Hz, 1H), 7.69 (d, J = 8.8 Hz, 1H), 7.42(t, J = 7.6 Hz, 1H), 5.23 (s. 2H) | 313.0 | 313.1 [M + 1] | A | |
| 111 | ¹H NMR (400 MHz, DMSO-d$_6$): δ 12.94 (br, 1H), 8.22 (d, J = 8.8 Hz, 1H), 8.09 (d, J = 8.0 Hz, 1H), 7.62 (d, J = 8.8 Hz, 1H), 7.60 (s, 1H), 7.29(d, J = 8.0 Hz, 1H), 5.31 (s, 2H), 3.08-3.01 (m, 1H), 1.27 (d, J = 6.8 Hz, 6 H) | 408.0 | 408.0 [M + 1] | A | |
| 112 | ¹H NMR (400 MHz, DMSO-d$_6$): δ 8.22 (d, J = 8.4 Hz, 1H), 8.06 (d, J = 8.0 Hz, 1H), 7.62 (d, J = 8.4 Hz, 1H), 7.59 (s, 1H), 7.20 (d, J = 8.0 Hz, 1H), 5.28 (s, 2H), 2.46 (s, 3 H) ppm | 380.0 | 380.1 [M + H] | A | |
| 114 | ¹H NMR (400 MHz, DMSO-d$_6$): δ 13.21 (s, 1H), 8.21 (d, J = 12 Hz, 1H), 8.12 (d, J = 12.0 Hz, 1H), 7.64 (d, J = 8.0 Hz, 1H), 7.56 (d, J = 8.0 Hz, 1H), 6.62 (s, 1H), 5.24 (s, 1H), 2.74-2.72 (m, 2H), 2.56-2.50 (m, 2H), 2.03-1.99 (m, 2H) ppm | 388.0 | 388.1 [M + H] | A | |

TABLE 2-continued

| Cmpd No. | ¹H NMR | Mass + H (calc) | HMass found | hSTING IC$_{50}$ (uM) | mSTING IC$_{50}$ (uM) |
|---|---|---|---|---|---|
| 115 | ¹H NMR (400 MHz, DMSO-d$_6$): δ 8.22 (d, J = 8.6 Hz, 1H), 8.11 (d, J = 8.2 Hz, 1H), 7.63 (d, J = 8.6 Hz, 1H), 7.49 (s, 1H), 7.29 (d, J = 8.2 Hz, 1H), 5.21 (s, 2H), 2.69 (m, 1 H), 1.85-1.72 (m, 5 H), 1.57-1.22 (m, 5H) ppm | 404.1 | 404.1 [M + H] | A | |
| 116 | ¹H NMR (400 MHz, DMSO-d$_6$): δ 13.14 (s, 1H), 8.21 (d, J = 8.0 Hz, 1H), 8.11 (d, J = 8.0 Hz, 1H), 7.64 (d, J = 8.0 Hz, 1H), 7.57 (d, J = 8.0 Hz, 1H), 6.47 (s, 1H), 5.23 (s, 1H), 2.50-2.45 (m, 2H), 2.26-2.25 (m, 2H), 1.77-1.75 (m, 2H), 1.66-1.64 (m, 2H) ppm | 402.1 | 402.1 [M + H] | A | |
| 117 | ¹H NMR (400 MHz, DMSO-d$_6$): δ 13.11 (s, 1H), 8.16 (d, J = 8.4 Hz, 1H), 7.90 (d, J = 8.8 Hz, 1H), 7.55 (d, J = 8.4 Hz, 1H), 7.27 (d, J = 6.0 Hz, 1H), 6.62-6.60 (m, 1H), 6.30 (s, 1H), 5.00 (s, 2H), 3.99-3.94 (m, 1H), 2.42-2.35 (m, 2H), 1.93-1.87 (m, 2H), 1.81-1.75(m, 2H) ppm | 391.1 | 391.2 [M + H] | A | |
| 118 | ¹H NMR (400 MHz, DMSO-d$_6$): δ 13.11 (s, 1H), 8.16 (d, J = 8.4 Hz, 1H), 7.88 (d, J = 8.8 Hz, 1H), 7.55 (d, J = 8.4 Hz, 1H), 7.00 (d, J = 6.0 Hz, 1H), 6.68-6.65 (m, 1H), 6.38(s, 1H), 5.01 (s, 2H), 3.83-3.80 (m, 1H), 2.00-1.94 (m, 2H), 1.69 (d, J = 6.4 Hz, 2H), 1.60-1.48 (m, 4H) ppm | 405.1 | 405.2 [M + H] | A | |
| 119 | ¹H NMR (400 MHz, DMSO-d$_6$): δ 8.14 (d, J = 8.4 Hz, 1H), 7.88 (d, J = 8.8 Hz, 1H), 7.52 (d, J = 8.4 Hz, 1H), 6.79 (d, J = 7.2 Hz, 1H), 6.64-6.61 (m, 1H), 6.44 (s, 1H), 4.90 (s, 2H), 3.70-3.64 (m, 1H), 1.18 (d, J = 6.4 Hz, 6 H) ppm | 379.1 | 379.2 [M + H] | A | |
| 120 | ¹H NMR (400 MHz, DMSO-d$_6$): δ 8.35 (s, 1H), 8.20 (d, J = 7.6 Hz, 1H), 7.85 (t, J = 8.0 Hz, 1H), 7.70 (d, J = 8.8 Hz, 1H), 7.41 (t, J = 7.6 Hz, 1H), 5.19 (s. 2H) ppm | 356.0 | 356.0 [M + H] | NA | |
| 121 | ¹H NMR (400 MHz, DMSO-d$_6$): δ 8.22 (d, J = 8.8 Hz, 1H), 7.97 (s, 1H), 7.63-7.56 (m, 3H), 5.08 (s, 2H), 2.41 (s, 3H) ppm | 336.0 | 336.2 [M + H] | C | |
| 122 | ¹H NMR (400 MHz, DMSO-d$_6$): δ 8.58 (d, J = 8.6 Hz, 1H), 7.89 (d, J = 8.6 Hz, 1H), 7.55 (d, J = 8.6 Hz, 1H), 6.91 (bs, 1H), 6.64 (d, J = 8.6 Hz, 1H), 6.31 (s, 1H), 4.99 (s, 2 H), 1.94 (m, 2 H), 1.68-1.50 (m, 11 H) ppm | 433.1 | 433.1 [M + 1] | A | |
| 123 | ¹H NMR (400 MHz, DMSO-d$_6$): δ 13.04 (s, 1H), 8.15 (d, J = 7.6 Hz, 1H), 7.89 (d, J = 7.6 Hz, 1H), 7.55 (d, J= 7.2 Hz, 1H), 6.97 (s, 1H), 6.64 (d, J = 7.6 Hz, 1H), 6.39 (s, 1H), 5.04 (s, 2H), 3.14 (s, 2H), 1.21 (s, 3H) ppm | 365.0 | 365.1 [M + H] | A | |
| 124 | ¹H NMR (400 MHz, DMSO-d$_6$): δ 8.20 (d, J = 8.0 Hz, 1 H), 7.48 (t, J = 8.4 Hz, 3 H), 7.17 (d, J = 6.8 Hz 1 H), 5.74 (s, 1 H), 5.95 (s, 2 H), 3.33-3.30 (m, 1 H), 2.00-1.93 (m, 2 H), 1.78-1.68 (m, 2 H), 1.43-1.30 (m, 2 H), 1.28-1.18 (m, 4 H) ppm | 419.1 | 419.1 [M + H] | NA | |
| 125 | ¹H NMR (400 MHz, DMSO-d$_6$): δ 8.43 (d, J = 2.0 Hz, 1H), 8.27 (d, J = 8.8 Hz, 1H), 8.17 (dd, J = 8.9, 2.8 Hz, 1H), 7.80-7.78 (m, 3H), 7.67 (d, J = 8.6 Hz, 1H), 7.54-7.51 (m, 2H), 7.43-7.40 (m, 1H), 4.02 (s, 2H) ppm | 398.0 | 398.1 [M + H] | A | |
| 226 | ¹H NMR (400 MHz, DMSO-d$_6$): δ 13.08 (s, 1H), 8.24 (d, J = 8.8 Hz, 1H), 8.11 (d, J = 8.8 Hz, 1H), 7.26 (d, J = 8.8 Hz, 1H), 7.00-6.95 (m, 2H), 5.15 (s, 2H), 4.01 (s, 3H), 3.90 (s, 3H) ppm | 348.1 | 348.2 [M + H] | D | |
| 227 | ¹H NMR (400 MHz, DMSO-d$_6$): δ 8.18 (d, J = 8.8 Hz, 1H), 8.04 (s, 1H), 7.75 (s, 1H), 7.58 (d, J = 8.8 Hz, 1H), 4.84 (s, 2H), 2.44, (s, 3H). | 370.0 | 370.1 [M + 1] | B | |
| 228 | ¹H NMR (400 MHz, DMSO-d$_6$): δ 8.07 (d, J = 8.8 Hz, 1H), 7.64 (s, 1H), 7.55-7.51 (m, 2H), 4.75 (s, 2H), 2.66 (s, 3H) ppm | 354.0 | 354.0 [M + H] | D | |

TABLE 2-continued

| Cmpd No. | $^1$H NMR | Mass + (calc) | HMass found | hSTING IC$_{50}$ (uM) | mSTING IC$_{50}$ (uM) |
|---|---|---|---|---|---|
| 229 | $^1$H NMR (400 MHz, DMSO-d$_6$): δ 8.14 (d, J = 8.8 Hz, 1H), 7.87 (d, J = 8.8 Hz, 1H), 7.51 (d, J = 8.8 Hz, 1H), 6.79 (bs, 1H), 6.75 (d, J = 8.8 Hz, 1H), 6.54 (s, 1H), 4.96 (s, 2H), 2.96 (d, J = 5.6 Hz, 2H), 0.96 (s, 9H) ppm | 407.1 | 407.2 [M + H] | A | | mSTING IC$_{50}$: "A" < 10 μM; "B" = 10-50 μM; "C" = 50-100 μM; "D" > 100 μM.
hSTING IC$_{50}$: "A" < 100 μM; "B" = 100-500 μM; "C" = 500-1000 μM; "D" > 1000 μM.
NA: not active in the assay performed

Example 62: Radiometric Filtration Binding Competition Assay

A radiometric filtration binding competition assay was performed to quantify the binding affinity of compounds of the present application for the human or mouse STING protein, or associated HAQ human isoform. The competition format filtration binding assay detects the ability of small molecule compounds from binding to and inhibiting the subsequent binding of a tritiated [H3]2'3'cGAMP high affinity STING ligand. The resulting dose response was fit by non-linear regression to determine an IC$_{50}$ value, from which a K$_i$ value for each compound was extrapolated.

Briefly, the recombinant C-terminal ligand binding domain of the human STING protein (140-379) or mouse STING protein (139-328) [0.5 μM] was incubated in the presence of a compound of the present application (8 point, 2 fold dilution starting at 300 μM) for 30 min or under control conditions. H3 labeled 2'3'cGAMP [25 nM] was then added and allowed to reach binding equilibrium (1 hour). The resulting complexes were then filtered, dried, and scintillation fluid was added and the remaining radio signal was measured to determine the degree of compound ligand inhibition. This assay format was optimized for both the WT and HAQ isoforms of the human protein and the mouse orthologue protein.

Assay Development
Parameters Optimized:
 a. Form of protein: 6×HIS-SUMO tag or untagged
 b. Concentration of target protein: Minimum concentration that achieved >80 max signal
 c. Assay DMSO concentration: 10%-0.1%
 d. Assay Buffer: Base (Tris or phosphate), Salt concentration, +/−Tween (0.1-2%)
 e. Synthesis of Probe: (1) Enzymatic incorporation of a S$^{35}$-ATP and cold GTP into a 2'3'cGAMP product using a mouse cGAS enzyme with subsequent purification. (2) Tritium incorporation into 2'3'cGAMP
 f. Probe Concentration: Minimum concentration that achieved max assay window
 g. Assay Format: Scintillation Proximity Bead or Filtration Binding Plate
 h. Assay Plate: 384 vs 96 well format
 i. Assay incubation times for successive incubation steps

| | 2'3'cGAMP control | | | |
|---|---|---|---|---|
| Target Protein | K$_d$ [nM] | K$_i$ [nM] | Z-factor | Assay Window |
| hSTING-WT | 11 ± 4 | 61 ± 9 | 0.75 | 21.5 |
| hSTING-HAQ | 10 ± 4 | 50.5 ± 8 | 0.78 | 22.3 |
| mSTING | 16 ± 5 | 362.5 ± 21 | 0.65 | 27 |

| Assay Parameter | Assay Component | STX Assay |
|---|---|---|
| Principle | | [Filtration Based Direct Competition Assay |
| Recombinant Target Protein | Expression Vector | pET |
| | Expression Construct | 6XHIS-SUMO-hSTING (140-379) |
| | Protein coding gene | E. Coli Expression Codon Optimized hSTING (140-379) |
| | Expression Cell Line | BL-21(DE3) E. coli |
| | Purification Strategy | (1) Talon Metal Affinity Resin (2) Desalting (H).Trap) (3) Concentrate (6) Gel Filtration (Superdex 200) (7) Concentrate and Store (8) QC by Analytical SEC, SDS-PAGE |
| | Storage Buffer | 20 mM PBS, pH 8.0, 150 mM NaCl, 0.2% tween-20 and 10% glycerol (hSTING) |
| | Working Assay Concentration | 0.5 μM |
| Probe | Probe Radio Label | H$^3$ |
| | Probe concentration | 25 nM |
| Controls | ZPE | + Buffer |
| | HPE | + 10 μM 2'3'cGAMP |
| | Positive Control | 2'3'cGAMP (20 μM-310 nM) |
| | Negative Control | DMXAA (150 μM-150 nM) |

-continued

| Assay Parameter | Assay Component | STX Assay |
|---|---|---|
| Buffer | Assay Buffer | 1x PBS + 1% DMSO |
| | Plate | 96 Well GF/C unifilter Plate |
| Readout | Instrument | PE Microbeta |
| | Signal | Scintillation (CPM) |
| | Normalized Signal | % inhibition = (ϕ X − ϕ ZPE))/(ϕ HPE − ϕ ZPE) * 100 |

Biological activities of the compounds of the application are shown in Table 3.

WT-hSWAT: WT_FBA_HIS-SUMO-hSWAT IC50 (μM) ("WT"=Wild-type); HAQ-hSWAT: HAQ_FBA_HIS-SUMO-hSWAT IC50 (μM) ("HAQ"=human HAQ allele of STING protein); and WT-mSWAT: MOUSE_FBA_HIS-SUMO-mnSWAT IC50 (μM) which is the mouse isoform of STING protein.

TABLE 3

| Cmpd No. | NMR Peak listmgs | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| 13 | $^1$H NMR (400 MHz, DMSO-d$_6$): δ 13.26 (br, 1 H), 8.23 (d, J = 8.8 Hz, 1 H), 8.19 (dd, J = 8.0 Hz, 1 H), 7.82 (m, 1 H), 7.67 (d, J = 8.4 Hz, 1 H), 7.64 (d, J = 8.8 Hz, 1 H), 7.39 (m, 1 H), 5.18 (s, 2 H). | 322.1 [M + H] | D | | D |
| 100 | $^1$H NMR (400 MHz, DMSO-d$_6$): δ 8.18 (d, J = 7.2 Hz, 2 H), 7.78 (d, J = 3.2 Hz, 2 H), 7.66 (d, J = 8.0 Hz, 1 H), 7.40 (m, 1 H), 5.31 (q, J = 7.2 Hz, 1 H), 1.64 (d, J = 7.2 Hz, 3 H). | 336.2 [M + H] | D | | |
| 101 | $^1$H NMR (400 MHz, DMSO-d$_6$): δ 8.18 (d, J = 8.4 Hz, 2 H), 7.79 (d, J = 3.2 Hz, 2 H), 7.66 (d, J = 8.8 Hz, 1 H), 7.40 (m, 1 H), 5.31 (q, J = 7.2 Hz, 1 H), 1.64 (d, J = 7.2 Hz, 3 H). | 336.2 [M + H] | D | | |
| 108 | $^1$H NMR (400 MHz, DMSO-d$_6$): δ 12.97 (br, 1 H), 8.18-8.13 (m, 2 H), 7.80-7.78 (m, 3 H), 7.37 (t, J = 7.2 Hz, 1 H), 5.29 (s, 2 H), δ 12.97 (br, 1 H), 8.18-8.13 (m, 2 H), 7.80-7.78 (m, 3 H), 7.37 (t, J = 7.2 Hz, 1 H), 5.29 (s, 2 H) | 409.9 [M + H] | D | | C |
| 109 | $^1$H NMR (400 MHz, DMSO-d$_6$): δ 13.13 (br, 1 H), 8.37 (d, J = 2.4 Hz, 1 H), 8.26 (d, J = 8.4 Hz, 1 H), 8.13-8.10 (m, 1 H), 7.85 (d, J = 9.2 Hz, 1 H), 7.70-7.64 (m, 3 H), 7.37 (d, J = 8.0 Hz, 2 H), 5.32 (s, 2 H), 2.99-2.92 (m, 1 H), 1.28-1.24 (m, 6 H), | 484.1 [M + H] | B | | |
| 110 | $^1$H NMR (400 MHz, DMSO-d$_6$): δ 8.14 (d, J = 8.4 Hz, 1 H), 7.84 (d, J = 8.2 Hz, 1 H), 7.47 (d, J = 8.0 Hz, 1 H), 6.67 (s, 1 H), 6.59 (d, J = 8.2 Hz, 1 H), 6.52 (s, 1H), 4.85 (s, 2 H), 1.94-1.91 (m, 2H), 1.68-1.52 (m, 2 H), 1.51-1.36 (m, 1 H), 1.23-1.17 (m, 6H). | 465.1 [M + H] | A | B | A |
| 111 | $^1$H NMR (400 MHz, DMSO-d$_6$): δ 12.95 (s, 1 H), 8.22 (d, J = 8.4 Hz, 1 H), 8.09 (d, J = 8.0 Hz, 1 H), 7.63 (d, J = 8.4 Hz, 1 H), 7.60 (s, 1 H), 7.29 (d, J = 8.4 Hz, 1 H), 5.32 (s, 2H), 3.06-3.01 (m, 1 H), 1.27 (d, J = 6.8 Hz, 6H), δ 8.18 (d, J = 8.4 Hz, 1 H), 8.04 (d, J = 8.8 Hz, 1 H), 7.56 (s, 1 H), 7.50 (d, J = 8.8 Hz, 1 H), 7.19 (d, J = 8.4 Hz, 1 H), 4.83 (s, 2 H), 2.98-3.05 (m, 1 H), 1.26 (d, J = 7.2 Hz, 6H). | 408.0 [M + H], 408 [M + H], 408.1 [M + H] | B | C | B |
| 112 | $^1$H NMR (400 MHz, DMSO-d$_6$): δ 12.94 (br, 1 H), 8.23 (d, J = 8.4 Hz, 1 H), 8.07 (d, J = 8.0 Hz, 1 H), 7.63 (d, J = 8.4 Hz, 1 H), 7.59 (s, 1 H), 7.21 (d, J = 8.0 Hz, 1 H), 5.28 (s, 2 H), 2.46 (s, 3 H) | 382.1 [M + H] | B | | |
| 113 | $^1$H NMR (400 MHz, DMSO-d$_6$): δ 8.20-8.18 (m, 1 H), 8.10-8.17 (m, 1 H), 7.58-7.55 (m, 1 H), 7.24-7.23 (m, 1 H), 4.87 (s, 2 H), 3.12-3.09 (m, 1 H), 2.06-2.05 (m, 2 H), 1.81-1.80 (m, 2 H), 1.67-1.64 (m, 4 H), δ 8.20-8.18 (m, 1 H), 8.10-8.17 (m, 1 H), 7.58-7.55 (m, 1 H), 7.24-7.23 (m, 1 H), 4.87 (s, 2 H), 3.12-3.09 (m, 1 | 390.0 [M + H], 390.2 [M + H] | B | | A |

TABLE 3-continued

| Cmpd No. | NMR Peak listings | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| | H), 2 06-2.05 (m, 2 H), 1.81-1.80 (m, 2 H), 1.67-1.64 (m, 4 H), δ 13.21 (s, 1 H), 8.20 (d, J = 8.4 Hz, 1 H), 8.10 (d, J = 8.4 Hz, 1 H), 7.62 (d, J = 8.4 Hz, 1 H), 7.50 (s, 1 H), 7.29 (dd, 1 H), 5.16 (s, 2 H), 3.14 (m, 1 H), 2.06 (m, 2 H), 1.80 (m, 2 H), 1.68(m, 4 H). | | | | |
| 115 | $^1$H NMR (400 MHz, DMSO-d$_6$): δ 13.12 (br, 1 H), 8.21 (d, J = 8 Hz, 1 H), 8.11 (d, J = 8 Hz, 1 H), 7.64-7.57 (m, 1 H), 7.48 (s, 1 H), 7.29 (d, J = 8 Hz, 1 H), 5.21 (s, 2 H), 2.71-2.68 (m, 1H), 1.84-1.82 (m, 4 H), 1.75-1.72 (m, 1 H), 1.54-1.36 (m, 4 H), 1.31-1.23 (m, 1 H) | 404.1 [M + H] | B | C | A |
| 122 | $^1$H NMR (400 MHz, DMSO-d$_6$): δ 8.16 (d, J = 8.8 Hz, 1 H), 7.88 (d, J = 8.4 Hz, 1 H), 7.55 (d, J = 8.4 Hz, 1 H), 6.90 (s, 1 H), 6.64 (d, J = 8.0 Hz, 1 H), 6.31 (s, 1 H), 4.99 (s, 2 H), 1.95-1.91 (m, 2 H), 1.68-1.50(m, 11 H) | 433.1 [M + H] | B | | |
| 125 | $^1$H NMR (400 MHz, DMSO-d$_6$): δ 13.26 (br, 1 H), 8.43 (d, J = 2.0 Hz, 1 H), 8.27 (d, J = 8.4 Hz, 1 H), 8.20-8.15 (m, 1 H), 7.81-7.75 (m, 3 H), 7.66 (d, J = 8.4 Hz 1 H), 7.56-7.50 (m, 2 H), 7.41 (t, J = 7.2 Hz, 1 H), 5.23 (s, 2 H) | 398.1 [M + H] | B | | |
| 130 | $^1$H NMR (400 MHz, DMSO-d$_6$): δ 13.10 (brs, 1 H), 8.30 (dd, J = 1.6 Hz, 1 H), 8.20 (dd, J = 1.2 Hz, 1 H), 8.11 (dd, J = 1.6 Hz, 1 H), 7.82-7.79 (m, 1 H), 7.69-7.67 (m, 1 H), 7.37-7.29 (m, 2 H), 5.30 (s, 2 H). | 332.1 [M + H] | D | | |
| 131 | $^1$H NMR (400 MHz, DMSO-d$_6$): δ 12.94 (brs, 1 H), 8.24 (d, J =7.2 Hz, 1H), 7.91 (d, J = 7.6 Hz, 1 H), 7.80-7.76 (m, 1 H), 7.59 (d, J = 6.6 Hz, 1 H), 7.43 (d, J = 8.0 Hz, 1 H), 7.35-7.28 (m, 2 H), 5.06 (s, 2 H), 3.88 (s, 3 H), | 284.2 [M + H] | D | | |
| 132 | $^1$H NMR (400 MHz, DMSO-d$_6$): δ 12.47 (s, 1 H), 7.93 (d, J = 7.6 Hz, 2 H), 7.57 (d, J = 6.4 Hz, 2 H), 7.28 (m, 2 H), 4.64 (s, 2 H), 2.57 (s, 6 H). | 282.3 [M + H] | C | | |
| 133 | $^1$H NMR (400 MHz, DMSO-d$_6$): δ 13.02 (br, 1 H), 8.07 (d, J = 8.8 Hz, 1 H), 7.59-7.55 (m, 2 H), 7.51-7.48 (m, 1 H), 5.12 (s, 2 H), 3.85 (s, 3 H), 2.63 (s, 3 H). | 366.1 [M + H] | C | | |
| 134 | $^1$H NMR (400 MHz, DMSO-d$_6$): δ 12.81 (s, 1 H), 8.02 (d, J = 8.4 Hz, 1 H), 7.83 (d, J = 8.4 Hz, 1 H), 7.63 (d, J = 8.4 Hz, 1 H), 7.27 (d, J = 8.0 Hz, 1 H), 5.07 (d, J = 18.0 Hz, 1 H), 5.48 (d, J = 18.0 Hz, 1 H), 2.42 (s, 3 H), 2.38 (s, 3 H). | 350.1 [M + H] | B | | |
| 135 | $^1$H NMR (400 MHz, DMSO-d$_6$): δ 13.09 (brs, 1 H), 8.09 (d, J = 8.4 Hz, 1 H), 7.64-7.60 (m, 3 H), 5.16 (s, 2 H), 2.66 (d, J = 2.4 Hz, 3 H). | 354.1 [M + H] | C | | |
| 136 | $^1$H NMR (400 MHz, DMSO-d$_6$): δ 12.86 (s, 1 H), 8.20 (t, J = 6.8 Hz, 1 H), 8.16 (d, J = 8.8 Hz, 1 H), 7.81 (t, J = 8.4 Hz, 1 H), 7.63 (d, J = 8.4 Hz, 1 H), 7.38 (d, J = 8.8 Hz, 1 H), 7.36 (t, J = 7.2 Hz, 1 H), 4.89 (s, 2 H), 2.73 (s, 6 H). | 331.3 [M + 1] | B | | |
| 137 | $^1$H NMR (400 MHz, DMSO-d$_6$): δ 13.16 (br, 1 H), 8.19 (d, J = 8.8 Hz, 1 H), 8.07 (d, J = 8.4 Hz, 1 H), 7.64 (d, J = 8.8 Hz, 1 H), 7.39 (s, 1 H), 7.28-7.24 (m, 1 H), 5.23 (s, 2H), 2.60 (s, 3 H) | 368.0 [M + H] | C | | |
| 138 | $^1$H NMR (400 MHz, DMSO-d$_6$): δ 8.14 (d, J = 8.8 Hz, 1 H), 7.87 (d, J = 8.8 Hz, 1 H), 7.51 (d, J = 8.8 Hz, 1 H), 6.79 (s, 1 H), 6.75 (d, J = 8.8 Hz, 1 H), 6.54 (s, 1 H), 4.90 (s, 2 H), 2.96 (d, J = 5.6 Hz, 2 H), 0.96 (s, 9H) | 407.2 [M + H] | B | | |
| 139 | $^1$H NMR (400 MHz, DMSO-d$_6$): δ 13.10 (br, 1 H), 8.15 (d, J = 8.4 Hz, 1 H), 7.87 (d, J = 8.8 Hz, 1 H), 7.54 (d, J = 8.4 Hz, 1 H), 6.81 (br, 1 H), 6.64 (dd, J = 9.0 Hz, 1 | 447.2 [M + H] | B | | |

TABLE 3-continued

| Cmpd No. | NMR Peak listings | Mass found | WT-hSWAT IC$_{50}$ (µM) | HAQ-hSWAT IC$_{50}$ (µM) | WT-mSWAT IC$_{50}$ (µM) |
|---|---|---|---|---|---|
| | H), 6.36 (s, 1 H), 5.00 (s, 2 H), 3.49 (m, 1 H), 1.99 (d, J = 13.2 Hz, 1 H), 1.72 (d, J = 11.6 Hz, 1 H), 1.52-1.63 (m, 2H), 1.36 (d, J = 13.6 Hz, 1 H), 0.99-1.16 (m, 3 H), 1.02 (s, 3H), 0.94 (s, 3H). | | | | |
| 140 | $^1$H NMR (400 MHz, DMSO-d$_6$): δ 13.09 (br, 1 H), 8.15 (d, J = 8.4 Hz, 1 H), 7.90-7.86 (m, 1 H), 7.54 (d, J = 8.4 Hz, 1 H), 6.88-6.81 (m, 1 H), 6.74 (d, J = 8.0 Hz, 0.5 H), 6.64 (d, J = 9.2 Hz, 0.5 H), 6.44 (s, 0.5 H), 6.40 (s, 0.5 H), 5.01 (s, 2 H), 2.07-1.98 (m, 1 H), 1.74-1.58 (m, 6H), 1.49-1.43 (m, 2 H), 1.23-1.20 (m, 1 H), 0.94-0.90 (m, 3 H) | 433.1 [M + H] | B | | |
| 141 | $^1$H NMR (400 MHz, DMSO-d$_6$): δ 13.08 (br, 1 H), 8.17 (d, J = 8.0 Hz, 2 H), 7.78 (s, 2 H), 7.66 (d, J = 8.4 Hz, 1 H), 7.40 (m, 1 H), 5.31 (q, J = 6.8 Hz, 1 H), 1.64 (d, J = 6.8 Hz, 3 H). | 336.0 [M + H] | D | | |
| 142 | $^1$H NMR (400 MHz, DMSO-d$_6$): δ 13.09 (s, 1 H), 8.16 (d, J = 10.0 Hz, 1H), 7.90 (d, J = 8.4 Hz, 1 H), 7.56 (d, J = 10.0 Hz, 1 H), 6.94 (d, J = 7.6 Hz, 1 H), 6.70 (d, J = 8.8 Hz, 1 H), 6.47 (s, 1 H), 5.04 (s, 2 H), 3.92 (d, J = 12 Hz, 2 H), 3.64-3.58 (m, 1 H), 3.44(t, J = 11.6 Hz, 2 H), 1.93 (d, J = 12.4 Hz, 2 H), 1.48-1.40 (m, 2 H). | 421.1 [M + H] | C | | |
| 143 | $^1$H NMR (400 MHz, DMSO-d$_6$): δ 8.62 (s, 1 H), 8.15 (d, J = 8.8 Hz, 1 H), 7.92 (d, J = 8.8 Hz, 1 H), 7.56 (d, J = 8.8 Hz, 1 H), 7.05 (d, J = 7.2 Hz, 1 H), 6.70 (d J = 7.6 Hz, 1 H), 6.52 (s, 1 H), 5.04 (s, 2 H), 3.73-3.71(m, 1 H), 3.02 (t, J = 11.6 Hz, 2 H), 2.09 (d, J = 10.8 Hz, 2 H), 1.65-1.57 (m, 2 H) (2H are estimated to be in the water peak), $^1$H NMR (400 MHz, CD$_3$OD): δ 8.26 (d, J = 8.4 Hz, 1 H), 8.05 (d, J = 8.8 Hz, 1 H), 7.50 (d, J = 8.4 Hz, 1 H), 6.74 (d, J = 8.8 Hz, 1 H), 6.57 (s, 1 H), 5.06 (s, 2 H), 3.77-3.83 (m, 1 H), 3.46-3.49 (m, 2 H), 3.17-3.23 (m, 2 H), 2 28-2.32 (m, 2 H), 1 70-1.79 (m, 2 H). | 420.1 [M + H] | D | | |
| 144 | $^1$H NMR (400 MHz, DMSO-d$_6$): δ 8.20 (d, J = 8.8 Hz, 1 H), 8.14 (d, J = 8.8 Hz, 1H), 7.57 (d, J = 8.8 Hz, 1 H), 7.46 (d, J = 7.6 Hz, 1 H), 7.31-7.25 (m, 3H), 7.17 (t, J = 7.6 Hz, 1 H), 6.89 (t, J = 7.2 Hz, 1 H), 4.90 (s, 2 H), 4.11-4.06 (m, 2 H), 3.18-3.14 (m, 2 H), | 439.3 [M + H] | C | | |
| 145 | $^1$H NMR (400 MHz, DMSO-d$_6$): δ 13.24 (s, 1 H), 8.33 (d, J = 8.0 Hz, 1 H), 8.13 (d, J = 8.4 Hz, 1 H), 7.86 (d, J = 8.0 Hz, 1 H), 7.51 (s, 1 H), 7.34 (d, J = 8.4 Hz, 1 H), 5.26 (s, 2 H), 3.08-2.99 (m, 1 H), 1.27 (d, J = 7.2 Hz, 6 H). | 355.1 [M + H] | C | | |
| 146 | $^1$H NMR (400 MHz, DMSO-d$_6$): δ 8.18-8.25 (m, 2 H), 7.82 (m, 2 H), 7.62 (m, 2 H), 7.32-7.38 (m, 2 H), 5.03 (s, 2 H) | 321.2 [M + H] | | | |
| 147 | $^1$H NMR (400 MHz, DMSO-d$_6$): δ 12.98 (br, 1 H), 8.21 (d, J = 8.4 Hz, 1 H), 8.07 (d, J = 8.4 Hz, 1 H), 7.63-7.58 (m, 2 H), 7.25 (d, J = 8.4 Hz, 1 H), 5.29 (s, 2 H), 2.67 (t, J = 11.2 Hz, 1 H), 1.83-1.81 (m, 4 H), 1.75-1.71 (m, 1 H), 1.51-1.25 (m, 5 H). | 448.0 [M + H] | A | B | A |
| 148 | $^1$H NMR (400 MHz, CD$_3$OD): δ 8.28 (d, J = 8.4 Hz, 1 H), 7.99 (d, J = 8.8 Hz, 1 H), 7.51 (d, J = 8.4 Hz, 1 H), 6.75 (d, J = 8.8 Hz, 1 H), 6.56 (s, 1 H), 5.13 (s, 2 H), 3.06 (s, 2 H), 1.02 (s, 9 H), $^1$H NMR (400 MHz, DMSO-d$_6$): δ 12.90 (s, 1 H), 8.15 (d, J = 8.4 Hz, 1 H), 7.84 (d, J = 8.8 Hz, 1 H), 7.54 (d, J = 8.4 Hz, 1 H), 6.82-6.74 (m, 2 H), 6.57 (s, 1 H), 5.12 (s, 2 H), 2.99 (d, J = 6.0 Hz, 2 H), 0.97 (s, 9 H). | 453.2 [M + H], 451.1 [M + H] | B | | |

TABLE 3-continued

| Cmpd No. | NMR Peak listmgs | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| 149 | $^1$H NMR (400 MHz, DMSO-d$_6$): δ 13.19 (br, 1 H), 8.20 (d, J = 8.4 Hz, 1 H), 8.08 (d, J = 8.4 Hz, 1 H), 7.64 (d, J = 8.8 Hz, 1 H), 7.48 (s, 1 H), 7.29-7.26 (m, 1 H), 5.20 (s, 2 H), 3.86-3.78 (m, 1H), 1.34 (d, J = 6.8 Hz, 6 H) | 396.0 [M + H] | C | | |
| 150 | $^1$H NMR (400 MHz, DMSO-d$_6$): δ 13.14 (br, 1 H), 8.16 (d, J = 8.4 Hz, 1 H), 7.91 (d, J = 8.8 Hz, 1 H), 7.56 (d, J = 8.4 Hz, 1 H), 7.01 (m, 3 H), 6.71 (dd, J = 9.0 Hz, 1 H), 6.55 (m, 3 H), 5.06 (s, 2 H), 3.41 (m, 4 H), 3.28 (t, J = 6.8 Hz, 2 H), 3.28 (t, J = 8 0 Hz, 2 H). | 482.2 [M + H] | C | | |
| 151 | $^1$H NMR (400 MHz, DMSO-d$_6$): δ 13.16 (s, 1 H), 8.23-8.27 (m, 2 H), 7.89 (s, 1 H), 7.71-7.58(m, 4 H), 7.44 (t, J = 7.6 Hz, 1 H), 7.29 (d, J = 7.2 Hz, 1 H), 5.35 (s, 2 H), 2.43 (s, 3 H)., δ 13.15 (s, 1 H), 8.27-8.23 (m, 2 H), 7.89(s, 1 H), 7.71-7.64 (m, 3 H), 7.62 (d, J = 8.0 Hz, 1 H), 7.44 (t, J = 7.6 Hz, 1 H), 7.29 (d, J = 7.2 Hz, 1 H), 5.35 (s, 2 H), 2.42 (s, 3 H). | 412.1 [M + H] | B | B | A |
| 152 | $^1$H NMR (400 MHz, DMSO-d$_6$): δ 13.37 (s, 1 H), 8.26-8.22 (m, 2 H), 7.95 (s, 1 H), 7.72-7.64 (m, 4 H), 7.61-7.55 (m, 1 H), 7.33-7.29 (m, 1 H), 5.26 (s, 2 H). | 416.1 [M + H] | B | | B |
| 153 | $^1$H NMR (400 MHz, DMSO-d$_6$): δ 8.21 (d, J = 8.0 Hz, 2 H), 7.96 (s, 1 H), 7.82 (m, 2 H), 7.57 (m, 2 H), 7.34 (m, 2 H), 4.88 (s, 2 H), | 416.2 [M + H] | B | | |
| 154 | $^1$H NMR (400 MHz, DMSO-d$_6$): δ 8.21 (d, J = 8.0 Hz, 2 H), 7.97 (s, 1 H), 7.69 (d, J = 8.0 Hz, 2 H), 7.55-7.60 (m, 2 H), 7.34 (d, J = 8.0 Hz, 2 H), 4.84 (s, 2 H), 2.38 (s, 3 H). | 412.2 [M + H] | C | | |
| 155 | $^1$H NMR (400 MHz, DMSO-d$_6$): δ 8.22-8.26 (m, 2 H), 7.96 (s, 1 H), 7.92 (s, 1 H), 7.77 (d, J = 7.2 Hz, 1 H), 7.62-7.70 (m, 2 H), 7.52-7.58 (m, 2 H), 5.22 (s, 2 H). | 430.0 [M − 1] | C | | |
| 156 | $^1$H NMR (400 MHz, DMSO-d$_6$): δ 8.22 (dd, J = 8.0 Hz, J = 5.1 Hz, 2 H), 8.00 (s, 1 H), 7.82 (d, J = 8.0 Hz, 2 H), 7.55-7.61 (m, 4 H), 4.83 (s, 2 H), | 432.0 [M + H] | C | | A |
| 157 | $^1$H NMR (400 MHz, DMSO-d$_6$): δ 13.21 (s, 1 H), 8.21 (d, J = 8.4 Hz, 1 H), 8.11 (d, J = 8.4 Hz, 1 H), 7.63 (d, J = 8.4 Hz, 1 H), 7.57 (s, 1 H), 7.45-7.49 (m, 1 H), 6.41 (s, 1 H), 5.22 (s, 2 H), 2.23-2.28 (m, 4 H), 1.40 (t, 2H), 0.99 (s, 6 H). | 430.1 [M + H] | B | | |
| 158 | $^1$H NMR (400 MHz, DMSO-d$_6$): δ 13.12 (s, 1 H), 8.21 (d, J = 8.8 Hz, 1 H), 8.10 (d, J = 8.0 Hz, 1 H), 7.63 (d, J = 8.4 Hz, 1 H), 7.49 (s, 1 H), 7.28 (d, J = 8.4 Hz, 1 H), 5.22 (s, 2 H), 2.88 (t, 1 H), 1.80-1.83 (m, 1H), 1.57-1.64 (m, 2 H), 1.33-1.52 (m, 4 H), 1.17-1.24 (m, 1 H), 1.02 (s, 3 H), 0.96 (s, 3 H). | 432.1 [M + H] | A | | |
| 159 | $^1$H NMR (400 MHz, DMSO-d$_6$): δ 13.15 (s, 1 H), 8.21 (d, J = 8.8 Hz, 1 H), 8.11 (d, J = 8.4 Hz, 1 H), 7.65-7.59 (m, 2 H), 7.51 (d, J = 8.4 Hz, 1 H), 6.45-6.40 (m, 1 h), 5.24 (s, 2 H), 2.48-2.43 (m, 2 H), 2.08-2.02 (m, 2 H), 1.52 (t, J = 6.0 Hz, 2 H), 0.97 (s, 6 H). | 430.2 [M + H] | B | B | A |
| 160 | $^1$H NMR (400 MHz, DMSO-d$_6$): δ 13.13 (s, 1 H), 8.21 (d, J = 8.4 Hz, 1 H), 8.11 (d, J = 8.0 Hz, 1 H), 7.63 (d, J = 8.4 Hz, 1 H), 7.51 (s, 1 H), 7.32 (d, J = 8.0 Hz, 1 H), 5.22 (s, 2 H), 2.63-2.54 (m, 1 H), 1.72-1.62 (m, 4 H), 1.52-1.44 (m, 2 H), 1.41-1.30 (m, 2 H)), 1.00 (s, 3 H), 0.96 (s, 3 H). | 432.2 [M + H] | B | | |
| 161 | $^1$H NMR (400 MHz, DMSO-d$_6$): δ 8.27-8.22(m, 2 H), 8.13 (s, 1 H), 8.10 (d, J = 8.0 Hz, 1 H), 8.04 (s, 1 H), 7.83(d, J = 7.6 Hz, 1 H), 7.77 (t, J = 8.0 Hz, 1 H), 7.69 | 466.1 [M + H] | B | | |

TABLE 3-continued

| Cmpd No. | NMR Peak listmgs | Mass found | WT-hSWAT IC$_{50}$ (µM) | HAQ-hSWAT IC$_{50}$ (µM) | WT-mSWAT IC$_{50}$ (µM) |
|---|---|---|---|---|---|
| | (d, J = 8.4 Hz, 1 H), 7.61 (d, J = 8.8 Hz, 1 H), 5.06 (s, 2 H). | | | | |
| 162 | $^1$H NMR (400 MHz, DMSO-d$_6$): δ 8.32 (s, 1 H), 8.28 (d, J = 8.8 Hz, 1 H), 8.23 (d, J = 8.8 Hz, 1 H), 8.16 (d, J = 8.0 Hz, 1 H), 8.08-7.99 (m, 2 H), 7.63 (d, J = 8.4 Hz, 1 H), 7.59 (d, J = 7.6 Hz, 1 H), 5.12 (s, 2 H). | 433.0 [M + H] | C | | |
| 163 | $^1$H NMR (400 MHz, DMSO-d$_6$): δ 13.14 (s, 1 H), 8.26-8.22 (m, 2 H), 7.92 (s, 1 H), 7.73-7.65 (m, 3 H), 7.61-7.57 (m, 1 H), 7.46 (t, J = 8.0 Hz, 1 H), 5.37 (s, 2 H), 2.31 (s, 3H). | 430.1 [M + H] | B | | |
| 164 | $^1$H NMR (400 MHz, DMSO-d$_6$): δ 13.15 (s, 1 H), 8.26-8.23 (m, 2 H), 7.95-7.91 (m, 2 H), 7.73-7.70 (m, 2 H), 7.67 (d, J = 8.4 Hz, 1 H), 7.53 (d, J = 8.0 Hz, 1 H), 5.38 (s, 2 H), 2.41 (s, 3 H). | 446.0 [M + H] | B | | |
| 165 | $^1$H NMR (400 MHz, DMSO-d$_6$): δ 8.37 (d, J = 8.0 Hz, 1 H), 8.23 (d, J = 8.0 Hz, 1 H), 8.09 (s, 1H), 7.69-7.72 (m, 2 H), 5.31 (s, 2H) | 390.1 [M + H] | D | | |
| 166 | $^1$H NMR (400 MHz, DMSO-d$_6$): δ 8.26 (d, J = 8.4 Hz, 1 H), 8.19 (d, J = 8.8 Hz, 1 H), 7.97 (s, 1 H), 7.59 (d, J = 8.8 Hz, 1 H), 7.45 (d, J = 8.4 Hz, 1 H), 7.14 (t, J = 15.2 Hz, 1 H), 4.90 (s, 1 H). | 372.3 [M + H] | D | | |
| 167 | $^1$H NMR (400 MHz, DMSO-d$_6$): δ 8.37 (d, J = 8.8 Hz, 1 H), 8.32 (d, J = 8.8 Hz, 1 H), 7.57-7.74 (m, 3 H), 5.11-5.35 (m, 2 H). | 488.0 [M + H] | D | | |
| 168 | $^1$H NMR (400 MHz, DMSO-d$_6$): δ 8.28 (d, J = 8.8 Hz, 1 H), 8.17 (d, J = 8.4 Hz, 1 H), 7.86 (s, 1 H), 7.58 (d, J = 8.4 Hz, 1 H), 7.52 (dd, J = 8.8. 1.6 Hz, 1 H), 5.15 (s, 2H), 1.25 (s, 6 H). | 402.0 [M + Na] | C | | |
| 169 | $^1$H NMR (400 MHz, DMSO-d$_6$): δ 12.84 (brs, 1 H), 8.13-8.08 (m, 2 H), 7.76 (d, J = 8.4 Hz, 1 H), 7.60 (s, 1 H), 7.29-7.27 (m, 1 H), 5.29 (s, 2 H), 3.06-3.03 (m, 1 H), 1.28-1.17 (m, 6 H). | 354.0 [M + H] | B | | |
| 170 | $^1$H NMR (400 MHz, DMSO-d$_6$): δ 13.23 (s, 1 H), 8.14-8.08 (m, 2 H), 7.76 (d, J = 8.4 Hz, 1 H), 7.51 (s, 1 H), 7.29 (d, J = 8.4 Hz, 1 H), 5.17 (s, 2 H), 3.10-3.01 (m, 1 H), 1.27 (d, J = 6.8 Hz, 6 H). | 408.1 [M + H] | B | | |
| 171 | $^1$H NMR (400 MHz, CD$_3$OD): δ 8.42 (d, J = 8.4 Hz, 1 H), 8.33 (d, J = 8.0 Hz, 1 H), 7.70 (s, 1 H), 7.49 (s, 1 H), 7.33 (dd, J = 8.4 Hz, 1 H), 7.23 (d, J = 8.0 Hz, 1 H), 5.97 (q, J = 7.2 Hz, 1 H), 2.54 (s, 3 H), 1.86 (d, J = 7.2 Hz, 3 H). | 316.2 [M + H] | D | | |
| 172 | $^1$H NMR (400 MHz, DMSO-d$_6$): δ 12.86 (br, 1 H), 8.10 (d, J = 8.4 Hz, 1 H), 7.67-7.58 (m, 3 H), 7.28 (d, J = 7.2 Hz, 1 H), 5.23 (s, 2 H), 4.01-3.98 (m, 1 H), 1.82-1.73 (m, 5 H), 1.42-1.40 (m, 4 H), 1.30-1.25 (m, 1 H). | 448.0 [M + H] | A | B | |
| 173 | $^1$H NMR (400 MHz, DMSO-d$_6$): δ 13.15 (s, 1 H), 8.35 (m, 1 H), 8.20 (dd, 1 H), 7.81 (m, 1 H), 7.67 (d, J = 8.4, 1 H), 7.39 (m, 2 H), 5.30 (s, 2 H) | 352.2 [M + H] | D | | |
| 174 | $^1$H NMR (400 MHz, DMSO-d$_6$): δ 8.17 (d, J = 8.4 Hz, 1 H), 8.10 (d, J = 8.0 Hz, 1 H), 7.56 (m, 2 H), 7.29 (d, J = 8.0 Hz, 1 H), 3.96 (s, 3 H), 3.10 (m, 1 H), 1.31 (d, J = 6.8 Hz, 6 H). | 320.2 [M + H] | D | | |
| 175 | $^1$H NMR (400 MHz, DMSO-d$_6$): δ 8.16 (d, J = 8.4 Hz, 1 H), 7.86 (d, J = 8.8 Hz, 1 H), 7.53 (d, J = 8.4 Hz, 1 H), 7.22 (d, J = 6.0 Hz, 1 H), 6.58 (dd, J = 8.8 Hz, 1 H), 6.38 (s, 1 H), 5.04 (s, 2 H), 4.02-3.94 (m, 1 H), 2.42-2.36 (m, 2 H), 1.92-1.85 (m, 2 H), 1.78-1.72 (m, 2 H). | 435.1 [M + H] | B | | |
| 176 | $^1$H NMR (400 MHz, DMSO-d$_6$): δ 12.98 (s, 1 H), 8.22 (d, J = 8.4 Hz, 1 H), 8.10 | 422.1 [M + H] | B | B | A |

TABLE 3-continued

| Cmpd No. | NMR Peak listmgs | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| | (d, J = 8.4 Hz, 1 H), 7.68-7.60 (m, 2 H), 7.47-7.31 (m, 1 H), 5.31 (s, 2 H), 1.35 (s, 9 H). | | | | |
| 177 | $^1$H NMR (400 MHz, DMSO-d$_6$): δ 8.23-8.26 (m, 2 H), 8.03 (s, 1 H), 7.83-7.83 (m, 2 H), 7.64-7.70 (m, 2 H), 7.53-7.57 (m, 2 H), 7.46-7.50 (m, 1 H), 5.42 (s, 2 1H). | 441.8 [M + H] | B | C | B |
| 178 | $^1$H NMR (400 MHz, DMSO-d$_6$): δ 13.30 (s, 1 H), 8.24 (dd, 1 H), 8.07 (d, J = 8.8, 1 H), 7.82 (m, 1 H), 7.61 (d, J = 8.8, 1 H), 7.45 (d, J = 8.8, 1 H), 7.31 (t, J = 7.2, 1 H), 5.30 (s, 2 H), 3.77 (s, 3H). | 318.3 [M + H] | D | | D |
| 179 | $^1$H NMR (400 MHz, DMSO-d$_6$): δ 13.41 (s, 1 H), 8.32 (d, J = 8.8 Hz, 1 H), 8.23 (d, J = 8 0 Hz, 1 H), 7.70 (m, 2 H), 7.37 (d, J = 8.4 Hz, 1 H), 7.21 (d, J = 8.0 Hz, 1 H), 6.06 (br, 1 H), 2.49 (s, 3 H), 1.73 (d, J = 6.8 Hz, 3 H). | 316.1 [M + H] | C | | |
| 180 | $^1$H NMR (400 MHz, DMSO-d$_6$): δ 13.41 (s, 1 H), 8.32 (d, J = 8.4 Hz, 1 H), 8.23 (d, J = 8.4 Hz, 1 H), 7.70 (m, 2 H), 7.37 (d, J = 8.4 Hz, 1 H), 7.21 (d, J = 8.0 Hz, 1 H), 6.05 (m, 1 H), 2.49 (s, 3 H), 1.73 (d, J = 7.2 Hz, 3 H). | 316.1 [M + H] | B | | |
| 181 | $^1$H NMR (400 MHz, DMSO-d$_6$): δ 13.21 (s, 1 H), 9.14 (s, 1 H), 8.19 (d, J = 8.8 Hz, 1 H), 8.04 (d, J = 8.4 Hz, 1 H), 7.59 (d, J = 8.4 Hz, 1 H), 7.36 (t, J = 8.0 Hz, 2 H), 7.27 (d, J = 8.0 Hz, 2 H), 7.07-6.99 (m, 3 H), 4.98 (s, 2H). | 413.2 [M + H] | A | B | A |
| 182 | $^1$H NMR (400 MHz, DMSO-d$_6$): δ 13.25 (br, 1 H), 8.21-8.24 (m, 2 H), 8.09 (s, 1 H), 7.84 (d, J = 7.2 Hz, 2 H), 7.64 (d, J = 8.4 Hz, 1 H), 6.95 (d, J = 2.4 Hz, 1 H), 5.27 (s, 2 H). | 388.3 [M + H] | C | | |
| 183 | $^1$H NMR (400 MHz, DMSO-d$_6$): δ 13.07 (s, 1 H), 8.45 (s, 1 H), 8.16-8.22 (m, 2 H), 7.90 (s, 1 H), 7.84 (s, 1 H), 7 64-7.67 (m, 2 H), 7.14 (s, 1 H), 5.36 (s, 2 H). | 388.2 [M + H] | B | | B |
| 184 | $^1$H NMR (400 MHz, DMSO-d$_6$): δ 13.20 (br, 1 H), 8.22 (t, J = 8.8 Hz, 2 H), 8.02 (s, 1 H), 7.81-7.84 (m, 2 H), 7.64 (d, J = 8.4 Hz, 1 H), 6.92 (d, J = 2.4 Hz, 1 H), 5.26 (s, 2 H), 3.94 (s, 3 H). | 402.3 [M + H] | D | | |
| 186 | $^1$H NMR (400 MHz, DMSO-d$_6$): δ 13.23 (br, 1 H), 8.21 (q, J = 4.4 Hz, 2 H), 7.92 (m, 2 H), 7.73 (d, J = 8.4 Hz, 1 H), 7.65 (d, J = 8.4 Hz, 1 H), 7.29 (d, J = 3.2 Hz, 1 H), 6.71 (q, J = 1.6 Hz, 1 H), 5.25 (s, 2 H) | 388.1 [M + H] | B | | |
| 187 | $^1$H NMR (400 MHz, DMSO-d$_6$): δ 13.31 (s, 1 H), 8.30 (d, J = 8.4 Hz, 1 H), 8.27-8.21 (m, 2 H), 8.09-8.05 (m, 1 H), 8.00-7.95 (m, 1 H), 7.94 (d, J = 8.8 Hz, 1 H), 7.68 (d, J = 8.4 Hz, 1 H), 5.26 (s, 2 H). | 405.2 [M + H] | C | | |
| 188 | $^1$H NMR (400 MHz, DMSO-d$_6$): δ 13.27 (br, 1 H), 8.36 (d, J = 8.4 Hz, 1 H), 8.25 (d, J = 8.4 Hz, 1 H), 8.16 (s, 1 H), 7.70-7.83 (m, 4 H), 5.29 (s, 2 H), 3.94 (s, 3 H). | 402.3 [M + H] | D | | |
| 189 | $^1$H NMR (400 MHz, DMSO-d$_6$): δ 13.17 (s, 1 H), 8.88 (m, 2 H), 8.33 (d, J = 8.4 Hz, 1 H), 8.24 (d, J = 8.4 Hz, 1 H), 8.13 (s, 1 H), 8.10 (m, 2 H), 7.85 (d, J = 8.4 Hz, 1 H), 7.69 (d, J = 8.4 Hz, 2 H), 5.40 (s, 1 H) | 399.1 [M + H] | C | | |
| 190 | $^1$H NMR (400 MHz, DMSO-d$_6$): δ 9.01 (s, 1 H), 8.66 (d, J = 4.8 Hz, 1 H), 8.26-8.20 (m, 3 H), 8.07 (s, 1 H), 7.66 (d, J = 8.4 Hz, 1 H), 7.59-7.54 (m, 2 H), 4.90 (s, 2 H). | 399.1 [M + H] | D | | |
| 191 | $^1$H NMR (400 MHz, DMSO-d$_6$): δ 8.19 (d, J = 8.4 Hz, 1 H), 8.10 (d, J = 8 Hz, 1 H), 7.71 (s, 1 H), 7.54 (d, J1 = 8.8 Hz, 1 H), 7.30 (d, J = 8.4 Hz, 1 H), 5.43 (d, J = | 366.3 [M + H] | D | | |

TABLE 3-continued

| Cmpd No. | NMR Peak listmgs | Mass found | WT-hSWAT IC$_{50}$ (µM) | HAQ-hSWAT IC$_{50}$ (µM) | WT-mSWAT IC$_{50}$ (µM) |
|---|---|---|---|---|---|
| | 4.4 Hz, 1 H), 4.89 (s, 2 H), 4.82-4.85 (m, 1 H), 1.36 (d, J = 6.4 Hz, 3 H), | | | | |
| 192 | $^1$H NMR (400 MHz, DMSO-d$_6$): δ 13.02 (brs, 1 H), 8.41 (d, J = 8.4 Hz, 1 H), 8.11 (d, J = 8.0 Hz, 1 H), 7.65-7.62 (m, 2 H), 7.30 (d, J = 7.6 Hz, 1 H), 5.05 (brs, 2 H), 3.07-3.03 (m, 1 H), 1.26 (d, J = 6.8 Hz, 6 H). | 398.2 [M + H] | B | B | C |
| 193 | $^1$H NMR (400 MHz, CDCl$_3$): δ 8.03-7.94 (m, 2 H), 7.37 (d, J = 8.4 Hz, 1 H), 7.28 (d, J = 8.4 Hz, 1 H), 5.18 (d, J = 18.0 Hz, 1 H), 4.46 (d, J = 18.0 Hz, 1 H), 3.30-3.21 (m, 1 H), 2.53 (s, 3 H), 1.30 (d, J = 6.8 Hz, 3 H), 1.22 (d, J = 6.8 Hz, 3 H). | 378.1 [M + H] | B | | D |
| 194 | $^1$H NMR (400 MHz, CD$_3$OD): δ 8.28 (d, J = 8.4 Hz, 1 H), 8.17 (d, J = 8.4 Hz, 1 H), 7.74-7.72 (m, 1 H), 7.63-7.76 (m, 1 H), 7.54-7.52 (m, 1 H), 5.35 (s, 2 H), 3.08-3.06 (m, 1 H), 1.34 (d, J = 7.2 Hz, 6 H), | 456.0 [M + H] | C | | |
| 195 | $^1$H NMR (400 MHz, CD$_3$OD): δ 8.26 (d, J = 8.4 Hz, 1 H), 8.07-7.93 (m, 2 H), 7.49 (s, 1 H), 7.30 (d, J = 8.0 Hz, 1 H), 5.10 (s, 2 H), 3.13-3.04 (m, 1 H), 1.34 (d, J = 6.4 Hz, 6 H) | 456.2 [M + H] | D | | |
| 196 | $^1$H NMR (400 MHz, DMSO-d$_6$): δ 13.00 (br, 1 H), 8.20 (d, J = 8.4 Hz, 1 H), 8.04 (d, J = 8.4 Hz, 1 H), 7.63 (d, J = 8.4 Hz, 1 H), 7.50 (s, 1 H), 7.23 (d, J = 8.4 Hz, 1 H), 5.32 (s, 2 H), 2.60 (s, 3 H) | 412.0 [M + H] | B | | |
| 197 | $^1$H NMR (400 MHz, DMSO-d$_6$): δ 8.33 (d, J = 8.8 Hz, 1 H), 8.29-8.24 (m, 1 H), 7.87-7.81 (m, 1 H), 7.59-7.52 (m, 2 H), 7.41 (t, J = 7.6 Hz, 1 H), 5.53 (s, 2 H), 5.18 (s, 1 H). | 312.1 [M + H] | D | D | |
| 198 | $^1$H NMR (400 MHz, DMSO-d$_6$): δ 8.16 (d, J = 8.4 Hz, 1 H), 7.94 (d, J = 8.8 Hz, 1 H), 7.56 (d, J = 8.4 Hz, 1 H), 6.94 (dd, J = 9.2 Hz, J2 = 1.2 Hz, 1 H), 6.87 (s, 1 H), 5.23 (s, 2 H), 3.46 (s, 4 H), 1.61 (s, 6 H) | 448.8 [M + H] | C | | C |
| 201 | $^1$H NMR (400 MHz, DMSO-d$_6$): δ 12.88 (s, 1 H), 8.16 (d, J = 7.6 Hz, 1 H), 7.95 (d, J = 8.8 Hz, 1 H), 7.55 (d, J = 8.0 Hz, 1 H), 6.64 (d, J = 8.4 Hz, 1 H), 6.46 (s, 1 H), 5.20 (s, 2 H), 3.38 (s, 4 H), 2.00 (s, 4 H) | 435.0 [M + H] | C | | |
| 202 | $^1$H NMR (400 MHz, DMSO-d$_6$): δ 8.16 (d, J = 8.0 Hz, 1 H), 7.94 (d, J = 8.8 Hz, 1 H), 7.53 (d, J = 8.0 Hz, 1 H), 6.65 (d, J = 7.6 Hz, 1 H), 6.46 (s, 1 H), 5.10 (s, 2 H), 4.07 (d, J = 4.8 Hz, 1 H), 3 48-3.46 (m, 2 H), 2.07-2.01 (m, 3 H), 1.73 (s, 1H), 1.15 (d, J = 4.8 Hz, 3H) | 451.0 [M + H] | B | | |
| 203 | $^1$H NMR (400 MHz, DMSO-d$_6$): δ 8.16-8.14 (m, 1 H), 7.94-7.92 (m, 1 H), 7.55-7.52 (m, 1 H), 6.64 (s, 1 H), 6.46 (s, 1 H), 5.12 (s, 2 H), 4.07 (d, J = 3.6 Hz, 1 H), 3.49-3.44 (m, 2 H), 2.11-1.97 (m, 3 H), 1.71 (s, 1H), 1.15 (s, 3H) | 451.0 [M + H] | B | | |
| 204 | $^1$H NMR (400 MHz, DMSO-d$_6$): δ 13.19 (s, 1 H), 8.17 (d, J = 8.8 Hz, 1 H), 8.05 (d, J = 8.4 Hz, 1 H), 7.49-7.41 (m, 3 H), 5.16 (s, 2 H), 3.77 (s, 3 H), 1.36 (s, 9 H), δ 13.41 (s, 1 H), 8.17 (d, J = 8.8 Hz, 1 H), 8.05 (d, J = 8.8 Hz, 1 H), 7.49-7.42 (m, 3 H), 5.16 (s, 2 H), 3.76 (s, 3 H), 1.36 (s, 9 H). | 374.4 [M + H], 374.3 [M + H] | A | B | A |
| 205 | $^1$H NMR (400 MHz, DMSO-d$_6$): δ 12.07 (s, 1 H), 8.17-8.20 (m, 1 H), 7.93 (d, J = 8.4 Hz, 1 H), 7.84 (t, J = 7.2 Hz, 1 H), 7.65 (d, J = 8.8 Hz, 2 H), 7.39 (t, J = 7.6 Hz, 1 H), 4.66 (t, J = 7.2 Hz, 2 H), 1.89 (t, J = 7.0 Hz, 2 H), 1.55 (t, J = 7.2 Hz, 2 H) | 350.1 [M + H] | D | | |
| 206 | $^1$H NMR (400 MHz, DMSO-d$_6$): δ 13.08 (br, 1 H), 9.10 (s, 1 H), 8.20 (d, J = 8.4 Hz, 1 H), 8.02 (d, J = 8.8 Hz, 1 H), 7.58 | 457.1 [M + H] | B | | A |

TABLE 3-continued

| Cmpd No. | NMR Peak listings | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| | (d, J = 8.8 Hz, 1 H), 7.36 (t, J = 7.6 Hz, 2 H), 7.26 (d, J = 8.0 Hz, 2 H), 7.05 (d, J = 10.0 Hz, 2 H), 6.98 (d, J = 9.2 Hz, 1 H), 5.04 (s, 2 H). | | | | |
| 207 | $^1$H NMR (400 MHz, DMSO-d$_6$): δ 13.20 (brs, 1 H), 9.08 (s, 1 H), 8.08-8.01 (m, 2 H), 7.41-7.34 (m, 3 H), 7.28-7.27 (m, 2 H), 7.06-6.96 (m, 3 H), 4.93 (s, 2 H), 3.73 (s, 3 H), δ 9.09 (brs, 1 H), 8.07-8.01 (m, 2 H), 7.37-7.31 (m, 3 H), 7.26-7.24 (m, 2 H), 7.06 (s, 1 H), 7.02-6.98 (m, 2 H), 4.89 (brs, 2 H), 3.74 (s, 3 H). | 409.2 [M + H] | A | B | A |
| 209 | $^1$H NMR (400 MHz, DMSO-d$_6$): δ 13.16 (br, 1 H), 8.24-8.17 (m, 2 H), 7.72 (d, J = 8.4 Hz, 1 H), 7.52 (t, J = 7.6 Hz, 1 H), 7.72 (d, J = 8.4 Hz, 1 H), 7.30 (t, J = 7.6 Hz, 1 H), 5.52 (s, 2 H) | 292.1 [M − 1] | D | | |
| 210 | $^1$H NMR (400 MHz, DMSO-d$_6$): δ 13.11 (s, 1 H), 8.15-8.07 (m, 2 H), 7.59 (s, 1 H), 7.41 (d, J = 8.4 Hz, 1 H), 7.20 (d, J = 8.0 Hz, 1 H), 5.51 (s, 2 H), 3.12-3.02 (m, 1 H), 1.30 (d, J = 6.8 Hz, 6 H) | 334.2 [M − 1] | B | | |
| 212 | $^1$H NMR (400 MHz, DMSO-d$_6$): δ 12.96 (brs, 1 H), 8.25-8.19 (m, 2 H), 7.84-7.77 (m, 2 H), 7.57 (d, J = 8.4 Hz, 1 H), 7.37 (t, J = 8.0 Hz, 1 H), 5.41 (s, 2 H), 2.33 (s, 3 H) | 334.1 [M + H] | C | D | C |
| 213 | $^1$H NMR (400 MHz, DMSO-d$_6$): δ 13.21 (br, 1 H), 8.21 (d, J = 8.4 Hz, 1 H), 8.10 (d, J = 8.4 Hz, 1 H), 7.63 (d, J = 8.8 Hz, 1 H), 7.58 (s, 1 H), 7.47 (d, J = 8.4 Hz, 1 H), 6.34 (s, 1 H), 5.21 (s, 2 H), 4.75 (s, 1 H), 4.02 (s, 1 H), 2.10 (m, 2 H), 1.89 (m, 2 H), 1.65 (m, 2 H) | 418.2 [M + H] | C | | B |
| 214 | $^1$H NMR (400 MHz, DMSO-d$_6$): δ 13.20 (br, 1 H), 8.22 (d, J = 8.4 Hz, 1 H), 8.12 (d, J = 8.0 Hz, 1 H), 7.63 (d, J = 8.8 Hz, t H), 7.47 (s, 1 H), 7.29 (d, J = 8.0 Hz, 1 H), 5.18 (s, 2 H), 4.40 (s, 1 H), 3.92 (s, 1 H), 2.69 (m, 1 H), 1.90 (m, 2 H), 1.77 (m, 2 H), 1.57 (m, 4 H) | 420.1 [M + H] | B | | |
| 215 | $^1$H NMR (400 MHz, DMSO-d$_6$): δ 12.98 (s, 1 H), 8.22 (d, J = 7.6 Hz, 1 H), 8.12 (d, J = 7.6 Hz, 1 H), 7.67 (s, 1 H), 7.54 (d, J = 7.6 Hz, 1 H), 7.44 (d, J = 7.6 Hz, 1 H), 5.39 (s, 2 H), 2.34 (s, 3 H), 1.36 (s, 9 H) | 390.2 [M + H] | A | A | A |
| 216 | $^1$H NMR (400 MHz, DMSO-d$_6$): δ 13.24 (s, 1 H), 10.36 (s, 1 H), 8.60 (d, J = 4.8 Hz, 2 H), 8.42 (s, 1 H), 8.23 (d, J = 8.4 Hz, 1 H), 8.11 (d, J = 8.8 Hz, 1 H), 7.68 (d, J = 8.4 Hz, 1 H), 7.61 (d, J = 8.4 Hz, 1 H), 7.03 (t, J = 4.4 Hz, 1 H), 5.06 (s, 2 H). | 415.1 [M + H] | B | B | A |
| 217 | $^1$H NMR (400 MHz, DMSO-d$_6$): δ 13.27 (s, 1 H), 10.22 (s, 1 H), 8.37 (s, 1 H), 8.27 (d, J = 1.2 Hz, 1 H), 8.21-8.25 (m, 2 H), 8.14 (d, J = 8.8 Hz, 1 H), 8.11 (d, J = 2.4 Hz, 1 H), 7.62 (d, J = 8.8 Hz, 1 H), 7.57-7.59 (dd, J = 8.8 Hz, 1.6 Hz, 1H), 5.06 (s, 2 H). | 415.1 [M + H] | B | C | A |
| 218 | $^1$H NMR (400 MHz, DMSO-d$_6$): δ 9.09 (s, 1 H), 8.21-8.19 (m, 1 H), 8.05-8.03 (m, 1 H), 7.60-7.58 (m, 1 H), 7.29 (d, J = 3.2 Hz, 2 H), 7.20 (s, 2 H), 6.94 (s, 2 H), 4.96 (s, 2 H). | 431.1 [M + H] | A | B | A |
| 219 | $^1$H NMR (400 MHz, DMSO-d$_6$): δ 13.19 (brs, 1 H), 8.15 (d, J = 8.8 Hz, 1 H), 8.05 (d, J = 8.8 Hz, 1 H), 7.47-7.44 (m, 3 H), 6.45 (s, 1 H), 5.17 (s, 2 H), 3.77 (s, 3 H), 2.46-2.45 (m, 2 H), 2.25-2.24 (m, 2 H), 1.77-1.75 (m, 2 H), 1.66-1.64 (m, 2 H). | 398.2 [M + H] | A | B | A |
| 220 | $^1$H NMR (400 MHz, DMSO-d$_6$): δ 13.14 (brs, 1 H), 8.15 (d, J = 8.4 Hz, 1 H), 8.05 (d, J = 8.8 Hz, 1 H), 7.43 (d, J = 8.8 Hz, 1 H), 7.40 (s, 1 H), 7.27 (d, J = 8.4 Hz, 1 H), 5.13 (s, 2 H), 3.76 (s, 3 H), 2.73-2.67 (m, 1 H), 1.84-1.82 (m, 4 H), 1.75-1.72 | 400.3 [M + H] | A | B | B |

TABLE 3-continued

| Cmpd No. | NMR Peak listings | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| | (m, 1 H), 1.55-1.31 (m, 4 H), 1.28-1.25 (m, 1 H). | | | | |
| 221 | $^1$H NMR (400 MHz, DMSO-d$_6$): δ 13.20 (s, 1 H), 8.90 (d, J = 4.0 Hz, 1 H), 8.21-8.18 (m, 1 H), 8.03 (s, 1 H), 7.61-7.40 (m, 3 H), 7.13-7.10 (m, 1 H), 6.85 (s, 1 H), 6.77-6.76 (m, 1 H), 4.94 (s, 2 H). | 449.1 [M + H] | A | B | |
| 223 | $^1$H NMR (400 MHz, DMSO-d$_6$): δ 13.13 (br, 1 H), 9.82 (s, 1 H), 8.22 (t, J = 8.8 Hz, 2 H), 7.80 (s, 1 H), 7.65 (m, 4 H), 6.92 (d, J = 8.4 Hz, 2 H), 5.31 (s, 2 H) | 414.1 [M + H] | B | B | A |
| 224 | 1$^1$H NMR (400 MHz, DMSO-d$_6$): δ 3.22 (br, 1 H), 8.16 (d, J = 8.8 Hz, 1 H), 8.04 (d, J = 8.8 Hz, 1 H), 7.45 (m, 3 H), 5.24 (s, 2 H), 3.92 (q, J = 6.8 Hz, 2 H), 1.36 (m, 12 H) | 388.3 [M + H] | B | | |
| 225 | $^1$H NMR (400 MHz, DMSO-d$_6$): δ 12.96 (br, 1 H), 8.16 (d, J = 8.4 Hz, 1 H), 8.04 (d, J = 8.8 Hz, 1 H), 7.66 (s, 1 H), 7.45 (m, 2 H), 5.54 (s, 2 H), 4.50 (m, 1 H), 1.36 (s, 9 H), 1.23 (d, J = 6.0 Hz, 6 H) | 402.4 [M + 1] | A | | B |
| 226 | $^1$H NMR (400 MHz, DMSO-d$_6$): δ 8.76 (br, 1 H), 8.74 (br, 1 H), 8.24 (d, J = 8.4 Hz, 1 H), 8.07 (d, J = 8.8 Hz, 1 H), 7.48 (d, J = 5.2 Hz, 1 H), 7.39 (s, 1 H), 7.28 (d, J = 8.4 Hz, 1 H), 5.10 (s, 2 H), 3.74 (s, 3 H), 3.44-3.41 (m, 2 H), 3.10-3.01 (m, 3 H), 2.03-1.99 (m, 2 H), 1.92-1.36 (m, 2 H). | 401.3 [M + 1] | C | | |
| 227 | $^1$H NMR (400 MHz, DMSO-d$_6$): δ 8.98 (brs, 1 H), 8.61 (brs, 1 H), 8.22 (d, J = 8.0 Hz, 1 H), 8.06 (d, J = 8.4 Hz, 1 H), 7.50 (s, 1 H), 7.46 (d, J = 8.8 Hz, 1 H), 7.33 (d, J = 8.4 Hz, 1 H), 5.14 (s, 2 H), 3.77 (s, 3 H), 3.56-3.55 (m, 1 H), 3.22-3.10 (m, 3 H), 2.96-2.91 (m, 1 H), 1.96-1.94 (m, 2 H), 1.83-1.80 (m, 2 H). | 401.2 [M + 1] | D | | |
| 228 | $^1$H NMR (400 MHz, DMSO-d$_6$): δ 8.15 (d, J = 8.8 Hz, 1 H), 8.03 (d, J = 8.4 Hz, 1 H), 7.64 (s, 1 H), 7.43 (d, J = 8.8 Hz, 2 H), 5.46 (s, 2 H), 4.60-4.56 (m, 1 H), 2.27-2.15 (m, 4 H), 1.68-1 66 (m, 1 H), 1.41-1.40 (m, 1 H), 1.36 (s, 9H). | 414.2 [M + 1] | B | | |
| 229 | $^1$H NMR (400 MHz, DMSO-d$_6$): δ 8.26 (d, J = 8.4 Hz, 1 H), 8.20 (d, J = 8 Hz, 1 H), 7.74 (t, J = 7.2 Hz, 1 H), 7.60 (d, J = 8.8 Hz, 1 H), 7.40 (d, J = 8.8 Hz, 1 H), 7.30 (t, J = 7.2 Hz, 1 H), 4.85 (s, 2 H), 4.74 (s, 2 H), 3.46 (s, 3 H). | 332.2 [M + 1] | D | | |
| 231 | $^1$H NMR (400 MHz, DMSO-d$_6$): δ 8.12 (d, J = 8.4 Hz, 1 H), 8.04 (d, J = 8.8 Hz, 1 H), 7.45 (d, J = 8.8 Hz, 1 H), 7.31 (s, 1 H), 7.25 (d, J = 8.4 Hz, 1 H), 5.14 (s, 2 H), 3.76 (s, 3 H), 3.19-3.15 (m, 2 H), 1.33 (t, J = 7.2. 3 H). | 378.1 [M + 1] | B | | A |
| 232 | $^1$H NMR (400 MHz, DMSO-d$_6$): δ 13.21 (s, 1 H), 8.12 (d, J = 8.4 Hz, 1 H), 8.03 (d, J = 8.8 Hz, 1 H), 7.44 ((d, J = 8.8 Hz, 1 H), 7.36 (s, 1 H), 7.26 (d, J = 8.4 Hz, 1 H), 5.13 (s, 2 H), 3.84-3.78 (m, 1H), 3.76 (s, 3 H), 1.34 (d, J = 6.4 Hz, 6 H). | 392.3 [M + 1] | C | | A |
| 233 | $^1$H NMR (400 MHz, DMSO-d$_6$): δ 8.10 (d, J = 8.4 Hz, 1 H), 8.03 (d, J = 8.4 Hz, 1 H), 7.44 (d, J = 8.8 Hz, 1 H), 7.34 (s, 1 H), 7.24 (d, J = 8.4 Hz, 1 H), 5.10 (s, 2 H), 3.76 (s, 3 H), 3.56 (m, 1 H), 2.02 (m, 2 H), 1.74 (m, 2 H), 1.60 (m, 1H), 1.42 (m, 4 H), 1.27 (m, 1 H). | 432.4 [M + 1] | A | | |
| 234 | $^1$H NMR (400 MHz, DMSO-d$_6$): δ 8.21 (d, J = 8.8 Hz, 1 H), 8.13 (d, J = 8.8 Hz, 1 H), 7.37 (d, J = 8.8 Hz, 1 H), 7.29 (s, 1 H), 7.21 (d, J = 8.4 Hz, 1 H), 5.06 (s, 2 H), 3.86 (s, 3 H), 2.65 (s, 3 H). | 364.2 [M + 1] | B | | A |
| 235 | $^1$H NMR (400 MHz, DMSO-d$_6$): δ 13.16(s, 1 H), 9.44(s, 1 H), 8.97(s, 1 H), 8.06 (d, J = 8.8 Hz, 1 H), 8.02 (d, J = 8.8 | 425.2 [M + 1] | A | | A |

TABLE 3-continued

| Cmpd No. | NMR Peak listmgs | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| | Hz, 1 H), 7.40 (d, J = 8.8 Hz, 1 H), 7.12 (t, J = 8 0 Hz, 1 H), 7.01 (d, J = 8.8 Hz, 1 H), 6.94 (s, 1 H), 6.72 (d, J = 9.2 Hz, 1 H), 6.66 (s, 1 H), 6 45 (d, J = 7.6 Hz, 1 H), 4.92 (s, 2 H), 3.73 (s, 3 H). | | | | |
| 236 | $^1$H NMR (400 MHz, DMSO-d$_6$): δ 13.16 (s, 1 H), 9.32 (s, 1 H), 8.76 (s, 1 H), 8.00 (d, J = 8.4 Hz, 2 H), 7.38 (d, J = 8.8 Hz, 1 H), 7.09 (d, J = 8.8 Hz, 2 H), 6.83-6.77 (m, 3 H), 6.71 (s, 1 H), 4.88 (s, 2 H), 3.72 (s, 3 H). | 425.2 [M + 1] | A | | |
| 238 | $^1$H NMR (400 MHz, DMSO-d$_6$): δ 8.29 (d, J = 8.4 Hz, 1 H), 8.07 (d, J = 8.4 Hz, 1 H), 7.76 (s, 1 H), 762 (m, 3 H), 7.46 (d, J = 8.8 Hz, 1 H), 7.43 (t, J = 7.6 Hz, 1 H), 7.28 (d, J = 7.6 Hz, 1 H), 5.26 (s, 2 H), 3.78 (s, 3H), 2.42 (s, 3 H). | 408.3 [M + 1] | A | | |
| 240 | $^1$H NMR (400 MHz, DMSO-d$_6$): δ 13.06 (s, 1 H), 8.47 (s, 1 H), 8.10 (s, 1 H), 7.94 (s, 1 H), 7.46 (d, J = 8.4 Hz, 1 H), 7.41-7.37 (m, 1 H), 5.23 (s, 2 H), 3.11-3.00 (m, 1 H), 1.30 (d, J = 6.8 Hz, 6H) | 334.1 [M − 1] | B | | |
| 243 | $^1$H NMR (400 MHz, DMSO-d$_6$): δ 8.54 (d, J = 5.6 Hz, 1 H), 8.40 (dd, J = 1.6 Hz, 8.0 Hz, 1 H), 8.30 (d, J = 8.8 Hz, 1 H), 8.17 (d, J = 8.4 Hz, 1 H), 8.09 (d, J = 5.6 Hz, 1 H), 7.83 (t, J = 8.0 Hz, 1 H), 7.57-7.45 (m, 4 H), 7.36 (1. J = 7.6 Hz, 1 H), 6.35 (d, J = 8.4 Hz, 1 H), 4.01 (d, J = 15.2 Hz, 1 H), 3.84 (d, J = 15.2 Hz, 1 H), | 431.3 [M + 1] | B | | C |
| 244 | $^1$H NMR (400 MHz, DMSO-d$_6$): δ 13.19 (s, 1 H), 8.24 (dd, J = 1.6 Hz, 8.0 Hz, 1 H), 8.07 (d, J = 8.4 Hz, 1 H), 7.84-7.80 (m, 1 H), 7.59 (d, J = 8.8 Hz, 1 H), 7.47 (d, J = 8.8 Hz, 1 H), 7.37 (m, 1 H), 5.19 (s, 2 H), 3.92 (q, J = 6.8 Hz, 2 H), 1.38 (t, J = 6.8 Hz, 3 H). | 332.1 [M + 1] | C | | B |
| 245 | $^1$H NMR (400 MHz, DMSO-d$_6$): δ 13.14 (s, 1 H), 8.17 (d, J = 8.0 Hz, 1 H), 8.06 (d, J = 8.8 Hz, 1 H), 7.46-7.39 (m, 2 H), 7.30 (d, J = 8.4 Hz, 1 H), 5.14 (s, 2 H), 3.76 (s, 3 H), 3 12-3.02 (m, 1 H), 1.27 (d, J = 6.8 Hz, 6 H). | 360.3 [M + 1] | B | | |
| 246 | $^1$H NMR (400 MHz, DMSO-d$_6$): δ 12.97 (s, 1 H), 8.24-8.21 (m, 1 H), 8.04 (d, J = 8.4 Hz, 1 H), 7.80-7.78 (m, 2 H), 7.47 (d, J = 8.4 Hz, 1 H), 7.37-7.33 (m, 1 H), 5.51 (s, 2 H), 4.48-4.45 (m, 1 H), 1.23 (d, J = 6.4 Hz, 6 H). | 346.3 [M + 1] | C | | |
| 247 | $^1$H NMR (400 MHz, DMSO-d$_6$): δ 13.00 (s, 1 H), 8.24-8.22 (m, 1 H), 8.04 (d, J = 8.4 Hz, 1 H), 7.81-7.79 (m, 2 H), 7.46 (d, J = 8.4 Hz, 1 H), 7.38-7.36 (m, 1 H), 5.49 (s, 2 H), 4.58-4.55 (m, 1 H), 2.50-2.15 (m, 4 H), 1.68-1.65 (m, 1 H), 1.40-1.37 (m, 1 H). | 358.3 [M + 1] | C | | |
| 248 | $^1$H NMR (400 MHz, DMSO-d$_6$): δ 8.04 (d, J = 8.4 Hz, 1 H), 7.81 (d, J = 10.4 Hz, 1 H), 7.54 (d, J = 6.0 Hz, 1 H), 7.44 (d, J = 9.6 Hz, 1 H), 5.11 (s, 2 H), 3.77 (s, 3 H), 1.29 (d, J = 6.8 Hz, 6 H). | 378.3 [M + 1] | D | | |
| 249 | $^1$H NMR (400 MHz, DMSO-d$_6$): δ 8.43 (d, J = 8.4 Hz, 1 H), 8.14 (s, 1 H), 8.07 (d, J = 8.8 Hz, 1 H), 7.81 (d, J = 7.2 Hz, 1 H), 7.50 (d, J = 8.8 Hz, 1 H), 5.14 (s, 2 H), 3.79 (s, 3 H), 3.34 (s, 3 H). | 396.0 [M + 1] | D | | |
| 250 | $^1$H NMR (400 MHz, DMSO-d$_6$): δ 9.01 (s, 1 H), 8.06-8.00 (m, 2 H), 7.38 (d, J = 8.4 Hz, 1 H), 7.29-7.26 (m, 2 H), 7.19-7.14 (m, 2 H), 6.93-6.91 (m, 2 H), 4.88 (s, 2 H), 3.73 (s, 3 H). | 427.2 [M + 1] | A | | A |
| 251 | $^1$H NMR (400 MHz, DMSO-d$_6$): δ 9.14 (s, 1 H), 8.07-8.01 (m, 2 H), 7.34-7.30 (m, 3 H), 7.25-7.23 (m, 2 H), 7.11 (s, 1 H), 6.96 (d, J = 8.4 Hz, 1 H), 4.81 (s, 2 H), 3.75 (s, 3 H). | 443.2 [M + 1] | B | | A |

TABLE 3-continued

| Cmpd No. | NMR Peak listmgs | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| 252 | $^1$H NMR (400 MHz, DMSO-d$_6$): δ 8.13 (d, J = 8.0 Hz, 1 H), 8.04 (d, J = 8.8 Hz, 1 H), 7.50 (s, 1 H), 7.31-7.37 (m, 2 H), 6.49 (s, 1 H), 4.99 (s, 2 H), 4.48 (s, 2 H), 3.79 (s, 3 H), 3.74 (s, 2 H), 2.28 (s, 2 H). | 400.3 [M + 1] | B | | |
| 253 | $^1$H NMR (400 MHz, DMSO-d$_6$): δ 8.14 (d, J = 8.4 Hz, 1 H), 8.04 (d, J = 8.4 Hz, 1 H), 7.50 (s, 1 H), 7.39 (d, J = 8.8 Hz, 1 H), 7.25 (d, J = 8.0 Hz, 1 H), 5.07 (s, 2 H), 3.85 (d, J = 11.2 Hz, 2 H), 3.78 (s, 3 H), 3.60 (t, J = 6.8 Hz, 2 H), 2.90-2.95 (m, 1 H), 1.74-1.81 (m, 2 H), 1.64(s, 2 H). | 402.3 [M + 1] | B | | B |
| 254 | $^1$H NMR (400 MHz, DMSO-d$_6$): δ 8.18 (d, J = 8.4 Hz, 1 H), 8.06 (d, J = 8.5 Hz, 1 H), 7.51-7.44 (m, 3 H), 6.55 (s, 1 H), 5.17 (s, 2 H), 4.28 (s, 2 H), 3.86-3.84 (m, 2 H), 3.77 (s, 3 H), 2.50 (s, 2H). | 400.4 [M + 1] | B | | |
| 255 | $^1$H NMR (400 MHz, DMSO-d$_6$): δ 8.17 (d, J = 8.0 Hz, 1 H), 8.06 (d, J = 8.4 Hz, 1 H), 7.45 (s, 1 H), 7.40 (d, J = 8.4 Hz, 1 H), 7.26 (d, 8.4 Hz, 1 H), 5.03 (s, 2 H), 3.96-3.94 (m, 2 H), 3.77 (s, 3 H), 3.47-3.41 (m, 2 H), 2.94-2.90 (m, 1 H), 1.73-1.71 (m, 4 H). | 402.4 [M + 1] | B | | |
| 256 | $^1$H NMR (400 MHz, DMSO-d$_6$): δ 8.32(d, J = 8.4 Hz, 1 H), 8.23 (dd, J = 1.6 Hz, J = 8.0 Hz, 1 H), 7.71 (1, J = 7.2 Hz, 1 H), 7.58-7.49 (m, 5 H), 7.39-7.31 (m, 3 H), 4.46 (s, 2 H). | 364.3 [M + 1] | C | | B |
| 257 | $^1$H NMR (400 MHz, DMSO-d$_6$): δ 9.78 (s, 1 H), 9.21 (s, 1 H), 8.20 (d, J = 8.8 Hz, 1 H), 8.05 (d, J = 9.2 Hz, 1H), 7.59 (d, J = 8.4 Hz, 1 H), 7.29 (t, J = 8.0 Hz, 1 H), 7.13 (s, 1 H), 7.05-7.02 (m, 3 H), 6.89 (d, J = 9.6 Hz, 1 H), 5.01 (s, 2 H), 3.03 (s, 3 H). | 506.0 [M + 1] | B | | A |
| 258 | $^1$H NMR (400 MHz, DMSO-d$_6$): δ 10.68 (br, 1 H), 8.28 (s, 1 H), 8.19 (d, J = 8.8 Hz, 1 H), 8.13 (s, 1 H), 8.05 (d, J = 8.8 Hz, 1 H), 7.98 (s, 1 H), 766 (d, J = 8.4 Hz, 1 H), 7.53 (d, J = 8.8 Hz, 1 H), 4.81 (s, 2 H). | 451.2 [M + 1] | B | | |
| 259 | $^1$H NMR (400 MHz, DMSO-d$_6$): δ 13.00 (s, 1 H), 9.04 (s, 1 H), 8.20(d, J = 8.8 Hz, 1 H), 8.02 (d, J = 8.8 Hz, 1 H), 7.51 (d, J = 8.4 Hz, 1 H), 7.27-7.30 (m, 2 H), 7.19 (t, J = 8.8 Hz, 2 H), 7.01 (s, 1 H), 6.92 (d, J = 8.8 Hz, 1 H), 5.01 (s, 2 H), 2.28 (s, 3H) | 443.2 [M + 1] | A | | |
| 260 | $^1$H NMR (400 MHz, DMSO-d$_6$): δ 12.96 (s, , 1 H), 8.24 (d, J = 8.4 Hz, 1 H), 8.13 (d, J = 8.4 Hz, 1 H), 7.64 (s, 1 H), 7.57 (d, J = 8.4, 1 H), 7.46 (dd, J = 1.2 Hz , 8.4 Hz, 1 H), 5.33 (s, 2 H), 2.77-2.75 (m, 2H), 1.38 (s, 9H), 0.93 (t, J = 7.2, 3H) | 404.1 [M + 1] | A | | |
| 261 | $^1$H NMR (400 MHz, DMSO-d$_6$): δ 8.16 (d, J = 8.0 Hz, 1 H), 8.06 (d, J = 8.8 Hz, 1 H), 7.40 (d, J = 8.8 Hz, 1 H), 7.30-7.23 (m, 2 H), 5.04 (br, 2 H), 3.75 (s, 3 H), 3.04-2.95 (m, 1 H), 1.26 (d, J = 7.2 Hz, 6 H). | 491.2 [M + 1] | B | | B |
| 262 | $^1$H NMR (400 MHz, DMSO-d$_6$): δ 8.18 (d, J = 8.4 Hz, 1 H), 8.07 (d, J = 8.4 Hz, 1 H), 7.47-7.43 (m, 2 H), 7.40 (s, 1 H), 5.12 (s, 2 H), 3.74 (s, 3 H), 3.28 (s, 3 H), 1.36 (s, 9 H). | 451.3 [M + 1] | B | | A |
| 263 | $^1$H NMR (400 MHz, DMSO-d$_6$): δ13.3 (br, 1 H), 10.1 (s, 1 H), 8.38 (s, 1 H), 8.23-8.04 (m, 5 H), 7.64 (d, J = 8.4 Hz, 1 H), 7.44 (d, J = 8.8 Hz, 1 H), 5.04 (s, 2 H), 3.78 (s, 3H). | 411.3 [M + 1] | B | | A |
| 264 | $^1$H NMR (400 MHz, DMSO-d$_6$): δ 13.11 (br, 1 H), 8.21 (d, J = 8.8 Hz, 1 H), 8.10 (d, J = 8.4 Hz, 1 H), 7.63 (d, J = 8.8 Hz, 1 H), 7.50 (s, 1 H), 7.29 (d, J = 8.4 Hz, 1 H), 5.20 (s, 2 H), 4.61 (d, J = 4.4 Hz, 1 H), | 418.2 [M − 1] | A | | |

TABLE 3-continued

| Cmpd No. | NMR Peak listmgs | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| | 3.48 (m, 1 H), 2.63 (m, 1 H), 1.96 (m, 2 H), 1.82 (m, 2 H), 1.55 (m, 2 H), 1.34 (m, 2 H) | | | | |
| 265 | $^1$H NMR (400 MHz, DMSO-d$_6$): 8.24-8.21 (m, 1 H), 8.09 (d, J = 9.2 Hz, 1 H), 7.78-7.74 (m, 1 H), 7.50 (d, J = 8.4 Hz, 1 H), 7.33-7.22 (m, 1 H), 7.21 (d, J = 8.8 Hz, 1 H), 5.00 (s, 2 H), 3.97 (s, 3 H), 3.72 (s, 3 H). | 314.3 [M + 1] | D | | |
| 266 | $^1$H NMR (400 MHz, DMSO-d$_6$): δ 13.20 (s, 1 H), 9.22 (s, 1 H), 8.10 (d, J = 8.8 Hz, 1 H), 8.02 (d, J = 8.8 Hz, 1 H), 7.41 (d, J = 8.8 Hz, 1 H), 7.35-7.34 (m, 4 H), 7.05-7.02 (m, 1 H), 6.97 (s, 1 H), 4.96 (s, 2 H), 3.74 (s, 3H. | 493.3 [M + 1] | A | | A |
| 267 | $^1$H NMR (400 MHz, DMSO-d$_6$): δ 8.63 (s, 1 H), 8.06-8.061(m, 2 H), 7.53-7.50 (m, 2 H), 7.35-7.31 (m, 2 H), 7.13-7.11 (m, 2 H), 6.91 (d, J = 8.8 Hz, 1 H), 4.81 (s, 2 H), 3.75 (s, 3 H) | 443.3 [M + 1] | A | | A |
| 268 | $^1$H NMR (400 MHz, DMSO-d$_6$): δ 8.29 (s, 1 H), 8.04 (d, J = 8.4 Hz, 1 H), 7.58 (s, 1 H), 7.41 (d, J = 8.4 Hz, 1 H), 5.04 (s, 2 H), 3.78 (s, 1 H), 3.30-3.35 (m, 1 H), 1.25 (d, J = 6.8 Hz, 6 H) | 438.2 [M + 1] | B | | C |
| 269 | $^1$H NMR (400 MHz, DMSO-d$_6$): δ 8.26 (d, J = 8.4 Hz, 1 H), 8.08 (d, J = 7.2 Hz, 1 H) 7.72-7.64 (m, 3 H), 7.60 (d, J = 8.4 Hz, 1 H), 7.45 (d, J = 8.8 Hz, 1 H), 6.93 (d, J = 8.8 Hz, 2 H), 5.26 (s, 2 H), 3.79 (s, 3 H) | 410.3 [M + 1] | A | | A |
| 270 | $^1$H NMR (400 MHz, DMSO-d$_6$): δ 9.70 (s, 1 H), 8.29 (d, J = 8.4 Hz, 1 H), 8.08 (d, J = 8.4 Hz, 1 H), 7.70 (s, 1 H), 7.62-7.58 (m, 1 H), 7.47 (d, J = 8.8 Hz, 1 H), 7.34 (t, J = 7.8 Hz, 1 H), 7.25-7.16 (m, 2 H), 6.90-6.86 (m, 1 H), 5.25 (s, 2 H), 3.78 (s, 3 H) | 410.3 [M + 1] | A | | A |
| 271 | $^1$H NMR (400 MHz, DMSO-d$_6$): δ 12.9 (s, 1 H), 9.80 (s, 1 H), 8.21 (t, J = 8.4 Hz, 2 H), 7.92 (s, 1 H), 7.72-7.65 (m, 2 H), 7.60 (d, J = 8.4 Hz, 1 H), 7.56 (d, J = 8.4 Hz, 1 H), 6.92 (d, J = 8.4 Hz, 2 H), 5.54 (s, 2 H), 2.36 (s, 3H) | 426.2 [M + 1] | A | | A |
| 272 | $^1$H NMR (400 MHz, DMSO-d$_6$): δ 13.24 (s, 1 H), 8.24 (dd, J = 1.6, 8.0 Hz, 1 H), 8.10 (d, J = 8.4 Hz, 1 H), 7.84-7.80 (m, 1 H), 7.63 (d, J = 8.4 Hz, 1 H), 7.48 (d, J = 8.4 Hz, 1 H), 7.37 (t, J = 7.6 Hz, 1 H), 5.27 (s, 2 H), 4.71 (d, J = 2 Hz, 2 H), 3.60 (t, J = 2.4 Hz, 1 H). | 342.1 [M + 1] | C | | D |
| 273 | $^1$H NMR (400 MHz, DMSO-d$_6$): δ 13.14 (s, 1 H), 8.25 (dd, J = 0.8, 8.0 Hz, 1 H), 8.07 (d, J = 8.8 Hz, 1 H), 7.84-7.80 (m, 1 H), 7.61 (d, J = 8.8 Hz, 1 H), 7.47 (d, J = 8.4 Hz, 1 H), 7.37 (t, J = 7.6 Hz, 1 H), 6.11-6.04 (m, 1 H), 5.44-5.39 (dd, J = 1.6, 17.2 Hz, 1 H), 5.28 (d, J = 15.6 Hz, 1 H), 5.24 (s, 2 H), 4.44 (d, J = 6.0 Hz, 2 H), | 344.2 [M + 1] | B | | B |
| 274 | $^1$H NMR (400 MHz, DMSO-d$_6$): δ 8.23 (d, J = 8.0 Hz, 1 H), 8.07 (d, J = 8.8 Hz, 1 H), 7.69-7.56 (m, 4 H), 7.45 (d, J = 8.4 Hz, 1 H), 6.87 (d, J = 8.4 Hz, 2 H), 5.25 (s, 2 H), 3.78 (s, 3 H) | 409.3 [M + 1] | A | | A |
| 275 | $^1$H NMR (400 MHz, DMSO-d$_6$): δ 8.31 (d, J = 8.4 Hz, 1 H), 8.08 (d, J = 8.8 Hz, 1 H), 7.69 (s, 1 H), 7.58 (d, J = 8.4 Hz, 1 H), 7.48 (d, J = 8.8 Hz, 1 H), 7.37 (t, J = 7.8 Hz, 1 H), 7.31-7.22 (m, 2 H), 7.001-6.92 (m, 1 H), 5.23 (s, 2 H), 3.78 (s, 3 H) | 409.3 [M + 1] | B | | A |
| 276 | $^1$H NMR (400 MHz, DMSO-d$_6$): δ 10.31 (s, 1 H), 8.60 (d, J = 4.8 Hz, 2 H), 8.42 (s, 1 H), 8.24 (d, J = 8.4 Hz, 1 H), 8.10 (d, J = 8.8 Hz, 1 H), 7.70 (d, J = 8.8 Hz, 1 H), 7.54 (d, J = 8.4 Hz, 1 H), 7.02 (t, J = 4.8 Hz, 1 H), 5.18 (s, 2 H), 2.31 (s, 3 H). | 427.2 [M + 1] | A | | A |
| 277 | $^1$H NMR (400 MHz, DMSO-d$_6$): δ 8.43 (s, 1 H), 8.21 (d, J = 8.4 Hz, 1 H), 8.06 (d, | 384.3 [M + 1] | A | | |

TABLE 3-continued

| Cmpd No. | NMR Peak listings | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| | J = 8.4 Hz, 1 H), 7.78-7.81 (m, 2 H), 7.60 (d, J = 8.4 Hz, 1 H), 7.43 (d, J = 8.8 Hz, 1 H), 7.13 (s, 1 H), 5.25 (s, 2 H), 3.78 (s, 3 H) | | | | |
| 278 | $^1$H NMR (400 MHz, DMSO-d$_6$): δ 9.01-9.02 (m, 2 H), 8.40-8.44 (m, 3 H), 8.08 (d, J = 8.4 Hz, 1 H), 7.87-7.89 (m, 2 H), 7.50 (d, J = 8.8 Hz, 1 H), 5.34 (s, 2 H) 3.80 (s, 3 H). | 395.3 [M + 1] | B | | |
| 279 | $^1$H NMR (400 MHz, DMSO-d$_6$): δ 8.20 (d, J = 8.4 Hz, 1 H), 8.08 (d, J = 8.0 Hz, 1 H), 7.60 (s, 1 H), 7.54 (d, J = 8.4 Hz, 1 H), 7.18 (d, J = 8.0 Hz, 1 H), 5.41 (s, 2 H), 2.47 (s, 3H), 2.32(s, 3 H). | 348.2 [M + 1] | B | | B |
| 280 | $^1$H NMR (400 MHz, DMSO-d$_6$): δ 13.16 (s, 1 H), 8.13 (d, J = 8.0 Hz, 1 H), 8.06 (d, J = 8.4 Hz, 1 H), 7.47-7.40 (m, 2 H), 7.20 (d, J = 8.0 Hz, 1 H), 5.10 (s, 2 H), 3.77 (s, 3 H), 2.48 (s, 3 H). | 332.2 [M + 1] | B | | |
| 281 | $^1$H NMR (400 MHz, DMSO-d$_6$): δ 8.18 (d, J = 8.0 Hz, 1 H), 8.09 (d, J = 8.0 Hz, 1 H), 7.58 (s, 1 H), 7.48 (d, J = 8.4 Hz, 1 H), 7.22 (d, J = 7.6 Hz, 1 H), 5.22 (s, 2 H), 3.02 (m, 1 H), 2.31 (s, 3 H), 1.26 (d, J = 6.8 Hz, 6 H) | 376.2 [M + 1] | A | | A |
| 282 | $^1$H NMR (400 MHz, DMSO-d$_6$): δ 8.13 (d, J = 8.4 Hz, 1 H), 8.05 (d, J = 8.8 Hz, 1 H), 7.45 (d, J = 8.8 Hz, 1 H), 7.41 (s, 1 H), 7.20 (d, J = 7.6 Hz, 1 H), 5.19 (s, 2 H), 3.95-3.90 (m, 2 H), 2.48 (s, 3 H), 1.38 (t, J = 7.2 Hz, 3 H). | 346.2 [M + 1] | B | | |
| 283 | $^1$H NMR (400 MHz, DMSO-d$_6$): δ 7.99 (d, J = 8.4 Hz, 1 H), 7.92 (d, J = 8.8 Hz, 1 H), 7.35 (d, J = 8.8 Hz, 1 H), 6.61-6.58 (m, 1 H), 6.41 (s, 1 H), 6.35 (s, 2 H), 4.87 (s, 2 H), 3.73 (s, 3 H) | 333.1 [M + 1] | C | | |
| 284 | $^1$H NMR (400 MHz, DMSO-d$_6$): δ 13.17 (s, 1 H), 8.25 (dd, J = 1.6. 8.0 Hz, 1 H), 8.06 (d, J = 8.4 Hz, 1 H), 7.84-7.80 (m, 1 H), 7.61 (d, J = 8.4 Hz, 1 H), 7.46 (dd, J = 1.2, 8.8 Hz, 1 H), 7.37 (t, J = 7.2 Hz, 1 H), 5.25 (s, 2 H), 3.82 (t, J = 6.8 Hz, 2 H), 1.85-1.79 (m, 2 H), 1.00 (t, J = 7.2 Hz, 3 H). | 346.2 [M + 1] | D | | |
| 285 | $^1$H NMR (400 MHz, DMSO-d$_6$): δ 8.14 (d, J = 8.0 Hz, 1 H), 8.08 (d, J = 8.4 Hz, 1 H), 7.55 (d, J = 7.2 Hz, 2 H), 7.48 (t, J = 4.4 Hz, 2 H), 7.42-7.36 (m, 3 H), 7.20 (d, J = 8.4 Hz, 1 H), 5.38 (s, 2 H), 4.94 (s, 2 H), 2.49 (s, 3 H). | 408.3 [M + 1] | B | | B |
| 286 | $^1$H NMR (400 MHz, DMSO-d$_6$): 13-34 (brs, 1 H), 8.86 (s, 1 H), 8.01-8.09 (m, 2 H), 7.57 (d, J = 8.0 Hz, 1 H), 7.36-7.46 (m, 3 H), 7.17-7.22 (m, 1 H), 7.95-7.00 (m, 2 H), 4.91 (brs, 2 H), 3.74 (s, 3 H) | 493.3 [M + 1] | A | | A |
| 287 | $^1$H NMR (400 MHz, DMSO-d$_6$): δ 13.04 (brs, 1 H), 8.25-8.30 (m, 2 H), 7.77-7.82 (m, 1 H), 7.54-7.57 (m, 2 H), 7.37 (t, J = 7.6 Hz, 1 H), 7.32 (t, J = 8.0 Hz, 2 H), 7.07 (t, J = 7.2 Hz, 1 H), 6.76 (d, J = 8.0 Hz, 2 H), 5.10 (s, 2 H) | 380.3 [M + 1] | D | | |
| 288 | $^1$H NMR (400 MHz, DMSO-d$_6$): 13.17 (brs, 1 H), 8.17 (d, J = 8.4 Hz, 1 H), 8.05 (d, J = 8.8 Hz, 1 H), 7.45 (d, J = 8.8 Hz, 1H), 7.45 (s, 1 H), 7.30 (d, J = 8.4 Hz, 1 H), 5.22 (s, 2 H), 3.95-3.89 (m, 2 H), 3.10-3.03 (m, 1 H), 1.38 (t, J = 7.2. 3 H), 1.27 (d, J = 3.2 Hz, 6 H) | 374.2 [M + 1] | A | | A |
| 289 | $^1$H NMR (400 MHz, DMSO-d$_6$): 12.70 (brs, 1 H), 8.31 (d, J = 8.8 Hz, 1 H), 8.16 (d, J = 8.0 Hz, 1 H), 7.58-7.51 (m, 4 H), 7.39 (m, J = 6.8 Hz, 2 H), 7.34 (s, 1 H), 7.26 (d, J = 8.4 Hz, 1 H), 4.52 (s, 2 H), 3.02-2.95 (m, 1 H), 1.22 (d, J = 6.8 Hz, 6 H). | 406.2 [M − 1] | A | | A |

TABLE 3-continued

| Cmpd No. | NMR Peak listmgs | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| 290 | $^1$H NMR (400 MHz, DMSO-d$_6$): 8.21 (d, J = 8.4 Hz, 1 H), 8.10 (d, J = 8.8 Hz, 1 H), 7.64 (s, 1 H), 7.50 (d, J = 8.4 Hz, 1 H), 7.39 (d, J = 8.4 Hz, 1 H), 5.10 (s, 2 H), 3.30 (t, J = 6.4 Hz, 1 H), 1.33 (s, 9 H), 0.92 (d, J = 6.8 Hz, 6 H). | 418.3 [M + 1] | A | | B |
| 291 | $^1$H NMR (400 MHz, DMSO-d$_6$): 10.20 (br, 1 H), 8.33 (s, 1 H), 8.23 (s, 1 H), 8.16 (d, J = 8.4 Hz, 1 H), 8.06-8.10 (m, 2 H), 8.03 (s, 1 H), 7.64 (d, J = 8.8 Hz, 1 H), 7.44 (d, J = 8.4 Hz, 1 H), 5.06 (s, 2 H), 2.32 (s, 3 H). | 427.2 [M + 1] | A | | A |
| 292 | $^1$H NMR (400 MHz, DMSO-d$_6$): 13.2 (brs, 1 H), 8.00-7.93 (m, 2 H), 7.36 (d, J = 8.8 Hz, 1 H), 7.19 (d, J = 5.6 Hz, 1 H), 16.61-6.59 (m, 1 H), 6.21 (s, 1 H), 4.94 (s, 2 H), 3.99-3.97 (m, 1 H), 3.73 (s, 3 H), 2.38-2.34 (m, 2 H), 1.93-1.74 (m, 4 H), | 387.1 [M + 1] | A | | A |
| 293 | $^1$H NMR (400 MHz, DMSO-d$_6$): 13.20 (s, 1 H), 8.00-7.92 (m, 2 H), 7.35 (d, J = 8.4 Hz, 1 H), 6.92 (d, J = 4.8 Hz, 1 H), 6.65 (d, J = 8.8 Hz, 1 H), 6.30 (s, 1H), 4.95 (s, 2 H), 3.82-3-3.83 (m, 1 H), 3.73 (s, 3 H), 1.98-1.95 (m, 2 H), 1.70-1.51 (m, 6 H) | 401.1 [M + 1] | A | | A |
| 294 | $^1$H NMR (400 MHz, DMSO-d$_6$): 8.15 (d, J = 8.0 Hz, 1 H), 8.07 (d, J = 8.8 Hz, 1 H), 7.44 (s, 1 H), 7.35 (d, J = 8.4 Hz, 1 H), 7.18 (d, J = 8.4 Hz, 1 H), 4.87 (s, 2 H), 3.78 (s, 3 H), 2.74 (d, J = 7.6 Hz, 2 H), 7.25 (t, J = 7.6 Hz, 3 H). | 346.2 [M + 1] | B | | B |
| 295 | $^1$H NMR (400 MHz, DMSO-d$_6$): 12.92 (brs, 1 H), 8.17 (d, J = 9.6 Hz, 1 H), 7.98 (d, J = 8.8 Hz, 1 H), 7.77 (d, J = 7.2 Hz, 1 H), 7.72 (d, J = 8.4 Hz, 1 H), 7.44 (d, J = 8.4 Hz, 1 H), 7.37 (d, J = 6.8 Hz, 2 H), 7.33 (t, J = 7.2 Hz, 1 H), 7.24 (t, J = 7.2 Hz, 1 H), 7.16 (d, J = 18.0 Hz, 1 H), 5.65 (d, J = 18.8 Hz, 1 H), 5.44 (d, J = 18.8 Hz, 1 H), 5.31 (dd, J = 5.6 Hz, J = 13.2 Hz, 1 H), 1.59 (d, J = 6.4 Hz, 3H), | 408.3 [M + 1] | C | | D |
| 296 | $^1$H NMR (400 MHz, DMSO-d$_6$): 12.97 (s, 1 H), 8.17 (d, J = 7.2 Hz, 1 H), 7.98 (d, J = 8.8 Hz, 1 H), 7.81-7.64 (m, 2 H), 7.44 (d, J = 8.8 Hz, 1 H), 7.40-7.30 (m, 3 H), 7.25-7.11 (m, 3 H), 5.69-5.38 (m, 2 H), 5.35-5.26 (m, 1 H), 1.59 (d, J = 6.4 Hz, 3 H). | 408.3 [M + 1] | D | | D |
| 297 | $^1$H NMR (400 MHz, DMSO-d$_6$): δ 9.08 (s, 1 H), 8.14 (d, J = 8.4 Hz, 1 H), 8.01 (d, J = 8.8 Hz, 2 H), 7.94 (d, J = 7.2 Hz, 1 H), 7.69 (d, J = 8.4 Hz, 1 H), 7.52 (m, 4 H), 7.28 (d, J = 8.4 Hz, 1 H), 7.19 (s, 1 H), 6.86 (d, J = 8.4 Hz, 1 H), 4.75 (brs, 2 H), 3.74 (s, 3 H), | 459.4 [M + 1] | A | | A |
| 298 | $^1$H NMR (400 MHz, DMSO-d$_6$): 8.32 (s, 1 H), 8.14 (d, J = 8.4 Hz, 2 H), 7.37 (d, J = 7.6 Hz, 1 H), 7.31 (d, J = 8.4 Hz, 1 H), 7.07 (d, J = 8.0 Hz, 2 H), 6.99 (s, 1 H), 6.94 (m, 1 H), 6.88 (d, J = 8.8 Hz, 1 H), 4.78 (brs, 2 H), 3.82 (s, 3 H), 3.73 (s, 3 H) | 439.3 [M + 1] | B | | A |
| 299 | $^1$H NMR (400 MHz, DMSO-d$_6$): 8.01-7.94 (m, 2 H), 7.36 (d, J = 8.8 Hz, 1 H), 6.65-6.62 (m, 1 H), 6.26 (s, 1 H), 5.00 (s, 2 H), 3.74 (s, 3 H), 2.80 (s, 3 H) | 347.1 [M + 1] | B | | |
| 300 | $^1$H NMR (400 MHz, DMSO-d$_6$): 8.00-7.92 (m, 2 H), 7.33 (d, J = 8.4 Hz, 1 H), 6.73-6.62 (m, 2 H), 6.34 (s, 1 H), 4.93 (s, 2 H), 3.74-3.67(m, 4 H), 1.16 (d, J = 6.0 Hz, 6 H) | 373.2 [M − 1] | B | | |
| 301 | $^1$H NMR (400 MHz, DMSO-d$_6$): 13.41 (s, 1 H), 9.11 (s, 1 H), 8.26 (d, J = 8.4 Hz, 1 H), 8.15 (d, J = 8.8 Hz, 1 H), 7.81 (s, 1 H), 7.39-7.22 (m, 5 H), 7.08-6.99 (m, 2 | 379.2 [M + 1] | B | | A |

TABLE 3-continued

| Cmpd No. | NMR Peak listmgs | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| | H), 6.92 (s, 1 H), 5.37 (s, 1 H), 4.87 (s, 1 H) | | | | |
| 302 | $^1$H NMR (400 MHz, DMSO-d$_6$): 8.25 (d, J = 7.2 Hz, 1 H), 8.08 (d, J = 8.8 Hz, 1 H), 7.82 (t, J = 7.2 Hz, 1 H), 7.68 (d, J = 8.4 Hz, 1 H), 7.47 (d, J = 8.4 Hz, 1 H), 7.37 (t, J = 7.2 Hz, 1 H), 5.49 (brs, 2 H), 4.07-4.11 (m, 1 H), 3.69-3.78 (m, 2 H), 1.15-1.23 (m, 3 H) | 362.3 [M + 1] | D | | D |
| 303 | $^1$H NMR (400 MHz, DMSO-d$_6$): 13.19 (s, 1 H), 8.25 (dd, J1 = 1.6 Hz, J2 = 8 Hz, 1 H), 8.07 (d, J = 8.8 Hz, 1 H), 7.82-7.80 (m, 1 H), 7.61 (d, J = 8.4 Hz, 1 H), 7.47 (d, J = 8.8 Hz, 1 H), 7.39-7.35 (m, 1 H), 5.25 (s, 2 H), 3.87-3.83 (m, 2 H), 1.83-1.76 (m, 2 H), 1.47-1.42 (m, 2 H), 1.33-1.23 (m, 4 H), 0.90-0.86 (m, 3 H) | 388.3 [M + 1] | B | | C |
| 304 | $^1$H NMR (400 MHz, DMSO-d$_6$): 12.93 (brs, 1 H), 8.22 (d, J = 8.8 Hz, 1 H), 8.09 (d, J = 8.0 Hz, 1 H), 7.57 (d, J = 8.8 Hz, 2H), 7.20 (d, J = 8.0 Hz, 1 H), 5.38 (s, 2 H), 2.77 (q, J = 7.2, 14.4 Hz, 2 H), 2.47 (s, 3 H), 0.91 (t, J = 7.2, 3 H) | 362.1 [M + 1] | B | | A |
| 305 | $^1$H NMR (400 MHz, DMSO-d$_6$): 13.34 (brs, 1 H), 8.26 (d, J = 8.4 Hz, 1 H), 8.21-8.16 (m, 1 H), 7.85-7.79 (m, 1 H), 7.62-7.54 (m, 2 H), 7.36 (t, J = 7.2 Hz, 1 H), 5.11 (s, 2 H), 4.91 (s, 2H) | 343.2 [M + 1] | D | | D |
| 306 | $^1$H NMR (400 MHz, DMSO-d$_6$): 13.17 (s, 1 H), 8.16 (d, J = 7.2 Hz, 1 H), 8.05 (d, J = 8.0 Hz, 1 H), 7.46-7.41 (m, 2 H), 7.25 (d, J = 7.2 Hz, 1 H), 5.20 (s, 2 H), 3.92 (d, J = 6.4 Hz, 2 H), 2.78 (d, J = 6.8, 2 H), 1.38-1.25 (m, 6 H). | 360.1 [M + 1] | A | | A |
| 307 | $^1$H NMR (400 MHz, DMSO-d$_6$): 12.84 (brs, 1 H), 8.13 (d, J = 8.8 Hz, 1 H), 8.09 (d, J = 8.0 Hz, 1 H), 7.47 (s, 1 H), 7.36 (d, J = 8.8 Hz, 1 H), 7.16 (d, J = 8.4 Hz, 1 H), 5.07-4.94 (m, 2 H), 3.14-2.94 (m, 2 H), 2.89 (s, 3 H), 2.48 (s, 3 H), 0.73 (s, 3 H). | 359.4 [M + 1] | B | | B |
| 308 | $^1$H NMR (400 MHz, DMSO-d$_6$): 12.81 (brs, 1 H), 8.14 (d, J = 8.4 Hz, 1 H), 8.09 (d, J = 8.0 Hz, 1 H), 7.43 (s, 1 H), 7.35 (d, J = 8.4 Hz, 1 H), 7.17 (d, J = 7.6 Hz, 1 H), 4.87 (s, 2H), 2.72(s, 6 H), 2.48 (s, 3 H). | 345.3 [M + 1] | A | | A |
| 309 | $^1$H NMR (400 MHz, DMSO-d$_6$): 13.02 (brs, 1 H), 8.19 (d, J = 8.4 Hz, 1 H), 8.10-8.08 (m, 2 H), 7.58 (d, J = 8.8 Hz, 1 H), 7.54-7.52 (m, 1H), 5.47 (s, 2 H), 2.34 (s, 3 H). | 412.1 [M + 1] | B | | B |
| 310 | $^1$H NMR (400 MHz, DMSO-d$_6$): 8.14 (d, J = 7.6 Hz, 1 H), 7.99 (d, J = 8.8 Hz, 1 H), 7.77 (d, J = 3.6 Hz, 2 H), 7.30 (d, J = 8.4 Hz, 2 H), 7.08 (t, J = 7.6 Hz, 5 H), 5.39-5.17 (m, 2 H), 4.14-4.04 (m, 2 H), 3.04 (s, 3 H). | 407.3 [M + 1] | C | | D |
| 311 | $^1$H NMR (400 MHz, DMSO-d$_6$): 13.09 (s, 1 H), 8.13 (d, J = 8.0 Hz, 1 H), 8.05 (d, J = 8.8 Hz, 1 H), 7.46-7.42 (m, 2 H), 7.20 (d, J = 8.0 Hz, 1 H), 6.13-6.04 (m, 1 H), 5.42 (d, J = 17.2 Hz, 1 H), 5.28 (d, J = 10.4 Hz, 1 H), 5.23 (s, 2 H), 4.43 (d, J = 5.2 Hz, 2 H), 2.48 (s, 3 H) | 358.2 [M + 1] | B | | A |
| 312 | $^1$H NMR (400 MHz, DMSO-d$_6$): 8.25 (d, J = 7.6 Hz, 1 H), 8.11 (d, J = 8.4 Hz, 1 H), 7.81 (t, J = 7.6 Hz, 1 H), 7.56 (d, J = 8.8 Hz, 1 H), 7.47 (d, J = 8.4 Hz, 1 H), 7.36 (t, J = 7.2 Hz, 1 H), 5.24 (brs, 2 H), 4.57 (s, 2 H), 2.22 (s, 3 H). | 360.1 [M + 1] | D | | D |
| 313 | $^1$H NMR (400 MHz, DMSO-d$_6$): 8.07 (d, J = 8.0 Hz, 1 H), 7.74-7.70 (m, 1 H), 7.53 (d, J = 8.4 Hz, 1 H), 7.32-7.28 (m, J = 8.0, 1 H), 7.00 (s, 1 H), 4.94 (s, 2 H), 3.87 (s, 3 H), 3.65 (s, 3H). | 348.1 [M + 1] | D | | D |
| 314 | $^1$H NMR (400 MHz, DMSO-d$_6$): 8.27 (dd, J = 1.6, 8.0 Hz, 1 H), 7.90-7.86 (m, 1 | 334.0 [M + 1] | D | | C |

TABLE 3-continued

| Cmpd No. | NMR Peak listmgs | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| | H), 7.64 (d, J = 8.8 Hz, 1 H), 7.42 (t, J = 7.6 Hz, 1 H), 6.84 (s, 1 H), 5.13 (s, 2 H), 3.66 (s, 3 H). | | | | |
| 315 | $^1$H NMR (400 MHz, DMSO-d$_6$): 10.76 (brs, 1 H), 8.20 (d, J = 6.8. 1 H), 8.20 (t, J = 7.2, 1 H), 7.69 (s, 1 H), 7.59 (d, J = 8.8. 1 H), 7.25 (t, J = 7.2, 1 H), 4.99 (s, 2 H), 3.78 (s, 3 H) | 334.0 [M + 1] | D | | D |
| 316 | $^1$H NMR (400 MHz, DMSO-d$_6$): 8.32 (dd, J = 8.0 Hz, 1 H), 7.77-7.73 (m, 1 H), 7.61 (s, 1 H), 7.52 (d, J = 8.4 Hz, 1 H), 7.29 (t, J = 7.6 Hz, 1 H), 5.01 (s, 2 H), 3.83 (s, 3H). | 333.0 [M + 1] | D | | D |
| 317 | $^1$H NMR (400 MHz, DMSO-d$_6$): 9.86 (brs, 1 H), 8.04 (d, J = 8.4 Hz, 1 H), 7.59 (s, 1 H), 7.38 (d, J = 8.8 Hz, 1 H), 7.32 (s, 1 H), 5.14 (s, 2 H), 3.75 (s, 3 H), 3.24-3.19 (m, 1H), 1.23 (s, 6H) | 376.1 [M + 1] | D | | D |
| 318 | $^1$H NMR (400 MHz, DMSO-d$_6$): 13.3 (brs, 1 H), 8.07 (d, J = 8.8 Hz, 1 H), 7.61 (s, 1 H), 7.41 (d, J = 7.6 Hz, 2 H), 5.17 (s, 2 H), 3.91 (s, 3 H), 3.76 (s, 3 H), 3.46-3.43 (m, 1 H), 1.34 (d, J = 6.8 Hz,, 6 H) | 390.1 [M + 1] | C | | D |
| 319 | $^1$H NMR (400 MHz, DMSO-d$_6$): 8.07(s, 1 H), 8.05 (s, 1 H), 7.45 (s, 1 H), 7.43 (s, 1 H), 5.19 (s, 2 H), 3.76 (s, 3 H), 2.81 (m, 1 H), 2.50 (s, 6H), 1.27 (d, 6 H) | 403.3 [M + 1] | D | | D |
| 320 | $^1$H NMR (400 MHz, DMSO-d$_6$): 8.15-8.13 (d, J = 8.8 Hz, 1 H), 7.60 (s, 1 H), 7.47 (s, 1 H), 7.27-7.25 (d, J = 8.8 Hz, 1 H), 5.05 (s, 2 H), 3.87 (s, 3 H), 3.19-3.16 (m, 1 H), 1.34 (d, 6 H). | 375.4 [M + 1] | C | | D |
| 321 | $^1$H NMR (400 MHz, DMSO-d$_6$): 8.13 (d, J = 8.4 Hz, 1 H), 8.05 (d, J = 8.8 Hz, 1 H), 7.46 (d, J = 8.8 Hz, 1 H), 7.42 (s, 1 H), 7.21 (d, J = 8.0 Hz, 1 H), 5.27 (s, 2 H), 4.23-4.18 (m, 2 H), 3.95-3.89 (m, 2 H), 2.48 (s, 3 H), 1.34 (t, J = 6.8 Hz, 3 H), 1.23 (t, J = 7.2 Hz, 3 H). | 374.2 [M + 1] | D | | D |
| 322 | $^1$H NMR (400 MHz, DMSO-d$_6$): 8.13 (d, J = 8.0 Hz, 1 H), 8.05 (d, J = 8.8 Hz, 1 H), 7.46 (d, J = 8.8 Hz, 1 H), 7.43 (s, 1 H), 7.21 (d, J = 8.4 Hz, 1 H), 5.25 (s, 2 H), 3.93-3.88 (m, 2 H), 3.78 (s, 3 H), 2.48 (s, 3 H), 1.33 (t, J = 6.8 Hz, 3H). | 360.2 [M + 1] | D | | D |
| 323 | $^1$H NMR (400 MHz, DMSO-d$_6$): 13.07 (brs, 1 H), 8.25 (d, J = 7.2 Hz, 1 H), 8.08 (d, J = 8.8 Hz, 1 H), 7.86-7.78 (m, 1 H), 7.68 (d, J = 8.8 Hz, 1 H), 7.47 (d, J = 8.8 Hz, 1 H), 7.39-7.35 (m, 1 H), 5.50 (s, 2 H), 4.97 (s, 1 H), 4.07 (s, 1 H), 3.77-3.69 (m, 2 H), 1.19 (d, J = 6.0 Hz, 3 H) | 362.2 [M + 1] | A | | A |
| 324 | $^1$H NMR (400 MHz, DMSO-d$_6$): δ 12.91 (brs, 1 H), 8.13 (d, J = 8.8 Hz, 1 H), 8.12 (d, J = 8.4 Hz, 1 H), 7.51 (s, 1 H), 7.44 (d, J = 8.4 Hz, 1 H), 7.36 (d, J = 8.4 Hz, 1 H), 4.89 (s, 2 H), 2.73 (s, 3 H), 2.73 (s, 3 H), 1.36 (s, 9 H) | 387.1 [M + 1] | A | | A |
| 325 | $^1$H NMR (400 MHz, DMSO-d$_6$): 8.12 (d, J = 8.0 Hz, 1 H), 8.04 (d, J = 8.4 Hz, 1 H), 7.45-7.43 (m, 2 H), 7.19 (d, J = 8.0 Hz, 1 H), 5.33 (s, 2 H), 3.72 (d, J = 7.2 Hz, 2 H), 2.48 (s, 3 H), 1.33-1.29 (m, 1 H), 0.56-0.51 (m, 2 H), 0.34-0.30 (m, 2 H). | 372.3 [M + 1] | C | | C |
| 326 | $^1$H NMR (400 MHz, DMSO-d$_6$): 8.30 (d, J = 8.4 Hz, 1 H), 8.11 (d, J = 8.4 Hz 1 H), 7.55-7.50 (m, 4 H), 7.37-7.32 (m, 3 H), 7.15 (d, J = 8.0 Hz, 1 H), 4.34 (s, 2 H), 2.39 (s, 3 H). | 378.1 [M + 1] | A | | A |
| 327 | $^1$H NMR (400 MHz, DMSO-d$_6$): 13.02 (brs, 1 H), 8.17 (d, J = 8.4 Hz, 1 H), 8.06 (d, J = 8.8 Hz, 1 H), 7.49 (s, 1 H), 7.45 (d, J = 8.8 Hz, 1 H), 7.29 (d, J = 8.0 Hz, 1 H), 5.53 (s, 2 H), 4.95 (s, 1 H), 4.14-4.03 (m, 1 H), 3.79-3.66 (m, 2 H) 3.12-3.01 | 404.2 [M + 1] | D | | D |

TABLE 3-continued

| Cmpd No. | NMR Peak listings | Mass found | WT-hSWAT IC$_{50}$ (μM) | HAQ-hSWAT IC$_{50}$ (μM) | WT-mSWAT IC$_{50}$ (μM) |
|---|---|---|---|---|---|
|  | (m, 1 H), 1.27 (d, J = 6.8 Hz, 6 H), 1.21 (d, J = 6.4 Hz, 3 H), |  |  |  |  |
| 328 | $^1$H NMR (400 MHz, DMSO-d$_6$): 8·24 (d, J = 8.0 Hz, 1 H), 8.07 (d, J = 8.8 Hz, 1 H), 7.81 (t, J = 8.6 Hz, 1 H), 7.66 (d, J = 8.8 Hz, 1 H), 7.46 (d, J = 8.8 Hz, 1 H), 7.36 (d, J = 7.6 Hz, 1 H), 5.37 (s, 2 H), 3.94 (t, J = 5.0 Hz, 2 H), 3.76 (t, J = 5.0 Hz, 2 H) | 348.0 [M + 1] | D |  | D |
| 329 | $^1$H NMR (400 MHz, DMSO-d$_6$): 8.25 (dd, J = 1.6, 8.0 Hz, 1 H), 8.07 (d, J = 8.8 Hz, 1 H), 7.82-7.80 (m, 1 H), 7.62 (d, J = 8.8 Hz, 1 H), 7.47 (d, J = 8.8 Hz, 1 H), 7.37 (t, J = 7.2 Hz, 1 H), 5.28 (s, 2 H), 3.93 (t, J = 6.8 Hz, 2 H), 3.60 (1. J = 6 4 Hz, 2H), 1.99-1.94 (m, 2 H). | 362.0 [M + 1] | D |  | D |
| 330 | $^1$H NMR (400 MHz, DMSO-d$_6$): 8.22 (d, J = 9.6 Hz, 1 H), 8.07 (d, J = 8.8 Hz. 1 H), 7.73 (t, J = 8.4 Hz, 1 H), 7.62 (d, J = 8.4 Hz, 1 H), 7.36 (d, J = 8.4 Hz, 1 H), 7.28 (t, J = 7.2 Hz, 1 H), 4.94 (s, 2 H), 4.04 (t, J = 4.8 Hz, 2 H), 3.70 (t, J = 4.8 Hz, 2 H), 3.31 (s, 3 H). | 361.0 [M + 1] | D |  | D |
| 332 | $^1$H NMR (400 MHz, DMSO-d$_6$): 12 87 (brs, 1 H), 9.06 (s, 1 H), 8.11 (d, J = 8.8 Hz, 1 H), 8.04 (d, J = 8.8 Hz, 1 H), 7.32-7.37 (m, 3 H), 7.26-7.28 (m, 2 H), 6.98-7.03 (m, 3 H), 4.72 (s, 2 H), 2.11 (s, 6 H) | 422.1 [M + 1] | A |  | A |
| 333 | $^1$H NMR (400 MHz, DMSO-d$_6$): 12.60 (brs, 1 H), 7.93 (d, J = 8.8 Hz, 1 H), 7.77 (d, J = 7.6 Hz, 1 H), 7.46 (t, J = 7.6 Hz, 2 H), 7.37 (t, J = 8.0 Hz, 1 H), 5.24 (s, 2 H), 4.00 (s, 3 H), 3.87 (s, 3 H) | 348.0 [M + 1] | D |  | D |
| 334 | $^1$H NMR (400 MHz, DMSO-d$_6$): 12.74 (brs, 1 H), 8.69 (s, 1 H), 8.57 (s, 1 H), 8.37 (d, J = 8.4 Hz, 1 H), 8.25 (d, J = 8.0 Hz, 1 H), 7.89 (d, J = 7.6 Hz, 1 H), 7.74 (t, J = 7.6 Hz, 1 H), 7.62-7.55 (m, 2 H), 7.47 (d, J = 8.8 Hz, 1 H), 7.36 (t, J = 7.6 Hz, 1 H), 4.55 (s, 2 H) | 365.1 [M + 1] | D |  |  |
| 336 | $^1$H NMR (400 MHz, DMSO-d$_6$): 8.24 (d, J = 8.4 Hz, 1 H), 7.92 (d, J = 8.8 Hz, 1 H), 7.55-7.45 (m, 5 H), 7.35 (d, J = 6.4 Hz, 2 H), 6.60 (dd, J = 8.8 Hz, 1 H), 6.16 (s, 1 H), 4.34 (s, 2 H), 3.70-3.64(m, 1 H), 1.12 (d , J = 6.0, 6 H) | 421.2 [M + 1] | A |  |  |
| 338 | $^1$H NMR (400 MHz, CD$_3$OD): δ 8.23 (d, J = 8.4 Hz, 1 H), 8.14 (d, J = 8.8 Hz, 1 H), 7.34-7.36 (m, 2 H), 7.20 (d, J = 8.4 Hz, 1 H), 5.07 (s, 2 H), 3.85 (s, 3H), 2.53 (s, 3 H). | 356.1 [M + 1] | C |  |  |
| 339 | $^1$H NMR (400 MHz, DMSO-d$_6$): δ = 11.49 (s, 1H), 8.14 (d, J = 8.4 Hz, 1H), 8.06 (d, .J = 8.4 Hz, 1H), 7.44 (d, .J = 8.4 Hz, 1H), 7.37 (s, 1H), 7.20 (d, J = 8.0 Hz, 1H), 4.94 (s, 2 H), 3.77 (s, 3H), 3.68 (s, 3H), 2.49 (s, 3H). | 361.3 [M + 1] | D |  |  |
| 346 | $^1$H NMR (400 MHz, DMSO-d$_6$): δ 13.16 (s, 1 H), 8.26 (d, J = 8.0 Hz, 1 H), 7.80 (t, J = 7.6 Hz, 1 H), 7.68 (s, 1 H), 7.60 (d, J = 8.8 Hz, 1 H), 7.35 (d, J = 1.6 Hz, 1 H), 5.11 (s, 2 H), 3.98 (s, 3 H), 3.78 (s, 3 H) | 348.1 [M + 1] |  |  |  |
| 347 | $^1$H NMR (400 MHz, CD$_3$OD), δ 8.21 (d, J = 8.0 Hz, 1 H), 8.12 (d, J = 8.4 Hz, 1 H), 7.36-7.38 (m, 2 H), 7.20 (d, J = 8.4 Hz, 1 H), 5.06 (s, 2 H), 3.85 (s, 3H), 3.28 (s, 3H), 2.52 (s, 3H) | 409.1 [M + 1] | C |  |  |
| 348 | $^1$H NMR (400 MHz, CD$_3$OD), δ 8.23 (d, J = 8.4 Hz, 1 H), 8.14 (d, J = 8.8 Hz, 1 H), 7.35-7.40 (m, 2 H), 7.19 (d, J = 8.4 Hz, 1 H), 5.10 (s, 2 H), 3.89 (s, 3 H), 2.99-3.02 (m, 1 H), 2.53 (s, 3 H), 1.17-1.20 (m, 2 H), 0.96-1.01 (m, 2 H) | 435.3 [M + 1] | C |  |  |
| 349 | $^1$H NMR (400 MHz, DMSO-d$_6$): δ 12.15 (brs, 1 H), 8.14 (d, J = 6.4 Hz, 1 H), 8.04 (d, J = 7.2 Hz, 1 H), 7.44 (d, J = 7.2 Hz, 1 H), 7.31 (s, 1 H), 7.20 (d, J = 6.4 Hz, 1 H), | 423.2 [M + 1] | D |  |  |

TABLE 3-continued

| Cmpd No. | NMR Peak listmgs | Mass found | WT-hSWAT IC$_{50}$ (μM) | HAQ-hSWAT IC$_{50}$ (μM) | WT-mSWAT IC$_{50}$ (μM) |
|---|---|---|---|---|---|
| | 5.14 (s, 2 H), 3.73 (s, 3 H), 3.46-3.47 (m, 2 H), 2.48 (s, 3 H), 1.33 (t, 3 H) | | | | |
| 350 | $^1$H NMR (400 MHz, DMSO-d$_6$): δ 12.17 (br, 1 H), 8.24 (d, J = 8.8 HZ, 1 H), 8.11 (d, J = 8.0 Hz, 1 H), 7.65 (d, J = 8.8 Hz, 1 H), 7.43 (s, 1 H), 7.30 (s, J = 8.4 Hz, 1 H), 5.29 (s, 2 H), 3.07 (s, 3 H), 3.06-3.02 (m, 1 H), 1.28 (d, J = 6.8 Hz, 6 H) | 485.0 [M + 1] | C | | |
| 351 | $^1$H NMR (400 MHz, DMSO-d$_6$): δ 12.60 (br, 1 H), 8.19 (d, J = 8.8 Hz, 1 H), 8.10 (d, J = 8.0 Hz, 1 H), 7.81 (d, J = 8.0 Hz, 2 H), 7.60 (d, 7.2 Hz, 1 H), 7.42 (d, J = 8.0 Hz, 2 H), 7.28 (d, 8.0 Hz, 1 H), 7.13 (s, 1 H), 5.96 (s, 2 H), 2.94-2.87 (m, 1 H), 2.35 (s, 3 H), 1.18 (d, J = 6.8 Hz, 6 H) | 517.2 [M + 1] | B | | |
| 352 | $^1$H NMR (400 MHz, DMSO-d$_6$): δ 12.28 (br, 1 H), 8.24 (d, J = 8.4 Hz, 1 H), 8.14 (d, J = 8.0 Hz, 1 H), 7.66 (d, J = 8.4 Hz, 1 H), 7.37 (s, 1 H), 7.33 (d, J = 8.4 Hz, 1 H), 5.22 (s, 2 H), 3.21 (s, 3 H), 3.06-3.03 (m, 1 H), 1.27 (d, J = 6.8 Hz, 6 H) | 441.3 [M + 1] | B | | |
| 353 | $^1$H NMR (400 MHz, DMSO-d$_6$): δ 10.88 (s, 1 H), 8.98 (s, 1 H), 8.17-8.25 (m, 2 H), 7.80-7.83 (m, 1 H), 7.63 (d, J = 8.4 Hz, 2 H), 7.38 (t, 7.6 Hz, 1 H), 5.00 (s, 2 H) | 337.0 [M + 1] | C | | |

WT_FBA_HIS-SUMO-hSWAT IC50 (μM); HAQ_FBA_HIS-SUMO-hSWAT IC50 (μM); and MOUSE_FBA_HIS-SUMO-mSWAT IC50 (μM): "A" < 20 μM; "B" = 20-100 μM; "C" = 100-300 μM; "D" > 300 μM.

Example 63: STING Differential Scanning Fluorimetry (DSF) Assay

A STING DSF assay was performed to determine protein thermostability shift in response to small molecule ligand binding. A STING thermostability shift assay based on differential scanning fluorimetry was used to measure (1) the net shift in melting temperature $(\Delta T_m)_{between}$ the apo and ligand-bound states of the STING protein and (2) the concentration of the thermal denaturation transition (EC50) as a surrogate measure of binding affinity (K). Briefly, recombinant mouse or human STING protein (aa140-379) comprising the C-terminal binding domain (R232-WT or HAQ isoforms) were purified by affinity chromatography and further processed to remove the purification tag, followed by gel filtration to achieve purity >95%. Protein in assay buffer was transferred to a 384 well plate and incubated with the hydrophobic fluorescent dye SYBR Orange. A temperature ramp was applied to the plate and the resulting dye fluorescence was plotted as a function of temperature. The first derivative of this function (dF/dT) was then used to extrapolate the melting temperature of the protein at various concentrations of compound and determine the thermal denaturation profile of a protein/compound complex.

Assay Parameters Optimized
1. Protein construct (affinity tag removal vs SUMO-fusion construct)
2. Protein concentration
3. Dye concentration
4. Buffer
5. Thermal ramp velocity
6. DMSO tolerance
7. Compound titration parameters
8. HPE and ZPE controls Final Assay Parameters
1. hSTING-R232 or hSTING-HAQ (aa140-379), mSTING-R232 (aa139-378)
2. 5 μM purified Target STING Protein
3. 8 μM Sypro Orange Dye
4. Buffer: 100 mM NaCl, 30 mM HEPES, pH 7.5
5. Thermal Ramp: 0.5° C./min
6. <1% DMSO
7. 11 point, 2 fold dilution, duplicate, 300 μM high concentrations
8. HPE (100 μM 2'3'cGAMP), ZPE (DMSO 1%)

Biological activities based on DSF assay of the compounds of the present application are depicted in Table 4 below.

TABLE 4

| Cmpd No. | WT_DSF_hSWAT Tm Shift (° C.) | HAQ_DSF_hSWAT Tm Shift (° C.) | MOUSE DSF_6xHIS-SUMO Tm Shift (° C.) |
|---|---|---|---|
| 13 | B | | C |
| 100 | A | | |
| 101 | A | | |
| 108 | C | | C |
| 109 | B | | B |
| 110 | D | D | D |
| 111 | D | D | C |
| 112 | B | | C |
| 113 | C | C | D |
| 115 | C | C | D |
| 122 | C | | D |
| 125 | C | | B |
| 130 | B | | C |
| 131 | A | | A |
| 132 | A | | A |
| 133 | A | | B |
| 134 | A | | |
| 135 | A | | B |
| 136 | D | | |
| 137 | C | | |
| 138 | C | | C |

TABLE 4-continued

| Cmpd No. | WT_DSF_hSWAT Tm Shift (° C.) | HAQ_DSF_hSWAT Tm Shift (° C.) | MOUSE DSF_6xHIS-SUMO Tm Shift (° C.) |
|---|---|---|---|
| 139 | C | | D |
| 140 | C | | D |
| 141 | | | A |
| 142 | C | | C |
| 143 | B | | B |
| 144 | C | | C |
| 145 | A | | A |
| 146 | | | B |
| 147 | D | D | D |
| 148 | C | | C |
| 149 | C | | |
| 150 | C | | C |
| 151 | B | C | C |
| 152 | C | | C |
| 153 | C | | D |
| 154 | C | | D |
| 155 | C | | D |
| 156 | B | | C |
| 157 | C | | D |
| 158 | C | | D |
| 159 | A | A | C |
| 160 | B | B | D |
| 161 | B | B | D |
| 162 | A | | C |
| 163 | C | | D |
| 164 | B | B | D |
| 165 | B | | C |
| 166 | B | | |
| 167 | A | | |
| 168 | A | | |
| 169 | C | | C |
| 170 | B | | C |
| 171 | A | | B |
| 172 | A | | A |
| 173 | B | | C |
| 174 | B | | B |
| 175 | D | | D |
| 176 | D | D | D |
| 177 | C | | |
| 178 | C | | C |
| 179 | A | | B |
| 180 | A | | B |
| 181 | D | | D |
| 182 | C | | |
| 183 | C | | |
| 184 | C | | |
| 186 | C | | |
| 187 | B | | |
| 188 | A | | |
| 189 | C | | C |
| 190 | C | | |
| 191 | B | | |
| 192 | A | | B |
| 193 | A | | |
| 194 | C | | |
| 195 | C | | |
| 196 | D | | |
| 197 | C | | |
| 198 | C | | |
| 201 | C | | |
| 202 | C | | |
| 203 | C | | |
| 204 | D | D | |
| 205 | A | | |
| 206 | D | | D |
| 207 | D | D | D |
| 209 | A | | |
| 210 | A | | |
| 212 | C | | |
| 213 | C | | |
| 214 | D | | |
| 215 | D | D | |
| 216 | C | | D |
| 217 | D | D | |
| 218 | | D | D |
| 219 | D | | |
| 220 | D | D | |
| 221 | D | D | |
| 223 | C | D | |
| 225 | D | | D |
| 226 | C | | |
| 227 | C | | |
| 228 | C | | |
| 229 | B | | |
| 231 | D | | D |
| 232 | D | | D |
| 233 | D | | |
| 234 | D | | D |
| 235 | D | | D |
| 236 | D | | |
| 238 | D | | |
| 243 | A | | |
| 244 | D | | C |
| 245 | D | | |
| 246 | C | | |
| 247 | A | | |
| 248 | B | | |
| 249 | B | | |
| 250 | D | | D |
| 251 | D | | D |
| 252 | D | | |
| 253 | D | | |
| 254 | D | | |
| 255 | C | | |
| 256 | C | | |
| 257 | D | | D |
| 258 | D | | |
| 259 | D | | |
| 260 | D | | |
| 261 | C | | |
| 262 | D | | D |
| 263 | D | | D |
| 264 | C | | |
| 265 | B | | |
| 266 | D | | D |
| 267 | D | | D |
| 268 | C | | |
| 269 | D | | D |
| 270 | D | | D |
| 271 | D | | |
| 272 | B | | |
| 273 | C | | |
| 274 | D | | D |
| 275 | D | | |
| 276 | D | | |
| 277 | D | | |
| 278 | D | | |
| 279 | D | | |
| 280 | D | | |
| 281 | D | | |
| 282 | D | | |
| 283 | C | | |
| 284 | C | | |
| 285 | D | | |
| 286 | D | | |
| 287 | B | | |
| 288 | D | | D |
| 289 | D | | C |
| 290 | D | | |
| 291 | D | | D |
| 292 | D | | D |
| 293 | D | | D |
| 294 | D | | C |
| 295 | A | | |
| 296 | A | | |
| 297 | D | | D |
| 298 | D | | D |
| 299 | C | | |
| 300 | C | | |
| 301 | C | | |
| 302 | A | | |
| 303 | C | | |
| 304 | D | | |
| 305 | B | | |

TABLE 4-continued

| Cmpd No. | WT_DSF_hSWAT Tm Shift (° C.) | HAQ_DSF_hSWAT Tm Shift (° C.) | MOUSE DSF_6xHIS-SUMO Tm Shift (° C.) |
|---|---|---|---|
| 306 | D | | D |
| 307 | D | | D |
| 308 | D | | D |
| 309 | D | | C |
| 310 | A | | A |
| 311 | D | | C |
| 312 | B | | B |
| 313 | B | | |
| 314 | C | | C |
| 315 | B | | |
| 316 | B | | |
| 317 | B | | |
| 318 | C | | B |
| 319 | A | | |
| 320 | A | | |
| 321 | B | | |
| 322 | B | | |
| 323 | D | | D |
| 324 | D | | D |
| 325 | C | | C |
| 326 | D | | D |
| 327 | C | | C |
| 328 | B | | C |
| 329 | B | | C |
| 330 | B | | B |
| 332 | D | | D |
| 333 | B | | B |
| 334 | C | | |
| 336 | D | | |
| 338 | C | | |
| 339 | B | | |
| 347 | C | | |
| 348 | C | | |
| 349 | C | | |
| 350 | C | C | |
| 351 | A | A | |
| 352 | C | | |
| 353 | A | | |

WT_DSF_hSWAT Tm Shift (° C.) and HAQ_DSF_hSWAT Tm Shift (° C.): "A" < 0° C.; "B" = 0-2° C.; "C" = 2-7° C.; "D" > 7° C.
MOUSE DSF_6xHIS-SUMO Tm Shift (° C.): "A" < 0° C.; "B" = 0-5° C.; "C" = 5-15° C.; "D" > 15° C.

Example 64: Cell Based Reporter Assays of IRF or IFN-Beta Activation

Cell reporter assays were developed to measure the ability of compounds of the application to agonize the STING protein and activate both IRF/IFN and the NFkB signaling pathways in the myeloid derived cell line THP-1, which is commercially available from several suppliers. Briefly, THP-1 monocytes were transfected and selected for stable integration of 2 reporter constructs. Clones incorporating stably integrated vectors were further selected by antibiotic resistance to blastocidin and zeocin. The reporter constructs included: (1) firefly luciferase reporter gene under the control of an ISG54 promoter fused to five interferon (IFN)-stimulated response elements to measure IRF transcription factor binding activity and (2) secreted embryonic alkaline phosphatase reporter gene under transcription control of an IFN-beta minimal promoter fused to 5 copies of the NFkB consensus transcriptional response element and 3 copies of the c-Rel binding site.

The resulting THP-1 cell line was further modified to incorporate 3 amino acid point mutations (H71R A230G Q293R). This modification of the native TMEM173 gene in THP-1 cells (HAQ) was designed to produce a cell reporter that expressed the most common allelic variant in the human population (THP-1 R232, available from InvivoGen). Alternatively, the TMEM173 gene was knocked out to provide a congenic control to counter-screen for compound activation that was independent of the STING protein (THP-1 STING KO).

Once cell lines were established, reporter assay protocols were developed and optimized to screen small molecule compounds for agonist activity. Assay optimization for efficacy and Z' value included titration of the following parameters:

Assay Optimization Parameters
1. Cell pre-activation with PMA
2. Cell seeding density
3. DMSO tolerance
4. Media selection
5. FBS concentration
6. Incubation time
7. Co-Assessment of cell viability by CTG assay
8. Appropriate HPE and ZPE controls
9. Dose Response Titration Final Assay SOP Conditions
1. No pre-activation with PMA
2. 5×10^4 cells/well in 96 well plate format
3. <0.5% DMSO
4. RPMI 1640+2.5 mg/ml glucose
5. 10% FBS
6. 14-18 hr incubation
7. Cell Titer Glo reagent (Promega) following supernatant removal
8. $HPE_{IRF}$ (100 μM 2'3'cGAMP), $HPE_{NFkB}$ (50 nM PM3CSK4), ZPE (DMSO 0.5%)
9. 8 point, 2 fold, duplicate starting at 150 μM Assay Performance

| | Z' Value (IRF-luc) | | Z' Value (NFkB-SEAP) | |
|---|---|---|---|---|
| Cell Line | Z' | Assay Window | Z' | Assay Window |
| THP-1 | 0.91 | >200 | 0.82 | >15 |
| THP-1 R232 | 0.86 | >120 | 0.96 | >30 |
| THP-1 STING KO | N/A | N/A | 0.91 | >30 |

Biological activities based on the cell reporter assays for the compounds of the present application are depicted in Table 5 below.

TABLE 5

| Cmpd No. | THP1-dual-KI R232_IRF(Luciferase) IC50 (uM) | THP1-dual-KI R232_IRF(Luciferase)_Activity Maximum measured (%) |
|---|---|---|
| 108 | C | B |
| 109 | D | A |
| 110 | B | D |
| 111 | B | D |
| 112 | C | B |
| 113 | B | B |
| 115 | B | C |
| 122 | B | D |
| 125 | C | A |
| 132 | D | A |
| 134 | D | A |
| 135 | D | A |
| 137 | C | C |
| 138 | B | D |
| 139 | C | A |
| 140 | B | B |
| 142 | D | A |
| 144 | D | A |

TABLE 5-continued

| Cmpd No. | THP1-dual-KI R232_IRF(Luciferase) IC50 (uM) | THP1-dual-KI R232_IRF(Luciferase)_Activity Maximum measured (%) |
|---|---|---|
| 145 | D | A |
| 147 | B | D |
| 148 | C | C |
| 149 | C | A |
| 150 | D | B |
| 151 | C | A |
| 152 | A | B |
| 153 | A | B |
| 154 | D | B |
| 155 | B | A |
| 156 | D | A |
| 157 | B | A |
| 158 | B | A |
| 159 | A | B |
| 160 | B | B |
| 161 | D | A |
| 162 | D | A |
| 163 | B | B |
| 169 | B | D |
| 170 | C | C |
| 171 | D | A |
| 174 | D | A |
| 175 | C | D |
| 176 | A | D |
| 177 | D | A |
| 181 | B | D |
| 183 | B | C |
| 186 | D | C |
| 189 | D | B |
| 192 | D | A |
| 197 | D | A |
| 201 | C | B |
| 202 | C | B |
| 203 | B | D |
| 204 | A | D |
| 207 | B | D |
| 210 |   | A |
| 215 | A | D |
| 216 | B | D |
| 217 | B | D |
| 218 | C | D |
| 220 | B | D |
| 221 | C | D |
| 223 | D | A |
| 225 | A | D |
| 227 |   | A |
| 228 |   | A |
| 229 |   | A |
| 231 | A | D |
| 232 | B | D |
| 233 | A | D |
| 234 | A | D |
| 235 |   | A |
| 238 | A | D |
| 243 |   | A |
| 244 | B | D |
| 250 | B | D |
| 251 | C | C |
| 254 | A | D |
| 253 | B | D |
| 257 |   | A |
| 258 | D | A |
| 261 | A | A |
| 262 | A | D |
| 263 | D | A |
| 264 | D | B |
| 265 |   | A |
| 266 | B | D |
| 267 | A | D |
| 268 | B | D |
| 269 | B | D |
| 270 | C | D |
| 271 | B | D |
| 272 |   | A |
| 273 | A | D |
| 274 | B | D |
| 275 | C | D |
| 276 | B | D |
| 277 | A | D |
| 278 | C | D |
| 279 | B | D |
| 280 | B | D |
| 281 | A | D |
| 282 | A | D |
| 283 |   | A |
| 284 | C | B |
| 285 | B | C |
| 286 | A | D |
| 287 | D | A |
| 288 | A | D |
| 289 | A | D |
| 290 | C | C |
| 291 | D | A |
| 292 | A | D |
| 293 | A | D |
| 294 | A | D |
| 295 | D | A |
| 296 | D | A |
| 297 | B | D |
| 298 | B | D |
| 299 | B | D |
| 300 | B | D |
| 301 | D | A |
| 302 | D | A |
| 303 | B | B |
| 304 | B | D |
| 305 | D | A |
| 306 | A | D |
| 307 | A | D |
| 308 | A | D |
| 309 | B | D |
| 310 | B | B |
| 311 | A | D |
| 312 | D | A |
| 313 | D | A |
| 314 | A | D |
| 315 | D | A |
| 316 | D | A |
| 317 | D | A |
| 318 | C | B |
| 319 | D | A |
| 320 | D | A |
| 321 | B | B |
| 322 | A | B |
| 323 | B | A |
| 324 | A | D |
| 325 | C | C |
| 326 | A | D |
| 327 | D | A |
| 328 | D | A |
| 329 | D | A |
| 330 | D | A |
| 332 | A | D |
| 333 | B | B |
| 334 | D | A |
| 336 | A | D |
| 338 | C | C |
| 339 | A | C |
| 347 | A | D |
| 348 | A | D |
| 349 | A | D |
| 350 | D | A |
| 351 | D | A |
| 352 | B | D |

THP1-dual-KI R232_IRF(Luciferase) IC50 (μM): "A" < 50 μM; "B" = 50-100 μM; "C" = 100-150 μM; "D" > 150 μM.
THP1-dual-KI R232_IRF(Luciferase)_Activity Maximum measured (%): "A" < 5%; "B" = 5-25%; "C" = 25-50%; "D" > 50%.

EQUIVALENTS

Those skilled in the art will recognize, or be able to ascertain using no more than routine experimentation, many equivalents to the specific embodiments and methods described herein. Such equivalents are intended to be encompassed by the scope of the present application.

All patents, patent applications, and literature references cited herein are hereby expressly incorporated by reference.

The invention claimed is:

1. A compound of Formula I:

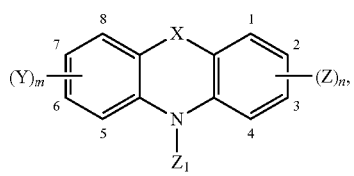

(I)

or a pharmaceutically acceptable salt or ester thereof, wherein

X is $C(R_X)_2$, O, S, CH=CH, or a bond;

each $R_X$ is independently H, $CH_3$, $CF_3$, $CF_2H$, or F, or two $R_X$ together form =O, =$CH_2$, or =$CF_2$, or two $R_X$, together with the carbon atom to which they are bonded, form a cyclopropyl;

$Z_1$ is $(C(R_Z)_2)_p$-$T_1$;

p is 1, 2, 3, 4, 5, or 6;

each $R_Z$ is independently H, $C_1$-$C_4$ alkyl, $C_1$-$C_4$ alkyl substituted with one or more halogen, or halogen;

$T_1$ is $C(O)R_1$, $C(O)OR_1$, $C(O)N(R_1)_2$, $NR_1C(O)R_1$, $C(S)R_1$, $C(S)N(R_1)_2$, $NR_1C(S)R_1$, $C(O)NHS(O)_2R_S$, $C(O)NHCOR_1$, $C(O)NHOH$, or $C(O)NHCN$;

$R_S$ is $R_1$, $C_3$-$C_8$ cycloalkyl, heterocyclyl comprising one 5- or 6-membered rings and 1-2 heteroatoms selected from N, O, and S, or $C_6$-$C_{10}$ aryl, wherein the cycloalkyl, heterocyclyl, or aryl is optionally substituted with one or more groups independently selected from $C_1$-$C_4$ alkyl;

each $R_1$ is independently H, $C_1$-$C_4$ alkyl, or $C_1$-$C_4$ alkyl substituted with one or more halogen;

m is 0, 1, or 2;

each Y is independently $C_1$-$C_6$ alkyl, $C_2$-$C_6$ alkenyl, $C_2$-$C_6$ alkynyl, halogen, CN, OH, O—($C_1$-$C_6$ alkyl), S—($C_1$-$C_6$ alkyl), O—($C_2$-$C_4$ alkenyl), O—($C_2$-$C_4$ alkynyl), $NH_2$, NH—$C_1$-$C_6$ alkyl, N—($C_1$-$C_6$ alkyl)$_2$, S(O)—($C_1$-$C_6$ alkyl), S(O)$_2$—($C_1$-$C_6$ alkyl), or Q-T, wherein the alkyl, alkenyl, or alkynyl moiety is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$, or two Y, together with the two adjacent carbon atoms to which they are bonded, form a 5- to 7-membered carbocycle or phenyl;

n is 2, 3, or 4;

each Z is independently $C_1$-$C_6$ alkyl, $C_2$-$C_6$ alkenyl, $C_2$-$C_6$ alkynyl, halogen, OH, O—($C_1$-$C_6$ alkyl), S—($C_1$-$C_6$ alkyl), O—($C_2$-$C_4$ alkenyl), O—($C_2$-$C_4$ alkynyl), $NH_2$, NH—$C_1$-$C_6$ alkyl, N—($C_1$-$C_6$ alkyl)$_2$, S(O)—($C_1$-$C_6$ alkyl), S(O)$_2$—($C_1$-$C_6$ alkyl), or Q-T, wherein the alkyl, alkenyl, or alkynyl moiety is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$;

each Q is independently a bond, NH, N($C_1$-$C_3$ alkyl), O, S, S(O), S(O)$_2$, Q', NH-Q', N($C_1$-$C_3$ alkyl)-Q', O-Q', S-Q', S(O)-Q', or S(O)$_2$-Q';

each Q' is independently a carbon linker comprising one or more $C(R_Q)_2$, $C(R_Q)_2$—$C(R_Q)_2$, $CR_Q$=$CR_Q$, or C≡C;

each $R_Q$ is independently H or $C_1$-$C_3$ alkyl;

each T is independently C(O)—$C_1$-$C_6$ alkyl, C(O)O—$C_1$-$C_6$ alkyl, $C_3$-$C_8$ cycloalkyl, $C_3$-$C_8$ cycloalkenyl, heterocyclyl comprising one or two 5- or 6-membered rings and 1-4 heteroatoms selected from N, O, and S, $C_6$-$C_{10}$ aryl, or heteroaryl comprising one or two 5- or 6-membered rings and 1-4 heteroatoms selected from N, O, and S, wherein the cycloalkyl, cycloalkenyl, heterocyclyl, aryl, or heteroaryl is optionally substituted with one or more $R_T$;

each $R_T$ is independently $C_1$-$C_6$ alkyl, $C_1$-$C_6$ haloalkyl, OH, CN, halogen, O—($C_1$-$C_6$ alkyl), O—($C_1$-$C_6$ haloalkyl), S—($C_1$-$C_6$ alkyl), $NH_2$, NH—$C_1$-$C_6$ alkyl, N—($C_1$-$C_6$ alkyl)$_2$, $NHS(O)_2$—($C_1$-$C_6$ alkyl), $(CH_2)_q$—$C_3$-$C_8$ cycloalkyl, $(CH_2)_q$-heterocyclyl, $(CH_2)_q$-phenyl, or $(CH_2)_q$-heteroaryl, wherein the heterocyclyl or heteroaryl comprises one or two 5- or 6-membered rings and 1-4 heteroatoms selected from N, O, and S; and q is 0, 1, 2, or 3, and wherein the compound of Formula I is substituted with Z at least at the 3-position and the 4-position.

2. The compound of claim 1, wherein X is $C(R_X)_2$.

3. The compound of claim 1, wherein each $R_X$ is H.

4. The compound of claim 1, wherein two $R_X$ together form =O, =$CH_2$, or =$CF_2$.

5. The compound of claim 1, wherein two $R_X$ together form =O.

6. The compound of claim 1, wherein each $R_Z$ is H, $C_1$-$C_4$ alkyl, or halogen.

7. The compound of claim 1, wherein $T_1$ is $C(O)R_1$, $C(O)OR_1$, $C(O)N(R_1)_2$, or $NR_1C(O)R_1$.

8. The compound of claim 1, wherein $T_1$ is $C(O)OR_1$, $C(O)N(R_1)_2$, $C(O)NHS(O)_2R_S$, $C(O)NHCOR_1$, $C(O)NHOH$, or $C(O)NHCN$.

9. The compound of claim 1, wherein each $R_1$ is H.

10. The compound of claim 1, wherein m is 0 or 1.

11. The compound of claim 1, wherein at least one Y is $C_1$-$C_6$ alkyl, $C_2$-$C_6$ alkenyl, $C_2$-$C_6$ alkynyl, halogen, OH, O—($C_1$-$C_6$ alkyl), O—($C_2$-$C_4$ alkenyl), O—($C_2$-$C_4$ alkynyl), S—($C_1$-$C_6$ alkyl), S(O)—($C_1$-$C_6$ alkyl), S(O)$_2$—($C_1$-$C_6$ alkyl), $NH_2$, NH—$C_1$-$C_6$ alkyl, N—($C_1$-$C_6$ alkyl)$_2$, or Q-T, wherein the alkyl, alkenyl, or alkynyl is optionally substituted with one or more groups independently selected from OH, $NH_2$, $N_3$, halogen, O—($C_1$-$C_6$ alkyl), S—($C_1$-$C_6$ alkyl), NH—$C_1$-$C_6$ alkyl, and N—($C_1$-$C_6$ alkyl)$_2$.

12. The compound of claim 1, wherein two Y, together with the two adjacent carbon atoms to which they are bonded, form a cyclopentyl, cyclohexyl, cycloheptyl, cyclopentenyl, cyclohexenyl, cycloheptenyl, cyclopentynyl, cyclohexynyl, or cycloheptynyl.

13. The compound of claim 1, wherein at least one Z is Q-T, $C_1$-$C_6$ alkyl, halogen, OH, O—($C_1$-$C_6$ alkyl), O—($C_2$-$C_4$ alkenyl), O—($C_2$-$C_4$ alkynyl), S—($C_1$-$C_6$ alkyl), S(O)—($C_1$-$C_6$ alkyl), S(O)$_2$—($C_1$-$C_6$ alkyl), $NH_2$, NH—$C_1$-$C_6$ alkyl, or N—($C_1$-$C_6$ alkyl)$_2$.

14. The compound of claim 1, wherein at least one Z is halogen.

15. The compound of claim 1, wherein Q is NH, O, S, Q', NH-Q', N($C_1$-$C_3$ alkyl)-Q', O-Q', S-Q', S(O)-Q', or S(O)$_2$-Q'.

16. The compound of claim 1, wherein Q' is a carbon linker comprising one or more $C(R_Q)_2$—$C(R_Q)_2$, $C(R_Q)_2$, and $CR_Q$=$CR_Q$.

17. The compound of claim 1, wherein T is cyclopropyl, cyclobutyl, cyclobutenyl, cyclopentyl, cyclopentenyl, cyclohexyl, cyclohexenyl, cycloheptyl, cycloheptenyl, cyclooctyl, or cyclooctenyl, each of which is optionally substituted with one or more $R_T$.

18. The compound of claim 1, wherein T is heterocyclyl comprising one or two 5- or 6-membered rings and 1-4 heteroatoms selected from N, O, and S or heteroaryl comprising one or two 5- or 6-membered rings and 1-4 heteroatoms selected from N, O, and S, each optionally substituted with one or more $R_T$.

19. The compound of claim 1, wherein T is $C_6$-$C_{10}$ aryl optionally substituted with one or more $R_T$.

20. The compound of claim 1, of Formula I5a1, I5b1, I5c1, or I5d1:

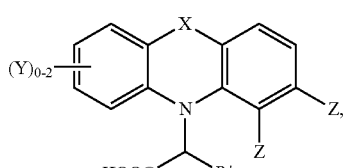
(I5a1)

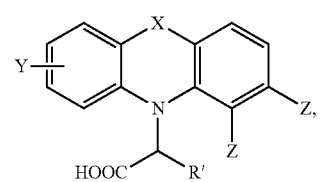
(I5b1)

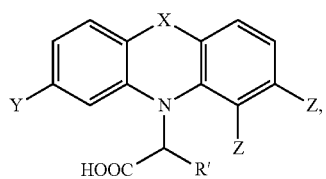
(I5c1)

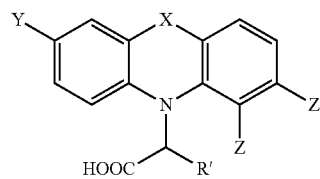
(I5d1)

or a pharmaceutically acceptable salt or ester thereof, wherein R' is H or methyl.

21. The compound of claim 1, selected from the following:

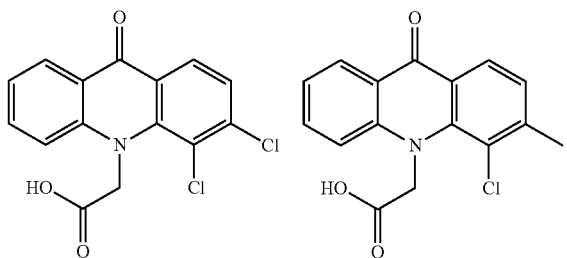

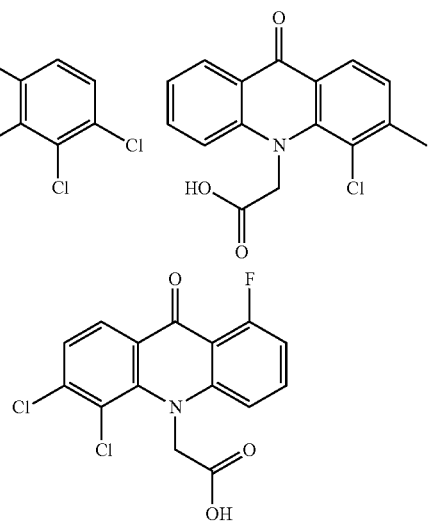

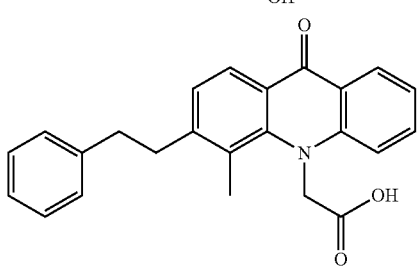

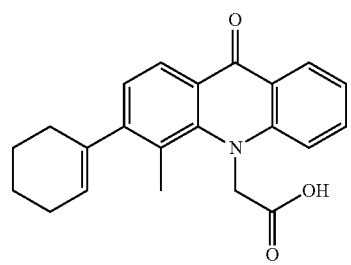

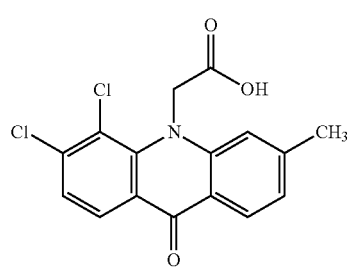

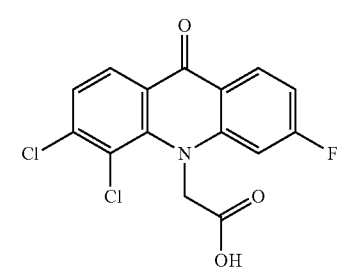

315
-continued
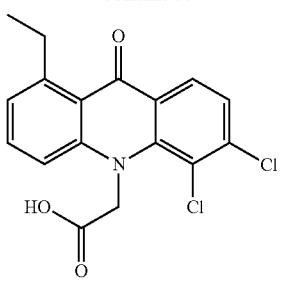
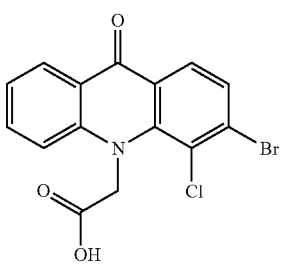
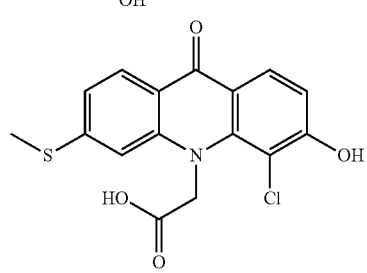
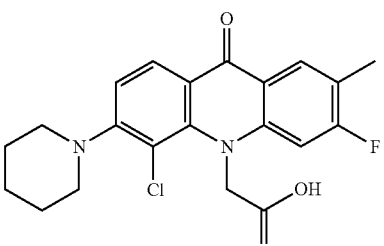
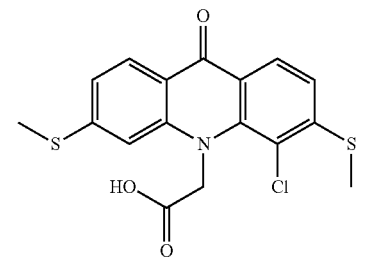
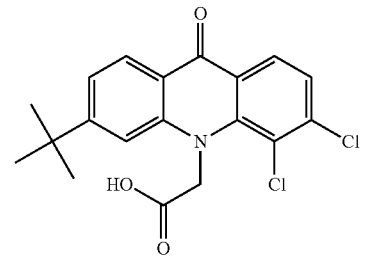
316
-continued
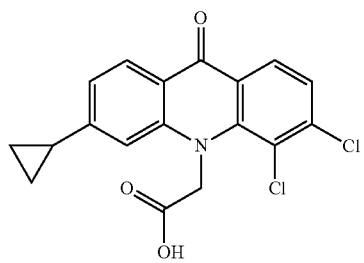
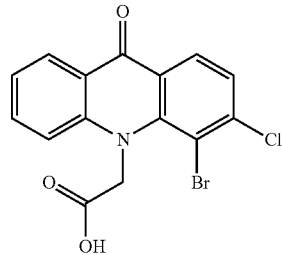
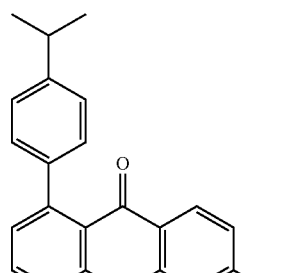
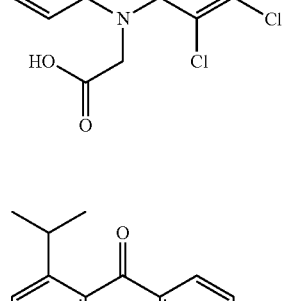
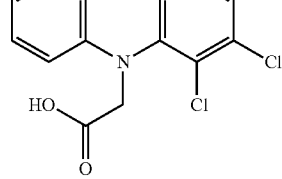
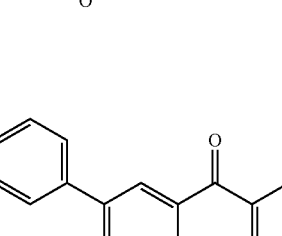

317
-continued
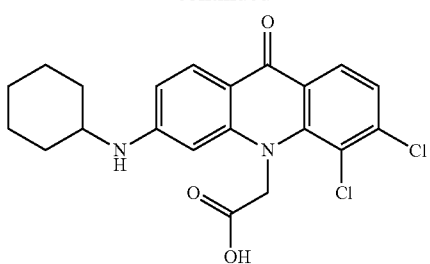
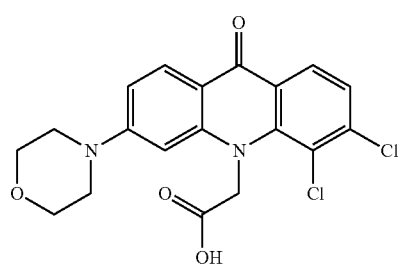
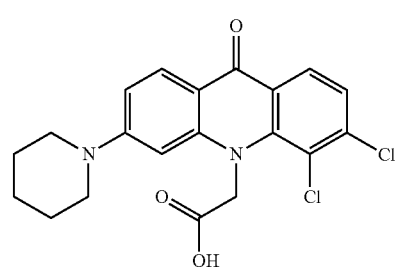
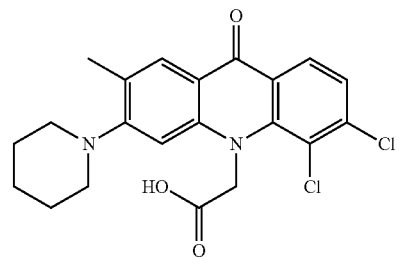
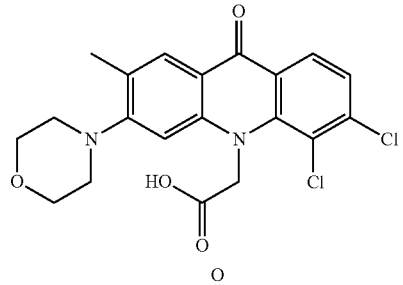
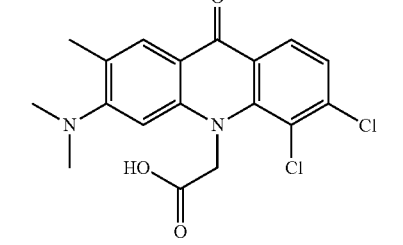
318
-continued
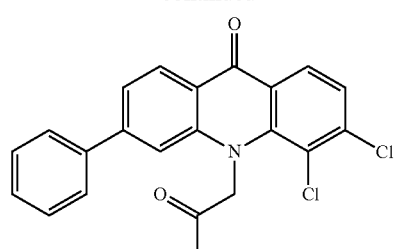
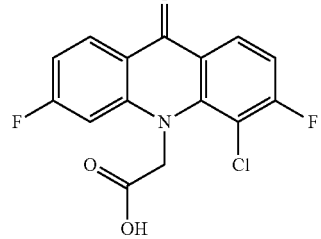
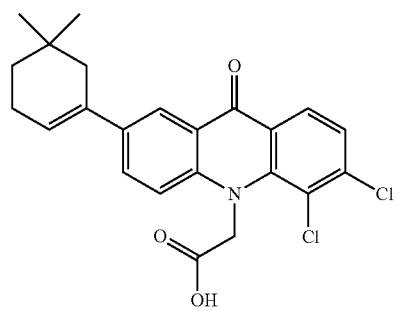
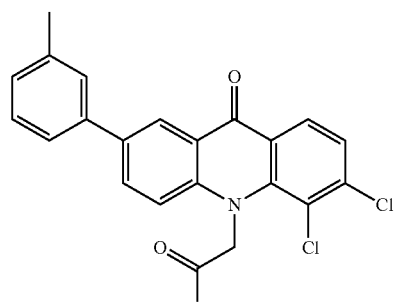
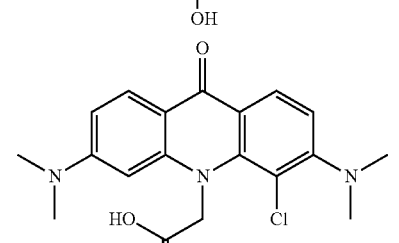
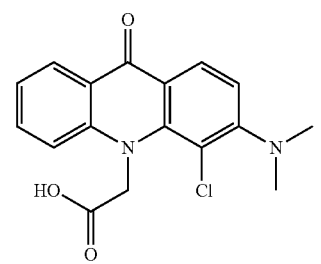

319
-continued
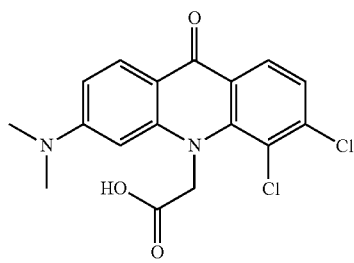
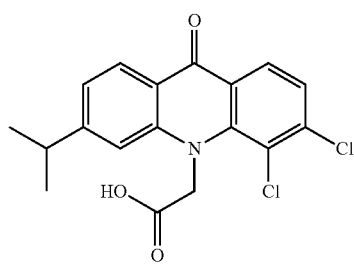
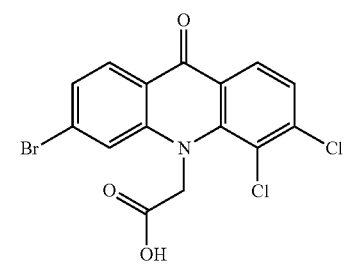
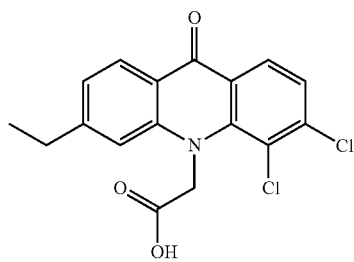
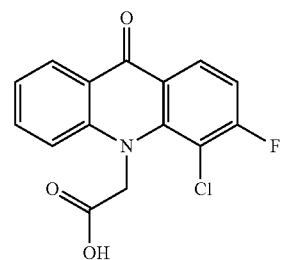
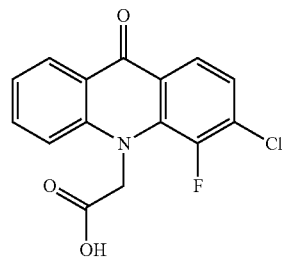
320
-continued
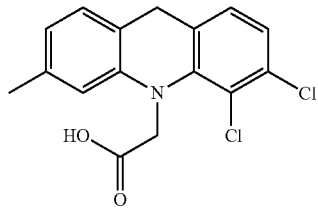
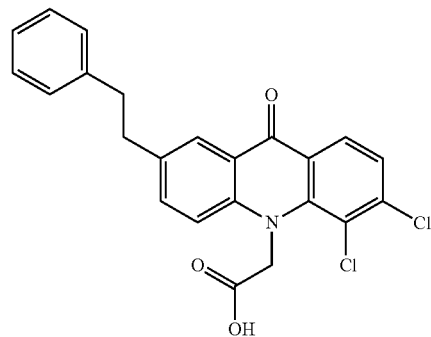
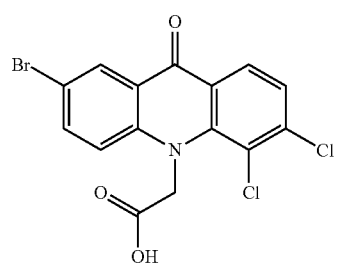
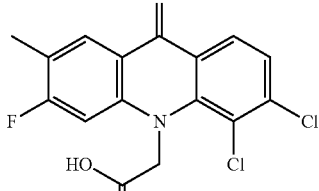
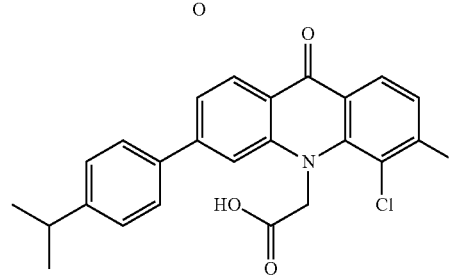
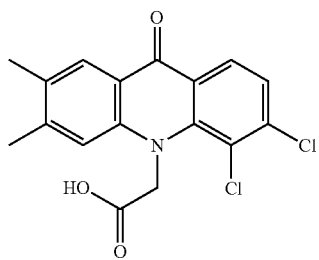

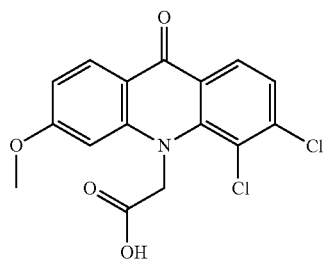
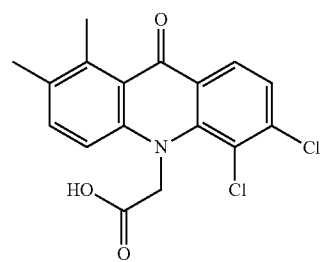
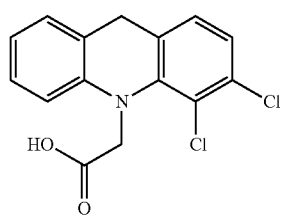
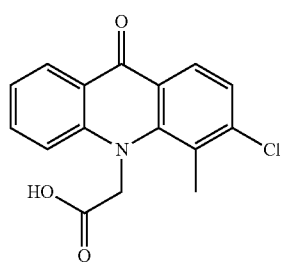
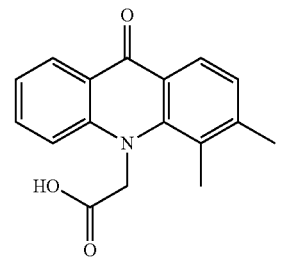
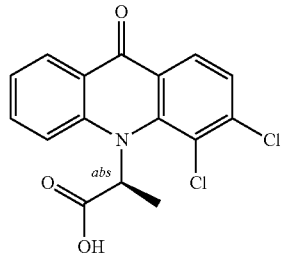
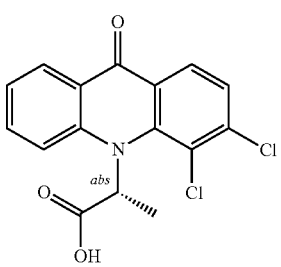
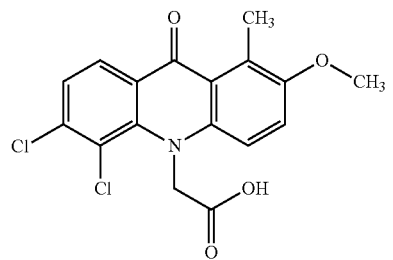
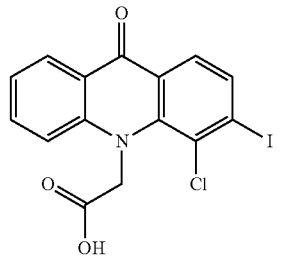
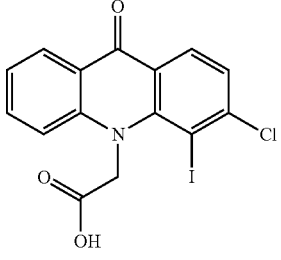
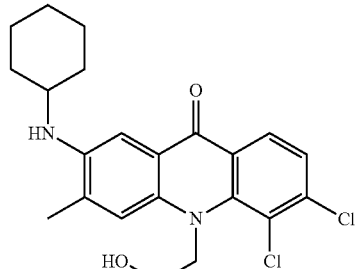
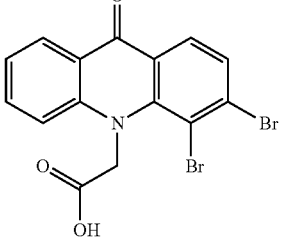

323
-continued
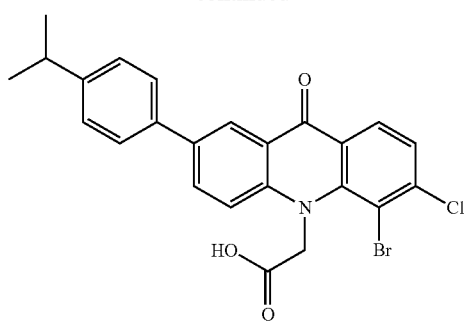
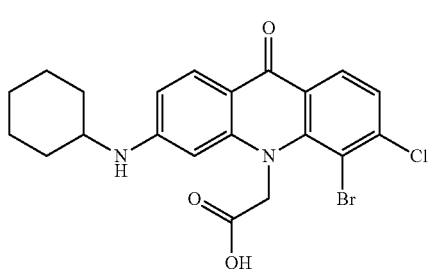
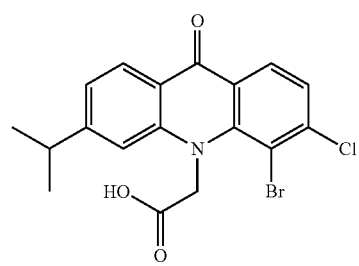
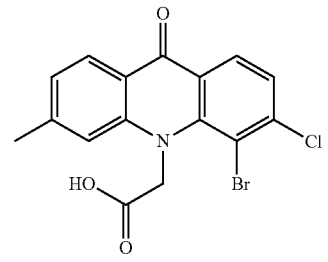
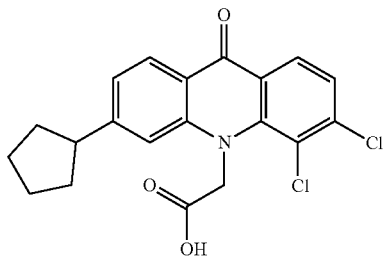
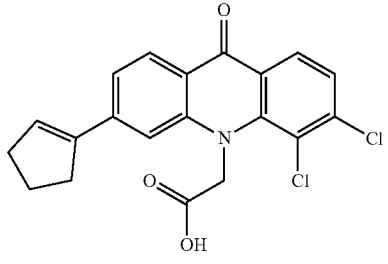
324
-continued
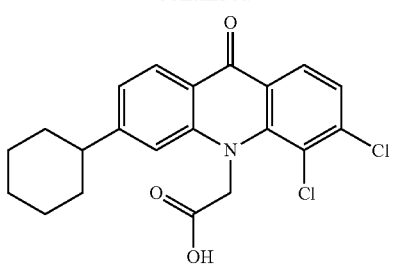
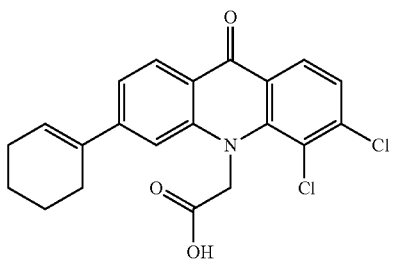
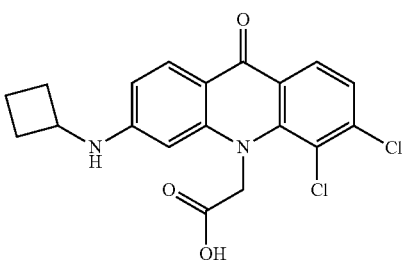
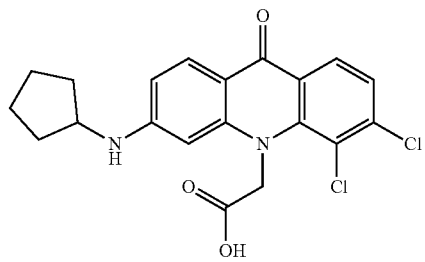
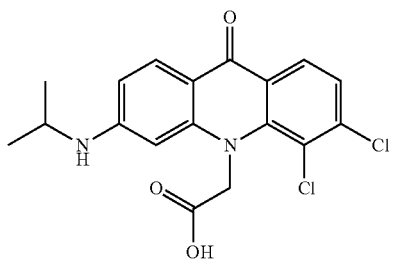
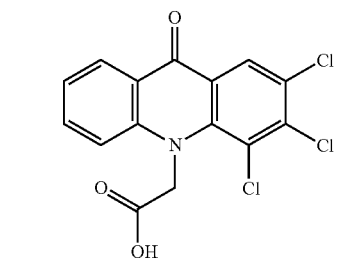

325
-continued
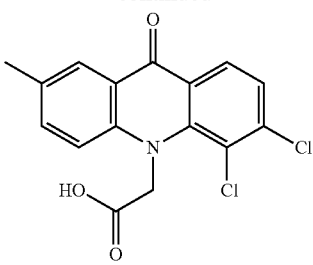
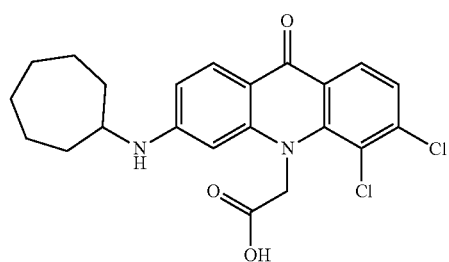
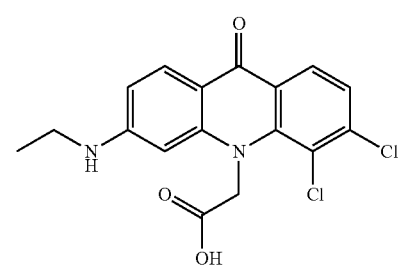
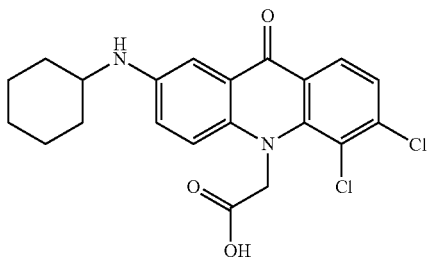
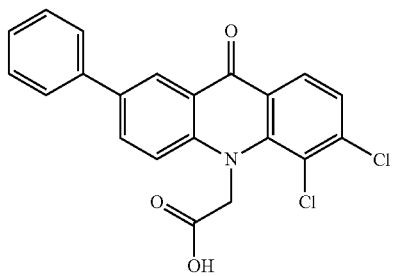
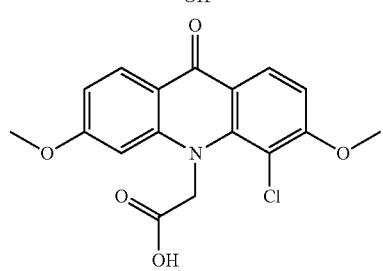
326
-continued
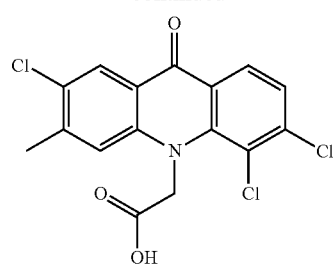
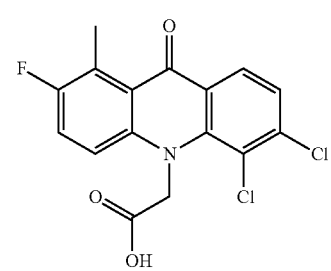
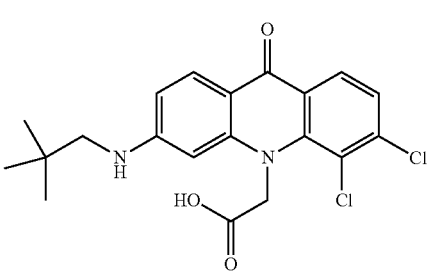
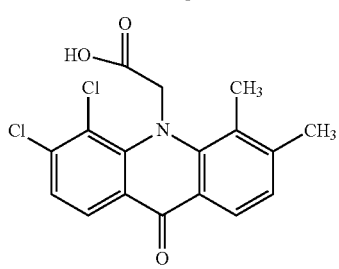
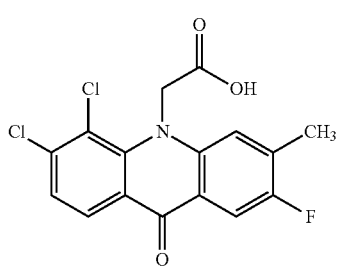
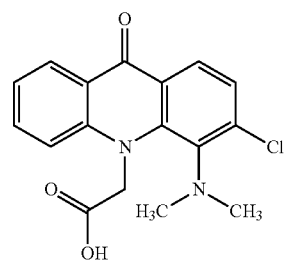

327
-continued
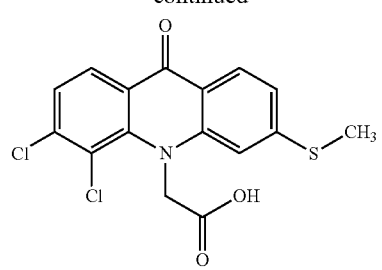
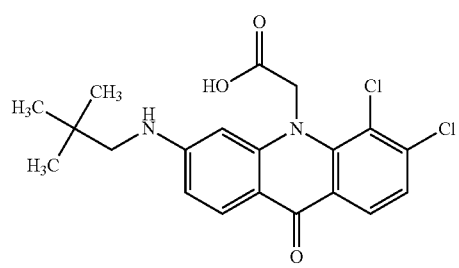
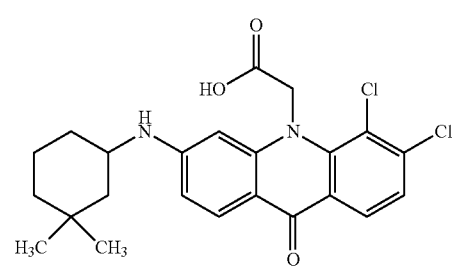
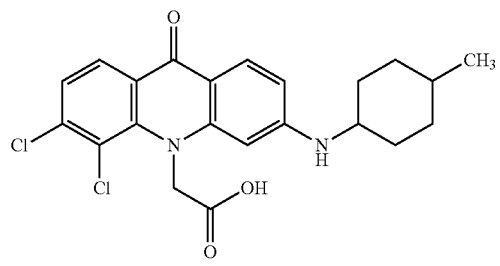
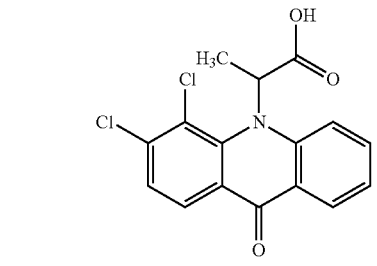
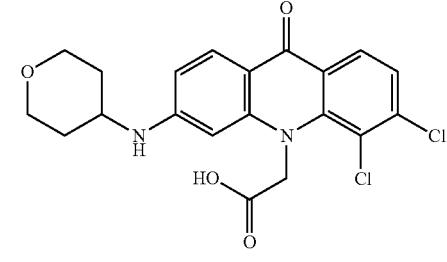
328
-continued
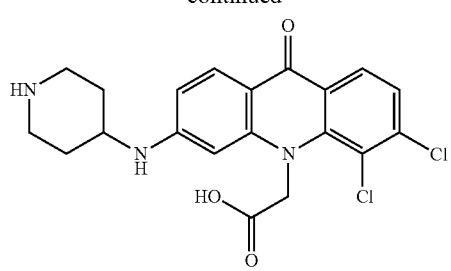
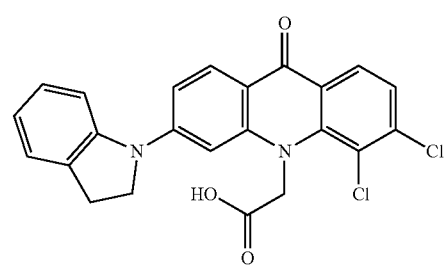
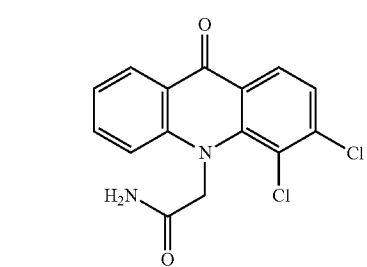
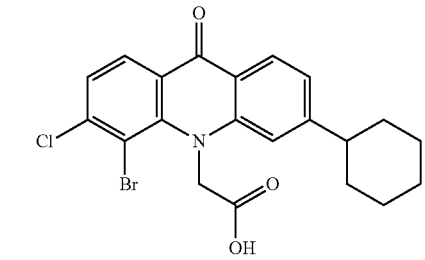
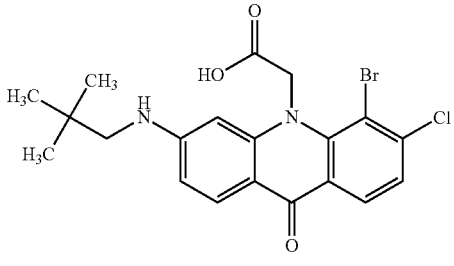
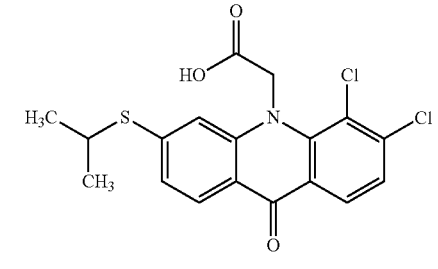

329
-continued
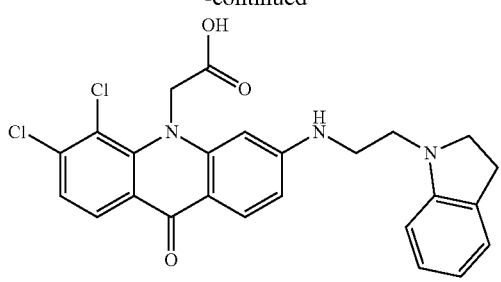
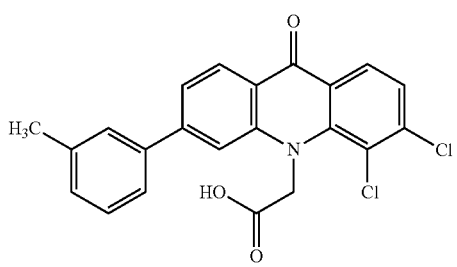
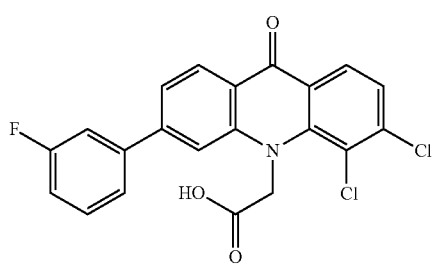
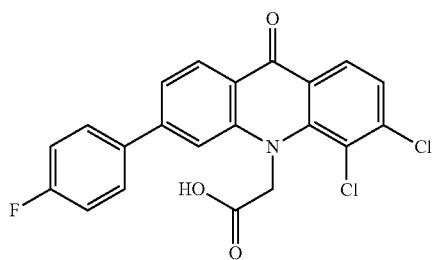
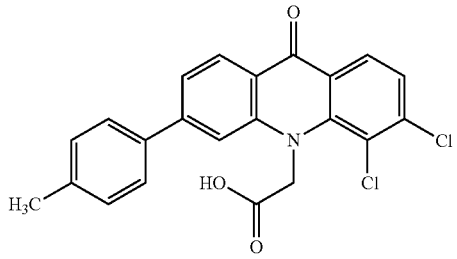
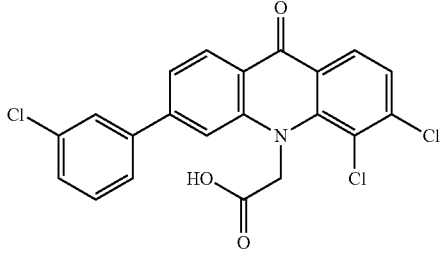
330
-continued
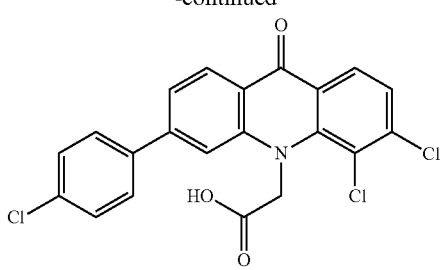
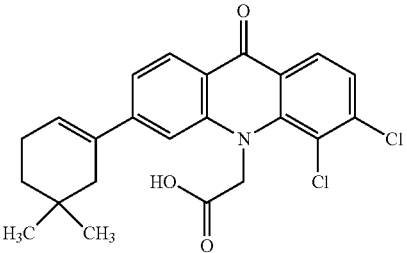
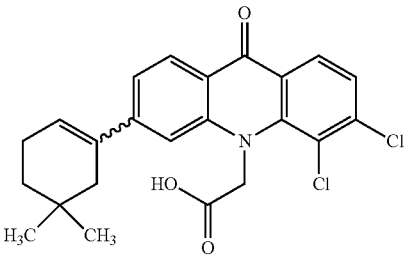
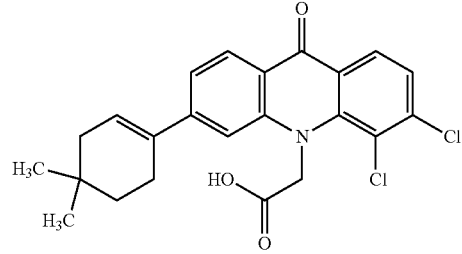
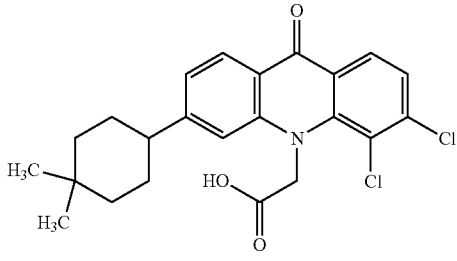

331
-continued
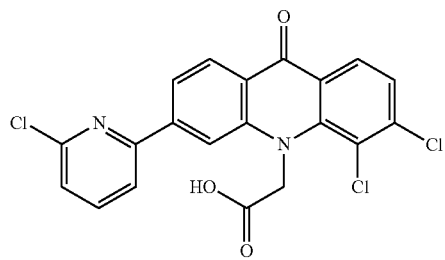
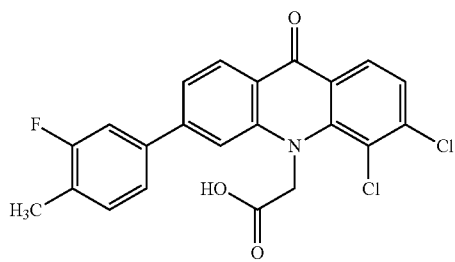
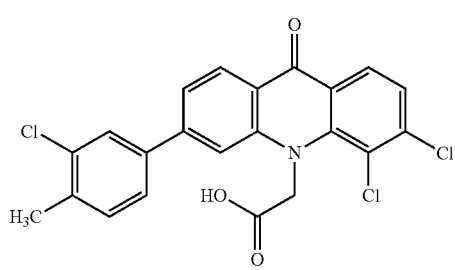
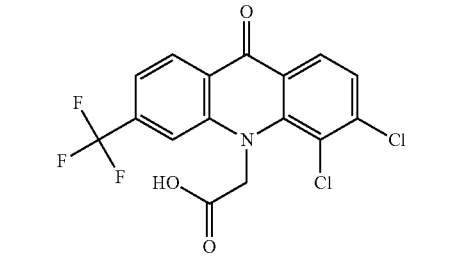
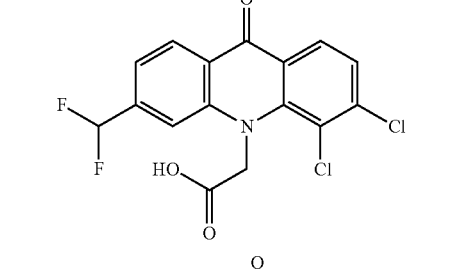
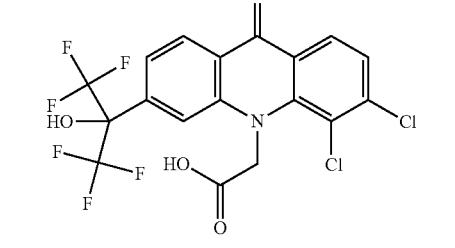
332
-continued
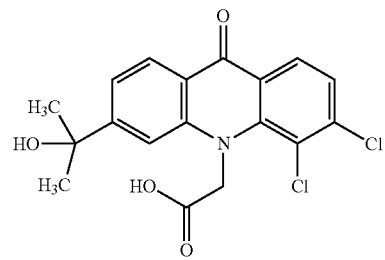
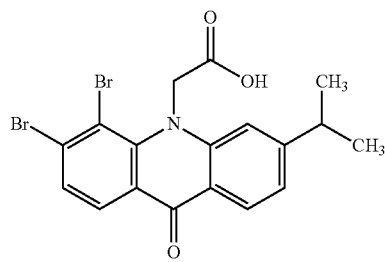
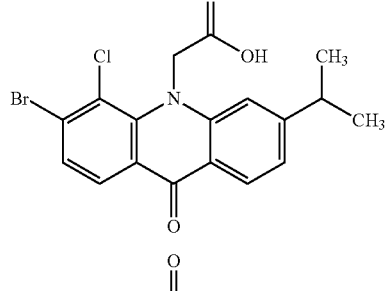
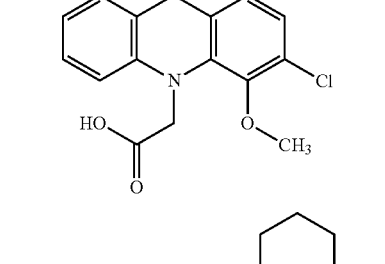
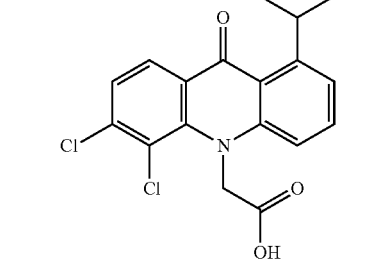
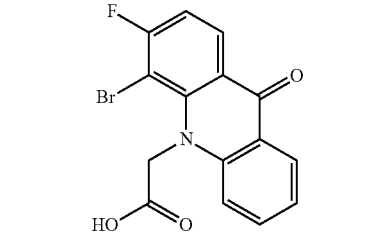

333
-continued
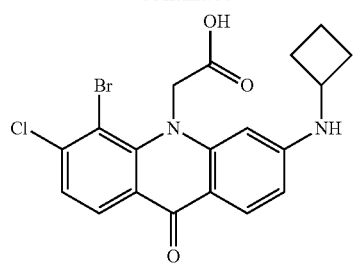
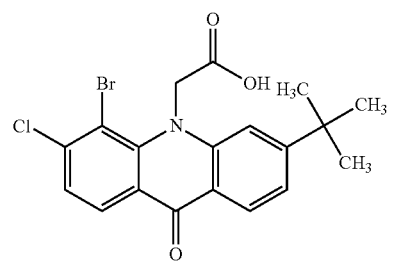
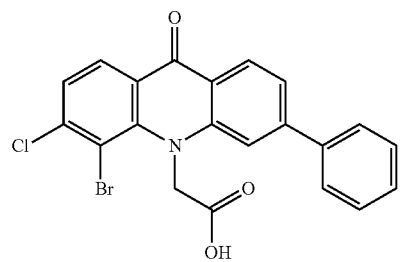
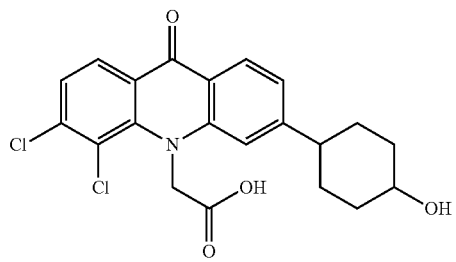
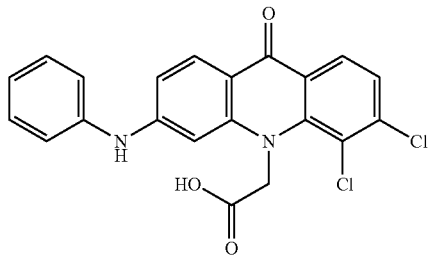
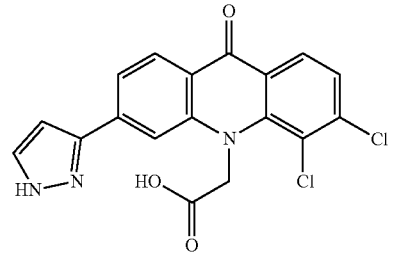
334
-continued
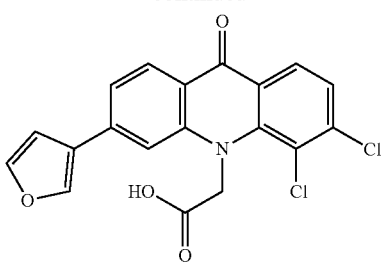
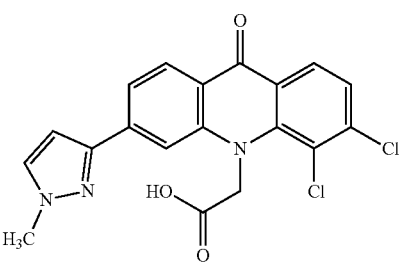
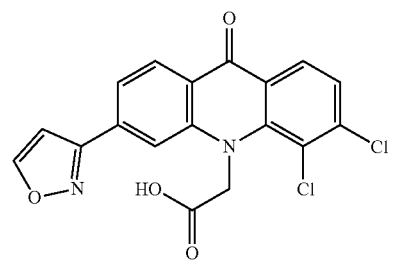
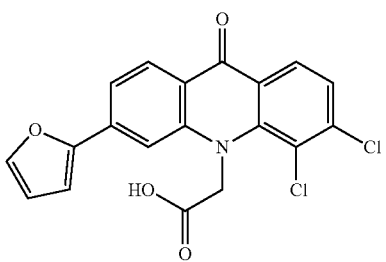
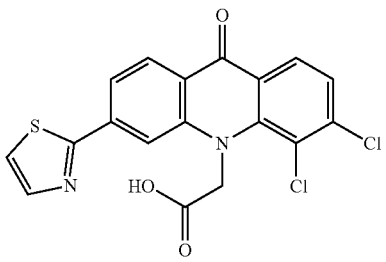
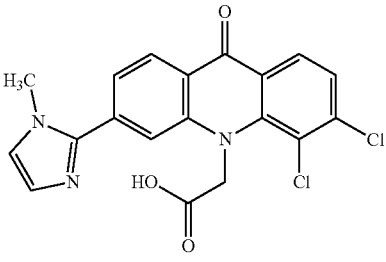

-continued
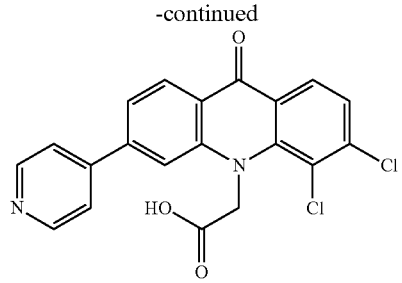
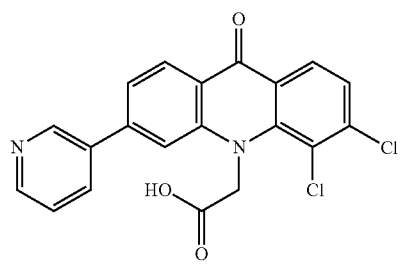
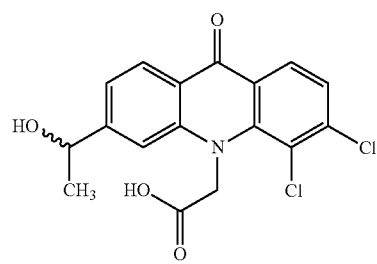
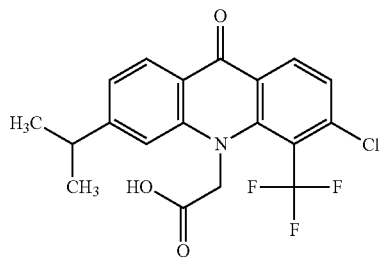
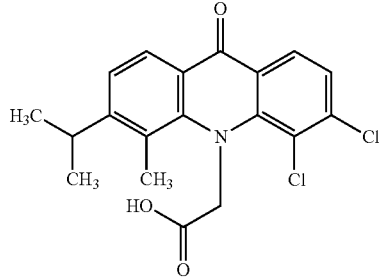
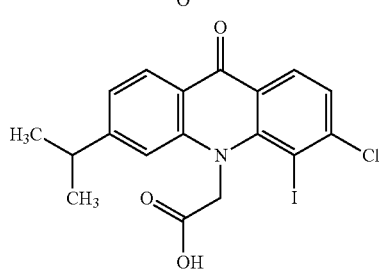
-continued
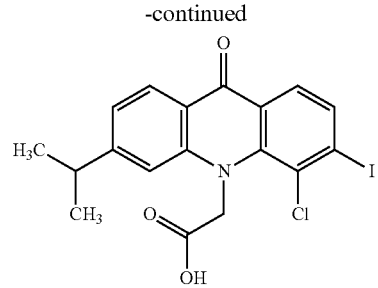
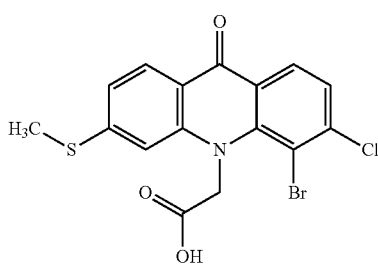
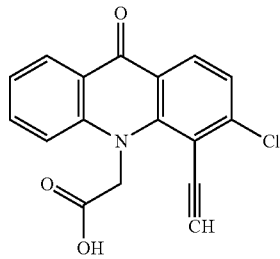
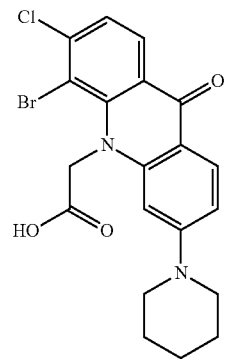
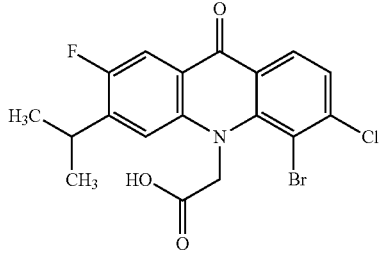
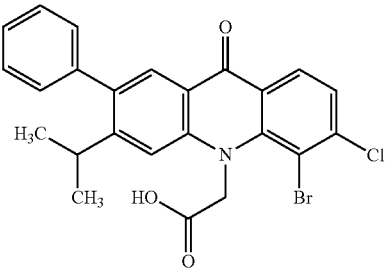

337
-continued
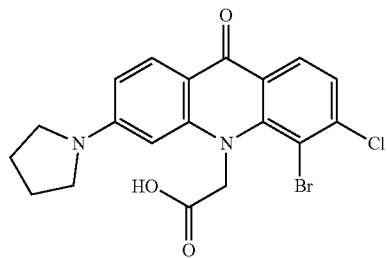
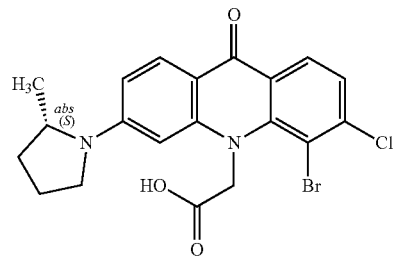
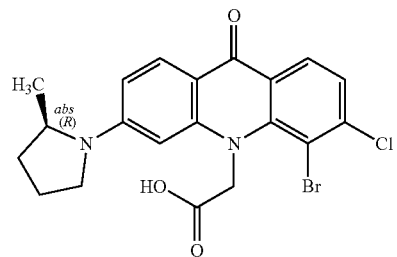
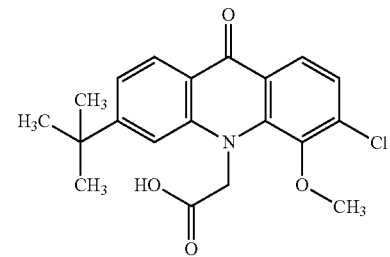
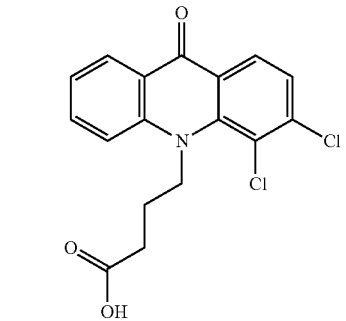
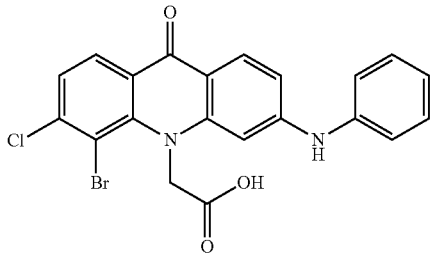
338
-continued
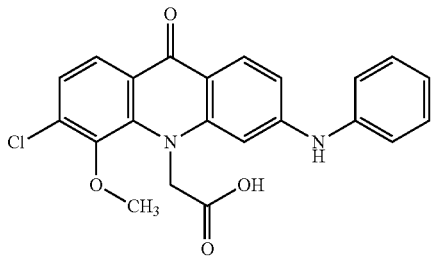
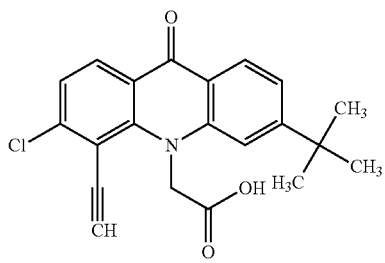
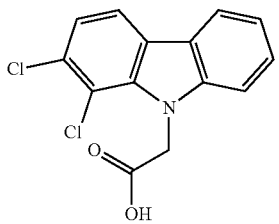
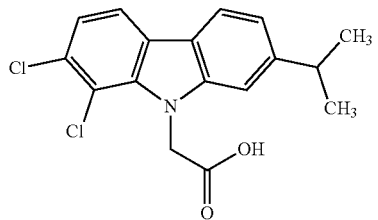
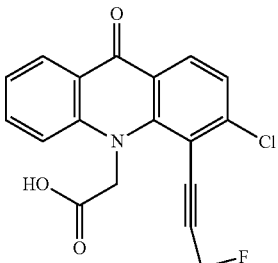
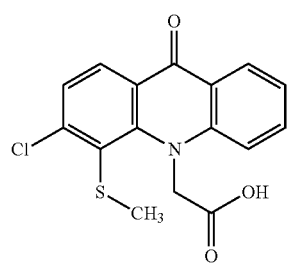

339
-continued
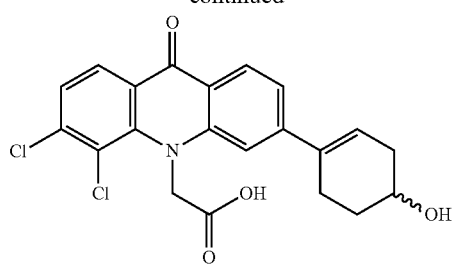
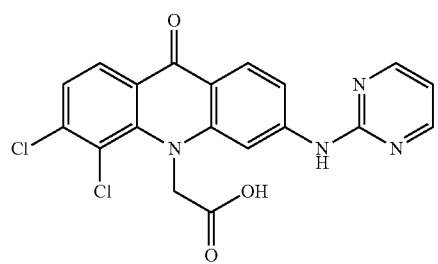
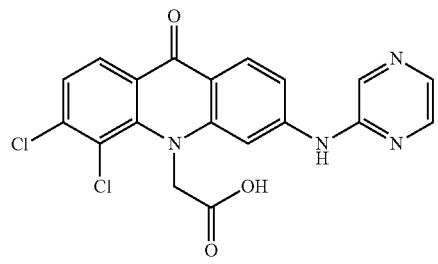
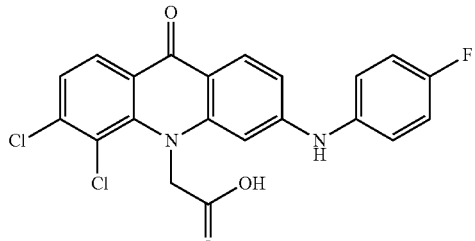
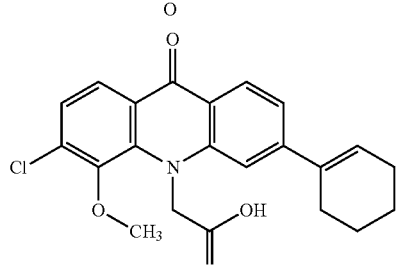
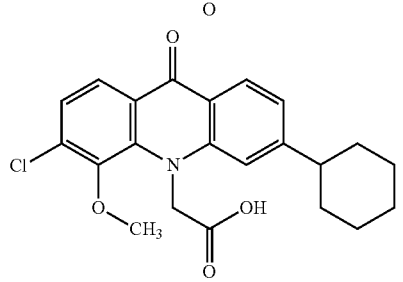
340
-continued
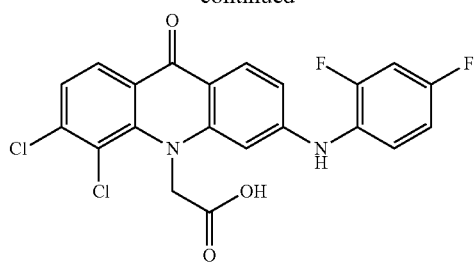
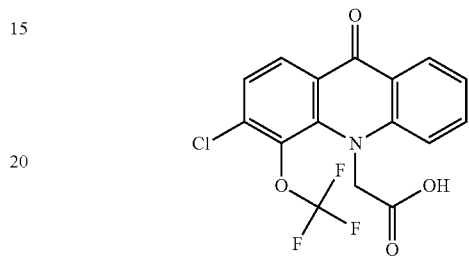
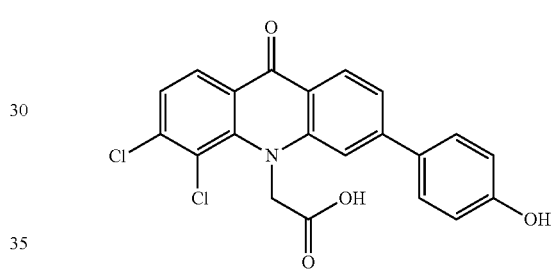
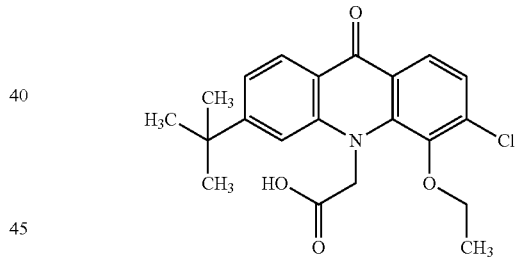
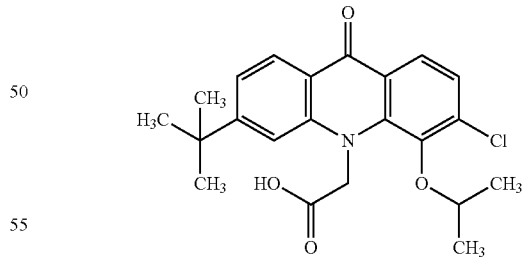
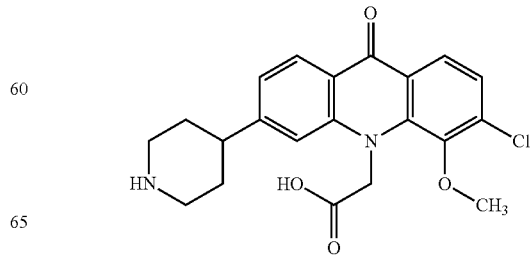

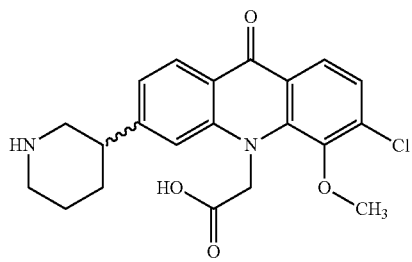
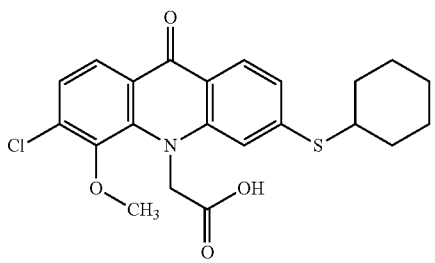
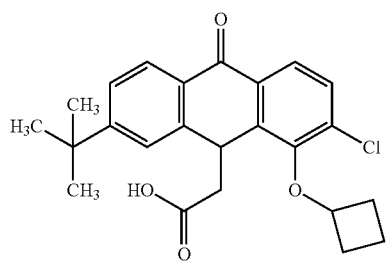
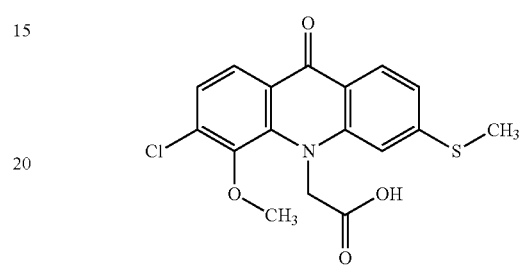
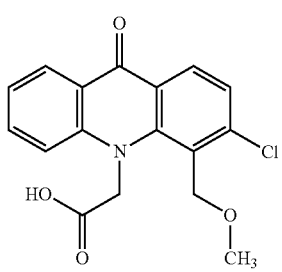
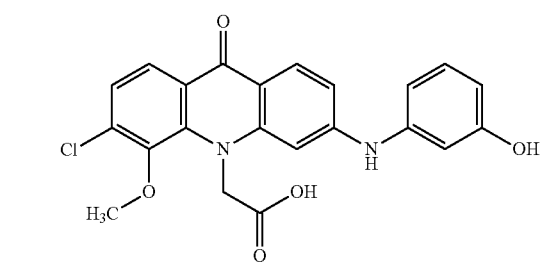
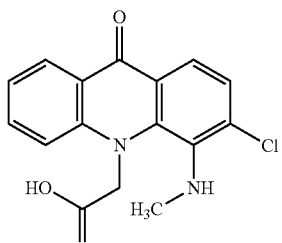
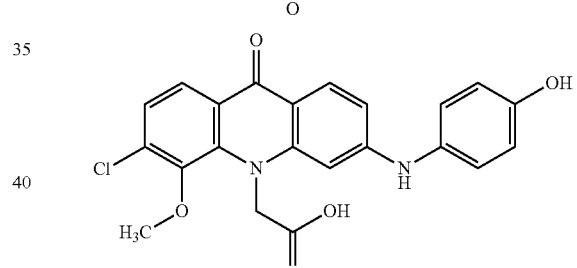
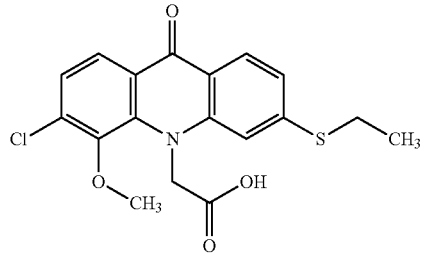
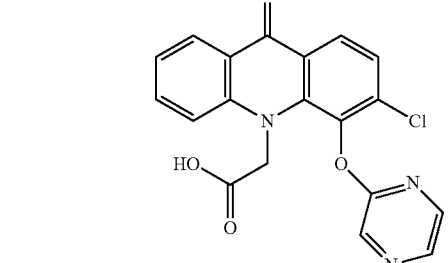
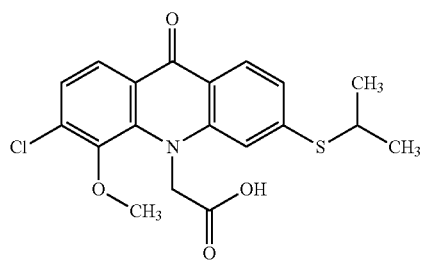
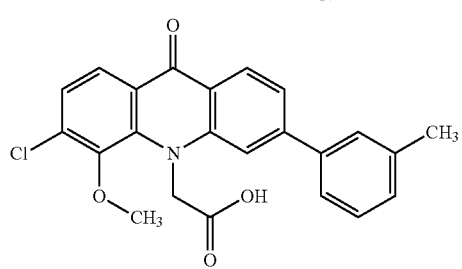

-continued
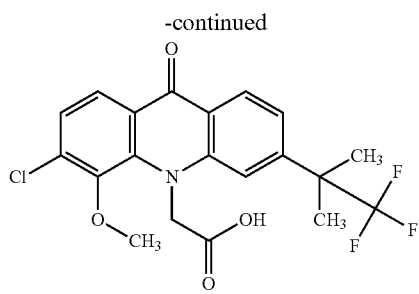
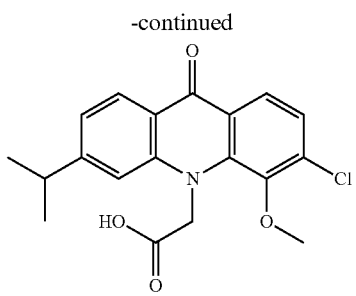
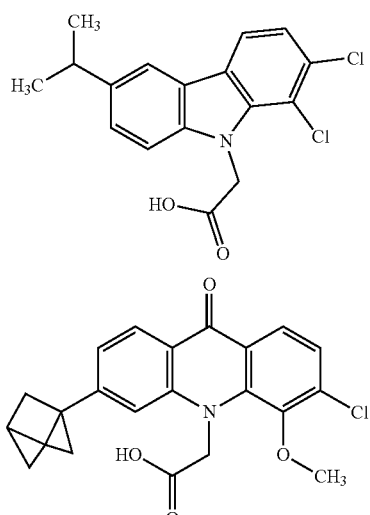
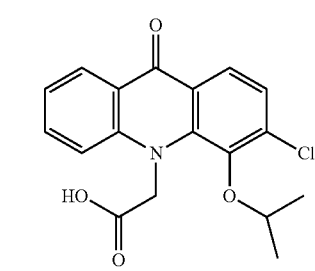
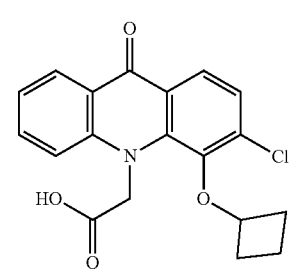
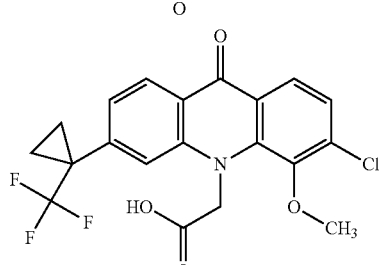
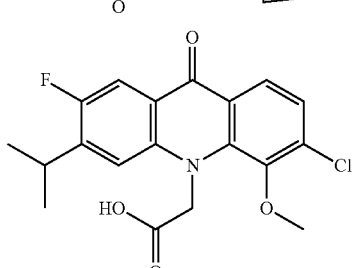
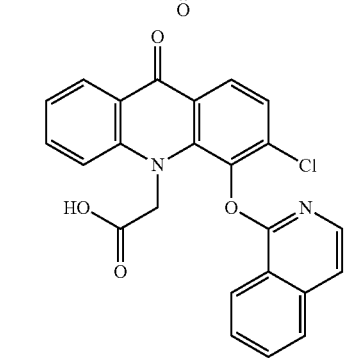
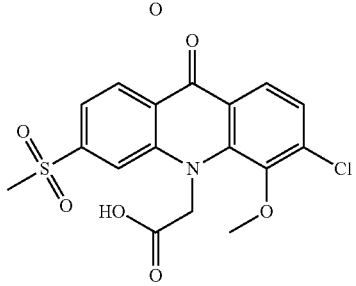
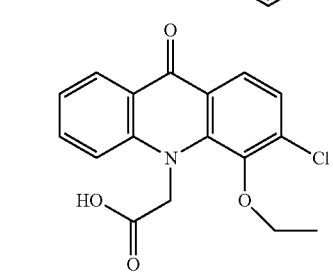
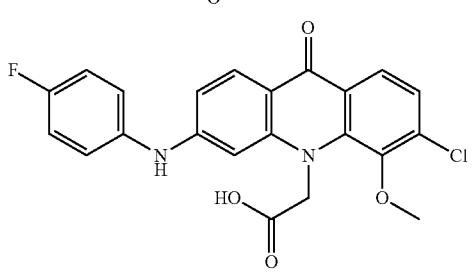

345
-continued
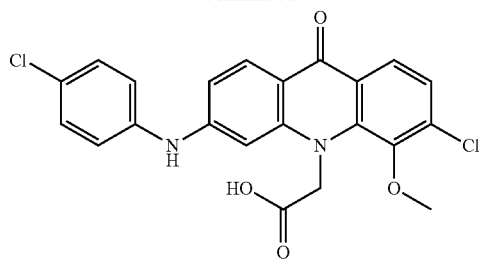
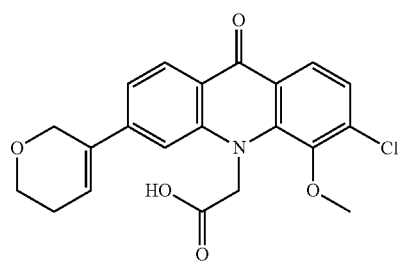
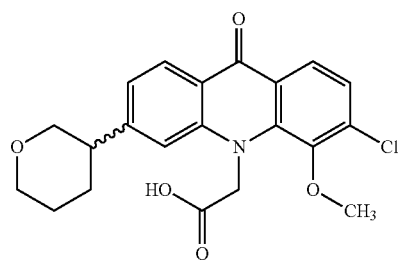
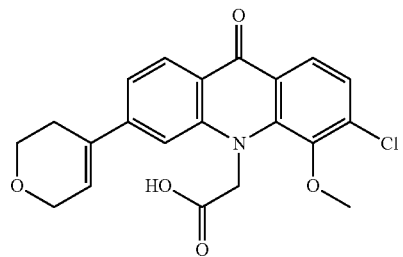
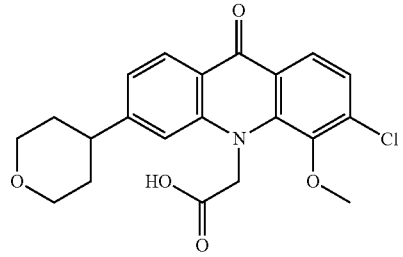
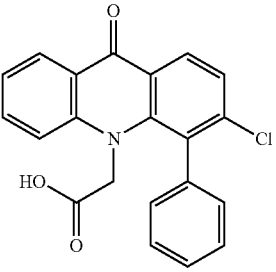
346
-continued
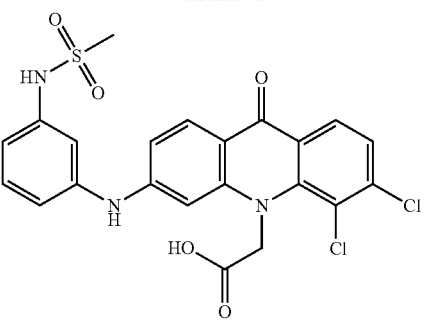
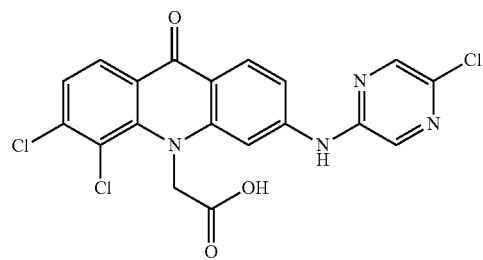
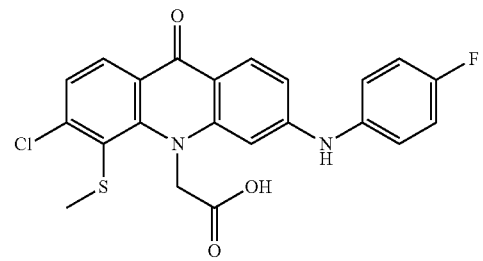
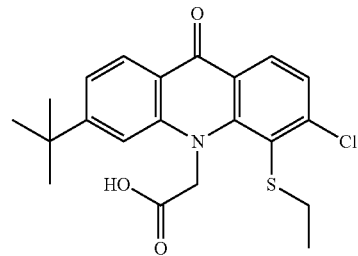
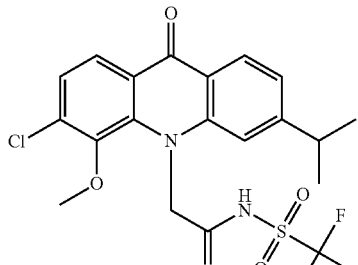
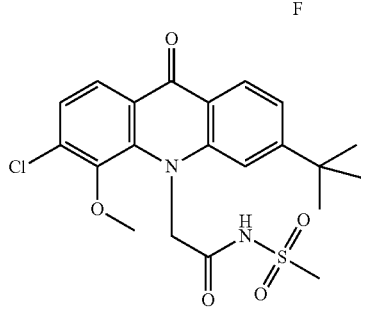

347
-continued
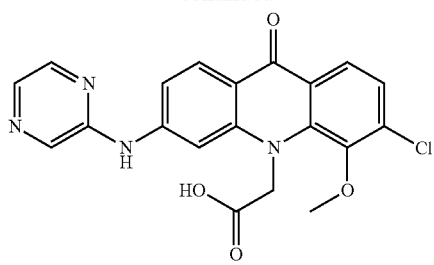
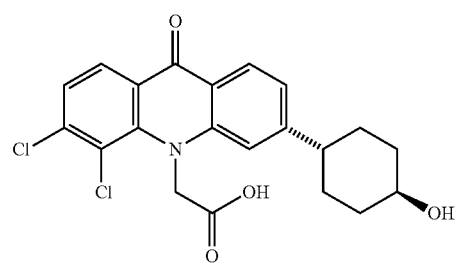
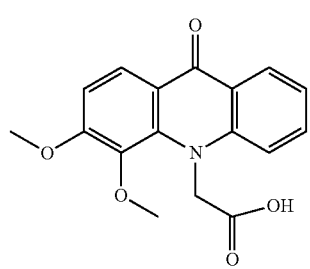
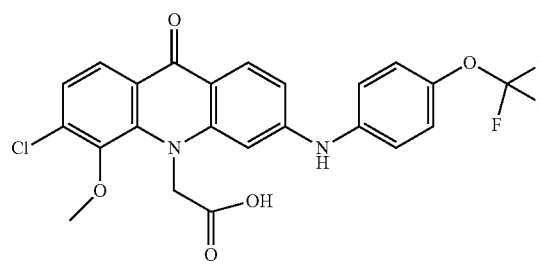
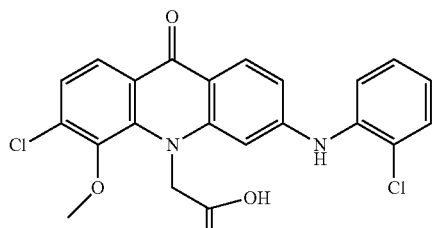
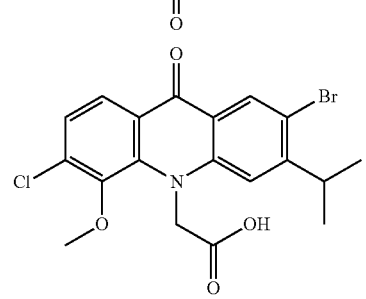
348
-continued
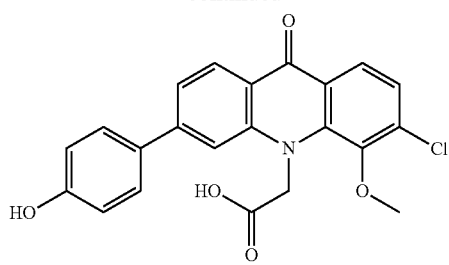
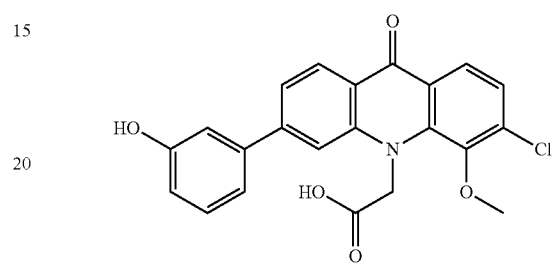
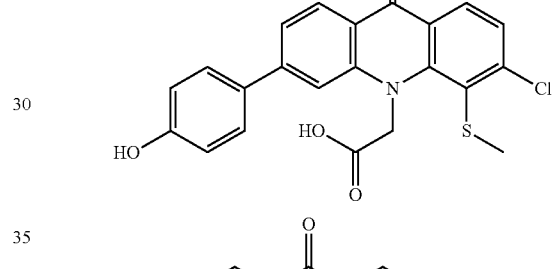
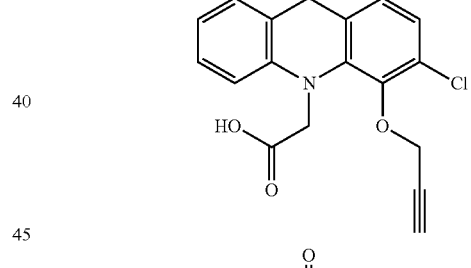
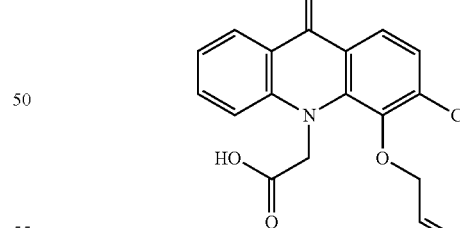
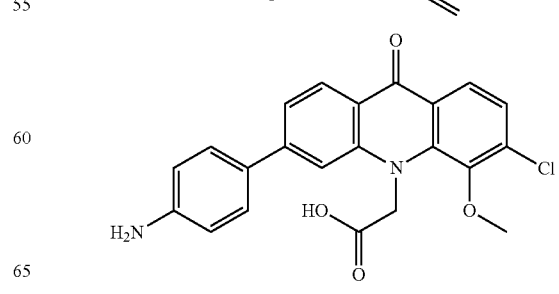

-continued
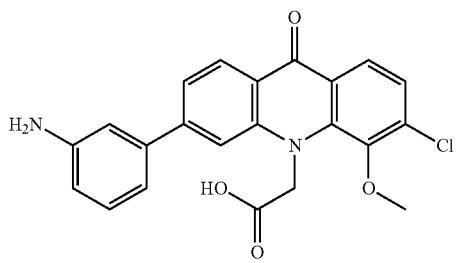
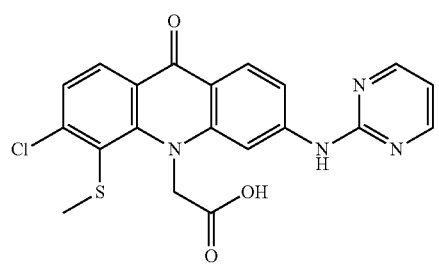
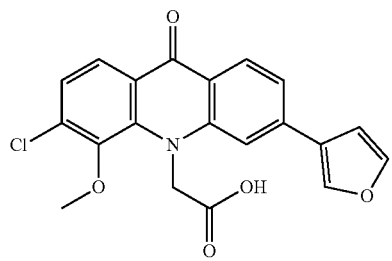
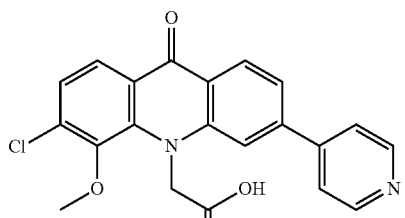
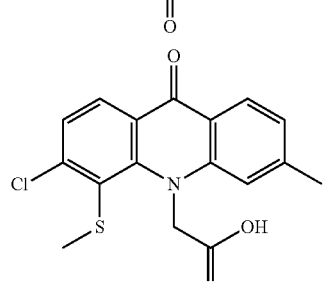
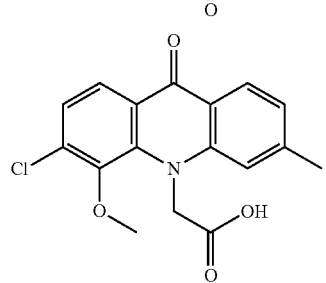
-continued
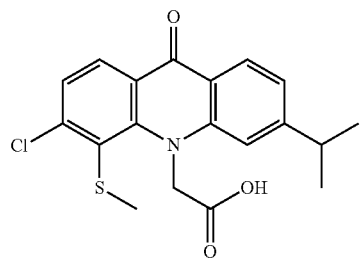
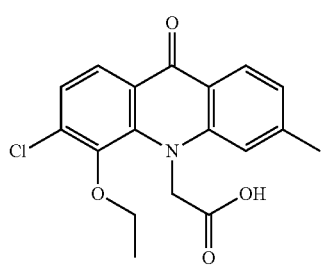
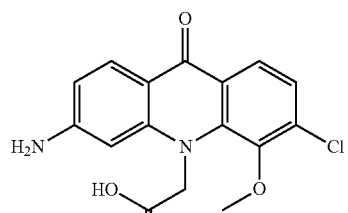
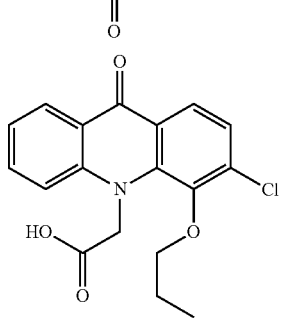
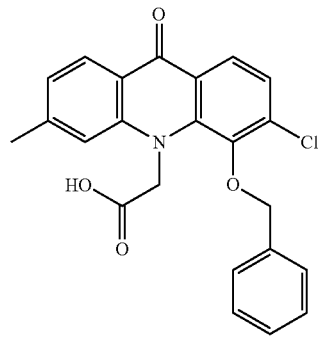
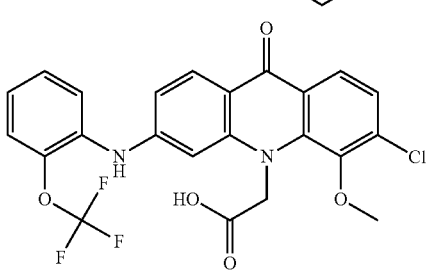

351
-continued
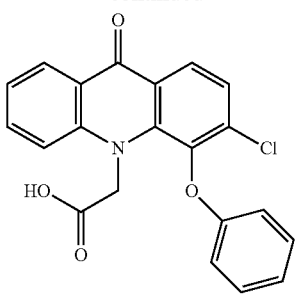
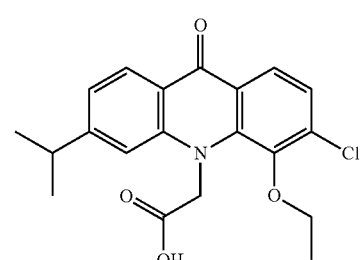
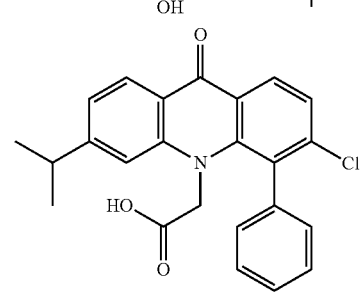
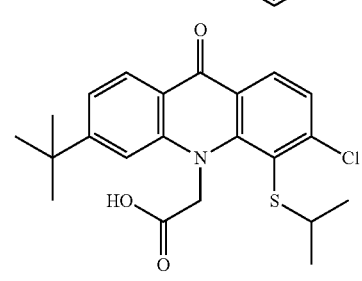
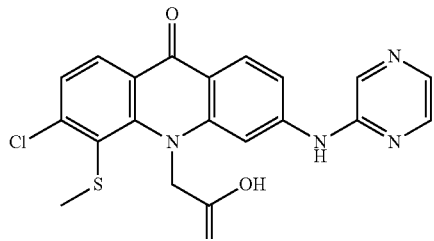
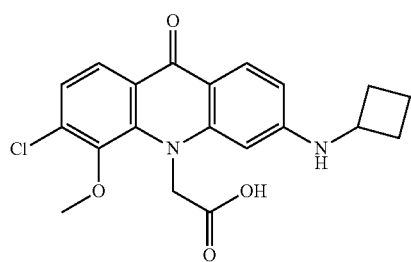
352
-continued
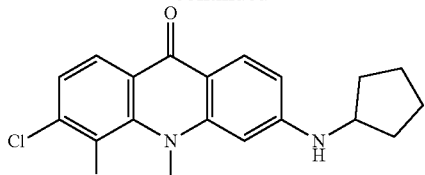
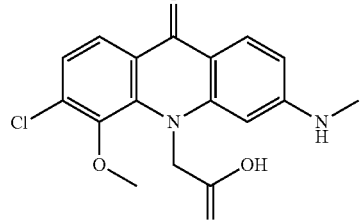
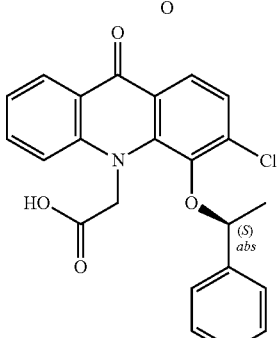
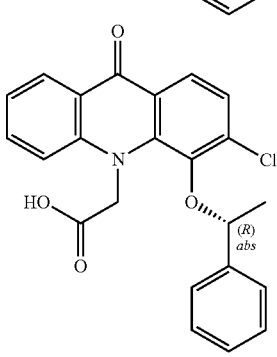
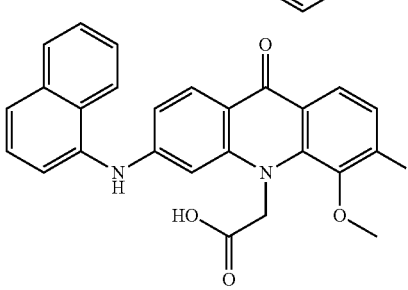
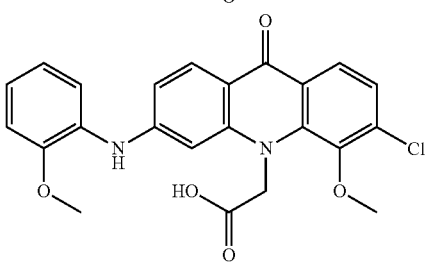

353
-continued
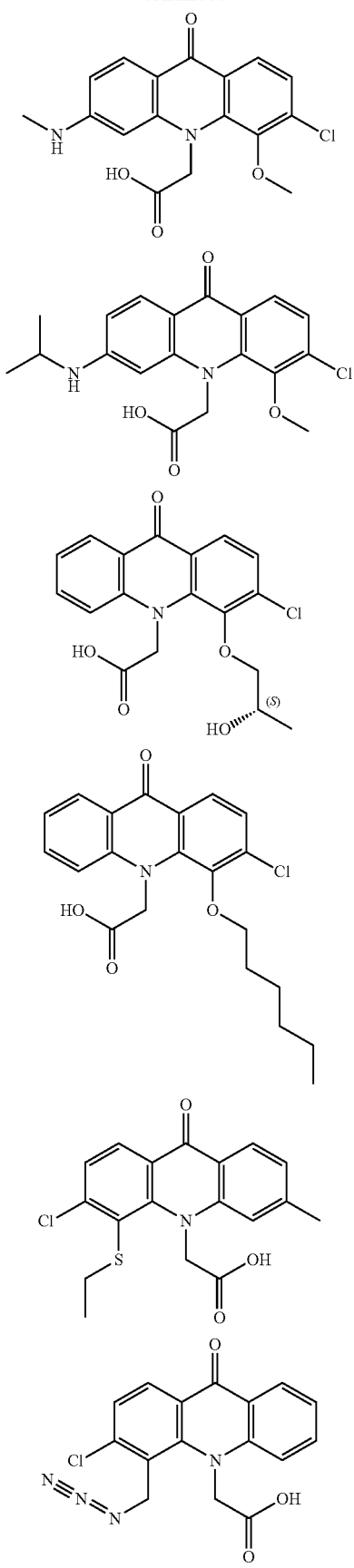
354
-continued
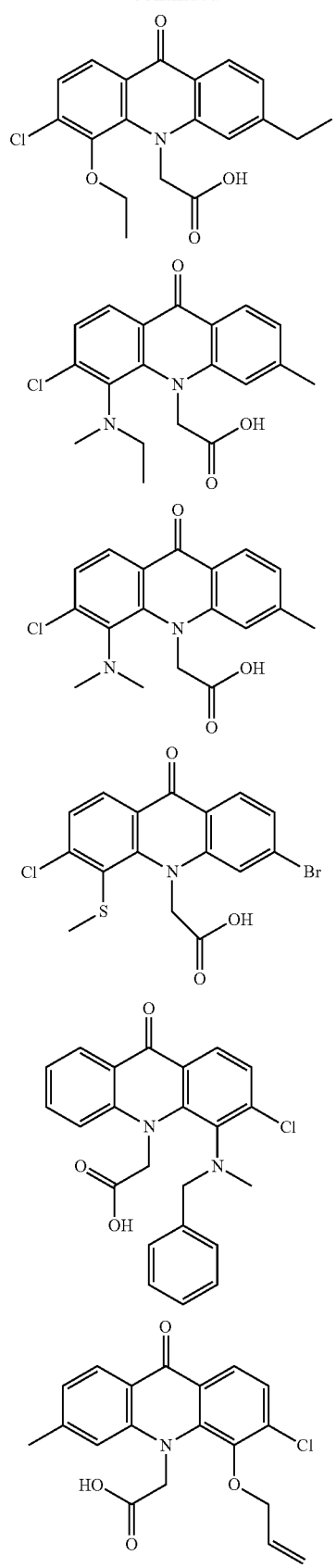

355
-continued
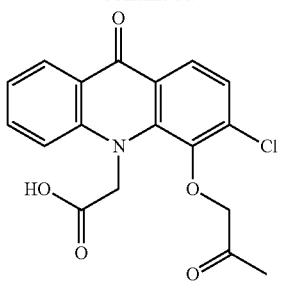 [SMILES: CC(=O)COc1c(Cl)ccc2c(=O)c3ccccc3n(CC(=O)O)c12]
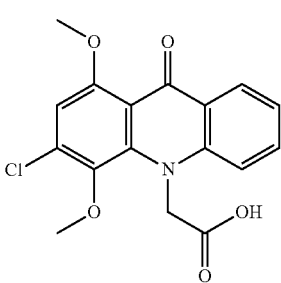 [SMILES: COc1cc(Cl)c(OC)c2c1c(=O)c1ccccc1n2CC(=O)O]
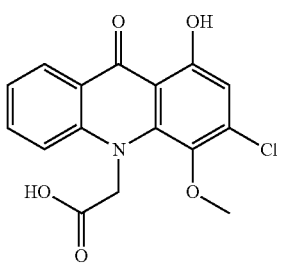 [SMILES: COc1c(Cl)cc(O)c2c(=O)c3ccccc3n(CC(=O)O)c12]
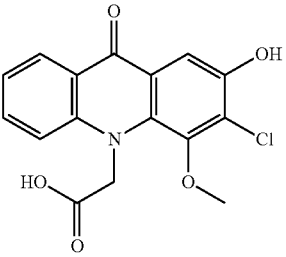 [SMILES: COc1c(Cl)c(O)cc2c(=O)c3ccccc3n(CC(=O)O)c12]
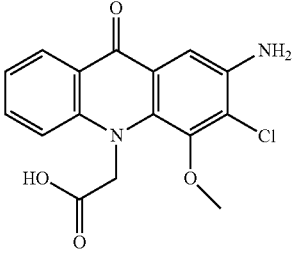 [SMILES: COc1c(Cl)c(N)cc2c(=O)c3ccccc3n(CC(=O)O)c12]
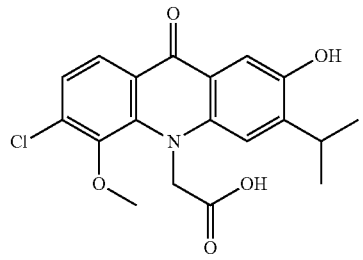 [SMILES: COc1c(Cl)ccc2c(=O)c3cc(O)c(C(C)C)cc3n(CC(=O)O)c12]
356
-continued
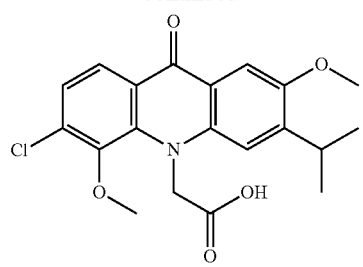 [SMILES: COc1cc2c(=O)c3ccc(Cl)c(OC)c3n(CC(=O)O)c2cc1C(C)C]
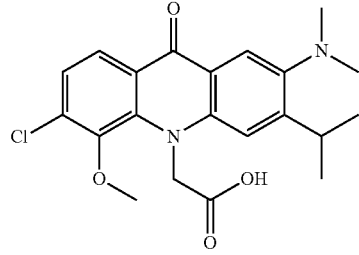 [SMILES: COc1c(Cl)ccc2c(=O)c3cc(N(C)C)c(C(C)C)cc3n(CC(=O)O)c12]
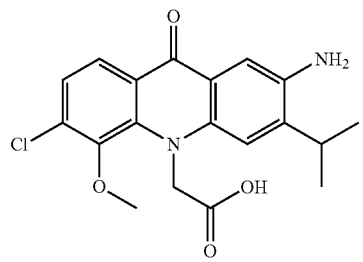 [SMILES: COc1c(Cl)ccc2c(=O)c3cc(N)c(C(C)C)cc3n(CC(=O)O)c12]
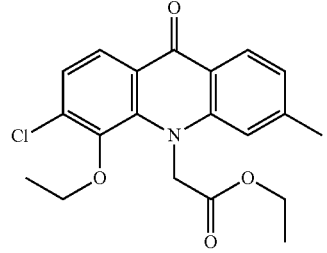 [SMILES: CCOC(=O)Cn1c2cc(C)ccc2c(=O)c2ccc(Cl)c(OCC)c21]
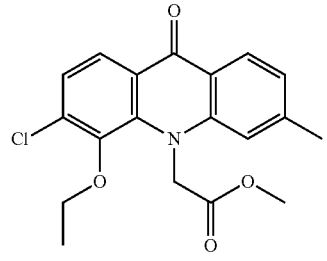 [SMILES: CCOc1c(Cl)ccc2c(=O)c3ccc(C)cc3n(CC(=O)OC)c12]
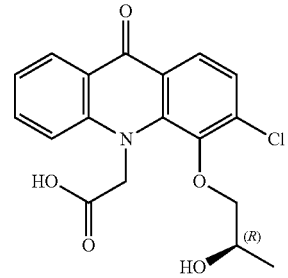

357
-continued
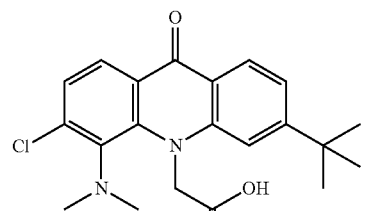
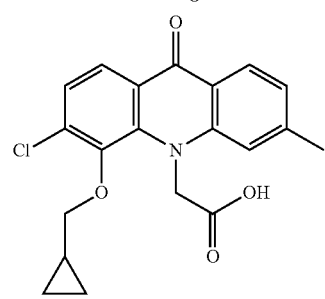
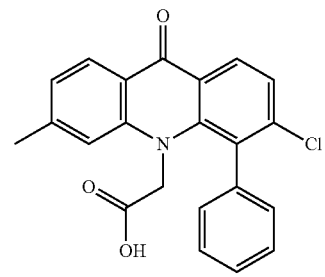 [SMILES: Cc1ccc2c(=O)c3ccc(Cl)c(-c4ccccc4)c3n(CC(=O)O)c2c1]
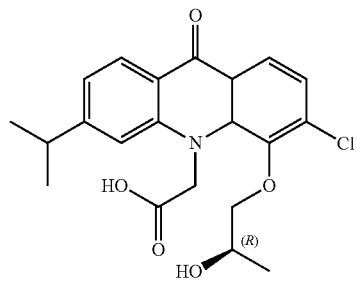
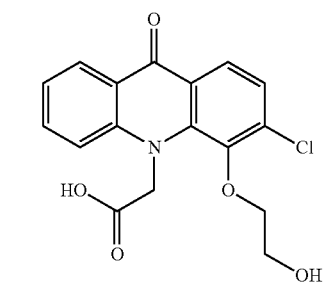 [SMILES: O=C(O)Cn1c2ccccc2c(=O)c2ccc(Cl)c(OCCO)c21]
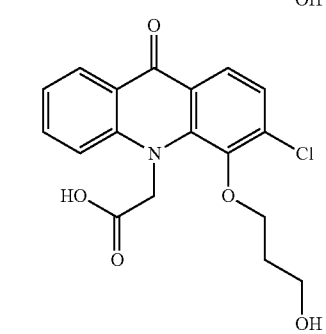
358
-continued
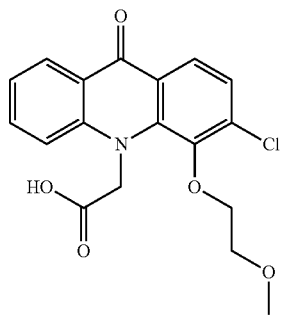 [SMILES: COCCOc1c(Cl)ccc2c(=O)c3ccccc3n(CC(=O)O)c12]
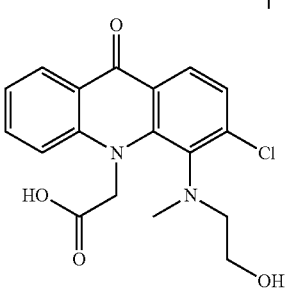
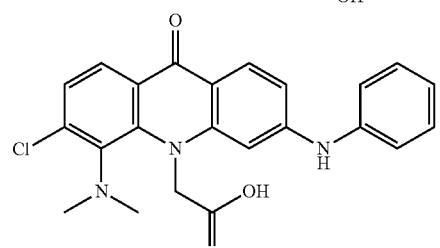
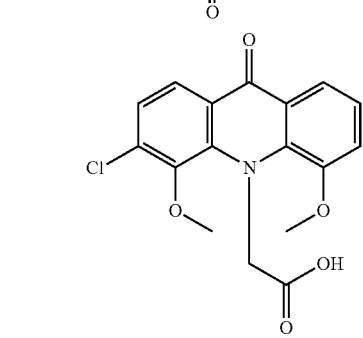
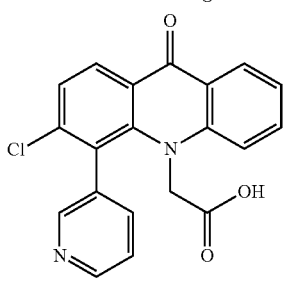
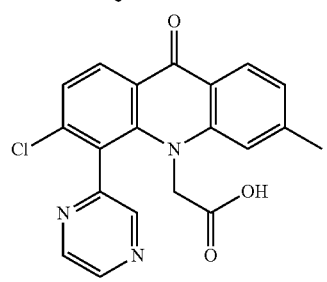

359
-continued
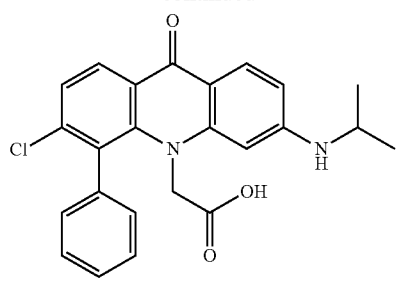 [SMILES: CC(C)Nc1ccc2c(=O)c3ccc(Cl)c(-c4ccccc4)c3n(CC(=O)O)c2c1]
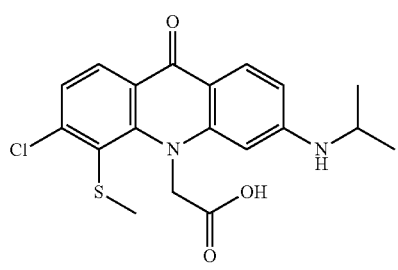 [SMILES: CSc1c(Cl)ccc2c(=O)c3ccc(NC(C)C)cc3n(CC(=O)O)c12]
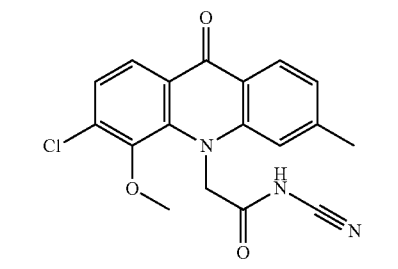 [SMILES: COc1c(Cl)ccc2c(=O)c3ccc(C)cc3n(CC(=O)NC#N)c12]
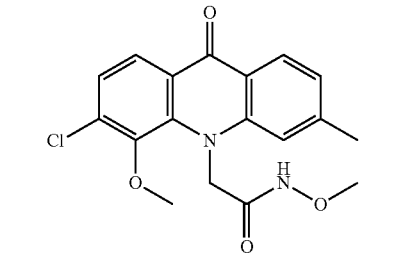 [SMILES: CONC(=O)Cn1c2cc(C)ccc2c(=O)c2ccc(Cl)c(OC)c21]
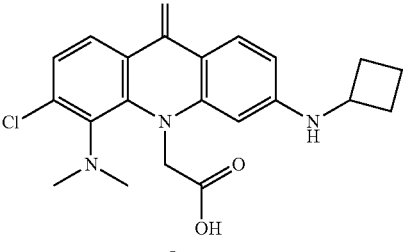
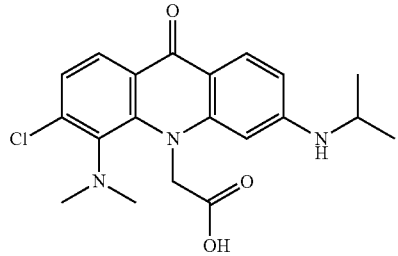 [SMILES: CC(C)Nc1ccc2c(=O)c3ccc(Cl)c(N(C)C)c3n(CC(=O)O)c2c1]
360
-continued
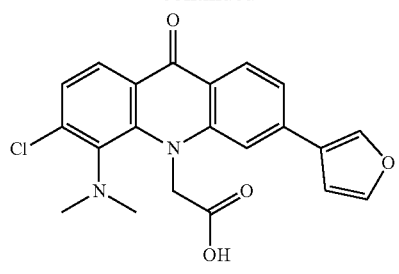 [SMILES: CN(C)c1c(Cl)ccc2c(=O)c3ccc(-c4ccoc4)cc3n(CC(=O)O)c12]
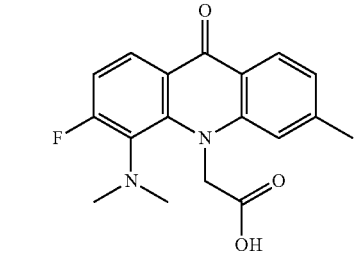 [SMILES: Cc1ccc2c(=O)c3ccc(F)c(N(C)C)c3n(CC(=O)O)c2c1]
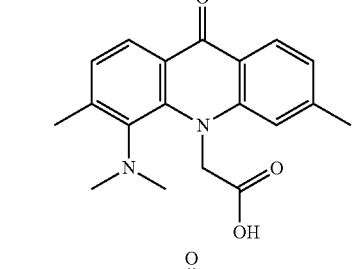
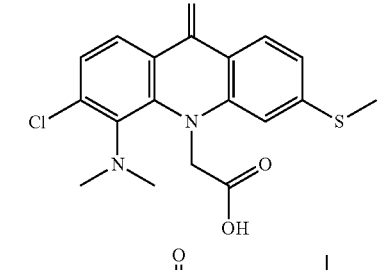
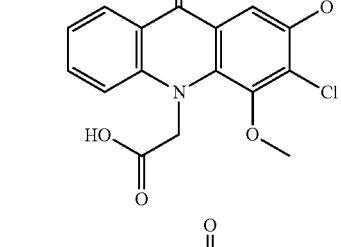
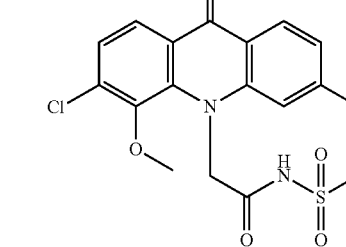

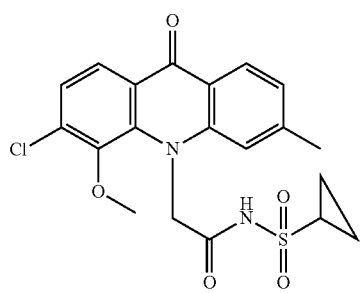
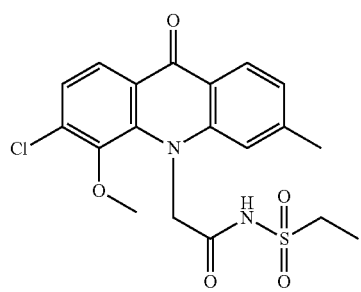
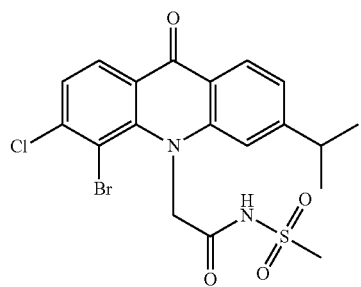
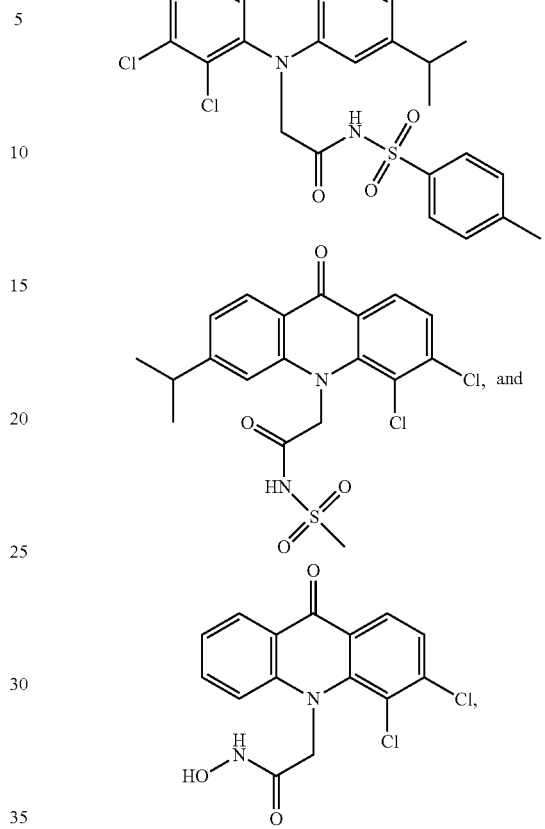

or a pharmaceutically acceptable salt or ester thereof.

22. A pharmaceutical composition comprising a therapeutically effective amount of a compound of claim 1, or a pharmaceutically acceptable salt or ester thereof, and a pharmaceutically acceptable carrier.

23. A method of modulating a stimulator of interferon genes (STING) protein, comprising administering to a subject in need thereof an effective amount of a compound of claim 1 or a pharmaceutically acceptable salt or ester thereof.

* * * * *